US012559734B2

(12) United States Patent
Beaudoin et al.

(10) Patent No.: US 12,559,734 B2
(45) Date of Patent: Feb. 24, 2026

(54) REVERSE TRANSCRIPTASE MUTANTS WITH INCREASED ACTIVITY AND THERMOSTABILITY

(71) Applicant: Integrated DNA Techonolgies, Inc., Coralville, IA (US)

(72) Inventors: Sarah Franz Beaudoin, Iowa City, IA (US); Christopher Anthony Vakulskas, North Liberty, IA (US)

(73) Assignee: INTEGRATED DNA TECHNOLOGIES, INC., Coralville, IA (US)

( * ) Notice: Subject to any disclaimer, the term of this patent is extended or adjusted under 35 U.S.C. 154(b) by 946 days.

(21) Appl. No.: 17/578,275

(22) Filed: Jan. 18, 2022

(65) Prior Publication Data

US 2022/0135955 A1 May 5, 2022

Related U.S. Application Data

(63) Continuation-in-part of application No. 17/380,982, filed on Jul. 20, 2021.

(60) Provisional application No. 63/054,228, filed on Jul. 20, 2020.

(51) Int. Cl.
*C12N 9/12* (2006.01)

(52) U.S. Cl.
CPC ........ *C12N 9/12* (2013.01); *C12Y 207/07049* (2013.01)

(58) Field of Classification Search
CPC ...................................................... C12N 9/12
See application file for complete search history.

(56) References Cited

U.S. PATENT DOCUMENTS

| | | | |
|---|---|---|---|
| 9,663,770 B2 * | 5/2017 | Rogers ................... | C12P 19/34 |
| 2014/0045244 A1 | 2/2014 | Park et al. | |
| 2014/0286907 A1 * | 9/2014 | Sarkis .................. | C12N 9/1276 |
| | | | 435/456 |
| 2014/0363854 A1 | 12/2014 | Smith et al. | |
| 2016/0340657 A1 | 11/2016 | Hogrefe et al. | |
| 2017/0298403 A1 | 10/2017 | Janulaitis et al. | |

FOREIGN PATENT DOCUMENTS

| | | |
|---|---|---|
| CN | 106 906 237 | 6/2017 |
| WO | WO 2007/022045 | 2/2007 |
| WO | WO 2015/075842 | 5/2015 |

OTHER PUBLICATIONS

Shinnick. Nucleotide sequence of Moloney murine leukaemia virus. Nature. Oct. 15-21, 1981;293(5833):543-8.*
Lim. Crystal structure of the moloney murine leukemia virus RNase H domain. J Virol. Sep. 2006;80(17):8379-89.*
Fransceus. J Ind Microbiol Biotechnol. May 2017;44(4-5):687-69.*
Sanavia. Computational and Structural Biotechnology Journal, vol. 18, 2020, pp. 1968-1979.*

(Continued)

*Primary Examiner* — Yong D Pak
(74) *Attorney, Agent, or Firm* — McDonnell Boehnen Hulbert & Berghoff LLP

(57) ABSTRACT

The disclosure provides Moloney murine leukemia virus (MMLV) reverse transcriptase (RTase) mutants. The disclosure as provides suitable amino acid positions in MMLV RTase for mutagenesis and methods and kits for using MMLV RTase mutants to synthesize cDNA from RNA templates.

14 Claims, 4 Drawing Sheets

Specification includes a Sequence Listing.

(56) References Cited

OTHER PUBLICATIONS

Studer. Residue mutations and their impact on protein structure and function: detecting beneficial and pathogenic changes. Biochem. J. (2013) 449, 581-594.*

Crowther et al. "Structural and energetic characterization of nucleic-acid binding to the fingers domain of Moloney rnurine leukemia virus reverse transcriptase" Proteins: Structure, Function, and Bioinformatics 57(1):15-26 (Oct. 2004).

Konishi et al., "Stabilization of Moloney murine leukemia virus reverse transcriptase by site-directed mutagenesis of surface residue Val433", Bioscience, Biotechnology, and Biochemistry, vol. 78, No. 1, pp. 75-78 (Jan. 2014).

The International Search Report for International Application No. PCT/US2021/042407; mailed Feb. 2, 2022, pp. 1-5.

* cited by examiner

REVERSE TRANSCRIPTASE MUTANTS WITH INCREASED ACTIVITY AND THERMOSTABILITY

CROSS-REFERENCE TO RELATED APPLICATIONS

This application is a continuation-in-part of U.S. application Ser. No. 17/380,982, filed on Jul. 20, 2021, which claims the benefit under 35 U.S.C. § 119(e) of U.S. Provisional Application No. 63/054,228, filed on Jul. 20, 2020. Each of the above-identified applications are hereby incorporated by reference herein in their entireties for all purposes.

REFERENCE TO AN ELECTRONIC SEQUENCE LISTING

The instant application contains a Sequence Listing which has been submitted electronically as a text file in ASCII format and is hereby incorporated by reference in its entirety. The name of the ASCII text file is "20-1076-US-CIP_Sequence-Listing_ST25_FINAL.txt."

FIELD OF THE DISCLOSURE

The disclosure relates to Moloney murine leukemia virus (MMLV) reverse transcriptase (RTase) mutants. The disclosure also relates to suitable amino acid positions in MMLV RTase for mutagenesis and methods for using MMLV RTase mutants to synthesize cDNA from RNA templates.

BACKGROUND

Reverse transcriptase (RTase) enzymes have revolutionized molecular biology. RTase is a critical component of the reverse transcription polymerase chain reaction (RT-PCR) allowing the production of complementary DNA (cDNA) from RNA. The cDNA produced in reverse transcription reactions can be used in a wide range of downstream applications, including quantitative PCR, gene expression analysis, isolated RNA sequencing, gene cloning, and cDNA library creation.

RTases, first derived from retroviruses, facilitate the reverse transcription of RNA into cDNA by utilizing RNA-dependent polymerase and RNase H, a non-sequence-specific endonuclease enzyme that catalyzes cleavage of RNA in an RNA/DNA duplex. This results in virus replication and integration of the viral sequence into host DNA thereby allowing for the proliferation of the virus along with host DNA. Within the laboratory setting, RTases from Moloney murine leukemia virus (MMLV), avian myeloblastosis virus (AMV), and human immunodeficiency virus type 1 (HIV-1) are the most commonly used RTase for cDNA synthesis.

RTases for research applications are often mutated multi-generational MMLV and AMV RTases that have been optimized for laboratory procedures. Mutations in the RTases alter properties of the enzymes, including thermostability, RTase activity, 5' mRNA coverage, and RNase H activity.

AMV RTases are thermostable and less sensitive to thermal degradation than MMLV RTase and are preferred for RNA having a strong secondary structure. In addition, AMV RTases are often suitable for use with RNA molecules that are five kilobases or longer because of the heat stability of AMV RTases. However, the high temperatures required to resolve strong secondary structures or long RNA strands can negatively impact RNA integrity and fidelity of transcription. AMV also possess an intrinsic RNase activity that degrades RNA in an RNA/DNA hybrid, which can result in reduced total cDNA and reduced full-length cDNA yield.

MMLV RTase is characterized by low RNase H activity and a higher fidelity as compared to AMV RTase. The reduced RNase H activity allows MMLV RTases to be used for the reverse transcription of long RNAs (>5 kb). However, the RNase H activity of MMLV RTase limits the efficiency of synthesizing long cDNA in vitro. Mutations in MMLV RTase have been introduced to reduce RNase H activity. In addition, because the optimal temperature for MMLV RTase activity is ~37° C., the enzyme lacks the ability to effectively reverse transcribe RNAs with strong secondary structures. The use of MMLV RTase at elevated temperatures can compromise cDNA length and yield as a result of lower enzyme activity. MMLV RTase mutants that substitute $Mn^{2+}$ for $Mg^{2+}$ in the reaction mixture attempt to overcome these limitations, but are characterized by inefficiency and error.

Thus, despite the unique properties of AMV and MMLV RTases, there exists a need for an RTase that combines the beneficial attributes of AMV and MMLV RTases. Consistent with this, the present application discloses MMLV RTase mutants, isolated through rational mutagenesis of MMLV RTase, that exhibit increased RTase activity and thermostability as compared to RTases, including RNase H minus constructs, that are currently available in the art.

SUMMARY

The disclosure provides Moloney murine leukemia virus (MMLV) reverse transcriptase (RTase) mutants. The disclosure also provides suitable amino acid positions in MMLV RTase for mutagenesis and methods and kits for using MMLV RTase mutants to synthesize cDNA from RNA templates.

One aspect of the disclosure provides an isolated Moloney murine leukemia virus (MMLV) reverse transcriptase (RTase) mutant comprising the amino acid sequence of SEQ ID NO: 717, wherein the amino acid sequence of the MMLV RTase mutant further comprises at least two amino acid substitutions that are: (a) a glutamine to arginine substitution at position 68 (Q68R); (b) a glutamine to arginine substitution at position 79 (Q79R); (c) a leucine to tyrosine at position 82 (L82Y); (d) a leucine to arginine substitution at position 99 (L99R); (e) a leucine to isoleucine at position 280 (L280I); (f) a glutamic acid to aspartic acid substitution at position 282 (E282D); (g) a glutamine to glutamic acid substitution at position 299 (Q299E); (h) threonine to lysine at position 306 (T306K); (i) a valine to asparagine at position 433 (V433N); (j) a valine to arginine at position 433 (V433R); (k) an isoleucine to glutamic acid at position 593 (I593E); or (l) an isoleucine to tryptophan at position 593 (I593W).

Another aspect of the disclosure provides an isolated nucleic acid molecule comprising a nucleotide sequence encoding an MMLV RTase mutant of the disclosure.

Other aspects of the disclosure provide a composition or a kit comprising an MMLV RTase mutant of the disclosure.

Other aspects of the disclosure provide methods for synthesizing complementary deoxyribonucleic acid (cDNA) or methods for performing reverse transcription-polymerase chain reaction (RT-PCR) using an MMLV RTase mutant of the disclosure.

Specific embodiments of the disclosure will become evident from the following more detailed description and the claims.

DETAILED DESCRIPTION

Figure 1A:
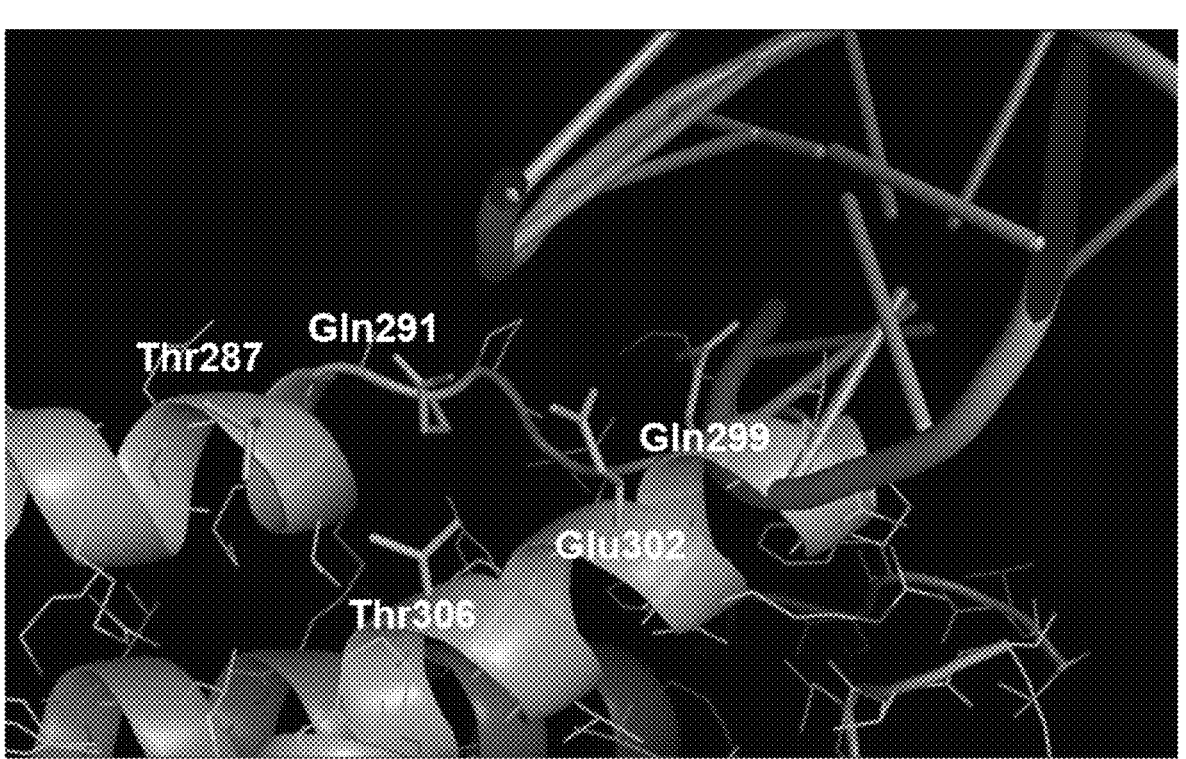
FIGS. 1A-1C are schematics showing reverse transcriptase mutagenesis selection by rational design. Amino acid positions for mutagenesis were chosen at the substrate binding site (FIGS. 1A and 1B) or near the substrate binding site (FIG. 1C).

The disclosure relates to Moloney murine leukemia virus (MMLV) reverse transcriptase (RTase) mutants. The disclosure also relates to suitable amino acid positions in MMLV RTase for mutagenesis and methods and kits for using MMLV RTase mutants to synthesize cDNA from RNA templates.

The MMLV RTase mutants of the disclosure, which have been identified and isolated, at least in part, through rational mutagenesis of a base construct of MMLV RTase, were found to have increased RTase activity and thermostability as compared to wild-type MMLV RTase and certain MMLV RTase mutants, including RNase H minus RTases, that are currently available in the art.

Reference will now be made in detail to exemplary embodiments of the claimed invention. While the claimed invention will be described in conjunction with the exemplary embodiments, it will be understood that it is not intended to limit the claimed invention to those embodiments. To the contrary, it is intended to cover alternatives, modifications, and equivalents, as may be included within the spirit and scope of the claimed invention, as defined by the appended claims.

Those of ordinary skill in the art may make modifications and variations to the embodiments described herein without departing from the spirit or scope of the claimed invention. In addition, although certain methods and materials are described herein, other methods and materials that are similar or equivalent to those described herein can also be used to practice the claimed invention.

In addition, any of the compositions or methods provided, disclosed, or described herein can be combined with one or more of any of the other compositions and methods provided, disclosed, or described herein.

1. Definitions

Unless defined otherwise, all technical and scientific terms used herein have the meaning commonly understood by a person skilled in the art to which the claimed invention belongs. The terminology used herein is for describing particular embodiments only and is not intended to be limiting of the claimed invention. All technical and scientific terms used herein have the same meaning.

The following references provide those of skill in the art with a general understanding of many of the terms used herein (unless defined otherwise herein): Singleton et al., Dictionary of Microbiology and Molecular Biology, 3rd ed.

(Wiley, 2006); Walker, The Cambridge Dictionary of Science and Technology (Cambridge University Press, 1990); Rieger et al., Glossary of Genetics: Classical and Molecular, 5th ed. (Springer Verlag, 1991); and Hale et al., Harper Collins Dictionary of Biology (HarperCollins Publishers, 1991). Generally, the procedures or methods described herein and the like are common methods used in the art. Such standard techniques can be found in reference manuals such as, for example, Green et al., Molecular Cloning: A Laboratory Manual, 4th ed. (Cold Spring Harbor Laboratory Press, 2012), and Ausubel, Current Protocols in Molecular Biology (John Wiley & Sons Inc., 2004).

The following terms may have meanings ascribed to them below, unless specified otherwise. However, it should be understood that other meanings known or understood by those having ordinary skill in the art are also possible, and within the scope of the claimed invention. All publications, patent applications, patents, and other references mentioned or discussed herein are expressly incorporated by reference in their entireties. In the case of conflict, the present specification, including definitions, will control. In addition, the materials, methods, and examples are illustrative only and not intended to be limiting.

As used herein, the singular forms "a," "and," and "the" include plural references, unless the context clearly dictates otherwise.

As used herein, the term "or" means, and is used interchangeably with, the term "and/or," unless context clearly indicates otherwise.

As used herein, the term "including" means, and is used interchangeably with, the phrase "including but not limited to."

As used herein, the term "such as" means, and is used interchangeably with, the phrase "such as, for example" or "such as but not limited."

Unless specifically stated or obvious from context, as used herein, the term "about" is understood as within a range of normal tolerance in the art, for example, within two standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "nucleic acid molecule" and "polynucleotide" refer to a polymer or large biomolecule comprised of nucleotides. The term "nucleic acid" includes deoxyribonucleic acid (DNA), ribonucleic acid (RNA), and analogs thereof. Non-limiting examples of nucleic acid molecules include DNA (e.g., genomic DNA, cDNA), RNA molecules (e.g., mRNA, rRNA, cRNA, tRNA), and chimeras thereof. A nucleic acid molecule can be obtained by cloning techniques or synthesized, using techniques that are known to those of skill in the art. DNA can be double-stranded or single-stranded (coding strand or non-coding strand, i.e., antisense). A nucleic acid backbone may comprise a variety of linkages known in the art, including one or more of sugar-phosphodiester linkages, peptide-nucleic acid bonds (referred to as "peptide nucleic acids" (PNA)), phosphorothioate linkages, methylphosphonate linkages, or combinations thereof. Sugar moieties of the nucleic acid may be ribose or deoxyribose, or similar compounds having known substitutions, for example, 2' methoxy substitutions (containing a 2'-O-methylribofuranosyl moiety) and/or 2' halide substitutions. Nitrogenous bases may be conventional bases (adenine (A), guanine (G), thymine (T), cytosine (C), and uracil (U)), known analogs thereof (e.g., inosine), known derivatives of purine or pyrimidine bases, or "abasic" residues in which the backbone includes no nitrogenous base for one or more residues. A nucleic acid may comprise only conventional sugars, bases, and linkages, as found in RNA and DNA, or may include both conventional components and substitutions (e.g., conventional bases linked via a methoxy backbone, or a nucleic acid including conventional bases and one or more base analogs). An "isolated nucleic acid molecule," as is generally understood by those of skill in the art and as used herein, refers to a polymer of nucleotides, and includes but is not limited to DNA and RNA.

As used herein, the term "probe" refers to a nucleic acid oligonucleotide that hybridizes specifically to a target sequence in a nucleic acid or its complement, under conditions that promote hybridization, thereby allowing detection of the target sequence or its amplified nucleic acid. Detection may either be direct (i.e., resulting from a probe hybridizing directly to the target or amplified sequence) or indirect (i.e., resulting from a probe hybridizing to an intermediate molecular structure that links the probe to the target or amplified sequence). A probe's "target" generally refers to a sequence within an amplified nucleic acid sequence (i.e., a subset of the amplified sequence) that hybridizes specifically to at least a portion of the probe sequence by standard hydrogen bonding or "base pairing." Sequences that are "sufficiently complementary" allow stable hybridization of a probe sequence to a target sequence, even if the two sequences are not completely complementary. A probe may be labeled or unlabeled. A probe can be produced by molecular cloning of a specific DNA sequence or it can be synthesized. Probes for use in the methods disclosed herein can be readily designed and used by those of skill in the art.

As used herein, the term "primer" refers to a nucleic acid oligonucleotide that hybridizes specifically to a target sequence in a nucleic acid or its complement, and which is capable of priming the synthesis of a nascent nucleic acid in a template-dependent process. Primers may be provided in double-stranded or single-stranded form. Primers for use in the methods disclosed herein can be readily designed and used by those of skill in the art.

Probes or primers for use in the methods disclosed herein may be of any suitable length, depending on the particular assay format and the particular needs and targeted sequences employed. For example, the probes or primers for use in the methods disclosed herein are at least 10 nucleotides in length, or at least 15, 20, 25, 30, or more than 30 nucleotides in length, and they may be adapted to be especially suited for a chosen nucleic acid amplification system and/or hybridization system used. Longer probes and primers are also within the scope of the disclosure.

A "transcribed polynucleotide" or "nucleotide transcript" is a polynucleotide (e.g., mRNA, hnRNA, cDNA, or analog of such RNA or cDNA) that is complementary to or having a high percentage of identity (e.g., at least 80% identity) with all or a portion of a mature mRNA made by transcription of a marker of the disclosure and normal post-transcriptional processing (e.g., splicing), if any, of the RNA transcript, and reverse transcription of the RNA transcript.

As used herein, the terms "reverse transcriptase," "RTase," or "RT" refer to an enzyme that is used to generate complementary (cDNA) from an RNA template in a process known as "reverse transcription." The term reverse transcriptase, as used herein, also refers to any enzyme that exhibits reverse transcription activity. Reverse transcriptases can be derived from a variety of sources including but not limited to viruses including retroviruses and DNA polymerases exhibiting transcriptase activity. Such retroviruses include but are not limited to Moloney murine leukemia virus (MMLV), avian myeloblastosis virus (AMV), and human immunodeficiency virus (HIV).

Reverse transcriptase activity can be measured by incubating an RTase in a buffer containing an RNA template and deoxynucleotides. One of skill in the art will recognize that a wide range of conditions can be used to perform reverse transcription reactions and multiple methods exist for measuring the quantity of cDNA produced during reverse transcription.

Reverse transcriptases of the disclosure include reverse transcriptases having one or a combination of the properties described herein. Such properties include but are not limited to increased activity, enhanced DNA synthesis, enhanced stability or enhanced thermostability, reduced or eliminated RNase H activity, reduced terminal deoxynucleotidyl transferase activity, increased accuracy or increased fidelity, increased specificity, or altered half-life, for example when compared to a base construct. As used herein, the term "base construct" refers to the initial RTase from which the RTase mutants of the disclosure are prepared (e.g. for example a wild-type RTase or a modified wild-type RTase).

As used herein, the terms "accuracy" and "fidelity" are used interchangeably and refer to ability of an RTase to accurately replicate a desired template; i.e., the ability of the RTase to accurately perform cDNA synthesis in a reverse transcription reaction. The "fidelity" or "accuracy" of a reverse transcriptase can be assessed by determining the frequency of incorrect nucleotide incorporation into the synthesized cDNA molecule, which may be referred to as the enzyme's error rate. As used herein, the term "increased fidelity" refers to RTase mutants of the disclosure that exhibit an error rate lower than that of the base construct. For example, the RTase mutants as disclosed herein can exhibit an error rate that is 10%, 15%, 20%, 25%, 30%, 35%, 40%, 45%, 50%, 55%, 60%, 65%, 70%, 75%, 80%, 85%, 90%, 95% 100%, or 200% lower than, or at least 2-fold, 3-fold, 4-fold, 5-fold, or 10-fold, or more than 10-fold lower than the error rate of the RTase base construct . . . .

As used herein, the term "specificity" refers to a decrease in mis-priming by an RTase during cDNA synthesis. An RTase mutant's specificity can be assessed by performing a reverse transcription reaction at a particular temperature, including higher temperatures, and comparing the amount of mis-priming in that reaction with the amount of mis-priming in a reaction performed with the wild-type RTase (or the RTase base construct) under identical conditions.

As used herein with respect to the RTase molecules of the disclosure, the terms "stable" and "thermostable" are used interchangeably and refer to an enzyme that is resistant to heat inactivation and remains active at temperatures in excess of 37° C. (e.g., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 70° C., or higher temperatures). For example, in one embodiment the disclosure provides an RTase mutant having activity with a longer half-life than that of the base construct RTase at an elevated temperature. Thus, RTase mutants with "enhanced thermostability" can refer to RTase mutants of the disclosure that exhibit an increase in thermostability at temperatures of about 50° C. up to about 90° C. as compared to the base construct RTase. In some embodiments, the thermostability of the RTase mutant is at least 1.5 fold or greater as compared to the thermostability of the base construct RTase. Comparisons of cDNA produced by a base construct and RTase mutant are compared using identical reaction conditions for the base construct and RTase mutant reactions. Reaction conditions can include but are not limited to salt concentration, buffer concentration, pH, divalent metal ion concentration, temperature, nucleoside triphosphate concentration, template concentration, RTase concentration, primer concentration, time, and in one-step PCR, the quantitative PCR primer and probe concentrations.

As used herein, the term "enhanced DNA synthesis" refers to an RTase enzyme that produces more DNA (e.g. cDNA) than the base RTase construct. In some embodiments, DNA synthesis can be measured by quantitative PCR at standard reaction conditions, as compared to the base construct RTase. Consistent with assessments of thermostability, quantitative comparisons are made under similar or the same reaction conditions and the amount of cDNA synthesized using the base construct RTase is compared to the amount of cDNA produced using the RTase mutant (see Tables 4-7). In some embodiments, the RTase mutant of the disclosure with enhanced DNA synthesis may produce about 5% to about 200% more cDNA than the base construct RTase. In some embodiments, the RTase mutant of the disclosure with enhanced DNA synthesis has at least 10%, 15%, 20%, 25%, 30%, 35%, 40%, 45%, 50%, 55%, 60%, 65%, 70%, 75%, 80%, 85%, 90%, 95%, 100%, or 200% more than, or at least 2-fold, 3-fold, 4-fold, 5-fold, or 10-fold, or more than 10-fold more DNA synthesis than the RTase base construct DNA synthesis.

Reverse transcriptase activity, as described herein, was evaluated in a one-step or two-step procedure. The one-step procedure combines reverse transcription and quantitative PCR in a single reaction. The method is performed by including Gene Expression Master Mix, RTase, RNA, a fluorescent probe, and primers and probes as described in Example 3. The two-step procedure comprises reverse transcription followed by quantitative PCR. In the reverse transcription step, RTase is added to a mixture containing RNA, gene specific primers, first strand synthesis buffer, and RNase. The resultant cDNA is then quantified in a second step wherein the cDNA is combined with Gene Expression Master Mix, primers and probes, and a fluorescent marker. The cDNA produced in either the one-step and two-step procedures is quantified, and the mean and standard deviation reported as shown herein in Tables 4-7.

As used herein, "RNase H activity" refers to cleavage of RNA in DNA-RNA duplexes via a hydrolytic mechanism to produce 5' phosphate terminated oligonucleotides. RNase H activity does not include degradation of single-stranded nucleic acids, duplex DNA, or double-stranded RNA. As used herein, the phrase "substantially lacks RNase H activity" means having less than 10%, 5%, 1%, 0.5%, or 0.1% of the activity of a wild type enzyme. As used herein, the phrase "lacks RNase H activity" means having undetectable RNase H activity or having less than about 1%, 0.5%, or 0.1% of the RNase H activity of a wild type enzyme.

As used herein, the term "mutation" refers to a change introduced into the nucleic acid sequence encoding a protein that changes the amino acid sequence of the protein, including but not limited to substitutions, insertions, deletions, point mutations, transpositions, inversions, frame shifts, nonsense mutations, truncations, or other forms of aberrations. A mutation may produce no discernible changes or result in a new property, function, or trait of the mutated protein. An RTase mutant of the disclosure may have one or more mutations in the nucleic acid sequence encoding the RTase mutant resulting in one or more mutations in the amino acid sequence of the RTase mutant. A mutation can result in one or more amino acids being substituted for an alternate amino acid residue, including Ala, Arg, Asn, Asp, Cys, Gln, Glu, Gly, His, Ile, Leu, Lys, Met, Phe, Pro, Ser, Thr, Trp, Tyr, and/or Val. The resulting amino acid mutations may impart altered functional and biological properties to the RTase mutant including but not limited to increased activity, enhanced DNA synthesis, enhanced stability or enhanced thermostability, reduced or eliminated RNase H activity, reduced terminal deoxynucleotidyl transferase activity, increased accuracy or increased fidelity, increased specificity, or altered half-life.

As used herein, the terms "detecting," "detection," "determining," and the like refer to assays performed for identification of the quantity of cDNA synthesis as a marker of RTase activity. The amount of marker expression or activity detected in the sample can be the same as, decreased, or increased as compared to the amount of marker expression or activity detected using the RTase base construct. One of skill in the art will understand that amount of cDNA can be quantified using multiple techniques.

The term "increased," as used herein with regard to RTase activity, refers to the level of RTase activity of an RTase mutant as compared to the RTase base construct. An RTase mutant has "increased" RTase activity if the level of its RTase activity, as measured by the quantity of cDNA synthesized or as measured by other methods known in the art, is more than the RTase base construct activity. For example, the RTase activity of the RTase mutant is increased if the RTase activity is at least 10%, 15%, 20%, 25%, 30%, 35%, 40%, 45%, 50%, 55%, 60%, 65%, 70%, 75%, 80%, 85%, 90%, 95%, or 100% more than, or at least 2-fold, 3-fold, 4-fold, 5-fold, or 10-fold, or more than 10-fold more than the RTase base construct activity.

The term "decreased," as used herein with regard to RTase activity, refers to the level of RTase activity of an RTase mutant as compared to the RTase base construct. An RTase mutant has "decreased" RTase activity if the level of its RTase activity, as measured by the quantity of cDNA synthesized or as measured by other methods known in the art is less than the RTase base construct activity. For example, the RTase activity of the RTase mutant is decreased if the RTase activity is at least 95%, 90%, 85%, 80%, 75%, 70%, 65%, 60%, 55%, 50%, 45%, 40%, 35%, 30%, 25%, 20%, 15%, 10%, or 5% less than, or at least 2-fold, 3-fold, 4-fold, 5-fold, 10-fold, or more than 10-fold less than the RTase base construct activity.

As used herein, the term "amplification" refers to any known in vitro procedure for obtaining multiple copies of a target nucleic acid sequence or its complement or fragments thereof. In vitro amplification refers to production of an amplified nucleic acid that may contain less than the complete target region sequence or its complement. Known in vitro amplification methods include, for example, transcription-mediated amplification, replicase-mediated amplification, polymerase chain reaction (PCR) amplification, ligase chain reaction (LCR) amplification, and strand-displacement amplification (SDA, including multiple strand-displacement amplification method (MSDA)). Replicase-mediated amplification uses self-replicating RNA molecules, and a replicase such as Q-β-replicase. PCR amplification uses DNA polymerase, primers, and thermal cycling to synthesize multiple copies of the two complementary strands of DNA or cDNA. PCR involves denaturation of a double-stranded DNA molecule, followed by annealing of DNA primers directed to the sequence of interest, and amplification/extension of the newly formed DNA strand. LCR amplification uses at least four separate oligonucleotides to amplify a target and its complementary strand by using multiple cycles of hybridization, ligation, and denaturation. SDA is a method in which a primer contains a recognition site for a restriction endonuclease that permits the endonuclease to nick one strand of a hemimodified DNA duplex that includes the target sequence, followed by amplification in a series of primer extension and strand displacement steps. Other strand-displacement amplification methods known in the art (e.g., MSDA) do not require endonuclease nicking. Those of skill in the art will understand that the oligonucleotide primer sequences of the disclosure may be readily used in any in vitro amplification method based on primer extension by a polymerase. As commonly known in the art, oligonucleotides are designed to bind to a complementary sequence under selected conditions.

As used herein, "real time PCR" or "quantitative PCR" refers to a PCR method wherein the amount of product being formed can be monitored using florescent probes and quantified by tracking the fluorescent signal produced, above a threshold level. Real time PCR can be performed in a one-step reaction that includes the reverse transcription step in a simultaneous reaction (i.e., real time PCR or RT-PCR) or in a two-step reaction in which the reverse transcription step and PCR steps are performed consecutively.

As used herein, the term "complementary" refers to the broad concept of sequence complementarity between regions of two nucleic acid strands or between two regions of the same nucleic acid strand. A first region of a nucleic acid is complementary to a second region of the same or a different nucleic acid if, when the two regions are arranged in an antiparallel fashion, at least one nucleotide of the first region is capable of base pairing with a nucleotide of the second region. In some embodiments, the first region comprises a first portion and the second region comprises a second portion, whereby, when the first and second portions are arranged in an antiparallel fashion, at least about 50%, 75%, 80%, 85%, 90%, 95%, 96%, 97%, 98%, or 99% of the nucleotides of the first portion are capable of base pairing with nucleotides in the second portion. In another embodiment, all nucleotides of the first portion are capable of base pairing with nucleotides in the second portion.

Polypeptide and polynucleotide sequences may be aligned, and percentages of identical amino acids or nucleotides in a specified region may be determined against another polypeptide or polynucleotide sequence, using computer algorithms that are publicly available. The percent identity of a polynucleotide or polypeptide sequence is determined by aligning polynucleotide and polypeptide sequences using appropriate algorithms, such as BLASTN or BLASTP, respectively, set to default parameters; identifying the number of identical nucleic or amino acids over the aligned portions; dividing the number of identical nucleic or amino acids by the total number of nucleic or amino acids of the polynucleotide or polypeptide of the disclosure; and then multiplying by 100 to determine the percent identity.

As used herein, the terms "sample" and "biological sample" include a specimen or culture obtained from any source. Biological samples can be obtained from cerebrospinal fluid, lacrimal fluid, blood (including any blood product, such as whole blood, plasma, serum, or specific types of cells of the blood), urine, saliva, and the like. Biological samples also include tissue samples, such as biopsy tissues or pathological tissues that have previously been fixed (e.g., formaline snap frozen, cytological processing).

2. Reverse Transcriptases

The disclosure relates to Moloney murine leukemia virus (MMLV) reverse transcriptase (RTase) mutants. The MMLV RTase mutants of the disclosure are prepared by modifying the sequence of an MMLV RTase base construct (SEQ ID NO: 637). In one embodiment, the MMLV RTase mutant of the disclosure comprises the amino acid sequence of SEQ ID NO: 637, wherein the amino acid sequence of the MMLV RTase mutant further comprises at least one amino acid substitution that is: (a) an isoleucine to arginine, lysine, or methionine substitution at position 61 (I61R, I61K, or I61M); (b) a glutamine to arginine, lysine, or isoleucine substitution at position 68 (Q68R, Q68K, or Q68I); (c) a glutamine to arginine, histidine, or isoleucine substitution at position 79 (Q79R, Q79H, or Q79I); (d) a leucine to arginine, lysine, or asparagine substitution at position 99 (L99R, L99K, or L99N); (e) a glutamic acid to aspartic acid, methionine, or typtophan substitution at position 282 (E282D, E282M, or E282W); and/or (f) an arginine to alanine substitution at position 298 (R298A).

In another embodiment, the MMLV RTase mutant of the disclosure comprises the amino acid sequence of SEQ ID NO: 637, wherein the amino acid sequence of the MMLV RTase mutant further comprises at least two amino acid substitutions that are: (a) an isoleucine to arginine substitution at position 61 and a glutamic acid to aspartic acid substitution at position 282 (I61R/E282D); (b) a leucine to arginine at substitution position 99 and a glutamic acid to aspartic acid substitution at position 282 (L99R/E282D); (c) a glutamine to arginine substitution at position 68 and a glutamic acid to aspartic acid substitution at position 282 (Q68R/E282D); (d) a glutamine to arginine substitution at position 79 and a glutamic acid to aspartic acid substitution at position 282 (Q79R/E282D); (e) a glutamic acid to aspartic acid substitution at position 282 and an arginine to alanine substitution at position 298 (E282D/R298A); (f) an isoleucine to arginine substitution at position 61 and a leucine to arginine substitution at position 99 (I61R/L99R); (g) an isoleucine to arginine substitution at position 61 and a glutamine to arginine substitution at position 68 (I61R/Q68R); (h) an isoleucine to arginine substitution at position 61 and a glutamine to arginine substitution at position 79 (I61R/Q79R); (i) an isoleucine to arginine substitution at position 61 and an arginine to alanine substitution at position 298 (I61R/R298A); (j) a glutamine to arginine substitution at position 68 and a leucine to arginine substitution at position 99 (Q68R/L99R); (k) a glutamine to arginine substitution at position 79 and a leucine to arginine substitution at position 99 (Q79R/L99R); (1) a leucine to arginine at substitution position 99 and an arginine to alanine substitution at position 298 (L99R/R298A); (m) a glutamine to arginine substitution at position 68 and a glutamine to arginine substitution at position 79 (Q68R/Q79R); (n) a glutamine to arginine substitution at position 68 and an arginine to alanine substitution at position 298 (Q68R/R298A); or (o) a glutamine to arginine substitution at position 79 and an arginine to alanine substitution at position 298 (Q79R/R298A).

In another embodiment, the MMLV RTase mutant of the disclosure comprises the amino acid sequence of SEQ ID NO: 637, wherein the amino acid sequence of the MMLV RTase mutant further comprises at least three amino acid substitutions that are: (a) a glutamine to arginine substitution at position 68, a leucine to arginine substitution at position 99, and a glutamic acid to aspartic acid substitution at position 282 (Q68R/L99R/E282D); (b) a glutamine to arginine substitution at position 79, a leucine to arginine substitution at position 99, and a glutamic acid to aspartic acid substitution at position 282 (Q79R/L99R/E282D); (c) a glutamine to arginine substitution at position 68, a glutamine to arginine substitution at position 68, and a glutamic acid to aspartic acid substitution at position 282 (Q68R/Q79R/E282D); or (d) a glutamine to arginine substitution at position 68, a glutamine to arginine substitution at position 68, and a leucine to arginine substitution at position 99 (Q68R/Q79R/L99R).

In another embodiment, the MMLV RTase mutant of the disclosure comprises the amino acid sequence of SEQ ID NO: 637, wherein the amino acid sequence of the MMLV RTase mutant further comprises at least four amino acid substitutions that are: (a) a glutamine to arginine substitution at position 68, a glutamine to arginine substitution at position 79, a leucine to arginine substitution at position 99, and a glutamic acid to aspartic acid substitution at position 282 (Q68R/Q79R/L99R/E282D); (b) a glutamine to arginine substitution at position 68, a glutamine to arginine substitution at position 79, a leucine to lysine substitution at position 99, and a glutamic acid to aspartic acid substitution at position 282 (Q68R/Q79R/L99K/E282D); (c) a glutamine to arginine substitution at position 68, a glutamine to arginine substitution at position 79, a leucine to asparagine substitution at position 99, and a glutamic acid to aspartic acid substitution at position 282 (Q68R/Q79R/L99N/E282D); (d) a glutamine to isoleucine substitution at position 68, a glutamine to arginine substitution at position 79, a leucine to arginine substitution at position 99, and a glutamic acid to aspartic acid substitution at position 282 (Q68I/Q79R/L99R/E282D); (e) a glutamine to lysine substitution at position 68, a glutamine to arginine substitution at position 79, a leucine to arginine substitution at position 99, and a glutamic acid to aspartic acid substitution at position 282 (Q68K/Q79R/L99R/E282D); (f) a glutamine to arginine substitution at position 68, a glutamine to histidine substitution at position 79, a leucine to arginine substitution at position 99, and a glutamic acid to aspartic acid substitution at position 282 (Q68R/Q79H/L99R/E282D); (g) a glutamine to arginine substitution at position 68, a glutamine to isoleucine substitution at position 79, a leucine to arginine substitution at position 99, and a glutamic acid to aspartic acid substitution at position 282 (Q68R/Q79I/L99R/E282D); (h) a glutamine to arginine substitution at position 68, a glutamine to arginine substitution at position 79, a leucine to arginine substitution at position 99, and a glutamic acid to methionine substitution at position 282 (Q68R/Q79R/L99R/E282M); (i) a glutamine to arginine substitution at position 68, a glutamine to arginine substitution at position 79, a leucine to arginine substitution at position 99, and a glutamic acid to tryptophan substitution at position 282 (Q68R/Q79R/L99R/E282W); or (j) a glutamine to isoleucine substitution at position 68, a glutamine to histidine substitution at position 79, a leucine to lysine substitution at position 99, and a glutamic acid to methionine substitution at position 282 (Q68I/Q79H/L99K/E282M).

In another embodiment, the MMLV RTase mutant of the disclosure comprises the amino acid sequence of SEQ ID NO: 637, wherein the amino acid sequence of the MMLV RTase mutant further comprises at least five amino acid substitutions that are: (a) an isoleucine to lysine substitution at position 61, a glutamine to arginine substitution at position 68, a glutamine to arginine substitution at position 79, a leucine to arginine substitution at position 99, and a glutamic acid to aspartic acid substitution at position 282 (I61K/Q68R/Q79R/L99R/E282D); (b) an isoleucine to methionine substitution at position 61, a glutamine to arginine substitution at position 68, a glutamine to arginine substitution at position 79, a leucine to arginine substitution at position 99, and a glutamic acid to aspartic acid substitution at position 282 (I61M/Q68R/Q79R/L99R/E282D); or (c) an isoleucine to methionine substitution at position 61, a glutamine to isoleucine substitution at position 68, a glutamine to histidine substitution at position 79, a leucine to lysine substitution at position 99, and a glutamic acid to methionine substitution at position 282 (I61M/Q68IR/Q79H/L99K/E282M).

In another embodiment, the MMLV RTase mutant of the disclosure comprises the amino acid sequence of SEQ ID NO: 637, wherein the amino acid sequence of the MMLV RTase mutant further comprises at least five or more amino acid substitutions that are: (a) a glutamine to arginine substitution at position 68, a glutamine to arginine substitution at position 79, a leucine to arginine substitution at position 99, a glutamic acid to aspartic acid substitution at position 282, a glutamine to glutamic acid substitution at position 299, a valine to arginine substitution at position 433, and a isoleucine to glutamic acid at position 593 (Q68R/Q79R/L99R/E282D/Q299E/V433R/I593E): (b) a glutamine to arginine substitution at position 68, a glutamine to arginine substitution at position 79, a leucine to arginine substitution at position 82, a leucine to arginine substitution at position 99, a glutamic acid to aspartic acid substitution at position 282, a glutamine to glutamic acid substitution at position 299, a valine to arginine substitution at position 433, and a isoleucine to glutamic acid at position 593 (Q68R/Q79R/L82R/L99R/E282D/Q299E/V433R/I593E); (c) a glutamine to arginine substitution at position 68, a glutamine to arginine substitution at position 79, a leucine to arginine substitution at position 82, a leucine to arginine substitution at position 99, a glutamic acid to aspartic acid substitution at position 282, a glutamine to glutamic acid substitution at position 299, a threonine to glutamic acid substitution at position 332, and a isoleucine to glutamic acid at position 593 (Q68R/Q79R/L82R/L99R/E282D/Q299E/T332E/I593E); (d) a glutamine to arginine substitution at position 68, a glutamine to arginine substitution at position 79, a leucine to arginine substitution at position 82, a leucine to arginine substitution at position 99, a glutamic acid to aspartic acid substitution at position 282, a glutamine to glutamic acid substitution at position 299, a threonine to glutamic acid substitution at position 332, a valine to arginine substitution at position 433, and a isoleucine to glutamic acid at position 593 (Q68R/Q79R/L82R/L99R/E282D/Q299E/T332E/V433R/I593E).

In another embodiment, the MMLV RTase mutant of the disclosure comprises the amino acid sequence of SEQ ID NO: 717, wherein the amino acid sequence of the MMLV RTase mutant further comprises at least two amino acid substitutions that are: (a) a glutamine to arginine substitution at position 68 (Q68R); (b) a glutamine to arginine substitution at position 79 (Q79R); (c) a leucine to tyrosine at position 82 (L82Y); (d) a leucine to arginine substitution at position 99 (L99R); (e) a leucine to isoleucine at position 280 (L280I); (f) a glutamic acid to aspartic acid substitution at position 282 (E282D); (g) a glutamine to glutamic acid substitution at position 299 (Q299E); (h) threonine to lysine at position 306 (T306K); (i) a valine to asparagine at position 433 (V433N); (j) a valine to arginine at position 433 (V433R); (k) an isoleucine to glutamic acid at position 593 (I593E); or (1) an isoleucine to tryptophan at position 593 (I593W).

In another embodiment, the MMLV RTase mutant of the disclosure comprises the amino acid sequence of SEQ ID NO: 717, wherein the amino acid sequence of the MMLV RTase mutant further comprises the amino acid substitutions: (a) a glutamine to arginine substitution at position 68 (Q68R); (b) a glutamine to arginine substitution at position 79 (Q79R); (c) a leucine to tyrosine substitution at position 82 (L82Y); (d) a leucine to arginine substitution at position 99 (L99R); (e) a leucine to isoleucine substitution at position 280 (L280I); (f) a glutamic acid to aspartic acid substitution at position 282 (E282D); (g) a glutamine to glutamic acid substitution at position 299 (Q299E); (h) a threonine to lysine substitution at position 306 (T306K); (i) a valine to asparagine substitution at position 433 (V433N); and (j) an isoleucine to tryptophan substitution at position 593 (I593W).

In another embodiment, the MMLV RTase mutant of the disclosure comprises the amino acid sequence of SEQ ID NO: 717, wherein the amino acid sequence of the MMLV RTase mutant further comprises the amino acid substitutions: (a) a glutamine to arginine substitution at position 68 (Q68R); (b) a glutamine to arginine substitution at position 79 (Q79R); (c) a leucine to tyrosine substitution at position 82 (L82Y); (d) a leucine to arginine substitution at position 99 (L99R); (e) a leucine to isoleucine substitution at position 280 (L280I); (f) a glutamic acid to aspartic acid substitution at position 282 (E282D); (g) a glutamine to glutamic acid substitution at position 299 (Q299E); (h) a threonine to lysine substitution at position 306 (T306K); (i) a valine to arginine substitution at position 433 (V433R); and (j) an isoleucine to glutamic acid substitution at position 593 (I593E).

In one embodiment the RTase mutant amino acid sequence comprises a mutant selected from Tables 3, 8, 9, 12, 21, 22, or 38. In one aspect, the RTase mutant amino acid sequence comprises a mutant selected from the amino acid sequences of SEQ ID NO: 638, SEQ ID NO: 639, SEQ ID NO: 640, SEQ ID NO: 641, SEQ ID NO: 642, SEQ ID NO: 643, SEQ ID NO: 644, SEQ ID NO: 645, SEQ ID NO: 646, SEQ ID NO: 647, SEQ ID NO: 648, SEQ ID NO: 649, SEQ ID NO: 650, SEQ ID NO: 651, SEQ ID NO: 652, SEQ ID NO: 653, SEQ ID NO: 654, SEQ ID NO: 655, SEQ ID NO: 656, SEQ ID NO: 657, SEQ ID NO: 658, SEQ ID NO: 659, SEQ ID NO: 660, SEQ ID NO: 661, SEQ ID NO: 662, SEQ ID NO: 663, SEQ ID NO: 664, SEQ ID NO: 665, SEQ ID NO: 666, SEQ ID NO: 667, SEQ ID NO: 668, SEQ ID NO: 669, SEQ ID NO: 679, SEQ ID NO: 671, SEQ ID NO: 672, SEQ ID NO: 673, SEQ ID NO: 674, SEQ ID NO: 675, SEQ ID NO: 676, SEQ ID NO: 677, SEQ ID NO: 678, SEQ ID NO: 679, SEQ ID NO: 670, SEQ ID NO: 671, SEQ ID NO: 672, SEQ ID NO: 673, SEQ ID NO: 674, SEQ ID NO: 675, SEQ ID NO: 676, SEQ ID NO: 677, SEQ ID NO: 678, SEQ ID NO: 679, SEQ ID NO: 680, SEQ ID NO: 681, SEQ ID NO: 682, SEQ ID NO: 683, SEQ ID NO: 684, SEQ ID NO: 685, SEQ ID NO: 686, SEQ ID NO: 687, SEQ ID NO: 688, SEQ ID NO: 689, SEQ ID NO: 690, SEQ ID NO: 691, SEQ ID NO: 692, SEQ ID NO: 693, SEQ ID NO: 694, SEQ ID NO: 695, SEQ ID NO: 696, SEQ ID NO: 697, SEQ ID NO: 698, SEQ ID NO: 699, SEQ ID NO: 716, SEQ ID NO: 717, SEQ ID NO: 718, SEQ ID NO: 719, SEQ ID NO: 720, SEQ ID NO: 721, SEQ ID NO: 722, SEQ ID NO: 723, SEQ ID NO: 724, SEQ ID NO: 725, SEQ ID NO: 726, SEQ ID NO: 727, SEQ ID NO: 728, SEQ ID NO: 729, SEQ ID NO: 730, or SEQ ID NO: 731.

In one embodiment the RTase mutant amino acid sequence comprises a C-terminal extension. In one aspect the C-terminal extension comprises a peptide sequence. In another embodiment an isolated polypeptide encodes a RTase mutant with a C-terminal extension The claimed invention is based, at least in part, on the discovery that certain single and double amino acid mutations introduced into an MMLV RTase sequence, as disclosed herein, result in an MMLV RTase with increased or enhanced thermostability and/or RTase activity. Accordingly, methods for synthesizing the MMLV RTase mutants and methods for performing reverse transcription-polymerase chain reaction (RT-PCR) are also provided herein. Further provided are kits comprising the isolated MMLV RTase single, double, triple, or more mutations.

In certain embodiments, the mutated RTase is derived from the retrovirus Moloney murine leukemia virus (MMLV). In other embodiments, a mutated RTase of the disclosure could be derived from the RTase from a retrovirus other than MMLV, such as avian myeloblastosis virus (AMV) or human immunodeficiency virus type 1 (HIV-1), by introducing the same mutations into an RTase base construct obtained from the other retrovirus.

In certain embodiments, the RTase mutants of the disclosure are obtained by genetic engineering techniques that are well known in the art. For example, site-directed and random mutagenesis can be used to generate the RTase mutants of the disclosure.

In one embodiment of the disclosure, an RTase mutant of the disclosure is part of a composition.

3. Mutagenesis

The RTase mutants of the disclosure can be prepared by standard methods disclosed herein or known in the art. In one embodiment, the nucleic acid sequence of the RTase base construct (SEQ ID NO: 637) is modified to create a nucleic acid sequence encoding an RTase mutant. One of skill in the art will recognize that colonies with the appropriate strains can be used to grow and express an RTase mutant of interest, and following cell harvest and protein isolation, the RTase mutant can be used in cDNA synthesis techniques. Non-limiting examples of mutagenesis and cDNA synthesis are described herein in Examples 1-3.

As used herein, the term "mutagenesis" refers to the introduction of a genetic change in the nucleic acid sequence of a cell, wherein the alteration is then inherited by each cell. One of skill in the art will understand that mutations in a given nucleic acid sequence can be introduced using a variety of methods. One of skill in the art will further recognize that mutagenesis methods seek to mutate a target gene or target polynucleotide. The target gene may encode any one or more desired proteins. Mutagenesis methods commonly use a synthetic oligonucleotide that carries the desired sequence modification. The mutagenic oligonucleotide is incorporated into the DNA sequence using in vitro enzymatic DNA synthesis and is propagated in a mutant or wild-type bacterium.

Site directed mutagenesis, wherein targeted mutations are introduced into one or more desired positions of a template polynucleotide, may be achieved using primer extension mutagenesis. This technique requires the use of a specific primer that contains one or more desired mutations relative to the template polynucleotide. The mutagenesis primer can be a synthetic oligonucleotide or a PCR product. The mutated primer may include one or more substitutions, deletions, additions, or combinations thereof.

Mutated reverse transcriptases may also be generated using random mutagenesis, wherein random mutations are introduced into the mutagenesis primer during synthesis. Randomly mutagenized oligonucleotides may also be used as mutagenesis primers.

In another embodiment, the mutated reverse transcriptases of the disclosure can be developed using error-prone rolling circle amplification (RCA). In this technique, the fidelity of a DNA polymerase is decreased by performing the RCA in the presence of $MnCl_2$ or by decreasing the amount of input DNA.

4. cDNA Synthesis

The disclosure also relates to the activity of MMLV RTases, as measured by the quantity of cDNA produced by the MMLV RTases disclosed herein. cDNA can be prepared using one-step or two-step procedures and can be obtained from a variety of template molecules. As used herein, the term "template molecule" refers to a biological molecule that carries the genetic code for use in making a new nucleic acid strand. For example, in DNA replication, the unwound double helix and each single-stranded DNA molecule is used as a template to synthesize a complementary strand. Reverse transcription generates cDNA from RNA. One of skill in the art will understand that cDNA molecules may be prepared from a variety of nucleic acid template molecules. In one embodiment, the nucleic acid template can be single-stranded or double-stranded DNA. In one embodiment, RNA can be used in cDNA synthesis. In certain embodiments, the MMLV RTase mutants of the disclosure exhibit increased or enhanced thermostability and/or RTase activity as compared to an RTase base construct. In other embodiments, the MMLV RTase mutants of the disclosure exhibit altered half-life, reduced or eliminated RNase H activity, reduced terminal deoxynucleotidyl transferase activity, increased accuracy or fidelity, or increased specificity.

The disclosure also provides methods for synthesizing cDNA using the MMLV RTase mutants of the disclosure that have single or double amino acid mutations. The MMLV RTase mutants of the disclosure may be used in methods that produce a first strand cDNA or a first and second strand cDNA. One of skill in the art will understand that first and second strand cDNA may form a double-stranded DNA molecule, which may include a full-length cDNA sequence and cDNA libraries.

The cDNA molecules that have been reverse transcribed by the MMLV RTase mutants of the disclosure may be isolated, or the reaction mixture containing the cDNA molecules may be directly used in downstream applications or for further analysis or manipulation. Amplification methods that may be used to practice the methods of the disclosure are described herein and are well known in the art. Reverse transcription reactions may be carried out using non-specific primers, such as an anchored oligo-dT primer, or random sequence primers, or using a target-specific primer complementary to the RNA for each genetic probe being monitored, or using thermostable DNA polymerases (such as AMV RTase or MMLV RTase).

Amplification methods utilize pairs of primers that selectively hybridize to nucleic acids corresponding to a specific nucleotide sequence of interest that are contacted with the isolated nucleic acid under conditions that permit selective hybridization. Once hybridized, the nucleic acid:primer complex is contacted with one or more enzymes that facilitate template-dependent nucleic acid synthesis. Multiple rounds of amplification, also referred to as "cycles," are conducted until a sufficient amount of amplification product is produced. Next, the amplification product is detected. In certain methods, the detection may be performed by visual means. Alternatively, the detection may involve indirect identification of the product via chemiluminescence, radioactive scintigraphy of incorporated radiolabel or fluorescent label, or even via a system using electrical or thermal impulse signals.

Methods based on ligation of two (or more) oligonucleotides in the presence of a nucleic acid having the sequence of the resulting "di-oligonucleotide," thereby amplifying the di-oligonucleotide, also may be used in the amplification step of the disclosure.

In some embodiments of the disclosure, the detection process can utilize a hybridization technique, for example, wherein a specific primer or probe is selected to anneal to a target biomarker of interest, and thereafter detection of selective hybridization is made. As commonly known in the art, the oligonucleotide probes and primers can be designed by taking into consideration the melting point of hybridization thereof with its targeted sequence.

One of skill in the art will recognize that cDNA molecules made using the MMLV RTase mutants of the disclosure can be used in a variety of additional downstream applications. For example, amplification methods may include one-step PCR, two-step PCR, real-time or quantitative PCR, hot-start PCR, nested PCR, touch down PCR, differential display PCR (DDRT-PCR), microarray technologies, inverse PCR, Rapid amplification of PCR ends (RACE or anchored PCR), multiplex PCR, and site directed PCR mutagenesis. Synthesized cDNA and cDNA libraries created with the MMLV RTase mutants of the disclosure can be used in cloning and/or sequencing for further characterization. One of skill in the art will recognize that nucleic acid amplification using cDNA prepared with the MMLV RTase mutants of the disclosure may include additional techniques not listed herein.

To enable hybridization to occur under the methods presented above, oligonucleotide primers and probes should comprise an oligonucleotide sequence that has at least 70%, 75%, 80%, 85%, 90%, 95%, 96%, 97%, 98%, 99%, or 100% identity to a portion of the sequence of interest.

5. Biological Samples

The MMLV RTase mutants and associated methods of the disclosure may be practiced with any suitable biological sample from which RNA or DNA can be isolated. In one embodiment of the disclosure, the biological sample may be a bodily fluid or tissue obtained from either a diseased or a healthy subject. In some embodiments of the disclosure, the biological sample may be a bodily fluid, including but not limited to whole blood, plasma, serum, feces, or urine. In another embodiment, the methods of the disclosure may be practiced with any suitable samples that are freshly isolated or that have been frozen or stored after having been collected from a subject, for example, with a known diagnosis, treatment, and/or outcome history. Samples may be collected by any non-invasive means, such as, for example, fine needle aspiration or needle biopsy, or alternatively, by an invasive method, including, for example, surgical biopsy. In such embodiments, RNA or DNA can be extracted from a biological sample (e.g., blood serum) before analysis. Methods of RNA and DNA extraction are well known in the art.

A number of kits for use in extracting RNA (i.e., total RNA or mRNA) from bodily fluids or tissues (e.g., blood serum) and are known in the art and commercially available. One of ordinary skill in the art can easily select an appropriate kit for a particular situation.

In certain embodiments of the disclosure, after extraction, mRNA is amplified, and transcribed into cDNA, which can then serve as template for multiple rounds of transcription by the appropriate RNA polymerase. Amplification methods that may be used to practice the methods of the disclosure are described herein and are well known in the art. Reverse transcription reactions may be carried out using non-specific primers, such as an anchored oligo-dT primer, or random sequence primers, or using a target-specific primer complementary to the RNA for each genetic probe being monitored, or using thermostable DNA polymerases, such as MMLV RTase or the MMLV RTase mutants of the disclosure.

In certain embodiments, the RNA isolated from a biological sample (e.g., after amplification and/or conversion to cDNA or cRNA) is labeled with a detectable agent before being analyzed. The role of a detectable agent is to facilitate detection of RNA or to allow visualization of hybridized nucleic acid fragments (e.g., nucleic acid fragments hybridized to genetic probes in an array-based assay). In some embodiments, the detectable agent is selected such that it generates a signal which can be measured and whose intensity is related to the amount of labeled nucleic acids present in the sample being analyzed.

Methods for labeling nucleic acid molecules are well known in the art. A review of labeling protocols and label detection techniques can be found in Kricka, *Ann. Clin. Biochem.* 39: 114-29 (2002); van Gijlswijk et al., *Expert Rev. Mol. Diagn.* 1: 81-91 (2001); and Joos et al., *J. Biotechnol.* 35: 135-53 (1994). Standard nucleic acid labeling methods include incorporation of radioactive agents; direct attachment of fluorescent dyes or of enzymes; chemical modifications of nucleic acid fragments making them detectable immunochemically or by other affinity reactions; and enzyme-mediated labeling methods, such as random priming, nick translation, PCR, and tailing with terminal transferase.

Any of a wide variety of detectable agents can be used to practice the methods of the disclosure. Suitable detectable agents include but are not limited to various ligands, radionuclides, fluorescent dyes, chemiluminescent agents, microparticles (such as, for example, quantum dots, nanocrystals, and phosphors), enzymes (such as, for example, those used in an ELISA, i.e., horseradish peroxidase, beta-galactosidase, luciferase, and alkaline phosphatase), colorimetric labels, magnetic labels, biotin, digoxigenin, or other haptens and proteins for which antisera or monoclonal antibodies are available.

6. Kits

The disclosure also provides kits for use in reverse transcription or related technologies. These kits include one or more of the following: an MMLV RTase mutant enzyme, reagents and buffers for conducting a reverse transcriptase reaction, a box, vial tubes, ampules, and the like. Kits can also include instructions for use of the kit for practicing any of the methods disclosed herein or other methods known to those of skill in the art.

EXAMPLES

The claimed invention is further illustrated by the following Examples, which should not be construed as limiting.

Those of skill in the art will recognize that the claimed invention may be practiced with variations of the disclosed structures, materials, compositions, and methods, and such variations are regarded as within the scope of the claimed invention.

The RTases described herein were overexpressed in *E. coli*, purified to homogeneity, and tested for their ability to enhance RNA detection in the context of reverse transcriptase quantitative PCR (RT-qPCR).

Example 1. Preparation of Reverse Transcriptase Mutants by Site Directed Mutagenesis a. Cloning of MMLV RTase Mutants Created from Base Construct (RNase H Minus Construct)

Figure 1B:
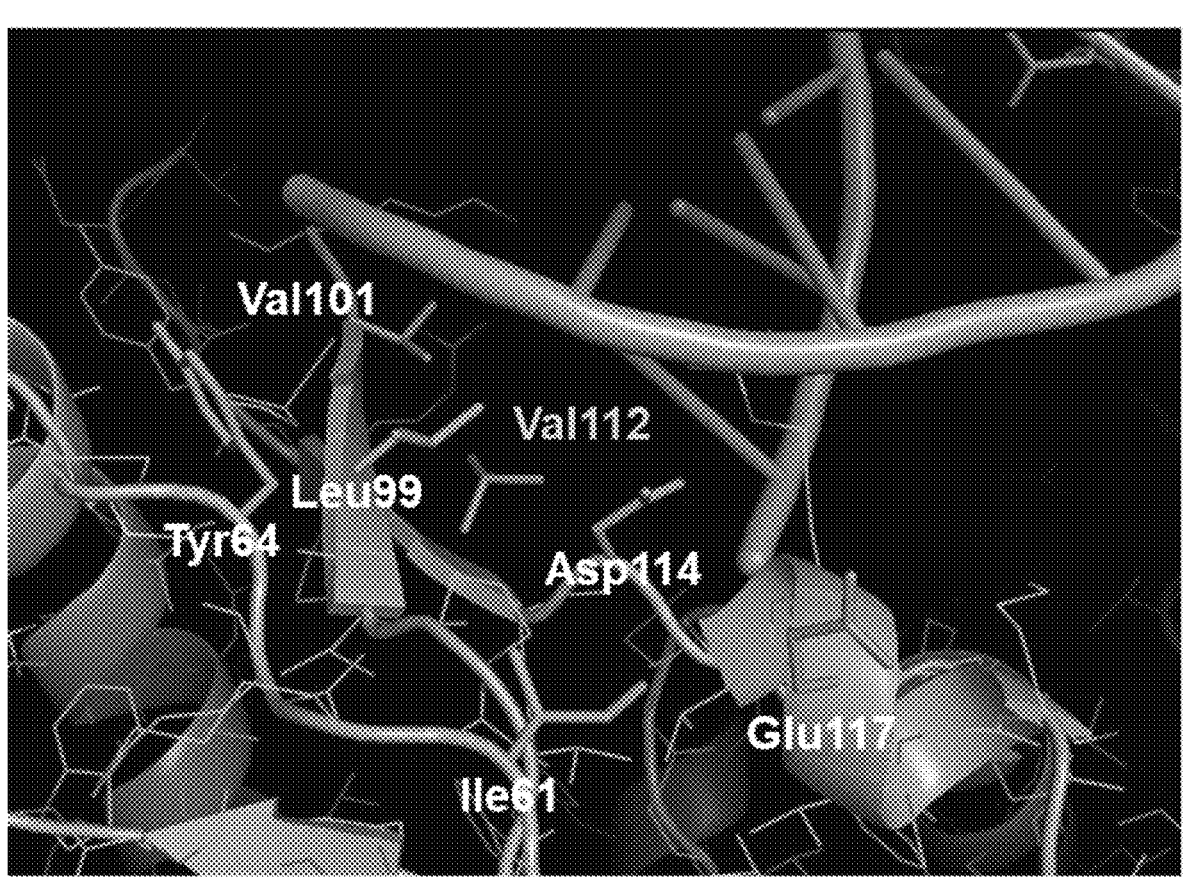
Figure 1C:
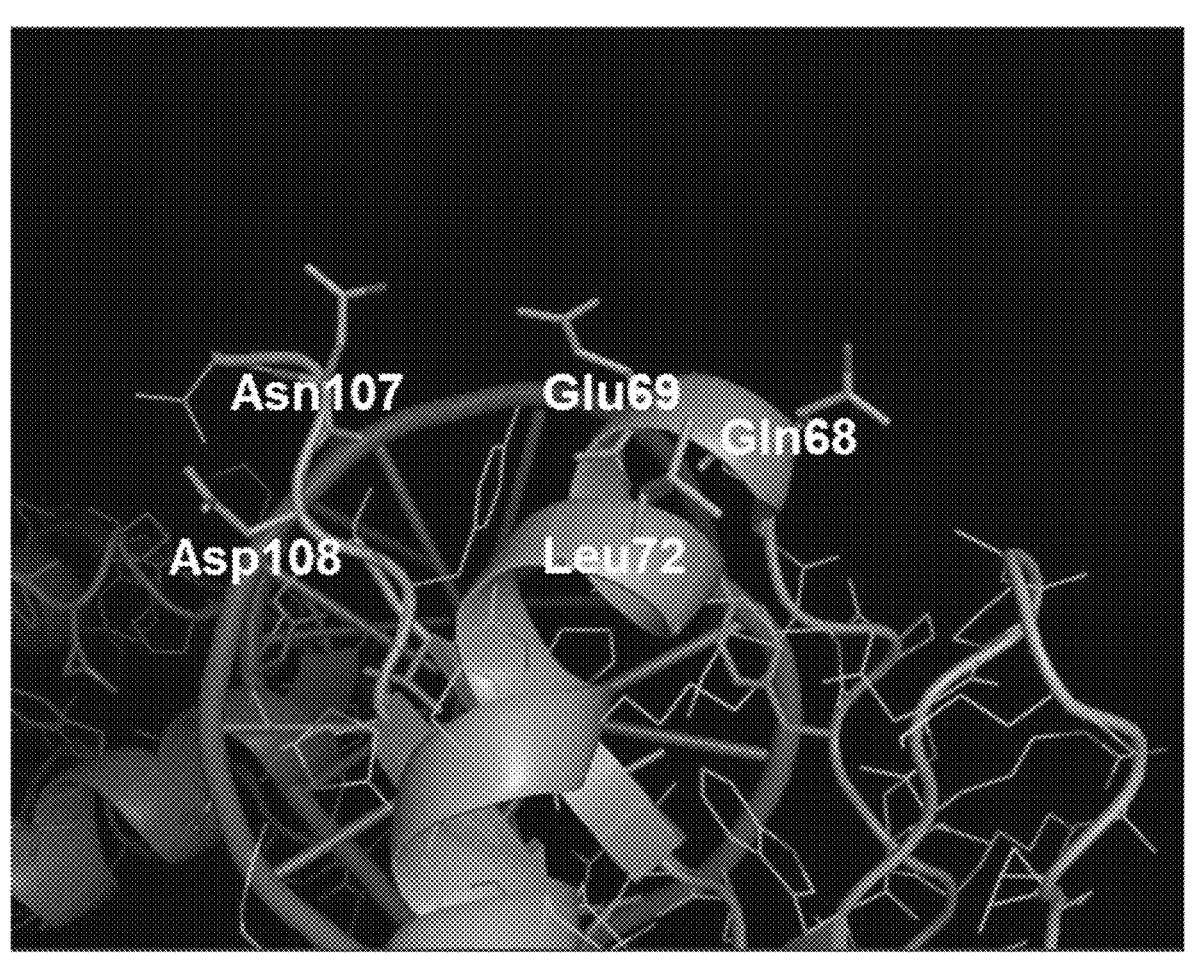

MMLV RTase mutants were prepared by first introducing three mutations (D524G, E562Q, and D583N) into the amino acid sequence of the wild-type, or naturally occurring, MMLV RTase to prepare an MMLV RTase base construct (SEQ TD NO: 637). The three mutations, which are contained in the SuperScript II RTase (Invitrogen), have been shown to reduce RNase H activity (see U.S. Pat. No. 5,405,776). The MMLV RTase base construct was optimized for *E. coli* expression and obtained as gBlocks® Gene Fragments (Integrated DNA Technologies) or by custom gene synthesis with the appropriate purification tag. Subsequent genes were amplified using standard PCR conditions and primers (see Tables 1 and 21). Amplified DNA was subjected to purification using a QIAquick PCR Purification kit (Qiagen, Catalog #28104), followed by gene fragment assembly into a pET28b expression plasmid. Plasmid DNA was isolated and sequenced to verify the desired sequence following transformation into *E. coli* cells. MMLV RTase mutations were selected by rational design (FIGS. 1A-1C) and introduced by site-directed mutagenesis, using standard PCR conditions and primers (see Tables 1 and 21). Resulting plasmids were transformed into *E. coli* BL21(DE3) cells for expression.

TABLE 1

Sequences of primers used for cloning of MMLV RTase base constructs and mutants into pET28b.

| SEQ ID NO: | Primer Name | Primer Sequence (5'-3') |
| --- | --- | --- |
| 1 | pET28b 5' Reverse | GGTATATCTCCTTCT TAAAGTTAAACAAAA TTATTTCTAGAGGGG AAT |
| 2 | pET28b 3' Forward | GATCCGGCTGCTAAC AAAGCC |
| 3 | MMLV 5' Primer | TTTTGTTTAACTTTA AGAAGGAGATATACC ATGGGCAGCAGCCAT CATCATC |
| 4 | MMLV 3' Primer | GCAGCCAACTCAGCT TCCTTTCGGGCTTTG TTAAAAATGCTCGCT AGTGTAGGGAGAGC |
| 5 | MMLV K53A Top SDM | AAGCACCGTTGATCA TCCCGTTAGCGGCAA CGTCTACACCTGTCT CTATCAAAC |

TABLE 1-continued

Sequences of primers used for cloning of
MMLV RTase base constructs and mutants
into pET28b.

| SEQ ID NO: | Primer Name | Primer Sequence (5'-3') |
|---|---|---|
| 6 | MMLV K53R Top SDM | AAGCACCGTTGATCA TCCCGTTACGTGCAA CGTCTACACCTGTCT CTATCAAAC |
| 7 | MMLV K53E Top SDM | AAGCACCGTTGATCA TCCCGTTAGAAGCAA CGTCTACACCTGTCT CTATCAAAC |
| 8 | MMLV T55A Top SDM | CCGTTGATCATCCCG TTAAAGGCAGCGTCT ACACCTGTCTCTATC AAACAGTACCCC |
| 9 | MMLV T55R Top SDM | CCGTTGATCATCCCG TTAAAGGCACGTTCT ACACCTGTCTCTATC AAACAGTACCCC |
| 10 | MMLV T55E Top SDM | CCGTTGATCATCCCG TTAAAGGCAGAATCT ACACCTGTCTCTATC AAACAGTACCCC |
| 11 | MMLV T57A Top SDM | ATCATCCCGTTAAAG GCAACGTCTGCGCCT GTCTCTATCAAACAG TACCCCATGAG |
| 12 | MMLV T57R Top SDM | ATCATCCCGTTAAAG GCAACGTCTCGTCCT GTCTCTATCAAACAG TACCCCATGAG |
| 13 | MMLV T57E Top SDM | ATCATCCCGTTAAAG GCAACGTCTGAACCT GTCTCTATCAAACAG TACCCCATGAG |
| 14 | MMLV V59A Top SDM | CCGTTAAAGGCAACG TCTACACCTGCGTCT ATCAAACAGTACCCC ATGAGTCAAGAGG |
| 15 | MMLV V59R Top SDM | CCGTTAAAGGCAACG TCTACACCTGCGTTCT ATCAAACAGTACCCC ATGAGTCAAGAGG |
| 16 | MMLV V59E Top SDM | CCGTTAAAGGCAACG TCTACACCTGAATCT ATCAAACAGTACCCC ATGAGTCAAGAGG |
| 17 | MMLV I61A Top SDM | TAAAGGCAACGTCTA CACCTGTCTCTGCGA AACAGTACCCCATGA GTCAAGAGG |
| 18 | MMLV I61R Top SDM | TAAAGGCAACGTCTA CACCTGTCTCTCGTA AACAGTACCCCATGA GTCAAGAGG |
| 19 | MMLV I61E Top SDM | TAAAGGCAACGTCTA CACCTGTCTCTGAAA AACAGTACCCCATGA GTCAAGAGG |

TABLE 1-continued

Sequences of primers used for cloning of
MMLV RTase base constructs and mutants
into pET28b.

| SEQ ID NO: | Primer Name | Primer Sequence (5'-3') |
|---|---|---|
| 20 | MMLV K62A Top SDM | GGCAACGTCTACACC TGTCTCTATCGCGCA GTACCCCATGAGTCA AGAGGC |
| 21 | MMLV K62R Top SDM | GGCAACGTCTACACC TGTCTCTATCCGTCA GTACCCCATGAGTCA AGAGGC |
| 22 | MMLV K62E Top SDM | GGCAACGTCTACACC TGTCTCTATCGAACA GTACCCCATGAGTCA AGAGGC |
| 23 | MMLV Q68A Top SDM | CTGTCTCTATCAAAC AGTACCCCATGAGTG CGGAGGCCCGCCTGG G |
| 24 | MMLV Q68R Top SDM | CTGTCTCTATCAAAC AGTACCCCATGAGTC GTGAGGCCCGCCTGG G |
| 25 | MMLV Q68E Top SDM | CTGTCTCTATCAAAC AGTACCCCATGAGTG AAGAGGCCCGCCTGG G |
| 26 | MMLV K75A Top SDM | GGCCCGCCTGGGGAT TGCGCCACATATTCA GCGCTTGCTGGACCA |
| 27 | MMLV K75R Top SDM | GGCCCGCCTGGGGAT TCGTCCACATATTCA GCGCTTGCTGGACCA |
| 28 | MMLV K75E Top SDM | GGCCCGCCTGGGGAT TGAACCACATATTCA GCGCTTGCTGGACCA |
| 29 | MMLV Q79A Top SDM | CGCCTGGGGATTAAG CCACATATTGCGCGC TTGCTGGACCAGGGG |
| 30 | MMLV Q79R Top SDM | CGCCTGGGGATTAAG CCACATATTCGTCGC TTGCTGGACCAGGGG |
| 31 | MMLV Q79E Top SDM | CGCCTGGGGATTAAG CCACATATTGAACGC TTGCTGGACCAGGGG |
| 32 | MMLV L99A Top SDM | CCGTGGAACACCCCC CTTGCGCCCGTGAAA AAGCCAGGTACAAAC |
| 33 | MMLV L99R Top SDM | CCGTGGAACACCCCC CTTCGTCCCGTGAAA AAGCCAGGTACAAAC |
| 34 | MMLV L99E Top SDM | CCGTGGAACACCCCC CTTGAACCCGTGAAA AAGCCAGGTACAAAC |
| 35 | MMLV V101A Top SDM | CACCCCCCTTCTGCC CGCGAAAAAGCCAGG TACAAACGATTATCG TCC |

TABLE 1-continued

TABLE 1-continued

Sequences of primers used for cloning of
MMLV RTase base constructs and mutants
into pET28b.

Sequences of primers used for cloning of
MMLV RTase base constructs and mutants
into pET28b.

| SEQ ID NO: | Primer Name | Primer Sequence (5'-3') |
|---|---|---|
| 36 | MMLV V101R Top SDM | CACCCCCCTTCTGCC CCGTAAAAAGCCAGG TACAAACGATTATCG TCC |
| 37 | MMLV V101E Top SDM | CACCCCCCTTCTGCC CGAAAAAAAGCCAGG TACAAACGATTATCG TCC |
| 38 | MMLV K102A Top SDM | CCCCCTTCTGCCCGT GGCGAAGCCAGGTAC AAACGATTATCGTCC |
| 39 | MMLV K102R Top SDM | CCCCCTTCTGCCCGT GCGTAAGCCAGGTAC AAACGATTATCGTCC |
| 40 | MMLV K102E Top SDM | CCCCCTTCTGCCCGT GGAAAAGCCAGGTAC AAACGATTATCGTCC |
| 41 | MMLV K103A Top SDM | CCCCCTTCTGCCCGT GAAAGCGCCAGGTAC AAACGATTATCGTCC AGTT |
| 42 | MMLV K103R Top SDM | CCCCCTTCTGCCCGT GAAACGTCCAGGTAC AAACGATTATCGTCC AGTT |
| 43 | MMLV K103E Top SDM | CCCCCTTCTGCCCGT GAAAGAACCAGGTAC AAACGATTATCGTCC AGTT |
| 44 | MMLV T106A Top SDM | GCCCGTGAAAAAGCC AGGTGCGAACGATTA TCGTCCAGTTCAAGA TCTTCG |
| 45 | MMLV T106R Top SDM | GCCCGTGAAAAAGCC AGGTCGTAACGATTA TCGTCCAGTTCAAGA TCTTCG |
| 46 | MMLV T106E Top SDM | GCCCGTGAAAAAGCC AGGTGAAAACGATTA TCGTCCAGTTCAAGA TCTTCG |
| 47 | MMLV N107A Top SDM | CCCGTGAAAAAGCCA GGTACAGCGGATTAT CGTCCAGTTCAAGAT CTTCGCG |
| 48 | MMLV N107R Top SDM | CCCGTGAAAAAGCCA GGTACACGTGATTAT CGTCCAGTTCAAGAT CTTCGCG |
| 49 | MMLV N107E Top SDM | CCCGTGAAAAAGCCAGGTAC AGAAGATTATCGTCCAGTTC AAGATCTTCGCG |
| 50 | MMLV Y109A Top SDM | CGTGAAAAAGCCAGGTACAA ACGATGCGCGTCCAGTTCAA GATCTTCGCG |
| 51 | MMLV Y109R Top SDM | CGTGAAAAAGCCAGGTACAA ACGATCGTCGTCCAGTTCAA GATCTTCGCG |
| 52 | MMLV Y109E Top SDM | CGTGAAAAAGCCAGGTACAA ACGATGAACGTCCAGTTCAA GATCTTCGCG |
| 53 | MMLVR110A Top SDM | CGTGAAAAAGCCAGGTACAA ACGATTATGCGCCAGTTCAA GATCTTCGCGAGG |
| 54 | MMLVR110K Top SDM | CGTGAAAAAGCCAGGTACAA ACGATTATAAACCAGTTCAA GATCTTCGCGAGG |
| 55 | MMLV R110E Top SDM | CGTGAAAAAGCCAGGTACAA ACGATTATGAACCAGTTCAA GATCTTCGCGAGG |
| 56 | MMLV V112A Top SDM | GCCAGGTACAAACGATTATC GTCCAGCGCAAGATCTTCGC GAGGTCAACAAAC |
| 57 | MMLV VI12R Top SDM | GCCAGGTACAAACGATTATC GTCCACGTCAAGATCTTCGC GAGGTCAACAAAC |
| 58 | MMLV V112E Top SDM | GCCAGGTACAAACGATTATC GTCCAGAACAAGATCTTCGC GAGGTCAACAAAC |
| 59 | MMLV K120A Top SDM | AGTTCAAGATCTTCGCGAGG TCAACGCGCGCGTAGAAGAC ATCCATCGAC |
| 60 | MMLV K120R Top SDM | AGTTCAAGATCTTCGCGAGG TCAACCGTCGCGTAGAAGAC ATCCATCGAC |
| 61 | MMLV K120E Top SDM | AGTTCAAGATCTTCGCGAGG TCAACGAACGCGTAGAAGAC ATCCATCGAC |
| 62 | MMLV E123A Top SDM | GCGAGGTCAACAAACGCGTA GCGGACATCCATCCGACTGT ACCTAATCC |
| 63 | MMLV E123R Top SDM | GCGAGGTCAACAAACGCGTA CGTGACATCCATCCGACTGT ACCTAATCC |
| 64 | MMLV E123D Top SDM | GCGAGGTCAACAAACGCGTA GATGACATCCATCCGACTGT ACCTAATCC |
| 65 | MMLV T128V Top SDM | ACGCGTAGAAGACATCCATC CGGTGGTACCTAATCCTTAT AATCTGTTATCAGGCCTGC |
| 66 | MMLV T128R Top SDM | ACGCGTAGAAGACATCCATC CGCGTGTACCTAATCCTTAT AATCTGTTATCAGGCCTGC |
| 67 | MMLV T128E Top SDM | ACGCGTAGAAGACATCCATC CGGAAGTACCTAATCCTTAT AATCTGTTATCAGGCCTGC |
| 68 | MMLV K193A Top SDM | CGTCTGCCCCAGGGCTTTGC GAACAGCCCCACATTGTTCG ATGAA |

TABLE 1-continued

Sequences of primers used for cloning of
MMLV RTase base constructs and mutants
into pET28b.

| SEQ ID NO: | Primer Name | Primer Sequence (5'-3') |
|---|---|---|
| 69 | MMLV K193R Top SDM | CGTCTGCCCCAGGGCTTTCG TAACAGCCCCACATTGTTCG ATGAA |
| 70 | MMLV K193E Top SDM | CGTCTGCCCCAGGGCTTTGA AAACAGCCCCACATTGTTCG ATGAA |
| 71 | MMLV E282A Top SDM | AGAAGGTCAACGTTGGCTGA CTGCGGCGCGTAAGGAGACC GTAATG |
| 72 | MMLV E282R Top SDM | AGAAGGTCAACGTTGGCTGA CTCGTGCGCGTAAGGAGACC GTAATG |
| 73 | MMLV E282D Top SDM | AGAAGGTCAACGTTGGCTGA CTGATGCGCGTAAGGAGACC GTAATG |
| 74 | MMLV A283V Top SDM | GAAGGTCAACGTTGGCTGAC TGAAGTGCGTAAGGAGACCG TAATGGGGC |
| 75 | MMLV A283R Top SDM | GAAGGTCAACGTTGGCTGAC TGAACGTCGTAAGGAGACCG TAATGGGGC |
| 76 | MMLV A283E Top SDM | GAAGGTCAACGTTGGCTGAC TGAAGAACGTAAGGAGACCG TAATGGGGC |
| 77 | MMLV Q291A Top SDM | GCGTAAGGAGACCGTAATGG GGGCGCCTACGCCTAAGACG CCACG |
| 78 | MMLV Q291R Top SDM | GCGTAAGGAGACCGTAATGG GGCGTCCTACGCCTAAGACG CCACG |
| 79 | MMLV Q291E Top SDM | GCGTAAGGAGACCGTAATGG GGGAACCTACGCCTAAGACG CCACG |
| 80 | MMLV T293A Top SDM | GAGACCGTAATGGGGCAGCC TGCGCCTAAGACGCCACGCC AGTTG |
| 81 | MMLV T293R Top SDM | GAGACCGTAATGGGGCAGCC TCGTCCTAAGACGCCACGCC AGTTG |
| 82 | MMLV T293E Top SDM | GAGACCGTAATGGGGCAGCC TGAACCTAAGACGCCACGCC AGTTG |
| 83 | MMLV K295A Top SDM | GTAATGGGGCAGCCTACGCC TGCGACGCCACGCCAGTTGC GTGAA |
| 84 | MMLV K295R Top SDM | GTAATGGGGCAGCCTACGCC TCGTACGCCACGCCAGTTGC GTGAA |
| 85 | MMLV K295E Top SDM | GTAATGGGGCAGCCTACGCC TGAAACGCCACGCCAGTTGC GTGAA |
| 86 | MMLV T296A Top SDM | TGGGGCAGCCTACGCCTAAG GCGCCACGCCAGTTGCGTGA ATTTT |

TABLE 1-continued

Sequences of primers used for cloning of
MMLV RTase base constructs and mutants
into pET28b.

| SEQ ID NO: | Primer Name | Primer Sequence (5'-3') |
|---|---|---|
| 87 | MMLV T296R Top SDM | TGGGGCAGCCTACGCCTAAG CGTCCACGCCAGTTGCGTGA ATTTT |
| 88 | MMLV T296E Top SDM | TGGGGCAGCCTACGCCTAAG GAACCACGCCAGTTGCGTGA ATTTT |
| 89 | MMLV R298A Top SDM | GCCTACGCCTAAGACGCCAG CGCAGTTGCGTGAATTTTTG GGCACAG |
| 90 | MMLV R298K Top SDM | GCCTACGCCTAAGACGCCAA AACAGTTGCGTGAATTTTTG GGCACAG |
| 91 | MMLV R298E Top SDM | GCCTACGCCTAAGACGCCAG AACAGTTGCGTGAATTTTTG GGCACAG |
| 92 | MMLV R30IA Top SDM | CCTAAGACGCCACGCCAGTT GGCGGAATTTTTGGGCACAG CGGGA |
| 93 | MMLV R301K Top SDM | CCTAAGACGCCACGCCAGTT GAAAGAATTTTTGGGCACAG CGGGA |
| 94 | MMLV R301E Top SDM | CCTAAGACGCCACGCCAGTT GGAAGAATTTTTGGGCACAG CGGGA |
| 95 | MMLV K329A Top SDM | GCACCCCTGTACCCCTTAAC AGCGACAGGGACGCTTTTCA ACTGG |
| 96 | MMLV K329R Top SDM | GCACCCCTGTACCCCTTAAC ACGTACAGGGACGCTTTTCA ACTGG |
| 97 | MMLV K329E Top SDM | GCACCCCTGTACCCCTTAAC AGAAACAGGGACGCTTTTCA ACTGG |
| 98 | MMLV K53A Btm SDM | GTTTGATAGAGACAGGTGTA GACGTTGCCGCTAACGGGAT GATCAACGGTGCTT |
| 99 | MMLV K53R Btm SDM | GTTTGATAGAGACAGGTGTA GACGTTGCACGTAACGGGAT GATCAACGGTGCTT |
| 100 | MMLV K53E Btm SDM | GTTTGATAGAGACAGGTGTA GACGTTGCTTCTAACGGGAT GATCAACGGTGCTT |
| 101 | MMLV T55A Btm SDM | GGGGTACTGTTTGATAGAGA CAGGTGTAGACGCTGCCTTT AACGGGATGATCAACGG |
| 102 | MMLV T55R Btm SDM | GGGGTACTGTTTGATAGAGA CAGGTGTAGAACGTGCCTTT AACGGGATGATCAACGG |
| 103 | MMLV T55E Btm SDM | GGGGTACTGTTTGATAGAGA CAGGTGTAGATTCTGCCTTT AACGGGATGATCAACGG |
| 104 | MMLV T57A Btm SDM | CTCATGGGGTACTGTTTGAT AGAGACAGGCGCAGACGTTG CCTTTAACGGGATGAT |

TABLE 1-continued

Sequences of primers used for cloning of
MMLV RTase base constructs and mutants
into pET28b.

| SEQ ID NO: | Primer Name | Primer Sequence (5'-3') |
|---|---|---|
| 105 | MMLV T57R Btm SDM | CTCATGGGGTACTGTTTGAT AGAGACAGGACGAGACGTTG CCTTTAACGGGATGAT |
| 106 | MMLV T57E Btm SDM | CTCATGGGGTACTGTTTGAT AGAGACAGGTTCAGACGTTG CCTTTAACGGGATGAT |
| 107 | MMLV V59A Btm SDM | CCTCTTGACTCATGGGGTAC TGTTTGATAGACGCAGGTGT AGACGTTGCCTTTAACGG |
| 108 | MMLV V59R Btm SDM | CCTCTTGACTCATGGGGTAC TGTTTGATAGAACGAGGTGT AGACGTTGCCTTTAACGG |
| 109 | MMLV V59E Btm SDM | CCTCTTGACTCATGGGGTAC TGTTTGATAGATTCAGGTGT AGACGTTGCCTTTAACGG |
| 110 | MMLV I61A Btm SDM | CCTCTTGACTCATGGGGTAC TGTTTCGCAGAGACAGGTGT AGACGTTGCCTTTA |
| 111 | MMLV I61R Btm SDM | CCTCTTGACTCATGGGGTAC TGTTTACAGAGACAGGTGT AGACGTTGCCTTTA |
| 112 | MMLV I61E Btm SDM | CCTCTTGACTCATGGGGTAC TGTTTTTCAGAGACAGGTGT AGACGTTGCCTTTA |
| 113 | MMLV K62A Btm SDM | GCCTCTTGACTCATGGGGTA CTGCGCGATAGAGACAGGTG TAGACGTTGCC |
| 114 | MMLV K62R Btm SDM | GCCTCTTGACTCATGGGGTA CTGACGCGATAGAGACAGGTG TAGACGTTGCC |
| 115 | MMLV K62E Btm SDM | GCCTCTTGACTCATGGGGTA CTGTTCGATAGAGACAGGTG TAGACGTTGCC |
| 116 | MMLV Q68A Btm SDM | CTGTCTCTATCAAACAGTAC CCCATGAGTGCGGAGGCCCG CCTGGG |
| 117 | MMLV Q68R Btm SDM | CTGTCTCTATCAAACAGTAC CCCATGAGTCGTGAGGCCCG CCTGGG |
| 118 | MMLV Q68E Btm SDM | CTGTCTCTATCAAACAGTAC CCCATGAGTGAAGAGGCCCG CCTGGG |
| 119 | MMLV K75A Btm SDM | TGGTCCAGCAAGCGCTGAAT ATGTGGCGCAATCCCCAGGC GGGCC |
| 120 | MMLV K75R Btm SDM | TGGTCCAGCAAGCGCTGAAT ATGTGGACGAATCCCCAGGC GGGCC |
| 121 | MMLV K75E Btm SDM | TGGTCCAGCAAGCGCTGAAT ATGTGGTTCAATCCCCAGGC GGGCC |
| 122 | MMLV Q79A Btm SDM | CCCCTGGTCCAGCAAGCGCG CAATATGTGGCTTAATCCCC AGGCG |

TABLE 1-continued

Sequences of primers used for cloning of
MMLV RTase base constructs and mutants
into pET28b.

| SEQ ID NO: | Primer Name | Primer Sequence (5'-3') |
|---|---|---|
| 123 | MMLV Q79R Btm SDM | CCCCTGGTCCAGCAAGCGAC GAATATGTGGCTTAATCCCC AGGCG |
| 124 | MMLV Q79E Btm SDM | CCCCTGGTCCAGCAAGCGTT CAATATGTGGCTTAATCCCC AGGCG |
| 125 | MMLV L99A Btm SDM | GTTTGTACCTGGCTTTTTCA CGGGCGCAAGGGGGGTGTTC CACGG |
| 126 | MMLV L99R Btm SDM | GTTTGTACCTGGCTTTTTCA CGGGACGAAGGGGGGTGTTC CACGG |
| 127 | MMLV L99E Btm SDM | GTTTGTACCTGGCTTTTTCA CGGGTTCAAGGGGGGTGTTC CACGG |
| 128 | MMLV V101A Btm SDM | GGACGATAATCGTTTGTACC TGGCTTTTTCGCGGGCAGAA GGGGGGTG |
| 129 | MMLV V101R Btm SDM | GGACGATAATCGTTTGTACC TGGCTTTTTACGGGGCAGAA GGGGGGTG |
| 130 | MMLV V101E Btm SDM | GGACGATAATCGTTTGTACC TGGCTTTTTTTCGGGCAGAA GGGGGGTG |
| 131 | MMLV K102A Btm SDM | GGACGATAATCGTTTGTACC TGGCTTCGCCACGGGCAGAA GGGGG |
| 132 | MMLV K102R Btm SDM | GGACGATAATCGTTTGTACC TGGCTTACGCACGGGCAGAA GGGGG |
| 133 | MMLV K102E Btm SDM | GGACGATAATCGTTTGTACC TGGCTTTTCCACGGGCAGAA GGGGG |
| 134 | MMLV K103 A Btm SDM | AACTGGACGATAATCGTTTG TACCTGGCGCTTTCACGGGC AGAAGGGGG |
| 135 | MMLV K103R Btm SDM | AACTGGACGATAATCGTTTG TACCTGGACGTTTCACGGGC AGAAGGGGG |
| 136 | MMLV K103E Btm SDM | AACTGGACGATAATCGTTTG TACCTGGTTCTTTCACGGGC AGAAGGGGG |
| 137 | MMLV T106A Btm SDM | CGAAGATCTTGAACTGGACG ATAATCGTTCGCACCTGGCT TTTTCACGGGC |
| 138 | MMLV T106R Btm SDM | CGAAGATCTTGAACTGGACG ATAATCGTTACGACCTGGCT TTTTCACGGGC |
| 139 | MMLV T106E Btm SDM | CGAAGATCTTGAACTGGACG ATAATCGTTTTCACCTGGCT TTTTCACGGGC |
| 140 | MMLV N107A Btm SDM | CGCGAAGATCTTGAACTGGA CGATAATCCGCTGTACCTGG CTTTTTCACGGG |

TABLE 1-continued

Sequences of primers used for cloning of
MMLV RTase base constructs and mutants
into pET28b.

| SEQ ID NO: | Primer Name | Primer Sequence (5'-3') |
|---|---|---|
| 141 | MMLV N107R Btm SDM | CGCGAAGATCTTGAACTGGA CGATAATCACGTGTACCTGG CTTTTTCACGGG |
| 142 | MMLV N107E Btm SDM | CGCGAAGATCTTGAACTGGA CGATAATCTTCTGTACCTGG CTTTTTCACGGG |
| 143 | MMLV Y109A Btm SDM | CGCGAAGATCTTGAACTGGA CGCGCATCGTTTGTACCTGG CTTTTTCACG |
| 144 | MMLV Y109R Btm SDM | CGCGAAGATCTTGAACTGGA CGACGATCGTTTGTACCTGG CTTTTTCACG |
| 145 | MMLV Y109E Btm SDM | CGCGAAGATCTTGAACTGGA CGTTCATCGTTTGTACCTGG CTTTTTCACG |
| 146 | MMLVR110A Btm SDM | CCTCGCGAAGATCTTGAACT GGCGCATAATCGTTTGTACC TGGCTTTTTCACG |
| 147 | MMLV R110K Btm SDM | CCTCGCGAAGATCTTGAACT GGTTTATAATCGTTTGTACC TGGCTTTTTCACG |
| 148 | MMLVR110E Btm SDM | CCTCGCGAAGATCTTGAACT GGTTCATAATCGTTTGTACC TGGCTTTTTCACG |
| 149 | MMLV V112A Btm SDM | GTTTGTTGACCTCGCGAAGA TCTTGCGCTGGACGATAATC GTTTGTACCTGGC |
| 150 | MMLV V112R Btm SDM | GTTTGTTGACCTCGCGAAGA TCTTGACGTGGACGATAATC GTTTGTACCTGGC |
| 151 | MMLV VI12E Btm SDM | GTTTGTTGACCTCGCGAAGA TCTTGTTCTGGACGATAATC GTTTGTACCTGGC |
| 152 | MMLV K120A Btm SDM | GTCGGATGGATGTCTTCTAC GCGCGCGTTGACCTCGCGAA GATCTTGAACT |
| 153 | MMLV K120R Btm SDM | GTCGGATGGATGTCTTCTAC GCGACGGTTGACCTCGCGAA GATCTTGAACT |
| 154 | MMLV K120E Btm SDM | GTCGGATGGATGTCTTCTAC GCGTTCGTTGACCTCGCGAA GATCTTGAACT |
| 155 | MMLV E123A Btm SDM | GGATTAGGTACAGTCGGATG GATGTCCGCTACGCGTTTGT TGACCTCGC |
| 156 | MMLV E123R Btm SDM | GGATTAGGTACAGTCGGATG GATGTCACGTACGCGTTTGT TGACCTCGC |
| 157 | MMLV E123D Btm SDM | GGATTAGGTACAGTCGGATG GATGTCATCTACGCGTTTGT TGACCTCGC |
| 158 | MMLV T128V Btm SDM | GCAGGCCTGATAACAGATTA TAAGGATTAGGTACCACCGG ATGGATGTCTTCTACGCGT |

TABLE 1-continued

Sequences of primers used for cloning of
MMLV RTase base constructs and mutants
into pET28b.

| SEQ ID NO: | Primer Name | Primer Sequence (5'-3') |
|---|---|---|
| 159 | MMLV T128R Btm SDM | GCAGGCCTGATAACAGATTA TAAGGATTAGGTACACGCGG ATGGATGTCTTCTACGCGT |
| 160 | MMLV T128E Btm SDM | GCAGGCCTGATAACAGATTA TAAGGATTAGGTACTTCCGG ATGGATGTCTTCTACGCGT |
| 161 | MMLV K193A Btm SDM | TTCATCGAACAATGTGGGGC TGTTCGCAAAGCCCTGGGGC AGACG |
| 162 | MMLV K193R Btm SDM | TTCATCGAACAATGTGGGGC TGTTACGAAAGCCCTGGGGC AGACG |
| 163 | MMLV K193E Btm SDM | TTCATCGAACAATGTGGGGC TGTTTTCAAAGCCCTGGGGC AGACG |
| 164 | MMLV E282A Btm SDM | CATTACGGTCTCCTTACGCG CCGCAGTCAGCCAACGTTGA CCTTCT |
| 165 | MMLV E282R Btm SDM | CATTACGGTCTCCTTACGCG CACGAGTCAGCCAACGTTGA CCTTCT |
| 166 | MMLV E282D Btm SDM | CATTACGGTCTCCTTACGCG CATCAGTCAGCCAACGTTGA CCTTCT |
| 167 | MMLV A283V Btm SDM | GCCCCATTACGGTCTCCTTA CGCACTTCAGTCAGCCAACG TTGACCTTC |
| 168 | MMLV A283R Btm SDM | GCCCCATTACGGTCTCCTTA CGACGTTCAGTCAGCCAACG TTGACCTTC |
| 169 | MMLV A283E Btm SDM | GCCCCATTACGGTCTCCTTA CGTTCTTCAGTCAGCCAACG TTGACCTTC |
| 170 | MMLV Q29IA Btm SDM | CGTGGCGTCTTAGGCGTAGG CGCCCCCATTACGGTCTCCT TACGC |
| 171 | MMLV Q291R Btm SDM | CGTGGCGTCTTAGGCGTAGG ACGCCCCATTACGGTCTCCT TACGC |
| 172 | MMLV Q291E Btm SDM | CGTGGCGTCTTAGGCGTAGG TTCCCCCATTACGGTCTCCT TACGC |
| 173 | MMLV T293A Btm SDM | CAACTGGCGTGGCGTCTTAG GCGCAGGCTGCCCCATTACG GTCTC |
| 174 | MMLV T293R Btm SDM | CAACTGGCGTGGCGTCTTAG GACGAGGCTGCCCCATTACG GTCTC |
| 175 | MMLV T293E Btm SDM | CAACTGGCGTGGCGTCTTAG GTTCAGGCTGCCCCATTACG GTCTC |
| 176 | MMLV K295A Btm SDM | TTCACGCAACTGGCGTGGCG TCGCAGGCGTAGGCTGCCCC ATTAC |

TABLE 1-continued

Sequences of primers used for cloning of
MMLV RTase base constructs and mutants
into pET28b.

| SEQ ID NO: | Primer Name | Primer Sequence (5'-3') |
|---|---|---|
| 177 | MMLV K295R Btm SDM | TTCACGCAACTGGCGTGGCG TACGAGGCGTAGGCTGCCCC ATTAC |
| 178 | MMLV K295E Btm SDM | TTCACGCAACTGGCGTGGCG TTTCAGGCGTAGGCTGCCCC ATTAC |
| 179 | MMLV T296A Btm SDM | AAAATTCACGCAACTGGCGT GGCGCCTTAGGCGTAGGCTG CCCCA |
| 180 | MMLV T296R Btm SDM | AAAATTCACGCAACTGGCGT GGACGCTTAGGCGTAGGCTG CCCCA |
| 181 | MMLV T296E Btm SDM | AAAATTCACGCAACTGGCGT GGTTCCTTAGGCGTAGGCTG CCCCA |
| 182 | MMLV R298A Btm SDM | CTGTGCCCAAAAATTCACGC AACTGCGCTGGCGTCTTAGG CGTAGGC |
| 183 | MMLV R298K Btm SDM | CTGTGCCCAAAAATTCACGC AACTGTTTTGGCGTCTTAGG CGTAGGC |
| 184 | MMLV R298E Btm SDM | CTGTGCCCAAAAATTCACGC AACTGTTCTGGCGTCTTAGG CGTAGGC |
| 185 | MMLV R301A Btm SDM | TCCCGCTGTGCCCAAAAATT CCGCCAACTGGCGTGGCGTC TTAGG |
| 186 | MMLV R301K Btm SDM | TCCCGCTGTGCCCAAAAATT CTTTCAACTGGCGTGGCGTC TTAGG |
| 187 | MMLV R301E Btm SDM | TCCCGCTGTGCCCAAAAATT CTTCCAACTGGCGTGGCGTC TTAGG |
| 188 | MMLV K329A Btm SDM | CCAGTTGAAAAGCGTCCCTG TCGCTGTTAAGGGGTACAGG GGTGC |
| 189 | MMLV K329R Btm SDM | CCAGTTGAAAAGCGTCCCTG TACGTGTTAAGGGGTACAGG GGTGC |
| 190 | MMLV K329E Btm SDM | CCAGTTGAAAAGCGTCCCTG TTTCTGTTAAGGGGTACAGG GGTGC |
| 191 | MMLV I61G Top SDM | TAAAGGCAACGTCTACACCT GTCTCTGGCAAACAGTACCC CATGAGTCAAGAGG |
| 192 | MMLV I61G Btm SDM | CCTCTTGACTCATGGGGTAC TGTTTGCCAGAGACAGGTGT AGACGTTGCCTTTA |
| 193 | MMLV I61L Top SDM | TAAAGGCAACGTCTACACCT GTCTCTCTGAAACAGTACCC CATGAGTCAAGAGG |
| 194 | MMLV I61L Btm SDM | CCTCTTGACTCATGGGGTAC TGTTTCAGAGAGACAGGTGT AGACGTTGCCTTTA |

TABLE 1-continued

Sequences of primers used for cloning of
MMLV RTase base constructs and mutants
into pET28b.

| SEQ ID NO: | Primer Name | Primer Sequence (5'-3') |
|---|---|---|
| 195 | MMLV 16IV Top SDM | TAAAGGCAACGTCTACACCT GTCTCTGTGAAACAGTACCC CATGAGTCAAGAGG |
| 196 | MMLV 16IV Btm SDM | CCTCTTGACTCATGGGGTAC TGTTTCACAGAGACAGGTGT AGACGTTGCCTTTA |
| 197 | MMLV 16IP Top SDM | TAAAGGCAACGTCTACACCT GTCTCTCCGAAACAGTACCC CATGAGTCAAGAGG |
| 198 | MMLV 16IP Btm SDM | CCTCTTGACTCATGGGGTAC TGTTTCGGAGAGACAGGTGT AGACGTTGCCTTTA |
| 199 | MMLV 161M Top SDM | TAAAGGCAACGTCTACACCT GTCTCTATGAAACAGTACCC CATGAGTCAAGAGG |
| 200 | MMLV 161M Btm SDM | CCTCTTGACTCATGGGGTAC TGTTTCATAGAGACAGGTGT AGACGTTGCCTTTA |
| 201 | MMLV 16IS Top SDM | TAAAGGCAACGTCTACACCT GTCTCTAGCAAACAGTACCC CATGAGTCAAGAGG |
| 202 | MMLV 16IS Btm SDM | CCTCTTGACTCATGGGGTAC TGTTTGCTAGAGACAGGTGT AGACGTTGCCTTTA |
| 203 | MMLV 16IT Top SDM | TAAAGGCAACGTCTACACCT GTCTCTACCAAACAGTACCC CATGAGTCAAGAGG |
| 204 | MMLV 16IT Btm SDM | CCTCTTGACTCATGGGGTAC TGTTTGGTAGAGACAGGTGT AGACGTTGCCTTTA |
| 205 | MMLV 161C Top SDM | TAAAGGCAACGTCTACACCT GTCTCTTGCAAACAGTACCC CATGAGTCAAGAGG |
| 206 | MMLV 161C Btm SDM | CCTCTTGACTCATGGGGTAC TGTTTGCAAGAGACAGGTGT AGACGTTGCCTTTA |
| 207 | MMLV 16IF Top SDM | TAAAGGCAACGTCTACACCT GTCTCTTTTAAACAGTACCC CATGAGTCAAGAGG |
| 208 | MMLV 161F Btm SDM | CCTCTTGACTCATGGGGTAC TGTTTAAAAGAGACA GGTGTAGACGTTGCCTTTA |
| 209 | MMLV 161Y Top SDM | TAAAGGCAACGTCTACACCT GTCTCTTATAAACAGTACCC CATGAGTCAAGAGG |
| 210 | MMLV 161Y Btm SDM | CCTCTTGACTCATGGGGTAC TGTTTATAAGAGACAGGTGT AGACGTTGCCTTTA |
| 211 | MMLV 161H Top SDM | TAAAGGCAACGTCTACACCT GTCTCTCATAAACAGTACCC CATGAGTCAAGAGG |
| 212 | MMLV 161H Btm SDM | CCTCTTGACTCATGGGGTAC TGTTTATGAGAGACAGGTGT AGACGTTGCCTTTA |

TABLE 1-continued

Sequences of primers used for cloning of
MMLV RTase base constructs and mutants
into pET28b.

| SEQ ID NO: | Primer Name | Primer Sequence (5'-3') |
|---|---|---|
| 213 | MMLV I61W Top SDM | TAAAGGCAACGTCTACACCT GTCTCTTGGAAACAGTACCC CATGAGTCAAGAGG |
| 214 | MMLV I61W Btm SDM | CCTCTTGACTCATGGGGTAC TGTTTCCAAGAGACAGGTGT AGACGTTGCCTTTA |
| 215 | MMLV I61D Top SDM | TAAAGGCAACGTCTACACCT GTCTCTGATAAACAGTACCC CATGAGTCAAGAGG |
| 216 | MMLV 16ID Btm SDM | CCTCTTGACTCATGGGGTAC TGTTTATCAGAGACAGGTGT AGACGTTGCCTTTA |
| 217 | MMLV 16IN Top SDM | TAAAGGCAACGTCTACACCT GTCTCTAACAAACAGTACCC CATGAGTCAAGAGG |
| 218 | MMLV 16IN Btm SDM | CCTCTTGACTCATGGGGTAC TGTTTGTTAGAGACAGGTGT AGACGTTGCCTTTA |
| 219 | MMLV 16IQ Top SDM | TAAAGGCAACGTCTACACCT GTCTCTCAGAAACAGTACCC CATGAGTCAAGAGG |
| 220 | MMLV 16IQ Btm SDM | CCTCTTGACTCATGGGGTAC TGTTTCTGAGAGACAGGTGT AGACGTTGCCTTTA |
| 221 | MMLV 16IK Top SDM | TAAAGGCAACGTCTACACCT GTCTCTAAAAAACAGTACCC CATGAGTCAAGAGG |
| 222 | MMLV 16IK Btm SDM | CCTCTTGACTCATGGGGTAC TGTTTTTTAGAGACAGGTGT AGACGTTGCCTTTA |
| 223 | MMLV Q68G Top SDM | CTGTCTCTATCAAACAGTAC CCCATGAGTGGCGAGGCCCG CCTGGG |
| 224 | MMLV Q68G Btm SDM | CCCAGGCGGGCCTCGCCACT CATGGGGTACTGTTTGATAG AGACAG |
| 225 | MMLV Q68L Top SDM | CTGTCTCTATCAAACAGTAC CCCATGAGTCTGGAGGCCCG CCTGGG |
| 226 | MMLV Q68L Btm SDM | CCCAGGCGGGCCTCCAGACT CATGGGGTACTGTTTGATAG AGACAG |
| 227 | MMLV Q68I Top SDM | CTGTCTCTATCAAACAGTAC CCCATGAGTATTGAGGCCCG CCTGGG |
| 228 | MMLV Q68I Btm SDM | CCCAGGCGGGCCTCAATACT CATGGGGTACTGTTT GATAGAGACAG |
| 229 | MMLV Q68V Top SDM | CTGTCTCTATCAAACAGTAC CCCATGAGTGTGGAGGCCCG CCTGGG |
| 230 | MMLV Q68V Btm SDM | CCCAGGCGGGCCTCCACACT CATGGGGTACTGTTTGATAG AGACAG |

TABLE 1-continued

Sequences of primers used for cloning of
MMLV RTase base constructs and mutants
into pET28b.

| SEQ ID NO: | Primer Name | Primer Sequence (5'-3') |
|---|---|---|
| 231 | MMLV Q68P Top SDM | CTGTCTCTATCAAACAGTAC CCCATGAGTCCGGAGGCCCG CCTGGG |
| 232 | MMLV Q68P Btm SDM | CCCAGGCGGGCCTCCGGACT CATGGGGTACTGTTTGATAG AGACAG |
| 233 | MMLV Q68M Top SDM | CTGTCTCTATCAAACAGTAC CCCATGAGTATGGAGGCCCG CCTGGG |
| 234 | MMLV Q68M Btm SDM | CCCAGGCGGGCCTCCATACT CATGGGGTACTGTTTGATAG AGACAG |
| 235 | MMLV Q68S Top SDM | CTGTCTCTATCAAACAGTAC CCCATGAGTAGCGAGGCCCG CCTGGG |
| 236 | MMLV Q68S Btm SDM | CCCAGGCGGGCCTCGCTACT CATGGGGTACTGTTTGATAG AGACAG |
| 237 | MMLV Q68T Top SDM | CTGTCTCTATCAAACAGTAC CCCATGAGTACCGAGGCCCG CCTGGG |
| 238 | MMLV Q68T Btm SDM | CCCAGGCGGGCCTCGGTACT CATGGGGTACTGTTTGATAG AGACAG |
| 239 | MMLV Q68C Top SDM | CTGTCTCTATCAAACAGTAC CCCATGAGTTGCGAGGCCCG CCTGGG |
| 240 | MMLV Q68C Btm SDM | CCCAGGCGGGCCTCGCAACT CATGGGGTACTGTTTGATAG AGACAG |
| 241 | MMLV Q68F Top SDM | CTGTCTCTATCAAACAGTAC CCCATGAGTTTTGAGGCCCG CCTGGG |
| 242 | MMLV Q68F Btm SDM | CCCAGGCGGGCCTCAAAACT CATGGGGTACTGTTTGATAG AGACAG |
| 243 | MMLV Q68Y Top SDM | CTGTCTCTATCAAACAGTAC CCCATGAGTTATGAGGCCCG CCTGGG |
| 244 | MMLV Q68Y Btm SDM | CCCAGGCGGGCCTCATAACT CATGGGGTACTGTTTGATAG AGACAG |
| 245 | MMLV Q68H Top SDM | CTGTCTCTATCAAACAGTAC CCCATGAGTCATGAGGCCCG CCTGGG |
| 246 | MMLV Q68H Btm SDM | CCCAGGCGGGCCTCATGACT CATGGGGTACTGTTTGATAG AGACAG |
| 247 | MMLV Q68W Top SDM | CTGTCTCTATCAAACAGTAC CCCATGAGTTGGGAGGCCCG CCTGGG |
| 248 | MMLV Q68W Btm SDM | CCCAGGCGGGCCTCCCAACT CATGGGGTACTGTTT GATAGAGACAG |

TABLE 1-continued

Sequences of primers used for cloning of
MMLV RTase base constructs and mutants
into pET28b.

| SEQ ID NO: | Primer Name | Primer Sequence (5'-3') |
|---|---|---|
| 249 | MMLV Q68D Top SDM | CTGTCTCTATCAAACAGTAC CCCATGAGTGATGAGGCCCG CCTGGG |
| 250 | MMLV Q68D Btm SDM | CCCAGGCGGGCCTCATCACT CATGGGGTACTGTTTGATAG AGACAG |
| 251 | MMLV Q68N Top SDM | CTGTCTCTATCAAACAGTAC CCCATGAGTAACGAGGCCCG CCTGGG |
| 252 | MMLV Q68N Btm SDM | CCCAGGCGGGCCTCGTTACT CATGGGGTACTGTTTGATAG AGACAG |
| 253 | MMLV Q68K Top SDM | CTGTCTCTATCAAACAGTAC CCCATGAGTAAAGAGGCCCG CCTGGG |
| 254 | MMLV Q68K Btm SDM | CCCAGGCGGGCCTCTTTACT CATGGGGTACTGTTTGATAG AGACAG |
| 255 | MMLV Q79G Top SDM | CGCCTGGGGATTAAGCCACA TATTGGCCGCTTGCTGGACC AGGGG |
| 256 | MMLV Q79G Btm SDM | CCCCTGGTCCAGCAAGCGGC CAATATGTGGCTTAATCCCC AGGCG |
| 257 | MMLV Q79L Top SDM | CGCCTGGGGATTAAGCCACA TATTCTGCGCTTGCTGGACC AGGGG |
| 258 | MMLV Q79L Btm SDM | CCCCTGGTCCAGCAAGCGCA GAATATGTGGCTTAATCCCC AGGCG |
| 259 | MMLV Q79I Top SDM | CGCCTGGGGATTAAGCCACA TATTATTCGCTTGCTGGACC AGGGG |
| 260 | MMLV Q79I Btm SDM | CCCCTGGTCCAGCAAGCGAA TAATATGTGGCTTAATCCCC AGGCG |
| 261 | MMLV Q79V Top SDM | CGCCTGGGGATTAAGCCACA TATTGTGCGCTTGCTGGACC AGGGG |
| 262 | MMLV Q79V Btm SDM | CCCCTGGTCCAGCAAGCGCA CAATATGTGGCTTAATCCCC AGGCG |
| 263 | MMLV Q79P Top SDM | CGCCTGGGGATTAAGCCACA TATTCCGCGCTTGCTGGACC AGGGG |
| 264 | MMLV Q79P Btm SDM | CCCCTGGTCCAGCAAGCGCG GAATATGTGGCTTAATCCCC AGGCG |
| 265 | MMLV Q79M Top SDM | CGCCTGGGGATTAAGCCACA TATTATGCGCTTGCTGGACC AGGGG |
| 266 | MMLV Q79M Btm SDM | CCCCTGGTCCAGCAAGCGCA TAATATGTGGCTTAATCCCC AGGCG |

TABLE 1-continued

Sequences of primers used for cloning of
MMLV RTase base constructs and mutants
into pET28b.

| SEQ ID NO: | Primer Name | Primer Sequence (5'-3') |
|---|---|---|
| 267 | MMLV Q79S Top SDM | CGCCTGGGGATTAAGCCACA TATTAGCCGCTTGCTGGACC AGGGG |
| 268 | MMLV Q79S Btm SDM | CCCCTGGTCCAGCAAGCGGC TAATATGTGGCTTAA TCCCCAGGCG |
| 269 | MMLV Q79T Top SDM | CGCCTGGGGATTAAGCCACA TATTACCCGCTTGCTGGACC AGGGG |
| 270 | MMLV Q79T Btm SDM | CCCCTGGTCCAGCAAGCGGG TAATATGTGGCTTAATCCCC AGGCG |
| 271 | MMLV Q79C Top SDM | CGCCTGGGGATTAAGCCACA TATTTGCCGCTTGCTGGACC AGGGG |
| 272 | MMLV Q79C Btm SDM | CCCCTGGTCCAGCAAGCGGC AAATATGTGGCTTAATCCCC AGGCG |
| 273 | MMLV Q79F Top SDM | CGCCTGGGGATTAAGCCACA TATTTTTCGCTTGCTGGACC AGGGG |
| 274 | MMLV Q79F Btm SDM | CCCCTGGTCCAGCAAGCGAA AAATATGTGGCTTAATCCCC AGGCG |
| 275 | MMLV Q79Y Top SDM | CGCCTGGGGATTAAGCCACA TATTTATCGCTTGCTGGACC AGGGG |
| 276 | MMLV Q79Y Btm SDM | CCCCTGGTCCAGCAAGCGAT AAATATGTGGCTTAATCCCC AGGCG |
| 277 | MMLV Q79H Top SDM | CGCCTGGGGATTAAGCCACA TATTCATCGCTTGCTGGACC AGGGG |
| 278 | MMLV Q79H Btm SDM | CCCCTGGTCCAGCAAGCGAT GAATATGTGGCTTAATCCCC AGGCG |
| 279 | MMLV Q79W Top SDM | CGCCTGGGGATTAAGCCACA TATTTGGCGCTTGCTGGACC AGGGG |
| 280 | MMLV Q79W Btm SDM | CCCCTGGTCCAGCAAGCGCC AAATATGTGGCTTAATCCCC AGGCG |
| 281 | MMLV Q79D Top SDM | CGCCTGGGGATTAAGCCACA TATTGATCGCTTGCTGGACC AGGGG |
| 282 | MMLV Q79D Btm SDM | CCCCTGGTCCAGCAAGCGAT CAATATGTGGCTTAATCCCC AGGCG |
| 283 | MMLV Q79N Top SDM | CGCCTGGGGATTAAGCCACA TATTAACCGCTTGCTGGACC AGGGG |
| 284 | MMLV Q79N Btm SDM | CCCCTGGTCCAGCAAGCGGT TAATATGTGGCTTAATCCCC AGGCG |

TABLE 1-continued

Sequences of primers used for cloning of
MMLV RTase base constructs and mutants
into pET28b.

| SEQ ID NO: | Primer Name | Primer Sequence (5'-3') |
|---|---|---|
| 285 | MMLV Q79K Top SDM | CGCCTGGGGATTAAGCCACA TATTAAACGCTTGCTGGACC AGGGG |
| 286 | MMLV Q79K Btm SDM | CCCCTGGTCCAGCAAGCGTT TAATATGTGGCTTAATCCCC AGGCG |
| 287 | MMLV L99G Top SDM | CCGTGGAACACCCCCCTTGG CCCCGTGAAAAAGCCAGGTA CAAAC |
| 288 | MMLV L99G Btm SDM | GTTTGTACCTGGCTTTTTCA CGGGGCCAAGGGGGG TGTTCCACGG |
| 289 | MMLV L99I Top SDM | CCGTGGAACACCCCCCTTAT TCCCGTGAAAAAGCCAGGTA CAAAC |
| 290 | MMLV L99I Btm SDM | GTTTGTACCTGGCTTTTTCA CGGGAATAAGGGGGGTGTTC CACGG |
| 291 | MMLV L99V Top SDM | CCGTGGAACACCCCCCTTGT GCCCGTGAAAAAGCCAGGTA CAAAC |
| 292 | MMLV L99V Btm SDM | GTTTGTACCTGGCTTTTTCA CGGGCACAAGGGGGGTGTTC CACGG |
| 293 | MMLV L99P Top SDM | CCGTGGAACACCCCCCTTCC GCCCGTGAAAAAGCCAGGTA CAAAC |
| 294 | MMLV L99P Btm SDM | GTTTGTACCTGGCTTTTTCA CGGGCGGAAGGGGGGTGTTC CACGG |
| 295 | MMLV L99M Top SDM | CCGTGGAACACCCCCCTTAT GCCCGTGAAAAAGCCAGGTA CAAAC |
| 296 | MMLV L99M Btm SDM | GTTTGTACCTGGCTTTTTCA CGGGCATAAGGGGGGTGTTC CACGG |
| 297 | MMLV L99S Top SDM | CCGTGGAACACCCCCCTTAG CCCCGTGAAAAAGCCAGGTA CAAAC |
| 298 | MMLV L99S Btm SDM | GTTTGTACCTGGCTTTTTCA CGGGGCTAAGGGGGGTGTTC CACGG |
| 299 | MMLV L99T Top SDM | CCGTGGAACACCCCCCTTAC CCCCGTGAAAAAGCCAGGTA CAAAC |
| 300 | MMLV L99T Btm SDM | GTTTGTACCTGGCTTTTTCA CGGGGGGTAAGGGGGGTGTTC CACGG |
| 301 | MMLV L99C Top SDM | CCGTGGAACACCCCCCTTTG CCCCGTGAAAAAGCCAGGTA CAAAC |
| 302 | MMLV L99C Btm SDM | GTTTGTACCTGGCTTTTTCA CGGGGCAAGGGGGGTGTTC CACGG |

TABLE 1-continued

Sequences of primers used for cloning of
MMLV RTase base constructs and mutants
into pET28b.

| SEQ ID NO: | Primer Name | Primer Sequence (5'-3') |
|---|---|---|
| 303 | MMLV L99F Top SDM | CCGTGGAACACCCCCCTTTT TCCCGTGAAAAAGCCAGGTA CAAAC |
| 304 | MMLV L99F Btm SDM | GTTTGTACCTGGCTTTTTCA CGGGAAAAAGGGGGGTGTTC CACGG |
| 305 | MMLV L99Y Top SDM | CCGTGGAACACCCCCCTTTA TCCCGTGAAAAAGCCAGGTA CAAAC |
| 306 | MMLV L99Y Btm SDM | GTTTGTACCTGGCTTTTTCA CGGGATAAAGGGGGGTGTTC CACGG |
| 307 | MMLV L99H Top SDM | CCGTGGAACACCCCCCTTCA TCCCGTGAAAAAGCCAGGTA CAAAC |
| 308 | MMLV L99H Btm SDM | GTTTGTACCTGGCTTTTTCA CGGGATGAAGGGGGG TGTTCCACGG |
| 309 | MMLV L99W Top SDM | CCGTGGAACACCCCCCTTTG GCCCGTGAAAAAGCCAGGTA CAAAC |
| 310 | MMLV L99W Btm SDM | GTTTGTACCTGGCTTTTTCA CGGGCCAAAGGGGGGTGTTC CACGG |
| 311 | MMLV L99D Top SDM | CCGTGGAACACCCCCCTTGA TCCCGTGAAAAAGCCAGGTA CAAAC |
| 312 | MMLV L99D Btm SDM | GTTTGTACCTGGCTTTTTCA CGGGATCAAGGGGGGTGTTC CACGG |
| 313 | MMLV L99N Top SDM | CCGTGGAACACCCCCCTTAA CCCCGTGAAAAAGCCAGGTA CAAAC |
| 314 | MMLV L99N Btm SDM | GTTTGTACCTGGCTTTTTCA CGGGGTTAAGGGGGGTGTTC CACGG |
| 315 | MMLV L99Q Top SDM | CCGTGGAACACCCCCCTTCA GCCCGTGAAAAAGCCAGGTA CAAAC |
| 316 | MMLV L99Q Btm SDM | GTTTGTACCTGGCTTTTTCA CGGGCTGAAGGGGGGTGTTC CACGG |
| 317 | MMLV L99K Top SDM | CCGTGGAACACCCCCCTTAA ACCCGTGAAAAAGCCAGGTA CAAAC |
| 318 | MMLV L99K Btm SDM | GTTTGTACCTGGCTTTTTCA CGGGTTTAAGGGGGGTGTTC CACGG |
| 319 | MMLV E282G Top SDM | AGAAGGTCAACGTTGGCTGA CTGGCGCGCGTAAGGAGACC GTAATG |
| 320 | MMLV E282G Btm SDM | CATTACGGTCTCCTTACGCG CGCCAGTCAGCCAACGTTGA CCTTCT |

TABLE 1-continued

Sequences of primers used for cloning of
MMLV RTase base constructs and mutants
into pET28b.

| SEQ ID NO: | Primer Name | Primer Sequence (5'-3') |
|---|---|---|
| 321 | MMLV E282L Top SDM | AGAAGGTCAACGTTGGCTGA CTCTGGCGCGTAAGGAGACC GTAATG |
| 322 | MMLV E282L Btm SDM | CATTACGGTCTCCTTACGCG CCAGAGTCAGCCAACGTTGA CCTTCT |
| 323 | MMLV E282I Top SDM | AGAAGGTCAACGTTGGCTGA CTATTGCGCGTAAGGAGACC GTAATG |
| 324 | MMLV E282I Btm SDM | CATTACGGTCTCCTTACGCG CAATAGTCAGCCAACGTTGA CCTTCT |
| 325 | MMLV E282V Top SDM | AGAAGGTCAACGTTGGCTGA CTGTGGCGCGTAAGGAGACC GTAATG |
| 326 | MMLV E282V Btm SDM | CATTACGGTCTCCTTACGCG CCACAGTCAGCCAACGTTGA CCTTCT |
| 327 | MMLV E282R Top SDM | AGAAGGTCAACGTTGGCTGA CTCCGGCGCGTAAGGAGACC GTAATG |
| 328 | MMLV E282P Btm SDM | CATTACGGTCTCCTTACGCG CCGGAGTCAGCCAAC GTTGACCTTCT |
| 329 | MMLV E282M Top SDM | AGAAGGTCAACGTTGGCTGA CTATGGCGCGTAAGGAGACC GTAATG |
| 330 | MMLV E282M Btm SDM | CATTACGGTCTCCTTACGCG CCATAGTCAGCCAACGTTGA CCTTCT |
| 331 | MMLV E282S Top SDM | AGAAGGTCAACGTTGGCTGA CTAGCGCGCGTAAGGAGACC GTAATG |
| 332 | MMLV E282S Btm SDM | CATTACGGTCTCCTTACGCG CGCTAGTCAGCCAACGTTGA CCTTCT |
| 333 | MMLV E282T Top SDM | AGAAGGTCAACGTTGGCTGA CTACCGCGCGTAAGGAGACC GTAATG |
| 334 | MMLV E282T Btm SDM | CATTACGGTCTCCTTACGCG CGGTAGTCAGCCAACGTTGA CCTTCT |
| 335 | MMLV E282C Top SDM | AGAAGGTCAACGTTGGCTGA CTTGCGCGCGTAAGGAGACC GTAATG |
| 336 | MMLV E282C Btm SDM | CATTACGGTCTCCTTACGCG CGCAAGTCAGCCAACGTTGA CCTTCT |
| 337 | MMLV E282F Top SDM | AGAAGGTCAACGTTGGCTGA CTTTTGCGCGTAAGGAGACC GTAATG |
| 338 | MMLV E282F Btm SDM | CATTACGGTCTCCTTACGCG CAAAAGTCAGCCAACGTTGA CCTTCT |

TABLE 1-continued

Sequences of primers used for cloning of
MMLV RTase base constructs and mutants
into pET28b.

| SEQ ID NO: | Primer Name | Primer Sequence (5'-3') |
|---|---|---|
| 339 | MMLV E282Y Top SDM | AGAAGGTCAACGTTGGCTGA CTTATGCGCGTAAGGAGACC GTAATG |
| 340 | MMLV E282Y Btm SDM | CATTACGGTCTCCTTACGCG CATAAGTCAGCCAACGTTGA CCTTCT |
| 341 | MMLV E282H Top SDM | AGAAGGTCAACGTTGGCTGA CTCATGCGCGTAAGGAGACC GTAATG |
| 342 | MMLV E282H Btm SDM | CATTACGGTCTCCTTACGCG CATGAGTCAGCCAACGTTGA CCTTCT |
| 343 | MMLV E282W Top SDM | AGAAGGTCAACGTTGGCTGA CTTGGGCGCGTAAGGAGACC GTAATG |
| 344 | MMLV E282W Btm SDM | CATTACGGTCTCCTTACGCG CCCAAGTCAGCCAACGTTGA CCTTCT |
| 345 | MMLV E282N Top SDM | AGAAGGTCAACGTTGGCTGA CTAACGCGCGTAAGGAGACC GTAATG |
| 346 | MMLV E282N Btm SDM | CATTACGGTCTCCTTACGCG CGTTAGTCAGCCAACGTTGA CCTTCT |
| 347 | MMLV E282Q Top SDM | AGAAGGTCAACGTTGGCTGA CTCAGGCGCGTAAGGAGACC GTAATG |
| 348 | MMLV E282Q Btm SDM | CATTACGGTCTCCTTACGCG CCTGAGTCAGCCAAC GTTGACCTTCT |
| 349 | MMLV E282K Top SDM | AGAAGGTCAACGTTGGCTGA CTAAAGCGCGTAAGGAGACC GTAATG |
| 350 | MMLV E282K Btm SDM | CATTACGGTCTCCTTACGCG CTTTAGTCAGCCAACGTTGA CCTTCT |
| 351 | MMLV R298G Top SDM | GCCTACGCCTAAGACGCCAG GCCAGTTGCGTGAATTTTTG GGCACAG |
| 352 | MMLV R298G Btm SDM | CTGTGCCCAAAAATTCACGC AACTGGCCTGGCGTCTTAGG CGTAGGC |
| 353 | MMLV R298L Top SDM | GCCTACGCCTAAGACGCCAC TGCAGTTGCGTGAATTTTTG GGCACAG |
| 354 | MMLV R298L Btm SDM | CTGTGCCCAAAAATTCACGC AACTGCAGTGGCGTCTTAGG CGTAGGC |
| 355 | MMLV R298I Top SDM | GCCTACGCCTAAGACGCCAA TTCAGTTGCGTGAATTTTTG GGCACAG |
| 356 | MMLV R298I Btm SDM | CTGTGCCCAAAAATTCACGC AACTGAATTGGCGTCTTAGG CGTAGGC |

TABLE 1-continued

Sequences of primers used for cloning of
MMLV RTase base constructs and mutants
into pET28b.

| SEQ ID NO: | Primer Name | Primer Sequence (5'-3') |
|---|---|---|
| 357 | MMLV R298V Top SDM | GCCTACGCCTAAGACGCCAG TGCAGTTGCGTGAATTTTTG GGCACAG |
| 358 | MMLV R298V Btm SDM | CTGTGCCCAAAAATTCACGC AACTGCACTGGCGTCTTAGG CGTAGGC |
| 359 | MMLV R298P Top SDM | GCCTACGCCTAAGACGCCAC CGCAGTTGCGTGAATTTTTG GGCACAG |
| 360 | MMLV R298P Btm SDM | CTGTGCCCAAAAATTCACGC AACTGCGGTGGCGTCTTAGG CGTAGGC |
| 361 | MMLV R298M Top SDM | GCCTACGCCTAAGACGCCAA TGCAGTTGCGTGAATTTTTG GGCACAG |
| 362 | MMLV R298M Btm SDM | CTGTGCCCAAAAATTCACGC AACTGCATTGGCGTCTTAGG CGTAGGC |
| 363 | MMLV R298S Top SDM | GCCTACGCCTAAGACGCCAA GCCAGTTGCGTGAATTTTTG GGCACAG |
| 364 | MMLV R298S Btm SDM | CTGTGCCCAAAAATTCACGC AACTGGCTTGGCGTCTTAGG CGTAGGC |
| 365 | MMLV R298T Top SDM | GCCTACGCCTAAGACGCCAA CCCAGTTGCGTGAATTTTTG GGCACAG |
| 366 | MMLV R298T Btm SDM | CTGTGCCCAAAAATTCACGC AACTGGGTTGGCGTCTTAGG CGTAGGC |
| 367 | MMLV R298C Top SDM | GCCTACGCCTAAGACGCCAT GCCAGTTGCGTGAATTTTTG GGCACAG |
| 368 | MMLV R298C Btm SDM | CTGTGCCCAAAAATTCACGC AACTGGCATGGCGTC TTAGGCGTAGGC |
| 369 | MMLV R298F Top SDM | GCCTACGCCTAAGACGCCAT TTCAGTTGCGTGAATTTTTG GGCACAG |
| 370 | MMLV R298F Btm SDM | CTGTGCCCAAAAATTCACGC AACTGAAATGGCGTCTTAGG CGTAGGC |
| 371 | MMLV R298Y Top SDM | GCCTACGCCTAAGACGCCAT ATCAGTTGCGTGAATTTTTG GGCACAG |
| 372 | MMLV R298Y Btm SDM | CTGTGCCCAAAAATTCACGC AACTGATATGGCGTCTTAGG CGTAGGC |
| 373 | MMLV R298H Top SDM | GCCTACGCCTAAGACGCCAC ATCAGTTGCGTGAATTTTTG GGCACAG |
| 374 | MMLV R298H Btm SDM | CTGTGCCCAAAAATTCACGC AACTGATGTGGCGTCTTAGG CGTAGGC |

TABLE 1-continued

Sequences of primers used for cloning of
MMLV RTase base constructs and mutants
into pET28b.

| SEQ ID NO: | Primer Name | Primer Sequence (5'-3') |
|---|---|---|
| 375 | MMLV R298W Top SDM | GCCTACGCCTAAGACGCCAT GGCAGTTGCGTGAATTTTTG GGCACAG |
| 376 | MMLV R298W Btm SDM | CTGTGCCCAAAAATTCACGC AACTGCCATGGCGTCTTAGG CGTAGGC |
| 377 | MMLV R298D Top SDM | GCCTACGCCTAAGACGCCAG ATCAGTTGCGTGAATTTTTG GGCACAG |
| 378 | MMLV R298D Btm SDM | CTGTGCCCAAAAATTCACGC AACTGATCTGGCGTCTTAGG CGTAGGC |
| 379 | MMLV R298N Top SDM | GCCTACGCCTAAGACGCCAA ACCAGTTGCGTGAATTTTTG GGCACAG |
| 380 | MMLV R298N Btm SDM | CTGTGCCCAAAAATTCACGC AACTGGTTTGGCGTCTTAGG CGTAGGC |
| 381 | MMLV R298Q Top SDM | GCCTACGCCTAAGACGCCAC AGCAGTTGCGTGAATTTTTG GGCACAG |
| 382 | MMLV R298Q Btm SDM | CTGTGCCCAAAAATTCACGC AACTGCTGTGGCGTCTTAGG CGTAGGC |
| 383 | MMLV I61R/Q68R Top SDM | AGGCAACGTCTACACCTGTC TCTCGTAAACAGTACCCCAT GAGTCGTGAGGCCCGCCTGG GG |
| 384 | MMLV I61R/Q68R Btm SDM | CCCCAGGCGGGCCTCACGAC TCATGGGGTACTGTTTACGA GAGACAGGTGTAGACGTTGC CT |
| 385 | MMLV I61K/Q68R Top SDM | AGGCAACGTCTACACCTGTC TCTAAAAAACAGTACCCCAT GAGTCGTGAGG |
| 386 | MMLV I61K/Q68R Btm SDM | CCTCACGACTCATGGGGTAC TGTTTTTTAGAGACAGGTGT AGACGTTGCCT |
| 387 | MMLV I61M/Q68R Top SDM | AGGCAACGTCTACACCTGTC TCTATGAAACAGTACCCCAT GAGTCGTGAGG |
| 388 | MMLV I61M/Q68R Btm SDM | CCTCACGACTCATGGGGTAC TGTTTCATAGAGACA GGTGTAGACGTTGCCT |
| 389 | MMLV I61M/Q68I Top SDM | AGGCAACGTCTACACCTGTC TCTATGAAACAGTACCCCAT GAGTATTGAGGCC |
| 390 | MMLV I61M/Q68I Btm SDM | GGCCTCAATACTCATGGGGT ACTGTTTCATAGAGACAGGT GTAGACGTTGCCT |
| 393 | MMLV 5' Primer | GTCTCTATCAAACAGTACCC CATGGCGCAAGAGGCCCGCC TGGG |

TABLE 1-continued

Sequences of primers used for cloning of
MMLV RTase base constructs and mutants
into pET28b.

| SEQ ID NO: | Primer Name | Primer Sequence (5'-3') |
|---|---|---|
| 394 | MMLV 3′ Primer | GTCTCTATCAAACAGTACCC CATGCGTCAAGAGGCCCGCC TGGG |
| 395 | MMLV G73A Top SDM | CATGAGTCAAGAGGCCCGCG AGGGGATTAAGCCACATATT CAGCG |
| 396 | MMLV G73R Top SDM | GAGTCAAGAGGCCCGCCTGG CGATTAAGCCACATATTCAG CGCTTGC |
| 397 | MMLV G73E Top SDM | GAGTCAAGAGGCCCGCCTGC GTATTAAGCCACATATTCAG CGCTTGC |
| 398 | MMLV P76A Top SDM | GAGTCAAGAGGCCCGCCTGG AGATTAAGCCACATATTCAG CGCTTGC |
| 399 | MMLV P76R Top SDM | GGCCCGCCTGGGGATTAAGG CGCATATTCAGCGCTTGCTG GACC |
| 400 | MMLV P76E Top SDM | GGCCCGCCTGGGGATTAAGC GTCATATTCAGCGCTTGCTG GACC |
| 401 | MMLV H77A Top SDM | GGCCCGCCTGGGGATTAAGG AGCATATTCAGCGCTTGCTG GACC |
| 402 | MMLV H77R Top SDM | CCGCCTGGGGATTAAGCCAG CGATTCAGCGCTTGCTGGAC CAG |
| 403 | MMLV H77E Top SDM | CCGCCTGGGGATTAAGCCAC GTATTCAGCGCTTGCTGGAC CAG |
| 404 | MMLV L82A Top SDM | CCGCCTGGGGATTAAGCCAG AGATTCAGCGCTTGCTGGAC CAG |
| 405 | MMLV L82R Top SDM | GATTAAGCCACATATTCAGC GCTTGGCGGACCAGGGGATC TTGGTCC |
| 406 | MMLV L82E Top SDM | GATTAAGCCACATATTCAGC GCTTGCGTGACCAGGGGATC TTGGTCC |
| 407 | MMLV D83A Top SDM | GATTAAGCCACATATTCAGC GCTTGGAGGACCAGGGGATC TTGGTCC |
| 408 | MMLV D83R Top SDM | GCCACATATTCAGCGCTTGC TGGCGCAGGGGATCTTGGTC CCATG |
| 409 | MMLV D83E Top SDM | GCCACATATTCAGCGCTTGC TGCGTCAGGGGATCTTGGTC CCATG |
| 410 | MMLV I125A Top SDM | GCCACATATTCAGCGCTTGC TGGAGCAGGGGATCT TGGTCCCATG |
| 411 | MMLV I125R Top SDM | AGGTCAACAAACGCGTAGAA GACGCGCATCCGACTGTACC TAATCCTTATAAT |

TABLE 1-continued

Sequences of primers used for cloning of
MMLV RTase base constructs and mutants
into pET28b.

| SEQ ID NO: | Primer Name | Primer Sequence (5'-3') |
|---|---|---|
| 412 | MMLV I125E Top SDM | AGGTCAACAAACGCGTAGAA GACCGTCATCCGACTGTACC TAATCCTTATAAT |
| 413 | MMLV V129A Top SDM | AGGTCAACAAACGCGTAGAA GACGAGCATCCGACTGTACC TAATCCTTATAAT |
| 414 | MMLV V129R Top SDM | GCGTAGAAGACATCCATCCG ACTGCGCCTAATCCTTATAA TCTGTTATCAGGC |
| 415 | MMLV V129E Top SDM | GCGTAGAAGACATCCATCCG ACTCGTCCTAATCCTTATAA TCTGTTATCAGGC |
| 416 | MMLV LI 98A Top SDM | GCGTAGAAGACATCCATCCG ACTGAGCCTAATCCTTATAA TCTGTTATCAGGC |
| 417 | MMLV LI98R Top SDM | AGGGCTTTAAAAACAGCCCC ACAGCGTTCGATGAAGCACT TCACCGTGA |
| 418 | MMLV L198E Top SDM | AGGGCTTTAAAAACAGCCCC ACACGTTTCGATGAAGCACT TCACCGTGA |
| 419 | MMLV E201A Top SDM | AGGGCTTTAAAAACAGCCCC ACAGAGTTCGATGAAGCACT TCACCGTGA |
| 420 | MMLV E201R Top SDM | TTTAAAAACAGCCCCACATT GTTCGATGCGGCACTTCACC GTGACTTAGCAG |
| 421 | MMLV E201D Top SDM | TTTAAAAACAGCCCCACATT GTTCGATCGTGCACTTCACC GTGACTTAGCAG |
| 422 | MMLV R205A Top SDM | TTTAAAAACAGCCCCACATT GTTCGATGATGCACTTCACC GTGACTTAGCAG |
| 423 | MMLV R205K Top SDM | CACATTGTTCGATGAAGCAC TTCACGCGGACTTAGCAGAC TTCCGTATCCA |
| 424 | MMLV R205E Top SDM | CACATTGTTCGATGAAGCAC TTCACAAAGACTTAGCAGAC TTCCGTATCCA |
| 425 | MMLV D209A Top SDM | GATGAAGCACTTCACCGTGA CTTAGAGGACTTCCGTATCC AACACCCAG |
| 426 | MMLV D209R Top SDM | AAGCACTTCACCGTGACTTA GCAGCGTTCCGTATCCAACA CCCAGACTT |
| 427 | MMLV D209E Top SDM | AAGCACTTCACCGTGACTTA GCACGTTCCGTATCCAACA CCCAGACTT |
| 428 | MMLV F210A Top SDM | AAGCACTTCACCGTGACTTA GCAGAGTTCCGTATCCAACA CCCAGACTT |
| 429 | MMLV F2I0R Top SDM | CACTTCACCGTGACTTAGCA GACGCGCGTATCCAACACCC AGACTTAATTC |

TABLE 1-continued

Sequences of primers used for cloning of MMLV RTase base constructs and mutants into pET28b.

| SEQ ID NO: | Primer Name | Primer Sequence (5'-3') |
|---|---|---|
| 430 | MMLV F210E Top SDM | CACTTCACCGTGACTTAGCA GACCGTCGTATCCAA CACCCAGACTTAATTC |
| 431 | MMLV R211A Top SDM | CACTTCACCGTGACTTAGCA GACGAGCGTATCCAACACCC AGACTTAATTC |
| 432 | MMLV R211K Top SDM | TTCACCGTGACTTAGCAGAC TTCGCGATCCAACACCCAGA CTTAATTCTGTTA |
| 433 | MMLV R21 IE Top SDM | TTCACCGTGACTTAGCAGAC TTCAAAATCCAACACCCAGA CTTAATTCTGTTA |
| 434 | MMLV 1212A Top SDM | TTCACCGTGACTTAGCAGAC TTCGAGATCCAACACCCAGA CTTAATTCTGTTA |
| 435 | MMLV I212R Top SDM | CCGTGACTTAGCAGACTTCC GTGCGCAACACCCAGACTTA ATTCTGTTACAG |
| 436 | MMLV I212E Top SDM | CCGTGACTTAGCAGACTTCC GTCGTCAACACCCAGACTTA ATTCTGTTACAG |
| 437 | MMLV Q213A Top SDM | CCGTGACTTAGCAGACTTCC GTGAGCAACACCCAGACTTA ATTCTGTTACAG |
| 438 | MMLV Q213R Top SDM | GTGACTTAGCAGACTTCCGT ATCGCGCACCCAGACTTAAT TCTGTTACAGTAT |
| 439 | MMLV Q213E Top SDM | GTGACTTAGCAGACTTCCGT ATCCGTCACCCAGACTTAAT TCTGTTACAGTAT |
| 440 | MMLV K348A Top SDM | GTGACTTAGCAGACTTCCGT ATCGAGCACCCAGACTTAAT TCTGTTACAGTAT |
| 441 | MMLV K348R Top SDM | AGCAAAAGGCGTATCAGGAG ATCGCGCAAGCTTTGTTGAC CGCACCC |
| 442 | MMLV K348E Top SDM | AGCAAAAGGCGTATCAGGAG ATCCGTCAAGCTTTGTTGAC CGCACCC |
| 443 | MMLV L352A Top SDM | AGCAAAAGGCGTATCAGGAG ATCGAGCAAGCTTTGTTGAC CGCACCC |
| 444 | MMLV L352R Top SDM | CGTATCAGGAGATCAAACAA GCTTTGGCGACCGCACCCGC GTTGGG |
| 445 | MMLV L352E Top SDM | CGTATCAGGAGATCAAACAA GCTTTGCGTACCGCACCCGC GTTGGG |
| 446 | MMLV K285A Top SDM | CGTATCAGGAGATCAAACAA GCTTTGGAGACCGCACCCGC GTTGGG |
| 447 | MMLV K285R Top SDM | GTTGGCTGACTGAAGCGCGT GCGGAGACCGTAATGGGGCA GC |

TABLE 1-continued

Sequences of primers used for cloning of MMLV RTase base constructs and mutants into pET28b.

| SEQ ID NO: | Primer Name | Primer Sequence (5'-3') |
|---|---|---|
| 448 | MMLV K285E Top SDM | GTTGGCTGACTGAAGCGCGT CGTGAGACCGTAATGGGGCA GC |
| 449 | MMLV Q299A Top SDM | GTTGGCTGACTGAAGCGCGT GAGGAGACCGTAATGGGGCA GC |
| 450 | MMLV Q299R Top SDM | TACGCCTAAGACGCCACGCG CGTTGCGTGAATTTT TGGGCACAGC |
| 451 | MMLV Q299E Top SDM | TACGCCTAAGACGCCACGCC GTTTGCGTGAATTTTTGGGC ACAGC |
| 452 | MMLV G308A Top SDM | TACGCCTAAGACGCCACGCG AGTTGCGTGAATTTTTGGGC ACAGC |
| 453 | MMLV G308R Top SDM | GCGTGAATTTTTGGGCACAG CGGCGTTCTGTCGTTTATGG ATTCCTGGG |
| 454 | MMLV G308E Top SDM | GCGTGAATTTTTGGGCACAG CGCGTTTCTGTCGTTTATGG ATTCCTGGG |
| 455 | MMLV R311A Top SDM | GCGTGAATTTTTGGGCACAG CGGAGTTCTGTCGTTTATGG ATTCCTGGG |
| 456 | MMLV R311K Top SDM | GGGCACAGCGGGATTCTGTG CGTTATGGATTCCTGGGTTC GCTGA |
| 457 | MMLV R311E Top SDM | GGGCACAGCGGGATTCTGTA AATTATGGATTCCTGGGTTC GCTGA |
| 458 | MMLV Y271A Top SDM | GGGCACAGCGGGATTCTGTG AGTTATGGATTCCTGGGTTC GCTGA |
| 459 | MMLV Y271R Top SDM | GTCAAAAACAGGTAAAGTAC CTTGGGGCGTTGCTGAAAGA AGGTCAACGTTGG |
| 460 | MMLV Y271E Top SDM | GTCAAAAACAGGTAAAGTAC CTTGGGCGTTTGCTGAAAGA AGGTCAACGTTGG |
| 461 | MMLV L280A Top SDM | GTCAAAAACAGGTAAAGTAC CTTGGGGAGTTGCTGAAAGA AGGTCAACGTTGG |
| 462 | MMLV L280R Top SDM | TGCTGAAAGAAGGTCAACGT TGGGCGACTGAAGCGCGTAA GGAGACC |
| 463 | MMLV L280E Top SDM | TGCTGAAAGAAGGTCAACGT TGGCGTACTGAAGCGCGTAA GGAGACC |
| 464 | MMLV L357A Top SDM | TGCTGAAAGAAGGTCAACGT TGGGGAGACTGAAGCGCGTAA GGAGACC |
| 465 | MMLV L357R Top SDM | TTTGTTGACCGCACCCGCGG CGGGTCTTCCGGATTTAACC AAGCC |

TABLE 1-continued

Sequences of primers used for cloning of
MMLV RTase base constructs and mutants
into pET28b.

| SEQ ID NO: | Primer Name | Primer Sequence (5'-3') |
|---|---|---|
| 466 | MMLV L357E Top SDM | TTTGTTGACCGCACCCGCGC GTGGTCTTCCGGATTTAACC AAGCC |
| 467 | MMLV T328A Top SDM | TTTGTTGACCGCACCCGCGG AGGGTCTTCCGGATTTAACC AAGCC |
| 468 | MMLV T328R Top SDM | CTGCACCCCTGTACCCCTTA GCGAAAACAGGGACGCTTTT CAACTGG |
| 469 | MMLV T328E Top SDM | CTGCACCCCTGTACCCCTTA CGTAAAACAGGGACGCTTTT CAACTGG |
| 470 | MMLV G331A Top SDM | CTGCACCCCTGTACCCCTTA GAGAAAACAGGGACG CTTTTCAACTGG |
| 471 | MMLV G331R Top SDM | CCCCTGTACCCCTTAACAAA AACAGCGACGCTTTTCAACT GGGGGCC |
| 472 | MMLV G331E Top SDM | CCCCTGTACCCCTTAACAAA AACACGTACGCTTTTCAACT GGGGGCC |
| 473 | MMLV T332A Top SDM | CCCCTGTACCCCTTAACT'L AAAACAGAGACGCTTTTCAA CTGGGGGCC |
| 474 | MMLV T332R Top SDM | CTGTACCCCTTAACAAAAAC AGGGGCGCTTTTCAACTGGG GGCCAGAC |
| 475 | MMLV T332E Top SDM | CTGTACCCCTTAACAAAAAC AGGGCGTCTTTTCAACTGGG GGCCAGAC |
| 476 | MMLV N335A Top SDM | CTGTACCCCTTAACAAAAAC AGGGGAGCTTTTCAACTGGG GGCCAGAC |
| All | MMLV N335R Top SDM | CCTTAACAAAAACAGGGACG CTTTTCGCGTGGGGGCCAGA CCAGCAAA |
| 478 | MMLV N335E Top SDM | CCTTAACAAAAACAGGGACG CTTTTCCGTTGGGGGCCAGA CCAGCAAA |
| 479 | MMLV E367A Top SDM | CTTCCGGATTTAACCAAGCC CTTTGCGCTGTTCGTTGATG AAAAACAGGGATAT |
| 480 | MMLV E367R Top SDM | CTTCCGGATTTAACCAAGCC CTTTCGTCTGTTCGTTGATG AAAAACAGGGATAT |
| 481 | MMLV E367D Top SDM | CTTCCGGATTTAACCAAGCC CTTTGATCTGTTCGTTGATG AAAAACAGGGATAT |
| 482 | MMLV F369A Top SDM | GATTTAACCAAGCCCTTTGA GCTGGCGGTTGATGAAAAAC AGGGATATGCAAAAG |
| 483 | MMLV F369R Top SDM | GATTTAACCAAGCCCTTTGA GCTGCGTGTTGATGAAAAAC AGGGATATGCAAAAG |

TABLE 1-continued

Sequences of primers used for cloning of
MMLV RTase base constructs and mutants
into pET28b.

| SEQ ID NO: | Primer Name | Primer Sequence (5'-3') |
|---|---|---|
| 484 | MMLV F369E Top SDM | GATTTAACCAAGCCCTTTGA GCTGGAGGTTGATGAAAAAC AGGGATATGCAAAAG |
| 485 | MMLV R389A Top SDM | CCCAAAAGTTAGGCCCGTGG GCGCGCCCTGTTGCTTACTT GAGTAA |
| 486 | MMLV R389K Top SDM | CCCAAAAGTTAGGCCCGTGG AAACGCCCTGTTGCTTACTT GAGTAA |
| 487 | MMLV R389E Top SDM | CCCAAAAGTTAGGCCCGTGG GAGCGCCCTGTTGCTTACTT GAGTAA |
| 488 | MMLV V433A Top SDM | AGTTGACGATGGGTCAACCC TTAGCGATCTTGGCTCCACA TGCTGTAGA |
| 489 | MMLV V433R Top SDM | AGTTGACGATGGGTCAACCC TTACGTATCTTGGCTCCACA TGCTGTAGA |
| 490 | MMLV V433E Top SDM | AGTTGACGATGGGTCAACCC TTAGAGATCTTGGCT CCACATGCTGTAGA |
| 491 | MMLV V476A Top SDM | GGATCGTGTACAATTTGGAC CAGTTGCGGCTTTGAATCCA GCTACTTTGCTTC |
| 492 | MMLV V476R Top SDM | GGATCGTGTACAATTTGGAC CAGTTCGTGCTTTGAATCCA GCTACTTTGCTTC |
| 493 | MMLV V476E Top SDM | GGATCGTGTACAATTTGGAC CAGTTGAGGCTTTGAATCCA GCTACTTTGCTTC |
| 494 | MMLV 1593A Top SDM | CGTTATGCTTTTGCAACAGC GCATGCGCATGGCGAAATTT ACCGCCGC |
| 495 | MMLV 1593R Top SDM | CGTTATGCTTTTGCAACAGC GCATCGTCATGGCGAAATTT ACCGCCGC |
| 496 | MMLV I593E Top SDM | CGTTATGCTTTTGCAACAGC GCATGAGCATGGCGAAATTT ACCGCCGC |
| 497 | MMLV E596A Top SDM | GCAACAGCGCATATCCATGG CGCGATTTACCGCCGCCGTG GTC |
| 498 | MMLV E596R Top SDM | GCAACAGCGCATATCCATGG CCGTATTTACCGCCGCCGTG GTC |
| 499 | MMLV E596D Top SDM | GCAACAGCGCATATCCATGG CGATATTTACCGCCGCCGTG GTC |
| 500 | MMLV 1597A Top SDM | CAACAGCGCATATCCATGGC GAAGCGTACCGCCGCCGTGG TCTG |
| 501 | MMLV 1597R Top SDM | CAACAGCGCATATCCATGGC GAACGTTACCGCCGCCGTGG TCTG |

TABLE 1-continued

Sequences of primers used for cloning of
MMLV RTase base constructs and mutants
into pET28b.

| SEQ ID NO: | Primer Name | Primer Sequence (5'-3') |
|---|---|---|
| 502 | MMLV I597E Top SDM | CAACAGCGCATATCCATGGC GAAGAGTACCGCCGCCGTGG TCTG |
| 503 | MMLV R650A Top SDM | AGCGGAGGCTCGTGGAAACG CGATGGCGGACCAAGCTGCC C |
| 504 | MMLV R650K Top SDM | AGCGGAGGCTCGTGGAAACA AAATGGCGGACCAAGCTGCC C |
| 505 | MMLV R650E Top SDM | AGCGGAGGCTCGTGGAAACG AGATGGCGGACCAAGCTGCC C |
| 506 | MMLV Q654A Top SDM | GTGGAAACCGTATGGCGGAC GCGGCTGCCCGTAAGGCGGC |
| 507 | MMLV Q654R Top SDM | GTGGAAACCGTATGGCGGAC CGTGCTGCCCGTAAGGCGGC |
| 508 | MMLV Q654E Top SDM | GTGGAAACCGTATGGCGGAC GAGGCTGCCCGTAAGGCGGC |
| 509 | MMLV R657A Top SDM | TATGGCGGACCAAGCTGCCG CGAAGGCGGCGATCACAGAG AC |
| 510 | MMLV R657K Top SDM | TATGGCGGACCAAGCTGCCA AAAAGGCGGCGATCA CAGAGAC |
| 511 | MMLV R657E Top SDM | TATGGCGGACCAAGCTGCCG AGAAGGCGGCGATCACAGAG AC |
| 512 | MMLV G73A Btm SDM | GCAAGCGCTGAATATGTGGC TTAATCGCCAGGCGGGCCTC TTGACTC |
| 513 | MMLV G73R Btm SDM | GCAAGCGCTGAATATGTGGC TTAATACGCAGGCGGGCCTC TTGACTC |
| 514 | MMLV G73E Btm SDM | GCAAGCGCTGAATATGTGGC TTAATCTCCAGGCGGGCCTC TTGACTC |
| 515 | MMLV P76A Btm SDM | GGTCCAGCAAGCGCTGAATA TGCGCCTTAATCCCCAGGCG GGCC |
| 516 | MMLV P76R Btm SDM | GGTCCAGCAAGCGCTGAATA TGACGCTTAATCCCCAGGCG GGCC |
| 517 | MMLV P76E Btm SDM | GGTCCAGCAAGCGCTGAATA TGCTCCTTAATCCCCAGGCG GGCC |
| 518 | MMLV H77A Btm SDM | CTGGTCCAGCAAGCGCTGAA TCGCTGGCTTAATCCCCAGG CGG |
| 519 | MMLV H77R Btm SDM | CTGGTCCAGCAAGCGCTGAA TACGTGGCTTAATCCCCAGG CGG |
| 520 | MMLV H77E Btm SDM | CTGGTCCAGCAAGCGCTGAA TCTCTGGCTTAATCCCCAGG CGG |

TABLE 1-continued

Sequences of primers used for cloning of
MMLV RTase base constructs and mutants
into pET28b.

| SEQ ID NO: | Primer Name | Primer Sequence (5'-3') |
|---|---|---|
| 521 | MMLV L82A Btm SDM | GGACCAAGATCCCCTGGTCC GCCAAGCGCTGAATATGTGG CTTAATC |
| 522 | MMLV L82R Btm SDM | GGACCAAGATCCCCTGGTCA CGCAAGCGCTGAATATGTGG CTTAATC |
| 523 | MMLV L82E Btm SDM | GGACCAAGATCCCCTGGTCC TCCAAGCGCTGAATATGTGG CTTAATC |
| 524 | MMLV D83A Btm SDM | CATGGGACCAAGATCCCCTG CGCCAGCAAGCGCTGAATAT GTGGC |
| 525 | MMLV D83R Btm SDM | CATGGGACCAAGATCCCCTG ACGCAGCAAGCGCTGAATAT GTGGC |
| 526 | MMLV D83E Btm SDM | CATGGGACCAAGATCCCCTG CTCCAGCAAGCGCTGAATAT GTGGC |
| 527 | MMLV I125A Btm SDM | ATTATAAGGATTAGGTACAG TCGGATGCGCGTCTTCTACG CGTTTGTTGACCT |
| 528 | MMLV I125R Btm SDM | ATTATAAGGATTAGGTACAG TCGGATGACGGTCTTCTACG CGTTTGTTGACCT |
| 529 | MMLV I125E Btm SDM | ATTATAAGGATTAGGTACAG TCGGATGCTCGTCTTCTACG CGTTTGTTGACCT |
| 530 | MMLV VI29A Btm SDM | GCCTGATAACAGATTATAAG GATTAGGCGCAGTCG GATGGATGTCTTCTACGC |
| 531 | MMLV V129R Btm SDM | GCCTGATAACAGATTATAAG GATTAGGACGAGTCGGATGG ATGTCTTCTACGC |
| 532 | MMLV V129E Btm SDM | GCCTGATAACAGATTATAAG GATTAGGCTCAGTCGGATGG ATGTCTTCTACGC |
| 533 | MMLV L198A Btm SDM | TCACGGTGAAGTGCTTCATC GAACGCTGTGGGGCTGTTTT TAAAGCCCT |
| 534 | MMLV L198R Btm SDM | TCACGGTGAAGTGCTTCATC GAAACGTGTGGGGCTGTTTT TAAAGCCCT |
| 535 | MMLV L198E Btm SDM | TCACGGTGAAGTGCTTCATC GAACTCTGTGGGGCTGTTTT TAAAGCCCT |
| 536 | MMLV E201A Btm SDM | CTGCTAAGTCACGGTGAAGT GCCGCATCGAACAATGTGGG GCTGTTTTTAAA |
| 537 | MMLV E201R Btm SDM | CTGCTAAGTCACGGTGAAGT GCACGCATCGAACAATGTGGG GCTGTTTTTAAA |
| 538 | MMLV E201D Btm SDM | CTGCTAAGTCACGGTGAAGT GCATCATCGAACAATGTGGG GCTGTTTTTAAA |

TABLE 1-continued

TABLE 1-continued

Sequences of primers used for cloning of
MMLV RTase base constructs and mutants
into pET28b.

Sequences of primers used for cloning of
MMLV RTase base constructs and mutants
into pET28b.

| SEQ ID NO: | Primer Name | Primer Sequence (5'-3') |
|---|---|---|
| 539 | MMLV R205A Btm SDM | TGGATACGGAAGTCTGCTAA GTCCGCGTGAAGTGCTTCAT CGAACAATGTG |
| 540 | MMLV R205K Btm SDM | TGGATACGGAAGTCTGCTAA GTCTTTGTGAAGTGCTTCAT CGAACAATGTG |
| 541 | MMLV R205E Btm SDM | TGGATACGGAAGTCTGCTAA GTCCTCGTGAAGTGCTTCAT CGAACAATGTG |
| 542 | MMLV D209A Btm SDM | AAGTCTGGGTGTTGGATACG GAACGCTGCTAAGTCACGGT GAAGTGCTT |
| 543 | MMLV D209R Btm SDM | AAGTCTGGGTGTTGGATACG GAAACGTGCTAAGTCACGGT GAAGTGCTT |
| 544 | MMLV D209E Btm SDM | AAGTCTGGGTGTTGGATACG GAACTCTGCTAAGTCACGGT GAAGTGCTT |
| 545 | MMLV F210A Btm SDM | GAATTAAGTCTGGGTGTTGG ATACGCGCGTCTGCTAAGTC ACGGTGAAGTG |
| 546 | MMLV F210R Btm SDM | GAATTAAGTCTGGGTGTTGG ATACGACGGTCTGCTAAGTC ACGGTGAAGTG |
| 547 | MMLV F210E Btm SDM | GAATTAAGTCTGGGTGTTGG ATACGCTCGTCTGCTAAGTC ACGGTGAAGTG |
| 548 | MMLV R211A Btm SDM | TAACAGAATTAAGTCTGGGT GTTGGATCGCGAAGTCTGCT AAGTCACGGTGAA |
| 549 | MMLV R211K Btm SDM | TAACAGAATTAAGTCTGGGT GTTGGATTTTGAAGTCTGCT AAGTCACGGTGAA |
| 550 | MMLV R211E Btm SDM | TAACAGAATTAAGTCTGGGT GTTGGATCTCGAAGT CTGCTAAGTCACGGTGAA |
| 551 | MMLV I212A Btm SDM | CTGTAACAGAATTAAGTCTG GGTGTTGCGCACGGAAGTCT GCTAAGTCACGG |
| 552 | MMLV 1212R Btm SDM | CTGTAACAGAATTAAGTCTG GGTGTTGACGACACGGAAGTCT GCTAAGTCACGG |
| 553 | MMLV 1212E Btm SDM | CTGTAACAGAATTAAGTCTG GGTGTTGCTCACGGAAGTCT GCTAAGTCACGG |
| 554 | MMLV Q213A Btm SDM | ATACTGTAACAGAATTAAGT CTGGGTGCGCGATACGGAAG TCTGCTAAGTCAC |
| 555 | MMLV Q213R Btm SDM | ATACTGTAACAGAATTAAGT CTGGGTGACGGATACGGAAG TCTGCTAAGTCAC |
| 556 | MMLV Q213E Btm SDM | ATACTGTAACAGAATTAAGT CTGGGTGCTCGATACGGAAG TCTGCTAAGTCAC |

| SEQ ID NO: | Primer Name | Primer Sequence (5'-3') |
|---|---|---|
| 557 | MMLV K348A Btm SDM | GGGTGCGGTCAACAAAGCTT GCGCGATCTCCTGATACGCC TTTTGCT |
| 558 | MMLV K348R Btm SDM | GGGTGCGGTCAACAAAGCTT GACGGATCTCCTGATACGCC TTTTGCT |
| 559 | MMLV K348E Btm SDM | GGGTGCGGTCAACAAAGCTT GCTCGATCTCCTGATACGCC TTTTGCT |
| 560 | MMLV L352A Btm SDM | CCCAACGCGGGTGCGGTCGC CAAAGCTTGTTTGATCTCCT GATACG |
| 561 | MMLV L352R Btm SDM | CCCAACGCGGGTGCGGTACG CAAAGCTTGTTTGATCTCCT GATACG |
| 562 | MMLV L352E Btm SDM | CCCAACGCGGGTGCGGTCTC CAAAGCTTGTTTGATCTCCT GATACG |
| 563 | MMLV K285A Btm SDM | GCTGCCCCATTACGGTCTCC GCACGCGCTTCAGTCAGCCA AC |
| 564 | MMLV K285R Btm SDM | GCTGCCCCATTACGGTCTCA CGACGCGCTTCAGTCAGCCA AC |
| 565 | MMLV K285E Btm SDM | GCTGCCCCATTACGGTCTCC TCACGCGCTTCAGTCAGCCA AC |
| 566 | MMLV Q299A Btm SDM | GCTGTGCCCAAAAATTCACG CAACGCGCGTGGCGTCTTAG GCGTA |
| 567 | MMLV Q299R Btm SDM | GCTGTGCCCAAAAATTCACG CAAACGGCGTGGCGTCTTAG GCGTA |
| 568 | MMLV Q299E Btm SDM | GCTGTGCCCAAAAATTCACG CAACTCGCGTGGCGTCTTAG GCGTA |
| 569 | MMLV G308A Btm SDM | CCCAGGAATCCATAAACGAC AGAACGCCGCTGTGCCCAAA AATTCACGC |
| 570 | MMLV G308R Btm SDM | CCCAGGAATCCATAAACGAC AGAAACGCGCTGTGC CCAAAAATTCACGC |
| 571 | MMLV G308E Btm SDM | CCCAGGAATCCATAAACGAC AGAACTCCGCTGTGCCCAAA AATTCACGC |
| 572 | MMLV R311A Btm SDM | TCAGCGAACCCAGGAATCCA TAACGCACAGAATCCCGCTG TGCCC |
| 573 | MMLV R311K Btm SDM | TCAGCGAACCCAGGAATCCA TAATTTACAGAATCCCGCTG TGCCC |
| 574 | MMLV R311E Btm SDM | TCAGCGAACCCAGGAATCCA TAACTCACAGAATCCCGCTG TGCCC |

TABLE 1-continued

Sequences of primers used for cloning of
MMLV RTase base constructs and mutants
into pET28b.

| SEQ ID NO: | Primer Name | Primer Sequence (5'-3') |
|---|---|---|
| 575 | MMLV Y271A Btm SDM | CCAACGTTGACCTTCTTTCA GCAACGCCCCAAGGTACTTT ACCTGTTTTTGAC |
| 576 | MMLV Y271R Btm SDM | CCAACGTTGACCTTCTTTCA GCAAACGCCCAAGGTACTTT ACCTGTTTTTGAC |
| 577 | MMLV Y271E Btm SDM | CCAACGTTGACCTTCTTTCA GCAACTCCCCAAGGTACTTT ACCTGTTTTTGAC |
| 578 | MMLV L280A Btm SDM | GGTCTCCTTACGCGCTTCAG TCGCCCAACGTTGACCTTCT TTCAGCA |
| 579 | MMLV L280R Btm SDM | GGTCTCCTTACGCGCTTCAG TACGCCAACGTTGACCTTCT TTCAGCA |
| 580 | MMLV L280E Btm SDM | GGTCTCCTTACGCGCTTCAG TCTCCCAACGTTGACCTTCT TTCAGCA |
| 581 | MMLV L357A Btm SDM | GGCTTGGTTAAATCCGGAAG ACCCGCCGCGGGTGCGGTCA ACAAA |
| 582 | MMLV L357R Btm SDM | GGCTTGGTTAAATCCGGAAG ACCACGCGCGGGTGCGGTCA ACAAA |
| 583 | MMLV L357E Btm SDM | GGCTTGGTTAAATCCGGAAG ACCCTCCGCGGGTGCGGTCA ACAAA |
| 584 | MMLV T328A Btm SDM | CCAGTTGAAAAGCGTCCCTG TTTTCGCTAAGGGGTACAGG GGTGCAG |
| 585 | MMLV T328R Btm SDM | CCAGTTGAAAAGCGTCCCTG TTTTACGTAAGGGGTACAGG GGTGCAG |
| 586 | MMLV T328E Btm SDM | CCAGTTGAAAAGCGTCCCTG TTTTCTCTAAGGGGTACAGG GGTGCAG |
| 587 | MMLV G331A Btm SDM | GGCCCCCAGTTGAAAAGCGT CGCTGTTTTTGTTAAGGGGT ACAGGGG |
| 588 | MMLV G331R Btm SDM | GGCCCCCAGTTGAAAAGCGT ACGTGTTTTTGTTAAGGGGT ACAGGGG |
| 589 | MMLV G331E Btm SDM | GGCCCCCAGTTGAAAAGCGT CTCTGTTTTTGTTAAGGGGT ACAGGGG |
| 590 | MMLV T332A Btm SDM | GTCTGGCCCCCAGTTGAAAA GCGCCCTGTTTTTG TTAAGGGGTACAG |
| 591 | MMLV T332R Btm SDM | GTCTGGCCCCCAGTTGAAAA GACGCCCTGTTTTTGTTAAG GGGTACAG |
| 592 | MMLV T332E Btm SDM | GTCTGGCCCCCAGTTGAAAA GCTCCCTGTTTTTGTTAAG GGGTACAG |
| 593 | MMLV N335A Btm SDM | TTTGCTGGTCTGGCCCCCAC GCGAAAAGCGTCCCTGTTTT TGTTAAGG |
| 594 | MMLV N335R Btm SDM | TTTGCTGGTCTGGCCCCCAA CGGAAAAGCGTCCCTGTTTT TGTTAAGG |
| 595 | MMLV N335E Btm SDM | TTTGCTGGTCTGGCCCCCAC TCGAAAAGCGTCCCTGTTTT TGTTAAGG |
| 596 | MMLV E367A Btm SDM | ATATCCCTGTTTTTCATCAA CGAACAGCGCAAAGGGCTTG GTTAAATCCGGAAG |
| 597 | MMLV E367R Btm SDM | ATATCCCTGTTTTTCATCAA CGAACAGACGAAAGGGCTTG GTTAAATCCGGAAG |
| 598 | MMLV E367D Btm SDM | ATATCCCTGTTTTTCATCAA CGAACAGATCAAAGGGCTTG GTTAAATCCGGAAG |
| 599 | MMLV F369A Btm SDM | CTTTTGCATATCCCTGTTTT TCATCAACCGCCAGCTCAAA GGGCTTGGTTAAATC |
| 600 | MMLV F369R Btm SDM | CTTTTGCATATCCCTGTTTT TCATCAACACGCAGCTCAAA GGGCTTGGTTAAATC |
| 601 | MMLV F369E Btm SDM | CTTTTGCATATCCCTGTTTT TCATCAACCTCCAGCTCAAA GGGCTTGGTTAAATC |
| 602 | MMLV R389A Btm SDM | TTACTCAAGTAAGCAACAGG GCGCGCCCACGGGCCTAACT TTTGGG |
| 603 | MMLV R389K Btm SDM | TTACTCAAGTAAGCAACAGG GCGTTTCCACGGGCCTAACT TTTGGG |
| 604 | MMLV R389E Btm SDM | TTACTCAAGTAAGCAACAGG GCGCTCCCACGGGCCTAACT TTTGGG |
| 605 | MMLV V433A Btm SDM | TCTACAGCATGTGGAGCCAA GATCGCTAAGGGTTGACCCA TCGTCAACT |
| 606 | MMLV V433R Btm SDM | TCTACAGCATGTGGAGCCAA GATACGTAAGGGTTGACCCA TCGTCAACT |
| 607 | MMLV V433E Btm SDM | TCTACAGCATGTGGAGCCAA GATCTCTAAGGGTTGACCCA TCGTCAACT |
| 608 | MMLV V476A Btm SDM | GAAGCAAAGTAGCTGGATTC AAAGCCGCAACTGGTCCAAA TTGTACACGATCC |
| 609 | MMLV V476R Btm SDM | GAAGCAAAGTAGCTGGATTC AAAGCACGAACTGGTCCAAA TTGTACACGATCC |
| 610 | MMLV V476E Btm SDM | GAAGCAAAGTAGCTGGATTC AAAGCCTCAACTGGT CCAAATTGTACACGATCC |

TABLE 1-continued

Sequences of primers used for cloning of
MMLV RTase base constructs and mutants
into pET28b.

| SEQ ID NO: | Primer Name | Primer Sequence (5'-3') |
|---|---|---|
| 611 | MMLV I593A Btm SDM | GCGGCGGTAAATTTCGCCAT GCGCATGCGCTGTTGCAAAA GCATAACG |
| 612 | MMLV I593R Btm SDM | GCGGCGGTAAATTTCGCCAT GACGATGCGCTGTTGCAAAA GCATAACG |
| 613 | MMLV I593E Btm SDM | GCGGCGGTAAATTTCGCCAT GCTCATGCGCTGTTGCAAAA GCATAACG |
| 614 | MMLV E596A Btm SDM | GACCACGGCGGCGGTAAATC GCGCCATGGATATGCGCTGT TGC |
| 615 | MMLV E596R Btm SDM | GACCACGGCGGCGGTAAATA CGGCCATGGATATGCGCTGT TGC |
| 616 | MMLV E596D Btm SDM | GACCACGGCGGCGGTAAATA TCGCCATGGATATGCGCTGT TGC |
| 617 | MMLV I597A Btm SDM | CAGACCACGGCGGCGGTACG CTTCGCCATGGATATGCGCT GTTG |
| 618 | MMLV I597R Btm SDM | CAGACCACGGCGGCGGTAAC GTTCGCCATGGATATGCGCT GTTG |
| 619 | MMLV I597E Btm SDM | CAGACCACGGCGGCGGTACT CTTCGCCATGGATATGCGCT GTTG |
| 620 | MMLV R650A Btm SDM | GGGCAGCTTGGTCCGCCATC GCGTTTCCACGAGCCTCCGC T |
| 621 | MMLV R650K Btm SDM | GGGCAGCTTGGTCCGCCATT TTGTTTCCACGAGCCTCCGC T |
| 622 | MMLV R650E Btm SDM | GGGCAGCTTGGTCCGCCATC TCGTTTCCACGAGCCTCCGC T |
| 623 | MMLV Q654A Btm SDM | GCCGCCTTACGGGCAGCCGC GTCCGCCATACGGTTTCCAC |
| 624 | MMLV Q654R Btm SDM | GCCGCCTTACGGGCAGCACG GTCCGCCATACGGTTTCCAC |
| 625 | MMLV Q654E Btm SDM | GCCGCCTTACGGGCAGCCTC GTCCGCCATACGGTTTCCAC |
| 626 | MMLV R657A Btm SDM | GTCTCTGTGATCGCCGCCTT CGCGGCAGCTTGGTCCGCCA TA |
| 627 | MMLV R657K Btm SDM | GTCTCTGTGATCGCCGCCTT TTTGGCAGCTTGGTCCGCCA TA |
| 628 | MMLV R657E Btm SDM | GTCTCTGTGATCGCCGCCTT CTCGGCAGCTTGGTCCGCCA TA |

TABLE 1-continued

Sequences of primers used for cloning of
MMLV RTase base constructs and mutants
into pET28b.

| SEQ ID NO: | Primer Name | Primer Sequence (5'-3') |
|---|---|---|
| 629 | MMLV L280R Top SDM V2 | ATTTGCTGAAAGAAGGTCAA CGTTGGCGTACTGATGCGCG TAAGGAGACC |
| 630 | MMLV L280R Btm SDM V2 | GGTCTCCTTACGCGCATCAG TACGCCAACGTTGACCTTCT TTCAGCAAAT |
| 631 | MMLV L82R Top SDM V2 | GGGATTAAGCCACATATTCG TCGCTTGCGTGACCAGGGGA TCTTGGTCCC |
| 632 | MMLV L82R Btm SDM V2 | GGGACCAAGATCCCCTGGTC ACGCAAGCGACGAATATGTG GCTTAATCCC |

Figure 2:
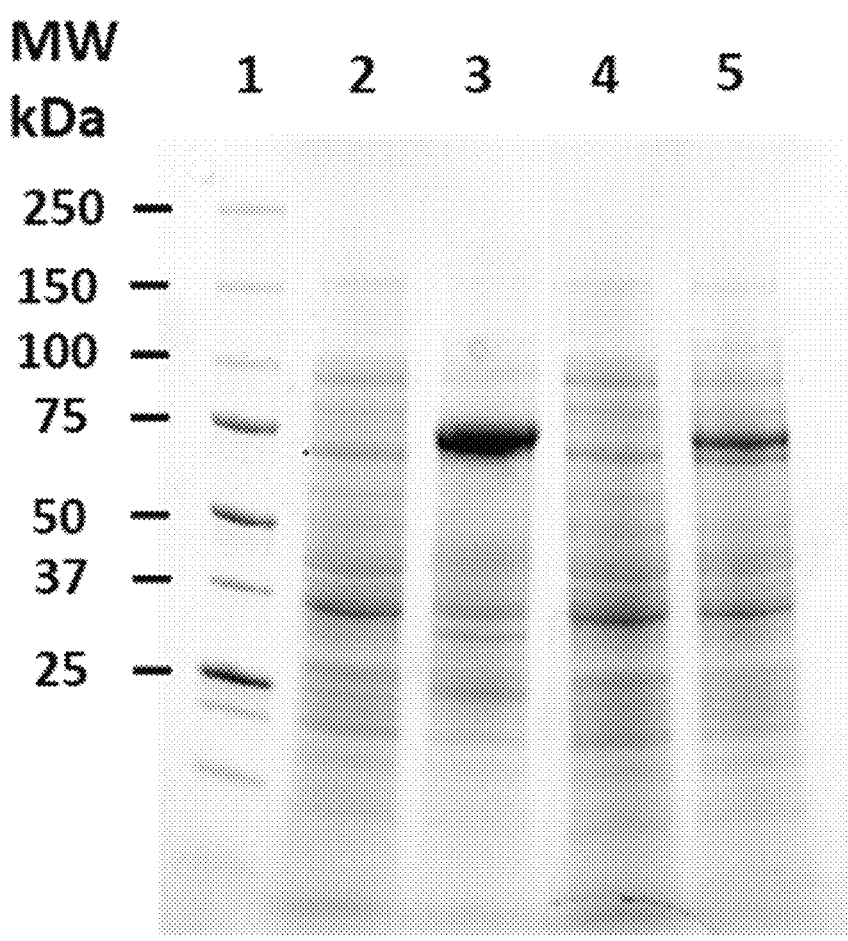
FIG. 2 shows Western blot analysis of test induction results in in BL21(DE3) cells for MMLV RT in TB medium. Lane 1—Precision Plus Protein Unstained Standards (Bio Rad, Cat #161-0363), Lane 2—Time=0 hour, Lane 3—Time=3 hours after induction at 37° C., Lane 4—Time=0 hour, Lane 5—Time=21 hours after induction at 18° C.

Example 2: Preparation of Reverse Transcriptase Mutants for Screening Increased Activity and Thermostability a. Overexpression of MMLV RTase and Mutant Variants A test induction was used to determine optimum growing conditions. A colony, with the appropriate strain, was used to inoculate Terrific Broth (TB) media (50 mL) with kanamycin (0.05 mg/mL) and grown at 37° C. until an OD of approximately 0.9 was reached. The 50 mL culture was divided in half to accommodate two induction temperatures. IPTG (1M; 12.5 μL) was used to induce protein expression, followed by growth at two induction temperatures for 21 hours. Aliquots (normalized to an OD of 1.25) were taken at 3 and 21 hours, cells were harvested at 13,000×g for one minute, and harvested cells were stored at −20° C. Cells were resuspended in 1×SDS-PAGE running buffer (270 μL) and 5×SDS-PAGE loading dye (70 μL). Samples were boiled for 5 minutes, sonicated, and loaded (15 μL) onto a 4-20% Mini-PROTEAN® TGX Stain-Free™ Protein Gel (Bio Rad, Cat #4568094). SDS-PAGE images are shown in FIG. 2.

b. Expression and Purification of MMLV RTase and Mutant Variants

A colony with the appropriate strain was used to inoculate TB media (1 mL, in a 96-well deep well plate) with kanamycin (0.05 mg/mL) and grown at 37° C. until an OD of approximately 0.9 was achieved followed by cooling of the plate on ice for 5 minutes. Protein expression was induced by the addition of 100 mM IPTG (5 μL), followed by growth at 18° C. for 21 hours. Cells were harvested by spinning samples at 4,700×g for 10 minutes.

Cell pellets were re-suspended in a lysis buffer (50 mM $NaPO_4$, pH 7.8, 5% glycerol, 300 mM NaCl, and 10 mM imidazole) and lysed by the addition of 1× BugBuster® (Millipore Sigma, Cat #70921) and incubation on an end-over-end mixer for 15 minutes at room temperature. Cell debris was removed by centrifuging the lysate at 16,000×g for 20 minutes at 4° C.

Cleared lysates were applied to a HisPur™ Ni-NTA spin plate (ThermoFisher, Cat #88230). Resin was equilibrated with Screening His-Bind buffer (50 mM $NaPO_4$, pH 7.8, 5% glycerol, 300 mM NaCl, and 10 mM imidazole) and samples loaded. Samples were washed three times with Screening His-Wash buffer (50 mM $NaPO_4$, pH 7.8, 5% glycerol, 300 mM NaCl, and 25 mM imidazole) and eluted using Screening His-Elution buffer (50 mM NaPO$_4$, pH 7.8, 5% glycerol, 300 mM NaCl, and 250 mM imidazole). Purified proteins were normalized to a set concentration (100 nM) for testing purposes.

Example 3: Evaluation of Reverse Transcriptase Mutants a. Evaluation of Ability of RTase Mutants to Synthesize DNA The ability of mutant RTase to synthesize cDNA from purified total RNA (DNased, isolated from HeLa cells) was compared to an MMLV RTase base construct (RNase H minus construct). Mutant MMLV RTases were tested in two formats: (1) standard two-step cDNA synthesis with gene specific primers, followed by qPCR, and (2) one-step addition of the RTase in Integrated DNA Technologies Prime-Time® Gene Expression Master Mix (GEM).

b. Standard Two-Step Procedure

RTases (2 µL, 100 nM) were added to a reaction mixture containing RNA (50 ng), dNTPs (100 µM), gene specific primer set (500 nM; see Table 2), first strand synthesis buffer (1×, 50 mM Tris-HCl, pH 8.3, 75 mM KCl, 3 mM MgCl$_2$, 10 mM DTT), and SuperaseIN (0.17 U/µL) in a 50 µL volume. The reaction was allowed to proceed at 50° C. for 15 minutes, followed by incubation at 80° C. for 10 minutes.

cDNA synthesized by RTase mutants was quantified by qPCR amplification using an assay that identified the SFRS9 gene in human cells. The assay master mix composition included GEM (1×), ROX (50 nM), SFRS9 primer set (500 nM; see Table 2), and SFRS9 probe (250 nM; see Table 2). Assay master mix and synthesized cDNA were mixed at a 4:1 ratio for a final volume of 20 µL. The reaction was run on qPCR (QuantStudio) for 40 cycles under the following cycle conditions: 95° C. hold for 3 minutes, 95° C. for 15 seconds, and 60° C. for one minute.

TABLE 2

| SEQ ID NO: | Primer Name | Primer Sequence (5'-3') |
|---|---|---|
| | Sequences of primers and probes used for qPCR assays. | |
| 633 | Hs SFRS9 Forward Primer | GTCGAGTATCTCAGAAAAGAAGACA |
| 634 | Hs SFRS9 Reverse Primer | CTCGGATGTAGGAAGTTTCACC |
| 635 | Hs SFRS9 Probe-SUN | /5SUN/ATGCCCTGC/ZEN/GTAAACTGGATGACA/3IABkFQ/ | c. One-Step Procedure in GEM

RTases (1 µL, 100 nM) were added to a reaction mixture containing RNA (10 ng), GEM (1×), ROX (50 nM), SFRS9 primer set (500 nM; see Table 2), and SFRS9 probe (250 nM; see Table 2) in a final volume of 20 µL. The reaction was run on a qPCR machine (QuantStudio) for 40 cycles using the following cycle conditions: 60° C. hold for 15 minutes, 95° C. hold for 3 minutes, 95° C. for 15 seconds, and 60° C. for one minute.

d. MMLV RTase Base Construct and Single Mutant Variants

As described in Example 1, MMLV RTase single mutant variants were prepared by introducing selected mutations into the MMLV RTase base construct by site-directed mutagenesis, using standard PCR conditions and primers. The sequences of the MMLV RTase base construct and single mutant variants are shown in Table 3. One of skill in the art will understand that the MMLV RTase amino acid sequences set forth in SEQ ID NO: 637 and SEQ ID NO: 717 (the latter of which is described in Example 6 below) are truncated forms of the full-length amino acid sequence of wild-type, or naturally occurring, MMLV RTase. In addition, a person having ordinary skill in the art will understand that a methionine residue is required to recombinantly produce the MMLV RTase base construct and mutants of the disclosure, and as such, that the MMLV RTase sequences disclosed herein (see, e.g., Table 3 below, Table 8 in Example 4, Tables 9 and 12 in Example 5, Table 22 in Example 6, and Table 38 in Example 9) include a methionine residue at the N-terminal end of the amino acid sequence. However, with respect to the present disclosure and for the purpose of identifying and numbering residues in the MMLV RTase amino acid sequence where mutations have been introduced, this methionine residue is considered to be amino acid residue 0 (i.e., is not counted) and the second amino acid residue (e.g., threonine in the MMLV RTase base construct set forth in SEQ ID NO: 637 and SEQ ID NO: 717) is considered to be amino acid residue 1.

TABLE 3

Sequences of MMLV RTase base construct and single mutant MMLV RTase constructs.

| SEQ ID NO: | Construct | Construct Sequence (DNA: 5'-3' or AA) |
|---|---|---|
| 636 | MMLV RTase | ATGACTTTAAATATTGAGGA TGAGCATCGTTTACATGAGA CATCAAAAGAACCCGACGTG AGCTTAGGGTCAACGTGGCT TTCTGACTTCCCCCAGGCGT GGGCGGAGACTGGCGGAATG GGGTTAGCTGTCCGCCAAGC ACCGTTGATCATCCCGTTAA AGGCAACGTCTACACCTGTC TCTATCAAACAGTACCCCAT GAGTCAAGAGGCCCGCCTGG GGATTAAGCCACATATTCAG CGCTTGCTGGACCAGGGGAT CTTGGTCCCATGTCAATCTC CGTGGAACACCCCCCTTCTG CCCGTGAAAAAGCCAGGTAC AAACGATTATCGTCCAGTTC AAGATCTTCGCGAGGTCAAC AAACGCGTAGAAGACATCCA TCCGACTGTACCTAATCCTT ATAATCTGTTATCAGGCCTG CCCCCATCGCACCAATGGTA TACAGTATTAGACTTGAAAG ACGCGTTCTTTTGCCTGCGT CTGCACCCAACGTCTCAGCC GCTGTTTGCGTTCGAATGGC GTGATCCTGAAATGGGAATT TCGGGTCAGTTAACCTGGAC TCGTCTGCCCCAGGGCTTTA AAAACAGCCCCACATTGTTC GATGAAGCACTTCACCGTGA CTTAGCAGACTTCCGTATCC AACACCCAGACTTAATTCTG TTACAGTATGTTGACGACCT TTTGTTGGCGGCAACGTCTG AACTTGACTGTCAGCAAGGC ACACGCGCGTTATTACAAAC GTTAGGTAACTTAGGATATC GTGCGTCCGCGAAAAAGGCG CAAATTTGTCAAAAACAGGT AAAGTACCTTGGGTATTTGC |

TABLE 3-continued

Sequences of MMLV RTase base construct
and single mutant MMLV RTase
constructs.

| SEQ ID NO: | Construct | Construct Sequence (DNA: 5'-3' or AA) |
|---|---|---|
| | | TGAAAGAAGGTCAACGTTGG CTGACTGAAGCGCGTAAGGA GACCGTAATGGGGCAGCCTA CGCCTAAGACGCCACGCCAG TTGCGTGAATTTTTGGGCAC AGCGGGATTCTGTCGTTTAT GGATTCCTGGGTTCGCTGAA ATGGCTGCACCCCTGTACCC CTTAACAAAACAGGGACGC TTTTCAACTGGGGGCCAGAC CAGCAAAAGGCGTATCAGGA GATCAAACAAGCTTTGTTGA CCGCACCCGCGTTGGGTCTT CCGGATTTAACCAAGCCCTT TGAGCTGTTCGTTGATGAAA AACAGGGATATGCAAAAGGA GTATTAACCCAAAAGTTAGG CCCGTGGCGTCGCCCTGTTG CTTACTTGAGTAAAAAATTG GATCCTGTCGCAGCAGGATG GCCACCGTGCTTGCGTATGG TCGCGGCAATTGCCGTTTTG ACAAAGGATGCAGGTAAGTT GACGATGGGTCAACCCTTAG TAATCTTGGCTCCACATGCT GTAGAAGCGTTAGTAAAGCA GCCCCCAGACCGCTGGCTTT CTAATGCGCGCATGACCCAC TATCAGGCGCTTCTGCTTGA TACGGATCGTGTACAATTTG GACCAGTTGTAGCTTTGAAT CCAGCTACTTTGCTTCCCCT TCCAGAAGAAGGACTTCAGC ACAATTGTTTAGATATTCTG GCCGAGGCACATGGGACGCG CCCTGATTTGACGGATCAGC CACTGCCTGATGCCGACCAT ACATGGTATACTGGCGGCAG TAGTCTTCTTCAAGAGGGGC AACGCAAGGCGGGAGCAGCC GTCACTACGGAGACCGAAGT TATCTGGGCCAAAGCGTTAC CCGCGGGAACATCCGCGCAA CGTGCACAGTTAATCGCTCT GACACAGGCCCTGAAGATGG CAGAGGGCAAAAAGTTGAAT GTCTACACCAACTCACGTTA TGCTTTTGCAACAGCGCATA TCCATGGCGAAATTTACCGC CGCCGTGGTCTGCTGACTAG TGAGGGTAAGGAAATTAAAA ATAAAGATGAGATTCTTGCG TTGTTAAAAGCTTTATTCTT ACCAAAACGCCTTTCGATCA TTCATTGCCCGGGGCATCAA AAGGGTCACTCAGCGGAGGC TCGTGGAAACCGTATGGCGG ACCAAGCTGCCCGTAAGGCG GCGCTACACAGAGACCCCGGA TACATCAACGCTGTTGATCG AAAACAGCTCTCCCTACACT AGCGAGCATTTTTAA |
| 637 | MMLV RTase | MTLNIEDEHRLHETSKEPDV SLGSTWLSDFPQAWAETGGM GLAVRQAPLIIPLKATSTPV SIKQYPMSQEARLGIKPHIQ RLLDQGILVPCQSPWNTPLL PVKKPGTNDYRPVQDLREVN KRVEDIHPTVPNPYNLLSGL PPSHQWYTVLDLKDAFFCLR LHPTSQPLFAFEWRDPEMGI |

TABLE 3-continued

Sequences of MMLV RTase base construct
and single mutant MMLV RTase
constructs.

| SEQ ID NO: | Construct | Construct Sequence (DNA: 5'-3' or AA) |
|---|---|---|
| | | SGQLTWTRLPQGFKNSPTLF DEALHRDLADFRIQHPDLIL LQYVDDLLLAATSELDCQQG TRALLQTLGNLGYRASAKKA QICQKQVKYLGYLLKEGQRW LTEARKETVMGQPTPKTPRQ LREFLGTAGFCRLWIPGFAE MAAPLYPLTKTGTLFNWGPD QQKAYQEIKQALLTAPALGL PDLTKPFELFVDEKQGYAKG VLTQKLGPWRRPVAYLSKKL DPVAAGWPPCLRMVAAIAVL TKDAGKLTMGQPLVILAPHA VEALVKQPPDRWLSNARMTH YQALLLDTDRVQFGPWALNP ATLLPLPEEGLQHNCLDILA EAHGTRPDLTDQPLPDADHT WYTGGSSLLQEGQRKAGAAV TTETEVIWAKALPAGTSAQR AQLIALTQALKMAEGKKLNV YTNSRYAFATAHIHGEIYRR RGLLTSEGKEIKNKDEILAL LKALFLPKRLSIIHCPGHQK GHSAEARGNRMADQAARKAA ITETPDTSTLLIENSSPYTS EHF |
| 638 | MMLV RTase with 161R mutation | MTLNIEDEHRLHETSKEPDV SLGSTWLSDFPQAWAETGGM GLAVRQAPLIIPLKATSTPV SRKQYPMSQEARLGIKPHIQ RLLDQGILVPCQSPWNTPLL PVKKPGTNDYRPVQDLREVN KRVEDIHPTVPNPYNLLSGL PPSHQWYTVLDLKDAFFCLR LHPTSQPLFAFEWRDPEMGI SGQLTWTRLPQGFKNSPT LFDEALHRDLADFRIQHPDL ILLQYVDDLLLAATSELDCQ QGTRALLQTLGNLGYRASAK KAQICQKQVKYLGYLLKEGQ RWLTEARKETVMGQPTPKTP RQLREFLGTAGFCRLWIPGF AEMAAPLYPLTKTGTLFNWG PDQQKAYQEIKQALLTAPAL GLPDLTKPFELFVDEKQGYA KGVLTQKLGPWRRPVAYLSK KLDPVAAGWPPCLRMVAAIA VLTKDAGKLTMGQPLVILAP HAVEALVKQPPDRWLSNARM THYQALLLDTDRVQFGPWAL NPATLLPLPEEGLQHNCLDI LAEAHGTRPDLTDQPLPDAD HTWYTGGSSLLQEGQRKAGA AVTTETEVIWAKALPAGTSA QRAQLIALTQALKMAEGKKL NVYTNSRYAFATAHIHGEIY RRRGLLTSEGKEIKNKDEIL ALLKALFLPKRLSIIHCPGH QKGHSAEARGNRMADQAARK AAITETPDTSTLLIENSSPY TSEHF |
| 639 | MMLV RTase with Q68R mutation | MTLNIEDEHRLHETSKEPDV SLGSTWLSDFPQAWAETGGM GLAVRQAPLIIPLKATSTPV SIKQYPMSREARLGIKPHIQ RLLDQGILVPCQSPWNTPLL PVKKPGTNDYRPVQDLREVN KRVEDIHPTVPNPYNLLSGL PPSHQWYTVLDLKDAFFCLR LHPTSQPLFAFEWRDPEMGI |

TABLE 3-continued

Sequences of MMLV RTase base construct
and single mutant MMLV RTase
constructs.

| SEQ ID NO: | Construct | Construct Sequence (DNA: 5'-3' or AA) |
|---|---|---|
| | | SGQLTWTRLPQGFKNSPTLF DEALHRDLADFRIQHPDLIL LQYVDDLLLAATSELDCQQG TRALLQTLGNLGYRASAKKA QICQKQVKYLGYLLKEGQRW LTEARKETVMGQPTPKTPRQ LREFLGTAGFCRLWIPGFAE MAAPLYPLTKTGTLFNWGPD QQKAYQEIKQALLTAPALGL PDLTKPFELFVDEKQGYAKG VLTQKLGPWRRPVAYLSKKL DPVAAGWPPCLRMVAAIAVL TKDAGKLTMGQPLVILAPHA VEALVKQPPDRWLSNARMTH YQALLLDTDRVQFGPWALNP ATLLPLPEEGLQHNCLDILA EAHGTRPDLTDQPLPDADHT WYTGGSSLLQEGQRKAGAAV TTETEVIWAKALPAGTSAQR AQLIALTQALKMAEGKKLNV YTNSRYAFATAHIHGEIYRR RGLLTSEGKEIKNKDEILAL LKALFLPKRLSIIHCPGHQK GHSAEARGNRMADQAARKAA ITETPDTSTLLIENSSPYTS EHF |
| 640 | MMLV RTase with Q79R mutation | MTLNIEDEHRLHETSKEPDV SLGSTWLSDFPQAWAETGGM GLAVRQAPLIIPLKATSTPV SIKQYPMSQEARLGIKPHIR RLLDQGILVPCQSPWNTPLL PVKKPGTNDYRPVQDLREVN KRVEDIHPTVPNPYNLLSGL PPSHQWYTVLDLKDAFFCLR LHPTSQPLFAFEWRDPEMGI SGQLTWTRLPQGFKNSPTLF DEALHRDLADFRIQHPDLIL LQYVDDLLLAATSELDCQQG TRALLQTLGNLGYRASAKKA QICQKQVKYLGYLLKEGQRW LTEARKETVMGQPTPKTPRQ LREFLGTAGFCRLWIPGFAE MAAPLYPLTK TGTLFNWGPDQQKAYQEIKQ ALLTAPALGLPDLTKPFELF VDEKQGYAKGVLTQKLGPWR RPVAYLSKKLDPVAAGWPPC LRMVAAIAVLTKDAGKLTMG QPLVILAPHAVEALVKQPPD RWLSNARMTHYQALLLDTDR VQFGPWALNPATLLPLPEEG LQHNCLDILAEAHGTRPDLT DQPLPDADHTWYTGGSSLLQ EGQRKAGAAVTTETEVIWAK ALPAGTSAQRAQLIALTQAL KMAEGKKLNVYTNSRYAFAT AHIHGEIYRRRGLLTSEGKE IKNKDEILALLKALFLPKRL SIIHCPGHQKGHSAEARGNR MADQAARKAAITETPDTSTL LIENSSPYTSEHF |
| 641 | MMLV RTase with L99R mutation | MTLNIEDEHRLHETSKEPDV SLGSTWLSDFPQAWAETGGM GLAVRQAPLIIPLKATSTPV SIKQYPMSQEARLGIKPHIQ RLLDQGILVPCQSPWNTPRL PVKKPGTNDYRPVQDLREVN KRVEDIHPTVPNPYNLLSGL PPSHQWYTVLDLKDAFFCLR LHPTSQPLFAFEWRDPEMGI |

TABLE 3-continued

Sequences of MMLV RTase base construct
and single mutant MMLV RTase
constructs.

| SEQ ID NO: | Construct | Construct Sequence (DNA: 5'-3' or AA) |
|---|---|---|
| | | SGQLTWTRLPQGFKNSPTLF DEALHRDLADFRIQHPDLIL LQYVDDLLLAATSELDCQQG TRALLQTLGNLGYRASAKKA QICQKQVKYLGYLLKEGQRW LTEARKETVMGQPTPKTPRQ LREFLGTAGFCRLWIPGFAE MAAPLYPLTKTGTLFNWGPD QQKAYQEIKQALLTAPALGL PDLTKPFELFVDEKQGYAKG VLTQKLGPWRRPVAYLSKKL DPVAAGWPPCLRMVAAIAVL TKDAGKLTMGQPLVILAPHA VEALVKQPPDRWLSNARMTH YQALLLDTDRVQFGPWALNP ATLLPLPEEGLQHNCLDILA EAHGTRPDLTDQPLPDADHT WYTGGSSLLQEGQRKAGAAV TTETEVIWAKALPAGTSAQR AQLIALTQALKMAEGKKLNV YTNSRYAFATAHIHGEIYRR RGLLTSEGKEIKNKDEILAL LKALFLPKRLSIIHCPGHQK GHSAEARGNRMADQAARKAA ITETPDTSTLLIENSSPYTS EHF |
| 642 | MMLV RTase with E282D mutation | MTLNIEDEHRLHETSKEPDV SLGSTWLSDFPQAWAETGGM GLAVRQAPLIIPLKATSTPV SIKQYPMSQEARLGIKPHIQ RLLDQGILVPCQSPWNTPLL PVKKPGTNDYRPVQDLREVN KRVEDIHPTVPNPYNLLSGL PPSHQWYTVLDLKDAFFCLR LHPTSQPLFAFEWRDPEMGI SGQLTWTRLPQGFKNSPTLF DEALHRDLADFRIQHPDLIL LQYVDDLLLAATSELDCQQG TRALLQTLGNLGYRASAKKA QICQKQVKYLGYLLKEGQRW LTDARKETVMGQPTPKTPRQ LREFLGTAGFCRLWIPGFAE MAAPLYPLTKTGTLFNWGPD QQKAYQEIKQALLTAPALGL PDLTKPFELFVDEKQGYAKG VLTQKLGPWRRPVAYLSKKL DPVAAGWPPCLRMVAAIAVL TKDAGKLTMGQPLVILAPHA VEALVKQPPDRWLSNARMTH YQ ALLLDTDRVQFGPWALNPAT LLPLPEEGLQHNCLDILAEA HGTRPDLTDQPLPDADHTWY TGGSSLLQEGQRKAGAAVTT ETEVIWAKALPAGTSAQRAQ LIALTQALKMAEGKKLNVYT NSRYAFATAHIHGEIYRRRG LLTSEGKEIKNKDEILALLK ALFLPKRLSIIHCPGHQKGH SAEARGNRMADQAARKAAIT ETPDTSTLLIENSSPYTSEH F |
| 643 | MMLV RTase with R298A mutation | MTLNIEDEHRLHETSKEPDV SLGSTWLSDFPQAWAETGGM GLAVRQAPLIIPLKATSTPV SIKQYPMSQEARLGIKPHIQ RLLDQGILVPCQSPWNTPLL PVKKPGTNDYRPVQDLREVN KRVEDIHPTVPNPYNLLSGL PPSHQWYTVLDLKDAFFCLR |

TABLE 3-continued

Sequences of MMLV RTase base construct
and single mutant MMLV RTase
constructs.

| SEQ ID NO: | Construct | Construct Sequence (DNA: 5'-3' or AA) |
|---|---|---|
| | | LHPTSQPLFAFEWRDPEMGI SGQLTWTRLPQGFKNSPTLF DEALHRDLADFRIQHPDLIL LQYVDDLLLAATSELDCQQG TRALLQTLGNLGYRASAKKA QICQKQVKYLGYLLKEGQRW LTEARKETVMGQPTPKTPAQ LREFLGTAGFCRLWIPGFAE MAAPLYPLTKTGTLFNWGPD QQKAYQEIKQALLTAPALGL PDLTKPFELFVDEKQGYAKG VLTQKLGPWRRPVAYLSKKL DPVAAGWPPCLRMVAAIAVL TKDAGKLTMGQPLVILAPHA VEALVKQPPDRWLSNARMTH YQALLLDTDRVQFGPWALNP ATLLPLPEEGLQHNCLDILA EAHGTRPDLTDQPLPDADHT WYTGGSSLLQEGQRKAGAAV TTETEVIWAKALPAGTSAQR AQLIALTQALKMAEGKKLNV YTNSRYAFATAHIHGEIYRR RGLLTSEGKEIKNKDEILAL LKALFLPKRLSIIHCPGHQK GHSAEARGNRMADQAARKAA ITETPDTSTLLIENSSPYTS EHF | e. Experimental Results

The two-step and one-step reactions for MMLV RTase base construct and MMLV RTase single mutant variants were analyzed and reported by copy number output based on a standard curve (see Tables 4 and 5). Six single mutant MMLV RTase variants were found to exhibit an increase in the overall activity and thermostability as compared to the MMLV RTase base construct. The six single mutant MMLV RTase variants were as follows: I61R, Q68R, Q79R, L99R, E282D, and R298A.

TABLE 4

Two-step cDNA synthesis by MMLV RT single mutants.
Data was generated via qPCR human normalizer
assay and translated by copy number.

| MMLV RT Variant | Quantity Mean | Quantity Standard Deviation |
|---|---|---|
| MMLV-II | 21,046.784 | 954.827 |
| MMLV-II A283V | 280.423 | 50.910 |
| MMLV-II A283R | 10,390.819 | 340.236 |
| MMLV-II A283E | 7,378.705 | 122.716 |
| MMLV-II E123A | 15,059.791 | 556.095 |
| MMLV-II E123R | 19,043.292 | 415.522 |
| MMLV-II E123D | 3,619.959 | 243.766 |
| MMLV-II E282A | 19,939.551 | 1,645.246 |
| MMLV-II E282R | 15,588.940 | 546.467 |
| MMLV-II E282D | 24,282.327 | 2,259.264 |
| MMLV-II I61A | 648.252 | 45.640 |
| MMLV-II I61R | 26,280.811 | 549.417 |
| MMLV-II I61E | 10,966.741 | 469.747 |
| MMLV-II K102A | 98.438 | 12.778 |
| MMLV-II K102R | 780.114 | 90.331 |
| MMLV-II K102E | 1,674.854 | 157.485 |
| MMLV-II K103A | 359.984 | 67.322 |
| MMLV-II K103R | 206.765 | 20.758 |
| MMLV-II K103E | 200.883 | 16.719 |
| MMLV-II K120A | 217.787 | 72.696 |
| MMLV-II K120R | 3,619.338 | 100.478 |

TABLE 4-continued

Two-step cDNA synthesis by MMLV RT single mutants.
Data was generated via qPCR human normalizer
assay and translated by copy number.

| MMLV RT Variant | Quantity Mean | Quantity Standard Deviation |
|---|---|---|
| MMLV-II K120E | 2,230.375 | 210.050 |
| MMLV-II K193A | 2,736.271 | 162.383 |
| MMLV-II K193R | 11,496.935 | 193.681 |
| MMLV-II K193E | 325.109 | 50.932 |
| MMLV-II K295A | 8,101.927 | 348.373 |
| MMLV-II K295R | 6,879.112 | 131.993 |
| MMLV-II K295E | 9,673.612 | 351.106 |
| MMLV-II K329A | 3,199.167 | 212.003 |
| MMLV-II K329R | 10,387.670 | 330.429 |
| MMLV-II K329E | 18,306.813 | 1,167.600 |
| MMLV-II K53A | 474.465 | 62.390 |
| MMLV-II K53R | 369.020 | 49.436 |
| MMLV-II K53E | 5,308.165 | 104.585 |
| MMLV-II K62A | 2,102.396 | 64.197 |
| MMLV-II K62R | 4,920.330 | 251.414 |
| MMLV-II K62E | 71.723 | 11.419 |
| MMLV-II K75A | 76.659 | 24.657 |
| MMLV-II K75R | 2,842.314 | 77.212 |
| MMLV-II K75E | 1,697.887 | 158.946 |
| MMLV-II L99A | 1,576.246 | 213.455 |
| MMLV-II L99R | 37,070.048 | 1,531.910 |
| MMLV-II L99E | 195.448 | 22.530 |
| MMLV-II N107A | 3,354.325 | 176.385 |
| MMLV-II N107R | 41.532 | 24.527 |
| MMLV-II N107E | 8,523.285 | 353.411 |
| MMLV-II Q291A | 14,093.444 | 576.318 |
| MMLV-II Q291R | 15,736.443 | 566.630 |
| MMLV-II Q291E | 1,480.309 | 93.187 |
| MMLV-II Q68A | n.d. | n.d. |
| MMLV-II Q68R | 20,158.035 | 722.022 |
| MMLV-II Q68E | 2,263.714 | 150.236 |
| MMLV-II Q79A | 2,317.484 | 43.518 |
| MMLV-II Q79R | 37,480.443 | 1,268.309 |
| MMLV-II Q79E | 489.184 | 39.449 |
| MMLV-II R110A | 1,815.710 | 7.917 |
| MMLV-II R110K | 502.172 | 38.619 |
| MMLV-II R110E | 383.331 | 38.162 |
| MMLV-II R298A | 44,477.013 | 3,036.502 |
| MMLV-II R298K | 14,925.202 | 186.581 |
| MMLV-II R298E | 1,150.932 | 56.107 |
| MMLV-II R301A | 2,745.075 | 82.646 |
| MMLV-II R301K | 12,813.899 | 568.898 |
| MMLV-II R301E | 1,583.826 | 198.913 |
| MMLV-II T106A | 16,641.642 | 179.631 |
| MMLV-II T106R | 2,248.217 | 71.295 |
| MMLV-II T106E | 10,302.113 | 250.531 |
| MMLV-II T128V | 7,034.032 | 351.446 |
| MMLV-II T128R | 3,465.069 | 143.456 |
| MMLV-II T128E | 10,709.019 | 110.124 |
| MMLV-II T293A | 4,612.880 | 167.335 |
| MMLV-II T293R | 13,753.879 | 319.851 |
| MMLV-II T293E | 12,893.457 | 223.100 |
| MMLV-II T296A | 2,192.531 | 76.071 |
| MMLV-II T296R | 893.449 | 51.913 |
| MMLV-II T296E | 473.936 | 102.414 |
| MMLV-II T55A | 5,774.471 | 223.173 |
| MMLV-II T55R | 3,284.089 | 314.651 |
| MMLV-II T55E | 6,143.058 | 429.507 |
| MMLV-II T57A | 6,129.791 | 285.070 |
| MMLV-II T57R | 888.244 | 11.952 |
| MMLV-II T57E | 1,487.448 | 71.681 |
| MMLV-II V101A | 552.130 | 98.391 |
| MMLV-II V101R | 4,754.017 | 107.434 |
| MMLV-II V101E | 1,388.699 | 87.091 |
| MMLV-II V112A | 2,085.594 | 72.265 |
| MMLV-II V112R | 377.194 | 41.722 |
| MMLV-II V112E | 210.825 | 17.715 |
| MMLV-II V59A | 628.779 | 15.216 |
| MMLV-II V59R | 6,662.173 | 210.234 |

TABLE 4-continued

Two-step cDNA synthesis by MMLV RT single mutants.
Data was generated via qPCR human normalizer
assay and translated by copy number.

| MMLV RT Variant | Quantity Mean | Quantity Standard Deviation |
| --- | --- | --- |
| MMLV-II V59E | 3,249.465 | 79.848 |
| MMLV-II Y109A | 101.656 | 6.717 |
| MMLV-II Y109R | 349.373 | 27.171 |
| MMLV-II Y109E | 1,029.589 | 45.189 |
| MMLV-IV | 71,572.714 | 4,656.679 |

TABLE 5

One-step cDNA synthesis by MMLV RT single mutants.
Data was generated via qPCR human normalizer assay
and data is translated by copy number.

| MMLV RT Variant | Quantity Mean | Quantity Standard Deviation |
| --- | --- | --- |
| MMLV-II | 20,638.973 | 614.785 |
| MMLV-II A283V | 8,802.753 | 220.902 |
| MMLV-II A283R | 14,379.575 | 337.562 |
| MMLV-II A283E | 16,396.614 | 203.476 |
| MMLV-II E123A | 17,975.218 | 259.986 |
| MMLV-II E123R | 20,652.508 | 515.600 |
| MMLV-II E123D | 14,452.672 | 242.000 |
| MMLV-II E282A | 19,017.751 | 827.419 |
| MMLV-II E282R | 17,180.421 | 204.739 |
| MMLV-II E282D | 20,735.271 | 420.881 |
| MMLV-II I61A | 7,450.147 | 348.788 |
| MMLV-II I61R | 25,123.507 | 2,977.836 |
| MMLV-II I61E | 17,441.860 | 1,662.749 |
| MMLV-II K102A | 9,342.754 | 120.846 |
| MMLV-II K102R | 10,563.589 | 255.139 |
| MMLV-II K102E | 13,925.008 | 307.601 |
| MMLV-II K103A | 9,429.555 | 437.351 |
| MMLV-II K103R | 9,009.846 | 155.888 |
| MMLV-II K103E | 7,985.278 | 189.792 |
| MMLV-II K120A | 8,593.433 | 438.722 |
| MMLV-II K120R | 12,558.793 | 407.946 |
| MMLV-II K120E | 12,268.574 | 303.495 |
| MMLV-II K193A | 12,977.263 | 537.992 |
| MMLV-II K193R | 13,446.766 | 2,337.906 |
| MMLV-II K193E | 8,536.558 | 182.514 |
| MMLV-II K295A | 13,506.491 | 1,613.467 |
| MMLV-II K295R | 13,944.407 | 1,839.608 |
| MMLV-II K295E | 15,021.823 | 650.111 |
| MMLV-II K329A | 13,284.541 | 246.298 |
| MMLV-II K329R | 15,935.899 | 970.971 |
| MMLV-II K329E | 20,628.859 | 884.254 |
| MMLV-II K53A | 10,868.676 | 161.435 |
| MMLV-II K53R | 9,908.252 | 632.663 |
| MMLV-II K53E | 20,666.775 | 518.895 |
| MMLV-II K62A | 9,454.043 | 732.242 |
| MMLV-II K62R | 14,532.171 | 63.450 |
| MMLV-II K62E | 8,341.361 | 436.076 |
| MMLV-II K75A | 9,084.502 | 113.100 |
| MMLV-II K75R | 13,106.462 | 331.663 |
| MMLV-II K75E | 11,191.849 | 565.160 |
| MMLV-II L99A | 12,876.076 | 49.507 |
| MMLV-II L99R | 27,167.197 | 142.371 |
| MMLV-II L99E | 6,534.199 | 2,730.598 |
| MMLV-II N107A | 13,563.421 | 349.378 |
| MMLV-II N107R | 8,654.167 | 497.167 |
| MMLV-II N107E | 16,675.075 | 172.596 |
| MMLV-II Q291A | 20,957.729 | 150.006 |
| MMLV-II Q291R | 17,980.723 | 346.436 |
| MMLV-II Q291E | 11,025.722 | 407.116 |
| MMLV-II Q68A | n.d. | n.d. |
| MMLV-II Q68R | 24,925.791 | 937.265 |
| MMLV-II Q68E | 12,844.484 | 165.039 |
| MMLV-II Q79A | 12,038.975 | 482.596 |
| MMLV-II Q79R | 28,458.521 | 296.595 |
| MMLV-II Q79E | 10,358.863 | 309.043 |
| MMLV-II R110A | 11,517.764 | 562.094 |
| MMLV-II R110K | 8,112.167 | 76.742 |

TABLE 5-continued

One-step cDNA synthesis by MMLV RT single mutants.
Data was generated via qPCR human normalizer assay
and data is translated by copy number.

| MMLV RT Variant | Quantity Mean | Quantity Standard Deviation |
| --- | --- | --- |
| MMLV-II R110E | 8,809.423 | 290.785 |
| MMLV-II R298A | 27,817.905 | 172.690 |
| MMLV-II R298K | 18,222.660 | 825.743 |
| MMLV-II R298E | 10,783.790 | 783.279 |
| MMLV-II R301A | 11,344.854 | 63.499 |
| MMLV-II R301K | 17,584.850 | 445.587 |
| MMLV-II R301E | 10,146.906 | 1,879.902 |
| MMLV-II T106A | 17,717.520 | 215.965 |
| MMLV-II T106R | 11,680.187 | 148.213 |
| MMLV-II T106E | 21,203.557 | 366.469 |
| MMLV-II T128V | 14,384.970 | 355.754 |
| MMLV-II T128R | 12,938.223 | 464.841 |
| MMLV-II T128E | 14,781.394 | 1,930.931 |
| MMLV-II T293A | 15,658.189 | 347.640 |
| MMLV-II T293R | 19,976.165 | 253.604 |
| MMLV-II T293E | 17,580.335 | 404.397 |
| MMLV-II T296A | 10,312.142 | 159.775 |
| MMLV-II T296R | 8,482.071 | 92.806 |
| MMLV-II T296E | 7,687.972 | 112.884 |
| MMLV-II T55A | 18,073.262 | 618.174 |
| MMLV-II T55R | 11,546.179 | 138.906 |
| MMLV-II T55E | 12,299.658 | 815.911 |
| MMLV-II T57A | 14,700.042 | 2,916.521 |
| MMLV-II T57R | 11,195.901 | 145.433 |
| MMLV-II T57E | 11,958.503 | 605.445 |
| MMLV-II V101A | 10,697.751 | 269.696 |
| MMLV-II VI01R | 8,934.765 | 53.924 |
| MMLV-II V101E | 11,295.874 | 296.506 |
| MMLV-II V112A | 12,854.738 | 356.724 |
| MMLV-II V112R | 6,331.802 | 303.453 |
| MMLV-II V112E | 7,643.184 | 448.446 |
| MMLV-II V59A | 9,520.143 | 339.954 |
| MMLV-II V59R | 18,523.053 | 499.377 |
| MMLV-II V59E | 16,029.631 | 137.454 |
| MMLV-II Y109A | 8,421.361 | 185.196 |
| MMLV-II Y109R | 8,581.961 | 129.732 |
| MMLV-II Y109E | 10,216.473 | 416.388 |
| MMLV-IV | 65,726.159 | 1,811.314 |

Example 4: Extension of Reverse Transcriptase Single Mutants

The amino acid positions that enclosed the MMLV RTase single mutants identified in Example 3 were further evaluated to include all possible amino acid substitutions at that position. The single mutants were cloned, overexpressed, and purified as described in Examples 1 and 2, and evaluated as described in Example 3. The two-step and one-step reactions for MMLV RTase base construct and MMLV RTase double mutant variants were analyzed and reported by copy number output based on a standard curve (see Tables 6 and 7). Ten single mutant MMLV RTase variants (see Table 8) were found to exhibit an increase in the overall activity and thermostability as compared to the MMLV RTase base construct. The ten single mutant MMLV RTase variants were as follows: I61K, I61M, Q68I, Q68K, Q79H, Q79I, L99K, L99N, E282M and E282W.

TABLE 6

Two-step cDNA synthesis by MMLV RT single mutants.
Data was generated via qPCR human normalizer
assay and translated by copy number.

| MMLV RT Variant | Quantity Mean | Quantity Standard Deviation |
|---|---|---|
| MMLV-II | 1,484.121 | 125.278 |
| MMLV-II E282C | 749.332 | 37.947 |
| MMLV-II E282F | 968.042 | 28.112 |
| MMLV-II E282G | 841.839 | 30.618 |
| MMLV-II E282H | 936.562 | 64.904 |
| MMLV-II E282I | 1,418.551 | 8.682 |
| MMLV-II E282K | 2,399.973 | 50.862 |
| MMLV-II E282L | 1,778.903 | 134.133 |
| MMLV-II E282M | 2,115.328 | 125.477 |
| MMLV-II E282N | 1,175.130 | 79.221 |
| MMLV-II E282P | 1,529.331 | 61.525 |
| MMLV-II E282Q | 1,856.418 | 24.118 |
| MMLV-II E282S | 673.670 | 44.770 |
| MMLV-II E282T | 994.318 | 24.066 |
| MMLV-II E282V | 748.877 | 29.053 |
| MMLV-II E282W | 2,469.404 | 141.080 |
| MMLV-II E282Y | 1,360.706 | 338.309 |
| MMLV-II I61C | 283.240 | 11.244 |
| MMLV-II I61D | 349.008 | 10.979 |
| MMLV-II I61F | 784.163 | 22.643 |
| MMLV-II I61G | 395.348 | 21.967 |
| MMLV-II I61H | 736.015 | 30.271 |
| MMLV-II I61K | 4,479.606 | 62.627 |
| MMLV-II I61L | 1,106.547 | 38.553 |
| MMLV-II I61M | 4,198.088 | 93.025 |
| MMLV-II I61N | 709.752 | 29.312 |
| MMLV-II I61P | 32.935 | 16.814 |
| MMLV-II I61Q | 1,311.695 | 145.810 |
| MMLV-II I61S | 797.783 | 50.626 |
| MMLV-II I61T | 628.173 | 33.371 |
| MMLV-II I61V | 1,439.915 | 27.490 |
| MMLV-II I61W | 442.039 | 29.310 |
| MMLV-II I61Y | 534.249 | 26.831 |
| MMLV-II L99C | 3,109.142 | 80.016 |
| MMLV-II L99D | 83.653 | 3.432 |
| MMLV-II L99F | 2,811.513 | 79.584 |
| MMLV-II L99G | 908.041 | 16.157 |
| MMLV-II L99H | 4,881.196 | 390.497 |
| MMLV-II L99I | 910.072 | 71.671 |
| MMLV-II L99K | 6,410.818 | 127.262 |
| MMLV-II L99M | 976.548 | 65.154 |
| MMLV-II L99N | 4,974.458 | 162.464 |
| MMLV-II L99P | 6.416 | 1.820 |
| MMLV-II L99Q | 3,908.473 | 337.167 |
| MMLV-II L99S | 3,793.955 | 86.959 |
| MMLV-II L99T | 4,189.211 | 27.640 |
| MMLV-II L99V | 964.081 | 48.105 |
| MMLV-II L99W | 1,614.660 | 40.442 |
| MMLV-II L99Y | 2,123.406 | 181.945 |
| MMLV-II Q68A | 1,184.702 | 7.676 |
| MMLV-II Q68C | 2,038.167 | 36.463 |
| MMLV-II Q68D | 1,613.880 | 77.796 |
| MMLV-II Q68F | 1,805.647 | 62.456 |
| MMLV-II Q68G | 2,262.873 | 69.688 |
| MMLV-II Q68H | 106.421 | 9.860 |
| MMLV-II Q68I | 2,675.446 | 73.874 |
| MMLV-II Q68K | 1,042.979 | 70.081 |
| MMLV-II Q68L | 1,070.742 | 57.215 |
| MMLV-II Q68M | 1,342.806 | 58.349 |
| MMLV-II Q68N | 1,993.946 | 65.808 |
| MMLV-II Q68P | 2,025.753 | 25.540 |
| MMLV-II Q68S | 1,895.984 | 26.959 |
| MMLV-II Q68T | 431.442 | 22.751 |
| MMLV-II Q68V | 1,534.710 | 110.794 |
| MMLV-II Q68W | 1,790.706 | 124.583 |
| MMLV-II Q79C | 2,477.812 | 107.510 |
| MMLV-II Q79D | 627.902 | 11.073 |
| MMLV-II Q79F | 1,786.571 | 126.904 |
| MMLV-II Q79G | 2,702.985 | 83.998 |
| MMLV-II Q79H | 2,851.710 | 57.501 |
| MMLV-II Q79I | 2,967.710 | 57.440 |
| MMLV-II Q79K | 1,346.751 | 64.513 |
| MMLV-II Q79L | 2,214.615 | 67.622 |
| MMLV-II Q79M | 1,847.181 | 31.384 |

TABLE 6-continued

Two-step cDNA synthesis by MMLV RT single mutants.
Data was generated via qPCR human normalizer
assay and translated by copy number.

| MMLV RT Variant | Quantity Mean | Quantity Standard Deviation |
|---|---|---|
| MMLV-II Q79N | 1,365.563 | 54.775 |
| MMLV-II Q79P | 674.074 | 42.100 |
| MMLV-II Q79S | 2,199.353 | 52.958 |
| MMLV-II Q79T | 1,523.163 | 77.025 |
| MMLV-II Q79V | 1,704.661 | 77.643 |
| MMLV-II Q79W | 2,186.489 | 31.470 |
| MMLV-II Q79Y | 2,326.023 | 123.508 |
| MMLV-II R298C | 79.970 | 9.815 |
| MMLV-II R298D | 0.000 | 0.000 |
| MMLV-II R298F | 84.760 | 9.362 |
| MMLV-II R298G | 357.027 | 15.726 |
| MMLV-II R298H | 269.257 | 20.814 |
| MMLV-II R298I | 130.983 | 5.364 |
| MMLV-II R298L | 199.612 | 5.843 |
| MMLV-II R298M | 172.013 | 18.710 |
| MMLV-II R298N | 199.678 | 2.660 |
| MMLV-II R298P | 122.098 | 5.900 |
| MMLV-II R298Q | 118.092 | 40.694 |
| MMLV-II R298S | 406.112 | 7.695 |
| MMLV-II R298T | 618.616 | 20.023 |
| MMLV-II R298V | 136.498 | 13.297 |
| MMLV-II R298W | 68.096 | 7.016 |
| MMLV-II R298Y | 162.713 | 7.854 |
| MMLV-IV | 6,830.294 | 376.878 |

TABLE 7

One-step cDNA synthesis by MMLV RT single mutants.
Data was generated via qPCR human normalizer assay
and data is translated by copy number.

| MMLV RT Variant | Quantity Mean | Quantity Standard Deviation |
|---|---|---|
| MMLV-II | 408.018 | 8.693 |
| MMLV-II E282C | 175.083 | 7.005 |
| MMLV-II E282F | 1,043.025 | 16.137 |
| MMLV-II E282G | 635.037 | 13.293 |
| MMLV-II E282H | 656.956 | 10.018 |
| MMLV-II E282I | 1,033.125 | 44.996 |
| MMLV-II E282K | 751.309 | 17.611 |
| MMLV-II E282L | 1,072.350 | 80.365 |
| MMLV-II E282M | 1,318.072 | 51.735 |
| MMLV-II E282N | 539.305 | 10.767 |
| MMLV-II E282P | 725.869 | 92.685 |
| MMLV-II E282Q | 626.674 | 12.129 |
| MMLV-II E282S | 354.956 | 34.850 |
| MMLV-II E282T | 485.477 | 45.783 |
| MMLV-II E282V | 594.047 | 27.898 |
| MMLV-II E282W | 913.290 | 61.145 |
| MMLV-II E282Y | 759.920 | 34.784 |
| MMLV-II I61C | 219.438 | 18.403 |
| MMLV-II I61D | 347.020 | 13.303 |
| MMLV-II I61F | 428.623 | 25.316 |
| MMLV-II I61G | 389.503 | 21.764 |
| MMLV-II I61H | 514.330 | 18.416 |
| MMLV-II I61K | 2,343.894 | 67.214 |
| MMLV-II I61L | 621.572 | 14.892 |
| MMLV-II I61M | 2,536.807 | 150.371 |
| MMLV-II I61N | 538.519 | 20.736 |
| MMLV-II I61P | 61.683 | 18.802 |
| MMLV-II I61Q | 701.471 | 32.487 |
| MMLV-II I61S | 611.977 | 30.430 |
| MMLV-II I61T | 534.254 | 31.643 |
| MMLV-II I61V | 881.608 | 20.662 |
| MMLV-II I61W | 428.440 | 17.964 |
| MMLV-II I61Y | 347.930 | 4.412 |
| MMLV-II L99C | 2,390.104 | 35.867 |
| MMLV-II L99D | 185.044 | 6.975 |
| MMLV-II L99F | 1,577.767 | 7.757 |
| MMLV-II L99G | 987.225 | 9.718 |
| MMLV-II L99H | 3,886.372 | 111.670 |

TABLE 7-continued

One-step cDNA synthesis by MMLV RT single mutants.
Data was generated via qPCR human normalizer assay
and data is translated by copy number.

| MMLV RT Variant | Quantity Mean | Quantity Standard Deviation |
| --- | --- | --- |
| MMLV-II L99I | 613.648 | 46.303 |
| MMLV-II L99K | 7,597.650 | 321.753 |
| MMLV-II L99M | 934.817 | 52.006 |
| MMLV-II L99N | 4,689.222 | 160.641 |
| MMLV-II L99P | 18.537 | 1.131 |
| MMLV-II L99Q | 2,394.744 | 64.077 |
| MMLV-II L99S | 3,293.831 | 111.802 |
| MMLV-II L99T | 3,505.113 | 101.670 |
| MMLV-II L99V | 677.756 | 49.356 |
| MMLV-II L99W | 839.088 | 50.301 |
| MMLV-II L99Y | 1,127.536 | 19.074 |
| MMLV-II Q68A | 827.617 | 30.689 |
| MMLV-II Q68C | 1,110.680 | 45.944 |
| MMLV-II Q68D | 1,045.802 | 25.488 |
| MMLV-II Q68F | 1,210.166 | 120.899 |
| MMLV-II Q68G | 907.279 | 30.688 |
| MMLV-II Q68H | 150.384 | 6.867 |
| MMLV-II Q68I | 1,550.372 | 76.712 |
| MMLV-II Q68K | 1,712.176 | 47.342 |
| MMLV-II Q68L | 651.039 | 51.426 |
| MMLV-II Q68M | 1,395.463 | 34.805 |
| MMLV-II Q68N | 1,241.364 | 25.780 |
| MMLV-II Q68P | 1,249.444 | 13.709 |
| MMLV-II Q68S | 1,125.260 | 21.324 |
| MMLV-II Q68T | 792.901 | 31.513 |
| MMLV-II Q68V | 1,026.654 | 24.972 |
| MMLV-II Q68W | 1,594.175 | 101.221 |
| MMLV-II Q79C | 1,948.151 | 87.341 |
| MMLV-II Q79D | 458.131 | 10.763 |
| MMLV-II Q79F | 1,623.675 | 50.723 |
| MMLV-II Q79G | 1,885.097 | 20.190 |
| MMLV-II Q79H | 2,508.763 | 149.926 |
| MMLV-II Q79I | 2,329.030 | 76.545 |
| MMLV-II Q79K | 1,861.302 | 24.320 |
| MMLV-II Q79L | 1,496.247 | 30.399 |
| MMLV-II Q79M | 1,496.469 | 38.178 |
| MMLV-II Q79N | 995.813 | 42.279 |
| MMLV-II Q79P | 526.914 | 23.216 |
| MMLV-II Q79S | 1,685.124 | 42.694 |
| MMLV-II Q79T | 966.505 | 8.377 |
| MMLV-II Q79V | 1,218.191 | 21.512 |
| MMLV-II Q79W | 1,962.326 | 37.135 |
| MMLV-II Q79Y | 2,218.504 | 56.938 |
| MMLV-II R298C | 45.500 | 1.456 |
| MMLV-II R298D | 0.000 | 0.000 |
| MMLV-II R298F | 104.825 | 5.133 |
| MMLV-II R298G | 323.542 | 14.052 |
| MMLV-II R298H | 253.202 | 47.711 |
| MMLV-II R298I | 205.982 | 8.304 |
| MMLV-II R298L | 213.674 | 15.199 |
| MMLV-II R298M | 176.347 | 12.484 |
| MMLV-II R298N | 142.969 | 39.198 |
| MMLV-II R298P | 188.995 | 3.689 |
| MMLV-II R298Q | 95.525 | 44.292 |
| MMLV-II R298S | 307.614 | 9.962 |
| MMLV-II R298T | 487.828 | 3.480 |
| MMLV-II R298V | 255.828 | 12.902 |
| MMLV-II R298W | 37.872 | 8.482 |
| MMLV-II R298Y | 153.333 | 25.137 |
| MMLV-IV | 19,407.721 | 466.310 |

TABLE 8

Sequences of single mutant MMLV
RTase variants.

| SEQ ID NO: | Construct | Construct Sequence (AA) |
| --- | --- | --- |
| 644 | MMLV RTase with 161K mutation | MTLNIEDEHRLHETSKEPDV SLGSTWLSDFPQAWAETGGM GLAVRQAPLIIPLKATSTPV SKKQYPMSQEARLGIKPHIQ RLLDQGILVPCQSPWNTPLL PVKKPGTNDYRPVQDLREVN KRVEDIHPTVPNPYNLLSGL PPSHQWYTVLDLKDAFFCLR LHPTSQPLFAFEWRDPEMGI SGQLTWTRLPQGFKNSPTLF DEALHRDLADFRIQHPDLIL LQYVDDLLLAATSELDCQQG TRALLQTLGNLGYRASAKKA QICQKQVKYLGYLLKEGQRW LTEARKETVMGQPTPKTPRQ LREFLGTAGFCRLWIPGFAE MAAPLYPLTKTGTLFNWGPD QQKAYQEIKQALLTAPALGL PDLTKPFELFVDEKQGYAKG VLTQKLGPWRRPVAYLSKKL DPVAAGWPPCLRMVAAIAVL TKDAGKLTMGQPLVILAPHA VEALVKQPPDRWLSNARMTH YQALLLDTDRVQFGPVVALN PATLLPLPEEGLQHNCLDIL AEAHGTRPDLTDQPLPDADH TWYTGGSSLLQEGQRKAGAA VTTETEVIWAKALPAGTSAQ RAQLIALTQALKMAEGKKLN VYTNSRYAFATAHIHGEIYR RRGLLTSEGKEIKNKDEILA LLKALFLPKRLSIIHCPGHQ KGHSAEARGNRMADQAARKA AITETPDTSTLLIENSSPYT SEHF |
| 645 | MMLV RTase with 161M mutation | MTLNIEDEHRLHETSKEPDV SLGSTWLSDFPQAWAETGGM GLAVRQAPLIIPLKATSTPV SMKQYPMSQEARLGIKPHIQ RLLDQGILVPCQSPWNTPLL PVKKPGTNDYRPVQDLREVN KRVEDIHPTVPNPYNLLSGL PPSHQWYTVLDLKDAFFCLR LHPTSQPLFAFEWRDPEMGI SGQLTWTRLPQGFKNSPTLF DEALHRDLADFRIQHPDLIL LQYVDDLLLAATSELDCQQG TRALLQTLGNLGYRASAKKA QICQKQVKYLGYLLKEGQRW LTEARKETVMGQPTPKTPRQ LREFLGTAGFCRLWIPGFAE MAAPLYPLTKTGTLFNWGPD QQKAYQEIKQALLTAPALGL PDLTKPFELFVDEKQGYAKG VLTQKLGPWRRPVAYLSKKL DPVAAGWPPCLRMVAAIAVL TKDAGKLTMGQPLVILAPHA VEALVKQPPDRWLSNARMTH YQALLLDTDRVQFGPVVALN PATLLPLPEEGLQHNCLDIL AEAHGTRPDLTDQPLPDADH TWYTGGSSLLQEGQRKAGAA VTTETEVIWAKALPAGTSAQ RAQLIALTQALKMAEGKKLN VYTNSRYAFATAHIHGEIYR RRGLLTSEGKEIKNKDEILA LLKALFLPKRLSIIHCPGHQ KGHSAEARGNRMADQAARKA AITETPDTSTLLIENSSPYT SEHF |

TABLE 8-continued

Sequences of single mutant MMLV
RTase variants.

| SEQ ID NO: | Construct | Construct Sequence (AA) |
|---|---|---|
| 646 | MMLV RTase with Q68I mutation | MTLNIEDEHRLHETSKEPDV SLGSTWLSDFPQAWAETGGM GLAVRQAPLIIPLKATSTPV SIKQYPMSIEARLGIKPHIQ RLLDQGILVPCQSPWNTPLL PVKKPGTNDYRPVQDLREVN KRVEDIHPTVPNPYNLLSGL PPSHQWYTVLDLKDAFFCLR LHPTSQPLFAFEWRDPEMGI SGQLTWTRLPQGFKNSPTLF DEALHRDLADFRIQHPDLIL LQYVDDLLLAATSELDCQQG TRALLQTLGNLGYRASAKKA QICQKQVKYLGYLLKEGQRW LTEARKETVMGQPTPKTPRQ LREFLGTAGFCRLWIPGFAE MAAPLYPLTKTGTLFNWGPD QQKAYQEIKQALLTAPALGL PDLTKPFELFVDEKQGYAKG VLTQKLGPWRRPVAYLSKKL DPVAAGWPPCLRMVAAIAVL TKDAGKLTMGQPLVILAPHA VEALVKQPPDRWLSNARMTH YQALLLDTDRVQFGPVVALN PATLLPLPEEGLQHNCLDIL AEAHGTRPDLTDQPLPDADH TWYTGGSSLLQEGQRKAGAA VTTETEVIWAKALPAGTSAQ RAQLIALTQALKMAEGKKLN VYTNSRYAFATAHIHGEIYR RRGLLTSEGKEIKNKDEILA LLKALFLPKRLSIIHCPGHQ KGHSAEARGNRMADQAARKA AITETPDTSTLLIENSSPYT SEHF |
| 647 | MMLV RTase with Q68K mutation | MTLNIEDEHRLHETSKEPDV SLGSTWLSDFPQAWAETGGM GLAVRQAPLIIPLKATSTPV SIKQYPMSKEARLGIKPHIQ RLLDQGILVPCQSPWNTPLL PVKKPGTNDYRPVQDLREVN KRVEDIHPTVPNPYNLLSGL PPSHQWYTVLDLKDAFFCLR LHPTSQPLFAFEWRDPEMGI SGQLTWTRLPQGFKNSPTLF DEALHRDLADFRIQHPDLIL LQYVDDLLLAATSELDCQQG TRALLQTLGNLGYRASAKKA QICQKQVKYLGYLLKEGQRW LTEARKETVMGQPTPKTPRQ LREFLGTAGFCRLWIPGFAE MAAPLYPLTKTGTLFNWGPD QQKAYQEIKQALLTAPALGL PDLTKPFELFVDEKQGYAKG VLTQKLGPWRRPVAYLSKKL DPVAAGWPPCLRMVAAIAVL TKDAGKLTMGQPLVILAPHA VEALVKQPPDRWLSNARMTH YQALLLDTDRVQFGPVVALN PATLLPLPEEGLQHNCLDIL AEAHGTRPDLTDQPLPDADH TWYTGGSSLLQEGQRKAGAA VTTETEVIWAKALPAGTSAQ RAQLIALTQALKMAEGKKLN VYTNSRYAFATAHIHGEIYR RRGLLTSEGKEIKNKDEILA LLKALFLPKRLSIIHCPGHQ KGHSAEARGNRMADQAARKA AITETPDTSTLLIENSSPYT SEHF |

TABLE 8-continued

Sequences of single mutant MMLV
RTase variants.

| SEQ ID NO: | Construct | Construct Sequence (AA) |
|---|---|---|
| 648 | MMLV RTase with Q79H mutation | MTLNIEDEHRLHETSKEPDV SLGSTWLSDFPQAWAETGGM GLAVRQAPLIIPLKATSTPV SIKQYPMSQEARLGIKPHIH RLLDQGILVPCQSPWNTPLL PVKKPGTNDYRPVQDLREVN KRVEDIHPTVPNPYNLLSGL PPSHQWYTVLDLKDAFFCLR LHPTSQPLFAFEWRDPEMGI SGQLTWTRLPQGFKNSPTLF DEALHRDLADFRIQHPDLIL LQYVDDLLLAATSELDCQQG TRALLQTLGNLGYRASAKKA QICQKQVKYLGYLLKEGQRW LTEARKETVMGQPTPKTPRQ LREFLGTAGFCRLWIPGFAE MAAPLYPLTKTGTLFNWGPD QQKAYQEIKQALLTAPALGL PDLTKPFELFVDEKQGYAKG VLTQKLGPWRRPVAYLSKKL DPVAAGWPPCLRMVAAIAVL TKDAGKLTMGQPLVILAPHA VEALVKQPPDRWLSNARMTH YQALLLDTDRVQFGPVVALN PATLLPLPEEGLQHNCLDIL AEAHGTRPDLTDQPLPDADH TWYTGGSSLLQEGQRKAGAA VTTETEVIWAKALPAGTSAQ RAQLIALTQALKMAEGKKLN VYTNSRYAFATAHIHGEIYR RRGLLTSEGKEIKNKDEILA LLKALFLPKRLSIIHCPGHQ KGHSAEARGNRMADQAARKA AITETPDTSTLLIENSSPYT SEHF |
| 649 | MMLV RTase with Q79I mutation | MTLNIEDEHRLHETSKEPDV SLGSTWLSDFPQAWAETGGM GLAVRQAPLIIPLKATSTPV SIKQYPMSQEARLGIKPHII RLLDQGILVPCQSPWNTPLL PVKKPGTNDYRPVQDLREVN KRVEDIHPTVPNPYNLLSGL PPSHQWYTVLDLKDAFFCLR LHPTSQPLFAFEWRDPEMGI SGQLTWTRLPQGFKNSPTLF DEALHRDLADFRIQHPDLIL LQYVDDLLLAATSELDCQQG TRALLQTLGNLGYRASAKKA QICQKQVKYLGYLLKEGQRW LTEARKETVMGQPTPKTPRQ LREFLGTAGFCRLWIPGFAE MAAPLYPLTKTGTLFNWGPD QQKAYQEIKQALLTAPALGL PDLTKPFELFVDEKQGYAKG VLTQKLGPWRRPVAYLSKKL DPVAAGWPPCLRMVAAIAVL TKDAGKLTMGQPLVILAPHA VEALVKQPPDRWLSNARMTH YQALLLDTDRVQFGPVVALN PATLLPLPEEGLQHNCLDIL AEAHGTRPDLTDQPLPDADH TWYTGGSSLLQEGQRKAGAA VTTETEVIWAKALPAGTSAQ RAQLIALTQALKMAEGKKLN VYTNSRYAFATAHIHGEIYR RRGLLTSEGKEIKNKDEILA LLKALFLPKRLSIIHCPGHQ KGHSAEARGNRMADQAARKA AITETPDTSTLLIENSSPYT SEHF |

TABLE 8-continued

Sequences of single mutant MMLV
RTase variants.

| SEQ ID NO: | Construct | Construct Sequence (AA) |
|---|---|---|
| 650 | MMLV RTase with L99K mutation | MTLNIEDEHRLHETSKEPDV SLGSTWLSDFPQAWAETGGM GLAVRQAPLIIPLKATSTP VSIKQYPMSQEA RLGIKPHIQRLLDQGILVPC QSPWNTPLKPVKKPGTNDYR PVQDLREVNKRVEDIHPTVP NPYNLLSGLPPSHQWYTVLD LKDAFFCLRLHPTSQPLFAF EWRDPEMGISGQLTWTRLPQ GFKNSPTLFDEALHRDLADF RIQHPDLILLQYVDDLLLAA TSELDCQQGTRALLQTLGNL GYRASAKKAQICQKQVKYLG YLLKEGQRWLTEARKETVMG QPTPKTPRQLREFLGTAGFC RLWIPGFAEMAAPLYPLTKT GTLFNWGPDQQKAYQEIKQA LLTAPALGLPDLTKPFELFV DEKQGYAKGVLTQKLGPWRR PVAYLSKKLDPVAAGWPPCL RMVAAIAVLTKDAGKLTMGQ PLVILAPHAVEALVKQPPDR WLSNARMTHYQALLLDTDRV QFGPVVALNPATLLPLPEEG LQHNCLDILAEAHGTRPDLT DQPLPDADHTWYTGGSSLLQ EGQRKAGAAVTTETEVIWAK ALPAGTSAQRAQLIALTQAL KMAEGKKLNVYTNSRYAFAT AHIHGEIYRRRGLLTSEGKE IKNKDEILALLKALFLPKRL SIIHCPGHQKGHSAEARGNR MADQAARKAAITETPDTSTL LIENSSPYTSEHF |
| 651 | MMLV RTase with L99N mutation | MTLNIEDEHRLHETSKEPDV SLGSTWLSDFPQAWAETGGM GLAVRQAPLIIPLKATSTPV SIKQYPMSQEARLGIKPHIQ RLLDQGILVPCQSPWNTPLN PVKKPGTNDYRPVQDLREVN KRVEDIHPTVPNPYNLLSGL PPSHQWYTVLDLKDAFFCLR LHPTSQPLFAFEWRDPEMGI SGQLTWTRLPQGFKNSPTLF DEALHRDLADFRIQHPDLIL LQYVDDLLLAATSELDCQQG TRALLQTLGNLGYRASAKKA QICQKQVKYLGYLLKEGQRW LTEARKETVMGQPTPKTPRQ LREFLGTAGFCRLWIPGFAE MAAPLYPLTKTGTLFNWGPD QQKAYQEIKQALLTAPALGL PDLTKPFELFVDEKQGYAKG VLTQKLGPWRRPVAYLSKKL DPVAAGWPPCLRMVAAIAVL TKDAGKLTMGQPLVILAPHA VEALVKQPPDRWLSNARMTH YQALLLDTDRVQFGPVVALN PATLLPLPEEGLQHNCLDIL AEAHGTRPDLTDQPLPDADH TWYTGGSSLLQEGQRKAGAA VTTETEVIWAKALPAGTSAQ RAQLIALTQALKMAEGKKLN VYTNSRYAFATAHIHGEIYR RRGLLTSEGKEIKNKDEILA LLKALFLPKRLSIIHCPGHQ KGHSAEARGNRMADQAARKA AITETPDTSTLLIENSSPYT SEHF |

TABLE 8-continued

Sequences of single mutant MMLV
RTase variants.

| SEQ ID NO: | Construct | Construct Sequence (AA) |
|---|---|---|
| 652 | MMLV RTase with E282M mutation | MTLNIEDEHRLHETSKEPDV SLGSTWLSDFPQAWAETGGM GLAVRQAPLIIPLKATSTPV SIKQYPMSQEARLGIKPHIQ RLLDQGILVPCQSPWNTPLL PVKKPGTNDYRPVQDLREVN KRVEDIHPTVPNPYNLLSGL PPSHQWYTVLDLKDAFFCLR LHPTSQPLFAFEWRDPEMGI SGQLTWTRLPQGFKNSPTLF DEALHRDLADFRIQHPDLIL LQYVDDLLLAATSELDCQQG TRALLQTLGNLGYRASAKKA QICQKQVKYLGYLLKEGQRW LTMARKETVMGQPTPKTPRQ LREFLGTAGFCRLWIPGFAE MAAPLYPLTKTGTLFNWGPD QQKAYQEIKQALLTAPALGL PDLTKPFELFVDEKQGYAKG VLTQKLGPWRRPVAYLSKKL DPVAAGWPPCLRMVAAIAVL TKDAGKLTMGQPLVILAPHA VEALVKQPPDRWLSNARMTH YQALLLDTDRVQFGPVVALN PATLLPLPEEGLQHNCLDIL AEAHGTRPDLTDQPLPDADH TWYTGGSSLLQEGQRKAGAA VTTETEVIWAKALPAGTSAQ RAQLIALTQALKMAEGKKLN VYTNSRYAFATAHIHGEIYR RRGLLTSEGKEIKNKDEILA LLKALFLPKRLSIIHCPGHQ KGHSAEARGNRMADQAARKA AITETPDTSTLLIENSSPYT SEHF |
| 653 | MMLV RTase with E282W mutation | MTLNIEDEHRLHETSKEPDV SLGSTWLSDFPQAWAETGGM GLAVRQAPLIIPLKATSTPV SIKQYPMSQEARLGIKPHIQ RLLDQGILVPCQSPWNTPLL PVKKPGTNDYRPVQDLREVN KRVEDIHPTVPNPYNLLSGL PPSHQWYTVLDLKDAFFCLR LHPTSQPLFAFEWRDPEMGI SGQLTWTRLPQGFKNSPTLF DEALHRDLADFRIQHPDLIL LQYVDDLLLAATSELDCQQG TRALLQTLGNLGYRASAKKA QICQKQVKYLGYLLKEGQRW LTWARKETVMGQPTPKTPRQ LREFLGTAGFCRLWIPGFAE MAAPLYPLTKTGTLFNWGPD QQKAYQEIKQALLTAPALGL PDLTKPFELFVDEKQGYAKG VLTQKLGPWRRPVAYLSKKL DPVAAGWPPCLRMVAAIAVL TKDAGKLTMGQPLVILAPHA VEALVKQPPDRWLSNARMTH YQALLLDTDRVQFGPVVALN PATLLPLPEEGLQHNCLDIL AEAHGTRPDLTDQPLPDADH TWYTGGSSLLQEGQRKAGAA VTTETEVIWAKALPAGTSAQ RAQLIALTQALKMAEGKKLN VYTNSRYAFATAHIHGEIYR RRGLLTSEGKEIKNKDEILA LLKALFLPKRLSIIHCPGHQ KGHSAEARGNRMADQAARKA AITETPDTSTLLIENSSPYT SEHF |

Example 5: Stacking of Reverse Transcriptase Mutants with Enhanced Activity a. MMLV RTase Double Mutants

The MMLV RTase single mutants identified in Example 3 were stacked to further improve the ability of MMLV RTase to synthesize cDNA from purified total RNA (DNased, isolated from HeLa cells) as compared to the MMLV RTase base construct (RNase H minus construct). Fifteen MMLV RTase double mutant variants (see Table 9) were cloned, overexpressed, and purified as described in Examples 1 and 2, and evaluated as described in Example 3. The two-step and one-step reactions for MMLV RTase base construct and MMLV RTase double mutant variants were analyzed and reported by copy number output based on a standard curve (see Tables 10 and 11).

Four of the fifteen MMLV RTase double mutant variants were found to exhibit increased overall activity and thermostability as compared to the other MMLV RTase double mutant variants, and almost all of the MMLV RTase double mutant variants exhibited increased overall activity and thermostability as compared to the MMLV RTase base construct. The four MMLV RTase double mutant variants that were found to exhibit the highest overall activity were E282D/L99R, L99R/Q68R, L99R/Q79R, and Q68R/Q79R.

TABLE 9

Sequences of double mutant MMLV RTase variants.

| SEQ ID NO: | Construct | Construct Sequence (AA) |
|---|---|---|
| 654 | MMLV RTase With I61R/E282D mutations | MTLNIEDEHRLHETSKEPDV SLGSTWLSDFPQAWAETGGM GLAVRQAPLIIPLKATSTPV SRKQYPMSQEARLGIKPHIQ RLLDQGILVPCQSPWNTPLL PVKKPGTNDYRPVQDLREVN KRVEDIHPTVPNPYNLLSGL PPSHQWYTVLDLKDAFFCLR LHPTSQPLFAFEWRDPEMGI SGQLTWTRLPQGFKNSPTLF DEALHRDLADFRIQHPDLIL LQYVDDLLLAATSELDCQQG TRALLQTLGNLGYRASAKKA QICQKQVKYLGYLLKEGQRW LTDARKETVMGQPTPKTPRQ LREFLGTAGFCRLWIPGFAE MAAPLYPLTKTGTLFNWGPD QQKAYQEIKQALLTAPALGL PDLTKPFELFVDEKQGYAKG VLTQKLGPWRRPVAYLSKKL DPVAAGWPPCLRMVAAIAVL TKDAGKLTMGQPLVILAPHA VEALVKQPPDRWLSNARMTH YQALLLDTDRVQFGPVVALN PATLLPLPEEGLQHNCLDIL AEAHGTRPDLTDQPLPDADH TWYTGGSSLLQEGQRKAGAA VTTETEVIWAKALPAGTSAQ RAQLIALTQALKMAEGKKLN VYTNSRYAFATAHIHGEIYR RRGLLTSEGKEIKNKDEILA LLKALFLPKRLSIIHCPGHQ KGHSAEARGNRMADQAARKA AITETPDTSTLLIENSSPYT SEHF |
| 655 | MMLV RTase with L99R/E282D mutations | MTLNIEDEHRLHETSKEPDV SLGSTWLSDFPQAWAETGGM GLAVRQAPLIIPLKATSTPV SIKQYPMSQEARLGIKPHIQ |

TABLE 9-continued

Sequences of double mutant MMLV RTase variants.

| SEQ ID NO: | Construct | Construct Sequence (AA) |
|---|---|---|
| | | RLLDQGILVPCQSPWNTPRL PVKKPGTNDYRPVQDLREVN KRVEDIHPTVPNPYNLLSGL PPSHQWYTVLDLKDAFFCLR LHPTSQPLFAFEWRDPEMGI SGQLTWTRLPQGFKNSPTLF DEALHRDLADFRIQHPDLIL LQYVDDLLLAATSELDCQQG TRALLQTLGNLGYRASAKKA QICQKQVKYLGYLLKEGQRW LTDARKETVMGQPTPKTPRQ LREFLGTAGFCRLWIPGFAE MAAPLYPLTKTGTLFNWGPD QQKAYQEIKQALLTAPALGL PDLTKPFELFVDEKQGYAKG VLTQKLGPWRRPVAYLSKKL DPVAAGWPPCLRMVAAIAVL TKDAGKLTMGQPLVILAPHA VEALVKQPPDRWLSNARMTH YQALLLDTDRVQFGPVVALN PATLLPLPEEGLQHNCLDIL AEAHGTRPDLTDQPLPDADH TWYTGGSSLLQEGQRKAGAA VTTETEVIWAKALPAGTSAQ RAQLIALTQALKMAEGKKLN VYTNSRYAFATAHIHGEIYR RRGLLTSEGKEIKNKDEILA LLKALFLPKRLSIIHCPGHQ KGHSAEARGNRMADQAARKA AITETPDTSTLLIENSSPYT SEHF |
| 656 | MMLV RTase with Q68R/E282D mutations | MTLNIEDEHRLHETSKEPDV SLGSTWLSDFPQAWAETGGM GLAVRQAPLIIPLKATSTPV SIKQYPMSREARLGIKPHIQ RLLDQGILVPCQSPWNTPLL PVKKPGTNDYRPVQDLREVN KRVEDIHPTVPNPYNLLSGL PPSHQWYTVLDLKDAFFCLR LHPTSQPLFAFEWRDPEMGI SGQLTWTRLPQGFKNSPTLF DEALHRDLADFRIQHPDLIL LQYVDDLLLAATSELDCQQG TRALLQTLGNLGYRASAKKA QICQKQVKYLGYLLKEGQRW LTDARKETVMGQPTPKTPRQ LREFLGTAGFCRLWIPGFAE MAAPLYPLTKTGTLFNWGPD QQKAYQEIKQALLTAPALGL PDLTKPFELFVDEKQGYAKG VLTQKLGPWRRPVAYLSKKL DPVAAGWPPCLRMVAAIAVL TKDAGKLTMGQPLVILAPHA VEALVKQPPDRWLSNARMTH YQALLLDTDRVQFGPVVALN PATLLPLPEEGLQHNCLDIL AEAHGTRPDLTDQPLPDADH TWYTGGSSLLQEGQRKAGAA VTTETEVIWAKALPAGTSAQ RAQLIALTQALKMAEGKKLN VYTNSRYAFATAHIHGEIYR RRGLLTSEGKEIKNKDEILA LLKALFLPKRLSIIHCPGHQ KGHSAEARGNRMADQAARKA AITETPDTSTLLIENSSPYT SEHF |
| 657 | MMLV RTase with Q79R/E282D mutations | MTLNIEDEHRLHETSKEPDV SLGSTWLSDFPQAWAETGGM GLAVRQAPLIIPLKATSTPV SIKQYPMSQEARLGIKPHIR RLLDQGILVPCQSPWNTPLL |

TABLE 9-continued

Sequences of double mutant
MMLV RTase variants.

| SEQ ID NO: | Construct | Construct Sequence (AA) |
|---|---|---|
| | | PVKKPGTNDYRPVQDLREVN |
| | | KRVEDIHPTVPNPYNLLSGL |
| | | PPSHQWYTVLDLKDAFFCLR |
| | | LHPTSQPLFAFEWRDPEMGI |
| | | SGQLTWTRLPQGFKNSPTLF |
| | | DEALHRDLADFRIQHPDLIL |
| | | LQYVDDLLLAATSELDCQQG |
| | | TRALLQTLGNLGYRASAKKA |
| | | QICQKQVKYLGYLLKEGQRW |
| | | LTDARKETVMGQPTPKTPRQ |
| | | LREFLGTAGFCRLWIPGFAE |
| | | MAAPLYPLTKTGTLFNWGPD |
| | | QQKAYQEIKQALLTAPALGL |
| | | PDLTKPFELFVDEKQGYAKG |
| | | VLTQKLGPWRRPVAYLSKKL |
| | | DPVAAGWPPCLRMVAAIAVL |
| | | TKDAGKLTMGQPLVILAPHA |
| | | VEALVKQPPDRWLSNARMTH |
| | | YQALLLDTDRVQFGPVVALN |
| | | PATLLPLPEEGLQHNCLDIL |
| | | AEAHGTRPDLTDQPLPDADH |
| | | TWYTGGSSLLQEGQRKAGAA |
| | | VTTETEVIWAKALPAGTSAQ |
| | | RAQLIALTQALKMAEGKKLN |
| | | VYTNSRYAFATAHIHGEIYR |
| | | RRGLLTSEGKEIKNKDEILA |
| | | LLKALFLPKRLSIIHCPGHQ |
| | | KGHSAEARGNRMADQAARKA |
| | | AITETPDTSTLLIENSSPYT |
| | | SEHF |
| 658 | MMLV RTase with E282D/R298A mutations | MTLNIEDEHRLHETSKEPDV |
| | | SLGSTWLSDFPQAWAETGGM |
| | | GLAVRQAPLIIPLKATSTPV |
| | | SIKQYPMSQEARLGIKPHIQ |
| | | RLLDQGILVPCQSPWNTPLL |
| | | PVKKPGTNDYRPVQDLREVN |
| | | KRVEDIHPTVPNPYNLLSGL |
| | | PPSHQWYTVLDLKDAFFCLR |
| | | LHPTSQPLFAFEWRDPEMGI |
| | | SGQLTWTRLPQGFKNSPTLF |
| | | DEALHRDLADFRIQHPDLIL |
| | | LQYVDDLLLAATSELDCQQG |
| | | TRALLQTLGNLGYRASAKKA |
| | | QICQKQVKYLGYLLKEGQRW |
| | | LTDARKETVMGQPTPKTPAQ |
| | | LREFLGTAGFCRLWIPGFAE |
| | | MAAPLYPLTKTGTLFNWGPD |
| | | QQKAYQEIKQALLTAPALGL |
| | | PDLTKPFELFVDEKQGYAKG |
| | | VLTQKLGPWRRPVAYLSKKL |
| | | DPVAAGWPPCLRMVAAIAVL |
| | | TKDAGKLTMGQPLVILAPHA |
| | | VEALVKQPPDRWLSNARMTH |
| | | YQALLLDTDRVQFGPVVALN |
| | | PATLLPLPEEGLQHNCLDIL |
| | | AEAHGTRPDLTDQPLPDADH |
| | | TWYTGGSSLLQEGQRKAGAA |
| | | VTTETEVIWAKALPAGTSAQ |
| | | RAQLIALTQALKMAEGKKLN |
| | | VYTNSRYAFATAHIHGEIYR |
| | | RRGLLTSEGKEIKNKDEILA |
| | | LLKALFLPKRLSIIHCPGHQ |
| | | KGHSAEARGNRMADQAARKA |
| | | AITETPDTSTLLIENSSPYT |
| | | SEHF |
| 659 | MMLV RTase with I61R/L99R mutations | MTLNIEDEHRLHETSKEPDV |
| | | SLGSTWLSDFPQAWAETGGM |
| | | GLAVRQAPLIIPLKATSTPV |
| | | SRKQYPMSQEARLGIKPHIQ |
| | | RLLDQGILVPCQSPWNTPLR |
| | | PVKKPGTNDYRPVQDLREVN |

TABLE 9-continued

Sequences of double mutant
MMLV RTase variants.

| SEQ ID NO: | Construct | Construct Sequence (AA) |
|---|---|---|
| | | KRVEDIHPTVPNPYNLLSGL |
| | | PPSHQWYTVLDLKDAFFCLR |
| | | LHPTSQPLFAFEWRDPEMGI |
| | | SGQLTWTRLPQGFKNSPTLF |
| | | DEALHRDLADFRIQHPDLIL |
| | | LQYVDDLLLAATSELDCQQG |
| | | TRALLQTLGNLGYRASAKKA |
| | | QICQKQVKYLGYLLKEGQRW |
| | | LTEARKETVMGQPTPKTPRQ |
| | | LREFLGTAGFCRLWIPGFAE |
| | | MAAPLYPLTKTGTLFNWGPD |
| | | QQKAYQEIKQALLTAPALGL |
| | | PDLTKPFELFVDEKQGYAKG |
| | | VLTQKLGPWRRPVAYLSKKL |
| | | DPVAAGWPPCLRMVAAIAVL |
| | | TKDAGKLTMGQPLVILAPHA |
| | | VEALVKQPPDRWLSNARMTH |
| | | YQALLLDTDRVQFGPVVALN |
| | | PATLLPLPEEGLQHNCLDIL |
| | | AEAHGTRPDLTDQPLPDADH |
| | | TWYTGGSSLLQEGQRKAGAA |
| | | VTTETEVIWAKALPAGTSAQ |
| | | RAQLIALTQALKMAEGKKLN |
| | | VYTNSRYAFATAHIHGEIYR |
| | | RRGLLTSEGKEIKNKDEILA |
| | | LLKALFLPKRLSIIHCPGHQ |
| | | KGHSAEARGNRMADQAARKA |
| | | AITETPDTSTLLIENSSPYT |
| | | SEHF |
| 660 | MMLV RTase with I61R/Q68R mutations | MTLNIEDEHRLHETSKEPDV |
| | | SLGSTWLSDFPQAWAETGGM |
| | | GLAVRQAPLIIPLKATSTPV |
| | | SRKQYPMSREARLGIKPHIQ |
| | | RLLDQGILVPCQSPWNTPLL |
| | | PVKKPGTNDYRPVQDLREVN |
| | | KRVEDIHPTVPNPYNLLSGL |
| | | PPSHQWYTVLDLKDAFFCLR |
| | | LHPTSQPLFAFEWRDPEMGI |
| | | SGQLTWTRLPQGFKNSPTLF |
| | | DEALHRDLADFRIQHPDLIL |
| | | LQYVDDLLLAATSELDCQQG |
| | | TRALLQTLGNLGYRASAKKA |
| | | QICQKQVKYLGYLLKEGQRW |
| | | LTEARKETVMGQPTPKTPRQ |
| | | LREFLGTAGFCRLWIPGFAE |
| | | MAAPLYPLTKTGTLFNWGPD |
| | | QQKAYQEIKQALLTAPALGL |
| | | PDLTKPFELFVDEKQGYAKG |
| | | VLTQKLGPWRRPVAYLSKKL |
| | | DPVAAGWPPCLRMVAAIAVL |
| | | TKDAGKLTMGQPLVILAPHA |
| | | VEALVKQPPDRWLSNARMTH |
| | | YQALLLDTDRVQFGPVVALN |
| | | PATLLPLPEEGLQHNCLDIL |
| | | AEAHGTRPDLTDQPLPDADH |
| | | TWYTGGSSLLQEGQRKAGAA |
| | | VTTETEVIWAKALPAGTSAQ |
| | | RAQLIALTQALKMAEGKKLN |
| | | VYTNSRYAFATAHIHGEIYR |
| | | RRGLLTSEGKEIKNKDEILA |
| | | LLKALFLPKRLSIIHCPGHQ |
| | | KGHSAEARGNRMADQAARKA |
| | | AITETPDTSTLLIENSSPYT |
| | | SEH |
| 661 | MMLV RTase with I61R/Q79R mutations | MTLNIEDEHRLHETSKEPDV |
| | | SLGSTWLSDFPQAWAETGGM |
| | | GLAVRQAPLIIPLKATSTPV |
| | | SRKQYPMSQEARLGIKPHIR |
| | | RLLDQGILVPCQSPWNTPLL |
| | | PVKKPGTNDYRPVQDLREVN |
| | | KRVEDIHPTVPNPYNLLSGL |

TABLE 9-continued

Sequences of double mutant
MMLV RTase variants.

| SEQ ID NO: | Construct | Construct Sequence (AA) |
|---|---|---|
| | | PPSHQWYTVLDLKDAFFCLR LHPTSQPLFAFEWRDPEMGI SGQLTWTRLPQGFKNSPTLF DEALHRDLADFRIQHPDLIL LQYVDDLLLAATSELDCQQG TRALLQTLGNLGYRASAKKA QICQKQVKYLGYLLKEGQRW LTEARKETVMGQPTPKTPRQ LREFLGTAGFCRLWIPGFAE MAAPLYPLTKTGTLFNWGPD QQKAYQEIKQALLTAPALGL PDLTKPFELFVDEKQGYAKG VLTQKLGPWRRPVAYLSKKL DPVAAGWPPCLRMVAAIAVL TKDAGKLTMGQPLVILAPHA VEALVKQPPDRWLSNARMTH YQALLLDTDRVQFGPVVALN PATLLPLPEEGLQHNCLDIL AEAHGTRPDLTDQPLPDADH TWYTGGSSLLQEGQRKAGAA VTTETEVIWAKALPAGTSAQ RAQLIALTQALKMAEGKKLN VYTNSRYAFATAHIHGEIYR RRGLLTSEGKEIKNKDEILA LLKALFLPKRLSIIHCPGHQ KGHSAEARGNRMADQAARKA AITETPDTSTLLIENSSPYT SEHF |
| 662 | MMLV RTase with I61R/R298A mutations | MTLNIEDEHRLHETSKEPDV SLGSTWLSDFPQAWAETGGM GLAVRQAPLIIPLKATSTPV SRKQYPMSQEARLGIKPHIQ RLLDQGILVPCQSPWNTPLL PVKKPGTNDYRPVQDLREVN KRVEDIHPTVPNPYNLLSGL PPSHQWYTVLDLKDAFFCLR LHPTSQPLFAFEWRDPEMGI SGQLTWTRLPQGFKNSPTLF DEALHRDLADFRIQHPDLIL LQYVDDLLLAATSELDCQQG TRALLQTLGNLGYRASAKKA QICQKQVKYLGYLLKEGQRW LTEARKETVMGQPTPKTPAQ LREFLGTAGFCRLWIPGFAE MAAPLYPLTKTGTLFNWGPD QQKAYQEIKQALLTAPALGL PDLTKPFELFVDEKQGYAKG VLTQKLGPWRRPVAYLSKKL DPVAAGWPPCLRMVAAIAVL TKDAGKLTMGQPLVILAPHA VEALVKQPPDRWLSNARMTH YQALLLDTDRVQFGPVVALN PATLLPLPEEGLQHNCLDIL AEAHGTRPDLTDQPLPDADH TWYTGGSSLLQEGQRKAGAA VTTETEVIWAKALPAGTSAQ RAQLIALTQALKMAEGKKLN VYTNSRYAFATAHIHGEIYR RRGLLTSEGKEIKNKDEILA LLKALFLPKRLSIIHCPGHQ KGHSAEARGNRMADQAARKA AITETPDTSTLLIENSSPYT SEHF |
| 663 | MMLV RTase with Q68R/L99R mutations | MTLNIEDEHRLHETSKEPDV SLGSTWLSDFPQAWAETGGM GLAVRQAPLIIPLKATSTPV SIKQYPMSREARLGIKPHIQ RLLDQGILVPCQSPWNTPLR PVKKPGTNDYRPVQDLREVN KRVEDIHPTVPNPYNLLSGL PPSHQWYTVLDLKDAFFCLR |

TABLE 9-continued

Sequences of double mutant
MMLV RTase variants.

| SEQ ID NO: | Construct | Construct Sequence (AA) |
|---|---|---|
| | | LHPTSQPLFAFEWRDPEMGI SGQLTWTRLPQGFKNSPTLF DEALHRDLADFRIQHPDLIL LQYVDDLLLAATSELDCQQG TRALLQTLGNLGYRASAKKA QICQKQVKYLGYLLKEGQRW LTEARKETVMGQPTPKTPRQ LREFLGTAGFCRLWIPGFAE MAAPLYPLTKTGTLFNWGPD QQKAYQEIKQALLTAPALGL PDLTKPFELFVDEKQGYAKG VLTQKLGPWRRPVAYLSKKL DPVAAGWPPCLRMVAAIAVL TKDAGKLTMGQPLVILAPHA VEALVKQPPDRWLSNARMTH YQALLLDTDRVQFGPVVALN PATLLPLPEEGLQHNCLDIL AEAHGTRPDLTDQPLPDADH TWYTGGSSLLQEGQRKAGAA VTTETEVIWAKALPAGTSAQ RAQLIALTQALKMAEGKKLN VYTNSRYAFATAHIHGEIYR RRGLLTSEGKEIKNKDEILA LLKALFLPKRLSIIHCPGHQ KGHSAEARGNRMADQAARKA AITETPDTSTLLIENSSPYT SEHF |
| 664 | MMLV RTase with Q79R/L99R mutations | MTLNIEDEHRLHETSKEPDV SLGSTWLSDFPQAWAETGGM GLAVRQAPLIIPLKATSTPV SIKQYPMSQEARLGIKPHIR RLLDQGILVPCQSPWNTPLR PVKKPGTNDYRPVQDLREVN KRVEDIHPTVPNPYNLLSGL PPSHQWYTVLDLKDAFFCLR LHPTSQPLFAFEWRDPEMGI SGQLTWTRLPQGFKNSPTLF DEALHRDLADFRIQHPDLIL LQYVDDLLLAATSELDCQQG TRALLQTLGNLGYRASAKKA QICQKQVKYLGYLLKEGQRW LTEARKETVMGQPTPKTPRQ LREFLGTAGFCRLWIPGFAE MAAPLYPLTKTGTLFNWGPD QQKAYQEIKQALLTAPALGL PDLTKPFELFVDEKQGYAKG VLTQKLGPWRRPVAYLSKKL DPVAAGWPPCLRMVAAIAVL TKDAGKLTMGQPLVILAPHA VEALVKQPPDRWLSNARMTH YQALLLDTDRVQFGPVVALN PATLLPLPEEGLQHNCLDIL AEAHGTRPDLTDQPLPDADH TWYTGGSSLLQEGQRKAGAA VTTETEVIWAKALPAGTSAQ RAQLIALTQALKMAEGKKLN VYTNSRYAFATAHIHGEIYR RRGLLTSEGKEIKNKDEILA LLKALFLPKRLSIIHCPGHQ KGHSAEARGNRMADQAARKA AITETPDTSTLLIENSSPYT SEHF |
| 665 | MMLV RTase with L99R/R298A mutations | MTLNIEDEHRLHETSKEPDV SLGSTWLSDFPQAWAETGGM GLAVRQAPLIIPLKATSTPV SIKQYPMSQEARLGIKPHIQ RLLDQGILVPCQSPWNTPLR PVKKPGTNDYRPVQDLREVN KRVEDIHPTVPNPYNLLSGL PPSHQWYTVLDLKDAFFCLR LHPTSQPLFAFEWRDPEMGI |

TABLE 9-continued

Sequences of double mutant
MMLV RTase variants.

| SEQ ID NO: | Construct | Construct Sequence (AA) |
|---|---|---|
| | | SGQLTWTRLPQGFKNSPTLF |
| | | DEALHRDLADFRIQHPDLIL |
| | | LQYVDDLLLAATSELDCQQG |
| | | TRALLQTLGNLGYRASAKKA |
| | | QICQKQVKYLGYLLKEGQRW |
| | | LTEARKETVMGQPTPKTPAQ |
| | | LREFLGTAGFCRLWIPGFAE |
| | | MAAPLYPLTKTGTLFNWGPD |
| | | QQKAYQEIKQALLTAPALGL |
| | | PDLTKPFELFVDEKQGYAKG |
| | | VLTQKLGPWRRPVAYLSKKL |
| | | DPVAAGWPPCLRMVAAIAVL |
| | | TKDAGKLTMGQPLVILAPHA |
| | | VEALVKQPPDRWLSNARMTH |
| | | YQALLLDTDRVQFGPVVALN |
| | | PATLLPLPEEGLQHNCLDIL |
| | | AEAHGTRPDLTDQPLPDADH |
| | | TWYTGGSSLLQEGQRKAGAA |
| | | VTTETEVIWAKALPAGTSAQ |
| | | RAQLIALTQALKMAEGKKLN |
| | | VYTNSRYAFATAHIHGEIYR |
| | | RRGLLTSEGKEIKNKDEILA |
| | | LLKALFLPKRLSIIHCPGHQ |
| | | KGHSAEARGNRMADQAARKA |
| | | AITETPDTSTLLIENSSPYT |
| | | SEHF |
| 666 | MMLV RTase with Q68R/Q79R mutations | MTLNIEDEHRLHETSKEPDV SLGSTWLSDFPQAWAETGGM GLAVRQAPLIIPLKATSTPV SIKQYPMSREARLGIKPHIR RLLDQGILVPCQSPWNTPLL PVKKPGTNDYRPVQDLREVN KRVEDIHPTVPNPYNLLSGL PPSHQWYTVLDLKDAFFCLR LHPTSQPLFAFEWRDPEMGI SGQLTWTRLPQGFKNSPTLF DEALHRDLADFRIQHPDLIL LQYVDDLLLAATSELDCQQG TRALLQTLGNLGYRASAKKA QICQKQVKYLGYLLKEGQRW LTEARKETVMGQPTPKTPRQ LREFLGTAGFCRLWIPGFAE MAAPLYPLTKTGTLFNWGPD QQKAYQEIKQALLTAPALGL PDLTKPFELFVDEKQGYAKG VLTQKLGPWRRPVAYLSKKL DPVAAGWPPCLRMVAAIAVL TKDAGKLTMGQPLVILAPHA VEALVKQPPDRWLSNARMTH YQALLLDTDRVQFGPVVALN PATLLPLPEEGLQHNCLDIL AEAHGTRPDLTDQPLPDADH TWYTGGSSLLQEGQRKAGAA VTTETEVIWAKALPAGTSAQ RAQLIALTQALKMAEGKKLN VYTNSRYAFATAHIHGEIYR RRGLLTSEGKEIKNKDEILA LLKALFLPKRLSIIHCPGHQ KGHSAEARGNRMADQAARKA AITETPDTSTLLIENSSPYT SEHF |
| 667 | MMLV RTase with Q68R/R298A mutations | MTLNIEDEHRLHETSKEPDV SLGSTWLSDFPQAWAETGGM GLAVRQAPLIIPLKATSTPV SIKQYPMSREARLGIKPHIQ RLLDQGILVPCQSPWNTPLL PVKKPGTNDYRPVQDLREVN KRVEDIHPTVPNPYNLLSGL PPSHQWYTVLDLKDAFFCLR LHPTSQPLFAFEWRDPEMGI SGQLTWTRLPQGFKNSPTLF |

TABLE 9-continued

Sequences of double mutant
MMLV RTase variants.

| SEQ ID NO: | Construct | Construct Sequence (AA) |
|---|---|---|
| | | DEALHRDLADFRIQHPDLIL |
| | | LQYVDDLLLAATSELDCQQG |
| | | TRALLQTLGNLGYRASAKKA |
| | | QICQKQVKYLGYLLKEGQRW |
| | | LTEARKETVMGQPTPKTPAQ |
| | | LREFLGTAGFCRLWIPGFAE |
| | | MAAPLYPLTKTGTLFNWGPD |
| | | QQKAYQEIKQALLTAPALGL |
| | | PDLTKPFELFVDEKQGYAKG |
| | | VLTQKLGPWRRPVAYLSKKL |
| | | DPVAAGWPPCLRMVAAIAVL |
| | | TKDAGKLTMGQPLVILAPHA |
| | | VEALVKQPPDRWLSNARMTH |
| | | YQALLLDTDRVQFGPVVALN |
| | | PATLLPLPEEGLQHNCLDIL |
| | | AEAHGTRPDLTDQPLPDADH |
| | | TWYTGGSSLLQEGQRKAGAA |
| | | VTTETEVIWAKALPAGTSAQ |
| | | RAQLIALTQALKMAEGKKLN |
| | | VYTNSRYAFATAHIHGEIYR |
| | | RRGLLTSEGKEIKNKDEILA |
| | | LLKALFLPKRLSIIHCPGHQ |
| | | KGHSAEARGNRMADQAARKA |
| | | AITETPDTSTLLIENSSPYT |
| | | SEHF |
| 668 | MMLV RTase with Q79R/R298A mutations | MTLNIEDEHRLHETSKEPDV SLGSTWLSDFPQAWAETGGM GLAVRQAPLIIPLKATSTPV SIKQYPMSQEARLGIKPHIR RLLDQGILVPCQSPWNTPLL PVKKPGTNDYRPVQDLREVN KRVEDIHPTVPNPYNLLSGL PPSHQWYTVLDLKDAFFCLR LHPTSQPLFAFEWRDPEMGI SGQLTWTRLPQGFKNSPTLF DEALHRDLADFRIQHPDLIL LQYVDDLLLAATSELDCQQG TRALLQTLGNLGYRASAKKA QICQKQVKYLGYLLKEGQRW LTEARKETVMGQPTPKTPAQ LREFLGTAGFCRLWIPGFAE MAAPLYPLTKTGTLFNWGPD QQKAYQEIKQALLTKPFELF VDEKQGYAKGVLTQKLGPWR RPVAYLSKKLDPVAAGWPPC LRMVAAIAVLTKDAGKLTMG QPLVILAPHAVEALVKQPPD RWLSNARMTHYQALLLDTDR VQFGPVVALNPATLLPLPEE GLQHNCLDILAEAHGTRPDL TDQPLPDADHTWYTGGSSLL QEGQRKAGAAVTTETEVIWA KALPAGTSAQRAQLIALTQA LKMAEGKKLNVYTNSRYAFA TAHIHGEIYRRRGLLTSEGK EIKNKDEILALLKALFLPKR LSIIHCPGHQKGHSAEARGN RMADQAARKAAITETPDTST LLIENSSPYTSEHFTAPALG LPDL |

TABLE 10

Two-Step cDNA synthesis by MMLV RT double mutants.
Data was generated via qPCR human normalizer assay
and data is translated by copy number.

| MMLV RT Variant | Quantity Mean | Quantity Standard Deviation |
|---|---|---|
| MMLV-II | 1,773.623 | 5.057 |
| MMLV-II E282D/I61R | 4,810.277 | 143.422 |
| MMLV-II E282D/L99R | 7,266.281 | 50.730 |
| MMLV-II E282D/Q68R | 5,186.392 | 69.563 |
| MMLV-II E282D/Q79R | 4,311.403 | 95.402 |
| MMLV-II E282D/R298A | 1,366.524 | 16.429 |
| MMLV-II I61R/L99R | 6,061.812 | 174.619 |
| MMLV-II I61R/Q68R | 5,899.316 | 39.879 |
| MMLV-II I61R/Q79R | 5,257.089 | 98.378 |
| MMLV-II I61R/R298A | 2,661.223 | 68.948 |
| MMLV-II L99R/Q68R | 7,750.519 | 94.408 |
| MMLV-II L99R/Q79R | 7,455.203 | 124.095 |
| MMLV-II L99R/R298A | 5,351.021 | 179.558 |
| MMLV-II Q68R/Q79R | 7,178.681 | 86.595 |
| MMLV-II Q68R/R298A | 4,524.340 | 84.703 |
| MMLV-II Q79R/R298A | 3,739.608 | 58.621 |
| MMLV-IV | 8,258.715 | 79.458 |

TABLE 11

One-Step cDNA synthesis by MMLV RT double mutants.
Data was generated via qPCR human normalizer assay
and data is translated by copy number.

| MMLV-RT Variant | Quantity Mean | Quantity Standard Deviation |
|---|---|---|
| MMLV-II | 859.127 | 24.795 |
| MMLV-II E282D/I61R | 2,948.906 | 49.177 |
| MMLV-II E282D/L99R | 4,814.957 | 239.110 |
| MMLV-II E282D/Q68R | 3,709.046 | 131.434 |
| MMLV-II E282D/Q79R | 3,694.187 | 98.772 |
| MMLV-II E282D/R298A | 794.643 | 39.913 |
| MMLV-II I61R/L99R | 3,443.713 | 180.210 |
| MMLV-II I61R/Q68R | 3,525.138 | 112.288 |
| MMLV-II I61R/Q79R | 3,125.990 | 120.996 |
| MMLV-II I61R/R298A | 2,006.208 | 83.559 |
| MMLV-II L99R/Q68R | 6,755.852 | 102.788 |
| MMLV-II L99R/Q79R | 6,709.502 | 35.997 |
| MMLV-II L99R/R298A | 2,128.451 | 55.565 |
| MMLV-II Q68R/Q79R | 6,343.821 | 140.779 |
| MMLV-II Q68R/R298A | 2,406.470 | 74.117 |
| MMLV-II Q79R/R298A | 2,301.759 | 22.849 |
| MMLV-IV | 15,411.857 | 333.388 | b. Cloning of MMLV RTase Triple and More Mutants

Following the double mutant variants, MMLV RTase single mutants were stacked further to improve the ability of MMLV RTase to synthesize cDNA from purified total RNA (DNased, isolated from HeLa cells) as compared to the MMLV RTase base construct (RNase H minus construct). Seventeen MMLV RTase triple or more mutant variants (see Table 12) were cloned as described in Example 1.

TABLE 12

Sequences of triple or more mutant
MMLV RTase variants.

| SEQ ID NO: | Construct | Construct Sequence (AA) |
|---|---|---|
| 669 | MMLV RTase with Q68R/ L99R/ E282D mutations | MTLNIEDEHRLHETSKEPDV SLGSTWLSDFPQAWAETGGM GLAVRQAPLIIPLKATSTPV SIKQYPMSREARLGIKPHIQ RLLDQGILVPCQSPWNTPLR PVKKPGTNDYRPVQDLREVN KRVEDIHPTVPNPYNLLSGL |

TABLE 12-continued

Sequences of triple or more mutant
MMLV RTase variants.

| SEQ ID NO: | Construct | Construct Sequence (AA) |
|---|---|---|
| | | PPSHQWYTVLDLKDAFFCLR LHPTSQPLFAFEWRDPEMGI SGQLTWTRLPQGFKNSPTLF DEALHRDLADFRIQHPDLIL LQYVDDLLLAATSELDCQQG TRALLQTLGNLGYRASAKKA QICQKQVKYLGYLLKEGQRW LTDARKETVMGQPTPKTPRQ LREFLGTAGFCRLWIPGFAE MAAPLYPLTKTGTLFNWGPD QQKAYQEIKQALLTAPALGL PDLTKPFELFVDEKQGYAKG VLTQKLGPWRRPVAYLSKKL DPVAAGWPPCLRMVAAIAVL TKDAGKLTMGQPLVILAPHA VEALVKQPPDRWLSNARMTH YQALLLDTDRVQFGPVVALN PATLLPLPEEGLQHNCLDIL AEAHGTRPDLTDQPLPDADH TWYTGGSSLLQEGQRKAGAA VTTETEVIWAKALPAGTSAQ RAQLIALTQALKMAEGKKLN VYTNSRYAFATAHIHGEIYR RRGLLTSEGKEIKNKDEILA LLKALFLPKRLSIIHCPGHQ KGHSAEARGNRMADQAARKA AITETPDTSTLLIENSSPYT SEHF |
| 670 | MMLV RTase with Q79R/ L99R/ E282D mutations | MTLNIEDEHRLHETSKEPDV SLGSTWLSDFPQAWAETGGM GLAVRQAPLIIPLKATSTPV SIKQYPMSQEARLGIKPHIR RLLDQGILVPCQSPWNTPLR PVKKPGTNDYRPVQDLREVN KRVEDIHPTVPNPYNLLSGL PPSHQWYTVLDLKDAFFCLR LHPTSQPLFAFEWRDPEMGI SGQLTWTRLPQGFKNSPTLF DEALHRDLADFRIQHPDLIL LQYVDDLLLAATSELDCQQG TRALLQTLGNLGYRASAKKA QICQKQVKYLGYLLKEGQRW LTDARKETVMGQPTPKTPRQ LREFLGTAGFCRLWIPGFAE MAAPLYPLTKTGTLFNWGPD QQKAYQEIKQALLTAPALGL PDLTKPFELFVDEKQGYAKG VLTQKLGPWRRPVAYLSKKL DPVAAGWPPCLRMVAAIAVL TKDAGKLTMGQPLVILAPHA VEALVKQPPDRWLSNARMTH YQALLLDTDRVQFGPVVALN PATLLPLPEEGLQHNCLDIL AEAHGTRPDLTDQPLPDADH TWYTGGSSLLQEGQRKAGAA VTTETEVIWAKALPAGTSAQ RAQLIALTQALKMAEGKKLN VYTNSRYAFATAHIHGEIYR RRGLLTSEGKEIKNKDEILA LLKALFLPKRLSIIHCPGHQ KGHSAEARGNRMADQAARKA AITETPDTSTLLIENSSPYT SEHF |
| 671 | MMLV RTase with Q68R/ Q79R/ E282D mutations | MTLNIEDEHRLHETSKEPDV SLGSTWLSDFPQAWAETGGM GLAVRQAPLIIPLKATSTPV SIKQYPMSREARLGIKPHIR RLLDQGILVPCQSPWNTPLL PVKKPGTNDYRPVQDLREVN KRVEDIHPTVPNPYNLLSGL PPSHQWYTVLDLKDAFFCLR |

TABLE 12-continued

Sequences of triple or more mutant
MMLV RTase variants.

| SEQ ID NO: | Construct | Construct Sequence (AA) |
|---|---|---|
| | | LHPTSQPLFAFEWRDPEMGI SGQLTWTRLPQGFKNSPTLF DEALHRDLADFRIQHPDLIL LQYVDDLLLAATSELDCQQG TRALLQTLGNLGYRASAKKA QICQKQVKYLGYLLKEGQRW LTDARKETVMGQPTPKTPRQ LREFLGTAGFCRLWIPGFAE MAAPLYPLTKTGTLFNWGPD QQKAYQEIKQALLTAPALGL PDLTKPFELFVDEKQGYAKG VLTQKLGPWRRPVAYLSKKL DPVAAGWPPCLRMVAAIAVL TKDAGKLTMGQPLVILAPHA VEALVKQPPDRWLSNARMTH YQALLLDTDRVQFGPVVALN PATLLPLPEEGLQHNCLDIL AEAHGTRPDLTDQPLPDADH TWYTGGSSLLQEGQRKAGAA VTTETEVIWAKALPAGTSAQ RAQLIALTQALKMAEGKKLN VYTNSRYAFATAHIHGEIYR RRGLLTSEGKEIKNKDEILA LLKALFLPKRLSIIHCPGHQ KGHSAEARGNRMADQAARKA AITETPDTSTLLIENSSPYT SEHF |
| 672 | MMLV RTase with Q68R/ Q79R/ L99R mutations | MTLNIEDEHRLHETSKEPDV SLGSTWLSDFPQAWAETGGM GLAVRQAPLIIPLKATSTPV SIKQYPMSREARLGIKPHIR RLLDQGILVPCQSPWNTPLR PVKKPGTNDYRPVQDLREVN KRVEDIHPTVPNPYNLLSGL PPSHQWYTVLDLKDAFFCLR LHPTSQPLFAFEWRDPEMGI SGQLTWTRLPQGFKNSPTLF DEALHRDLADFRIQHPDLIL LQYVDDLLLAATSELDCQQG TRALLQTLGNLGYRASAKKA QICQKQVKYLGYLLKEGQRW LTEARKETVMGQPTPKTPRQ LREFLGTAGFCRLWIPGFAE MAAPLYPLTKTGTLFNWGPD QQKAYQEIKQALLTAPALGL PDLTKPFELFVDEKQGYAKG VLTQKLGPWRRPVAYLSKKL DPVAAGWPPCLRMVAAIAVL TKDAGKLTMGQPLVILAPHA VEALVKQPPDRWLSNARMTH YQALLLDTDRVQFGPVVALN PATLLPLPEEGLQHNCLDIL AEAHGTRPDLTDQPLPDADH TWYTGGSSLLQEGQRKAGAA VTTETEVIWAKALPAGTSAQ RAQLIALTQALKMAEGKKLN VYTNSRYAFATAHIHGEIYR RRGLLTSEGKEIKNKDEILA LLKALFLPKRLSIIHCPGHQ KGHSAEARGNRMADQAARKA AITETPDTSTLLIENSSPYT SEHF |
| 673 | MMLV RTase with Q68R/ Q79R/ L99R/ E282D mutations | MTLNIEDEHRLHETSKEPDV SLGSTWLSDFPQAWAETGGM GLAVRQAPLIIPLKATSTPV SIKQYPMSREARLGIKPHIR RLLDQGILVPCQSPWNTPLR PVKKPGTNDYRPVQDLREVN KRVEDIHPTVPNPYNLLSGL PPSHQWYTVLDLKDAFFCLR LHPTSQPLFAFEWRDPEMGI |

TABLE 12-continued

Sequences of triple or more mutant
MMLV RTase variants.

| SEQ ID NO: | Construct | Construct Sequence (AA) |
|---|---|---|
| | | SGQLTWTRLPQGFKNSPTLF DEALHRDLADFRIQHPDLIL LQYVDDLLLAATSELDCQQG TRALLQTLGNLGYRASAKKA QICQKQVKYLGYLLKEGQRW LTDARKETVMGQPTPKTPRQ LREFLGTAGFCRLWIPGFAE MAAPLYPLTKTGTLFNWGPD QQKAYQEIKQALLTAPALGL PDLTKPFELFVDEKQGYAKG VLTQKLGPWRRPVAYLSKKL DPVAAGWPPCLRMVAAIAVL TKDAGKLTMGQPLVILAPHA VEALVKQPPDRWLSNARMTH YQALLLDTDRVQFGPVVALN PATLLPLPEEGLQHNCLDIL AEAHGTRPDLTDQPLPDADH TWYTGGSSLLQEGQRKAGAA VTTETEVIWAKALPAGTSAQ RAQLIALTQALKMAEGKKLN VYTNSRYAFATAHIHGEIYR RRGLLTSEGKEIKNKDEILA LLKALFLPKRLSIIHCPGHQ KGHSAEARGNRMADQAARKA AITETPDTSTLLIENSSPYT SEHF |
| 674 | MMLV RTase with Q68R/ Q79R/ L99K/ E282D mutations | MTLNIEDEHRLHETSKEPDV SLGSTWLSDFPQAWAETGGM GLAVRQAPLIIPLKATSTPV SIKQYPMSREARLGIKPHIR RLLDQGILVPCQSPWNTPLK PVKKPGTNDYRPVQDLREVN KRVEDIHPTVPNPYNLLSGL PPSHQWYTVLDLKDAFFCLR LHPTSQPLFAFEWRDPEMGI SGQLTWTRLPQGFKNSPTLF DEALHRDLADFRIQHPDLIL LQYVDDLLLAATSELDCQQG TRALLQTLGNLGYRASAKKA QICQKQVKYLGYLLKEGQRW LTDARKETVMGQPTPKTPRQ LREFLGTAGFCRLWIPGFAE MAAPLYPLTKTGTLFNWGPD QQKAYQEIKQALLTAPALGL PDLTKPFELFVDEKQGYAKG VLTQKLGPWRRPVAYLSKKL DPVAAGWPPCLRMVAAIAVL TKDAGKLTMGQPLVILAPHA VEALVKQPPDRWLSNARMTH YQALLLDTDRVQFGPVVALN PATLLPLPEEGLQHNCLDIL AEAHGTRPDLTDQPLPDADH TWYTGGSSLLQEGQRKAGAA VTTETEVIWAKALPAGTSAQ RAQLIALTQALKMAEGKKLN VYTNSRYAFATAHIHGEIYR RRGLLTSEGKEIKNKDEILA LLKALFLPKRLSIIHCPGHQ KGHSAEARGNRMADQAARKA AITETPDTSTLLIENSSPYT SEHF |
| 675 | MMLV RTase with Q68R/ Q79R/ L99N/ E282D mutations | MTLNIEDEHRLHETSKEPDV SLGSTWLSDFPQAWAETGGM GLAVRQAPLIIPLKATSTPV SIKQYPMSREARLGIKPHIR RLLDQGILVPCQSPWNTPLN PVKKPGTNDYRPVQDLREVN KRVEDIHPTVPNPYNLLSGL PPSHQWYTVLDLKDAFFCLR LHPTSQPLFAFEWRDPEMGI SGQLTWTRLPQGFKNSPTLF |

TABLE 12-continued

Sequences of triple or more mutant
MMLV RTase variants.

| SEQ ID NO: | Construct | Construct Sequence (AA) |
|---|---|---|
| | | DEALHRDLADFRIQHPDLIL |
| | | LQYVDDLLLAATSELDCQQG |
| | | TRALLQTLGNLGYRASAKKA |
| | | QICQKQVKYLGYLLKEGQRW |
| | | LTDARKETVMGQPTPKTPRQ |
| | | LREFLGTAGFCRLWIPGFAE |
| | | MAAPLYPLTKTGTLFNWGPD |
| | | QQKAYQEIKQALLTAPALGL |
| | | PDLTKPFELFVDEKQGYAKG |
| | | VLTQKLGPWRRPVAYLSKKL |
| | | DPVAAGWPPCLRMVAAIAVL |
| | | TKDAGKLTMGQPLVILAPHA |
| | | VEALVKQPPDRWLSNARMTH |
| | | YQALLLDTDRVQFGPVVALN |
| | | PATLLPLPEEGLQHNCLDIL |
| | | AEAHGTRPDLTDQPLPDADH |
| | | TWYTGGSSLLQEGQRKAGAA |
| | | VTTETEVIWAKALPAGTSAQ |
| | | RAQLIALTQALKMAEGKKLN |
| | | VYTNSRYAFATAHIHGEIYR |
| | | RRGLLTSEGKEIKNKDEILA |
| | | LLKALFLPKRLSIIHCPGHQ |
| | | KGHSAEARGNRMADQAARKA |
| | | AITETPDTSTLLIENSSPYT |
| | | SEHF |
| 676 | MMLV RTase with Q68I/ Q79R/ L99R/ E282D mutations | MTLNIEDEHRLHETSKEPDV SLGSTWLSDFPQAWAETGGM GLAVRQAPLIIPLKATSTPV SIKQYPMSIEARLGIKPHIR RLLDQGILVPCQSPWNTPLR PVKKPGTNDYRPVQDLREVN KRVEDIHPTVPNPYNLLSGL PPSHQWYTVLDLKDAFFCLR LHPTSQPLFAFEWRDPEMGI SGQLTWTRLPQGFKNSPTLF DEALHRDLADFRIQHPDLIL LQYVDDLLLAATSELDCQQG TRALLQTLGNLGYRASAKKA QICQKQVKYLGYLLKEGQRW LTDARKETVMGQPTPKTPRQ LREFLGTAGFCRLWIPGFAE MAAPLYPLTKTGTLFNWGPD QQKAYQEIKQALLTAPALGL PDLTKPFELFVDEKQGYAKG VLTQKLGPWRRPVAYLSKKL DPVAAGWPPCLRMVAAIAVL TKDAGKLTMGQPLVILAPHA VEALVKQPPDRWLSNARMTH YQALLLDTDRVQFGPVVALN PATLLPLPEEGLQHNCLDIL AEAHGTRPDLTDQPLPDADH TWYTGGSSLLQEGQRKAGAA VTTETEVIWAKALPAGTSAQ RAQLIALTQALKMAEGKKLN VYTNSRYAFATAHIHGEIYR RRGLLTSEGKEIKNKDEILA LLKALFLPKRLSIIHCPGHQ KGHSAEARGNRMADQAARKA AITETPDTSTLLIENSSPYT SEHF |
| 677 | MMLV RTase with Q68K/ Q79R/ L99R/ E282D mutations | MTLNIEDEHRLHETSKEPDV SLGSTWLSDFPQAWAETGGM GLAVRQAPLIIPLKATSTPV SIKQYPMSKEARLGIKPHIR RLLDQGILVPCQSPWNTPLR PVKKPGTNDYRPVQDLREVN KRVEDIHPTVPNPYNLLSGL PPSHQWYTVLDLKDAFFCLR LHPTSQPLFAFEWRDPEMGI SGQLTWTRLPQGFKNSPTLF DEALHRDLADFRIQHPDLIL |

TABLE 12-continued

Sequences of triple or more mutant
MMLV RTase variants.

| SEQ ID NO: | Construct | Construct Sequence (AA) |
|---|---|---|
| | | LQYVDDLLLAATSELDCQQG |
| | | TRALLQTLGNLGYRASAKKA |
| | | QICQKQVKYLGYLLKEGQRW |
| | | LTDARKETVMGQPTPKTPRQ |
| | | LREFLGTAGFCRLWIPGFAE |
| | | MAAPLYPLTKTGTLFNWGPD |
| | | QQKAYQEIKQALLTAPALGL |
| | | PDLTKPFELFVDEKQGYAKG |
| | | VLTQKLGPWRRPVAYLSKKL |
| | | DPVAAGWPPCLRMVAAIAVL |
| | | TKDAGKLTMGQPLVILAPHA |
| | | VEALVKQPPDRWLSNARMTH |
| | | YQALLLDTDRVQFGPVVALN |
| | | PATLLPLPEEGLQHNCLDIL |
| | | AEAHGTRPDLTDQPLPDADH |
| | | TWYTGGSSLLQEGQRKAGAA |
| | | VTTETEVIWAKALPAGTSAQ |
| | | RAQLIALTQALKMAEGKKLN |
| | | VYTNSRYAFATAHIHGEIYR |
| | | RRGLLTSEGKEIKNKDEILA |
| | | LLKALFLPKRLSIIHCPGHQ |
| | | KGHSAEARGNRMADQAARKA |
| | | AITETPDTSTLLIENSSPYT |
| | | SEHF |
| 678 | MMLV RTase with Q68R/ Q79H/ L99R/ E282D mutations | MTLNIEDEHRLHETSKEPDV SLGSTWLSDFPQAWAETGGM GLAVRQAPLIIPLKATSTPV SIKQYPMSREARLGIKPHIH RLLDQGILVPCQSPWNTPLR PVKKPGTNDYRPVQDLREVN KRVEDIHPTVPNPYNLLSGL PPSHQWYTVLDLKDAFFCLR LHPTSQPLFAFEWRDPEMGI SGQLTWTRLPQGFKNSPTLF DEALHRDLADFRIQHPDLIL LQYVDDLLLAATSELDCQQG TRALLQTLGNLGYRASAKKA QICQKQVKYLGYLLKEGQRW LTDARKETVMGQPTPKTPRQ LREFLGTAGFCRLWIPGFAE MAAPLYPLTKTGTLFNWGPD QQKAYQEIKQALLTAPALGL PDLTKPFELFVDEKQGYAKG VLTQKLGPWRRPVAYLSKKL DPVAAGWPPCLRMVAAIAVL TKDAGKLTMGQPLVILAPHA VEALVKQPPDRWLSNARMTH YQALLLDTDRVQFGPVVALN PATLLPLPEEGLQHNCLDIL AEAHGTRPDLTDQPLPDADH TWYTGGSSLLQEGQRKAGAA VTTETEVIWAKALPAGTSAQ RAQLIALTQALKMAEGKKLN VYTNSRYAFATAHIHGEIYR RRGLLTSEGKEIKNKDEILA LLKALFLPKRLSIIHCPGHQ KGHSAEARGNRMADQAARKA AITETPDTSTLLIENSSPYT SEHF |
| 679 | MMLV RTase with Q68R/ Q79I/ L99R/ E282D mutations | MTLNIEDEHRLHETSKEPDV SLGSTWLSDFPQAWAETGGM GLAVRQAPLIIPLKATSTPV SIKQYPMSREARLGIKPHII RLLDQGILVPCQSPWNTPLR PVKKPGTNDYRPVQDLREVN KRVEDIHPTVPNPYNLLSGL PPSHQWYTVLDLKDAFFCLR LHPTSQPLFAFEWRDPEMGI SGQLTWTRLPQGFKNSPTLF DEALHRDLADFRIQHPDLIL LQYVDDLLLAATSELDCQQG |

TABLE 12-continued

Sequences of triple or more mutant
MMLV RTase variants.

| SEQ ID NO: | Construct | Construct Sequence (AA) |
|---|---|---|
| | | TRALLQTLGNLGYRASAKKA QICQKQVKYLGYLLKEGQRW LTDARKETVMGQPTPKTPRQ LREFLGTAGFCRLWIPGFAE MAAPLYPLTKTGTLFNWGPD QQKAYQEIKQALLTAPALGL PDLTKPFELFVDEKQGYAKG VLTQKLGPWRRPVAYLSKKL DPVAAGWPPCLRMVAAIAVL TKDAGKLTMGQPLVILAPHA VEALVKQPPDRWLSNARMTH YQALLLDTDRVQFGPVVALN PATLLPLPEEGLQHNCLDIL AEAHGTRPDLTDQPLPDADH TWYTGGSSLLQEGQRKAGAA VTTETEVIWAKALPAGTSAQ RAQLIALTQALKMAEGKKLN VYTNSRYAFATAHIHGEIYR RRGLLTSEGKEIKNKDEILA LLKALFLPKRLSIIHCPGHQ KGHSAEARGNRMADQAARKA AITETPDTSTLLIENSSPYT SEHF |
| 680 | MMLV RTase with Q68R/ Q79R/ L99R/ E282M mutations | MTLNIEDEHRLHETSKEPDV SLGSTWLSDFPQAWAETGGM GLAVRQAPLIIPLKATSTPV SIKQYPMSREARLGIKPHIR RLLDQGILVPCQSPWNTPLR PVKKPGTNDYRPVQDLREVN KRVEDIHPTVPNPYNLLSGL PPSHQWYTVLDLKDAFFCLR LHPTSQPLFAFEWRDPEMGI SGQLTWTRLPQGFKNSPTLF DEALHRDLADFRIQHPDLIL LQYVDDLLLAATSELDCQQG TRALLQTLGNLGYRASAKKA QICQKQVKYLGYLLKEGQRW LTMARKETVMGQPTPKTPRQ LREFLGTAGFCRLWIPGFAE MAAPLYPLTKTGTLFNWGPD QQKAYQEIKQALLTAPALGL PDLTKPFELFVDEKQGYAKG VLTQKLGPWRRPVAYLSKKL DPVAAGWPPCLRMVAAIAVL TKDAGKLTMGQPLVILAPHA VEALVKQPPDRWLSNARMTH YQALLLDTDRVQFGPVVALN PATLLPLPEEGLQHNCLDIL AEAHGTRPDLTDQPLPDADH TWYTGGSSLLQEGQRKAGAA VTTETEVIWAKALPAGTSAQ RAQLIALTQALKMAEGKKLN VYTNSRYAFATAHIHGEIYR RRGLLTSEGKEIKNKDEILA LLKALFLPKRLSIIHCPGHQ KGHSAEARGNRMADQAARKA AITETPDTSTLLIENSSPYT SEHF |
| 681 | MMLV RTase with Q68R/ Q79R/ L99R/ E282W mutations | MTLNIEDEHRLHETSKEPDV SLGSTWLSDFPQAWAETGGM GLAVRQAPLIIPLKATSTPV SIKQYPMSREARLGIKPHIR RLLDQGILVPCQSPWNTPLR PVKKPGTNDYRPVQDLREVN KRVEDIHPTVPNPYNLLSGL PPSHQWYTVLDLKDAFFCLR LHPTSQPLFAFEWRDPEMGI SGQLTWTRLPQGFKNSPTLF DEALHRDLADFRIQHPDLIL LQYVDDLLLAATSELDCQQG TRALLQTLGNLGYRASAKKA |

| SEQ ID NO: | Construct | Construct Sequence (AA) |
|---|---|---|
| | | QICQKQVKYLGYLLKEGQRW LTWARKETVMGQPTPKTPRQ LREFLGTAGFCRLWIPGFAE MAAPLYPLTKTGTLFNWGPD QQKAYQEIKQALLTAPALGL PDLTKPFELFVDEKQGYAKG VLTQKLGPWRRPVAYLSKKL DPVAAGWPPCLRMVAAIAVL TKDAGKLTMGQPLVILAPHA VEALVKQPPDRWLSNARMTH YQALLLDTDRVQFGPVVALN PATLLPLPEEGLQHNCLDIL AEAHGTRPDLTDQPLPDADH TWYTGGSSLLQEGQRKAGAA VTTETEVIWAKALPAGTSAQ RAQLIALTQALKMAEGKKLN VYTNSRYAFATAHIHGEIYR RRGLLTSEGKEIKNKDEILA LLKALFLPKRLSIIHCPGHQ KGHSAEARGNRMADQAARKA AITETPDTSTLLIENSSPYT SEHF |
| 682 | MMLV RTase with 161K/ Q68R/ Q79R/ L99R/ E282D mutations | MTLNIEDEHRLHETSKEPDV SLGSTWLSDFPQAWAETGGM GLAVRQAPLIIPLKATSTPV SKKQYPMSREARLGIKPHIR RLLDQGILVPCQSPWNTPLR PVKKPGTNDYRPVQDLREVN KRVEDIHPTVPNPYNLLSGL PPSHQWYTVLDLKDAFFCLR LHPTSQPLFAFEWRDPEMGI SGQLTWTRLPQGFKNSPTLF DEALHRDLADFRIQHPDLIL LQYVDDLLLAATSELDCQQG TRALLQTLGNLGYRASAKKA QICQKQVKYLGYLLKEGQRW LTDARKETVMGQPTPKTPRQ LREFLGTAGFCRLWIPGFAE MAAPLYPLTKTGTLFNWGPD QQKAYQEIKQALLTAPALGL PDLTKPFELFVDEKQGYAKG VLTQKLGPWRRPVAYLSKKL DPVAAGWPPCLRMVAAIAVL TKDAGKLTMGQPLVILAPHA VEALVKQPPDRWLSNARMTH YQALLLDTDRVQFGPVVALN PATLLPLPEEGLQHNCLDIL AEAHGTRPDLTDQPLPDADH TWYTGGSSLLQEGQRKAGAA VTTETEVIWAKALPAGTSAQ RAQLIALTQALKMAEGKKLN VYTNSRYAFATAHIHGEIYR RRGLLTSEGKEIKNKDEILA LLKALFLPKRLSIIHCPGHQ KGHSAEARGNRMADQAARKA AITETPDTSTLLIENSSPYT SEHF |
| 683 | MMLV RTase with 161M/ Q68R/ Q79R/ L99R/ E282D mutations | MTLNIEDEHRLHETSKEPDV SLGSTWLSDFPQAWAETGGM GLAVRQAPLIIPLKATSTPV SMKQYPMSREARLGIKPHIR RLLDQGILVPCQSPWNTPLR PVKKPGTNDYRPVQDLREVN KRVEDIHPTVPNPYNLLSGL PPSHQWYTVLDLKDAFFCLR LHPTSQPLFAFEWRDPEMGI SGQLTWTRLPQGFKNSPTLF DEALHRDLADFRIQHPDLIL LQYVDDLLLAATSELDCQQG TRALLQTLGNLGYRASAKKA QICQKQVKYLGYLLKEGQRW |

TABLE 12-continued

| SEQ ID NO: | Construct | Construct Sequence (AA) |
|---|---|---|
| | | LTDARKETVMGQPTPKTPRQ LREFLGTAGFCRLWIPGFAE MAAPLYPLTKTGTLFNWGPD QQKAYQEIKQALLTAPALGL PDL TKPFELFVDEKQGYAKGVLT QKLGPWRRPVAYLSKKLDPV AAGWPPCLRMVAAIAVLTKD AGKLTMGQPLVILAPHAVEA LVKQPPDRWLSNARMTHYQA LLLDTDRVQFGPVVALNPAT LLPLPEEGLQHNCLDILAEA HGTRPDLTDQPLPDADHTWY TGGSSLLQEGQRKAGAAVTT ETEVIWAKALPAGTSAQRAQ LIALTQALKMAEGKKLNVYT NSRYAFATAHIHGEIYRRRG LLTSEGKEIKNKDEILALLK ALFLPKRLSIIHCPGHQKGH SAEARGNRMADQAARKAAIT ETPDTSTLLIENSSPYTSEH F |
| 684 | MMLV RTase with Q68I/ Q79H/ L99K/ E282M mutations | MTLNIEDEHRLHETSKEPDV SLGSTWLSDFPQAWAETGGM GLAVRQAPLIIPLKATSTPV SIKQYPMSIEARLGIKPHIH RLLDQGILVPCQSPWNTPLK PVKKPGTNDYRPVQDLREVN KRVEDIHPTVPNPYNLLSGL PPSHQWYTVLDLKDAFFCLR LHPTSQPLFAFEWRDPEMGI SGQLTWTRLPQGFKNSPTLF DEALHRDLADFRIQHPDLIL LQYVDDLLLAATSELDCQQG TRALLQTLGNLGYRASAKKA QICQKQVKYLGYLLKEGQRW LTMARKETVMGQPTPKTPRQ LREFLGTAGFCRLWIPGFAE MAAPLYPLTKTGTLFNWGPD QQKAYQEIKQALLTAPALGL PDLTKPFELFVDEKQGYAKG VLTQKLGPWRRPVAYLSKKL DPVAAGWPPCLRMVAAIAVL TKDAGKLTMGQPLVILAPHA VEALVKQPPDRWLSNARMTH YQALLLDTDRVQFGPVVALN PATLLPLPEEGLQHNCLDIL AEAHGTRPDLTDQPLPDADH TWYTGGSSLLQEGQRKAGAA VTTETEVIWAKALPAGTSAQ RAQLIALTQALKMAEGKKLN VYTNSRYAFATAHIHGEIYR RRGLLTSEGKEIKNKDEILA LLKALFLPKRLSIIHCPGHQ KGHSAEARGNRMADQAARKA AITETPDTSTLLIENSSPYT SEHF |
| 685 | MMLV RTase with I61M/ Q68I/ Q79H/ L99K/ E282M mutations | MTLNIEDEHRLHETSKEPDV SLGSTWLSDFPQAWAETGGM GLAVRQAPLIIPLKATSTPV SMKQYPMSIEARLGIKPHIH RLLDQGILVPCQSPWNTPLK PVKKPGTNDYRPVQDLREVN KRVEDIHPTVPNPYNLLSGL PPSHQWYTVLDLKDAFFCLR LHPTSQPLFAFEWRDPEMGI SGQLTWTRLPQGFKNSPTLF DEALHRDLADFRIQHPDLIL LQYVDDLLLAATSELDCQQG TRALLQTLGNLGYRASAKKA QICQKQVKYLGYLLKEGQRW |

TABLE 12-continued

| SEQ ID NO: | Construct | Construct Sequence (AA) |
|---|---|---|
| | | LTMARKETVMGQPTPKTPRQ LREFLGTAGFCRLWIPGFAE MAAPLYPLTKTGTLFNWGPD QQKAYQEIKQALLTAPALGL PDLTKPFELFVDEKQGYAKG VLTQKLGPWRRPVAYLSKKL DPVAAGWPPCLRMVAAIAVL TKDAGKLTMGQPLVILAPHA VEALVKQPPDRWLSNARMTH YQALLLDTDRVQFGPVVALN PATLLPLPEEGLQHNCLDIL AEAHGTRPDLTDQPLPDADH TWYTGGSSLLQEGQRKAGAA VTTETEVIWAKALPAGTSAQ RAQLIALTQALKMAEGKKLN VYTNSRYAFATAHIHGEIYR RRGLLTSEGKEIKNKDEILA LLKALFLPKRLSIIHCPGHQ KGHSAEARGNRMADQAARKA AITETPDTSTLLIENSSPYT SEHF | c. Expression and Purification of MMLV RTase and Mutant Variants

A colony with the appropriate strain was used to inoculate TB media (200 mL) with kanamycin (0.05 mg/mL) and grown at 37° C. until an OD of approximately 0.9 was achieved followed by cooling of the flask for 30 minutes at 4° C. Protein expression was induced by the addition of 1 M IPTG (100 μL), followed by growth at 18° C. for 21 hours. Cells were harvested by spinning samples at 4,700×g for 10 minutes.

Cell pellets were re-suspended in a lysis buffer (50 mM NaPO$_4$, pH 7.8, 5% glycerol, 300 mM NaCl, 10 mM imidazole, 5 mM DTT, 0.01% n-ocyl-β-D-glucopyranoside, DNaseI, 10 mM CaCl$_2$), lysozyme (1 mg/mL), and protease inhibitor). The sample was lysed on an Avestin Emulsiflex C3 pre-chilled to 4° C. at 15-20 kpsi with three passes. Cell debris was removed by centrifuging the lysate at 16,000×g for 30 minutes at 4° C.

Cleared lysates were applied to a HisTrap HP column (Cytiva Life Sciences, Cat #17524701). The resin was equilibrated with MMLV His-Bind buffer (50 mM NaPO$_4$, pH 7.8, 5% glycerol, 0.3 M NaCl, 10 mM imidazole, 1 mM DTT and 0.01% IGEPAL-CA), followed by sample loading. The samples were washed with MMLV His-Bind buffer, followed by a 25% B wash (B=MMLV His Elution buffer=50 mM NaPO4, pH 7.8, 5% glycerol, 0.3 M NaCl, 250 mM imidazole, 1 mM DTT and 0.01% IGEPAL-CA). The sample was eluted with 100% B for 10 CVs in 45 mL fractions.

Purified proteins were applied to a HiTrap Heparin HP column (Cytiva Life Sciences, Cat #17040601). The resin was equilibrated with MMLV Heparin-Bind buffer (50 mM Tris HCl pH 8.5, 75 mM NaCl, 1 mM DTT, 5% glycerol and 0.01% IGEPAL-CA), followed by sample loading. The sample was washed with MLV Heparin Bind buffer, followed by a 25% B wash (B=MLV Heparin Elution Buffer). The sample was eluted with 60% B for 10 CVs in 45 mL fractions.

Purified proteins were applied to a Bio-Scale™ Mini CHT™ Cartridge (Bio-Rad Laboratories, Cat #7324322). The resin was washed with 1 M NaOH, followed by equilibration with MMLV Heparin-Bind buffer and sample loading. The sample was washed with MLV Heparin Elution buffer, followed by MMLV Heparin Bind buffer. The sample was linearly eluted to 100% B2 (B2=MMLV HA Elution Buffer=250 mM KPO4 pH 7.5, 1 mM DTT, 5% glycerol and 0.01% IGEPAL-CA) for 15 CVs in 5 mL fractions.

Fractions containing purified protein were pooled and dialyzed in MMLV Storage Buffer (50 mM Tris-HCl (pH 7.5), 100 mM NaCl, 1 mM DTT, 50% (v/v) glycerol).

d. Evaluation of Ability of Purified MMLV RTase Mutant Variants to Synthesize DNA by Gene Specific Priming MMLV RTase base construct and MMLV RTase mutant variants evaluated as described in Example 3. Temperatures were adjusted for both two-step and one-step reactions to 55 and 60° C., respectively. The two-step and one-step reactions for MMLV RTase base construct and MMLV RTase mutant variants were analyzed and reported by Ct output from the qPCR (see Tables 13 and 14).

Six of the seventeen MMLV RTase triple or more mutant variants were found to exhibit increased overall activity and thermostability as compared to the other MMLV RTase stacked mutant variants, and almost all of the MMLV RTase stacked mutant variants exhibited increased overall activity and thermostability as compared to the MMLV RTase base construct. The six MMLV RTase mutant variants that were found to exhibit the highest overall activity were Q68R/L99R, Q68R/Q79R/L99R, Q68R/Q79R/L99R/E282D, Q68R/Q79R/L99K/E282D, Q68R/Q79R/L99R/E282W, I61M/Q68R/Q79R/L99R/E282D and Q68I/Q79H/L99K/E282M.

TABLE 13

Two-Step cDNA synthesis by MMLV RT triple and more mutants. Data was generated via qPCR human normalizer assay and data is reported by Ct value.

| MMLV RT Variant | Concentration of RTase (nM) | Ct Mean | Ct Standard Deviation |
|---|---|---|---|
| MMLV-II | 0.625 | 25.520 | 0.047 |
| MMLV-II L99R/E282D | 0.625 | 24.332 | 0.060 |
| MMLV-II Q68R/L99R | 0.625 | 22.207 | 0.097 |
| MMLV-II Q79R/L99R | 0.625 | 23.789 | 0.012 |
| MMLV-II Q68R/Q79R | 0.625 | 23.629 | 0.038 |
| MMLV-II Q68R/L99R/E282D | 0.625 | 22.855 | 0.079 |
| MMLV-II Q79R/L99R/E282D | 0.625 | 23.095 | 0.035 |
| MMLV-II Q68R/Q79R/E282D | 0.625 | 22.526 | 0.027 |
| MMLV-II Q68R/Q79R/L99R | 0.625 | 22.099 | 0.018 |
| MMLV-II Q68R/Q79R/L99R/E282D | 0.625 | 21.056 | 0.023 |
| MMLV-II Q68R/Q79R/L99K/E282D | 0.625 | 21.833 | 0.031 |
| MMLV-II Q68R/Q79R/L99N/E282D | 0.625 | 23.607 | 0.031 |
| MMLV-II Q68I/Q79R/L99R/E282D | 0.625 | 23.858 | 0.029 |
| MMLV-II Q68K/Q79R/L99R/E282D | 0.625 | 22.615 | 0.054 |
| MMLV-II Q68R/Q79H/L99R/E282D | 0.625 | 28.866 | 0.008 |
| MMLV-II Q68R/Q79I/L99R/E282D | 0.625 | 23.283 | 0.085 |
| MMLV-II Q68R/Q79R/L99R/E282M | 0.625 | 25.073 | 0.097 |
| MMLV-II Q68R/Q79R/L99R/E282W | 0.625 | 22.331 | 0.048 |
| MMLV-II I61K/Q68R/Q79R/L99R/E282D | 0.625 | 23.271 | 0.065 |
| MMLV-II I61M/Q68R/Q79R/L99R/E282D | 0.625 | 22.133 | 0.018 |
| MMLV-II Q68I/Q79H/L99K/E282M | 0.625 | 23.344 | 0.037 |

TABLE 13-continued

Two-Step cDNA synthesis by MMLV RT triple and more mutants. Data was generated via qPCR human normalizer assay and data is reported by Ct value.

| MMLV RT Variant | Concentration of RTase (nM) | Ct Mean | Ct Standard Deviation |
|---|---|---|---|
| MMLV-II I61M/Q68I/Q79H/L99K/E282M | 0.625 | 25.255 | 0.058 |
| MMLV-II | 2.5 | 22.154 | 0.052 |
| MMLV-II L99R/E282D | 2.5 | 21.501 | 0.054 |
| MMLV-II Q68R/L99R | 2.5 | 21.151 | 0.048 |
| MMLV-II Q79R/L99R | 2.5 | 21.229 | 0.163 |
| MMLV-II Q68R/Q79R | 2.5 | 21.228 | 0.054 |
| MMLV-II Q68R/L99R/E282D | 2.5 | 21.126 | 0.030 |
| MMLV-II Q79R/L99R/E282D | 2.5 | 21.418 | 0.033 |
| MMLV-II Q68R/Q79R/E282D | 2.5 | 21.011 | 0.052 |
| MMLV-II Q68R/Q79R/L99R | 2.5 | 20.953 | 0.041 |
| MMLV-II Q68R/Q79R/L99R/E282D | 2.5 | 21.113 | 0.108 |
| MMLV-II Q68R/Q79R/L99K/E282D | 2.5 | 20.906 | 0.081 |
| MMLV-II Q68R/Q79R/L99N/E282D | 2.5 | 21.196 | 0.029 |
| MMLV-II Q68I/Q79R/L99R/E282D | 2.5 | 21.369 | 0.009 |
| MMLV-II Q68K/Q79R/L99R/E282D | 2.5 | 20.960 | 0.030 |
| MMLV-II Q68R/Q79H/L99R/E282D | 2.5 | 26.167 | 0.038 |
| MMLV-II Q68R/Q79I/L99R/E282D | 2.5 | 21.012 | 0.056 |
| MMLV-II Q68R/Q79R/L99R/E282M | 2.5 | 21.277 | 0.036 |
| MMLV-II Q68R/Q79R/L99R/E282W | 2.5 | 20.944 | 0.020 |
| MMLV-II I61K/Q68R/Q79R/L99R/E282D | 2.5 | 21.320 | 0.009 |
| MMLV-II I61M/Q68R/Q79R/L99R/E282D | 2.5 | 21.095 | 0.013 |
| MMLV-II Q68I/Q79H/L99K/E282M | 2.5 | 21.329 | 0.047 |
| MMLV-II I61M/Q68I/Q79H/L99K/E282M | 2.5 | 22.159 | 0.031 |
| MMLV-II | 10 | 21.575 | 0.101 |
| MMLV-II L99R/E282D | 10 | 21.546 | 0.041 |
| MMLV-II Q68R/L99R | 10 | 21.343 | 0.021 |
| MMLV-II Q79R/L99R | 10 | 21.387 | 0.016 |
| MMLV-II Q68R/Q79R | 10 | 21.147 | 0.032 |
| MMLV-II Q68R/L99R/E282D | 10 | 21.265 | 0.076 |
| MMLV-II Q79R/L99R/E282D | 10 | 21.250 | 0.036 |
| MMLV-II Q68R/Q79R/E282D | 10 | 21.135 | 0.015 |
| MMLV-II Q68R/Q79R/L99R | 10 | 21.051 | 0.036 |
| MMLV-II Q68R/Q79R/L99R/E282D | 10 | 21.159 | 0.065 |
| MMLV-II Q68R/Q79R/L99K/E282D | 10 | 21.056 | 0.032 |
| MMLV-II Q68R/Q79R/L99N/E282D | 10 | 21.180 | 0.052 |
| MMLV-II Q68I/Q79R/L99R/E282D | 10 | 21.068 | 0.069 |
| MMLV-II Q68K/Q79R/L99R/E282D | 10 | 21.065 | 0.053 |
| MMLV-II Q68R/Q79H/L99R/E282D | 10 | 21.683 | 0.075 |
| MMLV-II Q68R/Q79I/L99R/E282D | 10 | 21.152 | 0.064 |
| MMLV-II Q68R/Q79R/L99R/E282M | 10 | 21.029 | 0.055 |
| MMLV-II Q68R/Q79R/L99R/E282W | 10 | 21.214 | 0.052 |
| MMLV-II I61K/Q68R/Q79R/L99R/E282D | 10 | 21.391 | 0.051 |
| MMLV-II I61M/Q68R/Q79R/L99R/E282D | 10 | 21.307 | 0.038 |
| MMLV-II Q68I/Q79H/L99K/E282M | 10 | 21.583 | 0.019 |
| MMLV-II I61M/Q68I/Q79H/L99K/E282M | 10 | 21.759 | 0.029 |

TABLE 14

One-Step cDNA synthesis by MMLV RT triple and more mutants. Data was generated via qPCR human normalizer assay and data is reported by Ct value.

| MMLV RT Variant | Concentration of RTase (nM) | Ct Mean | Ct Standard Deviation |
| --- | --- | --- | --- |
| MMLV-II | 0.625 | 22.153 | 0.122 |
| MMLV-II L99R/E282D | 0.625 | 21.713 | 0.111 |
| MMLV-II Q68R/L99R | 0.625 | 21.334 | 0.167 |
| MMLV-II Q79R/L99R | 0.625 | 21.398 | 0.069 |
| MMLV-II Q68R/Q79R | 0.625 | 21.546 | 0.096 |
| MMLV-II Q68R/L99R/E282D | 0.625 | 21.112 | 0.149 |
| MMLV-II Q79R/L99R/E282D | 0.625 | 21.260 | 0.104 |
| MMLV-II Q68R/Q79R/E282D | 0.625 | 21.014 | 0.102 |
| MMLV-II Q68R/Q79R/L99R | 0.625 | 20.338 | 0.042 |
| MMLV-II Q68R/Q79R/L99R/E282D | 0.625 | 19.537 | 0.120 |
| MMLV-II Q68R/Q79R/L99K/E282D | 0.625 | 20.516 | 0.131 |
| MMLV-II Q68R/Q79R/L99N/E282D | 0.625 | 20.960 | 0.023 |
| MMLV-II Q68I/Q79R/L99R/E282D | 0.625 | 21.325 | 0.088 |
| MMLV-II Q68K/Q79R/L99R/E282D | 0.625 | 20.602 | 0.038 |
| MMLV-II Q68R/Q79H/L99R/E282D | 0.625 | 23.889 | 0.042 |
| MMLV-II Q68R/Q79I/L99R/E282D | 0.625 | 21.375 | 0.035 |
| MMLV-II Q68R/Q79R/L99R/E282M | 0.625 | 21.805 | 0.054 |
| MMLV-II Q68R/Q79R/L99R/E282W | 0.625 | 20.229 | 0.085 |
| MMLV-II I61K/Q68R/Q79R/L99R/E282D | 0.625 | 20.972 | 0.037 |
| MMLV-II I61M/Q68R/Q79R/L99R/E282D | 0.625 | 20.225 | 0.042 |
| MMLV-II Q68I/Q79H/L99K/E282M | 0.625 | 20.578 | 0.061 |
| MMLV-II I61M/Q68I/Q79H/L99K/E282M | 0.625 | 21.107 | 0.101 |
| MMLV-II | 2.5 | 20.874 | 0.042 |
| MMLV-II L99R/E282D | 2.5 | 19.679 | 0.047 |
| MMLV-II Q68R/L99R | 2.5 | 19.152 | 0.024 |
| MMLV-II Q79R/L99R | 2.5 | 19.202 | 0.091 |
| MMLV-II Q68R/Q79R | 2.5 | 19.506 | 0.010 |
| MMLV-II Q68R/L99R/E282D | 2.5 | 19.142 | 0.060 |
| MMLV-II Q79R/L99R/E282D | 2.5 | 19.301 | 0.004 |
| MMLV-II Q68R/Q79R/E282D | 2.5 | 19.023 | 0.041 |
| MMLV-II Q68R/Q79R/L99R | 2.5 | 18.312 | 0.041 |
| MMLV-II Q68R/Q79R/L99R/E282D | 2.5 | 17.867 | 0.099 |
| MMLV-II Q68R/Q79R/L99K/E282D | 2.5 | 18.591 | 0.036 |
| MMLV-II Q68R/Q79R/L99N/E282D | 2.5 | 19.123 | 0.097 |
| MMLV-II Q68I/Q79R/L99R/E282D | 2.5 | 19.553 | 0.076 |
| MMLV-II Q68K/Q79R/L99R/E282D | 2.5 | 18.771 | 0.113 |
| MMLV-II Q68R/Q79H/L99R/E282D | 2.5 | 21.911 | 0.048 |
| MMLV-II Q68R/Q79I/L99R/E282D | 2.5 | 19.298 | 0.146 |
| MMLV-II Q68R/Q79R/L99R/E282M | 2.5 | 19.621 | 0.027 |
| MMLV-II Q68R/Q79R/L99R/E282W | 2.5 | 18.219 | 0.103 |
| MMLV-II I61K/Q68R/Q79R/L99R/E282D | 2.5 | 18.846 | 0.056 |
| MMLV-II I61M/Q68R/Q79R/L99R/E282D | 2.5 | 18.500 | 0.042 |
| MMLV-II Q68I/Q79H/L99K/E282M | 2.5 | 18.752 | 0.148 |
| MMLV-II I61M/Q68I/Q79H/L99K/E282M | 2.5 | 19.445 | 0.098 |
| MMLV-II | 10 | 18.239 | 0.025 |
| MMLV-II L99R/E282D | 10 | 17.293 | 0.021 |
| MMLV-II Q68R/L99R | 10 | 17.144 | 0.032 |

TABLE 14-continued

One-Step cDNA synthesis by MMLV RT triple and more mutants. Data was generated via qPCR human normalizer assay and data is reported by Ct value.

| MMLV RT Variant | Concentration of RTase (nM) | Ct Mean | Ct Standard Deviation |
| --- | --- | --- | --- |
| MMLV-II Q79R/L99R | 10 | 17.324 | 0.016 |
| MMLV-II Q68R/Q79R | 10 | 17.123 | 0.072 |
| MMLV-II Q68R/L99R/E282D | 10 | 17.082 | 0.088 |
| MMLV-II Q79R/L99R/E282D | 10 | 17.353 | 0.068 |
| MMLV-II Q68R/Q79R/E282D | 10 | 17.111 | 0.036 |
| MMLV-II Q68R/Q79R/L99R | 10 | 16.562 | 0.101 |
| MMLV-II Q68R/Q79R/L99R/E282D | 10 | 16.492 | 0.066 |
| MMLV-II Q68R/Q79R/L99K/E282D | 10 | 17.027 | 0.054 |
| MMLV-II Q68R/Q79R/L99N/E282D | 10 | 17.335 | 0.080 |
| MMLV-II Q68I/Q79R/L99R/E282D | 10 | 17.726 | 0.055 |
| MMLV-II Q68K/Q79R/L99R/E282D | 10 | 17.144 | 0.140 |
| MMLV-II Q68R/Q79H/L99R/E282D | 10 | 19.772 | 0.064 |
| MMLV-II Q68R/Q79I/L99R/E282D | 10 | 17.424 | 0.020 |
| MMLV-II Q68R/Q79R/L99R/E282M | 10 | 17.624 | 0.014 |
| MMLV-II Q68R/Q79R/L99R/E282W | 10 | 16.629 | 0.080 |
| MMLV-II I61K/Q68R/Q79R/L99R/E282D | 10 | 16.903 | 0.022 |
| MMLV-II I61M/Q68R/Q79R/L99R/E282D | 10 | 16.803 | 0.028 |
| MMLV-II Q6I/Q79H/L99K/E282M | 10 | 16.894 | 0.056 |
| MMLV-II I61M/Q68I/Q79H/L99K/E282M | 10 | 17.509 | 0.058 | e. Evaluation of Ability of Purified MMLV RTase Mutant Variants to Synthesize DNA by Oligo-dT or Random Priming MMLV RTase base construct and MMLV RTase mutant variants evaluated as described in Example 3. Oligo-dT or random hexamer priming conditions were adjusted for the two-step reactions and RTase concentration was normalized to 31 nM. The two-step reactions for MMLV RTase base construct and MMLV RTase mutant variants were analyzed and reported by Ct output from the qPCR (see Tables 15 and 16).

Nine of the seventeen MMLV RTase triple or more mutant variants were found to exhibit increased overall activity and thermostability as compared to the other MMLV RTase stacked mutant variants, and almost all of the MMLV RTase stacked mutant variants exhibited increased overall activity and thermostability as compared to the MMLV RTase base construct. The nine MMLV RTase mutant variants that were found to exhibit the highest overall activity were Q79R/L99R/E282D, Q68R/Q79R/L99R, Q68R/Q79R/L99R/E282D, Q68R/Q79R/L99K/E282D, Q68R/Q79R/L99N/E282D, Q68K/Q79R/L99R/E282D, Q68R/Q79R/L99R/E282M, M61K/Q68R/Q79R/L99R/E282D and 161M/Q68R/Q79R/L99R/E282D.

TABLE 15

Two-Step cDNA synthesis by MMLV RT triple and more mutants by Oligo-dT priming. Data was generated via qPCR human normalizer assay and data is reported by Ct value.

| MMLV RT Variant | Temperature of Reaction (° C.) | Ct Mean | Ct Standard Deviation |
|---|---|---|---|
| MMLV-II | 42 | 25.165 | 0.057 |
| MMLV-II L99R/E282D | 42 | 25.287 | 0.062 |
| MMLV-II Q68R/L99R | 42 | 25.026 | 0.035 |
| MMLV-II Q79R/L99R | 42 | 24.932 | 0.032 |
| MMLV-II Q68R/Q79R | 42 | 25.002 | 0.076 |
| MMLV-II Q68R/L99R/E282D | 42 | 24.964 | 0.068 |
| MMLV-II Q79R/L99R/E282D | 42 | 24.822 | 0.106 |
| MMLV-II Q68R/Q79R/E282D | 42 | 24.905 | 0.134 |
| MMLV-II Q68R/Q79R/L99R | 42 | 24.673 | 0.131 |
| MMLV-II Q68R/Q79R/L99R/E282D | 42 | 24.523 | 0.111 |
| MMLV-II Q68R/Q79R/L99K/E282D | 42 | 24.677 | 0.076 |
| MMLV-II Q68R/Q79R/L99N/E282D | 42 | 24.635 | 0.087 |
| MMLV-II Q68I/Q79R/L99R/E282D | 42 | 25.010 | 0.074 |
| MMLV-II Q68K/Q79R/L99R/E282D | 42 | 24.676 | 0.066 |
| MMLV-II Q68R/Q79H/L99R/E282D | 42 | 28.929 | 0.021 |
| MMLV-II Q68R/Q79I/L99R/E282D | 42 | 24.932 | 0.039 |
| MMLV-II Q68R/Q79R/L99R/E282M | 42 | 24.900 | 0.113 |
| MMLV-II Q68R/Q79R/L99R/E282W | 42 | 24.967 | 0.091 |
| MMLV-II I61K/Q68R/Q79R/L99R/E282D | 42 | 24.597 | 0.076 |
| MMLV-II I61M/Q68R/Q79R/L99R/E282D | 42 | 24.833 | 0.007 |
| MMLV-II Q68I/Q79H/L99K/E282M | 42 | 25.440 | 0.048 |
| MMLV-II I61M/Q68I/Q79H/L99K/E282M | 42 | 25.679 | 0.050 |
| MMLV-II | 55 | 34.223 | 0.406 |
| MMLV-II L99R/E282D | 55 | 34.732 | 3.729 |
| MMLV-II Q68R/L99R | 55 | 31.509 | 0.169 |
| MMLV-II Q79R/L99R | 55 | 31.831 | 0.019 |
| MMLV-II Q68R/Q79R | 55 | 32.633 | 1.094 |
| MMLV-II Q68R/L99R/E282D | 55 | 32.089 | 0.075 |
| MMLV-II Q79R/L99R/E282D | 55 | 32.134 | 0.081 |
| MMLV-II Q68R/Q79R/E282D | 55 | 34.639 | 3.791 |
| MMLV-II Q68R/Q79R/L99R | 55 | 29.559 | 0.029 |
| MMLV-II Q68R/Q79R/L99R/E282D | 55 | 28.013 | 0.136 |
| MMLV-II Q68R/Q79R/L99K/E282D | 55 | 29.712 | 0.090 |
| MMLV-II Q68R/Q79R/L99N/E282D | 55 | 30.442 | 0.224 |
| MMLV-II Q68I/Q79R/L99R/E282D | 55 | 32.857 | 0.378 |
| MMLV-II Q68K/Q79R/L99R/E282D | 55 | 31.186 | 0.630 |
| MMLV-II Q68R/Q79H/L99R/E282D | 55 | 37.338 | 1.882 |
| MMLV-II Q68R/Q79I/L99R/E282D | 55 | 31.830 | 0.120 |
| MMLV-II Q68R/Q79R/L99R/E282M | 55 | 31.682 | 0.181 |
| MMLV-II Q68R/Q79R/L99R/E282W | 55 | 32.256 | 0.228 |
| MMLV-II I61K/Q68R/Q79R/L99R/E282D | 55 | 30.362 | 0.129 |
| MMLV-II I61M/Q68R/Q79R/L99R/E282D | 55 | 31.473 | 0.070 |
| MMLV-II Q68I/Q79H/L99K/E282M | 55 | 32.892 | 0.286 |
| MMLV-II I61M/Q68I/Q79H/L99K/E282M | 55 | 33.872 | 0.131 |

TABLE 16

Two-Step cDNA synthesis by MMLV RT triple and more mutants by random hexamer priming. Data was generated via qPCR human normalizer assay and data is reported by Ct value.

| MMLV RT Variant | Temperature of Reaction (° C.) | Ct Mean | Ct Standard Deviation |
|---|---|---|---|
| MMLV-II | 42 | 24.675 | 0.054 |
| MMLV-II L99R/E282D | 42 | 24.864 | 0.043 |
| MMLV-II Q68R/L99R | 42 | 24.577 | 0.066 |
| MMLV-II Q79R/L99R | 42 | 24.630 | 0.103 |
| MMLV-II Q68R/Q79R | 42 | 24.496 | 0.050 |
| MMLV-II Q68R/L99R/E282D | 42 | 24.549 | 0.059 |
| MMLV-II Q79R/L99R/E282D | 42 | 24.625 | 0.013 |
| MMLV-II Q68R/Q79R/E282D | 42 | 24.623 | 0.083 |
| MMLV-II Q68R/Q79R/L99R | 42 | 24.494 | 0.070 |
| MMLV-II Q68R/Q79R/L99R/E282D | 42 | 24.422 | 0.035 |
| MMLV-II Q68R/Q79R/L99K/E282D | 42 | 24.517 | 0.066 |
| MMLV-II Q68R/Q79R/L99N/E282D | 42 | 24.324 | 0.059 |
| MMLV-II Q68I/Q79R/L99R/E282D | 42 | 24.488 | 0.070 |
| MMLV-II Q68K/Q79R/L99R/E282D | 42 | 24.501 | 0.041 |
| MMLV-II Q68R/Q79H/L99R/E282D | 42 | 26.574 | 0.029 |
| MMLV-II Q68R/Q79I/L99R/E282D | 42 | 24.496 | 0.055 |
| MMLV-II Q68R/Q79R/L99R/E282M | 42 | 24.382 | 0.043 |
| MMLV-II Q68R/Q79R/L99R/E282W | 42 | 24.617 | 0.109 |
| MMLV-II I61K/Q68R/Q79R/L99R/E282D | 42 | 24.391 | 0.045 |
| MMLV-II I61M/Q68R/Q79R/L99R/E282D | 42 | 24.426 | 0.028 |
| MMLV-II Q68I/Q79H/L99K/E282M | 42 | 24.660 | 0.027 |
| MMLV-II I61M/Q68I/Q79H/L99K/E282M | 42 | 24.949 | 0.052 |
| MMLV-II | 55 | 32.082 | 0.095 |
| MMLV-II L99R/E282D | 55 | 31.612 | 0.190 |
| MMLV-II Q68R/L99R | 55 | 30.349 | 0.041 |
| MMLV-II Q79R/L99R | 55 | 30.494 | 0.094 |
| MMLV-II Q68R/Q79R | 55 | 29.735 | 0.153 |
| MMLV-II Q68R/L99R/E282D | 55 | 30.724 | 0.045 |
| MMLV-II Q79R/L99R/E282D | 55 | 30.774 | 0.152 |
| MMLV-II Q68R/Q79R/E282D | 55 | 30.232 | 0.079 |
| MMLV-II Q68R/Q79R/L99R | 55 | 28.270 | 0.340 |
| MMLV-II Q68R/Q79R/L99R/E282D | 55 | 26.673 | 0.143 |
| MMLV-II Q68R/Q79R/L99K/E282D | 55 | 28.258 | 0.018 |
| MMLV-II Q68R/Q79R/L99N/E282D | 55 | 28.973 | 0.116 |
| MMLV-II Q68I/Q79R/L99R/E282D | 55 | 31.617 | 0.071 |
| MMLV-II Q68K/Q79R/L99R/E282D | 55 | 28.994 | 0.110 |
| MMLV-II Q68R/Q79H/L99R/E282D | 55 | 35.664 | 0.695 |
| MMLV-II Q68R/Q79I/L99R/E282D | 55 | 30.265 | 0.116 |
| MMLV-II Q68R/Q79R/L99R/E282M | 55 | 29.765 | 0.059 |
| MMLV-II Q68R/Q79R/L99R/E282W | 55 | 30.535 | 0.424 |
| MMLV-II I61K/Q68R/Q79R/L99R/E282D | 55 | 28.878 | 0.038 |
| MMLV-II I61M/Q68R/Q79R/L99R/E282D | 55 | 29.778 | 0.081 |
| MMLV-II Q68I/Q79H/L99K/E282M | 55 | 31.836 | 0.222 |
| MMLV-II I61M/Q68I/Q79H/L99K/E282M | 55 | 31.984 | 0.223 | f. Evaluation of Ability of Purified MMLV RTase Mutant Variants to Synthesize DNA Over a Wide Range of Temperatures MMLV RTase base construct and MMLV RTase mutant variants evaluated as described in Example 3. Oligo-dT or random hexamer priming conditions and reaction temperatures were adjusted for the two-step reactions and RTase concentration was normalized to 31 nM. The two-step reactions for MMLV RTase base construct and MMLV RTase mutant variants were analyzed and reported by Ct output from the qPCR (see Tables 17 and 18).

Six of the nine MMLV RTase triple or more mutant variants were found to exhibit high overall activity as compared to the other MMLV RTase stacked mutant variants over a wide range of temperatures, spanning from 37.0 to 65° C., regardless of which priming method used. All of the MMLV RTase stacked mutant variants exhibited increased overall activity and thermostability as compared to the MMLV RTase base construct. The six MMLV RTase mutant variants that were found to exhibit the highest overall activity at a wide range of temperatures were Q68R/Q79R/L99R, Q68R/Q79R/L99R/E282D, Q68R/Q79R/L99K/E282D, Q68R/Q79R/L99N/E282D, I61K/Q68R/Q79R/L99R/E282D and I61M/Q68R/Q79R/L99R/E282D.

TABLE 17

Two-Step cDNA synthesis by MMLV RT triple and more mutants by Oligo-dT priming. Data was generated via qPCR human normalizer assay and data is reported by Ct value.

| MMLV RT Variant | Temperature of Reaction (° C.) | Ct Mean | Ct Standard Deviation |
|---|---|---|---|
| MMLV-II | 37.0 | 26.593 | 0.020 |
| MMLV-II Q79R/L99R/E282D | 37.0 | 25.713 | 0.024 |
| MMLV-II Q68R/Q79R/L99R | 37.0 | 25.164 | 0.059 |
| MMLV-II Q68R/Q79R/L99R/E282D | 37.0 | 25.163 | 0.035 |
| MMLV-II Q68R/Q79R/L99K/E282D | 37.0 | 25.135 | 0.078 |
| MMLV-II Q68R/Q79R/L99N/E282D | 37.0 | 25.693 | 0.048 |
| MMLV-II Q68K/Q79R/L99R/E282D | 37.0 | 25.491 | 0.062 |
| MMLV-II Q68R/Q79R/L99R/E282M | 37.0 | 25.450 | 0.083 |
| MMLV-II I61K/Q68R/Q79R/L99R/E282D | 37.0 | 25.094 | 0.071 |
| MMLV-II I61M/Q68R/Q79R/L99R/E282D | 37.0 | 25.356 | 0.034 |
| MMLV-II | 37.8 | 26.623 | 0.062 |
| MMLV-II Q79R/L99R/E282D | 37.8 | 25.516 | 0.078 |
| MMLV-II Q68R/Q79R/L99R | 37.8 | 25.251 | 0.094 |
| MMLV-II Q68R/Q79R/L99R/E282D | 37.8 | 24.987 | 0.050 |
| MMLV-II Q68R/Q79R/L99K/E282D | 37.8 | 25.093 | 0.084 |
| MMLV-II Q68R/Q79R/L99N/E282D | 37.8 | 25.273 | 0.095 |
| MMLV-II Q68K/Q79R/L99R/E282D | 37.8 | 25.310 | 0.079 |
| MMLV-II Q68R/Q79R/L99R/E282M | 37.8 | 25.545 | 0.044 |
| MMLV-II I61K/Q68R/Q79R/L99R/E282D | 37.8 | 25.144 | 0.196 |
| MMLV-II I61M/Q68R/Q79R/L99R/E282D | 37.8 | 25.302 | 0.035 |
| MMLV-II | 39.5 | 26.430 | 0.074 |
| MMLV-II Q79R/L99R/E282D | 39.5 | 25.067 | 0.026 |
| MMLV-II Q68R/Q79R/L99R | 39.5 | 25.138 | 0.050 |
| MMLV-II Q68R/Q79R/L99R/E282D | 39.5 | 24.788 | 0.022 |
| MMLV-II Q68R/Q79R/L99K/E282D | 39.5 | 24.842 | 0.071 |

TABLE 17-continued

Two-Step cDNA synthesis by MMLV RT triple and more mutants by Oligo-dT priming. Data was generated via qPCR human normalizer assay and data is reported by Ct value.

| MMLV RT Variant | Temperature of Reaction (° C.) | Ct Mean | Ct Standard Deviation |
|---|---|---|---|
| MMLV-II Q68R/Q79R/L99N/E282D | 39.5 | 24.892 | 0.042 |
| MMLV-II Q68K/Q79R/L99R/E282D | 39.5 | 25.047 | 0.038 |
| MMLV-II Q68R/Q79R/L99R/E282M | 39.5 | 25.249 | 0.081 |
| MMLV-II I61K/Q68R/Q79R/L99R/E282D | 39.5 | 24.845 | 0.130 |
| MMLV-II I61M/Q68R/Q79R/L99R/E282D | 39.5 | 25.130 | 0.072 |
| MMLV-II | 42.0 | 25.485 | 0.052 |
| MMLV-II Q79R/L99R/E282D | 42.0 | 24.941 | 0.024 |
| MMLV-II Q68R/Q79R/L99R | 42.0 | 24.848 | 0.101 |
| MMLV-II Q68R/Q79R/L99R/E282D | 42.0 | 24.802 | 0.009 |
| MMLV-II Q68R/Q79R/L99K/E282D | 42.0 | 24.805 | 0.008 |
| MMLV-II Q68R/Q79R/L99N/E282D | 42.0 | 24.744 | 0.076 |
| MMLV-II Q68K/Q79R/L99R/E282D | 42.0 | 24.893 | 0.073 |
| MMLV-II Q68R/Q79R/L99R/E282M | 42.0 | 24.968 | 0.031 |
| MMLV-II I61K/Q68R/Q79R/L99R/E282D | 42.0 | 24.933 | 0.088 |
| MMLV-II I61M/Q68R/Q79R/L99R/E282D | 42.0 | 24.821 | 0.045 |
| MMLV-II | 45.2 | 25.776 | 0.028 |
| MMLV-II Q79R/L99R/E282D | 45.2 | 24.902 | 0.034 |
| MMLV-II Q68R/Q79R/L99R | 45.2 | 24.792 | 0.055 |
| MMLV-II Q68R/Q79R/L99R/E282D | 45.2 | 24.705 | 0.092 |
| MMLV-II Q68R/Q79R/L99K/E282D | 45.2 | 24.791 | 0.009 |
| MMLV-II Q68R/Q79R/L99N/E282D | 45.2 | 24.890 | 0.071 |
| MMLV-II Q68K/Q79R/L99R/E282D | 45.2 | 25.420 | 0.101 |
| MMLV-II Q68R/Q79R/L99R/E282M | 45.2 | 25.196 | 0.086 |
| MMLV-II I61K/Q68R/Q79R/L99R/E282D | 45.2 | 24.823 | 0.079 |
| MMLV-II I61M/Q68R/Q79R/L99R/E282D | 45.2 | 24.720 | 0.006 |
| MMLV-II | 47.8 | 27.932 | 0.049 |
| MMLV-II Q79R/L99R/E282D | 47.8 | 24.858 | 0.063 |
| MMLV-II Q68R/Q79R/L99R | 47.8 | 24.685 | 0.095 |
| MMLV-II Q68R/Q79R/L99R/E282D | 47.8 | 24.689 | 0.067 |
| MMLV-II Q68R/Q79R/L99K/E282D | 47.8 | 24.620 | 0.072 |
| MMLV-II Q68R/Q79R/L99N/E282D | 47.8 | 24.780 | 0.039 |
| MMLV-II Q68K/Q79R/L99R/E282D | 47.8 | 24.855 | 0.018 |
| MMLV-II Q68R/Q79R/L99R/E282M | 47.8 | 24.961 | 0.040 |
| MMLV-II I61K/Q68R/Q79R/L99R/E282D | 47.8 | 24.681 | 0.076 |
| MMLV-II I61M/Q68R/Q79R/L99R/E282D | 47.8 | 24.759 | 0.055 |
| MMLV-II | 49.2 | 30.393 | 0.118 |
| MMLV-II Q79R/L99R/E282D | 49.2 | 24.974 | 0.090 |
| MMLV-II Q68R/Q79R/L99R | 49.2 | 24.794 | 0.056 |
| MMLV-II Q68R/Q79R/L99R/E282D | 49.2 | 24.720 | 0.100 |
| MMLV-II Q68R/Q79R/L99K/E282D | 49.2 | 25.007 | 0.096 |
| MMLV-II Q68R/Q79R/L99N/E282D | 49.2 | 25.304 | 0.147 |
| MMLV-II Q68K/Q79R/L99R/E282D | 49.2 | 25.273 | 0.066 |

TABLE 17-continued

Two-Step cDNA synthesis by MMLV RT triple and more mutants by Oligo-dT priming. Data was generated via qPCR human normalizer assay and data is reported by Ct value.

| MMLV RT Variant | Temperature of Reaction (° C.) | Ct Mean | Ct Standard Deviation |
|---|---|---|---|
| MMLV-II Q68R/Q79R/L99R/E282M | 49.2 | 25.560 | 0.019 |
| MMLV-II I61K/Q68R/Q79R/L99R/E282D | 49.2 | 24.719 | 0.177 |
| MMLV-II I61M/Q68R/Q79R/L99R/E282D | 49.2 | 25.123 | 0.034 |
| MMLV-II | 50.0 | 30.870 | 0.210 |
| MMLV-II Q79R/L99R/E282D | 50.0 | 26.677 | 0.090 |
| MMLV-II Q68R/Q79R/L99R | 50.0 | 25.381 | 0.049 |
| MMLV-II Q68R/Q79R/L99R/E282D | 50.0 | 24.820 | 0.064 |
| MMLV-II Q68R/Q79R/L99K/E282D | 50.0 | 25.348 | 0.098 |
| MMLV-II Q68R/Q79R/L99N/E282D | 50.0 | 25.287 | 0.064 |
| MMLV-II Q68K/Q79R/L99R/E282D | 50.0 | 25.208 | 0.085 |
| MMLV-II Q68R/Q79R/L99R/E282M | 50.0 | 25.790 | 0.051 |
| MMLV-II I61K/Q68R/Q79R/L99R/E282D | 50.0 | 24.840 | 0.071 |
| MMLV-II I61M/Q68R/Q79R/L99R/E282D | 50.0 | 25.317 | 0.042 |
| MMLV-II | 51.0 | 27.914 | 0.002 |
| MMLV-II Q79R/L99R/E282D | 51.0 | 25.561 | 0.069 |
| MMLV-II Q68R/Q79R/L99R | 51.0 | 25.225 | 0.069 |
| MMLV-II Q68R/Q79R/L99R/E282D | 51.0 | 24.726 | 0.034 |
| MMLV-II Q68R/Q79R/L99K/E282D | 51.0 | 25.324 | 0.071 |
| MMLV-II Q68R/Q79R/L99N/E282D | 51.0 | 25.157 | 0.062 |
| MMLV-II Q68K/Q79R/L99R/E282D | 51.0 | 25.275 | 0.039 |
| MMLV-II Q68R/Q79R/L99R/E282M | 51.0 | 25.938 | 0.095 |
| MMLV-II I61K/Q68R/Q79R/L99R/E282D | 51.0 | 25.821 | 0.072 |
| MMLV-II I61M/Q68R/Q79R/L99R/E282D | 51.0 | 25.053 | 0.044 |
| MMLV-II | 51.9 | 28.602 | 0.059 |
| MMLV-II Q79R/L99R/E282D | 51.9 | 25.975 | 0.024 |
| MMLV-II Q68R/Q79R/L99R | 51.9 | 25.256 | 0.075 |
| MMLV-II Q68R/Q79R/L99R/E282D | 51.9 | 24.903 | 0.050 |
| MMLV-II Q68R/Q79R/L99K/E282D | 51.9 | 25.163 | 0.169 |
| MMLV-II Q68R/Q79R/L99N/E282D | 51.9 | 25.272 | 0.011 |
| MMLV-II Q68R/Q79R/L99R/E282D | 51.9 | 25.491 | 0.075 |
| MMLV-II Q68R/Q79R/L99R/E282M | 51.9 | 25.878 | 0.038 |
| MMLV-II I61K/Q68R/Q79R/L99R/E282D | 51.9 | 26.071 | 0.044 |
| MMLV-II I61M/Q68R/Q79R/L99R/E282D | 51.9 | 25.419 | 0.067 |
| MMLV-II | 53.8 | 26.412 | 0.082 |
| MMLV-II Q79R/L99R/E282D | 53.8 | 25.558 | 0.063 |
| MMLV-II Q68R/Q79R/L99R | 53.8 | 24.969 | 0.065 |
| MMLV-II Q68R/Q79R/L99R/E282D | 53.8 | 25.356 | 0.063 |
| MMLV-II Q68R/Q79R/L99K/E282D | 53.8 | 25.460 | 0.056 |
| MMLV-II Q68R/Q79R/L99N/E282D | 53.8 | 25.769 | 0.118 |
| MMLV-II Q68K/Q79R/L99R/E282D | 53.8 | 26.251 | 0.103 |
| MMLV-II Q68R/Q79R/L99R/E282M | 53.8 | 26.310 | 0.174 |
| MMLV-II I61K/Q68R/Q79R/L99R/E282D | 53.8 | 25.701 | 0.106 |
| MMLV-II I61M/Q68R/Q79R/L99R/E282D | 53.8 | 26.412 | 0.082 |
| MMLV-II | 56.5 | 29.343 | 0.085 |
| MMLV-II Q79R/L99R/E282D | 56.5 | 26.885 | 0.083 |
| MMLV-II Q68R/Q79R/L99R | 56.5 | 25.736 | 0.015 |
| MMLV-II Q68R/Q79R/L99R/E282D | 56.5 | 25.223 | 0.016 |
| MMLV-II Q68R/Q79R/L99K/E282D | 56.5 | 25.900 | 0.039 |
| MMLV-II Q68R/Q79R/L99N/E282D | 56.5 | 25.930 | 0.031 |
| MMLV-II Q68K/Q79R/L99R/E282D | 56.5 | 25.869 | 0.204 |
| MMLV-II Q68R/Q79R/L99R/E282M | 56.5 | 26.622 | 0.067 |
| MMLV-II I61K/Q68R/Q79R/L99R/E282D | 56.5 | 25.817 | 0.089 |
| MMLV-II I61M/Q68R/Q79R/L99R/E282D | 56.5 | 26.290 | 0.009 |
| MMLV-II | 59.9 | 29.693 | 0.047 |
| MMLV-II Q79R/L99R/E282D | 59.9 | 27.820 | 0.014 |
| MMLV-II Q68R/Q79R/L99R | 59.9 | 26.069 | 0.057 |
| MMLV-II Q68R/Q79R/L99R/E282D | 59.9 | 25.374 | 0.061 |
| MMLV-II Q68R/Q79R/L99K/E282D | 59.9 | 26.066 | 0.053 |
| MMLV-II Q68R/Q79R/L99N/E282D | 59.9 | 25.873 | 0.018 |
| MMLV-II Q68K/Q79R/L99R/E282D | 59.9 | 26.278 | 0.073 |
| MMLV-II Q68R/Q79R/L99R/E282M | 59.9 | 27.068 | 0.075 |
| MMLV-II I61K/Q68R/Q79R/L99R/E282D | 59.9 | 26.863 | 0.025 |
| MMLV-II I61M/Q68R/Q79R/L99R/E282D | 59.9 | 26.176 | 0.072 |
| MMLV-II | 62.6 | 29.731 | 0.092 |
| MMLV-II Q79R/L99R/E282D | 62.6 | 27.161 | 0.035 |
| MMLV-II Q68R/Q79R/L99R | 62.6 | 25.929 | 0.026 |
| MMLV-II Q68R/Q79R/L99R/E282D | 62.6 | 25.303 | 0.074 |
| MMLV-II Q68R/Q79R/L99K/E282D | 62.6 | 25.907 | 0.003 |
| MMLV-II Q68R/Q79R/L99N/E282D | 62.6 | 26.145 | 0.053 |
| MMLV-II Q68R/Q79R/L99R/E282D | 62.6 | 26.181 | 0.056 |
| MMLV-II Q68R/Q79R/L99R/E282M | 62.6 | 27.134 | 0.015 |
| MMLV-II I61K/Q68R/Q79R/L99R/E282D | 62.6 | 26.025 | 0.178 |
| MMLV-II I61M/Q68R/Q79R/L99R/E282D | 62.6 | 26.304 | 0.041 |
| MMLV-II | 64.2 | 26.809 | 0.080 |
| MMLV-II Q79R/L99R/E282D | 64.2 | 27.325 | 0.038 |
| MMLV-II Q68R/Q79R/L99R | 64.2 | 26.131 | 0.018 |
| MMLV-II Q68R/Q79R/L99R/E282D | 64.2 | 25.542 | 0.135 |
| MMLV-II Q68R/Q79R/L99K/E282D | 64.2 | 26.408 | 0.093 |
| MMLV-II Q68R/Q79R/L99N/E282D | 64.2 | 26.734 | 0.040 |
| MMLV-II Q68K/Q79R/L99R/E282D | 64.2 | 30.589 | 0.128 |
| MMLV-II Q68R/Q79R/L99R/E282M | 64.2 | 26.262 | 0.090 |
| MMLV-II I61K/Q68R/Q79R/L99R/E282D | 64.2 | 27.594 | 0.118 |
| MMLV-II I61M/Q68R/Q79R/L99R/E282D | 64.2 | 27.062 | 0.051 |
| MMLV-II | 65.0 | 30.277 | 0.050 |
| MMLV-II Q79R/L99R/E282D | 65.0 | 27.119 | 0.065 |
| MMLV-II Q68R/Q79R/L99R | 65.0 | 26.078 | 0.025 |

TABLE 17-continued

Two-Step cDNA synthesis by MMLV RT triple and more mutants by Oligo-dT priming. Data was generated via qPCR human normalizer assay and data is reported by Ct value.

| MMLV RT Variant | Temperature of Reaction (° C.) | Ct Mean | Ct Standard Deviation |
|---|---|---|---|
| MMLV-II Q68R/Q79R/L99R/E282D | 65.0 | 25.583 | 0.068 |
| MMLV-II Q68R/Q79R/L99K/E282D | 65.0 | 25.906 | 0.080 |
| MMLV-II Q68R/Q79R/L99N/E282D | 65.0 | 26.943 | 0.058 |
| MMLV-II Q68K/Q79R/L99R/E282D | 65.0 | 26.413 | 0.067 |
| MMLV-II Q68R/Q79R/L99R/E282M | 65.0 | 28.233 | 0.075 |
| MMLV-II I61K/Q68R/Q79R/L99R/E282D | 65.0 | 25.778 | 0.129 |
| MMLV-II I61M/Q68R/Q79R/L99R/E282D | 65.0 | 27.345 | 0.015 |

TABLE 18

Two-Step cDNA synthesis by MMLV RT triple and more mutants by random hexamer priming. Data was generated via qPCR human normalizer assay and data is reported by Ct value.

| MMLV RT Variant | Temperature of Reaction (° C.) | Ct Mean | Ct Standard Deviation |
|---|---|---|---|
| MMLV-II | 37.0 | 25.827 | 0.120 |
| MMLV-II Q79R/L99R/E282D | 37.0 | 25.616 | 0.094 |
| MMLV-II Q68R/Q79R/L99R | 37.0 | 24.747 | 0.041 |
| MMLV-II Q68R/Q79R/L99R/E282D | 37.0 | 24.595 | 0.034 |
| MMLV-II Q68R/Q79R/L99K/E282D | 37.0 | 24.917 | 0.078 |
| MMLV-II Q68R/Q79R/L99N/E282D | 37.0 | 24.817 | 0.024 |
| MMLV-II Q68K/Q79R/L99R/E282D | 37.0 | 24.757 | 0.032 |
| MMLV-II Q68R/Q79R/L99R/E282M | 37.0 | 24.754 | 0.062 |
| MMLV-II I61K/Q68R/Q79R/L99R/E282D | 37.0 | 24.883 | 0.106 |
| MMLV-II I61M/Q68R/Q79R/L99R/E282D | 37.0 | 24.776 | 0.028 |
| MMLV-II | 37.8 | 25.609 | 0.038 |
| MMLV-II Q79R/L99R/E282D | 37.8 | 25.300 | 0.061 |
| MMLV-II Q68R/Q79R/L99R | 37.8 | 24.822 | 0.037 |
| MMLV-II Q68R/Q79R/L99R/E282D | 37.8 | 24.690 | 0.044 |
| MMLV-II Q68R/Q79R/L99K/E282D | 37.8 | 24.884 | 0.033 |
| MMLV-II Q68R/Q79R/L99N/E282D | 37.8 | 24.665 | 0.022 |
| MMLV-II Q68K/Q79R/L99R/E282D | 37.8 | 24.846 | 0.021 |
| MMLV-II Q68R/Q79R/L99R/E282M | 37.8 | 24.882 | 0.043 |
| MMLV-II I61K/Q68R/Q79R/L99R/E282D | 37.8 | 24.846 | 0.059 |
| MMLV-II I61M/Q68R/Q79R/L99R/E282D | 37.8 | 24.723 | 0.023 |
| MMLV-II | 39.5 | 25.455 | 0.020 |
| MMLV-II Q79R/L99R/E282D | 39.5 | 24.790 | 0.109 |
| MMLV-II Q68R/Q79R/L99R | 39.5 | 24.712 | 0.050 |
| MMLV-II Q68R/Q79R/L99R/E282D | 39.5 | 24.543 | 0.005 |
| MMLV-II Q68R/Q79R/L99K/E282D | 39.5 | 24.714 | 0.035 |
| MMLV-II Q68R/Q79R/L99N/E282D | 39.5 | 24.520 | 0.084 |
| MMLV-II Q68K/Q79R/L99R/E282D | 39.5 | 24.752 | 0.047 |
| MMLV-II Q68R/Q79R/L99R/E282M | 39.5 | 24.850 | 0.054 |
| MMLV-II I61K/Q68R/Q79R/L99R/E282D | 39.5 | 24.698 | 0.059 |
| MMLV-II I61M/Q68R/Q79R/L99R/E282D | 39.5 | 24.682 | 0.024 |
| MMLV-II | 42.0 | 25.136 | 0.034 |
| MMLV-II Q79R/L99R/E282D | 42.0 | 24.760 | 0.052 |
| MMLV-II Q68R/Q79R/L99R | 42.0 | 24.637 | 0.037 |
| MMLV-II Q68R/Q79R/L99R/E282D | 42.0 | 24.449 | 0.008 |
| MMLV-II Q68R/Q79R/L99K/E282D | 42.0 | 24.650 | 0.068 |
| MMLV-II Q68R/Q79R/L99N/E282D | 42.0 | 24.477 | 0.055 |
| MMLV-II Q68K/Q79R/L99R/E282D | 42.0 | 24.624 | 0.029 |
| MMLV-II Q68R/Q79R/L99R/E282M | 42.0 | 24.627 | 0.044 |
| MMLV-II I61K/Q68R/Q79R/L99R/E282D | 42.0 | 24.718 | 0.083 |
| MMLV-II I61M/Q68R/Q79R/L99R/E282D | 42.0 | 24.532 | 0.021 |
| MMLV-II | 45.2 | 25.079 | 0.017 |
| MMLV-II Q79R/L99R/E282D | 45.2 | 24.624 | 0.026 |
| MMLV-II Q68R/Q79R/L99R | 45.2 | 24.525 | 0.021 |
| MMLV-II Q68R/Q79R/L99R/E282D | 45.2 | 24.430 | 0.014 |
| MMLV-II Q68R/Q79R/L99K/E282D | 45.2 | 24.525 | 0.037 |
| MMLV-II Q68R/Q79R/L99N/E282D | 45.2 | 34.853 | 0.705 |
| MMLV-II Q68K/Q79R/L99R/E282D | 45.2 | 24.653 | 0.055 |
| MMLV-II Q68R/Q79R/L99R/E282M | 45.2 | 24.552 | 0.060 |
| MMLV-II I61K/Q68R/Q79R/L99R/E282D | 45.2 | 24.595 | 0.027 |
| MMLV-II I61M/Q68R/Q79R/L99R/E282D | 45.2 | 24.493 | 0.016 |
| MMLV-II | 47.8 | 25.346 | 0.007 |
| MMLV-II Q79R/L99R/E282D | 47.8 | 24.521 | 0.097 |
| MMLV-II Q68R/Q79R/L99R | 47.8 | 24.605 | 0.018 |
| MMLV-II Q68R/Q79R/L99R/E282D | 47.8 | 24.333 | 0.107 |
| MMLV-II Q68R/Q79R/L99K/E282D | 47.8 | 24.516 | 0.043 |
| MMLV-II Q68R/Q79R/L99N/E282D | 47.8 | 24.527 | 0.026 |
| MMLV-II Q68K/Q79R/L99R/E282D | 47.8 | 24.539 | 0.064 |
| MMLV-II Q68R/Q79R/L99R/E282M | 47.8 | 24.631 | 0.019 |
| MMLV-II I61K/Q68R/Q79R/L99R/E282D | 47.8 | 24.227 | 0.260 |
| MMLV-II I61M/Q68R/Q79R/L99R/E282D | 47.8 | 24.441 | 0.030 |
| MMLV-II | 49.2 | 25.791 | 0.064 |
| MMLV-II Q79R/L99R/E282D | 49.2 | 24.700 | 0.033 |
| MMLV-II Q68R/Q79R/L99R | 49.2 | 24.658 | 0.008 |
| MMLV-II Q68R/Q79R/L99R/E282D | 49.2 | 24.471 | 0.069 |
| MMLV-II Q68R/Q79R/L99K/E282D | 49.2 | 24.590 | 0.024 |
| MMLV-II Q68R/Q79R/L99N/E282D | 49.2 | 24.482 | 0.099 |
| MMLV-II Q68K/Q79R/L99R/E282D | 49.2 | 24.549 | 0.028 |
| MMLV-II Q68R/Q79R/L99R/E282M | 49.2 | 24.753 | 0.030 |
| MMLV-II I61K/Q68R/Q79R/L99R/E282D | 49.2 | 24.499 | 0.157 |

TABLE 18-continued

Two-Step cDNA synthesis by MMLV RT triple and more mutants by random hexamer priming. Data was generated via qPCR human normalizer assay and data is reported by Ct value.

| MMLV RT Variant | Temperature of Reaction (° C.) | Ct Mean | Ct Standard Deviation |
|---|---|---|---|
| MMLV-II I61M/Q68R/Q79R/L99R/E282D | 49.2 | 24.559 | 0.033 |
| MMLV-II | 50.0 | 26.267 | 0.025 |
| MMLV-II Q79R/L99R/E282D | 50.0 | 24.729 | 0.047 |
| MMLV-II Q68R/Q79R/L99R | 50.0 | 24.462 | 0.040 |
| MMLV-II Q68R/Q79R/L99R/E282D | 50.0 | 24.412 | 0.035 |
| MMLV-II Q68R/Q79R/L99K/E282D | 50.0 | 24.438 | 0.090 |
| MMLV-II Q68R/Q79R/L99N/E282D | 50.0 | 24.509 | 0.050 |
| MMLV-II Q68K/Q79R/L99R/E282D | 50.0 | 24.405 | 0.059 |
| MMLV-II Q68R/Q79R/L99R/E282M | 50.0 | 24.547 | 0.041 |
| MMLV-II I61K/Q68R/Q79R/L99R/E282D | 50.0 | 24.504 | 0.005 |
| MMLV-II I61M/Q68R/Q79R/L99R/E282D | 50.0 | 24.481 | 0.009 |
| MMLV-II | 51.0 | 27.277 | 0.058 |
| MMLV-II Q79R/L99R/E282D | 51.0 | 25.694 | 0.104 |
| MMLV-II Q68R/Q79R/L99R | 51.0 | 24.579 | 0.037 |
| MMLV-II Q68R/Q79R/L99R/E282D | 51.0 | 24.364 | 0.019 |
| MMLV-II Q68R/Q79R/L99K/E282D | 51.0 | 24.849 | 0.041 |
| MMLV-II Q68R/Q79R/L99N/E282D | 51.0 | 24.899 | 0.121 |
| MMLV-II Q68K/Q79R/L99R/E282D | 51.0 | 24.980 | 0.048 |
| MMLV-II Q68R/Q79R/L99R/E282M | 51.0 | 25.292 | 0.065 |
| MMLV-II I61K/Q68R/Q79R/L99R/E282D | 51.0 | 25.147 | 0.100 |
| MMLV-II I61M/Q68R/Q79R/L99R/E282D | 51.0 | 25.034 | 0.075 |
| MMLV-II | 51.9 | 28.797 | 0.055 |
| MMLV-II Q79R/L99R/E282D | 51.9 | 26.585 | 0.011 |
| MMLV-II Q68R/Q79R/L99R | 51.9 | 25.021 | 0.036 |
| MMLV-II Q68R/Q79R/L99R/E282D | 51.9 | 24.763 | 0.028 |
| MMLV-II Q68R/Q79R/L99K/E282D | 51.9 | 25.392 | 0.012 |
| MMLV-II Q68R/Q79R/L99N/E282D | 51.9 | 25.543 | 0.087 |
| MMLV-II Q68K/Q79R/L99R/E282D | 51.9 | 25.549 | 0.058 |
| MMLV-II Q68R/Q79R/L99R/E282M | 51.9 | 26.025 | 0.065 |
| MMLV-II I61K/Q68R/Q79R/L99R/E282D | 51.9 | 26.087 | 0.024 |
| MMLV-II I61M/Q68R/Q79R/L99R/E282D | 51.9 | 25.756 | 0.054 |
| MMLV-II | 53.8 | 30.985 | 0.073 |
| MMLV-II Q79R/L99R/E282D | 53.8 | 29.356 | 0.044 |
| MMLV-II Q68R/Q79R/L99R | 53.8 | 26.370 | 0.041 |
| MMLV-II Q68R/Q79R/L99R/E282D | 53.8 | 25.580 | 0.049 |
| MMLV-II Q68R/Q79R/L99K/E282D | 53.8 | 26.682 | 0.029 |
| MMLV-II Q68R/Q79R/L99N/E282D | 53.8 | 26.438 | 0.031 |
| MMLV-II Q68K/Q79R/L99R/E282D | 53.8 | 27.024 | 0.042 |
| MMLV-II Q68R/Q79R/L99R/E282M | 53.8 | 28.314 | 0.051 |
| MMLV-II I61K/Q68R/Q79R/L99R/E282D | 53.8 | 27.489 | 0.025 |
| MMLV-II I61M/Q68R/Q79R/L99R/E282D | 53.8 | 27.871 | 0.118 |
| MMLV-II | 56.5 | 33.313 | 0.164 |
| MMLV-II Q79R/L99R/E282D | 56.5 | 32.626 | 0.113 |
| MMLV-II Q68R/Q79R/L99R | 56.5 | 30.047 | 0.089 |
| MMLV-II Q68R/Q79R/L99R/E282D | 56.5 | 29.183 | 0.155 |
| MMLV-II Q68R/Q79R/L99K/E282D | 56.5 | 30.750 | 0.051 |
| MMLV-II Q68R/Q79R/L99N/E282D | 56.5 | 30.403 | 0.095 |
| MMLV-II Q68K/Q79R/L99R/E282D | 56.5 | 31.707 | 0.111 |
| MMLV-II Q68R/Q79R/L99R/E282M | 56.5 | 31.878 | 0.093 |
| MMLV-II I61K/Q68R/Q79R/L99R/E282D | 56.5 | 32.235 | 0.291 |
| MMLV-II I61M/Q68R/Q79R/L99R/E282D | 56.5 | 32.395 | 0.105 |
| MMLV-II | 59.9 | 34.408 | 0.498 |
| MMLV-II Q79R/L99R/E282D | 59.9 | 36.798 | 2.131 |
| MMLV-II Q68R/Q79R/L99R | 59.9 | 33.997 | 0.035 |
| MMLV-II Q68R/Q79R/L99R/E282D | 59.9 | 32.009 | 0.051 |
| MMLV-II Q68R/Q79R/L99K/E282D | 59.9 | 33.685 | 0.317 |
| MMLV-II Q68R/Q79R/L99N/E282D | 59.9 | 33.083 | 0.163 |
| MMLV-II Q68K/Q79R/L99R/E282D | 59.9 | 34.160 | 0.066 |
| MMLV-II Q68R/Q79R/L99R/E282M | 59.9 | 33.650 | 0.161 |
| MMLV-II I61K/Q68R/Q79R/L99R/E282D | 59.9 | 33.341 | 0.096 |
| MMLV-II I61M/Q68R/Q79R/L99R/E282D | 59.9 | 34.439 | 0.222 |
| MMLV-II | 62.6 | 35.163 | 0.447 |
| MMLV-II Q79R/L99R/E282D | 62.6 | 37.138 | 1.603 |
| MMLV-II Q68R/Q79R/L99R | 62.6 | 34.108 | 0.604 |
| MMLV-II Q68R/Q79R/L99R/E282D | 62.6 | 32.539 | 0.060 |
| MMLV-II Q68R/Q79R/L99K/E282D | 62.6 | 34.175 | 0.421 |
| MMLV-II Q68R/Q79R/L99N/E282D | 62.6 | 33.726 | 0.622 |
| MMLV-II Q68K/Q79R/L99R/E282D | 62.6 | 34.376 | 0.408 |
| MMLV-II Q68R/Q79R/L99R/E282M | 62.6 | 33.792 | 0.231 |
| MMLV-II I61K/Q68R/Q79R/L99R/E282D | 62.6 | 33.768 | 0.387 |
| MMLV-II I61M/Q68R/Q79R/L99R/E282D | 62.6 | 34.428 | 0.085 |
| MMLV-II | 64.2 | 37.284 | 0.764 |
| MMLV-II Q79R/L99R/E282D | 64.2 | 36.661 | 0.192 |
| MMLV-II Q68R/Q79R/L99R | 64.2 | 34.463 | 0.213 |
| MMLV-II Q68R/Q79R/L99R/E282D | 64.2 | 32.992 | 0.023 |
| MMLV-II Q68R/Q79R/L99K/E282D | 64.2 | 34.805 | 0.472 |
| MMLV-II Q68R/Q79R/L99N/E282D | 64.2 | 34.060 | 0.043 |
| MMLV-II Q68K/Q79R/L99R/E282D | 64.2 | 34.508 | 0.302 |
| MMLV-II Q68R/Q79R/L99R/E282M | 64.2 | 34.481 | 0.078 |
| MMLV-II I61K/Q68R/Q79R/L99R/E282D | 64.2 | 34.231 | 0.253 |
| MMLV-II I61M/Q68R/Q79R/L99R/E282D | 64.2 | 35.049 | 0.885 |
| MMLV-II | 65.0 | 35.809 | 0.511 |
| MMLV-II Q79R/L99R/E282D | 65.0 | 35.932 | 0.372 |
| MMLV-II Q68R/Q79R/L99R | 65.0 | 34.979 | 0.856 |
| MMLV-II Q68R/Q79R/L99R/E282D | 65.0 | 33.293 | 0.319 |
| MMLV-II Q68R/Q79R/L99K/E282D | 65.0 | 34.974 | 0.536 |

TABLE 18-continued

Two-Step cDNA synthesis by MMLV RT triple and more mutants
by random hexamer priming. Data was generated via qPCR human
normalizer assay and data is reported by Ct value.

| MMLV RT Variant | Temperature of Reaction (° C.) | Ct Mean | Ct Standard Deviation |
|---|---|---|---|
| MMLV-II Q68R/Q79R/L99N/E282D | 65.0 | 34.862 | 0.268 |
| MMLV-II Q68K/Q79R/L99R/E282D | 65.0 | 34.363 | 0.201 |
| MMLV-II Q68R/Q79R/L99R/E282M | 65.0 | 34.687 | 0.666 |
| MMLV-II I61K/Q68R/Q79R/L99R/E282D | 65.0 | 34.246 | 0.563 |
| MMLV-II I61M/Q68R/Q79R/L99R/E282D | 65.0 | 34.872 | 0.467 |

Example 6: Reverse Transcriptase Mutant
Evaluation by Oligo dT or Random Priming This example demonstrates the procedure used to evaluate each mutant RTase's ability to synthesize cDNA from purified total RNA (DNased, isolated from HeLa cells) compared to the base construct of MMLV RTase. The mutant MMLV RTases were tested by two priming conditions: Oligo dT only and random hexamer priming using a standard two-step cDNA synthesis as described in Example 5.

The reactions were analyzed and reported by Ct value (Tables 19 and 20). Four mutant variants of MMLV RTase showed an increase in the overall activity using oligo dT priming compared to the base construct, Q299E, T332E and V433R. Eight mutant variants of MMLV RTase showed an increase in the overall activity using random priming compared to the base construct, P76R, L82R, I125R, Y271A, L280A, L280R, T328R and V433R.

TABLE 19

Two-Step cDNA Synthesis by MMLV-RT single mutants using
oligo dT priming. The data was generated via qPCR human
normalizer assay and data is reported by Ct value.

| MMLV-RT Variant | Ct Mean | Ct Standard Deviation |
|---|---|---|
| MMLV-II | 40.000 | 0.000 |
| MMLV-II D209A | 40.000 | 0.000 |
| MMLV-II D209E | 40.000 | 0.000 |
| MMLV-II D209R | 40.000 | 0.000 |
| MMLV-II D83 A | 40.000 | 0.000 |
| MMLV-II D83E | 40.000 | 0.000 |
| MMLV-II D83R | 40.000 | 0.000 |
| MMLV-II E201A | 40.000 | 0.000 |
| MMLV-II E201D | 40.000 | 0.000 |
| MMLV-II E201R | 40.000 | 0.000 |
| MMLV-II E367A | 40.000 | 0.000 |
| MMLV-II E367D | 40.000 | 0.000 |
| MMLV-II E367R | 40.000 | 0.000 |
| MMLV-II E596A | 40.000 | 0.000 |
| MMLV-II E596D | 40.000 | 0.000 |
| MMLV-II E596R | 40.000 | 0.000 |
| MMLV-II F210A | 40.000 | 0.000 |
| MMLV-II F210E | 40.000 | 0.000 |
| MMLV-II F210R | 40.000 | 0.000 |
| MMLV-II F369A | 40.000 | 0.000 |
| MMLV-II F369E | 40.000 | 0.000 |
| MMLV-II F369R | 40.000 | 0.000 |
| MMLV-II G308A | 40.000 | 0.000 |
| MMLV-II G308E | 40.000 | 0.000 |
| MMLV-II G308R | 40.000 | 0.000 |
| MMLV-II G331A | 40.000 | 0.000 |
| MMLV-II G331E | 40.000 | 0.000 |

TABLE 19-continued

Two-Step cDNA Synthesis by MMLV-RT single mutants using
oligo dT priming. The data was generated via qPCR human
normalizer assay and data is reported by Ct value.

| MMLV-RT Variant | Ct Mean | Ct Standard Deviation |
|---|---|---|
| MMLV-II G331R | 40.000 | 0.000 |
| MMLV-II G73A | 40.000 | 0.000 |
| MMLV-II G73E | 40.000 | 0.000 |
| MMLV-II G73R | 40.000 | 0.000 |
| MMLV-II H77A | 40.000 | 0.000 |
| MMLV-II H77E | 40.000 | 0.000 |
| MMLV-II H77R | 40.000 | 0.000 |
| MMLV-II I125A | 40.000 | 0.000 |
| MMLV-II I125E | 40.000 | 0.000 |
| MMLV-II I125R | 40.000 | 0.000 |
| MMLV-II I212A | 40.000 | 0.000 |
| MMLV-II I212E | 40.000 | 0.000 |
| MMLV-II I212R | 40.000 | 0.000 |
| MMLV-II I593A | 40.000 | 0.000 |
| MMLV-II I593E | 40.000 | 0.000 |
| MMLV-II I593R | 40.000 | 0.000 |
| MMLV-II I597A | 40.000 | 0.000 |
| MMLV-II I597E | 40.000 | 0.000 |
| MMLV-II I597R | 40.000 | 0.000 |
| MMLV-II K285A | 40.000 | 0.000 |
| MMLV-II K285E | 40.000 | 0.000 |
| MMLV-II K285R | 40.000 | 0.000 |
| MMLV-II K348A | 40.000 | 0.000 |
| MMLV-II K348E | 40.000 | 0.000 |
| MMLV-II K348R | 40.000 | 0.000 |
| MMLV-II L198A | 40.000 | 0.000 |
| MMLV-II L198E | 40.000 | 0.000 |
| MMLV-II L198R | 40.000 | 0.000 |
| MMLV-II L280A | 40.000 | 0.000 |
| MMLV-II L280E | 40.000 | 0.000 |
| MMLV-II L280R | 40.000 | 0.000 |
| MMLV-II L352A | 40.000 | 0.000 |
| MMLV-II L352E | 40.000 | 0.000 |
| MMLV-II L352R | 40.000 | 0.000 |
| MMLV-II L357A | 40.000 | 0.000 |
| MMLV-II L357E | 40.000 | 0.000 |
| MMLV-II L357R | 40.000 | 0.000 |
| MMLV-II L82A | 40.000 | 0.000 |
| MMLV-II L82E | 40.000 | 0.000 |
| MMLV-II L82R | 40.000 | 0.000 |
| MMLV-II N335A | 39.787 | 0.302 |
| MMLV-II N335E | 40.000 | 0.000 |
| MMLV-II N335R | 40.000 | 0.000 |
| MMLV-II P76A | 40.000 | 0.000 |
| MMLV-II P76E | 40.000 | 0.000 |
| MMLV-II P76R | 40.000 | 0.000 |
| MMLV-II Q213A | 40.000 | 0.000 |
| MMLV-II Q213E | 40.000 | 0.000 |
| MMLV-II Q213R | 40.000 | 0.000 |
| MMLV-II Q299A | 40.000 | 0.000 |
| MMLV-II Q299E | 37.177 | 3.993 |
| MMLV-II Q299R | 40.000 | 0.000 |
| MMLV-II Q654A | 40.000 | 0.000 |
| MMLV-II Q654E | 40.000 | 0.000 |
| MMLV-II Q654R | 40.000 | 0.000 |
| MMLV-II R205A | 40.000 | 0.000 |
| MMLV-II R205E | 39.947 | 0.075 |
| MMLV-II R205K | 40.000 | 0.000 |
| MMLV-II R211A | 40.000 | 0.000 |
| MMLV-II R211E | 40.000 | 0.000 |
| MMLV-II R211K | 40.000 | 0.000 |
| MMLV-II R311A | 40.000 | 0.000 |
| MMLV-II R311E | 40.000 | 0.000 |
| MMLV-II R311K | 40.000 | 0.000 |
| MMLV-II R389A | 40.000 | 0.000 |
| MMLV-II R389E | 40.000 | 0.000 |
| MMLV-II R389K | 40.000 | 0.000 |
| MMLV-II R650A | 40.000 | 0.000 |
| MMLV-II R650E | 40.000 | 0.000 |
| MMLV-II R650K | 40.000 | 0.000 |
| MMLV-II R657A | 40.000 | 0.000 |
| MMLV-II R657E | 39.965 | 0.050 |
| MMLV-II R657K | 40.000 | 0.000 |

TABLE 19-continued

Two-Step cDNA Synthesis by MMLV-RT single mutants using
oligo dT priming. The data was generated via qPCR human
normalizer assay and data is reported by Ct value.

| MMLV-RT Variant | Ct Mean | Ct Standard Deviation |
|---|---|---|
| MMLV-II S67A | 40.000 | 0.000 |
| MMLV-II S67E | 40.000 | 0.000 |
| MMLV-II S67R | 36.816 | 0.703 |
| MMLV-II T328A | 40.000 | 0.000 |
| MMLV-II T328E | 40.000 | 0.000 |
| MMLV-II T328R | 40.000 | 0.000 |
| MMLV-II T332A | 39.750 | 0.354 |
| MMLV-II T332E | 38.461 | 2.177 |
| MMLV-II T332R | 40.000 | 0.000 |
| MMLV-II V129A | 40.000 | 0.000 |
| MMLV-II V129E | 40.000 | 0.000 |
| MMLV-II V129R | 40.000 | 0.000 |
| MMLV-II V433A | 40.000 | 0.000 |
| MMLV-II V433E | 40.000 | 0.000 |
| MMLV-II V433R | 38.884 | 0.806 |
| MMLV-II V476A | 40.000 | 0.000 |
| MMLV-II V476E | 40.000 | 0.000 |
| MMLV-II V476R | 40.000 | 0.000 |
| MMLV-II Y271A | 40.000 | 0.000 |
| MMLV-II Y271E | 40.000 | 0.000 |
| MMLV-II Y271R | 40.000 | 0.000 |
| MMLV-IV | 31.467 | 0.190 |

TABLE 20

Two-Step cDNA Synthesis by MMLV-RT single mutants using
random priming. The data was generated via qPCR human
normalizer assay and data is reported by Ct value.

| MMLV-RT Variant | Ct Mean | Ct Standard Deviation |
|---|---|---|
| MMLV-II | 40.000 | 0.000 |
| MMLV-II D209A | 40.000 | 0.000 |
| MMLV-II D209E | 40.000 | 0.000 |
| MMLV-II D209R | 40.000 | 0.000 |
| MMLV-II D83A | 40.000 | 0.000 |
| MMLV-II D83E | 40.000 | 0.000 |
| MMLV-II D83R | 40.000 | 0.000 |
| MMLV-II E201A | 40.000 | 0.000 |
| MMLV-II E201D | 40.000 | 0.000 |
| MMLV-II E201R | 40.000 | 0.000 |
| MMLV-II E367A | 40.000 | 0.000 |
| MMLV-II E367D | 40.000 | 0.000 |
| MMLV-II E367R | 40.000 | 0.000 |
| MMLV-II E596A | 40.000 | 0.000 |
| MMLV-II E596D | 40.000 | 0.000 |
| MMLV-II E596R | 40.000 | 0.000 |
| MMLV-II F210A | 40.000 | 0.000 |
| MMLV-II F210E | 40.000 | 0.000 |
| MMLV-II F210R | 40.000 | 0.000 |
| MMLV-II F369A | 40.000 | 0.000 |
| MMLV-II F369E | 40.000 | 0.000 |
| MMLV-II F369R | 40.000 | 0.000 |
| MMLV-II G308A | 40.000 | 0.000 |
| MMLV-II G308E | 40.000 | 0.000 |
| MMLV-II G308R | 40.000 | 0.000 |
| MMLV-II G331A | 40.000 | 0.000 |
| MMLV-II G331E | 40.000 | 0.000 |
| MMLV-II G331R | 40.000 | 0.000 |
| MMLV-II G73A | 40.000 | 0.000 |
| MMLV-II G73E | 40.000 | 0.000 |
| MMLV-II G73R | 40.000 | 0.000 |
| MMLV-II H77A | 39.708 | 0.412 |
| MMLV-II H77E | 40.000 | 0.000 |
| MMLV-II H77R | 40.000 | 0.000 |
| MMLV-II I125A | 40.000 | 0.000 |
| MMLV-II I125E | 40.000 | 0.000 |
| MMLV-II I125R | 39.449 | 0.779 |
| MMLV-II I212A | 40.000 | 0.000 |

TABLE 20-continued

Two-Step cDNA Synthesis by MMLV-RT single mutants using
random priming. The data was generated via qPCR human
normalizer assay and data is reported by Ct value.

| MMLV-RT Variant | Ct Mean | Ct Standard Deviation |
|---|---|---|
| MMLV-II I212E | 40.000 | 0.000 |
| MMLV-II I212R | 40.000 | 0.000 |
| MMLV-II I593A | 40.000 | 0.000 |
| MMLV-II I593E | 40.000 | 0.000 |
| MMLV-II I593R | 40.000 | 0.000 |
| MMLV-II I597A | 40.000 | 0.000 |
| MMLV-II I597E | 40.000 | 0.000 |
| MMLV-II I597R | 40.000 | 0.000 |
| MMLV-II K285A | 40.000 | 0.000 |
| MMLV-II K285E | 40.000 | 0.000 |
| MMLV-II K285R | 39.783 | 0.308 |
| MMLV-II K348A | 40.000 | 0.000 |
| MMLV-II K348E | 40.000 | 0.000 |
| MMLV-II K348R | 40.000 | 0.000 |
| MMLV-II L198A | 40.000 | 0.000 |
| MMLV-II L198E | 40.000 | 0.000 |
| MMLV-II L198R | 40.000 | 0.000 |
| MMLV-II L280A | 39.503 | 0.703 |
| MMLV-II L280E | 40.000 | 0.000 |
| MMLV-II L280R | 38.762 | 1.751 |
| MMLV-II L352A | 39.778 | 0.313 |
| MMLV-II L352E | 40.000 | 0.000 |
| MMLV-II L352R | 40.000 | 0.000 |
| MMLV-II L357A | 40.000 | 0.000 |
| MMLV-II L357E | 40.000 | 0.000 |
| MMLV-II L357R | 40.000 | 0.000 |
| MMLV-II L82A | 40.000 | 0.000 |
| MMLV-II L82E | 39.673 | 0.462 |
| MMLV-II L82R | 38.926 | 1.518 |
| MMLV-II N335A | 39.876 | 0.175 |
| MMLV-II N335E | 40.000 | 0.000 |
| MMLV-II N335R | 39.861 | 0.196 |
| MMLV-II P76A | 40.000 | 0.000 |
| MMLV-II P76E | 40.000 | 0.000 |
| MMLV-II P76R | 39.535 | 0.658 |
| MMLV-II Q213A | 40.000 | 0.000 |
| MMLV-II Q213E | 40.000 | 0.000 |
| MMLV-II Q213R | 40.000 | 0.000 |
| MMLV-II Q299A | 40.000 | 0.000 |
| MMLV-II Q299E | 40.000 | 0.000 |
| MMLV-II Q299R | 40.000 | 0.000 |
| MMLV-II Q654A | 40.000 | 0.000 |
| MMLV-II Q654E | 40.000 | 0.000 |
| MMLV-II Q654R | 40.000 | 0.000 |
| MMLV-II R205A | 39.811 | 0.267 |
| MMLV-II R205E | 40.000 | 0.000 |
| MMLV-II R205K | 40.000 | 0.000 |
| MMLV-II R211A | 40.000 | 0.000 |
| MMLV-II R211E | 40.000 | 0.000 |
| MMLV-II R211K | 40.000 | 0.000 |
| MMLV-II R311A | 40.000 | 0.000 |
| MMLV-II R311E | 40.000 | 0.000 |
| MMLV-II R311K | 40.000 | 0.000 |
| MMLV-II R389A | 40.000 | 0.000 |
| MMLV-II R389E | 40.000 | 0.000 |
| MMLV-II R389K | 40.000 | 0.000 |
| MMLV-II R650A | 40.000 | 0.000 |
| MMLV-II R650E | 40.000 | 0.000 |
| MMLV-II R650K | 40.000 | 0.000 |
| MMLV-II R657A | 40.000 | 0.000 |
| MMLV-II R657E | 40.000 | 0.000 |
| MMLV-II R657K | 40.000 | 0.000 |
| MMLV-II S67A | 40.000 | 0.000 |
| MMLV-II S67E | 39.435 | 0.800 |
| MMLV-II S67R | 38.209 | 0.977 |
| MMLV-II T328A | 40.000 | 0.000 |
| MMLV-II T328E | 40.000 | 0.000 |
| MMLV-II T328R | 39.478 | 0.739 |
| MMLV-II T332A | 40.000 | 0.000 |
| MMLV-II T332E | 40.000 | 0.000 |
| MMLV-II T332R | 40.000 | 0.000 |
| MMLV-II V129A | 40.000 | 0.000 |
| MMLV-II V129E | 40.000 | 0.000 |

TABLE 20-continued

Two-Step cDNA Synthesis by MMLV-RT single mutants using random priming. The data was generated via qPCR human normalizer assay and data is reported by Ct value.

| MMLV-RT Variant | Ct Mean | Ct Standard Deviation |
|---|---|---|
| MMLV-II V129R | 40.000 | 0.000 |
| MMLV-II V433A | 40.000 | 0.000 |
| MMLV-II V433E | 40.000 | 0.000 |
| MMLV-II V433R | 38.071 | 1.452 |
| MMLV-II V476A | 40.000 | 0.000 |
| MMLV-II V476E | 40.000 | 0.000 |
| MMLV-II V476R | 40.000 | 0.000 |
| MMLV-II Y271A | 39.466 | 0.755 |
| MMLV-II Y271E | 40.000 | 0.000 |

TABLE 20-continued

Two-Step cDNA Synthesis by MMLV-RT single mutants using random priming. The data was generated via qPCR human normalizer assay and data is reported by Ct value.

| MMLV-RT Variant | Ct Mean | Ct Standard Deviation |
|---|---|---|
| MMLV-II Y271R | 40.000 | 0.000 |
| MMLV-IV | 31.850 | 0.183 |

In addition to the increased activity demonstrated in the MMLV RTase mutations Q299E, T332E, and V433R (Table 19), and the MMLV RTase mutations P76R, L82R, I125R, Y271A, L280A, L280R, T328R, and V433R (Table 20), further MMLV RTase mutations were selected by rational design and introduced by site-directed mutagenesis using standard PCR conditions and primers (Table 21).

TABLE 21

Sequences of primers used for cloning of MMLV RTase base construct and mutants into pET28b. All primers were ordered as DNA oligos from Integrated DNA Technologies.

| SEQ ID NO: | Primer Name | Primer Sequence (5'-3') |
|---|---|---|
| 700 | MMLV V433R SDM F | AGTTGACGATGGGTCAACCCTTACGTATCTTGGCTCCA CATGCTGTAGA |
| 701 | MMLV V433R SDM R | TCTACAGCATGTGGAGCCAAGATACGTAAGGGTTGAC CCATCGTCAACT |
| 702 | MMLV I593E SDM F | CGTTATGCTTTTGCAACAGCGCATGAGCATGGCGAAA TTTACCGCCGC |
| 703 | MMLV I593E SDM R | GCGGCGGTAAATTTCGCCATGCTCATGCGCTGTTGCAA AAGCATAACG |
| 704 | MMLV Q299E SDM F | TACGCCTAAGACGCCACGCGAGTTGCGTGAATTTTTG GGCACAGC |
| 705 | MMLV Q299E SDM R | GCTGTGCCCAAAAATTCACGCAACTCGCGTGGCGTCTT AGGCGTA |
| 706 | MMLV L82Y SDM F | GATTAAGCCACATATTCAGCGCTTGTATGACCAGGGG ATCTTGGTCC |
| 707 | MMLV L82Y SDM R | GGACCAAGATCCCCTGGTCATACAAGCGCTGAATATG TGGCTTAATC |
| 708 | MMLV L280I SDM F | TGCTGAAAGAAGGTCAACGTTGGATCACTGAAGCGCG TAAGGAGACC |
| 709 | MMLV L280I SDM R | GGTCTCCTTACGCGCTTCAGTGATCCAACGTTGACCTT CTTTCAGCA |
| 710 | MMLV V433N SDM F | AGTTGACGATGGGTCAACCCTTAAACATCTTGGCTCCA CATGCTGTAGA |
| 711 | MMLV V433N SDM R | TCTACAGCATGTGGAGCCAAGATGTTTAAGGGTTGAC CCATCGTCAACT |
| 712 | MMLV I593W SDM F | CGTTATGCTTTTGCAACAGCGCATTGGCATGGCGAAAT TTACCGCCGC |
| 713 | MMLV I593W SDM R | GCGGCGGTAAATTTCGCCATGCCAATGCGCTGTTGCA AAAGCATAACG |
| 714 | MMLV T306K TOP | GCCAGTTGCGTGAATTTTTGGGCAAAGCGGGATTCTGT CGTTTATGGATTCC |
| 715 | MMLV T306K BTM | GGAATCCATAAACGACAGAATCCCGCTTTGCCCAAAA ATTCACGCAACTGGC |

The resulting plasmids were transformed into *E. coli* BL21(DE3) cells for protein expression and proteins isolated through affinity and ion exchange chromatography (Table 22).

TABLE 22

Sequences of MMLV RTase base construct and mutant MMLV RTase constructs.

| SEQ ID NO: | Construct | Construct Sequence (DNA: 5'-3' or AA) |
| --- | --- | --- |
| 716 | MMLV-II RTase | ATGACTTTAAATATTGAGGATGAGCATCGTTTA CATGAGACATCAAAAGAACCCGACGTGAGCTTA GGGTCAACGTGGCTTTCTGACTTCCCCCAGGCG TGGGCGGAGACTGGCGGAATGGGGTTAGCTGTC CGCCAAGCACCGTTGATCATCCCGTTAAAGGCA ACGTCTACACCTGTCTCTATCAAACAGTACCCC ATGAGTCAAGAGGCCCGCCTGGGGATTAAGCCA CATATTCAGCGCTTGCTGGACCAGGGGATCTTG GTCCCATGTCAATCTCCGTGGAACACCCCCCTT CTGCCCGTGAAAAAGCCAGGTACAAACGATTAT CGTCCAGTTCAAGATCTTCGCGAGGTCAACAAA CGCGTAGAAGACATCCATCCGACTGTACCTAAT CCTTATAATCTGTTATCAGGCCTGCCCCCATCG CACCAATGGTATACAGTATTAGACTTGAAAGAC GCGTTCTTTTGCCTGCGTCTGCACCCAACGTCT CAGCCGCTGTTTGCGTTCGAATGGCGTGATCCT GAAATGGGAATTTCGGGTCAGTTAACCTGGACT CGTCTGCCCCAGGGCTTTAAAAACAGCCCCACA TTGTTCGATGAAGCACTTCACCGTGACTTAGCA GACTTCCGTATCCAACACCCAGACTTAATTCTG TTACAGTATGTTGACGACCTTTTGTTGGCGGCA ACGTCTGAACTTGACTGTCAGCAAGGCACACGC GCGTTATTACAAACGTTAGGTAACTTAGGATAT CGTGCGTCCGCGAAAAAGGCGCAAATTTGTCAA AAACAGGTAAAGTACCTTGGGTATTTGCTGAAA GAAGGTCAACGTTGGCTGACTGAAGCGCGTAAG GAGACCGTAATGGGGCAGCCTACGCCTAAGACG CCACGCCAGTTGCGTGAATTTTTGGGCACAGCG GGATTCTGTCGTTTATGGATTCCTGGGTTCGCT GAAATGGCTGCACCCCTGTACCCCTTAACAAAA ACAGGGACGCTTTTCAACTGGGGGCAGACCAG CAAAAGGCGTATCAGGAGATCAAACAAGCTTTG TTGACCGCACCCGCGTTGGGTCTTCCGGATTTA ACCAAGCCCTTTGAGCTGTTCGTTGATGAAAAA CAGGGATATGCAAAAGGAGTATTAACCCAAAAG TTAGGCCCGTGGCGTCGCCCTGTTGCTTACTTG AGTAAAAAATTGGATCCTGTCGCAGCAGGATGG CCACCGTGCTTGCGTATGGTCGCGGCAATTGCC GTTTTGACAAAGGATGCAGGTAAGTTGACGATG GGTCAACCCTTAGTAATCTTGGCTCCACATGCT GTAGAAGCGTTAGTAAAGCAGCCCCCAGACCGC TGGCTTTCTAATGCGCGCATGACCCACTATCAG GCGCTTCTGCTTGATACGGATCGTGTACAATTT GGACCAGTTGTAGCTTTGAATCCAGCTACTTTG CTTCCCCTTCCAGAAGAAGGACTTCAGCACAAT TGTTTAGATATTCTGGCCGAGGCACATGGGACG CGCCCTGATTTGACGGATCAGCCACTGCCTGAT GCCGACCATACATGGTATACTGGCGGCAGTAGT CTTCTTCAAGAGGGGCAACGCAAGGCGGGAGCA GCCGTCACTACGGAGACCGAAGTTATCTGGGCC AAAGCGTTACCCGCGGGAACATCCGCGCAACGT GCACAGTTAATCGCTCTGACACAGGCCCTGAAG ATGGCAGAGGGCAAAAAGTTGAATGTCTACACC AACTCACGTTATGCTTTTGCAACAGCGCATATC CATGGCGAAATTTACCGCCGCCGTGGTCTGCTG ACTAGTGAGGGTAAGGAAATTAAAAATAAAGAT GAGATTCTTGCGTTGTTAAAAGCTTTATTCTTA CCAAAACGCCTTTCGATCATTCATTGCCCGGGG CATCAAAAGGGTCACTCAGCGGAGGCTCGTGGA AACCGTATGGCGGACCAAGCTGCCCGTAAGGCG GCGATCACAGAGACCCCGGATACATCAACGCTG TTGATCGAAAACAGCTCTCCCTACACTAGCGAG CATTTTTAA |
| 717 | MMLV-II RTase | MTLNIEDEHRLHETSKEPDVSLGSTWLSDFPQA WAETGGMGLAVRQAPLIIPLKATSTPVSIKQYP MSQEARLGIKPHIQRLLDQGILVPCQSPWNTPL LPVKKPGTNDYRPVQDLREVNKRVEDIHPTVPN PYNLLSGLPPSHQWYTVLDLKDAFFCLRLHPTS |

TABLE 22-continued

Sequences of MMLV RTase base construct and mutant MMLV RTase
constructs.

| SEQ ID NO: | Construct | Construct Sequence (DNA: 5'-3' or AA) |
|---|---|---|
| | | QPLFAFEWRDPEMGISGQLTWTRLPQGFKNSPT<br>LFDEALHRDLADFRIQHPDLILLQYVDDLLLAA<br>TSELDCQQGTRALLQTLGNLGYRASAKKAQICQ<br>KQVKYLGYLLKEGQRWLTEARKETVMGQPTPKT<br>PRQLREFLGTAGFCRLWIPGFAEMAAPLYPLTK<br>TGTLFNWGPDQQKAYQEIKQALLTAPALGLPDL<br>TKPFELFVDEKQGYAKGVLTQKLGPWRRPVAYL<br>SKKLDPVAAGWPPCLRMVAAIAVLTKDAGKLTM<br>GQPLVILAPHAVEALVKQPPDRWLSNARMTHYQ<br>ALLLDTDRVQFGPVVALNPATLLPLPEEGLQHN<br>CLDILAEAHGTRPDLTDQPLPDADHTWYTGGSS<br>LLQEGQRKAGAAVTTETEVIWAKALPAGTSAQR<br>AQLIALTQALKMAEGKKLNVYTNSRYAFATAHI<br>HGEIYRRGLLTSEGKEIKNKDEILALLKALFL<br>PKRLSIIHCPGHQKGHSAEARGNRMADQAARKA<br>AITETPDTSTLLIENSSPYTSEHF |
| 718 | MMLV-II<br>Q68R/Q79R/L99R/<br>E282D/Q299E/V433N/<br>I593W | ATGACTTTAAATATTGAGGATGAGCATCGTTTA<br>CATGAGACATCAAAAGAACCCGACGTGAGCTTA<br>GGGTCAACGTGGCTTTCTGACTTCCCCCAGGCG<br>TGGGCGGAGACTGGCGGAATGGGGTTAGCTGTC<br>CGCCAAGCACCGTTGATCATCCCGTTAAAGGCA<br>ACGTCTACACCTGTCTCTATCAAACAGTACCCC<br>ATGAGTCGTGAGGCCCGCCTGGGGATTAAGCCA<br>CATATTCGTCGCTTGCTGGACCAGGGGATCTTG<br>GTCCCATGTCAATCTCCGTGGAACACCCCCCTT<br>CGTCCCGTGAAAAAGCCAGGTACAAACGATTAT<br>CGTCCAGTTCAAGATCTTCGCGAGGTCAACAAA<br>CGCGTAGAAGACATCCATCCGACTGTACCTAAT<br>CCTTATAATCTGTTATCAGGCCTGCCCCCATCG<br>CACCAATGGTATACAGTATTAGACTTGAAAGAC<br>GCGTTCTTTTGCCTGCGTCTGCACCCAACGTCT<br>CAGCCGCTGTTTGCGTTCGAATGGCGTGATCCT<br>GAAATGGGAATTTCGGGTCAGTTAACCTGGACT<br>CGTCTGCCCCAGGGCTTTAAAAACAGCCCCACA<br>TTGTTCGATGAAGCACTTCACCGTGACTTAGCA<br>GACTTCCGTATCCAACACCCAGACTTAATTCTG<br>TTACAGTATGTTGACGACCTTTTGTTGGCGGCA<br>ACGTCTGAACTTGACTGTCAGCAAGGCACACGC<br>GCGTTATTACAAACGTTAGGTAACTTAGGATAT<br>CGTGCGTCCGCGAAAAAGGCGCAAATTTGTCAA<br>AAACAGGTAAAGTACCTTGGGTATTTGCTGAAA<br>GAAGGTCAACGTTGGCTGACTGATGCGCGTAAG<br>GAGACCGTAATGGGGCAGCCTACGCCTAAGACG<br>CCACGCGAATTGCGTGAATTTTTGGGCACAGCG<br>GGATTCTGTCGTTTATGGATTCCTGGGTTCGCT<br>GAAATGGCTGCACCCCTGTACCCCTTAACAAAA<br>ACAGGGACGCTTTTCAACTGGGGGCCAGACCAG<br>CAAAAGGCGTATCAGGAGATCAAACAAGCTTTG<br>TTGACCGCACCCGCGTTGGGTCTTCCGGATTTA<br>ACCAAGCCCTTTGAGCTGTTCGTTGATGAAAAA<br>CAGGGATATGCAAAAGGAGTATTAACCCAAAAG<br>TTAGGCCCGTGGCGTCGCCCTGTTGCTTACTTG<br>AGTAAAAAATTGGATCCTGTCGCAGCAGGATGG<br>CCACCGTGCTTGCGTATGGTCGCGGCAATTGCC<br>GTTTTGACAAAGGATGCAGGTAAGTTGACGATG<br>GGTCAACCCTTACGTATCTTGGCTCCACATGCT<br>GTAGAAGCGTTAGTAAAGCAGCCCCCAGACCGC<br>TGGCTTTCTAATGCGCGCATGACCCACTATCAG<br>GCGCTTCTGCTTGATACGGATCGTGTACAATTT<br>GGACCAGTTGTAGCTTTGAATCCAGCTACTTTG<br>CTTCCCCTTCCAGAAGAAGGACTTCAGCACAAT<br>TGTTTAGATATTCTGGCCGAGGCACATGGGACG<br>CGCCCTGATTTGACGGATCAGCCACTGCCTGAT<br>GCCGACCATACATGGTATACTGGCGGCAGTAGT<br>CTTCTTCAAGAGGGGCAACGCAAGGCGGGAGCA<br>GCCGTCACTACGGAGACCGAAGTTATCTGGGCC<br>AAAGCGTTACCCGCGGGAACATCCGCGCAACGT<br>GCACAGTTAATCGCTCTGACACAGGCCCTGAAG<br>ATGGCAGAGGGCAAAAAGTTGAATGTCTACACC<br>AACTCACGTTATGCTTTTGCAACAGCGCATTGG<br>CATGGCGAAATTTACCGCCGCCGTGGTCTGCTG<br>ACTAGTGAGGGTAAGGAAATTAAAAATAAAGAT<br>GAGATTCTTGCGTTGTTAAAAGCTTTATTCTTA<br>CCAAAACGCCTTTCGATCATTCATTGCCCGGGG |

TABLE 22-continued

Sequences of MMLV RTase base construct and mutant MMLV RTase
constructs.

| SEQ ID NO: | Construct | Construct Sequence (DNA: 5'-3' or AA) |
|---|---|---|
| | | CATCAAAAGGGTCACTCAGCGGAGGCTCGTGGA<br>AACCGTATGGCGGACCAAGCTGCCCGTAAGGCG<br>GCGATCACAGAGACCCCGGATACATCAACGCTG<br>TTGATCGAAAACAGCTCTCCCTACACTAGCGAG<br>CATTTT |
| 719 | MMLV-II<br>Q68R/Q79R/L99R/<br>E282D/Q299E/V433N/<br>I593W | MTLNIEDEHRLHETSKEPDVSLGSTWLSDFPQA<br>WAETGGMGLAVRQAPLIIPLKATSTPVSIKQYP<br>MSREARLGIKPHIRRLLDQGILVPCQSPWNTPL<br>RPVKKPGTNDYRPVQDLREVNKRVEDIHPTVPN<br>PYNLLSGLPPSHQWYTVLDLKDAFFCLRLHPTS<br>QPLFAFEWRDPEMGISGQLTWTRLPQGFKNSPT<br>LFDEALHRDLADFRIQHPDLILLQYVDDLLLAA<br>TSELDCQQGTRALLQTLGNLGYRASAKKAQICQ<br>KQVKYLGYLLKEGQRWLTDARKETVMGQPTPKI<br>PRELREFLGTAGFCRLWIPGFAEMAAPLYPLTK<br>TGTLFNWGPDQQKAYQEIKQALLTAPALGLPDL<br>TKPFELFVDEKQGYAKGVLTQKLGPWRRPVAYL<br>SKKLDPVAAGWPPCLRMVAAIAVLTKDAGKLTM<br>GQPLRILAPHAVEALVKQPPDRWLSNARMTHYQ<br>ALLLDTDRVQFGPVVALNPATLLPLPEEGLQHN<br>CLDILAEAHGTRPDLTDQPLPDADHTWYTGGSS<br>LLQEGQRKAGAAVTTETEVIWAKALPAGTSAQR<br>AQLIALTQALKMAEGKKLNVYTNSRYAFATAHW<br>HGEIYRRRGLLTSEGKEIKNKDEILALLKALFL<br>PKRLSIIHCPGHQKGHSAEARGNRMADQAARKA<br>AITETPDTSTLLIENSSPYTSEHF |
| 720 | MMLV-II<br>Q68R/Q79R/L99R/<br>L280I/E282D/Q299E/<br>V433N/I593W | ATGACTTTAAATATTGAGGATGAGCATCGTTTA<br>CATGAGACATCAAAAGAACCCGACGTGAGCTTA<br>GGGTCAACGTGGCTTTCTGACTTCCCCCAGGCG<br>TGGGCGGAGACTGGCGGAATGGGGTTAGCTGTC<br>CGCCAAGCACCGTTGATCATCCCGTTAAAGGCA<br>ACGTCTACACCTGTCTCTATCAAACAGTACCCC<br>ATGAGTCGTGAGGCCCGCCTGGGGATTAAGCCA<br>CATATTCGTCGCTTGCTGGACCAGGGGATCTTG<br>GTCCCATGTCAATCTCCGTGGAACACCCCCCTT<br>CGTCCCGTGAAAAAGCCAGGTACAAACGATTAT<br>CGTCCAGTTCAAGATCTTCGCGAGGTCAACAAA<br>CGCGTAGAAGACATCCATCCGACTGTACCTAAT<br>CCTTATAATCTGTTATCAGGCCTGCCCCCATCG<br>CACCAATGGTATACAGTATTAGACTTGAAAGAC<br>GCGTTCTTTTGCCTGCGTCTGCACCCAACGTCT<br>CAGCCGCTGTTTGCGTTCGAATGGCGTGATCCT<br>GAAATGGGAATTTCGGGTCAGTTAACCTGGACT<br>CGTCTGCCCCAGGGCTTTAAAAACAGCCCCACA<br>TTGTTCGATGAAGCACTTCACCGTGACTTAGCA<br>GACTTCCGTATCCAACACCCAGACTTAATTCTG<br>TTACAGTATGTTGACGACCTTTTGTTGGCGGCA<br>ACGTCTGAACTTGACTGTCAGCAAGGCACACGC<br>GCGTTATTACAAACGTTAGGTAACTTAGGATAT<br>CGTGCGTCCGCGAAAAAGGCGCAAATTTGTCAA<br>AAACAGGTAAAGTACCTTGGGTATTTGCTGAAA<br>GAAGGTCAACGTTGGATTACTGATGCGCGTAAG<br>GAGACCGTAATGGGGCAGCCTACGCCTAAGACG<br>CCACGCGAATTGCGTGAATTTTTGGGCACAGCG<br>GGATTCTGTCGTTTATGGATTCCTGGGTTCGCT<br>GAAATGGCTGCACCCCTGTACCCCTTAACAAAA<br>ACAGGGACGCTTTTCAACTGGGGGCCAGACCAG<br>CAAAAGGCGTATCAGGAGATCAAACAAGCTTTG<br>TTGACCGCACCCGCGTTGGGTCTTCCGGATTTA<br>ACCAAGCCCTTTGAGCTGTTCGTTGATGAAAAA<br>CAGGGATATGCAAAAGGAGTATTAACCCAAAAG<br>TTAGGCCCGTGGCGTCGCCCTGTTGCTTACTTG<br>AGTAAAAAATTGGATCCTGTCGCAGCAGGATGG<br>CCACCGTGCTTGCGTATGGTCGCGGCAATTGCC<br>GTTTTGACAAAGGATGCAGGTAAGTTGACGATG<br>GGTCAACCCTTACGTATCTTGGCTCCACATGCT<br>GTAGAAGCGTTAGTAAAGCAGCCCCCAGACCGC<br>TGGCTTTCTAATGCGCGCATGACCCACTATCAG<br>GCGCTTCTGCTTGATACGGATCGTGTACAATTT<br>GGACCAGTTGTAGCTTTGAATCCAGCTACTTTG<br>CTTCCCCTTCCAGAAGAAGGACTTCAGCACAAT<br>TGTTTAGATATTCTGGCCGAGGCACATGGGACG<br>CGCCCTGATTTGACGGATCAGCCACTGCCTGAT |

TABLE 22-continued

Sequences of MMLV RTase base construct and mutant MMLV RTase
constructs.

| SEQ ID NO: | Construct | Construct Sequence (DNA: 5'-3' or AA) |
|---|---|---|
| | | GCCGACCATACATGGTATACTGGCGGCAGTAGT<br>CTTCTTCAAGAGGGGCAACGCAAGGCGGGAGCA<br>GCCGTCACTACGGAGACCGAAGTTATCTGGGCC<br>AAAGCGTTACCCGCGGGAACATCCGCGCAACGT<br>GCACAGTTAATCGCTCTGACACAGGCCCTGAAG<br>ATGGCAGAGGGCAAAAAGTTGAATGTCTACACC<br>ACTCACGTTATGCTTTTGCAACAGCGCATTGG<br>CATGGCGAAATTTACCGCCGCCGTGGTCTGCTG<br>ACTAGTGAGGGTAAGGAAATTAAAAATAAAGAT<br>GAGATTCTTGCGTTGTTAAAAGCTTTATTCTTA<br>CCAAAACGCCTTTCGATCATTCATTGCCCGGGG<br>CATCAAAAGGGTCACTCAGCGGAGGCTCGTGGA<br>AACCGTATGGCGGACCAAGCTGCCCGTAAGGCG<br>GCGATCACAGAGACCCCGGATACATCAACGCTG<br>TTGATCGAAAACAGCTCTCCCTACACTAGCGAG<br>CATTTT |
| 721 | MMLV-II<br>Q68R/Q79R/L99R/<br>L280I/E282D/Q299E/<br>V433N/I593W | MTLNIEDEHRLHETSKEPDVSLGSTWLSDFPQA<br>WAETGGMGLAVRQAPLIIPLKATSTPVSIKQYP<br>MSREARLGIKPHIRRLLDQGILVPCQSPWNTPL<br>RPVKKPGTNDYRPVQDLREVNKRVEDIHPTVPN<br>PYNLLSGLPPSHQWYTVLDLKDAFFCLRLHPTS<br>QPLFAFEWRDPEMGISGQLTWTRLPQGFKNSPT<br>LFDEALHRDLADFRIQHPDLILLQYVDDLLLAA<br>TSELDCQQGTRALLQTLGNLGYRASAKKAQICQ<br>KQVKYLGYLLKEGQRWITDARKETVMGQPTPKT<br>PRELREFLGTAGFCRLWIPGFAEMAAPLYPLTK<br>TGTLFNWGPDQQKAYQEIKQALLTAPALGLPDL<br>TKPFELFVDEKQGYAKGVLTQKLGPWRRPVAYL<br>SKKLDPVAAGWPPCLRMVAAIAVLTKDAGKLTM<br>GQPLRILAPHAVEALVKQPPDRWLSNARMTHYQ<br>ALLLDTDRVQFGPVVALNPATLLPLPEEGLQHN<br>CLDILAEAHGTRPDLTDQPLPDADHTWYTGGSS<br>LLQEGQRKAGAAVTTETEVIWAKALPAGTSAQR<br>AQLIALTQALKMAEGKKLNVYTNSRYAFATAHW<br>HGEIYRRGLLTSEGKEIKNKDEILALLKALFL<br>PKRLSIIHCPGHQKGHSAEARGNRMADQAARKA<br>AITETPDTSTLLIENSSPYTSEHF |
| 722 | MMLV-II<br>Q68R/Q79R/L82Y/<br>L99R/L280I/E282D/<br>Q299E/V433N/I593W | ATGACTTTAAATATTGAGGATGAGCATCGTTTA<br>CATGAGCATCAAAAGAACCCGACGTGAGCTTA<br>GGGTCAACGTGGCTTTCTGACTTCCCCCAGGCG<br>TGGGCGGAGACTGGCGGAATGGGGTTAGCTGTC<br>CGCCAAGCACCGTTGATCATCCCGTTAAAGGCA<br>ACGTCTACACCTGTCTCTATCAAACAGTACCCC<br>ATGAGTCGTGAGGCCCGCCTGGGGATTAAGCCA<br>CATATTCGTCGCTTGTATGACCAGGGGATCTTG<br>GTCCCATGTCAATCTCCGTGGAACACCCCCCTT<br>CGTCCCGTGAAAAAGCCAGGTACAAACGATTAT<br>CGTCCAGTTCAAGATCTTCGCGAGGTCAACAAA<br>CGCGTAGAAGACATCCATCCGACTGTACCTAAT<br>CCTTATAATCTGTTATCAGGCCTGCCCCCATCG<br>CACCAATGGTATACAGTATTAGACTTGAAAGAC<br>GCGTTCTTTTGCCTGCGTCTGCACCCAACGTCT<br>CAGCCGCTGTTTGCGTTCGAATGGCGTGATCCT<br>GAAATGGGAATTTCGGGTCAGTTAACCTGGACT<br>CGTCTGCCCCAGGGCTTTAAAAACAGCCCCACA<br>TTGTTCGATGAAGCACTTCACCGTGACTTAGCA<br>GACTTCCGTATCCAACACCCAGACTTAATTCTG<br>TTACAGTATGTTGACGACCTTTTGTTGGCGGCA<br>ACGTCTGAACTTGACTGTCAGCAAGGCACACGC<br>GCGTTATTACAAACGTTAGGTAACTTAGGATAT<br>CGTGCGTCCGCGAAAAAGGCGCAAATTTGTCAA<br>AAACAGGTAAAGTACCTTGGGTATTTGCTGAAA<br>GAAGGTCAACGTTGGATTACTGATGCGCGTAAG<br>GAGACCGTAATGGGGCAGCCTACGCCTAAGACG<br>CCACGCGAATTGCGTGAATTTTTGGGCACAGCG<br>GGATTCTGTCGTTTATGGATTCCTGGGTTCGCT<br>GAAATGGCTGCACCCCTGTACCCCTTAACAAAA<br>ACAGGGACGCTTTTCAACTGGGGGCCAGACCAG<br>CAAAAGGCGTATCAGGAGATCAAACAAGCTTTG<br>TTGACCGCACCCGCGTTGGGTCTTCCGGATTTA<br>ACCAAGCCCTTTGAGCTGTTCGTTGATGAAAAA<br>CAGGGATATGCAAAAGGAGTATTAACCCAAAAG<br>TTAGGCCCGTGGCGTCGCCCTGTTGCTTACTTG |

TABLE 22-continued

Sequences of MMLV RTase base construct and mutant MMLV RTase
constructs.

| SEQ ID NO: | Construct | Construct Sequence (DNA: 5'-3' or AA) |
|---|---|---|
| | | AGTAAAAAATTGGATCCTGTCGCAGCAGGATGG |
| | | CCACCGTGCTTGCGTATGGTCGCGGCAATTGCC |
| | | GTTTTGACAAAGGATGCAGGTAAGTTGACGATG |
| | | GGTCAACCCTTACGTATCTTGGCTCCACATGCT |
| | | GTAGAAGCGTTAGTAAAGCAGCCCCCAGACCGC |
| | | TGGCTTTCTAATGCGCGCATGACCCACTATCAG |
| | | GCGCTTCTGCTTGATACGGATCGTGTACAATTT |
| | | GGACCAGTTGTAGCTTTGAATCCAGCTACTTTG |
| | | CTTCCCCTTCCAGAAGAAGGACTTCAGCACAAT |
| | | TGTTTAGATATTCTGGCCGAGGCACATGGGACG |
| | | CGCCCTGATTTGACGGATCAGCCACTGCCTGAT |
| | | GCCGACCATACATGGTATACTGGCGGCAGTAGT |
| | | CTTCTTCAAGAGGGGCAACGCAAGGCGGGAGCA |
| | | GCCGTCACTACGGAGACCGAAGTTATCTGGGCC |
| | | AAAGCGTTACCCGCGGGAACATCCGCGCAACGT |
| | | GCACAGTTAATCGCTCTGACACAGGCCCTGAAG |
| | | ATGGCAGAGGGCAAAAAGTTGAATGTCTACACC |
| | | AACTCACGTTATGCTTTTGCAACAGCGCATTGG |
| | | CATGGCGAAATTTACCGCCGCCGTGGTCTGCTG |
| | | ACTAGTGAGGGTAAGGAAATTAAAAATAAAGAT |
| | | GAGATTCTTGCGTTGTTAAAAGCTTTATTCTTA |
| | | CCAAAACGCCTTTCGATCATTCATTGCCCGGGG |
| | | CATCAAAAGGGTCACTCAGCGGAGGCTCGTGGA |
| | | AACCGTATGGCGGACCAAGCTGCCCGTAAGGCG |
| | | GCGATCACAGAGACCCCGGATACATCAACGCTG |
| | | TTGATCGAAACAGCTCTCCCTACACTAGCGAG |
| | | CATTTT |
| 723 | MMLV-II Q68R/Q79R/L82Y/ L99R/L280I/E282D/ Q299E/V433N/I593W | MTLNIEDEHRLHETSKEPDVSLGSTWLSDFPQA WAETGGMGLAVRQAPLIIPLKATSTPVSIKQYP MSREARLGIKPHIRRLYDQGILVPCQSPWNTPL RPVKKPGTNDYRPVQDLREVNKRVEDIHPTVPN PYNLLSGLPPSHQWYTVLDLKDAFFCLRLHPTS QPLFAFEWRDPEMGISGQLTWTRLPQGFKNSPT LFDEALHRDLADFRIQHPDLILLQYVDDLLLAA TSELDCQQGTRALLQTLGNLGYRASAKKAQICQ KQVKYLGYLLKEGQRWITDARKETVMGQPTPKT PRELREFLGTAGFCRLWIPGFAEMAAPLYPLTK TGTLFNWGPDQQKAYQEIKQALLTAPALGLPDL TKPFELFVDEKQGYAKGVLTQKLGPWRRPVAYL SKKLDPVAAGWPPCLRMVAAIAVLTKDAGKLTM GQPLRILAPHAVEALVKQPPDRWLSNARMTHYQ ALLLDTDRVQFGPVVALNPATLLPLPEEGLQHN CLDILAEAHGTRPDLTDQPLPDADHTWYTGGSS LLQEGQRKAGAAVTTETEVIWAKALPAGTSAQR AQLIALTQALKMAEGKKLNVYTNSRYAFATAHW HGEIYRRGLLTSEGKEIKNKDEILALLKALFL PKRLSIIHCPGHQKGHSAEARGNRMADQAARKA AITETPDTSTLLIENSSPYTSEHF |
| 724 | MMLV-II Q68R/Q79R/L82Y/ L99R/L280I/E282D/ Q299E/T306K/V433N/ I593W | ATGACTTTAAATATTGAGGATGAGCATCGTTTA CATGAGACATCAAAAGAACCCGACGTGAGCTTA GGGTCAACGTGGCTTTCTGACTTCCCCCAGGCG TGGGCGGAGACTGGCGGAATGGGGTTAGCTGTC CGCCAAGCACCGTTGATCATCCCGTTAAAGGCA ACGTCTACACCTGTCTCTATCAAACAGTACCCC ATGAGTCGTGAGGCCCGCCTGGGGATTAAGCCA CATATTCGTCGCTTGTATGACCAGGGGATCTTG GTCCCATGTCAATCTCCGTGGAACACCCCCCTT CGTCCCGTGAAAAAGCCAGGTACAAACGATTAT CGTCCAGTTCAAGATCTTCGCGAGGTCAACAAA CGCGTAGAAGACATCCATCCGACTGTACCTAAT CCTTATAATCTGTTATCAGGCCTGCCCCCATCG CACCAATGGTATACAGTATTAGACTTGAAAGAC GCGTTCTTTTGCCTGCGTCTGCACCCAACGTCT CAGCCGCTGTTTGCGTTCGAATGGCGTGATCCT GAAATGGGAATTTCGGGTCAGTTAACCTGGACT CGTCTGCCCCAGGGCTTTAAAAACAGCCCCACA TTGTTCGATGAAGCACTTCACCGTGACTTAGCA GACTTCCGTATCCAACACCCAGACTTAATTCTG TTACAGTATGTTGACGACCTTTTGTTGGCGGCA ACGTCTGAACTTGACTGTCAGCAAGGCACACGC GCGTTATTACAAACGTTAGGTAACTTAGGATAT CGTGCGTCCGCGAAAAAGGCGCAAATTTGTCAA AAACAGGTAAAGTACCTTGGGTATTTGCTGAAA |

TABLE 22-continued

Sequences of MMLV RTase base construct and mutant MMLV RTase constructs.

| SEQ ID NO: | Construct | Construct Sequence (DNA: 5'-3' or AA) |
|---|---|---|
| | | GAAGGTCAACGTTGGATTACTGATGCGCGTAAG |
| | | GAGACCGTAATGGGGCAGCCTACGCCTAAGACG |
| | | CCACGCGAATTGCGTGAATTTTTGGGCAAAGCG |
| | | GGATTCTGTCGTTTATGGATTCCTGGGTTCGCT |
| | | GAAATGGCTGCACCCCTGTACCCCTTAACAAAA |
| | | ACAGGGACGCTTTTCAACTGGGGGCCAGACCAG |
| | | CAAAAGGCGTATCAGGAGATCAAACAAGCTTTG |
| | | TTGACCGCACCCGCGTTGGGTCTTCCGGATTTA |
| | | ACCAAGCCCTTTGAGCTGTTCGTTGATGAAAAA |
| | | CAGGGATATGCAAAAGGAGTATTAACCCAAAAG |
| | | TTAGGCCCGTGGCGTCGCCCTGTTGCTTACTTG |
| | | AGTAAAAAATTGGATCCTGTCGCAGCAGGATGG |
| | | CCACCGTGCTTGCGTATGGTCGCGGCAATTGCC |
| | | GTTTTGACAAAGGATGCAGGTAAGTTGACGATG |
| | | GGTCAACCCTTAAACATCTTGGCTCCACATGCT |
| | | GTAGAAGCGTTAGTAAAGCAGCCCCCAGACCGC |
| | | TGGCTTTCTAATGCGCGCATGACCCACTATCAG |
| | | GCGCTTCTGCTTGATACGGATCGTGTACAATTT |
| | | GGACCAGTTGTAGCTTTGAATCCAGCTACTTTG |
| | | CTTCCCCTTCCAGAAGAAGGACTTCAGCACAAT |
| | | TGTTTAGATATTCTGGCCGAGGCACATGGGACG |
| | | CGCCCTGATTTGACGGATCAGCCACTGCCTGAT |
| | | GCCGACCATACATGGTATACTGGCGGCAGTAGT |
| | | CTTCTTCAAGAGGGGCAACGCAAGGCGGGAGCA |
| | | GCCGTCACTACGGAGACCGAAGTTATCTGGGCC |
| | | AAAGCGTTACCCGCGGGAACATCCGCGCAACGT |
| | | GCACAGTTAATCGCTCTGACACAGGCCCTGAAG |
| | | ATGGCAGAGGGCAAAAAGTTGAATGTCTACACC |
| | | AACTCACGTTATGCTTTTGCAACAGCGCATTGG |
| | | CATGGCGAAATTTACCGCCGCCGTGGTCTGCTG |
| | | ACTAGTGAGGGTAAGGAAATTAAAAATAAAGAT |
| | | GAGATTCTTGCGTTGTTAAAAGCTTTATTCTTA |
| | | CCAAAACGCCTTTCGATCATTCATTGCCCGGGG |
| | | CATCAAAAGGGTCACTCAGCGGAGGCTCGTGGA |
| | | AACCGTATGGCGGACCAAGCTGCCCGTAAGGCG |
| | | GCGATCACAGAGACCCCGGATACATCAACGCTG |
| | | TTGATCGAAACAGCTCTCCCTACACTAGCGAG |
| | | CATTTT |
| 725 | MMLV-II Q68R/Q79R/L82Y/ L99R/L280I/E282D/ Q299E/T306K/V433N/ I593W | MTLNIEDEHRLHETSKEPDVSLGSTWLSDFPQA WAETGGMGLAVRQAPLIIPLKATSTPVSIKQYP MSREARLGIKPHIRRLYDQGILVPCQSPWNTPL RPVKKPGTNDYRPVQDLREVNKRVEDIHPTVPN PYNLLSGLPPSHQWYTVLDLKDAFFCLRLHPTS QPLFAFEWRDPEMGISGQLTWTRLPQGFKNSPT LFDEALHRDLADFRIQHPDLILLQYVDDLLLAA TSELDCQQGTRALLQTLGNLGYRASAKKAQICQ KQVKYLGYLLKEGQRWITDARKETVMGQPTPKT PRELREFLGKAGFCRLWIPGFAEMAAPLYPLTK TGTLFNWGPDQQKAYQEIKQALLTAPALGLPDL TKPFELFVDEKQGYAKGVLTQKLGPWRRPVAYL SKKLDPVAAGWPPCLRMVAAIAVLTKDAGKLTM GQPLNILAPHAVEALVKQPPDRWLSNARMTHYQ ALLLDTDRVQFGPVVALNPATLLPLPEEGLQHN CLDILAEAHGTRPDLTDQPLPDADHTWYTGGSS LLQEGQRKAGAAVTTETEVIWAKALPAGTSAQR AQLIALTQALKMAEGKKLNVYTNSRYAFATAHW HGEIYRRGLLTSEGKEIKNKDEILALLKALFL PKRLSIIHCPGHQKGHSAEARGNRMADQAARKA AITETPDTSTLLIENSSPYTSEHF |
| 726 | MMLV-II Q68R/Q79R/L99R/ E282D/Q299E/T306K/ V433R/I593E | ATGACTTTAAATATTGAGGATGAGCATCGTTTA CATGAGACATCAAAAGAACCCGACGTGAGCTTA GGGTCAACGTGGCTTTCTGACTTCCCCCAGGCG TGGGCGGAGACTGGCGGAATGGGGTTAGCTGTC CGCCAAGCACCGTTGATCATCCCGTTAAAGGCA ACGTCTACACCTGTCTCTATCAAACAGTACCCC ATGAGTCGTGAGGCCCGCCTGGGGATTAAGCCA CATATTCGTCGCTTGCTGGACCAGGGGATCTTG GTCCCATGTCAATCTCCGTGGAACACCCCCCTT CGTCCCGTGAAAAAGCCAGGTACAAACGATTAT CGTCCAGTTCAAGATCTTCGCGAGGTCAACAAA CGCGTAGAAGACATCCATCCGACTGTACCTAAT CCTTATAATCTGTTATCAGGCCTGCCCCCATCG CACCAATGGTATACAGTATTAGACTTGAAAGAC |

TABLE 22-continued

Sequences of MMLV RTase base construct and mutant MMLV RTase
constructs.

| SEQ ID NO: | Construct | Construct Sequence (DNA: 5'-3' or AA) |
|---|---|---|
| | | GCGTTCTTTTGCCTGCGTCTGCACCCAACGTCT<br>CAGCCGCTGTTTGCGTTCGAATGGCGTGATCCT<br>GAAATGGGAATTTCGGGTCAGTTAACCTGGACT<br>CGTCTGCCCCAGGGCTTTAAAAACAGCCCCACA<br>TTGTTCGATGAAGCACTTCACCGTGACTTAGCA<br>GACTTCCGTATCCAACACCCAGACTTAATTCTG<br>TTACAGTATGTTGACGACCTTTTGTTGGCGGCA<br>ACGTCTGAACTTGACTGTCAGCAAGGCACACGC<br>GCGTTATTACAAACGTTAGGTAACTTAGGATAT<br>CGTGCGTCCGCGAAAAAGGCGCAAATTTGTCAA<br>AAACAGGTAAAGTACCTTGGGTATTTGCTGAAA<br>GAAGGTCAACGTTGGCTGACTGATGCGCGTAAG<br>GAGACCGTAATGGGGCAGCCTACGCCTAAGACG<br>CCACGCGAATTGCGTGAATTTTTGGGCAAAGCG<br>GGATTCTGTCGTTTATGGATTCCTGGGTTCGCT<br>GAAATGGCTGCACCCCTGTACCCCTTAACAAAA<br>ACAGGGACGCTTTTCAACTGGGGGCCAGACCAG<br>CAAAAGGCGTATCAGGAGATCAAACAAGCTTTG<br>TTGACCGCACCCGCGTTGGGTCTTCCGGATTTA<br>ACCAAGCCCTTTGAGCTGTTCGTTGATGAAAAA<br>CAGGGATATGCAAAAGGAGTATTAACCCAAAAG<br>TTAGGCCCGTGGCGTCGCCCTGTTGCTTACTTG<br>AGTAAAAAATTGGATCCTGTCGCAGCAGGATGG<br>CCACCGTGCTTGCGTATGGTCGCGGCAATTGCC<br>GTTTTGACAAAGGATGCAGGTAAGTTGACGATG<br>GGTCAACCCTTACGTATCTTGGCTCCACATGCT<br>GTAGAAGCGTTAGTAAAGCAGCCCCCAGACCGC<br>TGGCTTTCTAATGCGCGCATGACCCACTATCAG<br>GCGCTTCTGCTTGATACGGATCGTGTGTACAATTT<br>GGACCAGTTGTAGCTTTGAATCCAGCTACTTTG<br>CTTCCCCTTCCAGAAGAAGGACTTCAGCACAAT<br>TGTTTAGATATTCTGGCCGAGGCACATGGGACG<br>CGCCCTGATTTGACGGATCAGCCACTGCCTGAT<br>GCCGACCATACATGGTATACTGGCGGCAGTAGT<br>CTTCTTCAAGAGGGGCAACGCAAGGCGGGAGCA<br>GCCGTCACTACGGAGACCGAAGTTATCTGGGCC<br>AAAGCGTTACCCGCGGGAACATCCGCGCAACGT<br>GCACAGTTAATCGCTCTGACACAGGCCCTGAAG<br>ATGGCAGAGGGCAAAAAGTTGAATGTCTACACC<br>AACTCACGTTATGCTTTTGCAACAGCGCATGAA<br>CATGGCGAAATTTACCGCCGCCGTGGTCTGCTG<br>ACTAGTGAGGGTAAGGAAATTAAAAATAAAGAT<br>GAGATTCTTGCGTTGTTAAAAGCTTTATTCTTA<br>CCAAAACGCCTTTCGATCATTCATTGCCCGGGG<br>CATCAAAAGGGTCACTCAGCGGAGGCTCGTGGA<br>AACCGTATGGCGGACCAAGCTGCCCGTAAGGCG<br>GCGATCACAGAGACCCCGGATACATCAACGCTG<br>TTGATCGAAACAGCTCTCCCTACACTAGCGAG<br>CATTTT |
| 727 | MMLV-II<br>Q68R/Q79R/L99R/<br>E282D/Q299E/T306K/<br>V433R/I593E | MTLNIEDEHRLHETSKEPDVSLGSTWLSDFPQA<br>WAETGGMGLAVRQAPLIIPLKATSTPVSIKQYP<br>MSREARLGIKPHIRRLLDQGILVPCQSPWNTPL<br>RPVKKPGTNDYRPVQDLREVNKRVEDIHPTVPN<br>PYNLLSGLPPSHQWYTVLDLKDAFFCLRLHPTS<br>QPLFAFEWRDPEMGISGQLTWTRLPQGFKNSPT<br>LFDEALHRDLADFRIQHPDLILLQYVDDLLLAA<br>TSELDCQQGTRALLQTLGNLGYRASAKKAQICQ<br>KQVKYLGYLLKEGQRWLTDARKETVMGQPTPKI<br>PRELREFLGKAGFCRLWIPGFAEMAAPLYPLTK<br>TGTLFNWGPDQQKAYQEIKQALLTAPALGLPDL<br>TKPFELFVDEKQGYAKGVLTQKLGPWRRPVAYL<br>SKKLDPVAAGWPPCLRMVAAIAVLTKDAGKLTM<br>GQPLRILAPHAVEALVKQPPDRWLSNARMTHYQ<br>ALLLDTDRVQFGPVVALNPATLLPLPEEGLQHN<br>CLDILAEAHGTRPDLTDQPLPDADHTWYTGGSS<br>LLQEGQRKAGAAVTTETEVIWAKALPAGTSAQR<br>AQLIALTQALKMAEGKKLNVYTNSRYAFATAHE<br>HGEIYRRRGLLTSEGKEIKNKDEILALLKALFL<br>PKRLSIIHCPGHQKGHSAEARGNRMADQAARKA<br>AITETPDTSTLLIENSSPYTSEHF |

TABLE 22-continued

Sequences of MMLV RTase base construct and mutant MMLV RTase constructs.

| SEQ ID NO: | Construct | Construct Sequence (DNA: 5'-3' or AA) |
| --- | --- | --- |
| 728 | MMLV-II Q68R/Q79R/L82Y/ L99R/L280I/E282D/ Q299E/V433R/I593E | ATGACTTTAAATATTGAGGATGAGCATCGTTTA CATGAGACATCAAAAGAACCCGACGTGAGCTTA GGGTCAACGTGGCTTTCTGACTTCCCCCAGGCG TGGGCGGAGACTGGCGGAATGGGGTTAGCTGTC CGCCAAGCACCGTTGATCATCCCGTTAAAGGCA ACGTCTACACCTGTCTCTATCAAACAGTACCCC ATGAGTCGTGAGGCCCGCCTGGGGATTAAGCCA CATATTCGTCGCTTGTATGACCAGGGGATCTTG GTCCCATGTCAATCTCCGTGGAACACCCCCCTT CGTCCCGTGAAAAAGCCAGGTACAAACGATTAT CGTCCAGTTCAAGATCTTCGCGAGGTCAACAAA CGCGTAGAAGACATCCATCCGACTGTACCTAAT CCTTATAATCTGTTATCAGGCCTGCCCCCATCG CACCAATGGTATACAGTATTAGACTTGAAAGAC GCGTTCTTTTGCCTGCGTCTGCACCCAACGTCT CAGCCGCTGTTTGCGTTCGAATGGCGTGATCCT GAAATGGGAATTTCGGGTCAGTTAACCTGGACT CGTCTGCCCCAGGGCTTTAAAAACAGCCCCACA TTGTTCGATGAAGCACTTCACCGTGACTTAGCA GACTTCCGTATCCAACACCCAGACTTAATTCTG TTACAGTATGTTGACGACCTTTTGTTGGCGGCA ACGTCTGAACTTGACTGTCAGCAAGGCACACGC GCGTTATTACAAACGTTAGGTAACTTAGGATAT CGTGCGTCCGCGAAAAAGGCGCAAATTTGTCAA AAACAGGTAAAGTACCTTGGGTATTTGCTGAAA GAAGGTCAACGTTGGATTACTGATGCGCGTAAG GAGACCGTAATGGGGCAGCCTACGCCTAAGACG CCACGCGAATTGCGTGAATTTTTGGGCACAGCG GGATTCTGTCGTTTATGGATTCCTGGGTTCGCT GAAATGGCTGCACCCCTGTACCCCTTAACAAAA ACAGGGACGCTTTTCAACTGGGGGCCAGACCAG CAAAAGGCGTATCAGGAGATCAAACAAGCTTTG TTGACCGCACCCGCGTTGGGTCTTCCGGATTTA ACCAAGCCCTTTGAGCTGTTCGTTGATGAAAAA CAGGGATATGCAAAAGGAGTATTAACCCAAAAG TTAGGCCCGTGGCGTCGCCCTGTTGCTTACTTG AGTAAAAAAATTGGATCCTGTCGCAGCAGGATGG CCACCGTGCTTGCGTATGGTCGCGGCAATTGCC GTTTTGACAAAGGATGCAGGTAAGTTGACGATG GGTCAACCCTTACGTATCTTGGCTCCACATGCT GTAGAAGCGTTAGTAAAGCAGCCCCCAGACCGC TGGCTTTCTAATGCGCGCATGACCCACTATCAG GCGCTTCTGCTTGATACGGATCGTGTACAATTT GGACCAGTTGTAGCTTTGAATCCAGCTACTTTG CTTCCCCTTCCAGAAGAAGGACTTCAGCACAAT TGTTTAGATATTCTGGCCGAGGCACATGGGACG CGCCCTGATTTGACGGATCAGCCACTGCCTGAT GCCGACCATACATGGTATACTGGCGGCAGTAGT CTTCTTCAAGAGGGGCAACGCAAGGCGGGAGCA GCCGTCACTACGGAGACCGAAGTTATCTGGGCC AAAGCGTTACCCGCGGGAACATCCGCGCAACGT GCACAGTTAATCGCTCTGACACAGGCCCTGAAG ATGGCAGAGGGCAAAAAGTTGAATGTCTACACC AACTCACGTTATGCTTTTGCAACAGCGCATGAA CATGGCGAAATTTACCGCCGCCGTGGTCTGCTG ACTAGTGAGGGTAAGGAAATTAAAAATAAAGAT GAGATTCTTGCGTTGTTAAAAGCTTTATTCTTA CCAAAACGCCTTTCGATCATTCATTGCCCGGGG CATCAAAAGGGTCACTCAGCGGAGGCTCGTGGA AACCGTATGGCGGACCAAGCTGCCCGTAAGGCG GCGATCACAGAGACCCCGGATACATCAACGCTG TTGATCGAAAACAGCTCTCCCTACACTAGCGAG CATTTT |
| 729 | MMLV-II Q68R/Q79R/L82Y/ L99R/L280I/E282D/ Q299E/V433R/I593E | MTLNIEDEHRLHETSKEPDVSLGSTWLSDFPQA WAETGGMGLAVRQAPLIIPLKATSTPVSIKQYP MSREARLGIKPHIRRLYDQGILVPCQSPWNTPL RPVKKPGTNDYRPVQDLREVNKRVEDIHPTVPN PYNLLSGLPPSHQWYTVLDLKDAFFCLRLHPTS QPLFAFEWRDPEMGISGQLTWTRLPQGFKNSPT LFDEALHRDLADFRIQHPDLILLQYVDDLLLAA TSELDCQQGTRALLQTLGNLGYRASAKKAQICQ KQVKYLGYLLKEGQRWITDARKETVMGQPTPKT PRELREFLGTAGFCRLWIPGFAEMAAPLYPLTK |

TABLE 22-continued

Sequences of MMLV RTase base construct and mutant MMLV RTase
constructs.

| SEQ ID NO: | Construct | Construct Sequence (DNA: 5'-3' or AA) |
|---|---|---|
| | | TGTLFNWGPDQQKAYQEIKQALLTAPALGLPDL |
| | | TKPFELFVDEKQGYAKGVLTQKLGPWRRPVAYL |
| | | SKKLDPVAAGWPPCLRMVAAIAVLTKDAGKLTM |
| | | GQPLRILAPHAVEALVKQPPDRWLSNARMTHYQ |
| | | ALLLDTDRVQFGPVVALNPATLLPLPEEGLQHN |
| | | CLDILAEAHGTRPDLTDQPLPDADHTWYTGGSS |
| | | LLQEGQRKAGAAVTTETEVIWAKALPAGTSAQR |
| | | AQLIALTQALKMAEGKKLNVYTNSRYAFATAHE |
| | | HGEIYRRRGLLTSEGKEIKNKDEILALLKALFL |
| | | PKRLSIIHCPGHQKGHSAEARGNRMADQAARKA |
| | | AITETPDTSTLLIENSSPYTSEHF |
| 730 | MMLV-II Q68R/Q79R/L82Y/ L99R/L280I/E282D/ Q299E/T306K/V433R/ I593E | ATGACTTTAAATATTGAGGATGAGCATCGTTTA CATGAGACATCAAAAGAACCCGACGTGAGCTTA GGGTCAACGTGGCTTTCTGACTTCCCCCAGGCG TGGGCGGAGACTGGCGGAATGGGGTTAGCTGTC CGCCAAGCACCGTTGATCATCCCGTTAAAGGCA ACGTCTACACCTGTCTCTATCAAACAGTACCCC ATGAGTCGTGAGGCCCGCCTGGGGATTAAGCCA CATATTCGTCGCTTGTATGACCAGGGGATCTTG GTCCCATGTCAATCTCCGTGGAACACCCCCCTT CGTCCCGTGAAAAAGCCAGGTACAAACGATTAT CGTCCAGTTCAAGATCTTCGCGAGGTCAACAAA CGCGTAGAAGACATCCATCCGACTGTACCTAAT CCTTATAATCTGTTATCAGGCCTGCCCCCATCG CACCAATGGTATACAGTATTAGACTTGAAAGAC GCGTTCTTTTGCCTGCGTCTGCACCCAACGTCT CAGCCGCTGTTTGCGTTCGAATGGCGTGATCCT GAAATGGGAATTTCGGGTCAGTTAACCTGGACT CGTCTGCCCCAGGGCTTTAAAAACAGCCCCACA TTGTTCGATGAAGCACTTCACCGTGACTTAGCA GACTTCCGTATCCAACACCCAGACTTAATTCTG TTACAGTATGTTGACGACCTTTTGTTGGCGGCA ACGTCTGAACTTGACTGTCAGCAAGGCACACGC GCGTTATTACAAACGTTAGGTAACTTAGGTATAT CGTGCGTCCGCGAAAAAGGCGCAAATTTGTCAA AAACAGGTAAAGTACCTTGGGTATTTGCTGAAA GAAGGTCAACGTTGGATTACTGATGCGCGTAAG GAGACCGTAATGGGGCAGCCTACGCCTAAGACG CCACGCGAATTGCGTGAATTTTTGGGCAAAGCG GGATTCTGTCGTTTATGGATTCCTGGGTTCGCT GAAATGGCTGCACCCCTGTACCCCTTAACAAAA ACAGGGACGCTTTTCAACTGGGGGCCAGACCAG CAAAAGGCGTATCAGGAGATCAAACAAGCTTTG TTGACCGCACCCGCGTTGGGTCTTCCGGATTTA ACCAAGCCCTTTGAGCTGTTCGTTGATGAAAAA CAGGGATATGCAAAAGGAGTATTAACCCAAAAG TTAGGCCCGTGGCGTCGCCCTGTTGCTTACTTG AGTAAAAAATTGGATCCTGTCGCAGCAGGATGG CCACCGTGCTTGCGTATGGTCGCGGCAATTGCC GTTTTGACAAAGGATGCAGGTAAGTTGACGATG GGTCAACCCTTACGTATCTTGGCTCCACATGCT GTAGAAGCGTTAGTAAAGCAGCCCCCAGACCGC TGGCTTTCTAATGCGCGCATGACCCACTATCAG GCGCTTCTGCTTGATACGGATCGTGTACAATTT GGACCAGTTGTAGCTTTGAATCCAGCTACTTTG CTTCCCCTTCCAGAAGAAGGACTTCAGCACAAT TGTTTAGATATTCTGGCCGAGGCACATGGGACG CGCCCTGATTTGACGGATCAGCCACTGCCTGAT GCCGACCATACATGGTATACTGGCGGCAGTAGT CTTCTTCAAGAGGGGCAACGCAAGGCGGGAGCA GCCGTCACTACGGAGACCGAAGTTATCTGGGCC AAAGCGTTACCCGCGGGAACATCCGCGCAACGT GCACAGTTAATCGCTCTGACACAGGCCCTGAAG ATGGCAGAGGGCAAAAAGTTGAATGTCTACACC AACTCACGTTATGCTTTTGCAACAGCGCATGAA CATGGCGAAATTTACCGCCGCCGTGGTCTGCTG ACTAGTGAGGGTAAGGAAATTAAAAATAAAGAT GAGATTCTTGCGTTGTTAAAAGCTTTATTCTTA CCAAAAACGCCTTTCGATCATTCATTGCCCGGGG CATCAAAAGGGTCACTCAGCGGAGGCTCGTGGA AACCGTATGGCGGACCAAGCTGCCCGTAAGGCG GCGATCACAGAGACCCCGGATACATCAACGCTG TTGATCGAAACAGCTCTCCCTACACTAGCGAG CATTTT |

TABLE 22-continued

Sequences of MMLV RTase base construct and mutant MMLV RTase constructs.

| SEQ ID NO: | Construct | Construct Sequence (DNA: 5'-3' or AA) |
|---|---|---|
| 731 | MMLV-II Q68R/Q79R/L82Y/ L99R/L280I/E282D/ Q299E/T306K/V433R/ I593E | MTLNIEDEHRLHETSKEPDVSLGSTWLSDFPQA WAETGGMGLAVRQAPLIIPLKATSTPVSIKQYP MSREARLGIKPHIRRLYDQGILVPCQSPWNTPL RPVKKPGTNDYRPVQDLREVNKRVEDIHPTVPN PYNLLSGLPPSHQWYTVLDLKDAFFCLRLHPTS QPLFAFEWRDPEMGISGQLTWTRLPQGFKNSPT LFDEALHRDLADFRIQHPDLILLQYVDDLLLAA TSELDCQQGTRALLQTLGNLGYRASAKKAQICQ KQVKYLGYLLKEGQRWITDARKETVMGQPTPKT PRELREFLGKAGFCRLWIPGFAEMAAPLYPLTK TGTLFNWGPDQQKAYQEIKQALLTAPALGLPDL TKPFELFVDEKQGYAKGVLTQKLGPWRRPVAYL SKKLDPVAAGWPPCLRMVAAIAVLTKDAGKLTM GQPLRILAPHAVEALVKQPPDRWLSNARMTHYQ ALLLDTDRVQFGPVVALNPATLLPLPEEGLQHN CLDILAEAHGTRPDLTDQPLPDADHTWYTGGSS LLQEGQRKAGAAVTTETEVIWAKALPAGTSAQR AQLIALTQALKMAEGKKLNVYTNSRYAFATAHE HGEIYRRRGLLTSEGKEIKNKDEILALLKALFL PKRLSIIHCPGHQKGHSAEARGNRMADQAARKA AITETPDTSTLLIENSSPYTSEHF |

For the standard two-step procedure, RTases (1 µL, 620 nM) were added to a reaction mixture containing RNA (20 ng), dNTPs (100 µM), oligo dT primer (5 ng/uL) or both random hexamers and oligo dT primers (5 ng/uL each), first strand synthesis buffer (1×, 50 mM potassium acetate, 20 mM tris-acetate, pH 7.9, 10 mM magnesium acetate, 0.6 M trehalose 100 µg/ml BSA, and 10 mM DTT), and Supera-seIN (0.17 U/µL) in a 20 µL volume. The reaction proceeded at 50 or 65° C. for 15 minutes, followed by 80° C. for 10 minutes.

The subsequent cDNA synthesized by the RTase mutants in this disclosure were quantified by qPCR amplification using an assay that identified the SFRS9 gene in human cells. The assay master mix was a composition of Integrated DNA Technologies PrimeTime© Gene Expression Master Mix (GEM, 1×), SFRS9 primer set (500 nM, Table 3) and SFRS9 probe (250 nM, Table 3). The assay master mix and synthesized cDNA were mixed at a 10:1 ratio for a final volume of 20 µL. The reaction proceeded on a qPCR (QuantStudio7 Flex) using the following method: 95° C. hold for 3 minutes, followed by 95° C. for 15 seconds and 60° C. for one minute for 40 cycles. The reactions were analyzed and reported by Ct value (Tables 23-25). All mutant variants of MMLV RTase showed an increase in the overall activity compared to the base construct and three mutant variants of MMLV RTase showed noteworthy activity compared to the others, Q68R/Q79R/L82Y/L99R/L280I/E282D/Q299E/T306K/V433R/I593W; Q68R/Q79R/L99R/E282D/Q299E/T306K/V433R/I593E; and Q68R/Q79R/L83Y/L99R/L280I/E282D/Q299E/T306K/V433R/I593E.

TABLE 23

Two-Step cDNA Synthesis by MMLV-RT mutants using oligo dT priming. The data was generated via qPCR human normalizer assay and data is reported by Ct value.

| MMLV-RT Variant | RT Temperature (° C.) | Ct Mean | Ct Standard Deviation |
|---|---|---|---|
| MMLV-II | 50 | 24.873 | 0.043 |
| | 65 | 35.817 | 0.630 |
| MMLV-II Q68R/Q79R/L99R/E282D | 50 | 24.932 | 0.058 |
| | 65 | 36.668 | 0.614 |
| MMLV-II Q68R/Q79R/L99R/E282D/Q299E/V433R/I593E | 50 | 24.750 | 0.036 |
| | 65 | 35.782 | 1.366 |
| MMLV-II Q68R/Q79R/L99R/E282D/Q299E/V433N/I593W | 50 | 24.586 | 0.035 |
| | 65 | 35.819 | 0.284 |
| MMLV-II Q68R/Q79R/L99R/E282D/L280EQ299E/V433N/I593W | 50 | 24.638 | 0.028 |
| | 65 | 34.319 | 0.343 |
| MMLV-II Q68R/Q79R/L82Y/L99R/E282D/L280I/Q299E/V433N/I593W | 50 | 24.681 | 0.019 |
| | 65 | 33.184 | 0.021 |

TABLE 24

Two-Step cDNA Synthesis by MMLV-RT mutants using oligo dT priming. The data was
generated via qPCR human normalizer assay and data is reported by Ct value.

| MMLV-RT Variant | RT Temperature (° C.) | Ct Mean | Ct Standard Deviation |
|---|---|---|---|
| MMLV-II | 50 | 24.887 | 0.041 |
| | 65 | 32.730 | 0.053 |
| MMLV-II Q68R/Q79R/L99R/E282D/Q299E/V433R/I593E | 50 | 25.061 | 0.126 |
| | 65 | 27.898 | 0.070 |
| MMLV-II Q68R/Q79R/L82Y/L99R/L280I/E282D/Q299E/V433N/I593W | 50 | 24.849 | 0.101 |
| | 65 | 26.607 | 0.077 |
| MMLV-II Q68R/Q79R/L82Y/L99R/L280I/E282D/Q299E/T306K/V433N/I593W | 50 | 25.110 | 0.154 |
| | 65 | 25.701 | 0.062 |
| MMLV-II Q68R/Q79R/L99R/E282D/Q299E/T306K/V433R/I593E | 50 | 24.990 | 0.088 |
| | 65 | 25.929 | 0.114 |
| MMLV-II Q68R/Q79R/L82Y/L99R/L280I/E282D/Q299E/V433R I593E | 50 | 25.133 | 0.114 |
| | 65 | 27.032 | 0.141 |
| MMLV-II Q68R/Q79R/L82Y/L99R/L280I/E282D/Q299E/T306K/ V433R/I593E | 50 | 24.817 | 0.122 |
| | 65 | 25.721 | 0.187 |

TABLE 25

Two-Step cDNA Synthesis by MMLV-RT mutants using random priming. The data was
generated via qPCR human normalizer assay and data is reported by Ct value.

| MMLV-RT Variant | RT Temperature (° C.) | Ct Mean | Ct Standard Deviation |
|---|---|---|---|
| MMLV-II | 50 | 25.048 | 0.075 |
| | 65 | 32.563 | 0.156 |
| MMLV-II Q68R/Q79R/L99R/E282D/Q299E/V433R/I593E | 50 | 25.002 | 0.027 |
| | 65 | 28.062 | 0.106 |
| MMLV-II Q68R/Q79R/L82Y/L99R/L280I/E282D/Q299E/V433N/ I593W | 50 | 25.016 | 0.179 |
| | 65 | 26.724 | 0.040 |
| MMLV-II Q68R/Q79R/L82Y/L99R/L280I/E282D/Q299E/T306K/ V433N/I593W | 50 | 24.973 | 0.021 |
| | 65 | 25.732 | 0.061 |
| MMLV-II Q68R/Q79R/L99R/E282D/Q299E/T306K/V433R/I593E | 50 | 24.982 | 0.030 |
| | 65 | 26.006 | 0.020 |
| MMLV-II Q68R/Q79R/L82Y/L99R/L280I/E282D/Q299E/V433R/I593E | 50 | 25.078 | 0.065 |
| | 65 | 27.080 | 0.122 |
| MMLV-II Q68R/Q79R/L82Y/L99R/L280I/E282D/Q299E/T306K/ V433R/I593E | 50 | 25.074 | 0.094 |
| | 65 | 25.784 | 0.100 |

Example 7. Reverse Transcriptase Mutant
Evaluation by Gene Specific Priming

This example demonstrates the procedure used to evaluate
each mutant RTase's ability to synthesize cDNA from puri-
fied RNA ultramers (Integrated DNA Technologies) com-
pared to the base construct of MMLV RTase. The mutant
MMLV RTases were tested by a one-step addition of the
RTase in GEM as described in Example 5. The reactions
were analyzed and reported by Ct value (Table 26). Twelve
mutant variants of MMLV RTase showed an increase in the
overall activity compared to the base construct, H77A,
D83E, D83R, Y271E, Q299E, G308E, F396A, V433R,
I593E, I597A, and I597R.

TABLE 26

One-Step cDNA Synthesis by MMLV-RT single mutants by gene
specific priming. The data was generated via qPCR human
normalizer assay and data is reported by Ct value.

| MMLV-RT Variant | Ct Mean | Ct Standard Deviation |
|---|---|---|
| MMLV-II | 29.065 | 0.277 |
| MMLV-II D209A | 29.583 | 0.166 |
| MMLV-II D209E | 28.900 | 0.088 |
| MMLV-II D209R | 29.266 | 0.068 |
| MMLV-II D83 A | 29.588 | 0.082 |
| MMLV-II D83E | 28.499 | 0.087 |
| MMLV-II D83R | 28.724 | 0.087 |
| MMLV-II E201A | 30.692 | 0.173 |
| MMLV-II E201D | 29.130 | 0.157 |
| MMLV-II E201R | 29.333 | 0.141 |
| MMLV-II E367A | 31.153 | 0.021 |
| MMLV-II E367D | 31.070 | 0.187 |
| MMLV-II E367R | 34.221 | 0.475 |

TABLE 26-continued

One-Step cDNA Synthesis by MMLV-RT single mutants by gene specific priming. The data was generated via qPCR human normalizer assay and data is reported by Ct value.

| MMLV-RT Variant | Ct Mean | Ct Standard Deviation |
|---|---|---|
| MMLV-II E596A | 29.150 | 0.121 |
| MMLV-II E596D | 30.494 | 0.081 |
| MMLV-II E596R | 31.787 | 0.227 |
| MMLV-II F210A | 33.639 | 0.196 |
| MMLV-II F210E | 34.982 | 0.065 |
| MMLV-II F210R | 37.201 | 1.986 |
| MMLV-II F369A | 29.055 | 0.063 |
| MMLV-II F369E | 36.856 | 0.508 |
| MMLV-II F369R | 36.149 | 0.308 |
| MMLV-II G308A | 30.226 | 0.170 |
| MMLV-II G308E | 28.772 | 0.121 |
| MMLV-II G308R | 40.000 | 0.000 |
| MMLV-II G331A | 30.412 | 0.137 |
| MMLV-II G331E | 31.321 | 0.160 |
| MMLV-II G331R | 31.340 | 0.020 |
| MMLV-II G73A | 30.741 | 0.125 |
| MMLV-II G73E | 34.319 | 0.369 |
| MMLV-II G73R | 29.721 | 0.061 |
| MMLV-II H77A | 28.581 | 0.070 |
| MMLV-II H77E | 29.475 | 0.107 |
| MMLV-II H77R | 29.726 | 0.120 |
| MMLV-II I125A | 29.812 | 0.043 |
| MMLV-II I125E | 30.712 | 0.147 |
| MMLV-II I125R | 30.324 | 0.012 |
| MMLV-II I212A | 29.586 | 0.086 |
| MMLV-II I212E | 29.459 | 0.073 |
| MMLV-II I212R | 29.037 | 0.092 |
| MMLV-II I593A | 30.560 | 0.101 |
| MMLV-II I593E | 27.779 | 0.056 |
| MMLV-II I593R | 29.268 | 0.012 |
| MMLV-II I597A | 28.983 | 0.024 |
| MMLV-II I597E | 29.583 | 0.143 |
| MMLV-II I597R | 28.671 | 0.103 |
| MMLV-II K285A | 32.375 | 0.158 |
| MMLV-II K285E | 37.065 | 0.044 |
| MMLV-II K285R | 30.564 | 0.075 |
| MMLV-II K348A | 34.241 | 0.516 |
| MMLV-II K348E | 34.533 | 0.432 |
| MMLV-II K348R | 29.703 | 0.225 |
| MMLV-II L198A | 31.900 | 0.054 |
| MMLV-II L198E | 34.193 | 0.167 |
| MMLV-II L198R | 30.819 | 0.077 |
| MMLV-II L280A | 35.724 | 0.175 |
| MMLV-II L280E | 40.000 | 0.000 |
| MMLV-II L280R | 40.000 | 0.000 |
| MMLV-II L352A | 28.936 | 0.043 |
| MMLV-II L352E | 30.177 | 0.059 |
| MMLV-II L352R | 29.371 | 0.063 |
| MMLV-II L357A | 38.802 | 1.694 |
| MMLV-II L357E | 40.000 | 0.000 |
| MMLV-II L357R | 40.000 | 0.000 |
| MMLV-II L82A | 31.245 | 0.035 |
| MMLV-II L82E | 31.384 | 0.122 |
| MMLV-II L82R | 29.682 | 0.116 |
| MMLV-II N335A | 29.668 | 0.086 |
| MMLV-II N335E | 29.113 | 0.058 |
| MMLV-II N335R | 32.323 | 5.429 |
| MMLV-II P76A | 29.463 | 0.123 |
| MMLV-II P76E | 30.030 | 0.163 |
| MMLV-II P76R | 29.443 | 0.028 |
| MMLV-II Q213A | 29.833 | 0.223 |
| MMLV-II Q213E | 29.677 | 0.196 |
| MMLV-II Q213R | 29.704 | 0.053 |
| MMLV-II Q299A | 31.314 | 0.200 |
| MMLV-II Q299E | 28.652 | 0.149 |
| MMLV-II Q299R | 31.711 | 0.062 |
| MMLV-II Q654A | 29.415 | 0.117 |
| MMLV-II Q654E | 30.523 | 0.057 |
| MMLV-II Q654R | 29.523 | 0.052 |
| MMLV-II R205A | 29.140 | 0.138 |
| MMLV-II R205E | 29.356 | 0.179 |
| MMLV-II R205K | 29.162 | 0.206 |
| MMLV-II R211A | 29.491 | 0.025 |

TABLE 26-continued

One-Step cDNA Synthesis by MMLV-RT single mutants by gene specific priming. The data was generated via qPCR human normalizer assay and data is reported by Ct value.

| MMLV-RT Variant | Ct Mean | Ct Standard Deviation |
|---|---|---|
| MMLV-II R211E | 30.049 | 0.205 |
| MMLV-II R211K | 30.196 | 0.147 |
| MMLV-II R311A | 31.237 | 0.425 |
| MMLV-II R311E | 40.000 | 0.000 |
| MMLV-II R311K | 29.857 | 0.091 |
| MMLV-II R389A | 32.173 | 0.151 |
| MMLV-II R389E | 32.717 | 0.105 |
| MMLV-II R389K | 31.944 | 0.166 |
| MMLV-II R650A | 29.734 | 0.060 |
| MMLV-II R650E | 31.012 | 0.074 |
| MMLV-II R650K | 29.404 | 0.094 |
| MMLV-II R657A | 31.470 | 0.133 |
| MMLV-II R657E | 32.785 | 0.145 |
| MMLV-II R657K | 29.468 | 0.274 |
| MMLV-II S67A | 29.268 | 0.090 |
| MMLV-II S67E | 30.157 | 0.254 |
| MMLV-II S67R | 27.274 | 0.054 |
| MMLV-II T328A | 40.000 | 0.000 |
| MMLV-II T328E | 37.699 | 1.627 |
| MMLV-II T328R | 37.169 | 0.848 |
| MMLV-II T332A | 29.219 | 0.075 |
| MMLV-II T332E | 29.714 | 0.057 |
| MMLV-II T332R | 30.462 | 0.130 |
| MMLV-II V129A | 29.305 | 0.077 |
| MMLV-II V129E | 31.188 | 0.181 |
| MMLV-II V129R | 30.383 | 0.081 |
| MMLV-II V433A | 30.483 | 0.059 |
| MMLV-II V433E | 30.106 | 0.144 |
| MMLV-II V433R | 29.297 | 0.457 |
| MMLV-II V476A | 31.295 | 0.244 |
| MMLV-II V476E | 34.664 | 0.364 |
| MMLV-II V476R | 31.223 | 0.166 |
| MMLV-II Y271A | 30.854 | 0.086 |
| MMLV-II Y271E | 28.620 | 0.068 |
| MMLV-II Y271R | 33.280 | 0.258 |
| MMLV-IV | 26.368 | 0.057 |

Example 8. Further Stacking of Reverse Transcriptase Mutants with Enhanced Activity This example demonstrates the procedure used to stack the enhanced mutants found in Examples 6 and 7 to further improve the MMLV RTase's ability to synthesize cDNA from purified total RNA (DNased, isolated from HeLa cells) compared to the base construct and previously found mutant MMLV RTase containing the following mutations: Q68R/Q79R/L99R/E282D. The stacked mutant MMLV RTases were cloned, overexpressed and purified as described in Examples 1 and 2 and tested as described in Examples 6 and 7. Both the two- and one-step reactions were analyzed and reported by Ct value (Tables 27-29). Six of the eight stacked mutant variants of MMLV RTase increased the overall activity and thermostability compared to the base construct, Q68R/Q79R/L99R/E282D/V433R, Q68R/Q79R/L99R/E282D/I593E, Q68R/Q79R/L99R/E282D/Q299E, Q68R/Q79R/L99R/E282D/T332E, Q68R/L82R/L99R/E282D and Q68R/Q79R/L82R/L99R/E282D. Sub sequentially, four of those six stacked mutant variants of MMLV RTase increased the overall activity and thermostability compared to the previously identified mutant RTase (Q68R/Q79R/L99R/E282D), Q68R/Q79R/L99R/E282D/I593E, Q68R/Q79R/L99R/E282D/Q299E, Q68R/L82R/L99R/E282D and Q68R/Q79R/L82R/L99R/E282D.

Following these stacked mutant variants, MMLV RTase mutations were stacked further to improve the ability of MMLV RTase to synthesize cDNA from purified total RNA (DNased, isolated from HeLa cells) as compared to the MMLV RTase base construct (RNase H minus construct). Eight MMLV RTase sextuple or more mutant variants were cloned as described in Example 1 and overexpressed and purified as in Example 5.

MMLV RTase base construct and MMLV RTase mutant variants evaluated as described in Example 3. Temperatures were adjusted for both two-step and one-step reactions to 42/55 and 50/60° C., respectively. The two-step first strand synthesis buffer was modified from 50 mM Tris-hydrochloride, pH 8.3, 75 mM potassium chloride, 3 mM magnesium chloride and 10 mM DTT to 50 mM potassium acetate, 20 mM Tris-acetate, pH 7.0, 10 mM magnesium acetate, 100 µg/ml bovine serum albumin and 10 mM DTT. The two-step and one-step reactions for MMLV RTase base construct and MMLV RTase mutant variants were analyzed and reported by Ct output from the qPCR (Tables 27-29).

Four of the eleven MMLV RTase sextuple or more mutant variants were found to exhibit increased overall activity and thermostability as compared to the other MMLV RTase stacked mutant variants, and almost all of the MMLV RTase stacked mutant variants exhibited increased overall activity and thermostability as compared to the MMLV RTase base construct. The four MMLV RTase mutant variants that were found to exhibit the highest overall activity were Q68R/Q79R/L99R/E282D/Q299E/V433R/V593E, Q68R2Q79R/L82R/L99R/E282D/Q299E/V433R/M593E, Q68R/Q79R/L82R/L99R/E282D/Q299E/T332E/593E, and Q68R/Q79R/L82R/L99R/E282D/Q299E/T332E/V433R/I593E.

TABLE 27

Two-Step cDNA Synthesis by MMLV-RT stacked mutants using oligo dT priming. The data was generated via qPCR human normalizer assay and data is reported by Ct value.

| MMLV-RT Variant | Ct Mean | Ct Standard Deviation |
|---|---|---|
| MMLV-II | 37.388 | 0.396 |
| MMLV-II Q68R/Q79R/L99R/E282D/V433R | 29.215 | 0.113 |
| MMLV-II Q68R/Q79R/L99R/E282D/I593E | 33.563 | 0.118 |
| MMLV-II Q68R/Q79R/L99R/E282D/Q299E | 31.902 | 0.169 |
| MMLV-II Q68R/Q79R/L99R/E282D/T332E | 33.988 | 0.108 |
| MMLV-II Q68R/Q79R/L99R/L280R | 40.000 | 0.000 |
| MMLV-II Q68R/Q79R/L99R/L280R/E282D | 40.000 | 0.000 |
| MMLV-II Q68R/L82R/L99R/E282D | 39.259 | 1.047 |
| MMLV-II Q68R/Q79R/L82R/L99R/E282D | 30.623 | 0.076 |
| MMLV-IV | 25.880 | 0.023 |

TABLE 28

Two-Step cDNA Synthesis by MMLV-RT stacked mutants using random priming. The data was generated via qPCR human normalizer assay and data is reported by Ct value.

| MMLV-RT Variant | Ct Mean | Ct Standard Deviation |
|---|---|---|
| MMLV-II | 36.638 | 1.014 |
| MMLV-II Q68R/Q79R/L99R/E282D/V433R | 40.000 | 0.000 |
| MMLV-II Q68R/Q79R/L99R/E282D/I593E | 32.331 | 0.111 |
| MMLV-II Q68R/Q79R/L99R/E282D/Q299E | 30.430 | 0.154 |
| MMLV-II Q68R/Q79R/L99R/E282D/T332E | 33.720 | 0.266 |
| MMLV-II Q68R/Q79R/L99R/L280R | 40.000 | 0.000 |
| MMLV-II Q68R/Q79R/L99R/L280R/E282D | 40.000 | 0.000 |
| MMLV-II Q68R/L82R/L99R/E282D | 35.325 | 0.422 |
| MMLV-II Q68R/Q79R/L82R/L99R/E282D | 31.928 | 0.177 |
| MMLV-IV | 25.840 | 0.049 |

TABLE 29

One-Step cDNA Synthesis by MMLV-RT stacked mutants by gene specific priming. The data was generated via qPCR human normalizer assay and data is reported by Ct value.

| MMLV-RT Variant | Ct Mean | Ct Standard Deviation |
|---|---|---|
| MMLV-II | 33.027 | 0.048 |
| MMLV-II Q68R/Q79R/L99R/E282D/V433R | 29.937 | 0.040 |
| MMLV-II Q68R/Q79R/L99R/E282D/I593E | 28.724 | 0.081 |
| MMLV-II Q68R/Q79R/L99R/E282D/Q299E | 29.341 | 0.022 |
| MMLV-II Q68R/Q79R/L99R/E282D/T332E | 30.330 | 0.036 |
| MMLV-II Q68R/Q79R/L99R/L280R | 40.000 | 0.000 |
| MMLV-II Q68R/Q79R/L99R/L280R/E282D | 40.000 | 0.000 |
| MMLV-II Q68R/L82R/L99R/E282D | 30.559 | 0.045 |
| MMLV-II Q68R/Q79R/L82R/L99R/E282D | 30.097 | 0.033 |
| MMLV-IV | 28.975 | 0.012 | a. Evaluation of Ability of Purified MMLV RTase Mutant Variants to Synthesize DNA Over a Wide Range of Temperatures MMLV RTase base construct MMLV RTase mutant variants evaluated as described in Example 5. Oligo-dT or random hexamer priming conditions and reaction temperatures were adjusted for the two-step reactions and RTase concentration was normalized to 31 nM. The two-step reactions for MMLV RTase base construct and MMLV RTase mutant variants were analyzed and reported by Ct output from the qPCR (see tables 25 and 26)

Five MMLV RTase mutants were found to exhibit high overall activity as compared to the MMLV RTase base construct over a wide range of temperatures, spanning from 37.0 to 51° C., regardless of which priming method used. All of the MMLV RTase stacked mutant variants exhibited increased overall activity and thermostability as compared to the MMLV RTase base construct. The five MMLV RTase mutant variants that were found to exhibit the highest overall activity at a wide range of temperatures were Q68R/Q79R/L99R/E282D, Q68R/Q79R/L99R/E282D/Q299E/V433R/I593E, Q68R/Q79R/L82R/L99R/E282D/Q299E/V433R/I593E, Q68R/Q79R/L82R/L99R/E282D/Q299E/T332E/I593E and Q68R/Q79R/L82R/L99R/E282D/Q299E/T332E/V433R/I593E

TABLE 30

Two-Step cDNA synthesis by MMLV RT quadruple and more mutants
by Oligo-dT priming. Data was generated via qPCR human
normalizer assay and data is reported by Ct value.

| MMLV RT Mutant | Temperature of Reaction (° C.) | Ct Mean | Ct SD |
|---|---|---|---|
| MMLV-II | 37.0 | 26.340 | 0.033 |
| MMLV-II | 37.8 | 26.130 | 0.061 |
| MMLV-II | 39.5 | 25.830 | 0.014 |
| MMLV-II | 42.0 | 25.753 | 0.041 |
| MMLV-II | 45.2 | 25.632 | 0.077 |
| MMLV-II | 47.8 | 25.935 | 0.026 |
| MMLV-II | 49.2 | 26.478 | 0.042 |
| MMLV-II | 50.0 | 29.461 | 0.120 |
| MMLV-II | 51.0 | 29.430 | 0.098 |
| MMLV-II | 51.9 | 31.123 | 0.066 |
| MMLV-II | 53.8 | 33.632 | 0.073 |
| MMLV-II | 56.5 | 36.499 | 0.385 |
| MMLV-II | 59.9 | 37.158 | 0.427 |
| MMLV-II | 62.6 | 37.464 | 0.440 |
| MMLV-II | 64.2 | 37.082 | 0.022 |
| MMLV-II | 65.0 | 37.518 | 0.370 |
| MMLV-II Q68R/Q79R/L99R/E282D | 37.0 | 25.688 | 0.031 |
| MMLV-II Q68R/Q79R/L99R/E282D | 37.8 | 25.734 | 0.032 |
| MMLV-II Q68R/Q79R/L99R/E282D | 39.5 | 25.613 | 0.040 |
| MMLV-II Q68R/Q79R/L99R/E282D | 42.0 | 25.528 | 0.032 |
| MMLV-II Q68R/Q79R/L99R/E282D | 45.2 | 25.525 | 0.029 |
| MMLV-II Q68R/Q79R/L99R/E282D | 47.8 | 25.471 | 0.105 |
| MMLV-II Q68R/Q79R/L99R/E282D | 49.2 | 25.491 | 0.047 |
| MMLV-II Q68R/Q79R/L99R/E282D | 50.0 | 25.608 | 0.061 |
| MMLV-II Q68R/Q79R/L99R/E282D | 51.0 | 25.679 | 0.006 |
| MMLV-II Q68R/Q79R/L99R/E282D | 51.9 | 25.969 | 0.032 |
| MMLV-II Q68R/Q79R/L99R/E282D | 53.8 | 27.251 | 0.053 |
| MMLV-II Q68R/Q79R/L99R/E282D | 56.5 | 33.619 | 0.195 |
| MMLV-II Q68R/Q79R/L99R/E282D | 59.9 | 36.635 | 0.059 |
| MMLV-II Q68R/Q79R/L99R/E282D | 62.6 | 36.929 | 0.500 |
| MMLV-II Q68R/Q79R/L99R/E282D | 64.2 | 37.515 | 0.478 |
| MMLV-II Q68R/Q79R/L99R/E282D | 65.0 | 37.107 | 0.285 |
| MMLV-II Q68R/Q79R/L99R/E282D/I593E | 37.0 | 26.133 | 0.054 |
| MMLV-II Q68R/Q79R/L99R/E282D/I593E | 37.8 | 26.029 | 0.012 |
| MMLV-II Q68R/Q79R/L99R/E282D/I593E | 39.5 | 25.850 | 0.047 |
| MMLV-II Q68R/Q79R/L99R/E282D/I593E | 42.0 | 25.793 | 0.012 |
| MMLV-II Q68R/Q79R/L99R/E282D/I593E | 45.2 | 25.614 | 0.018 |
| MMLV-II Q68R/Q79R/L99R/E282D/I593E | 47.8 | 25.658 | 0.005 |
| MMLV-II Q68R/Q79R/L99R/E282D/I593E | 49.2 | 25.663 | 0.024 |
| MMLV-II Q68R/Q79R/L99R/E282D/I593E | 50.0 | 25.791 | 0.041 |
| MMLV-II Q68R/Q79R/L99R/E282D/I593E | 51.0 | 25.877 | 0.067 |
| MMLV-II Q68R/Q79R/L99R/E282D/I593E | 51.9 | 26.602 | 0.038 |
| MMLV-II Q68R/Q79R/L99R/E282D/I593E | 53.8 | 29.535 | 0.086 |
| MMLV-II Q68R/Q79R/L99R/E282D/I593E | 56.5 | 35.912 | 0.439 |
| MMLV-II Q68R/Q79R/L99R/E282D/I593E | 59.9 | 37.158 | 0.566 |
| MMLV-II Q68R/Q79R/L99R/E282D/I593E | 62.6 | 37.187 | 0.158 |
| MMLV-II Q68R/Q79R/L99R/E282D/I593E | 64.2 | 37.958 | 0.236 |
| MMLV-II Q68R/Q79R/L99R/E282D/I593E | 65.0 | 36.861 | 0.416 |
| MMLV-II Q68R/Q79R/L99R/E282D/Q299E | 37.0 | 26.106 | 0.070 |
| MMLV-II Q68R/Q79R/L99R/E282D/Q299E | 37.8 | 26.024 | 0.092 |
| MMLV-II Q68R/Q79R/L99R/E282D/Q299E | 39.5 | 25.830 | 0.122 |
| MMLV-II Q68R/Q79R/L99R/E282D/Q299E | 42.0 | 25.788 | 0.025 |
| MMLV-II Q68R/Q79R/L99R/E282D/Q299E | 45.2 | 25.634 | 0.022 |
| MMLV-II Q68R/Q79R/L99R/E282D/Q299E | 47.8 | 25.681 | 0.016 |
| MMLV-II Q68R/Q79R/L99R/E282D/Q299E | 49.2 | 25.684 | 0.029 |
| MMLV-II Q68R/Q79R/L99R/E282D/Q299E | 50.0 | 25.743 | 0.096 |
| MMLV-II Q68R/Q79R/L99R/E282D/Q299E | 51.0 | 25.870 | 0.003 |
| MMLV-II Q68R/Q79R/L99R/E282D/Q299E | 51.9 | 26.301 | 0.033 |
| MMLV-II Q68R/Q79R/L99R/E282D/Q299E | 53.8 | 28.283 | 0.036 |
| MMLV-II Q68R/Q79R/L99R/E282D/Q299E | 56.5 | 34.732 | 0.445 |
| MMLV-II Q68R/Q79R/L99R/E282D/Q299E | 59.9 | 36.947 | 0.407 |
| MMLV-II Q68R/Q79R/L99R/E282D/Q299E | 62.6 | 37.140 | 0.280 |
| MMLV-II Q68R/Q79R/L99R/E282D/Q299E | 64.2 | 37.403 | 0.205 |
| MMLV-II Q68R/Q79R/L99R/E282D/Q299E | 65.0 | 37.347 | 0.438 |
| MMLV-II Q68R/Q79R/L82R/L99R/E282D | 37.0 | 25.961 | 0.170 |
| MMLV-II Q68R/Q79R/L82R/L99R/E282D | 37.8 | 26.065 | 0.085 |
| MMLV-II Q68R/Q79R/L82R/L99R/E282D | 39.5 | 25.909 | 0.028 |
| MMLV-II Q68R/Q79R/L82R/L99R/E282D | 42.0 | 25.802 | 0.055 |
| MMLV-II Q68R/Q79R/L82R/L99R/E282D | 45.2 | 25.632 | 0.087 |
| MMLV-II Q68R/Q79R/L82R/L99R/E282D | 47.8 | 25.728 | 0.065 |
| MMLV-II Q68R/Q79R/L82R/L99R/E282D | 49.2 | 25.612 | 0.165 |
| MMLV-II Q68R/Q79R/L82R/L99R/E282D | 50.0 | 25.795 | 0.038 |
| MMLV-II Q68R/Q79R/L82R/L99R/E282D | 51.0 | 25.830 | 0.009 |

TABLE 30-continued

Two-Step cDNA synthesis by MMLV RT quadruple and more mutants
by Oligo-dT priming. Data was generated via qPCR human
normalizer assay and data is reported by Ct value.

| MMLV RT Mutant | Temperature of Reaction (° C.) | Ct Mean | Ct SD |
|---|---|---|---|
| MMLV-II Q68R/Q79R/L82R/L99R/E282D | 51.9 | 26.477 | 0.037 |
| MMLV-II Q68R/Q79R/L82R/L99R/E282D | 53.8 | 28.496 | 0.040 |
| MMLV-II Q68R/Q79R/L82R/L99R/E282D | 56.5 | 34.329 | 0.177 |
| MMLV-II Q68R/Q79R/L82R/L99R/E282D | 59.9 | 36.564 | 0.315 |
| MMLV-II Q68R/Q79R/L82R/L99R/E282D | 62.6 | 37.152 | 0.322 |
| MMLV-II Q68R/Q79R/L82R/L99R/E282D | 64.2 | 37.340 | 0.585 |
| MMLV-II Q68R/Q79R/L82R/L99R/E282D | 65.0 | 38.351 | 1.016 |
| MMLV-II Q68R/Q79R/L99R/E282D/Q299E/V433R/I593E | 37.0 | 25.853 | 0.057 |
| MMLV-II Q68R/Q79R/L99R/E282D/Q299E/V433R/I593E | 37.8 | 25.898 | 0.016 |
| MMLV-II Q68R/Q79R/L99R/E282D/Q299E/V433R/I593E | 39.5 | 25.716 | 0.093 |
| MMLV-II Q68R/Q79R/L99R/E282D/Q299E/V433R/I593E | 42.0 | 25.669 | 0.064 |
| MMLV-II Q68R/Q79R/L99R/E282D/Q299E/V433R/I593E | 45.2 | 25.643 | 0.056 |
| MMLV-II Q68R/Q79R/L99R/E282D/Q299E/V433R/I593E | 47.8 | 25.680 | 0.016 |
| MMLV-II Q68R/Q79R/L99R/E282D/Q299E/V433R/I593E | 49.2 | 25.663 | 0.057 |
| MMLV-II Q68R/Q79R/L99R/E282D/Q299E/V433R/I593E | 50.0 | 25.708 | 0.045 |
| MMLV-II Q68R/Q79R/L99R/E282D/Q299E/V433R/I593E | 51.0 | 25.557 | 0.025 |
| MMLV-II Q68R/Q79R/L99R/E282D/Q299E/V433R/I593E | 51.9 | 26.015 | 0.125 |
| MMLV-II Q68R/Q79R/L99R/E282D/Q299E/V433R/I593E | 53.8 | 27.812 | 0.048 |
| MMLV-II Q68R/Q79R/L99R/E282D/Q299E/V433R/I593E | 56.5 | 34.073 | 0.217 |
| MMLV-II Q68R/Q79R/L99R/E282D/Q299E/V433R/I593E | 59.9 | 36.512 | 0.168 |
| MMLV-II Q68R/Q79R/L99R/E282D/Q299E/V433R/I593E | 62.6 | 37.182 | 0.167 |
| MMLV-II Q68R/Q79R/L99R/E282D/Q299E/V433R/I593E | 64.2 | 37.239 | 0.291 |
| MMLV-II Q68R/Q79R/L99R/E282D/Q299E/V433R/I593E | 65.0 | 36.573 | 0.232 |
| MMLV-II Q68R/Q79R/L82R/L99R/E282D/Q299E/V433R/I593E | 37.0 | 25.789 | 0.075 |
| MMLV-II Q68R/Q79R/L82R/L99R/E282D/Q299E/V433R/I593E | 37.8 | 25.784 | 0.103 |
| MMLV-II Q68R/Q79R/L82R/L99R/E282D/Q299E/V433R/I593E | 39.5 | 25.714 | 0.025 |
| MMLV-II Q68R/Q79R/L82R/L99R/E282D/Q299E/V433R/I593E | 42.0 | 25.713 | 0.027 |
| MMLV-II Q68R/Q79R/L82R/L99R/E282D/Q299E/V433R/I593E | 45.2 | 25.690 | 0.030 |
| MMLV-II Q68R/Q79R/L82R/L99R/E282D/Q299E/V433R/I593E | 47.8 | 25.662 | 0.026 |
| MMLV-II Q68R/Q79R/L82R/L99R/E282D/Q299E/V433R/I593E | 49.2 | 25.713 | 0.021 |
| MMLV-II Q68R/Q79R/L82R/L99R/E282D/Q299E/V433R/I593E | 50.0 | 25.551 | 0.092 |
| MMLV-II Q68R/Q79R/L82R/L99R/E282D/Q299E/V433R/I593E | 51.0 | 25.561 | 0.107 |
| MMLV-II Q68R/Q79R/L82R/L99R/E282D/Q299E/V433R/I593E | 51.9 | 25.975 | 0.125 |
| MMLV-II Q68R/Q79R/L82R/L99R/E282D/Q299E/V433R/I593E | 53.8 | 27.556 | 0.023 |
| MMLV-II Q68R/Q79R/L82R/L99R/E282D/Q299E/V433R/I593E | 56.5 | 33.934 | 0.249 |
| MMLV-II Q68R/Q79R/L82R/L99R/E282D/Q299E/V433R/I593E | 59.9 | 36.473 | 0.285 |
| MMLV-II Q68R/Q79R/L82R/L99R/E282D/Q299E/V433R/I593E | 62.6 | 37.411 | 0.377 |
| MMLV-II Q68R/Q79R/L82R/L99R/E282D/Q299E/V433R/I593E | 64.2 | 37.656 | 0.478 |
| MMLV-II Q68R/Q79R/L82R/L99R/E282D/Q299E/V433R/I593E | 65.0 | 37.950 | 1.451 |
| MMLV-II Q68R/Q79R/L82R/L99R/E282D/Q299E/T332E/I593E | 37.0 | 25.788 | 0.028 |

TABLE 30-continued

Two-Step cDNA synthesis by MMLV RT quadruple and more mutants
by Oligo-dT priming. Data was generated via qPCR human
normalizer assay and data is reported by Ct value.

| MMLV RT Mutant | Temperature of Reaction (° C.) | Ct Mean | Ct SD |
|---|---|---|---|
| MMLV-II Q68R/Q79R/L82R/L99R/E282D/Q299E/T332E/I593E | 37.8 | 25.680 | 0.229 |
| MMLV-II Q68R/Q79R/L82R/L99R/E282D/Q299E/T332E/I593E | 39.5 | 25.794 | 0.051 |
| MMLV-II Q68R/Q79R/L82R/L99R/E282D/Q299E/T332E/I593E | 42.0 | 25.415 | 0.270 |
| MMLV-II Q68R/Q79R/L82R/L99R/E282D/Q299E/T332E/I593E | 45.2 | 25.631 | 0.047 |
| MMLV-II Q68R/Q79R/L82R/L99R/E282D/Q299E/T332E/I593E | 47.8 | 25.672 | 0.027 |
| MMLV-II Q68R/Q79R/L82R/L99R/E282D/Q299E/T332E/I593E | 49.2 | 25.792 | 0.045 |
| MMLV-II Q68R/Q79R/L82R/L99R/E282D/Q299E/T332E/I593E | 50.0 | 25.759 | 0.022 |
| MMLV-II Q68R/Q79R/L82R/L99R/E282D/Q299E/T332E/I593E | 51.0 | 25.852 | 0.015 |
| MMLV-II Q68R/Q79R/L82R/L99R/E282D/Q299E/T332E/I593E | 51.9 | 26.425 | 0.033 |
| MMLV-II Q68R/Q79R/L82R/L99R/E282D/Q299E/T332E/I593E | 53.8 | 29.964 | 0.023 |
| MMLV-II Q68R/Q79R/L82R/L99R/E282D/Q299E/T332E/I593E | 56.5 | 36.532 | 0.113 |
| MMLV-II Q68R/Q79R/L82R/L99R/E282D/Q299E/T332E/I593E | 59.9 | 38.246 | 0.608 |
| MMLV-II Q68R/Q79R/L82R/L99R/E282D/Q299E/T332E/I593E | 62.6 | 37.333 | 0.446 |
| MMLV-II Q68R/Q79R/L82R/L99R/E282D/Q299E/T332E/I593E | 64.2 | 37.223 | 0.212 |
| MMLV-II Q68R/Q79R/L82R/L99R/E282D/Q299E/T332E/I593E | 65.0 | 36.930 | 0.527 |
| MMLV-II Q68R/Q79R/L82R/L99R/E282D/Q299E/T332E/V433R/ I593E | 37.0 | 25.863 | 0.014 |
| MMLV-II Q68R/Q79R/L82R/L99R/E282D/Q299E/T332E/V433R/ I593E | 37.8 | 25.649 | 0.036 |
| MMLV-II Q68R/Q79R/L82R/L99R/E282D/Q299E/T332E/V433R/ I593E | 39.5 | 25.573 | 0.057 |
| MMLV-II Q68R/Q79R/L82R/L99R/E282D/Q299E/T332E/V433R/ I593E | 42.0 | 25.453 | 0.023 |
| MMLV-II Q68R/Q79R/L82R/L99R/E282D/Q299E/T332E/V433R/ I593E | 45.2 | 25.447 | 0.083 |
| MMLV-II Q68R/Q79R/L82R/L99R/E282D/Q299E/T332E/V433R/ I593E | 47.8 | 25.413 | 0.061 |
| MMLV-II Q68R/Q79R/L82R/L99R/E282D/Q299E/T332E/V433R/ I593E | 49.2 | 25.542 | 0.035 |
| MMLV-II Q68R/Q79R/L82R/L99R/E282D/Q299E/T332E/V433R/ I593E | 50.0 | 25.567 | 0.060 |
| MMLV-II Q68R/Q79R/L82R/L99R/E282D/Q299E/T332E/V433R/ I593E | 51.0 | 25.741 | 0.093 |
| MMLV-II Q68R/Q79R/L82R/L99R/E282D/Q299E/T332E/V433R/ I593E | 51.9 | 26.231 | 0.225 |
| MMLV-II Q68R/Q79R/L82R/L99R/E282D/Q299E/T332E/V433R/ I593E | 53.8 | 28.556 | 0.142 |
| MMLV-II Q68R/Q79R/L82R/L99R/E282D/Q299E/T332E/V433R/ I593E | 56.5 | 35.202 | 0.208 |
| MMLV-II Q68R/Q79R/L82R/L99R/E282D/Q299E/T332E/V433R/ I593E | 59.9 | 36.991 | 0.419 |
| MMLV-II Q68R/Q79R/L82R/L99R/E282D/Q299E/T332E/V433R/ I593E | 62.6 | 37.168 | 0.463 |

TABLE 30-continued

Two-Step cDNA synthesis by MMLV RT quadruple and more mutants
by Oligo-dT priming. Data was generated via qPCR human
normalizer assay and data is reported by Ct value.

| MMLV RT Mutant | Temperature of Reaction (° C.) | Ct Mean | Ct SD |
|---|---|---|---|
| MMLV-II Q68R/Q79R/L82R/L99R/E282D/Q299E/T332E/V433R/ I593E | 64.2 | 37.670 | 0.410 |
| MMLV-II Q68R/Q79R/L82R/L99R/E282D/Q299E/T332E/V433R/ I593E | 65.0 | 37.680 | 0.273 |

TABLE 31

Two-Step cDNA synthesis by MMLV RT quadruple and more mutants
by Random priming. Data was generated via qPCR human normalizer
assay and data is reported by Ct value.

| MMLV RT Mutant | Temperature of Reaction (° C.) | Ct Mean | Ct SD |
|---|---|---|---|
| MMLV-II | 37.0 | 26.365 | 0.066 |
| MMLV-II | 37.8 | 26.390 | 0.006 |
| MMLV-II | 39.5 | 25.939 | 0.016 |
| MMLV-II | 42.0 | 25.798 | 0.029 |
| MMLV-II | 45.2 | 25.849 | 0.064 |
| MMLV-II | 47.8 | 26.647 | 0.050 |
| MMLV-II | 49.2 | 28.326 | 0.028 |
| MMLV-II | 50.0 | 29.340 | 0.010 |
| MMLV-II | 51.0 | 30.684 | 0.099 |
| MMLV-II | 51.9 | 32.462 | 0.163 |
| MMLV-II | 53.8 | 33.855 | 0.307 |
| MMLV-II | 56.5 | 35.376 | 0.461 |
| MMLV-II | 59.9 | 36.098 | 0.481 |
| MMLV-II | 62.6 | 36.391 | 0.367 |
| MMLV-II | 64.2 | 36.442 | 0.547 |
| MMLV-II | 65.0 | 35.871 | 0.301 |
| MMLV-II Q68R/Q79R/L99R/E282D | 37.0 | 25.699 | 0.009 |
| MMLV-II Q68R/Q79R/L99R/E282D | 37.8 | 25.674 | 0.038 |
| MMLV-II Q68R/Q79R/L99R/E282D | 39.5 | 25.594 | 0.029 |
| MMLV-II Q68R/Q79R/L99R/E282D | 42.0 | 25.496 | 0.016 |
| MMLV-II Q68R/Q79R/L99R/E282D | 45.2 | 25.431 | 0.011 |
| MMLV-II Q68R/Q79R/L99R/E282D | 47.8 | 25.420 | 0.036 |
| MMLV-II Q68R/Q79R/L99R/E282D | 49.2 | 25.481 | 0.023 |
| MMLV-II Q68R/Q79R/L99R/E282D | 50.0 | 25.646 | 0.035 |
| MMLV-II Q68R/Q79R/L99R/E282D | 51.0 | 25.979 | 0.012 |
| MMLV-II Q68R/Q79R/L99R/E282D | 51.9 | 26.591 | 0.053 |
| MMLV-II Q68R/Q79R/L99R/E282D | 53.8 | 28.345 | 0.091 |
| MMLV-II Q68R/Q79R/L99R/E282D | 56.5 | 32.976 | 0.109 |
| MMLV-II Q68R/Q79R/L99R/E282D | 59.9 | 34.407 | 0.158 |
| MMLV-II Q68R/Q79R/L99R/E282D | 62.6 | 35.130 | 0.014 |
| MMLV-II Q68R/Q79R/L99R/E282D | 64.2 | 34.866 | 0.258 |
| MMLV-II Q68R/Q79R/L99R/E282D | 65.0 | 35.317 | 0.299 |
| MMLV-II Q68R/Q79R/L99R/E282D/I593E | 37.0 | 26.079 | 0.036 |
| MMLV-II Q68R/Q79R/L99R/E282D/I593E | 37.8 | 25.951 | 0.015 |
| MMLV-II Q68R/Q79R/L99R/E282D/I593E | 39.5 | 25.801 | 0.055 |
| MMLV-II Q68R/Q79R/L99R/E282D/I593E | 42.0 | 25.602 | 0.087 |
| MMLV-II Q68R/Q79R/L99R/E282D/I593E | 45.2 | 25.424 | 0.038 |
| MMLV-II Q68R/Q79R/L99R/E282D/I593E | 47.8 | 25.520 | 0.011 |
| MMLV-II Q68R/Q79R/L99R/E282D/I593E | 49.2 | 25.674 | 0.046 |
| MMLV-II Q68R/Q79R/L99R/E282D/I593E | 50.0 | 25.922 | 0.015 |
| MMLV-II Q68R/Q79R/L99R/E282D/I593E | 51.0 | 26.351 | 0.014 |
| MMLV-II Q68R/Q79R/L99R/E282D/I593E | 51.9 | 27.411 | 0.092 |
| MMLV-II Q68R/Q79R/L99R/E282D/I593E | 53.8 | 30.482 | 0.048 |
| MMLV-II Q68R/Q79R/L99R/E282D/I593E | 56.5 | 33.914 | 0.075 |
| MMLV-II Q68R/Q79R/L99R/E282D/I593E | 59.9 | 35.443 | 0.191 |
| MMLV-II Q68R/Q79R/L99R/E282D/I593E | 62.6 | 35.872 | 0.445 |
| MMLV-II Q68R/Q79R/L99R/E282D/I593E | 64.2 | 36.107 | 0.011 |
| MMLV-II Q68R/Q79R/L99R/E282D/I593E | 65.0 | 35.715 | 0.299 |
| MMLV-II Q68R/Q79R/L99R/E282D/Q299E | 37.0 | 25.955 | 0.040 |
| MMLV-II Q68R/Q79R/L99R/E282D/Q299E | 37.8 | 25.934 | 0.023 |
| MMLV-II Q68R/Q79R/L99R/E282D/Q299E | 39.5 | 25.669 | 0.035 |
| MMLV-II Q68R/Q79R/L99R/E282D/Q299E | 42.0 | 25.523 | 0.016 |
| MMLV-II Q68R/Q79R/L99R/E282D/Q299E | 45.2 | 25.532 | 0.054 |

TABLE 31-continued

Two-Step cDNA synthesis by MMLV RT quadruple and more mutants by Random priming. Data was generated via qPCR human normalizer assay and data is reported by Ct value.

| MMLV RT Mutant | Temperature of Reaction (° C.) | Ct Mean | Ct SD |
|---|---|---|---|
| MMLV-II Q68R/Q79R/L99R/E282D/Q299E | 47.8 | 25.550 | 0.021 |
| MMLV-II Q68R/Q79R/L99R/E282D/Q299E | 49.2 | 25.620 | 0.030 |
| MMLV-II Q68R/Q79R/L99R/E282D/Q299E | 50.0 | 25.711 | 0.035 |
| MMLV-II Q68R/Q79R/L99R/E282D/Q299E | 51.0 | 26.215 | 0.056 |
| MMLV-II Q68R/Q79R/L99R/E282D/Q299E | 51.9 | 26.969 | 0.013 |
| MMLV-II Q68R/Q79R/L99R/E282D/Q299E | 53.8 | 29.622 | 0.060 |
| MMLV-II Q68R/Q79R/L99R/E282D/Q299E | 56.5 | 33.679 | 0.234 |
| MMLV-II Q68R/Q79R/L99R/E282D/Q299E | 59.9 | 35.253 | 0.144 |
| MMLV-II Q68R/Q79R/L99R/E282D/Q299E | 62.6 | 35.408 | 0.441 |
| MMLV-II Q68R/Q79R/L99R/E282D/Q299E | 64.2 | 35.586 | 0.139 |
| MMLV-II Q68R/Q79R/L99R/E282D/Q299E | 65.0 | 36.076 | 0.700 |
| MMLV-II Q68R/Q79R/L82R/L99R/E282D | 37.0 | 25.884 | 0.012 |
| MMLV-II Q68R/Q79R/L82R/L99R/E282D | 37.8 | 25.833 | 0.009 |
| MMLV-II Q68R/Q79R/L82R/L99R/E282D | 39.5 | 25.684 | 0.077 |
| MMLV-II Q68R/Q79R/L82R/L99R/E282D | 42.0 | 25.553 | 0.026 |
| MMLV-II Q68R/Q79R/L82R/L99R/E282D | 45.2 | 25.471 | 0.043 |
| MMLV-II Q68R/Q79R/L82R/L99R/E282D | 47.8 | 25.491 | 0.085 |
| MMLV-II Q68R/Q79R/L82R/L99R/E282D | 49.2 | 25.646 | 0.014 |
| MMLV-II Q68R/Q79R/L82R/L99R/E282D | 50.0 | 25.765 | 0.039 |
| MMLV-II Q68R/Q79R/L82R/L99R/E282D | 51.0 | 26.365 | 0.044 |
| MMLV-II Q68R/Q79R/L82R/L99R/E282D | 51.9 | 27.170 | 0.071 |
| MMLV-II Q68R/Q79R/L82R/L99R/E282D | 53.8 | 29.662 | 0.048 |
| MMLV-II Q68R/Q79R/L82R/L99R/E282D | 56.5 | 33.853 | 0.162 |
| MMLV-II Q68R/Q79R/L82R/L99R/E282D | 59.9 | 34.899 | 0.325 |
| MMLV-II Q68R/Q79R/L82R/L99R/E282D | 62.6 | 35.557 | 0.145 |
| MMLV-II Q68R/Q79R/L82R/L99R/E282D | 64.2 | 35.360 | 0.222 |
| MMLV-II Q68R/Q79R/L82R/L99R/E282D | 65.0 | 35.614 | 0.403 |
| MMLV-II Q68R/Q79R/L99R/E282D/Q299E/V433R/I593E | 37.0 | 25.706 | 0.031 |
| MMLV-II Q68R/Q79R/L99R/E282D/Q299E/V433R/I593E | 37.8 | 25.757 | 0.101 |
| MMLV-II Q68R/Q79R/L99R/E282D/Q299E/V433R/I593E | 39.5 | 25.435 | 0.036 |
| MMLV-II Q68R/Q79R/L99R/E282D/Q299E/V433R/I593E | 42.0 | 25.417 | 0.025 |
| MMLV-II Q68R/Q79R/L99R/E282D/Q299E/V433R/I593E | 45.2 | 25.425 | 0.023 |
| MMLV-II Q68R/Q79R/L99R/E282D/Q299E/V433R/I593E | 47.8 | 25.401 | 0.049 |
| MMLV-II Q68R/Q79R/L99R/E282D/Q299E/V433R/I593E | 49.2 | 25.467 | 0.009 |
| MMLV-II Q68R/Q79R/L99R/E282D/Q299E/V433R/I593E | 50.0 | 25.516 | 0.056 |
| MMLV-II Q68R/Q79R/L99R/E282D/Q299E/V433R/I593E | 51.0 | 25.880 | 0.039 |
| MMLV-II Q68R/Q79R/L99R/E282D/Q299E/V433R/I593E | 51.9 | 26.348 | 0.064 |
| MMLV-II Q68R/Q79R/L99R/E282D/Q299E/V433R/I593E | 53.8 | 28.506 | 0.018 |
| MMLV-II Q68R/Q79R/L99R/E282D/Q299E/V433R/I593E | 56.5 | 32.812 | 0.242 |
| MMLV-II Q68R/Q79R/L99R/E282D/Q299E/V433R/I593E | 59.9 | 34.123 | 0.163 |
| MMLV-II Q68R/Q79R/L99R/E282D/Q299E/V433R/I593E | 62.6 | 35.108 | 0.027 |
| MMLV-II Q68R/Q79R/L99R/E282D/Q299E/V433R/I593E | 64.2 | 34.796 | 0.171 |
| MMLV-II Q68R/Q79R/L99R/E282D/Q299E/V433R/I593E | 65.0 | 34.999 | 0.064 |
| MMLV-II Q68R/Q79R/L82R/L99R/E282D/Q299E/V433R/I593E | 37.0 | 25.711 | 0.080 |
| MMLV-II Q68R/Q79R/L82R/L99R/E282D/Q299E/V433R/I593E | 37.8 | 25.916 | 0.224 |
| MMLV-II Q68R/Q79R/L82R/L99R/E282D/Q299E/V433R/I593E | 39.5 | 25.665 | 0.052 |
| MMLV-II Q68R/Q79R/L82R/L99R/E282D/Q299E/V433R/I593E | 42.0 | 25.527 | 0.016 |
| MMLV-II Q68R/Q79R/L82R/L99R/E282D/Q299E/V433R/I593E | 45.2 | 25.504 | 0.065 |
| MMLV-II Q68R/Q79R/L82R/L99R/E282D/Q299E/V433R/I593E | 47.8 | 25.437 | 0.070 |

147

148

TABLE 31-continued

Two-Step cDNA synthesis by MMLV RT quadruple and more mutants
by Random priming. Data was generated via qPCR human normalizer
assay and data is reported by Ct value.

| MMLV RT Mutant | Temperature of Reaction (° C.) | Ct Mean | Ct SD |
|---|---|---|---|
| MMLV-II Q68R/Q79R/L82R/L99R/E282D/Q299E/V433R/I593E | 49.2 | 25.555 | 0.065 |
| MMLV-II Q68R/Q79R/L82R/L99R/E282D/Q299E/V433R/I593E | 50.0 | 25.571 | 0.028 |
| MMLV-II Q68R/Q79R/L82R/L99R/E282D/Q299E/V433R/I593E | 51.0 | 25.854 | 0.029 |
| MMLV-II Q68R/Q79R/L82R/L99R/E282D/Q299E/V433R/I593E | 51.9 | 26.259 | 0.057 |
| MMLV-II Q68R/Q79R/L82R/L99R/E282D/Q299E/V433R/I593E | 53.8 | 28.329 | 0.053 |
| MMLV-II Q68R/Q79R/L82R/L99R/E282D/Q299E/V433R/I593E | 56.5 | 32.962 | 0.212 |
| MMLV-II Q68R/Q79R/L82R/L99R/E282D/Q299E/V433R/I593E | 59.9 | 34.072 | 0.446 |
| MMLV-II Q68R/Q79R/L82R/L99R/E282D/Q299E/V433R/I593E | 62.6 | 34.931 | 0.205 |
| MMLV-II Q68R/Q79R/L82R/L99R/E282D/Q299E/V433R/I593E | 64.2 | 34.626 | 0.169 |
| MMLV-II Q68R/Q79R/L82R/L99R/E282D/Q299E/V433R/I593E | 65.0 | 35.085 | 0.230 |
| MMLV-II Q68R/Q79R/L82R/L99R/E282D/Q299E/T332E/I593E | 37.0 | 25.940 | 0.130 |
| MMLV-II Q68R/Q79R/L82R/L99R/E282D/Q299E/T332E/I593E | 37.8 | 25.793 | 0.129 |
| MMLV-II Q68R/Q79R/L82R/L99R/E282D/Q299E/T332E/I593E | 39.5 | 25.599 | 0.015 |
| MMLV-II Q68R/Q79R/L82R/L99R/E282D/Q299E/T332E/I593E | 42.0 | 25.504 | 0.016 |
| MMLV-II Q68R/Q79R/L82R/L99R/E282D/Q299E/T332E/I593E | 45.2 | 25.602 | 0.041 |
| MMLV-II Q68R/Q79R/L82R/L99R/E282D/Q299E/T332E/I593E | 47.8 | 25.604 | 0.058 |
| MMLV-II Q68R/Q79R/L82R/L99R/E282D/Q299E/T332E/I593E | 49.2 | 25.665 | 0.007 |
| MMLV-II Q68R/Q79R/L82R/L99R/E282D/Q299E/T332E/I593E | 50.0 | 25.821 | 0.068 |
| MMLV-II Q68R/Q79R/L82R/L99R/E282D/Q299E/T332E/I593E | 51.0 | 26.315 | 0.047 |
| MMLV-II Q68R/Q79R/L82R/L99R/E282D/Q299E/T332E/I593E | 51.9 | 27.036 | 0.059 |
| MMLV-II Q68R/Q79R/L82R/L99R/E282D/Q299E/T332E/I593E | 53.8 | 31.004 | 0.089 |
| MMLV-II Q68R/Q79R/L82R/L99R/E282D/Q299E/T332E/I593E | 56.5 | 33.765 | 0.274 |
| MMLV-II Q68R/Q79R/L82R/L99R/E282D/Q299E/T332E/I593E | 59.9 | 34.656 | 0.209 |
| MMLV-II Q68R/Q79R/L82R/L99R/E282D/Q299E/T332E/I593E | 62.6 | 35.561 | 0.468 |
| MMLV-II Q68R/Q79R/L82R/L99R/E282D/Q299E/T332E/I593E | 64.2 | 35.877 | 0.154 |
| MMLV-II Q68R/Q79R/L82R/L99R/E282D/Q299E/T332E/I593E | 65.0 | 35.659 | 0.477 |
| MMLV-II Q68R/Q79R/L82R/L99R/E282D/Q299E/T332E/V433R/I593E | 37.0 | 25.780 | 0.046 |
| MMLV-II Q68R/Q79R/L82R/L99R/E282D/Q299E/T332E/V433R/I593E | 37.8 | 25.652 | 0.026 |
| MMLV-II Q68R/Q79R/L82R/L99R/E282D/Q299E/T332E/V433R/I593E | 39.5 | 25.641 | 0.037 |
| MMLV-II Q68R/Q79R/L82R/L99R/E282D/Q299E/T332E/V433R/I593E | 42.0 | 25.507 | 0.005 |
| MMLV-II Q68R/Q79R/L82R/L99R/E282D/Q299E/T332E/V433R/I593E | 45.2 | 25.484 | 0.067 |
| MMLV-II Q68R/Q79R/L82R/L99R/E282D/Q299E/T332E/V433R/I593E | 47.8 | 25.438 | 0.027 |

TABLE 31-continued

Two-Step cDNA synthesis by MMLV RT quadruple and more mutants
by Random priming. Data was generated via qPCR human normalizer
assay and data is reported by Ct value.

| MMLV RT Mutant | Temperature of Reaction (° C.) | Ct Mean | Ct SD |
|---|---|---|---|
| MMLV-II Q68R/Q79R/L82R/L99R/E282D/Q299E/T332E/V433R/ I593E | 49.2 | 25.534 | 0.022 |
| MMLV-II Q68R/Q79R/L82R/L99R/E282D/Q299E/T332E/V433R/ I593E | 50.0 | 25.755 | 0.085 |
| MMLV-II Q68R/Q79R/L82R/L99R/E282D/Q299E/T332E/V433R/ I593E | 51.0 | 25.981 | 0.027 |
| MMLV-II Q68R/Q79R/L82R/L99R/E282D/Q299E/T332E/V433R/ I593E | 51.9 | 26.242 | 0.052 |
| MMLV-II Q68R/Q79R/L82R/L99R/E282D/Q299E/T332E/V433R/ I593E | 53.8 | 29.146 | 0.069 |
| MMLV-II Q68R/Q79R/L82R/L99R/E282D/Q299E/T332E/V433R/ I593E | 56.5 | 33.138 | 0.159 |
| MMLV-II Q68R/Q79R/L82R/L99R/E282D/Q299E/T332E/V433R/ I593E | 59.9 | 34.551 | 0.152 |
| MMLV-II Q68R/Q79R/L82R/L99R/E282D/Q299E/T332E/V433R /I593E | 62.6 | 35.186 | 0.322 |
| MMLV-II Q68R/Q79R/L82R/L99R/E282D/Q299E/T332E/V433R/ I593E | 64.2 | 35.550 | 0.368 |
| MMLV-II Q68R/Q79R/L82R/L99R/E282D/Q299E/T332E/V433R/ I593E | 65.0 | 35.459 | 0.295 |

Example 9: Extension of Reverse Transcriptase Single Mutants

The amino acid positions that enclosed the MMLV RTase single mutants identified in Examples 6 and 7 were further evaluated to include all possible amino acid substitutions at that position. The single mutants were cloned, overexpressed, and purified as described in Examples 1 and 2, and evaluated as described in Examples 6 and 7. The two-step and one-step reactions for MMLV RTase base construct and MMLV RTase double mutant variants were analyzed and reported by Ct output from the qPCR (Tables 32-34). Numerous single mutant MMLV RTase variants were found to exhibit an increase in the overall activity and thermostability as compared to the MMLV RTase base construct. The most prevalent among these were: L82F, L82K, L82T, L82Y, L280I, T332V, V433K, V433N, and I593W.

TABLE 32

Two-Step cDNA Synthesis by MMLV-RT single mutants using
Oligo-dT priming. The data was generated via qPCR human
normalizer assay and data is reported by Ct value.

| MMLV-RT Variant | Ct Mean | Ct Standard Deviation |
|---|---|---|
| MMLV-II | 40.000 | 0.000 |
| MMLV-II I593A | 40.000 | 0.000 |
| MMLV-II I593C | 37.874 | 0.991 |
| MMLV-II I593D | 40.000 | 0.000 |
| MMLV-II I593E | 40.000 | 0.000 |
| MMLV-II I593F | 40.000 | 0.000 |
| MMLV-II I593G | 39.748 | 0.356 |

TABLE 32-continued

Two-Step cDNA Synthesis by MMLV-RT single mutants using
Oligo-dT priming. The data was generated via qPCR human
normalizer assay and data is reported by Ct value.

| MMLV-RT Variant | Ct Mean | Ct Standard Deviation |
|---|---|---|
| MMLV-II I593H | 39.502 | 0.704 |
| MMLV-II I593K | 40.000 | 0.000 |
| MMLV-II I593L | 38.994 | 1.423 |
| MMLV-II I593M | 39.383 | 0.873 |
| MMLV-II I593N | 40.000 | 0.000 |
| MMLV-II I593P | 40.000 | 0.000 |
| MMLV-II I593Q | 40.000 | 0.000 |
| MMLV-II I593R | 40.000 | 0.000 |
| MMLV-II I593S | 39.614 | 0.545 |
| MMLV-II I593T | 37.709 | 0.520 |
| MMLV-II I593V | 40.000 | 0.000 |
| MMLV-II I593W | 30.504 | 0.073 |
| MMLV-II I593Y | 40.000 | 0.000 |
| MMLV-II L280A | 40.000 | 0.000 |
| MMLV-II L280C | 40.000 | 0.000 |
| MMLV-II L280D | 40.000 | 0.000 |
| MMLV-II L280E | 40.000 | 0.000 |
| MMLV-II L280F | 40.000 | 0.000 |
| MMLV-II L280G | 40.000 | 0.000 |
| MMLV-II L280H | 40.000 | 0.000 |
| MMLV-II L280I | 30.951 | 0.076 |
| MMLV-II L280K | 40.000 | 0.000 |
| MMLV-II L280M | 40.000 | 0.000 |
| MMLV-II L280N | 39.727 | 0.386 |
| MMLV-II L280P | 40.000 | 0.000 |
| MMLV-II L280Q | 40.000 | 0.000 |
| MMLV-II L280R | 39.994 | 0.009 |
| MMLV-II L280S | 40.000 | 0.000 |
| MMLV-II L280T | 40.000 | 0.000 |

TABLE 32-continued

Two-Step cDNA Synthesis by MMLV-RT single mutants using Oligo-dT priming. The data was generated via qPCR human normalizer assay and data is reported by Ct value.

| MMLV-RT Variant | Ct Mean | Ct Standard Deviation |
|---|---|---|
| MMLV-II L280V | 37.749 | 0.142 |
| MMLV-II L280W | 40.000 | 0.000 |
| MMLV-II L280Y | 40.000 | 0.000 |
| MMLV-II L82A | 40.000 | 0.000 |
| MMLV-II L82C | 39.565 | 0.615 |
| MMLV-II L82D | 40.000 | 0.000 |
| MMLV-II L82E | 40.000 | 0.000 |
| MMLV-II L82F | 39.347 | 0.924 |
| MMLV-II L82G | 40.000 | 0.000 |
| MMLV-II L82H | 40.000 | 0.000 |
| MMLV-II L82I | 40.000 | 0.000 |
| MMLV-II L82K | 37.136 | 0.593 |
| MMLV-II L82M | 38.649 | 1.260 |
| MMLV-II L82N | 40.000 | 0.000 |
| MMLV-II L82P | 40.000 | 0.000 |
| MMLV-II L82Q | 39.098 | 1.275 |
| MMLV-II L82R | 40.000 | 0.000 |
| MMLV-II L82S | 39.346 | 0.925 |
| MMLV-II L82T | 38.695 | 1.845 |
| MMLV-II L82V | 38.047 | 1.381 |
| MMLV-II L82W | 37.151 | 0.308 |
| MMLV-II L82Y | 35.014 | 0.421 |
| MMLV-II Q299A | 40.000 | 0.000 |
| MMLV-II Q299C | 40.000 | 0.000 |
| MMLV-II Q299D | 40.000 | 0.000 |
| MMLV-II Q299E | 39.061 | 1.328 |
| MMLV-II Q299F | 40.000 | 0.000 |
| MMLV-II Q299G | 40.000 | 0.000 |
| MMLV-II Q299H | 39.398 | 0.852 |
| MMLV-II Q299I | 39.183 | 1.155 |
| MMLV-II Q299K | 40.000 | 0.000 |
| MMLV-II Q299L | 39.474 | 0.743 |
| MMLV-II Q299M | 40.000 | 0.000 |
| MMLV-II Q299N | 40.000 | 0.000 |
| MMLV-II Q299P | 40.000 | 0.000 |
| MMLV-II Q299R | 40.000 | 0.000 |
| MMLV-II Q299S | 40.000 | 0.000 |
| MMLV-II Q299T | 40.000 | 0.000 |
| MMLV-II Q299V | 40.000 | 0.000 |
| MMLV-II Q299W | 40.000 | 0.000 |
| MMLV-II Q299Y | 40.000 | 0.000 |
| MMLV-II T332A | 39.087 | 1.291 |
| MMLV-II T332C | 38.956 | 1.476 |
| MMLV-II T332D | 40.000 | 0.000 |
| MMLV-II T332E | 39.554 | 0.631 |
| MMLV-II T332F | 40.000 | 0.000 |
| MMLV-II T332G | 37.321 | 2.009 |
| MMLV-II T332H | 39.215 | 1.110 |
| MMLV-II T332I | 39.344 | 0.927 |
| MMLV-II T332K | 40.000 | 0.000 |
| MMLV-II T332L | 40.000 | 0.000 |
| MMLV-II T332M | 37.775 | 1.632 |
| MMLV-II T332N | 37.326 | 0.834 |
| MMLV-II T332P | 40.000 | 0.000 |
| MMLV-II T332Q | 39.509 | 0.694 |
| MMLV-II T332R | 39.588 | 0.582 |
| MMLV-II T332S | 39.765 | 0.332 |
| MMLV-II T332V | 36.977 | 0.384 |
| MMLV-II T332W | 40.000 | 0.000 |
| MMLV-II T332Y | 40.000 | 0.000 |
| MMLV-II V433A | 40.000 | 0.000 |
| MMLV-II V433C | 37.504 | 0.682 |
| MMLV-II V433D | 40.000 | 0.000 |
| MMLV-II V433E | 35.189 | 0.336 |
| MMLV-II V433F | 39.379 | 0.878 |
| MMLV-II V433G | 39.482 | 0.732 |
| MMLV-II V433H | 40.000 | 0.000 |
| MMLV-II V433I | 39.781 | 0.310 |
| MMLV-II V433K | 35.770 | 0.623 |
| MMLV-II V433L | 39.015 | 0.744 |
| MMLV-II V433M | 39.119 | 1.247 |
| MMLV-II V433N | 33.981 | 0.185 |
| MMLV-II V433P | 40.000 | 0.000 |

TABLE 32-continued

Two-Step cDNA Synthesis by MMLV-RT single mutants using Oligo-dT priming. The data was generated via qPCR human normalizer assay and data is reported by Ct value.

| MMLV-RT Variant | Ct Mean | Ct Standard Deviation |
|---|---|---|
| MMLV-II V433Q | 40.000 | 0.000 |
| MMLV-II V433R | 37.230 | 1.247 |
| MMLV-II V433S | 37.850 | 0.846 |
| MMLV-II V433T | 37.564 | 1.895 |
| MMLV-II V433W | 37.770 | 1.622 |
| MMLV-II V433Y | 40.000 | 0.000 |
| MMLV-IV | 26.102 | 0.033 |

TABLE 33

Two-Step cDNA Synthesis by MMLV-RT single mutants using random priming. The data was generated via qPCR human normalizer assay and data is reported by Ct value.

| MMLV-RT Variant | Ct Mean | Ct Standard Deviation |
|---|---|---|
| MMLV-II | 40.000 | 0.000 |
| MMLV-II I593A | 40.000 | 0.000 |
| MMLV-II I593C | 40.000 | 0.000 |
| MMLV-II I593D | 39.992 | 0.012 |
| MMLV-II I593E | 40.000 | 0.000 |
| MMLV-II I593F | 39.189 | 1.147 |
| MMLV-II I593G | 40.000 | 0.000 |
| MMLV-II I593H | 40.000 | 0.000 |
| MMLV-II I593K | 40.000 | 0.000 |
| MMLV-II I593L | 40.000 | 0.000 |
| MMLV-II I593M | 40.000 | 0.000 |
| MMLV-II I593N | 40.000 | 0.000 |
| MMLV-II I593P | 40.000 | 0.000 |
| MMLV-II I593Q | 39.201 | 0.853 |
| MMLV-II I593R | 38.928 | 1.516 |
| MMLV-II I593S | 39.025 | 1.379 |
| MMLV-II I593T | 38.385 | 1.227 |
| MMLV-II I593V | 39.574 | 0.603 |
| MMLV-II I593W | 32.572 | 0.054 |
| MMLV-II I593Y | 40.000 | 0.000 |
| MMLV-II L280A | 40.000 | 0.000 |
| MMLV-II L280C | 40.000 | 0.000 |
| MMLV-II L280D | 40.000 | 0.000 |
| MMLV-II L280E | 40.000 | 0.000 |
| MMLV-II L280F | 40.000 | 0.000 |
| MMLV-II L280G | 40.000 | 0.000 |
| MMLV-II L280H | 40.000 | 0.000 |
| MMLV-II L280I | 34.152 | 0.276 |
| MMLV-II L280K | 40.000 | 0.000 |
| MMLV-II L280M | 39.973 | 0.038 |
| MMLV-II L280N | 40.000 | 0.000 |
| MMLV-II L280P | 40.000 | 0.000 |
| MMLV-II L280Q | 40.000 | 0.000 |
| MMLV-II L280R | 40.000 | 0.000 |
| MMLV-II L280S | 40.000 | 0.000 |
| MMLV-II L280T | 40.000 | 0.000 |
| MMLV-II L280V | 39.260 | 1.046 |
| MMLV-II L280W | 40.000 | 0.000 |
| MMLV-II L280Y | 40.000 | 0.000 |
| MMLV-II L82A | 40.000 | 0.000 |
| MMLV-II L82C | 40.000 | 0.000 |
| MMLV-II L82D | 40.000 | 0.000 |
| MMLV-II L82E | 39.672 | 0.463 |
| MMLV-II L82F | 36.854 | 0.708 |
| MMLV-II L82G | 40.000 | 0.000 |
| MMLV-II L82H | 37.705 | 0.557 |
| MMLV-II L82I | 39.231 | 1.087 |
| MMLV-II L82K | 39.437 | 0.443 |
| MMLV-II L82M | 40.000 | 0.000 |
| MMLV-II L82N | 40.000 | 0.000 |
| MMLV-II L82P | 40.000 | 0.000 |
| MMLV-II L82Q | 40.000 | 0.000 |
| MMLV-II L82R | 38.595 | 1.191 |

TABLE 33-continued

Two-Step cDNA Synthesis by MMLV-RT single mutants using random priming. The data was generated via qPCR human normalizer assay and data is reported By Ct value.

| MMLV-RT Variant | Ct Mean | Ct Standard Deviation |
|---|---|---|
| MMLV-II L82S | 40.000 | 0.000 |
| MMLV-II L82T | 38.449 | 1.192 |
| MMLV-II L82V | 39.438 | 0.795 |
| MMLV-II L82W | 39.178 | 1.163 |
| MMLV-II L82Y | 36.758 | 0.962 |
| MMLV-II Q299A | 40.000 | 0.000 |
| MMLV-II Q299C | 40.000 | 0.000 |
| MMLV-II Q299D | 38.003 | 1.414 |
| MMLV-II Q299E | 39.338 | 0.936 |
| MMLV-II Q299F | 40.000 | 0.000 |
| MMLV-II Q299G | 40.000 | 0.000 |
| MMLV-II Q299H | 40.000 | 0.000 |
| MMLV-II Q299I | 39.850 | 0.212 |
| MMLV-II Q299K | 40.000 | 0.000 |
| MMLV-II Q299L | 40.000 | 0.000 |
| MMLV-II Q299M | 40.000 | 0.000 |
| MMLV-II Q299N | 40.000 | 0.000 |
| MMLV-II Q299P | 40.000 | 0.000 |
| MMLV-II Q299R | 40.000 | 0.000 |
| MMLV-II Q299S | 40.000 | 0.000 |
| MMLV-II Q299T | 40.000 | 0.000 |
| MMLV-II Q299V | 40.000 | 0.000 |
| MMLV-II Q299W | 40.000 | 0.000 |
| MMLV-II Q299Y | 40.000 | 0.000 |
| MMLV-II T332A | 39.814 | 0.264 |
| MMLV-II T332C | 40.000 | 0.000 |
| MMLV-II T332D | 40.000 | 0.000 |
| MMLV-II T332E | 40.000 | 0.000 |
| MMLV-II T332F | 40.000 | 0.000 |
| MMLV-II T332G | 38.897 | 1.560 |
| MMLV-II T332H | 40.000 | 0.000 |
| MMLV-II T332I | 40.000 | 0.000 |
| MMLV-II T332K | 40.000 | 0.000 |
| MMLV-II T332L | 38.169 | 2.589 |
| MMLV-II T332M | 37.410 | 1.906 |
| MMLV-II T332N | 38.983 | 1.362 |
| MMLV-II T332P | 39.046 | 1.350 |
| MMLV-II T332Q | 40.000 | 0.000 |
| MMLV-II T332R | 40.000 | 0.000 |
| MMLV-II T332S | 40.000 | 0.000 |
| MMLV-II T332V | 38.650 | 1.326 |
| MMLV-II T332W | 40.000 | 0.000 |
| MMLV-II T332Y | 40.000 | 0.000 |
| MMLV-II V433A | 40.000 | 0.000 |
| MMLV-II V433C | 37.605 | 0.184 |
| MMLV-II V433D | 40.000 | 0.000 |
| MMLV-II V433E | 34.693 | 0.193 |
| MMLV-II V433F | 40.000 | 0.000 |
| MMLV-II V433G | 40.000 | 0.000 |
| MMLV-II V433H | 40.000 | 0.000 |
| MMLV-II V433I | 39.792 | 0.294 |
| MMLV-II V433K | 35.725 | 0.464 |
| MMLV-II V433L | 40.000 | 0.000 |
| MMLV-II V433M | 40.000 | 0.000 |
| MMLV-II V433N | 34.604 | 0.554 |
| MMLV-II V433P | 40.000 | 0.000 |
| MMLV-II V433Q | 38.844 | 1.001 |
| MMLV-II V433R | 38.817 | 0.839 |
| MMLV-II V433S | 38.202 | 1.372 |
| MMLV-II V433T | 37.573 | 0.623 |
| MMLV-II V433W | 37.611 | 1.690 |
| MMLV-II V433Y | 40.000 | 0.000 |
| MMLV-IV | 26.053 | 0.098 |

TABLE 34

One-Step cDNA Synthesis by MMLV-RT single mutants by gene specific priming. The data was generated via qPCR human normalizer assay and data is reported by Ct value.

| MMLV-RT Variant | Ct Mean | Ct Standard Deviation |
|---|---|---|
| MMLV-II | 32.775 | 0.189 |
| MMLV-II I593A | 32.438 | 0.209 |
| MMLV-II I593C | 32.680 | 0.053 |
| MMLV-II I593D | 31.775 | 0.237 |
| MMLV-II I593E | 30.635 | 0.048 |
| MMLV-II I593F | 30.411 | 0.008 |
| MMLV-II I593G | 30.904 | 0.098 |
| MMLV-II I593H | 29.686 | 0.131 |
| MMLV-II I593K | 31.832 | 0.259 |
| MMLV-II I593L | 32.289 | 0.273 |
| MMLV-II I593M | 32.162 | 0.078 |
| MMLV-II I593N | 31.410 | 0.251 |
| MMLV-II I593P | 34.728 | 0.201 |
| MMLV-II I593Q | 31.609 | 0.032 |
| MMLV-II I593R | 31.144 | 0.133 |
| MMLV-II I593S | 30.548 | 0.247 |
| MMLV-II I593T | 29.572 | 0.236 |
| MMLV-II I593V | 30.673 | 0.142 |
| MMLV-II I593W | 28.179 | 0.092 |
| MMLV-II I593Y | 30.858 | 0.067 |
| MMLV-II L280A | 36.160 | 0.729 |
| MMLV-II L280C | 32.097 | 0.261 |
| MMLV-II L280D | 40.000 | 0.000 |
| MMLV-II L280E | 39.115 | 1.251 |
| MMLV-II L280F | 34.573 | 0.371 |
| MMLV-II L280G | 40.000 | 0.000 |
| MMLV-II L280H | 37.255 | 0.322 |
| MMLV-II L280I | 29.267 | 1.032 |
| MMLV-II L280K | 34.274 | 0.095 |
| MMLV-II L280M | 32.746 | 0.223 |
| MMLV-II L280N | 39.677 | 0.457 |
| MMLV-II L280P | 33.045 | 0.095 |
| MMLV-II L280Q | 39.190 | 1.145 |
| MMLV-II L280R | 40.000 | 0.000 |
| MMLV-II L280S | 40.000 | 0.000 |
| MMLV-II L280T | 37.074 | 0.325 |
| MMLV-II L280V | 30.461 | 0.052 |
| MMLV-II L280W | 40.000 | 0.000 |
| MMLV-II L280Y | 40.000 | 0.000 |
| MMLV-II L82A | 31.729 | 0.308 |
| MMLV-II L82C | 31.131 | 0.192 |
| MMLV-II L82D | 34.280 | 0.227 |
| MMLV-II L82E | 32.973 | 0.430 |
| MMLV-II L82F | 29.760 | 0.030 |
| MMLV-II L82G | 33.066 | 0.217 |
| MMLV-II L82H | 30.098 | 0.078 |
| MMLV-II L82I | 31.605 | 0.083 |
| MMLV-II L82K | 29.258 | 0.015 |
| MMLV-II L82M | 30.280 | 0.027 |
| MMLV-II L82N | 33.074 | 0.323 |
| MMLV-II L82P | 38.754 | 1.762 |
| MMLV-II L82Q | 32.001 | 0.164 |
| MMLV-II L82R | 30.208 | 0.128 |
| MMLV-II L82S | 31.841 | 0.231 |
| MMLV-II L82T | 28.908 | 0.044 |
| MMLV-II L82V | 29.533 | 0.057 |
| MMLV-II L82W | 29.580 | 0.056 |
| MMLV-II L82Y | 28.934 | 0.073 |
| MMLV-II Q299A | 31.113 | 0.138 |
| MMLV-II Q299C | 35.953 | 0.542 |
| MMLV-II Q299D | 32.292 | 0.080 |
| MMLV-II Q299E | 31.663 | 0.027 |
| MMLV-II Q299F | 36.143 | 0.317 |
| MMLV-II Q299G | 31.929 | 0.131 |
| MMLV-II Q299H | 32.387 | 0.133 |
| MMLV-II Q299I | 37.763 | 1.582 |
| MMLV-II Q299K | 32.326 | 0.096 |
| MMLV-II Q299L | 34.807 | 0.180 |
| MMLV-II Q299M | 32.514 | 0.375 |
| MMLV-II Q299N | 34.040 | 0.186 |
| MMLV-II Q299P | 39.460 | 0.764 |
| MMLV-II Q299R | 33.044 | 0.354 |
| MMLV-II Q299S | 33.438 | 0.256 |

TABLE 34-continued

One-Step cDNA Synthesis by MMLV-RT single mutants by gene
specific priming. The data was generated via qPCR human
normalizer assay and data is reported by Ct value.

| MMLV-RT Variant | Ct Mean | Ct Standard Deviation |
|---|---|---|
| MMLV-II Q299T | 35.093 | 0.926 |
| MMLV-II Q299V | 35.114 | 1.045 |
| MMLV-II Q299W | 38.998 | 1.417 |
| MMLV-II Q299Y | 39.055 | 1.336 |
| MMLV-II T332A | 30.528 | 0.084 |
| MMLV-II T332C | 30.785 | 0.135 |
| MMLV-II T332D | 33.310 | 0.348 |
| MMLV-II T332E | 32.711 | 0.106 |
| MMLV-II T332F | 33.201 | 0.179 |
| MMLV-II T332G | 30.424 | 0.054 |
| MMLV-II T332H | 31.913 | 0.306 |
| MMLV-II T332I | 32.072 | 0.115 |
| MMLV-II T332K | 31.591 | 0.082 |
| MMLV-II T332L | 34.011 | 0.133 |
| MMLV-II T332M | 29.039 | 0.164 |
| MMLV-II T332N | 29.500 | 0.135 |
| MMLV-II T332P | 33.976 | 0.272 |
| MMLV-II T332Q | 31.599 | 0.041 |
| MMLV-II T332R | 32.950 | 0.130 |
| MMLV-II T332S | 31.003 | 0.341 |
| MMLV-II T332V | 29.835 | 0.061 |
| MMLV-II T332W | 35.431 | 0.099 |
| MMLV-II T332Y | 33.384 | 0.164 |
| MMLV-II V433A | 30.757 | 0.105 |
| MMLV-II V433C | 29.901 | 0.305 |
| MMLV-II V433D | 34.152 | 0.170 |
| MMLV-II V433E | 28.868 | 0.011 |
| MMLV-II V433F | 31.529 | 0.009 |
| MMLV-II V433G | 33.663 | 0.412 |
| MMLV-II V433H | 31.811 | 0.069 |
| MMLV-II V433I | 30.460 | 0.071 |
| MMLV-II V433K | 30.040 | 0.109 |
| MMLV-II V433L | 31.758 | 0.063 |
| MMLV-II V433M | 30.791 | 0.095 |
| MMLV-II V433N | 28.566 | 0.074 |
| MMLV-II V433P | 37.436 | 1.824 |
| MMLV-II V433Q | 30.586 | 0.104 |
| MMLV-II V433R | 30.773 | 0.080 |
| MMLV-II V433S | 29.768 | 0.074 |
| MMLV-II V433T | 29.096 | 0.107 |
| MMLV-II V433W | 29.130 | 0.064 |
| MMLV-II V433Y | 32.676 | 0.279 |
| MMLV-IV | 25.979 | 0.043 |

TABLE 35

Two-Step cDNA Synthesis by MMLV-RT stacked mutants using
oligo dT priming. The data was generated via qPCR human
normalizer assay and data is reported by Ct value.

| MMLV-RT Variant | Temperature (° C.) | Ct Mean | Ct Standard Deviation |
|---|---|---|---|
| MMLV-II | 42 | 25.207 | 0.025 |
| MMLV-II | 55 | 28.180 | 0.022 |
| MMLV-II | 42 | 25.287 | 0.068 |
| Q68R/Q79R/L99R/E282D | 55 | 26.442 | 0.044 |
| MMLV-II | 42 | 25.344 | 0.065 |
| Q68R/Q79R/L99R/E282D/V433R | 55 | 26.586 | 0.077 |
| MMLV-II | 42 | 25.266 | 0.112 |
| Q68R/Q79R/L99R/E282D/I593E | 55 | 27.389 | 0.069 |
| MMLV-II | 42 | 25.357 | 0.087 |
| Q68R/Q79R/L99R/E282D/Q299E | 55 | 26.953 | 0.034 |
| MMLV-II | 42 | 25.394 | 0.011 |
| Q68R/Q79R/L82R/L99R/E282D | 55 | 27.171 | 0.028 |
| MMLV-II | 42 | 25.371 | 0.061 |
| Q68R/Q79R/L99R/E282D/Q299E/I593E | 55 | 26.689 | 0.068 |
| MMLV-II | 42 | 25.258 | 0.035 |
| Q68R/Q79R/L82R/L99R/E282D/Q299E/I593E | 55 | 26.979 | 0.034 |
| MMLV-II | 42 | 25.171 | 0.006 |
| Q68R/Q79R/L99R/E282D/Q299E/V433R/I593E | 55 | 26.299 | 0.025 |
| MMLV-II | 42 | 25.146 | 0.052 |
| Q68R/Q79R/L82R/L99R/E282D/Q299E/V433R/I593E | 55 | 26.320 | 0.036 |
| MMLV-II | 42 | 25.176 | 0.044 |
| Q68R/Q79R/L82R/L99R/E282D/Q299E/T332E/I593E | 55 | 26.750 | 0.040 |
| MMLV-II | 42 | 25.110 | 0.046 |
| Q68R/Q79R/L82R/L99R/E282D/Q299E/T332E/V433R/I593E | 55 | 26.587 | 0.049 |
| MMLV-IV | 42 | 25.184 | 0.025 |
| MMLV-IV | 55 | 25.153 | 0.037 |
| SuperScript-IV | 42 | 25.082 | 0.073 |
| SuperScript-IV | 55 | 25.080 | 0.047 |

TABLE 36

Two-Step cDNA Synthesis by MMLV-RT stacked mutants using random priming. The data
was generated via qPCR human normalizer assay and data is reported by Ct value.

| MMLV-RT Variant | Temperature (C) | Ct Mean | Ct Standard Deviation |
|---|---|---|---|
| MMLV-II | 42 | 25.264 | 0.019 |
| MMLV-II | 55 | 28.443 | 0.014 |
| MMLV-II Q68R/Q79R/L99R/E282D | 42 | 25.399 | 0.040 |
|  | 55 | 26.484 | 0.072 |
| MMLV-II Q68R/Q79R/L99R/E282D/V433R | 42 | 25.324 | 0.063 |
|  | 55 | 26.794 | 0.065 |
| MMLV-II Q68R/Q79R/L99R/E282D/I593E | 42 | 25.278 | 0.025 |
|  | 55 | 27.616 | 0.058 |
| MMLV-II Q68R/Q79R/L99R/E282D/Q299E | 42 | 25.281 | 0.079 |
|  | 55 | 27.148 | 0.025 |
| MMLV-II Q68R/Q79R/L82R/L99R/E282D | 42 | 25.279 | 0.053 |
|  | 55 | 27.243 | 0.008 |
| MMLV-II Q68R/Q79R/L99R/E282D/Q299E/I593E | 42 | 25.409 | 0.065 |
|  | 55 | 26.704 | 0.066 |
| MMLV-II Q68R/Q79R/L82R/L99R/E282D/Q299E/I593E | 42 | 25.581 | 0.062 |
|  | 55 | 26.605 | 0.028 |
| MMLV-II Q68R/Q79R/L99R/E282D/Q299E/V433R/I593E | 42 | 25.355 | 0.158 |
|  | 55 | 26.305 | 0.066 |

TABLE 36-continued

Two-Step cDNA Synthesis by MMLV-RT stacked mutants using random priming. The data
was generated via qPCR human normalizer assay and data is reported by Ct value.

| MMLV-RT Variant | Temperature (C) | Ct Mean | Ct Standard Deviation |
|---|---|---|---|
| MMLV-II | 42 | 25.418 | 0.120 |
| Q68R/Q79R/L82R/L99R/E282D/Q299E/V433R/I593E | 55 | 26.403 | 0.055 |
| MMLV-II | 42 | 25.374 | 0.115 |
| Q68R/Q79R/L82R/L99R/E282D/Q299E/T332E/I593E | 55 | 26.747 | 0.065 |
| MMLV-II | 42 | 25.426 | 0.082 |
| Q68R/Q79R/L82R/L99R/E282D/Q299E/T332E/V433R/I593E | 55 | 26.481 | 0.017 |
| MMLV-IV | 42 | 25.394 | 0.162 |
| MMLV-IV | 55 | 25.185 | 0.022 |
| SuperScript-IV | 42 | 25.299 | 0.132 |
| SuperScript-IV | 55 | 25.214 | 0.021 |

TABLE 37

One-Step cDNA Synthesis by MMLV-RT stacked mutants by gene
specific priming. The data was generated via qPCR human
normalizer assay and data is reported by Ct value.

| MMLV-RT Variant | Temperature (° C.) | Concentration of RT (nM) | Ct Mean | Ct Standard Deviation |
|---|---|---|---|---|
| MMLV-II | 50 | 0.28 | 26.401 | 0.022 |
| | | 1.4 | 24.701 | 0.061 |
| | | 7.0 | 24.664 | 0.007 |
| | 60 | 0.28 | 31.134 | 0.205 |
| | | 1.4 | 28.109 | 0.042 |
| | | 7.0 | 27.644 | 0.061 |
| MMLV-II Q68R/Q79R/L99R/ E282D | 50 | 0.28 | 25.171 | 0.046 |
| | | 1.4 | 24.440 | 0.037 |
| | | 7.0 | 24.406 | 0.010 |
| | 60 | 0.28 | 28.848 | 0.114 |
| | | 1.4 | 25.905 | 0.066 |
| | | 7.0 | 25.618 | 0.057 |
| MMLV-II Q68R/Q79R/L99R/ E282D/V433R | 50 | 0.28 | 24.967 | 0.068 |
| | | 1.4 | 24.386 | 0.015 |
| | | 7.0 | 24.433 | 0.079 |
| | 60 | 0.28 | 28.516 | 0.051 |
| | | 1.4 | 25.803 | 0.063 |
| | | 7.0 | 25.620 | 0.035 |
| MMLV-II Q68R/Q79R/L99R/ E282D/I593E | 50 | 0.28 | 24.660 | 0.053 |
| | | 1.4 | 24.377 | 0.028 |
| | | 7.0 | 24.355 | 0.021 |
| | 60 | 0.28 | 27.488 | 0.074 |
| | | 1.4 | 25.413 | 0.049 |
| | | 7.0 | 25.209 | 0.136 |
| MMLV-II Q68R/Q79R/L99R/ E282D/Q299E | 50 | 0.28 | 25.044 | 0.094 |
| | | 1.4 | 24.422 | 0.023 |
| | | 7.0 | 24.528 | 0.055 |
| | 60 | 0.28 | 28.818 | 0.137 |
| | | 1.4 | 25.953 | 0.082 |
| | | 7.0 | 25.754 | 0.098 |
| MMLV-II Q68R/Q79R/L82R/ L99R/E282D | 50 | 0.28 | 25.014 | 0.152 |
| | | 1.4 | 24.467 | 0.020 |
| | | 7.0 | 24.507 | 0.046 |
| | 60 | 0.28 | 28.743 | 0.076 |
| | | 1.4 | 26.662 | 0.012 |
| | | 7.0 | 25.883 | 0.022 |
| MMLV-II Q68R/Q79R/L99R/ E282D/Q299E/I593E | 50 | 0.28 | 24.771 | 0.027 |
| | | 1.4 | 24.501 | 0.008 |
| | | 7.0 | 24.485 | 0.087 |
| | 60 | 0.28 | 27.721 | 0.057 |
| | | 1.4 | 25.836 | 0.030 |
| | | 7.0 | 25.199 | 0.016 |
| MMLV-II Q68R/Q79R/L82R/ L99R/E282D/Q299E/ I593E | 50 | 0.28 | 24.777 | 0.029 |
| | | 1.4 | 24.432 | 0.033 |
| | | 7.0 | 24.435 | 0.024 |
| | 60 | 0.28 | 27.854 | 0.035 |
| | | 1.4 | 25.613 | 0.028 |
| | | 7.0 | 25.072 | 0.030 |
| MMLV-II Q68R/Q79R/L99R/ | 50 | 0.28 | 24.550 | 0.003 |
| | | 1.4 | 24.333 | 0.033 |

TABLE 37-continued

One-Step cDNA Synthesis by MMLV-RT stacked mutants by gene
specific priming. The data was generated via qPCR human
normalizer assay and data is reported by Ct value.

| MMLV-RT Variant | Temperature (° C.) | Concentration of RT (nM) | Ct Mean | Ct Standard Deviation |
|---|---|---|---|---|
| E282D/Q299E/V433R/ | | 7.0 | 24.345 | 0.030 |
| I593E | 60 | 0.28 | 26.399 | 0.051 |
| | | 1.4 | 25.236 | 0.040 |
| | | 7.0 | 25.105 | 0.050 |
| MMLV-II | 50 | 0.28 | 24.562 | 0.047 |
| Q68R/Q79R/L82R/ | | 1.4 | 24.350 | 0.039 |
| L99R/E282D/Q299E/ | | 7.0 | 24.302 | 0.015 |
| V433R/I593E | 60 | 0.28 | 26.459 | 0.022 |
| | | 1.4 | 25.247 | 0.069 |
| | | 7.0 | 25.001 | 0.050 |
| MMLV-II | 50 | 0.28 | 24.614 | 0.047 |
| Q68R/Q79R/L82R/ | | 1.4 | 24.420 | 0.051 |
| L99R/E282D/Q299E/ | | 7.0 | 24.361 | 0.021 |
| T332E/I593E | 60 | 0.28 | 26.769 | 0.089 |
| | | 1.4 | 25.609 | 0.041 |
| | | 7.0 | 25.348 | 0.043 |
| MMLV-II | 50 | 0.28 | 24.594 | 0.075 |
| Q68R/Q79R/L82R/ | | 1.4 | 24.402 | 0.045 |
| L99R/E282D/Q299E/ | | 7.0 | 24.291 | 0.057 |
| T332E/V433R/I593E | 60 | 0.28 | 26.591 | 0.018 |
| | | 1.4 | 25.517 | 0.048 |
| | | 7.0 | 25.193 | 0.027 |
| MMLV-IV | 50 | 0.28 | 24.397 | 0.091 |
| | | 1.4 | 24.303 | 0.062 |
| | | 7.0 | 24.189 | 0.039 |
| | 60 | 0.28 | 25.807 | 0.045 |
| | | 1.4 | 25.180 | 0.037 |
| | | 7.0 | 24.625 | 0.011 |
| SuperScript-IV | 50 | 0.28 | 24.743 | 0.049 |
| | | 1.4 | 24.213 | 0.017 |
| | | 7.0 | 24.008 | 0.036 |
| | 60 | 0.28 | 26.124 | 0.103 |
| | | 1.4 | 24.681 | 0.070 |
| | | 7.0 | 24.180 | 0.082 |

TABLE 38

Sequences of quadruple or more mutant MMLV RTase variants.

| SEQ ID NO: | Construct | Construct Sequence (AA) |
|---|---|---|
| 686 | MMLV-II Q68R/Q79R/ L99R/E282D/ V433R | TLNIEDEHRLHETSKEPDVSLGSTWLSDFPQAWAE TGGMGLAVRQAPLIIPLKATSTPVSIKQYPMSREA RLGIKPHIRRLLDQGILVPCQSPWNTPLRPVKKPG TNDYRPVQDLREVNKRVEDIHPTVPNPYNLLSGLP PSHQWYTVLDLKDAFFCLRLHPTSQPLFAFEWRDP EMGISGQLTWTRLPQGFKNSPTLFDEALHRDLADF RIQHPDLILLQYVDDLLLAATSELDCQQGTRALLQ TLGNLGYRASAKKAQICQKQVKYLGYLLKEGQRWL TDARKETVMGQPTPKTPRQLREFLGTAGFCRLWIP GFAEMAAPLYPLTKTGTLFNWGPDQQKAYQEIKQA LLTAPALGLPDLTKPFELFVDEKQGYAKGVLTQKL GPWRRPVAYLSKKLDPVAAGWPPCLRMVAAIAVLT KDAGKLTMGQPLRILAPHAVEALVKQPPDRWLSNA RMTHYQALLLDTDRVQFGPVVALNPATLLPLPEEG LQHNCLDILAEAHGTRPDLTDQPLPDADHTWYTGG SSLLQEGQRKAGAAVTTETEVIWAKALPAGTSAQR AQLIALTQALKMAEGKKLNVYTNSRYAFATAHIHG EIYRRRGLLTSEGKEIKNKDEILALLKALFLPKRL SIIHCPGHQKGHSAEARGNRMADQAARKAAITETP DTSTLLIENSSPYTSEHF |
| 687 | MMLV-II Q68R/Q79R/ L99R/E282D/ I593E | TLNIEDEHRLHETSKEPDVSLGSTWLSDFPQAWAE TGGMGLAVRQAPLIIPLKATSTPVSIKQYPMSREA RLGIKPHIRRLLDQGILVPCQSPWNTPLRPVKKPG TNDYRPVQDLREVNKRVEDIHPTVPNPYNLLSGLP PSHQWYTVLDLKDAFFCLRLHPTSQPLFAFEWRDP EMGISGQLTWTRLPQGFKNSPTLFDEALHRDLADF RIQHPDLILLQYVDDLLLAATSELDCQQGTRALLQ TLGNLGYRASAKKAQICQKQVKYLGYLLKEGQRWL |

TABLE 38-continued

Sequences of quadruple or more mutant MMLV RTase variants.

| SEQ ID NO:Construct | | Construct Sequence (AA) |
|---|---|---|
| | | TDARKETVMGQPTPKTPRQLREFLGTAGFCRLWIP |
| | | GFAEMAAPLYPLTKTGTLFNWGPDQQKAYQEIKQA |
| | | LLTAPALGLPDLTKPFELFVDEKQGYAKGVLTQKL |
| | | GPWRRPVAYLSKKLDPVAAGWPPCLRMVAAIAVLT |
| | | KDAGKLTMGQPLVILAPHAVEALVKQPPDRWLSNA |
| | | RMTHYQALLLDTDRVQFGPVVALNPATLLPLPEEG |
| | | LQHNCLDILAEAHGTRPDLTDQPLPDADHTWYTGG |
| | | SSLLQEGQRKAGAAVTTETEVIWAKALPAGTSAQR |
| | | AQLIALTQALKMAEGKKLNVYINSRYAFATAHEHG |
| | | EIYRRRGLLTSEGKEIKNKDEILALLKALFLPKRL |
| | | SIIHCPGHQKGHSAEARGNRMADQAARKAAITETP |
| | | DTSTLLIENSSPYTSEHF |
| 688 | MMLV-II Q68R/Q79R/ L99R/E282D/ Q299E | TLNIEDEHRLHETSKEPDVSLGSTWLSDFPQAWAE |
| | | TGGMGLAVRQAPLIIPLKATSTPVSIKQYPMSREA |
| | | RLGIKPHIRRLLDQGILVPCQSPWNTPLRPVKKPG |
| | | TNDYRPVQDLREVNKRVEDIHPTVPNPYNLLSGLP |
| | | PSHQWYTVLDLKDAFFCLRLHPTSQPLFAFEWRDP |
| | | EMGISGQLTWTRLPQGFKNSPTLFDEALHRDLADF |
| | | RIQHPDLILLQYVDDLLLAATSELDCQQGTRALLQ |
| | | TLGNLGYRASAKKAQICQKQVKYLGYLLKEGQRWL |
| | | TDARKETVMGQPTPKTPRELREFLGTAGFCRLWIP |
| | | GFAEMAAPLYPLTKTGTLFNWGPDQQKAYQEIKQA |
| | | LLTAPALGLPDLTKPFELFVDEKQGYAKGVLTQKL |
| | | GPWRRPVAYLSKKLDPVAAGWPPCLRMVAAIAVLT |
| | | KDAGKLTMGQPLVILAPHAVEALVKQPPDRWLSNA |
| | | RMTHYQALLLDTDRVQFGPVVALNPATLLPLPEEG |
| | | LQHNCLDILAEAHGTRPDLTDQPLPDADHTWYTGG |
| | | SSLLQEGQRKAGAAVTTETEVIWAKALPAGTSAQR |
| | | AQLIALTQALKMAEGKKLNVYINSRYAFATAHIHG |
| | | EIYRRRGLLTSEGKEIKNKDEILALLKALFLPKRL |
| | | SIIHCPGHQKGHSAEARGNRMADQAARKAAITETP |
| | | DTSTLLIENSSPYTSEHF |
| 689 | MMLV-II Q68R/Q79R/ L99R/E282D/ T332E | TLNIEDEHRLHETSKEPDVSLGSTWLSDFPQAWAE |
| | | TGGMGLAVRQAPLIIPLKATSTPVSIKQYPMSREA |
| | | RLGIKPHIRRLLDQGILVPCQSPWNTPLRPVKKPG |
| | | TNDYRPVQDLREVNKRVEDIHPTVPNPYNLLSGLP |
| | | PSHQWYTVLDLKDAFFCLRLHPTSQPLFAFEWRDP |
| | | EMGISGQLTWTRLPQGFKNSPTLFDEALHRDLADF |
| | | RIQHPDLILLQYVDDLLLAATSELDCQQGTRALLQ |
| | | TLGNLGYRASAKKAQICQKQVKYLGYLLKEGQRWL |
| | | TDARKETVMGQPTPKTPRQLREFLGTAGFCRLWIP |
| | | GFAEMAAPLYPLTKTGELFNWGPDQQKAYQEIKQA |
| | | LLTAPALGLPDLTKPFELFVDEKQGYAKGVLTQKL |
| | | GPWRRPVAYLSKKLDPVAAGWPPCLRMVAAIAVLT |
| | | KDAGKLTMGQPLVILAPHAVEALVKQPPDRWLSNA |
| | | RMTHYQALLLDTDRVQFGPVVALNPATLLPLPEEG |
| | | LQHNCLDILAEAHGTRPDLTDQPLPDADHTWYTGG |
| | | SSLLQEGQRKAGAAVTTETEVIWAKALPAGTSAQR |
| | | AQLIALTQALKMAEGKKLNVYTNSRYAFATAHIHG |
| | | EIYRRRGLLTSEGKEIKNKDEILALLKALFLPKRL |
| | | SIIHCPGHQKGHSAEARGNRMADQAARKAAITETP |
| | | DTSTLLIENSSPYTSEHF |
| 690 | MMLV-II Q68I/Q79I/ L99R/L280R | TLNIEDEHRLHETSKEPDVSLGSTWLSDFPQAWAE |
| | | TGGMGLAVRQAPLIIPLKATSTPVSIKQYPMSREA |
| | | RLGIKPHIRRLLDQGILVPCQSPWNTPLRPVKKPG |
| | | TNDYRPVQDLREVNKRVEDIHPTVPNPYNLLSGLP |
| | | PSHQWYTVLDLKDAFFCLRLHPTSQPLFAFEWRDP |
| | | EMGISGQLTWTRLPQGFKNSPTLFDEALHRDLADF |
| | | RIQHPDLILLQYVDDLLLAATSELDCQQGTRALLQ |
| | | TLGNLGYRASAKKAQICQKQVKYLGYLLKEGQRWR |
| | | TEARKETVMGQPTPKTPRQLREFLGTAGFCRLWIP |
| | | GFAEMAAPLYPLTKTGTLFNWGPDQQKAYQEIKQA |
| | | LLTAPALGLPDLTKPFELFVDEKQGYAKGVLTQKL |
| | | GPWRRPVAYLSKKLDPVAAGWPPCLRMVAAIAVLT |
| | | KDAGKLTMGQPLVILAPHAVEALVKQPPDRWLSNA |
| | | RMTHYQALLLDTDRVQFGPVVALNPATLLPLPEEG |
| | | LQHNCLDILAEAHGTRPDLTDQPLPDADHTWYTGG |
| | | SSLLQEGQRKAGAAVTTETEVIWAKALPAGTSAQR |
| | | AQLIALTQALKMAEGKKLNVYTNSRYAFATAHIHG |
| | | EIYRRRGLLTSEGKEIKNKDEILALLKALFLPKRL |
| | | SIIHCPGHQKGHSAEARGNRMADQAARKAAITETP |
| | | DTSTLLIENSSPYTSEHF |

TABLE 38-continued

Sequences of quadruple or more mutant MMLV RTase variants.

| SEQ ID NO:Construct | | Construct Sequence (AA) |
|---|---|---|
| 691 | MMLV-II Q68R/Q79R/ L99R/L280R/ E282D | TLNIEDEHRLHETSKEPDVSLGSTWLSDFPQAWAE TGGMGLAVRQAPLIIPLKATSTPVSIKQYPMSREA RLGIKPHIRRLLDQGILVPCQSPWNTPLRPVKKPG TNDYRPVQDLREVNKRVEDIHPTVPNPYNLLSGLP PSHQWYTVLDLKDAFFCLRLHPTSQPLFAFEWRDP EMGISGQLTWTRLPQGFKNSPTLFDEALHRDLADF RIQHPDLILLQYVDDLLLAATSELDCQQGTRALLQ TLGNLGYRASAKKAQICQKQVKYLGYLLKEGQRWR TDARKETVMGQPTPKTPRQLREFLGTAGFCRLWIP GFAEMAAPLYPLTKTGTLFNWGPDQQKAYQEIKQA LLTAPALGLPDLTKPFELFVDEKQGYAKGVLTQKL GPWRRPVAYLSKKLDPVAAGWPPCLRMVAAIAVLT KDAGKLTMGQPLVILAPHAVEALVKQPPDRWLSNA RMTHYQALLLDTDRVQFGPVVALNPATLLPLPEEG LQHNCLDILAEAHGTRPDLTDQPLPDADHTWYTGG SSLLQEGQRKAGAAVTTETEVIWAKALPAGTSAQR AQLIALTQALKMAEGKKLNVYTNSRYAFATAHIHG EIYRRRGLLTSEGKEIKNKDEILALLKALFLPKRL SIIHCPGHQKGHSAEARGNRMADQAARKAAITETP DTSTLLIENSSPYTSEHF |
| 692 | MMLV-II Q68R/L82R/ L99R/E282D | TLNIEDEHRLHETSKEPDVSLGSTWLSDFPQAWAE TGGMGLAVRQAPLIIPLKATSTPVSIKQYPMSREA RLGIKPHIQRLRDQGILVPCQSPWNTPLRPVKKPG TNDYRPVQDLREVNKRVEDIHPTVPNPYNLLSGLP PSHQWYTVLDLKDAFFCLRLHPTSQPLFAFEWRDP EMGISGQLTWTRLPQGFKNSPTLFDEALHRDLADF RIQHPDLILLQYVDDLLLAATSELDCQQGTRALLQ TLGNLGYRASAKKAQICQKQVKYLGYLLKEGQRWL TDARKETVMGQPTPKTPRQLREFLGTAGFCRLWIP GFAEMAAPLYPLTKTGTLFNWGPDQQKAYQEIKQA LLTAPALGLPDLTKPFELFVDEKQGYAKGVLTQKL GPWRRPVAYLSKKLDPVAAGWPPCLRMVAAIAVLT KDAGKLTMGQPLVILAPHAVEALVKQPPDRWLSNA RMTHYQALLLDTDRVQFGPVVALNPATLLPLPEEG LQHNCLDILAEAHGTRPDLTDQPLPDADHTWYTGG SSLLQEGQRKAGAAVTTETEVIWAKALPAGTSAQR AQLIALTQALKMAEGKKLNVYTNSRYAFATAHIHG EIYRRRGLLTSEGKEIKNKDEILALLKALFLPKRL SIIHCPGHQKGHSAEARGNRMADQAARKAAITETP DTSTLLIENSSPYTSEHF |
| 693 | MMLV-II Q68R/Q79R/ L82R/L99R/ E282D | TLNIEDEHRLHETSKEPDVSLGSTWLSDFPQAWAE TGGMGLAVRQAPLIIPLKATSTPVSIKQYPMSREA RLGIKPHIRRLRDQGILVPCQSPWNTPLRPVKKPG TNDYRPVQDLREVNKRVEDIHPTVPNPYNLLSGLP PSHQWYTVLDLKDAFFCLRLHPTSQPLFAFEWRDP EMGISGQLTWTRLPQGFKNSPTLFDEALHRDLADF RIQHPDLILLQYVDDLLLAATSELDCQQGTRALLQ TLGNLGYRASAKKAQICQKQVKYLGYLLKEGQRWL TDARKETVMGQPTPKTPRQLREFLGTAGFCRLWIP GFAEMAAPLYPLTKTGTLFNWGPDQQKAYQEIKQA LLTAPALGLPDLTKPFELFVDEKQGYAKGVLTQKL GPWRRPVAYLSKKLDPVAAGWPPCLRMVAAIAVLT KDAGKLTMGQPLVILAPHAVEALVKQPPDRWLSNA RMTHYQALLLDTDRVQFGPVVALNPATLLPLPEEG LQHNCLDILAEAHGTRPDLTDQPLPDADHTWYTGG SSLLQEGQRKAGAAVTTETEVIWAKALPAGTSAQR AQLIALTQALKMAEGKKLNVYTNSRYAFATAHIHG EIYRRRGLLTSEGKEIKNKDEILALLKALFLPKRL SIIHCPGHQKGHSAEARGNRMADQAARKAAITETP DTSTLLIENSSPYTSEHF |
| 694 | MMLV-II Q68R/Q79R/ L99R/E282D/ Q299E/I593E | TLNIEDEHRLHETSKEPDVSLGSTWLSDFPQAWAE TGGMGLAVRQAPLIIPLKATSTPVSIKQYPMSREA RLGIKPHIRRLLDQGILVPCQSPWNTPLRPVKKPG TNDYRPVQDLREVNKRVEDIHPTVPNPYNLLSGLP PSHQWYTVLDLKDAFFCLRLHPTSQPLFAFEWRDP EMGISGQLTWTRLPQGFKNSPTLFDEALHRDLADF RIQHPDLILLQYVDDLLLAATSELDCQQGTRALLQ TLGNLGYRASAKKAQICQKQVKYLGYLLKEGQRWL TDARKETVMGQPTPKTPRELREFLGTAGFCRLWIP GFAEMAAPLYPLTKTGTLFNWGPDQQKAYQEIKQA LLTAPALGLPDLTKPFELFVDEKQGYAKGVLTQKL GPWRRPVAYLSKKLDPVAAGWPPCLRMVAAIAVLT KDAGKLTMGQPLVILAPHAVEALVKQPPDRWLSNA |

TABLE 38-continued

Sequences of quadruple or more mutant MMLV RTase variants.

| SEQ ID NO: | Construct | Construct Sequence (AA) |
|---|---|---|
| | | RMTHYQALLLDTDRVQFGPVVALNPATLLPLPEEG LQHNCLDILAEAHGTRPDLTDQPLPDADHTWYTGG SSLLQEGQRKAGAAVTTETEVIWAKALPAGTSAQR AQLIALTQALKMAEGKKLNVYTNSRYAFATAHEHG EIYRRRGLLTSEGKEIKNKDEILALLKALFLPKRL SIIHCPGHQKGHSAEARGNRMADQAARKAAITETP DTSTLLIENSSPYTSEHF |
| 695 | MMLV-II Q68R/Q79R/ L82R/L99R/ E282D/Q299E/ I593E | TLNIEDEHRLHETSKEPDVSLGSTWLSDFPQAWAE TGGMGLAVRQAPLIIPLKATSTPVSIKQYPMSREA RLGIKPHIRRLRDQGILVPCQSPWNTPLRPVKKPG TNDYRPVQDLREVNKRVEDIHPTVPNPYNLLSGLP PSHQWYTVLDLKDAFFCLRLHPTSQPLFAFEWRDP EMGISGQLTWTRLPQGFKNSPTLFDEALHRDLADF RIQHPDLILLQYVDDLLLAATSELDCQQGTRALLQ TLGNLGYRASAKKAQICQKQVKYLGYLLKEGQRWL TDARKETVMGQPTPKTPRELREFLGTAGFCRLWIP GFAEMAAPLYPLTKTGTLFNWGPDQQKAYQEIKQA LLTAPALGLPDLTKPFELFVDEKQGYAKGVLTQKL GPWRRPVAYLSKKLDPVAAGWPPCLRMVAAIAVLT KDAGKLTMGQPLVILAPHAVEALVKQPPDRWLSNA RMTHYQALLLDTDRVQFGPVVALNPATLLPLPEEG LQHNCLDILAEAHGTRPDLTDQPLPDADHTWYTGG SSLLQEGQRKAGAAVTTETEVIWAKALPAGTSAQR AQLIALTQALKMAEGKKLNVYTNSRYAFATAHEHG EIYRRRGLLTSEGKEIKNKDEILALLKALFLPKRL SIIHCPGHQKGHSAEARGNRMADQAARKAAITETP DTSTLLIENSSPYTSEHF |
| 696 | MMLV-II Q68R/Q79R/ L99R/E282D/ Q299E/V433R/ I593E | TLNIEDEHRLHETSKEPDVSLGSTWLSDFPQAWAE TGGMGLAVRQAPLIIPLKATSTPVSIKQYPMSREA RLGIKPHIRRLLDQGILVPCQSPWNTPLRPVKKPG TNDYRPVQDLREVNKRVEDIHPTVPNPYNLLSGLP PSHQWYTVLDLKDAFFCLRLHPTSQPLFAFEWRDP EMGISGQLTWTRLPQGFKNSPTLFDEALHRDLADF RIQHPDLILLQYVDDLLLAATSELDCQQGTRALLQ TLGNLGYRASAKKAQICQKQVKYLGYLLKEGQRWL TDARKETVMGQPTPKTPRELREFLGTAGFCRLWIP GFAEMAAPLYPLTKTGTLFNWGPDQQKAYQEIKQA LLTAPALGLPDLTKPFELFVDEKQGYAKGVLTQKL GPWRRPVAYLSKKLDPVAAGWPPCLRMVAAIAVLT KDAGKLTMGQPLRILAPHAVEALVKQPPDRWLSNA RMTHYQALLLDTDRVQFGPVVALNPATLLPLPEEG LQHNCLDILAEAHGTRPDLTDQPLPDADHTWYTGG SSLLQEGQRKAGAAVTTETEVIWAKALPAGTSAQR AQLIALTQALKMAEGKKLNVYINSRYAFATAHEHG EIYRRRGLLTSEGKEIKNKDEILALLKALFLPKRL SIIHCPGHQKGHSAEARGNRMADQAARKAAITETP DTSTLLIENSSPYTSEHF |
| 697 | MMLV-II Q68R/Q79R/ L82R/L99R/ E282D/Q299E/ V433R/I593E | TLNIEDEHRLHETSKEPDVSLGSTWLSDFPQAWAE TGGMGLAVRQAPLIIPLKATSTPVSIKQYPMSREA RLGIKPHIRRLRDQGILVPCQSPWNTPLRPVKKPG TNDYRPVQDLREVNKRVEDIHPTVPNPYNLLSGLP PSHQWYTVLDLKDAFFCLRLHPTSQPLFAFEWRDP EMGISGQLTWTRLPQGFKNSPTLFDEALHRDLADF RIQHPDLILLQYVDDLLLAATSELDCQQGTRALLQ TLGNLGYRASAKKAQICQKQVKYLGYLLKEGQRWL TDARKETVMGQPTPKTPRELREFLGTAGFCRLWIP GFAEMAAPLYPLTKTGTLFNWGPDQQKAYQEIKQA LLTAPALGLPDLTKPFELFVDEKQGYAKGVLTQKL GPWRRPVAYLSKKLDPVAAGWPPCLRMVAAIAVLT KDAGKLTMGQPLRILAPHAVEALVKQPPDRWLSNA RMTHYQALLLDTDRVQFGPVVALNPATLLPLPEEG LQHNCLDILAEAHGTRPDLTDQPLPDADHTWYTGG SSLLQEGQRKAGAAVTTETEVIWAKALPAGTSAQR AQLIALTQALKMAEGKKLNVYINSRYAFATAHEHG EIYRRRGLLTSEGKEIKNKDEILALLKALFLPKRL SIIHCPGHQKGHSAEARGNRMADQAARKAAITETP DTSTLLIENSSPYTSEHF |
| 698 | MMLV-II Q68R/Q79R/ L82R/L99R/ E282D/Q299E/ T332E/I593E | TLNIEDEHRLHETSKEPDVSLGSTWLSDFPQAWAE TGGMGLAVRQAPLIIPLKATSTPVSIKQYPMSREA RLGIKPHIRRLRDQGILVPCQSPWNTPLRPVKKPG TNDYRPVQDLREVNKRVEDIHPTVPNPYNLLSGLP PSHQWYTVLDLKDAFFCLRLHPTSQPLFAFEWRDP |

TABLE 38-continued

Sequences of quadruple or more mutant MMLV RTase variants.

| SEQ ID NO:Construct | | Construct Sequence (AA) |
|---|---|---|
| | | EMGISGQLTWTRLPQGFKNSPTLFDEALHRDLADF |
| | | RIQHPDLILLQYVDDLLLAATSELDCQQGTRALLQ |
| | | TLGNLGYRASAKKAQICQKQVKYLGYLLKEGQRWL |
| | | TDARKETVMGQPTPKTPRELREFLGTAGFCRLWIP |
| | | GFAEMAAPLYPLTKTGELFNWGPDQQKAYQEIKQA |
| | | LLTAPALGLPDLTKPFELFVDEKQGYAKGVLTQKL |
| | | GPWRRPVAYLSKKLDPVAAGWPPCLRMVAAIAVLT |
| | | KDAGKLTMGQPLVILAPHAVEALVKQPPDRWLSNA |
| | | RMTHYQALLLDTDRVQFGPVVALNPATLLPLPEEG |
| | | LQHNCLDILAEAHGTRPDLTDQPLPDADHTWYTGG |
| | | SSLLQEGQRKAGAAVTTETEVIWAKALPAGTSAQR |
| | | AQLIALTQALKMAEGKKLNVYINSRYAFATAHEHG |
| | | EIYRRRGLLTSEGKEIKNKDEILALLKALFLPKRL |
| | | SIIHCPGHQKGHSAEARGNRMADQAARKAAITETP |
| | | DTSTLLIENSSPYTSEHF |
| 699 | MMLV-II Q68R/Q79R/ L82R/L99R/ E282D/Q299E/ T332E/V433R/ I593E | TLNIEDEHRLHETSKEPDVSLGSTWLSDFPQAWAE TGGMGLAVRQAPLIIPLKATSTPVSIKQYPMSREA RLGIKPHIRRLRDQGILVPCQSPWNTPLRPVKKPG TNDYRPVQDLREVNKRVEDIHPTVPNPYNLLSGLP PSHQWYTVLDLKDAFFCLRLHPTSQPLFAFEWRDP EMGISGQLTWTRLPQGFKNSPTLFDEALHRDLADF RIQHPDLILLQYVDDLLLAATSELDCQQGTRALLQ TLGNLGYRASAKKAQICQKQVKYLGYLLKEGQRWL TDARKETVMGQPTPKTPRELREFLGTAGFCRLWIP GFAEMAAPLYPLTKTGELFNWGPDQQKAYQEIKQA LLTAPALGLPDLTKPFELFVDEKQGYAKGVLTQKL GPWRRPVAYLSKKLDPVAAGWPPCLRMVAAIAVLT KDAGKLTMGQPLRILAPHAVEALVKQPPDRWLSNA RMTHYQALLLDTDRVQFGPVVALNPATLLPLPEEG LQHNCLDILAEAHGTRPDLTDQPLPDADHTWYTGG SSLLQEGQRKAGAAVTTETEVIWAKALPAGTSAQR AQLIALTQALKMAEGKKLNVYINSRYAFATAHEHG EIYRRRGLLTSEGKEIKNKDEILALLKALFLPKRL SIIHCPGHQKGHSAEARGNRMADQAARKAAITETP DTSTLLIENSSPYTSEHF |

BIBLIOGRAPHY

1. Coffin et al., "The discovery of reverse transcriptase," *Ann. Rev. Virol.* 3(1): 29-51 (2016).
2. Hogrefe et al., "Mutant reverse transcriptase and methods of use," U.S. Pat. No. 9,783,791.
3. Kotewicz et al., "Cloned genes encoding reverse transcriptase lacking RNase H activity," U.S. Pat. No. 5,405,776.
4. Kotewicz et al., "Isolation of cloned Moloney murine leukemia virus reverse transcriptase lacking ribonuclease H activity," *Nucleic Acids Res.* 16(1): 265-77 (1988).
5. Rogers et al., "Novel Reverse Transcriptases for Use in High Temperature Nucleic Acid Synthesis." U.S. Patent Application Publication No. US 2015/0210989 A1.

What is claimed is:

1. An isolated Moloney murine leukemia virus (MMLV) reverse transcriptase (RTase) mutant comprising an amino acid sequence as set forth in any one of SEQ ID NOs: 725, 727, and 731.

2. The isolated MMLV RTase mutant of claim 1, wherein the MMLV RTase mutant comprises the amino acid sequence as set forth in SEQ ID NO: 727.

3. The isolated MMLV RTase mutant of claim 1, wherein the MMLV RTase mutant comprises the amino acid sequence as set forth in SEQ ID NO: 725.

4. The isolated MMLV RTase mutant of claim 1, wherein the MMLV RTase mutant comprises the amino acid sequence as set forth in SEQ ID NO: 731.

5. The MMLV RTase mutant of claim 1, wherein the MMLV RTase mutant lacks RNase H activity.

6. The MMLV RTase mutant of claim 1, wherein the MMLV RTase mutant possesses at least one of the following characteristics: enhanced DNA synthesis, increased fidelity, or enhanced thermostability when compared to wild-type MMLV RTase.

7. A composition comprising the isolated MMLV RTase mutant of claim 1.

8. The composition of claim 7, wherein the isolated MMLV RTase mutant lacks RNase H activity.

9. The composition of claim 8, wherein the isolated MMLV RTase mutant possesses at least one of the following characteristics: enhanced DNA synthesis, increased fidelity, or enhanced thermostability.

10. A kit comprising the isolated MMLV RTase mutant of mutant of claim 1.

11. The kit of claim 10, wherein the isolated MMLV RTase mutant lacks RNAse H activity.

12. The kit of claim 11, wherein the isolated MMLV RTase mutant possesses at least one of the following characteristics: enhanced DNA synthesis, increased fidelity, or enhanced thermostability.

13. A method for synthesizing complementary deoxyribonucleic acid (cDNA) comprising:

(a) providing the isolated MMLV RTase mutant of claim 1; and (b) contacting the isolated MMLV RTase mutant with a nucleic acid template to permit synthesis of cDNA.

14. A method for performing reverse transcription-polymerase chain reaction (RTPCR) comprising:

(a) providing the isolated MMLV RTase mutant of claim 1; and (b) contacting the isolated MMLV RTase mutant with a nucleic acid template to replicate and amplify the nucleic acid template.

* * * * *

SEQUENCE LISTING

<160> NUMBER OF SEQ ID NOS: 731

<210> SEQ ID NO 1
<211> LENGTH: 69
<212> TYPE: DNA
<213> ORGANISM: Artificial Sequence
<220> FEATURE:
<223> OTHER INFORMATION: Synthetic oligonucleotide

<400> SEQUENCE: 1
ggtatatctc cttcttaaag ttaaacaaaa ttatttctag aggggaatga tccggctgct      60
aacaaagcc                                                             69

<210> SEQ ID NO 2
<211> LENGTH: 21
<212> TYPE: DNA
<213> ORGANISM: Artificial Sequence
<220> FEATURE:

<223> OTHER INFORMATION: Synthetic oligonucleotide

<400> SEQUENCE: 2
gatccggctg ctaacaaagc c                                                 21

<210> SEQ ID NO 3
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 3
ttttgtttaa ctttaagaag gagatatacc atgggcagca gccatcatca tc              52

<210> SEQ ID NO 4
<211> LENGTH: 59
<212> TYPE: DNA
<213> ORGANISM: Artificial Sequence
<220> FEATURE:
<223> OTHER INFORMATION: Synthetic oligonucleotide

<400> SEQUENCE: 4
gcagccaact cagcttcctt tcgggctttg ttaaaaatgc tcgctagtgt agggagagc        59

<210> SEQ ID NO 5
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 5
aagcaccgtt gatcatcccg ttagcggcaa cgtctacacc tgtctctatc aaac            54

<210> SEQ ID NO 6
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 6
aagcaccgtt gatcatcccg ttacgtgcaa cgtctacacc tgtctctatc aaac            54

<210> SEQ ID NO 7
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 7
aagcaccgtt gatcatcccg ttagaagcaa cgtctacacc tgtctctatc aaac            54

<210> SEQ ID NO 8
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 8
ccgttgatca tcccgttaaa ggcagcgtct acacctgtct ctatcaaaca gtacccc          57

```
<210> SEQ ID NO 9
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 9
ccgttgatca tcccgttaaa ggcacgttct acacctgtct ctatcaaaca gtacccc           57

<210> SEQ ID NO 10
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 10
ccgttgatca tcccgttaaa ggcagaatct acacctgtct ctatcaaaca gtacccc           57

<210> SEQ ID NO 11
<211> LENGTH: 56
<212> TYPE: DNA
<213> ORGANISM: Artificial Sequence
<220> FEATURE:
<223> OTHER INFORMATION: Synthetic oligonucleotide

<400> SEQUENCE: 11
atcatcccgt taaaggcaac gtctgcgcct gtctctatca aacagtaccc catgag           56

<210> SEQ ID NO 12
<211> LENGTH: 56
<212> TYPE: DNA
<213> ORGANISM: Artificial Sequence
<220> FEATURE:
<223> OTHER INFORMATION: Synthetic oligonucleotide

<400> SEQUENCE: 12
atcatcccgt taaaggcaac gtctcgtcct gtctctatca aacagtaccc catgag           56

<210> SEQ ID NO 13
<211> LENGTH: 56
<212> TYPE: DNA
<213> ORGANISM: Artificial Sequence
<220> FEATURE:
<223> OTHER INFORMATION: Synthetic oligonucleotide

<400> SEQUENCE: 13
atcatcccgt taaaggcaac gtctgaacct gtctctatca aacagtaccc catgag           56

<210> SEQ ID NO 14
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 14
ccgttaaagg caacgtctac acctgcgtct atcaaacagt accccatgag tcaagagg          58

<210> SEQ ID NO 15
<211> LENGTH: 58
<212> TYPE: DNA
<213> ORGANISM: Artificial Sequence
<220> FEATURE:
<223> OTHER INFORMATION: Synthetic oligonucleotide
```

-continued

<400> SEQUENCE: 15
ccgttaaagg caacgtctac acctcgttct atcaaacagt accccatgag tcaagagg        58

<210> SEQ ID NO 16
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 16
ccgttaaagg caacgtctac acctgaatct atcaaacagt accccatgag tcaagagg        58

<210> SEQ ID NO 17
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 17
taaaggcaac gtctacacct gtctctgcga aacagtaccc catgagtcaa gagg            54

<210> SEQ ID NO 18
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 18
taaaggcaac gtctacacct gtctctcgta aacagtaccc catgagtcaa gagg            54

<210> SEQ ID NO 19
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 19
taaaggcaac gtctacacct gtctctgaaa aacagtaccc catgagtcaa gagg            54

<210> SEQ ID NO 20
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 20
ggcaacgtct acacctgtct ctatcgcgca gtaccccatg agtcaagagg c              51

<210> SEQ ID NO 21
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 21
ggcaacgtct acacctgtct ctatccgtca gtaccccatg agtcaagagg c              51

<210> SEQ ID NO 22
<211> LENGTH: 51

-continued

```
<212> TYPE: DNA
<213> ORGANISM: Artificial Sequence
<220> FEATURE:
<223> OTHER INFORMATION: Synthetic oligonucleotide

<400> SEQUENCE: 22
ggcaacgtct acacctgtct ctatcgaaca gtaccccatg agtcaagagg c          51

<210> SEQ ID NO 23
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 23
ctgtctctat caaacagtac cccatgagtg cggaggcccg cctggg               46

<210> SEQ ID NO 24
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 24
ctgtctctat caaacagtac cccatgagtc gtgaggcccg cctggg               46

<210> SEQ ID NO 25
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 25
ctgtctctat caaacagtac cccatgagtg aagaggcccg cctggg               46

<210> SEQ ID NO 26
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 26
ggcccgcctg gggattgcgc cacatattca gcgcttgctg gacca               45

<210> SEQ ID NO 27
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 27
ggcccgcctg gggattcgtc cacatattca gcgcttgctg gacca               45

<210> SEQ ID NO 28
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 28
```

-continued

```
ggcccgcctg gggattgaac cacatattca gcgcttgctg gacca                    45

<210> SEQ ID NO 29
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 29
cgcctgggga ttaagccaca tattgcgcgc ttgctggacc agggg                    45

<210> SEQ ID NO 30
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 30
cgcctgggga ttaagccaca tattcgtcgc ttgctggacc agggg                    45

<210> SEQ ID NO 31
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 31
cgcctgggga ttaagccaca tattgaacgc ttgctggacc agggg                    45

<210> SEQ ID NO 32
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 32
ccgtggaaca ccccccttgc gcccgtgaaa aagccaggta caaac                    45

<210> SEQ ID NO 33
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 33
ccgtggaaca ccccccttcg tcccgtgaaa aagccaggta caaac                    45

<210> SEQ ID NO 34
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 34
ccgtggaaca ccccccttga acccgtgaaa aagccaggta caaac                    45

<210> SEQ ID NO 35
<211> LENGTH: 48
<212> TYPE: DNA
<213> ORGANISM: Artificial Sequence
```

-continued

```
<220> FEATURE:
<223> OTHER INFORMATION: Synthetic oligonucleotide

<400> SEQUENCE: 35
cacccccctt ctgcccgcga aaaagccagg tacaaacgat tatcgtcc                48

<210> SEQ ID NO 36
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 36
cacccccctt ctgccccgta aaaagccagg tacaaacgat tatcgtcc                48

<210> SEQ ID NO 37
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 37
cacccccctt ctgcccgaaa aaaagccagg tacaaacgat tatcgtcc                48

<210> SEQ ID NO 38
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 38 ccccttctg cccgtggcga agccaggtac aaacgattat cgtcc                    45

<210> SEQ ID NO 39
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 39 ccccttctg cccgtgcgta agccaggtac aaacgattat cgtcc                    45

<210> SEQ ID NO 40
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 40 ccccttctg cccgtggaaa agccaggtac aaacgattat cgtcc                    45

<210> SEQ ID NO 41
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 41 ccccttctg cccgtgaaag cgccaggtac aaacgattat cgtccagtt               49
```

-continued

```
<210> SEQ ID NO 42
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 42
cccccttctg cccgtgaaac gtccaggtac aaacgattat cgtccagtt                      49

<210> SEQ ID NO 43
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 43
cccccttctg cccgtgaaag aaccaggtac aaacgattat cgtccagtt                      49

<210> SEQ ID NO 44
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 44
gcccgtgaaa aagccaggtg cgaacgatta tcgtccagtt caagatcttc g                   51

<210> SEQ ID NO 45
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 45
gcccgtgaaa aagccaggtc gtaacgatta tcgtccagtt caagatcttc g                   51

<210> SEQ ID NO 46
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 46
gcccgtgaaa aagccaggtg aaaacgatta tcgtccagtt caagatcttc g                   51

<210> SEQ ID NO 47
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 47
cccgtgaaaa agccaggtac agcggattat cgtccagttc aagatcttcg cg                  52

<210> SEQ ID NO 48
<211> LENGTH: 52
<212> TYPE: DNA
<213> ORGANISM: Artificial Sequence
<220> FEATURE:
<223> OTHER INFORMATION: Synthetic oligonucleotide
```

-continued

```
<400> SEQUENCE: 48
cccgtgaaaa agccaggtac acgtgattat cgtccagttc aagatcttcg cg          52

<210> SEQ ID NO 49
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 49
cccgtgaaaa agccaggtac agaagattat cgtccagttc aagatcttcg cg          52

<210> SEQ ID NO 50
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 50
cgtgaaaaag ccaggtacaa acgatgcgcg tccagttcaa gatcttcgcg             50

<210> SEQ ID NO 51
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 51
cgtgaaaaag ccaggtacaa acgatcgtcg tccagttcaa gatcttcgcg             50

<210> SEQ ID NO 52
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 52
cgtgaaaaag ccaggtacaa acgatgaacg tccagttcaa gatcttcgcg             50

<210> SEQ ID NO 53
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 53
cgtgaaaaag ccaggtacaa acgattatgc gccagttcaa gatcttcgcg agg         53

<210> SEQ ID NO 54
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 54
cgtgaaaaag ccaggtacaa acgattataa accagttcaa gatcttcgcg agg         53

<210> SEQ ID NO 55
```

-continued

```
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 55
cgtgaaaaag ccaggtacaa acgattatga accagttcaa gatcttcgcg agg          53

<210> SEQ ID NO 56
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 56
gccaggtaca aacgattatc gtccagcgca agatcttcgc gaggtcaaca aac          53

<210> SEQ ID NO 57
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 57
gccaggtaca aacgattatc gtccacgtca agatcttcgc gaggtcaaca aac          53

<210> SEQ ID NO 58
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 58
gccaggtaca aacgattatc gtccagaaca agatcttcgc gaggtcaaca aac          53

<210> SEQ ID NO 59
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 59
agttcaagat cttcgcgagg tcaacgcgcg cgtagaagac atccatccga c            51

<210> SEQ ID NO 60
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 60
agttcaagat cttcgcgagg tcaaccgtcg cgtagaagac atccatccga c            51

<210> SEQ ID NO 61
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 61
```
agttcaagat cttcgcgagg tcaacgaacg cgtagaagac atccatccga c 51

<210> SEQ ID NO 62
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 62
gcgaggtcaa caaacgcgta gcggacatcc atccgactgt acctaatcc 49

<210> SEQ ID NO 63
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 63
gcgaggtcaa caaacgcgta cgtgacatcc atccgactgt acctaatcc 49

<210> SEQ ID NO 64
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 64
gcgaggtcaa caaacgcgta gatgacatcc atccgactgt acctaatcc 49

<210> SEQ ID NO 65
<211> LENGTH: 59
<212> TYPE: DNA
<213> ORGANISM: Artificial Sequence
<220> FEATURE:
<223> OTHER INFORMATION: Synthetic oligonucleotide

<400> SEQUENCE: 65
acgcgtagaa gacatccatc cggtggtacc taatccttat aatctgttat caggcctgc 59

<210> SEQ ID NO 66
<211> LENGTH: 59
<212> TYPE: DNA
<213> ORGANISM: Artificial Sequence
<220> FEATURE:
<223> OTHER INFORMATION: Synthetic oligonucleotide

<400> SEQUENCE: 66
acgcgtagaa gacatccatc cgcgtgtacc taatccttat aatctgttat caggcctgc 59

<210> SEQ ID NO 67
<211> LENGTH: 59
<212> TYPE: DNA
<213> ORGANISM: Artificial Sequence
<220> FEATURE:
<223> OTHER INFORMATION: Synthetic oligonucleotide

<400> SEQUENCE: 67
acgcgtagaa gacatccatc cggaagtacc taatccttat aatctgttat caggcctgc 59

<210> SEQ ID NO 68
<211> LENGTH: 45
<212> TYPE: DNA

-continued

```
<213> ORGANISM: Artificial Sequence
<220> FEATURE:
<223> OTHER INFORMATION: Synthetic oligonucleotide

<400> SEQUENCE: 68
cgtctgcccc agggctttgc gaacagcccc acattgttcg atgaa                        45

<210> SEQ ID NO 69
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 69
cgtctgcccc agggctttcg taacagcccc acattgttcg atgaa                        45

<210> SEQ ID NO 70
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 70
cgtctgcccc agggctttga aaacagcccc acattgttcg atgaa                        45

<210> SEQ ID NO 71
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 71
agaaggtcaa cgttggctga ctgcggcgcg taaggagacc gtaatg                       46

<210> SEQ ID NO 72
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 72
agaaggtcaa cgttggctga ctcgtgcgcg taaggagacc gtaatg                       46

<210> SEQ ID NO 73
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 73
agaaggtcaa cgttggctga ctgatgcgcg taaggagacc gtaatg                       46

<210> SEQ ID NO 74
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 74
gaaggtcaac gttggctgac tgaagtgcgt aaggagaccg taatggggc                    49
```

```
<210> SEQ ID NO 75
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 75
gaaggtcaac gttggctgac tgaacgtcgt aaggagaccg taatggggc                49

<210> SEQ ID NO 76
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 76
gaaggtcaac gttggctgac tgaagaacgt aaggagaccg taatggggc                49

<210> SEQ ID NO 77
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 77
gcgtaaggag accgtaatgg gggcgcctac gcctaagacg ccacg                     45

<210> SEQ ID NO 78
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 78
gcgtaaggag accgtaatgg ggcgtcctac gcctaagacg ccacg                     45

<210> SEQ ID NO 79
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 79
gcgtaaggag accgtaatgg gggaacctac gcctaagacg ccacg                     45

<210> SEQ ID NO 80
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 80
gagaccgtaa tggggcagcc tgcgcctaag acgccacgcc agttg                     45

<210> SEQ ID NO 81
<211> LENGTH: 45
<212> TYPE: DNA
<213> ORGANISM: Artificial Sequence
<220> FEATURE:
```

-continued

<223> OTHER INFORMATION: Synthetic oligonucleotide

<400> SEQUENCE: 81
gagaccgtaa tggggcagcc tcgtcctaag acgccacgcc agttg                    45

<210> SEQ ID NO 82
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 82
gagaccgtaa tggggcagcc tgaacctaag acgccacgcc agttg                    45

<210> SEQ ID NO 83
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 83
gtaatggggc agcctacgcc tgcgacgcca cgccagttgc gtgaa                    45

<210> SEQ ID NO 84
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 84
gtaatggggc agcctacgcc tcgtacgcca cgccagttgc gtgaa                    45

<210> SEQ ID NO 85
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 85
gtaatggggc agcctacgcc tgaaacgcca cgccagttgc gtgaa                    45

<210> SEQ ID NO 86
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 86
tggggcagcc tacgcctaag gcgccacgcc agttgcgtga atttt                    45

<210> SEQ ID NO 87
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 87
tggggcagcc tacgcctaag cgtccacgcc agttgcgtga atttt                    45

-continued

```
<210> SEQ ID NO 88
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 88
tggggcagcc tacgcctaag gaaccacgcc agttgcgtga atttt                    45

<210> SEQ ID NO 89
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 89
gcctacgcct aagacgccag cgcagttgcg tgaatttttg ggcacag                  47

<210> SEQ ID NO 90
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 90
gcctacgcct aagacgccaa aacagttgcg tgaatttttg ggcacag                  47

<210> SEQ ID NO 91
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 91
gcctacgcct aagacgccag aacagttgcg tgaatttttg ggcacag                  47

<210> SEQ ID NO 92
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 92
cctaagacgc cacgccagtt ggcggaattt ttgggcacag cggga                    45

<210> SEQ ID NO 93
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 93
cctaagacgc cacgccagtt gaaagaattt ttgggcacag cggga                    45

<210> SEQ ID NO 94
<211> LENGTH: 45
<212> TYPE: DNA
<213> ORGANISM: Artificial Sequence
<220> FEATURE:
<223> OTHER INFORMATION: Synthetic oligonucleotide
```

-continued

<400> SEQUENCE: 94
cctaagacgc cacgccagtt ggaagaattt ttgggcacag cggga                          45

<210> SEQ ID NO 95
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 95
gcacccctgt accccttaac agcgacaggg acgcttttca actgg                          45

<210> SEQ ID NO 96
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 96
gcacccctgt accccttaac acgtacaggg acgcttttca actgg                          45

<210> SEQ ID NO 97
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 97
gcacccctgt accccttaac agaaacaggg acgcttttca actgg                          45

<210> SEQ ID NO 98
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 98
gtttgataga gacaggtgta gacgttgccg ctaacgggat gatcaacggt gctt               54

<210> SEQ ID NO 99
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 99
gtttgataga gacaggtgta gacgttgcac gtaacgggat gatcaacggt gctt               54

<210> SEQ ID NO 100
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 100
gtttgataga gacaggtgta gacgttgctt ctaacgggat gatcaacggt gctt               54

<210> SEQ ID NO 101
<211> LENGTH: 57

```
<212> TYPE: DNA
<213> ORGANISM: Artificial Sequence
<220> FEATURE:
<223> OTHER INFORMATION: Synthetic oligonucleotide

<400> SEQUENCE: 101
ggggtactgt ttgatagaga caggtgtaga cgctgccttt aacgggatga tcaacgg        57

<210> SEQ ID NO 102
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 102
ggggtactgt ttgatagaga caggtgtaga acgtgccttt aacgggatga tcaacgg        57

<210> SEQ ID NO 103
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 103
ggggtactgt ttgatagaga caggtgtaga ttctgccttt aacgggatga tcaacgg        57

<210> SEQ ID NO 104
<211> LENGTH: 56
<212> TYPE: DNA
<213> ORGANISM: Artificial Sequence
<220> FEATURE:
<223> OTHER INFORMATION: Synthetic oligonucleotide

<400> SEQUENCE: 104
ctcatggggt actgtttgat agagacaggc gcagacgttg cctttaacgg gatgat         56

<210> SEQ ID NO 105
<211> LENGTH: 56
<212> TYPE: DNA
<213> ORGANISM: Artificial Sequence
<220> FEATURE:
<223> OTHER INFORMATION: Synthetic oligonucleotide

<400> SEQUENCE: 105
ctcatggggt actgtttgat agagacagga cgagacgttg cctttaacgg gatgat         56

<210> SEQ ID NO 106
<211> LENGTH: 56
<212> TYPE: DNA
<213> ORGANISM: Artificial Sequence
<220> FEATURE:
<223> OTHER INFORMATION: Synthetic oligonucleotide

<400> SEQUENCE: 106
ctcatggggt actgtttgat agagacaggt tcagacgttg cctttaacgg gatgat         56

<210> SEQ ID NO 107
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 107
```

-continued cctcttgact catggggtac tgtttgatag acgcaggtgt agacgttgcc tttaacgg    58

<210> SEQ ID NO 108
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 108
cctcttgact catggggtac tgtttgatag aacgaggtgt agacgttgcc tttaacgg    58

<210> SEQ ID NO 109
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 109
cctcttgact catggggtac tgtttgatag attcaggtgt agacgttgcc tttaacgg    58

<210> SEQ ID NO 110
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 110
cctcttgact catggggtac tgtttcgcag agacaggtgt agacgttgcc ttta    54

<210> SEQ ID NO 111
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 111
cctcttgact catggggtac tgtttacgag agacaggtgt agacgttgcc ttta    54

<210> SEQ ID NO 112
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 112
cctcttgact catggggtac tgtttttcag agacaggtgt agacgttgcc ttta    54

<210> SEQ ID NO 113
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 113
gcctcttgac tcatggggta ctgcgcgata gagacaggtg tagacgttgc c    51

<210> SEQ ID NO 114
<211> LENGTH: 51
<212> TYPE: DNA
<213> ORGANISM: Artificial Sequence -continued

```
<220> FEATURE:
<223> OTHER INFORMATION: Synthetic oligonucleotide

<400> SEQUENCE: 114
gcctcttgac tcatgggta ctgacggata gagacaggtg tagacgttgc c          51

<210> SEQ ID NO 115
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 115
gcctcttgac tcatgggta ctgttcgata gagacaggtg tagacgttgc c          51

<210> SEQ ID NO 116
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 116
ctgtctctat caaacagtac cccatgagtg cggaggcccg cctggg          46

<210> SEQ ID NO 117
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 117
ctgtctctat caaacagtac cccatgagtc gtgaggcccg cctggg          46

<210> SEQ ID NO 118
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 118
ctgtctctat caaacagtac cccatgagtg aagaggcccg cctggg          46

<210> SEQ ID NO 119
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 119
tggtccagca agcgctgaat atgtggcgca atcccaggc gggcc          45

<210> SEQ ID NO 120
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 120
tggtccagca agcgctgaat atgtggacga atcccaggc gggcc          45
```

-continued

```
<210> SEQ ID NO 121
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 121
tggtccagca agcgctgaat atgtggttca atccccaggc gggcc                      45

<210> SEQ ID NO 122
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 122
cccctggtcc agcaagcgcg caatatgtgg cttaatcccc aggcg                      45

<210> SEQ ID NO 123
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 123
cccctggtcc agcaagcgac gaatatgtgg cttaatcccc aggcg                      45

<210> SEQ ID NO 124
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 124
cccctggtcc agcaagcgtt caatatgtgg cttaatcccc aggcg                      45

<210> SEQ ID NO 125
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 125
gtttgtacct ggctttttca cgggcgcaag gggggtgttc cacgg                      45

<210> SEQ ID NO 126
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 126
gtttgtacct ggctttttca cgggacgaag gggggtgttc cacgg                      45

<210> SEQ ID NO 127
<211> LENGTH: 45
<212> TYPE: DNA
<213> ORGANISM: Artificial Sequence
<220> FEATURE:
<223> OTHER INFORMATION: Synthetic oligonucleotide
```

```
<400> SEQUENCE: 127
gtttgtacct ggctttttca cgggttcaag gggggtgttc cacgg                              45

<210> SEQ ID NO 128
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 128
ggacgataat cgtttgtacc tggctttttc gcgggcagaa ggggggtg                           48

<210> SEQ ID NO 129
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 129
ggacgataat cgtttgtacc tggcttttta cggggcagaa ggggggtg                           48

<210> SEQ ID NO 130
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 130
ggacgataat cgtttgtacc tggctttttt tcgggcagaa ggggggtg                           48

<210> SEQ ID NO 131
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 131
ggacgataat cgtttgtacc tggcttcgcc acgggcagaa ggggg                             45

<210> SEQ ID NO 132
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 132
ggacgataat cgtttgtacc tggcttacgc acgggcagaa ggggg                             45

<210> SEQ ID NO 133
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 133
ggacgataat cgtttgtacc tggctttttcc acgggcagaa ggggg                            45

<210> SEQ ID NO 134
```

```
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 134
aactggacga taatcgtttg tacctggcgc tttcacgggc agaaggggg              49

<210> SEQ ID NO 135
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 135
aactggacga taatcgtttg tacctggacg tttcacgggc agaaggggg              49

<210> SEQ ID NO 136
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 136
aactggacga taatcgtttg tacctggttc tttcacgggc agaaggggg              49

<210> SEQ ID NO 137
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 137
cgaagatctt gaactggacg ataatcgttc gcacctggct ttttcacggg c          51

<210> SEQ ID NO 138
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 138
cgaagatctt gaactggacg ataatcgtta cgacctggct ttttcacggg c          51

<210> SEQ ID NO 139
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 139
cgaagatctt gaactggacg ataatcgttt tcacctggct ttttcacggg c          51

<210> SEQ ID NO 140
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 140
```
cgcgaagatc ttgaactgga cgataatccg ctgtacctgg cttttcacg gg          52

<210> SEQ ID NO 141
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 141
cgcgaagatc ttgaactgga cgataatcac gtgtacctgg cttttcacg gg          52

<210> SEQ ID NO 142
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 142
cgcgaagatc ttgaactgga cgataatctt ctgtacctgg cttttcacg gg          52

<210> SEQ ID NO 143
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 143
cgcgaagatc ttgaactgga cgcgcatcgt ttgtacctgg cttttcacg          50

<210> SEQ ID NO 144
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 144
cgcgaagatc ttgaactgga cgacgatcgt ttgtacctgg cttttcacg          50

<210> SEQ ID NO 145
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 145
cgcgaagatc ttgaactgga cgttcatcgt ttgtacctgg cttttcacg          50

<210> SEQ ID NO 146
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 146
cctcgcgaag atcttgaact ggcgcataat cgtttgtacc tggctttttc acg          53

<210> SEQ ID NO 147
<211> LENGTH: 53
<212> TYPE: DNA

<210> SEQ ID NO 148
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 147
cctcgcgaag atcttgaact ggtttataat cgtttgtacc tggctttttc acg             53

<210> SEQ ID NO 148
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 148
cctcgcgaag atcttgaact ggttcataat cgtttgtacc tggctttttc acg             53

<210> SEQ ID NO 149
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 149
gtttgttgac ctcgcgaaga tcttgcgctg gacgataatc gtttgtacct ggc             53

<210> SEQ ID NO 150
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 150
gtttgttgac ctcgcgaaga tcttgacgtg gacgataatc gtttgtacct ggc             53

<210> SEQ ID NO 151
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 151
gtttgttgac ctcgcgaaga tcttgttctg gacgataatc gtttgtacct ggc             53

<210> SEQ ID NO 152
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 152
gtcggatgga tgtcttctac gcgcgcgttg acctcgcgaa gatcttgaac t               51

<210> SEQ ID NO 153
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 153
gtcggatgga tgtcttctac gcgacggttg acctcgcgaa gatcttgaac t               51

-continued

<210> SEQ ID NO 154
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 154
gtcggatgga tgtcttctac gcgttcgttg acctcgcgaa gatcttgaac t          51

<210> SEQ ID NO 155
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 155
ggattaggta cagtcggatg gatgtccgct acgcgtttgt tgacctcgc          49

<210> SEQ ID NO 156
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 156
ggattaggta cagtcggatg gatgtcacgt acgcgtttgt tgacctcgc          49

<210> SEQ ID NO 157
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 157
ggattaggta cagtcggatg gatgtcatct acgcgtttgt tgacctcgc          49

<210> SEQ ID NO 158
<211> LENGTH: 59
<212> TYPE: DNA
<213> ORGANISM: Artificial Sequence
<220> FEATURE:
<223> OTHER INFORMATION: Synthetic oligonucleotide

<400> SEQUENCE: 158
gcaggcctga taacagatta taaggattag gtaccaccgg atggatgtct tctacgcgt          59

<210> SEQ ID NO 159
<211> LENGTH: 59
<212> TYPE: DNA
<213> ORGANISM: Artificial Sequence
<220> FEATURE:
<223> OTHER INFORMATION: Synthetic oligonucleotide

<400> SEQUENCE: 159
gcaggcctga taacagatta taaggattag gtacacgcgg atggatgtct tctacgcgt          59

<210> SEQ ID NO 160
<211> LENGTH: 59
<212> TYPE: DNA
<213> ORGANISM: Artificial Sequence
<220> FEATURE:

<223> OTHER INFORMATION: Synthetic oligonucleotide

<400> SEQUENCE: 160
gcaggcctga taacagatta taaggattag gtacttccgg atggatgtct tctacgcgt          59

<210> SEQ ID NO 161
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 161
ttcatcgaac aatgtggggc tgttcgcaaa gccctggggc agacg                         45

<210> SEQ ID NO 162
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 162
ttcatcgaac aatgtggggc tgttacgaaa gccctggggc agacg                         45

<210> SEQ ID NO 163
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 163
ttcatcgaac aatgtggggc tgttttcaaa gccctggggc agacg                         45

<210> SEQ ID NO 164
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 164
cattacggtc tccttacgcg ccgcagtcag ccaacgttga ccttct                        46

<210> SEQ ID NO 165
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 165
cattacggtc tccttacgcg cacgagtcag ccaacgttga ccttct                        46

<210> SEQ ID NO 166
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 166
cattacggtc tccttacgcg catcagtcag ccaacgttga ccttct                        46

-continued

```
<210> SEQ ID NO 167
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 167
gccccattac ggtctcctta cgcacttcag tcagccaacg ttgaccttc                 49

<210> SEQ ID NO 168
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 168
gccccattac ggtctcctta cgacgttcag tcagccaacg ttgaccttc                 49

<210> SEQ ID NO 169
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 169
gccccattac ggtctcctta cgttcttcag tcagccaacg ttgaccttc                 49

<210> SEQ ID NO 170
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 170
cgtggcgtct taggcgtagg cgcccccatt acggtctcct tacgc                     45

<210> SEQ ID NO 171
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 171
cgtggcgtct taggcgtagg acgccccatt acggtctcct tacgc                     45

<210> SEQ ID NO 172
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 172
cgtggcgtct taggcgtagg ttcccccatt acggtctcct tacgc                     45

<210> SEQ ID NO 173
<211> LENGTH: 45
<212> TYPE: DNA
<213> ORGANISM: Artificial Sequence
<220> FEATURE:
<223> OTHER INFORMATION: Synthetic oligonucleotide
```

-continued

<400> SEQUENCE: 173
caactggcgt ggcgtcttag gcgcaggctg ccccattacg gtctc                    45

<210> SEQ ID NO 174
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 174
caactggcgt ggcgtcttag gacgaggctg ccccattacg gtctc                    45

<210> SEQ ID NO 175
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 175
caactggcgt ggcgtcttag gttcaggctg ccccattacg gtctc                    45

<210> SEQ ID NO 176
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 176
ttcacgcaac tggcgtggcg tcgcaggcgt aggctgcccc attac                    45

<210> SEQ ID NO 177
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 177
ttcacgcaac tggcgtggcg tacgaggcgt aggctgcccc attac                    45

<210> SEQ ID NO 178
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 178
ttcacgcaac tggcgtggcg tttcaggcgt aggctgcccc attac                    45

<210> SEQ ID NO 179
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 179
aaaattcacg caactggcgt ggcgccttag gcgtaggctg cccca                    45

<210> SEQ ID NO 180
<211> LENGTH: 45

```
<212> TYPE: DNA
<213> ORGANISM: Artificial Sequence
<220> FEATURE:
<223> OTHER INFORMATION: Synthetic oligonucleotide

<400> SEQUENCE: 180
aaaattcacg caactggcgt ggacgcttag gcgtaggctg cccca                      45

<210> SEQ ID NO 181
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 181
aaaattcacg caactggcgt ggttccttag gcgtaggctg cccca                      45

<210> SEQ ID NO 182
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 182
ctgtgcccaa aaattcacgc aactgcgctg gcgtcttagg cgtaggc                    47

<210> SEQ ID NO 183
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 183
ctgtgcccaa aaattcacgc aactgttttg gcgtcttagg cgtaggc                    47

<210> SEQ ID NO 184
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 184
ctgtgcccaa aaattcacgc aactgttctg gcgtcttagg cgtaggc                    47

<210> SEQ ID NO 185
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 185
tcccgctgtg cccaaaaatt ccgccaactg gcgtggcgtc ttagg                      45

<210> SEQ ID NO 186
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 186
```

```
tcccgctgtg cccaaaaatt ctttcaactg gcgtggcgtc ttagg                   45

<210> SEQ ID NO 187
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 187
tcccgctgtg cccaaaaatt cttccaactg gcgtggcgtc ttagg                    45

<210> SEQ ID NO 188
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 188
ccagttgaaa agcgtccctg tcgctgttaa ggggtacagg ggtgc                    45

<210> SEQ ID NO 189
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 189
ccagttgaaa agcgtccctg tacgtgttaa ggggtacagg ggtgc                    45

<210> SEQ ID NO 190
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 190
ccagttgaaa agcgtccctg tttctgttaa ggggtacagg ggtgc                    45

<210> SEQ ID NO 191
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 191
taaaggcaac gtctacacct gtctctggca aacagtaccc catgagtcaa gagg          54

<210> SEQ ID NO 192
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 192
cctcttgact catggggtac tgtttgccag agacaggtgt agacgttgcc ttta          54

<210> SEQ ID NO 193
<211> LENGTH: 54
<212> TYPE: DNA
<213> ORGANISM: Artificial Sequence
```

-continued

```
<220> FEATURE:
<223> OTHER INFORMATION: Synthetic oligonucleotide

<400> SEQUENCE: 193
taaaggcaac gtctacacct gtctctctga aacagtaccc catgagtcaa gagg        54

<210> SEQ ID NO 194
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 194
cctcttgact catggggtac tgtttcagag agacaggtgt agacgttgcc ttta        54

<210> SEQ ID NO 195
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 195
taaaggcaac gtctacacct gtctctgtga aacagtaccc catgagtcaa gagg        54

<210> SEQ ID NO 196
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 196
cctcttgact catggggtac tgtttcacag agacaggtgt agacgttgcc ttta        54

<210> SEQ ID NO 197
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 197
taaaggcaac gtctacacct gtctctccga aacagtaccc catgagtcaa gagg        54

<210> SEQ ID NO 198
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 198
cctcttgact catggggtac tgtttcggag agacaggtgt agacgttgcc ttta        54

<210> SEQ ID NO 199
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 199
taaaggcaac gtctacacct gtctctatga aacagtaccc catgagtcaa gagg        54
```

<210> SEQ ID NO 200
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 200
cctcttgact catggggtac tgtttcatag agacaggtgt agacgttgcc ttta          54

<210> SEQ ID NO 201
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 201
taaaggcaac gtctacacct gtctctagca aacagtaccc catgagtcaa gagg          54

<210> SEQ ID NO 202
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 202
cctcttgact catggggtac tgtttgctag agacaggtgt agacgttgcc ttta          54

<210> SEQ ID NO 203
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 203
taaaggcaac gtctacacct gtctctacca aacagtaccc catgagtcaa gagg          54

<210> SEQ ID NO 204
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 204
cctcttgact catggggtac tgtttggtag agacaggtgt agacgttgcc ttta          54

<210> SEQ ID NO 205
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 205
taaaggcaac gtctacacct gtctcttgca aacagtaccc catgagtcaa gagg          54

<210> SEQ ID NO 206
<211> LENGTH: 54
<212> TYPE: DNA
<213> ORGANISM: Artificial Sequence
<220> FEATURE:
<223> OTHER INFORMATION: Synthetic oligonucleotide -continued

<400> SEQUENCE: 206
cctcttgact catggggtac tgtttgcaag agacaggtgt agacgttgcc ttta          54

<210> SEQ ID NO 207
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 207
taaaggcaac gtctcacct gtctctttta aacagtaccc catgagtcaa gagg           54

<210> SEQ ID NO 208
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 208
cctcttgact catggggtac tgtttaaaag agacaggtgt agacgttgcc ttta          54

<210> SEQ ID NO 209
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 209
taaaggcaac gtctcacct gtctcttata aacagtaccc catgagtcaa gagg           54

<210> SEQ ID NO 210
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 210
cctcttgact catggggtac tgtttataag agacaggtgt agacgttgcc ttta          54

<210> SEQ ID NO 211
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 211
taaaggcaac gtctcacct gtctctcata aacagtaccc catgagtcaa gagg           54

<210> SEQ ID NO 212
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 212
cctcttgact catggggtac tgtttatgag agacaggtgt agacgttgcc ttta          54

<210> SEQ ID NO 213

-continued

```
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 213
taaaggcaac gtctacacct gtctcttgga aacagtaccc catgagtcaa gagg          54

<210> SEQ ID NO 214
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 214
cctcttgact catggggtac tgtttccaag agacaggtgt agacgttgcc ttta          54

<210> SEQ ID NO 215
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 215
taaaggcaac gtctacacct gtctctgata aacagtaccc catgagtcaa gagg          54

<210> SEQ ID NO 216
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 216
cctcttgact catggggtac tgtttatcag agacaggtgt agacgttgcc ttta          54

<210> SEQ ID NO 217
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 217
taaaggcaac gtctacacct gtctctaaca aacagtaccc catgagtcaa gagg          54

<210> SEQ ID NO 218
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 218
cctcttgact catggggtac tgtttgttag agacaggtgt agacgttgcc ttta          54

<210> SEQ ID NO 219
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 219
```

-continued taaaggcaac gtctacacct gtctctcaga aacagtaccc catgagtcaa gagg            54

<210> SEQ ID NO 220
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 220
cctcttgact catggggtac tgtttctgag agacaggtgt agacgttgcc ttta            54

<210> SEQ ID NO 221
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 221
taaaggcaac gtctacacct gtctctaaaa aacagtaccc catgagtcaa gagg            54

<210> SEQ ID NO 222
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 222
cctcttgact catggggtac tgttttttag agacaggtgt agacgttgcc ttta            54

<210> SEQ ID NO 223
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 223
ctgtctctat caaacagtac cccatgagtg gcgaggcccg cctggg            46

<210> SEQ ID NO 224
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 224
cccaggcggg cctcgccact catggggtac tgtttgatag agacag            46

<210> SEQ ID NO 225
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 225
ctgtctctat caaacagtac cccatgagtc tggaggcccg cctggg            46

<210> SEQ ID NO 226
<211> LENGTH: 46
<212> TYPE: DNA

```
<213> ORGANISM: Artificial Sequence
<220> FEATURE:
<223> OTHER INFORMATION: Synthetic oligonucleotide

<400> SEQUENCE: 226
cccaggcggg cctccagact catggggtac tgtttgatag agacag                        46

<210> SEQ ID NO 227
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 227
ctgtctctat caaacagtac cccatgagta ttgaggcccg cctggg                        46

<210> SEQ ID NO 228
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 228
cccaggcggg cctcaatact catggggtac tgtttgatag agacag                        46

<210> SEQ ID NO 229
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 229
ctgtctctat caaacagtac cccatgagtg tggaggcccg cctggg                        46

<210> SEQ ID NO 230
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 230
cccaggcggg cctccacact catggggtac tgtttgatag agacag                        46

<210> SEQ ID NO 231
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 231
ctgtctctat caaacagtac cccatgagtc cggaggcccg cctggg                        46

<210> SEQ ID NO 232
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 232
cccaggcggg cctccggact catggggtac tgtttgatag agacag                        46
```

-continued

<210> SEQ ID NO 233
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 233
ctgtctctat caaacagtac cccatgagta tggaggcccg cctggg                          46

<210> SEQ ID NO 234
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 234
cccaggcggg cctccatact catggggtac tgtttgatag agacag                          46

<210> SEQ ID NO 235
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 235
ctgtctctat caaacagtac cccatgagta gcgaggcccg cctggg                          46

<210> SEQ ID NO 236
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 236
cccaggcggg cctcgctact catggggtac tgtttgatag agacag                          46

<210> SEQ ID NO 237
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 237
ctgtctctat caaacagtac cccatgagta ccgaggcccg cctggg                          46

<210> SEQ ID NO 238
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 238
cccaggcggg cctcggtact catggggtac tgtttgatag agacag                          46

<210> SEQ ID NO 239
<211> LENGTH: 46
<212> TYPE: DNA
<213> ORGANISM: Artificial Sequence
<220> FEATURE:

<223> OTHER INFORMATION: Synthetic oligonucleotide

<400> SEQUENCE: 239
ctgtctctat caaacagtac cccatgagtt gcgaggcccg cctggg                    46

<210> SEQ ID NO 240
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 240
cccaggcggg cctcgcaact catggggtac tgtttgatag agacag                    46

<210> SEQ ID NO 241
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 241
ctgtctctat caaacagtac cccatgagtt ttgaggcccg cctggg                    46

<210> SEQ ID NO 242
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 242
cccaggcggg cctcaaaact catggggtac tgtttgatag agacag                    46

<210> SEQ ID NO 243
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 243
ctgtctctat caaacagtac cccatgagtt atgaggcccg cctggg                    46

<210> SEQ ID NO 244
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 244
cccaggcggg cctcataact catggggtac tgtttgatag agacag                    46

<210> SEQ ID NO 245
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 245
ctgtctctat caaacagtac cccatgagtc atgaggcccg cctggg                    46

243

244

-continued

```
<210> SEQ ID NO 246
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 246
cccaggcggg cctcatgact catggggtac tgtttgatag agacag                46

<210> SEQ ID NO 247
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 247
ctgtctctat caaacagtac cccatgagtt gggaggcccg cctggg                46

<210> SEQ ID NO 248
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 248
cccaggcggg cctcccaact catggggtac tgtttgatag agacag                46

<210> SEQ ID NO 249
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 249
ctgtctctat caaacagtac cccatgagtg atgaggcccg cctggg                46

<210> SEQ ID NO 250
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 250
cccaggcggg cctcatcact catggggtac tgtttgatag agacag                46

<210> SEQ ID NO 251
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 251
ctgtctctat caaacagtac cccatgagta acgaggcccg cctggg                46

<210> SEQ ID NO 252
<211> LENGTH: 46
<212> TYPE: DNA
<213> ORGANISM: Artificial Sequence
<220> FEATURE:
<223> OTHER INFORMATION: Synthetic oligonucleotide
```

-continued

```
<400> SEQUENCE: 252
cccaggcggg cctcgttact catggggtac tgtttgatag agacag                46

<210> SEQ ID NO 253
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 253
ctgtctctat caaacagtac cccatgagta aagaggcccg cctggg                46

<210> SEQ ID NO 254
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 254
cccaggcggg cctctttact catggggtac tgtttgatag agacag                46

<210> SEQ ID NO 255
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 255
cgcctgggga ttaagccaca tattggccgc ttgctggacc agggg                 45

<210> SEQ ID NO 256
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 256
cccctggtcc agcaagcggc caatatgtgg cttaatcccc aggcg                 45

<210> SEQ ID NO 257
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 257
cgcctgggga ttaagccaca tattctgcgc ttgctggacc agggg                 45

<210> SEQ ID NO 258
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 258
cccctggtcc agcaagcgca gaatatgtgg cttaatcccc aggcg                 45

<210> SEQ ID NO 259
<211> LENGTH: 45
```

<212> TYPE: DNA
<213> ORGANISM: Artificial Sequence
<220> FEATURE:
<223> OTHER INFORMATION: Synthetic oligonucleotide

<400> SEQUENCE: 259
cgcctgggga ttaagccaca tattattcgc ttgctggacc agggg                    45

<210> SEQ ID NO 260
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 260
cccctggtcc agcaagcgaa taatatgtgg cttaatcccc aggcg                    45

<210> SEQ ID NO 261
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 261
cgcctgggga ttaagccaca tattgtgcgc ttgctggacc agggg                    45

<210> SEQ ID NO 262
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 262
cccctggtcc agcaagcgca caatatgtgg cttaatcccc aggcg                    45

<210> SEQ ID NO 263
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 263
cgcctgggga ttaagccaca tattccgcgc ttgctggacc agggg                    45

<210> SEQ ID NO 264
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 264
cccctggtcc agcaagcgcg gaatatgtgg cttaatcccc aggcg                    45

<210> SEQ ID NO 265
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 265

-continued

--- cgcctgggga ttaagccaca tattatgcgc ttgctggacc agggg                                    45

<210> SEQ ID NO 266
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 266
cccctggtcc agcaagcgca taatatgtgg cttaatcccc aggcg                                     45

<210> SEQ ID NO 267
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 267
cgcctgggga ttaagccaca tattagccgc ttgctggacc agggg                                     45

<210> SEQ ID NO 268
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 268
cccctggtcc agcaagcggc taatatgtgg cttaatcccc aggcg                                     45

<210> SEQ ID NO 269
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 269
cgcctgggga ttaagccaca tattacccgc ttgctggacc agggg                                     45

<210> SEQ ID NO 270
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 270
cccctggtcc agcaagcggg taatatgtgg cttaatcccc aggcg                                     45

<210> SEQ ID NO 271
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 271
cgcctgggga ttaagccaca tatttgccgc ttgctggacc agggg                                     45

<210> SEQ ID NO 272
<211> LENGTH: 45
<212> TYPE: DNA
<213> ORGANISM: Artificial Sequence -continued

```
<220> FEATURE:
<223> OTHER INFORMATION: Synthetic oligonucleotide

<400> SEQUENCE: 272
cccctggtcc agcaagcggc aaatatgtgg cttaatcccc aggcg                    45

<210> SEQ ID NO 273
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 273
cgcctgggga ttaagccaca tatttttcgc ttgctggacc agggg                    45

<210> SEQ ID NO 274
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 274
cccctggtcc agcaagcgaa aaatatgtgg cttaatcccc aggcg                    45

<210> SEQ ID NO 275
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 275
cgcctgggga ttaagccaca tatttatcgc ttgctggacc agggg                    45

<210> SEQ ID NO 276
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 276
cccctggtcc agcaagcgat aaatatgtgg cttaatcccc aggcg                    45

<210> SEQ ID NO 277
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 277
cgcctgggga ttaagccaca tattcatcgc ttgctggacc agggg                    45

<210> SEQ ID NO 278
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 278
cccctggtcc agcaagcgat gaatatgtgg cttaatcccc aggcg                    45
```

<210> SEQ ID NO 279
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 279
cgcctgggga ttaagccaca tatttggcgc ttgctggacc agggg                    45

<210> SEQ ID NO 280
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 280
cccctggtcc agcaagcgcc aaatatgtgg cttaatcccc aggcg                    45

<210> SEQ ID NO 281
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 281
cgcctgggga ttaagccaca tattgatcgc ttgctggacc agggg                    45

<210> SEQ ID NO 282
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 282
cccctggtcc agcaagcgat caatatgtgg cttaatcccc aggcg                    45

<210> SEQ ID NO 283
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 283
cgcctgggga ttaagccaca tattaaccgc ttgctggacc agggg                    45

<210> SEQ ID NO 284
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 284
cccctggtcc agcaagcggt taatatgtgg cttaatcccc aggcg                    45

<210> SEQ ID NO 285
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 285
cgcctgggga ttaagccaca tattaaacgc ttgctggacc agggg                    45

<210> SEQ ID NO 286
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 286
cccctggtcc agcaagcgtt taatatgtgg cttaatcccc aggcg                    45

<210> SEQ ID NO 287
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 287
ccgtggaaca cccccccttgg ccccgtgaaa aagccaggta caaac                    45

<210> SEQ ID NO 288
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 288
gtttgtacct ggctttttca cggggccaag gggggtgttc cacgg                    45

<210> SEQ ID NO 289
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 289
ccgtggaaca ccccccttat tcccgtgaaa aagccaggta caaac                     45

<210> SEQ ID NO 290
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 290
gtttgtacct ggctttttca cgggaataag gggggtgttc cacgg                     45

<210> SEQ ID NO 291
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 291
ccgtggaaca ccccccttgt gcccgtgaaa aagccaggta caaac                     45

<210> SEQ ID NO 292

-continued

```
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 292
gtttgtacct ggcttttttca cgggcacaag gggggtgttc cacgg                    45

<210> SEQ ID NO 293
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 293
ccgtggaaca cccccttcc gcccgtgaaa aagccaggta caaac                      45

<210> SEQ ID NO 294
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 294
gtttgtacct ggcttttttca cgggcggaag gggggtgttc cacgg                    45

<210> SEQ ID NO 295
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 295
ccgtggaaca cccccttat gcccgtgaaa aagccaggta caaac                      45

<210> SEQ ID NO 296
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 296
gtttgtacct ggcttttttca cgggcataag gggggtgttc cacgg                    45

<210> SEQ ID NO 297
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 297
ccgtggaaca cccccttag ccccgtgaaa aagccaggta caaac                      45

<210> SEQ ID NO 298
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 298
```

```
gtttgtacct ggctttttca cggggctaag gggggtgttc cacgg                         45

<210> SEQ ID NO 299
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 299
ccgtggaaca ccccccttac ccccgtgaaa aagccaggta caaac                         45

<210> SEQ ID NO 300
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 300
gtttgtacct ggctttttca cgggggtaag gggggtgttc cacgg                         45

<210> SEQ ID NO 301
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 301
ccgtggaaca cccccctttg ccccgtgaaa aagccaggta caaac                         45

<210> SEQ ID NO 302
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 302
gtttgtacct ggctttttca cggggcaaag gggggtgttc cacgg                         45

<210> SEQ ID NO 303
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 303
ccgtggaaca cccccctttt tcccgtgaaa aagccaggta caaac                         45

<210> SEQ ID NO 304
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 304
gtttgtacct ggctttttca cgggaaaaag gggggtgttc cacgg                         45

<210> SEQ ID NO 305
<211> LENGTH: 45
<212> TYPE: DNA
```

-continued

<213> ORGANISM: Artificial Sequence
<220> FEATURE:
<223> OTHER INFORMATION: Synthetic oligonucleotide

<400> SEQUENCE: 305
ccgtggaaca ccccccttta tcccgtgaaa aagccaggta caaac                            45

<210> SEQ ID NO 306
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 306
gtttgtacct ggctttttca cgggataaag gggggtgttc cacgg                            45

<210> SEQ ID NO 307
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 307
ccgtggaaca ccccccttca tcccgtgaaa aagccaggta caaac                            45

<210> SEQ ID NO 308
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 308
gtttgtacct ggctttttca cgggatgaag gggggtgttc cacgg                            45

<210> SEQ ID NO 309
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 309
ccgtggaaca cccccctttg gcccgtgaaa aagccaggta caaac                            45

<210> SEQ ID NO 310
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 310
gtttgtacct ggctttttca cgggccaaag gggggtgttc cacgg                            45

<210> SEQ ID NO 311
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 311
ccgtggaaca ccccccttga tcccgtgaaa aagccaggta caaac                            45

<210> SEQ ID NO 312
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 312
gtttgtacct ggcttttttca cgggatcaag gggggtgttc cacgg                        45

<210> SEQ ID NO 313
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 313
ccgtggaaca ccccccttaa ccccgtgaaa aagccaggta caaac                        45

<210> SEQ ID NO 314
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 314
gtttgtacct ggcttttttca cggggttaag gggggtgttc cacgg                        45

<210> SEQ ID NO 315
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 315
ccgtggaaca ccccccttca gcccgtgaaa aagccaggta caaac                        45

<210> SEQ ID NO 316
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 316
gtttgtacct ggctttttca cgggctgaag gggggtgttc cacgg                        45

<210> SEQ ID NO 317
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 317
ccgtggaaca ccccccttaa acccgtgaaa aagccaggta caaac                        45

<210> SEQ ID NO 318
<211> LENGTH: 45
<212> TYPE: DNA
<213> ORGANISM: Artificial Sequence
<220> FEATURE:

-continued

<223> OTHER INFORMATION: Synthetic oligonucleotide

<400> SEQUENCE: 318
gtttgtacct ggctttttca cgggtttaag gggggtgttc cacgg                     45

<210> SEQ ID NO 319
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 319
agaaggtcaa cgttggctga ctggcgcgcg taaggagacc gtaatg                    46

<210> SEQ ID NO 320
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 320
cattacggtc tccttacgcg cgccagtcag ccaacgttga ccttct                    46

<210> SEQ ID NO 321
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 321
agaaggtcaa cgttggctga ctctggcgcg taaggagacc gtaatg                    46

<210> SEQ ID NO 322
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 322
cattacggtc tccttacgcg ccagagtcag ccaacgttga ccttct                    46

<210> SEQ ID NO 323
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 323
agaaggtcaa cgttggctga ctattgcgcg taaggagacc gtaatg                    46

<210> SEQ ID NO 324
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 324
cattacggtc tccttacgcg caatagtcag ccaacgttga ccttct                    46

-continued

```
<210> SEQ ID NO 325
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 325
agaaggtcaa cgttggctga ctgtggcgcg taaggagacc gtaatg                      46

<210> SEQ ID NO 326
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 326
cattacggtc tccttacgcg ccacagtcag ccaacgttga ccttct                      46

<210> SEQ ID NO 327
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 327
agaaggtcaa cgttggctga ctccggcgcg taaggagacc gtaatg                      46

<210> SEQ ID NO 328
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 328
cattacggtc tccttacgcg ccggagtcag ccaacgttga ccttct                      46

<210> SEQ ID NO 329
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 329
agaaggtcaa cgttggctga ctatggcgcg taaggagacc gtaatg                      46

<210> SEQ ID NO 330
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 330
cattacggtc tccttacgcg ccatagtcag ccaacgttga ccttct                      46

<210> SEQ ID NO 331
<211> LENGTH: 46
<212> TYPE: DNA
<213> ORGANISM: Artificial Sequence
<220> FEATURE:
<223> OTHER INFORMATION: Synthetic oligonucleotide
```

-continued

```
<400> SEQUENCE: 331
agaaggtcaa cgttggctga ctagcgcgcg taaggagacc gtaatg                    46

<210> SEQ ID NO 332
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 332
cattacggtc tccttacgcg cgctagtcag ccaacgttga ccttct                    46

<210> SEQ ID NO 333
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 333
agaaggtcaa cgttggctga ctaccgcgcg taaggagacc gtaatg                    46

<210> SEQ ID NO 334
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 334
cattacggtc tccttacgcg cggtagtcag ccaacgttga ccttct                    46

<210> SEQ ID NO 335
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 335
agaaggtcaa cgttggctga cttgcgcgcg taaggagacc gtaatg                    46

<210> SEQ ID NO 336
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 336
cattacggtc tccttacgcg cgcaagtcag ccaacgttga ccttct                    46

<210> SEQ ID NO 337
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 337
agaaggtcaa cgttggctga cttttgcgcg taaggagacc gtaatg                    46

<210> SEQ ID NO 338
<211> LENGTH: 46
```

```
<212> TYPE: DNA
<213> ORGANISM: Artificial Sequence
<220> FEATURE:
<223> OTHER INFORMATION: Synthetic oligonucleotide

<400> SEQUENCE: 338
cattacggtc tccttacgcg caaaagtcag ccaacgttga ccttct                    46

<210> SEQ ID NO 339
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 339
agaaggtcaa cgttggctga cttatgcgcg taaggagacc gtaatg                    46

<210> SEQ ID NO 340
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 340
cattacggtc tccttacgcg cataagtcag ccaacgttga ccttct                    46

<210> SEQ ID NO 341
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 341
agaaggtcaa cgttggctga ctcatgcgcg taaggagacc gtaatg                    46

<210> SEQ ID NO 342
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 342
cattacggtc tccttacgcg catgagtcag ccaacgttga ccttct                    46

<210> SEQ ID NO 343
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 343
agaaggtcaa cgttggctga cttgggcgcg taaggagacc gtaatg                    46

<210> SEQ ID NO 344
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 344
```

```
cattacggtc tccttacgcg cccaagtcag ccaacgttga ccttct                      46
```

```
<210> SEQ ID NO 345
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 345
agaaggtcaa cgttggctga ctaacgcgcg taaggagacc gtaatg                      46
```

```
<210> SEQ ID NO 346
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 346
cattacggtc tccttacgcg cgttagtcag ccaacgttga ccttct                      46
```

```
<210> SEQ ID NO 347
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 347
agaaggtcaa cgttggctga ctcaggcgcg taaggagacc gtaatg                      46
```

```
<210> SEQ ID NO 348
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 348
cattacggtc tccttacgcg cctgagtcag ccaacgttga ccttct                      46
```

```
<210> SEQ ID NO 349
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 349
agaaggtcaa cgttggctga ctaaagcgcg taaggagacc gtaatg                      46
```

```
<210> SEQ ID NO 350
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 350
cattacggtc tccttacgcg ctttagtcag ccaacgttga ccttct                      46
```

```
<210> SEQ ID NO 351
<211> LENGTH: 47
<212> TYPE: DNA
<213> ORGANISM: Artificial Sequence
```

-continued

<220> FEATURE:
<223> OTHER INFORMATION: Synthetic oligonucleotide

<400> SEQUENCE: 351
gcctacgcct aagacgccag gccagttgcg tgaatttttg ggcacag                    47

<210> SEQ ID NO 352
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 352
ctgtgcccaa aaattcacgc aactggcctg gcgtcttagg cgtaggc                    47

<210> SEQ ID NO 353
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 353
gcctacgcct aagacgccac tgcagttgcg tgaatttttg ggcacag                    47

<210> SEQ ID NO 354
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 354
ctgtgcccaa aaattcacgc aactgcagtg gcgtcttagg cgtaggc                    47

<210> SEQ ID NO 355
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 355
gcctacgcct aagacgccaa ttcagttgcg tgaatttttg ggcacag                    47

<210> SEQ ID NO 356
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 356
ctgtgcccaa aaattcacgc aactgaattg gcgtcttagg cgtaggc                    47

<210> SEQ ID NO 357
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 357
gcctacgcct aagacgccag tgcagttgcg tgaatttttg ggcacag                    47

-continued

```
<210> SEQ ID NO 358
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 358
ctgtgcccaa aaattcacgc aactgcactg gcgtcttagg cgtaggc              47

<210> SEQ ID NO 359
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 359
gcctacgcct aagacgccac cgcagttgcg tgaattttg ggcacag               47

<210> SEQ ID NO 360
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 360
ctgtgcccaa aaattcacgc aactgcggtg gcgtcttagg cgtaggc              47

<210> SEQ ID NO 361
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 361
gcctacgcct aagacgccaa tgcagttgcg tgaattttg ggcacag               47

<210> SEQ ID NO 362
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 362
ctgtgcccaa aaattcacgc aactgcattg gcgtcttagg cgtaggc              47

<210> SEQ ID NO 363
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 363
gcctacgcct aagacgccaa gccagttgcg tgaattttg ggcacag               47

<210> SEQ ID NO 364
<211> LENGTH: 47
<212> TYPE: DNA
<213> ORGANISM: Artificial Sequence
<220> FEATURE:
<223> OTHER INFORMATION: Synthetic oligonucleotide
```

<400> SEQUENCE: 364
ctgtgcccaa aaattcacgc aactggcttg gcgtcttagg cgtaggc          47

<210> SEQ ID NO 365
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 365
gcctacgcct aagacgccaa cccagttgcg tgaatttttg ggcacag          47

<210> SEQ ID NO 366
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 366
ctgtgcccaa aaattcacgc aactgggttg gcgtcttagg cgtaggc          47

<210> SEQ ID NO 367
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 367
gcctacgcct aagacgccat gccagttgcg tgaatttttg ggcacag          47

<210> SEQ ID NO 368
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 368
ctgtgcccaa aaattcacgc aactggcatg gcgtcttagg cgtaggc          47

<210> SEQ ID NO 369
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 369
gcctacgcct aagacgccat ttcagttgcg tgaatttttg ggcacag          47

<210> SEQ ID NO 370
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 370
ctgtgcccaa aaattcacgc aactgaaatg gcgtcttagg cgtaggc          47

<210> SEQ ID NO 371

```
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 371
gcctacgcct aagacgccat atcagttgcg tgaatttttg ggcacag                    47

<210> SEQ ID NO 372
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 372
ctgtgcccaa aaattcacgc aactgatatg gcgtcttagg cgtaggc                    47

<210> SEQ ID NO 373
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 373
gcctacgcct aagacgccac atcagttgcg tgaatttttg ggcacag                    47

<210> SEQ ID NO 374
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 374
ctgtgcccaa aaattcacgc aactgatgtg gcgtcttagg cgtaggc                    47

<210> SEQ ID NO 375
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 375
gcctacgcct aagacgccat ggcagttgcg tgaatttttg ggcacag                    47

<210> SEQ ID NO 376
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 376
ctgtgcccaa aaattcacgc aactgccatg gcgtcttagg cgtaggc                    47

<210> SEQ ID NO 377
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 377
```

-continued gcctacgcct aagacgccag atcagttgcg tgaatttttg ggcacag                    47

<210> SEQ ID NO 378
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 378
ctgtgcccaa aaattcacgc aactgatctg gcgtcttagg cgtaggc                    47

<210> SEQ ID NO 379
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 379
gcctacgcct aagacgccaa accagttgcg tgaatttttg ggcacag                    47

<210> SEQ ID NO 380
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 380
ctgtgcccaa aaattcacgc aactggtttg gcgtcttagg cgtaggc                    47

<210> SEQ ID NO 381
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 381
gcctacgcct aagacgccac agcagttgcg tgaatttttg ggcacag                    47

<210> SEQ ID NO 382
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 382
ctgtgcccaa aaattcacgc aactgctgtg gcgtcttagg cgtaggc                    47

<210> SEQ ID NO 383
<211> LENGTH: 62
<212> TYPE: DNA
<213> ORGANISM: Artificial Sequence
<220> FEATURE:
<223> OTHER INFORMATION: Synthetic oligonucleotide

<400> SEQUENCE: 383
aggcaacgtc tacacctgtc tctcgtaaac agtaccccat gagtcgtgag gcccgcctgg    60
gg                                                                    62

<210> SEQ ID NO 384

-continued

```
<211> LENGTH: 62
<212> TYPE: DNA
<213> ORGANISM: Artificial Sequence
<220> FEATURE:
<223> OTHER INFORMATION: Synthetic oligonucleotide

<400> SEQUENCE: 384
ccccaggcgg gcctcacgac tcatggggta ctgtttacga gagacaggtg tagacgttgc      60
ct                                                                      62

<210> SEQ ID NO 385
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 385
aggcaacgtc tacacctgtc tctaaaaaac agtaccccat gagtcgtgag g               51

<210> SEQ ID NO 386
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 386
cctcacgact catggggtac tgtttttttag agacaggtgt agacgttgcc t              51

<210> SEQ ID NO 387
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 387
aggcaacgtc tacacctgtc tctatgaaac agtaccccat gagtcgtgag g               51

<210> SEQ ID NO 388
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 388
cctcacgact catggggtac tgtttcatag agacaggtgt agacgttgcc t               51

<210> SEQ ID NO 389
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 389
aggcaacgtc tacacctgtc tctatgaaac agtaccccat gagtattgag gcc             53

<210> SEQ ID NO 390

<400> SEQUENCE: 390

000
```

-continued

<210> SEQ ID NO 391

<400> SEQUENCE: 391

000

<210> SEQ ID NO 392

<400> SEQUENCE: 392

000

<210> SEQ ID NO 393
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 393
gtctctatca aacagtaccc catggcgcaa gaggcccgcc tggg                     44

<210> SEQ ID NO 394
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 394
gtctctatca aacagtaccc catgcgtcaa gaggcccgcc tggg                     44

<210> SEQ ID NO 395
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 395
catgagtcaa gaggcccgcg aggggattaa gccacatatt cagcg                    45

<210> SEQ ID NO 396
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 396
gagtcaagag gcccgcctgg cgattaagcc acatattcag cgcttgc                  47

<210> SEQ ID NO 397
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 397
gagtcaagag gcccgcctgc gtattaagcc acatattcag cgcttgc                  47

<210> SEQ ID NO 398
<211> LENGTH: 47
<212> TYPE: DNA
<213> ORGANISM: Artificial Sequence -continued
<220> FEATURE:
<223> OTHER INFORMATION: Synthetic oligonucleotide

<400> SEQUENCE: 398
gagtcaagag gcccgcctgg agattaagcc acatattcag cgcttgc                47

<210> SEQ ID NO 399
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 399
ggcccgcctg gggattaagg cgcatattca gcgcttgctg gacc                44

<210> SEQ ID NO 400
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 400
ggcccgcctg gggattaagc gtcatattca gcgcttgctg gacc                44

<210> SEQ ID NO 401
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 401
ggcccgcctg gggattaagg agcatattca gcgcttgctg gacc                44

<210> SEQ ID NO 402
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 402
ccgcctgggg attaagccag cgattcagcg cttgctggac cag                 43

<210> SEQ ID NO 403
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 403
ccgcctgggg attaagccac gtattcagcg cttgctggac cag                 43

<210> SEQ ID NO 404
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 404
ccgcctgggg attaagccag agattcagcg cttgctggac cag                 43

<210> SEQ ID NO 405
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 405
gattaagcca catattcagc gcttggcgga ccaggggatc ttggtcc                      47

<210> SEQ ID NO 406
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 406
gattaagcca catattcagc gcttgcgtga ccaggggatc ttggtcc                      47

<210> SEQ ID NO 407
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 407
gattaagcca catattcagc gcttggagga ccaggggatc ttggtcc                      47

<210> SEQ ID NO 408
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 408
gccacatatt cagcgcttgc tggcgcaggg gatcttggtc ccatg                        45

<210> SEQ ID NO 409
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 409
gccacatatt cagcgcttgc tgcgtcaggg gatcttggtc ccatg                        45

<210> SEQ ID NO 410
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 410
gccacatatt cagcgcttgc tggagcaggg gatcttggtc ccatg                        45

<210> SEQ ID NO 411
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 411
aggtcaacaa acgcgtagaa gacgcgcatc cgactgtacc taatccttat aat          53

<210> SEQ ID NO 412
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 412
aggtcaacaa acgcgtagaa gaccgtcatc cgactgtacc taatccttat aat          53

<210> SEQ ID NO 413
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 413
aggtcaacaa acgcgtagaa gacgagcatc cgactgtacc taatccttat aat          53

<210> SEQ ID NO 414
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 414
gcgtagaaga catccatccg actgcgccta atccttataa tctgttatca ggc          53

<210> SEQ ID NO 415
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 415
gcgtagaaga catccatccg actcgtccta atccttataa tctgttatca ggc          53

<210> SEQ ID NO 416
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 416
gcgtagaaga catccatccg actgagccta atccttataa tctgttatca ggc          53

<210> SEQ ID NO 417
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 417
agggctttaa aaacagcccc acagcgttcg atgaagcact tcaccgtga          49

<210> SEQ ID NO 418

-continued

```
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 418
agggctttaa aaacagcccc acacgtttcg atgaagcact tcaccgtga                49

<210> SEQ ID NO 419
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 419
agggctttaa aaacagcccc acagagttcg atgaagcact tcaccgtga                49

<210> SEQ ID NO 420
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 420
tttaaaaaca gccccacatt gttcgatgcg gcacttcacc gtgacttagc ag            52

<210> SEQ ID NO 421
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 421
tttaaaaaca gccccacatt gttcgatcgt gcacttcacc gtgacttagc ag            52

<210> SEQ ID NO 422
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 422
tttaaaaaca gccccacatt gttcgatgat gcacttcacc gtgacttagc ag            52

<210> SEQ ID NO 423
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 423
cacattgttc gatgaagcac ttcacgcgga cttagcagac ttccgtatcc a             51

<210> SEQ ID NO 424
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 424
```

-continued cacattgttc gatgaagcac ttcacaaaga cttagcagac ttccgtatcc a          51

<210> SEQ ID NO 425
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 425
gatgaagcac ttcaccgtga cttagaggac ttccgtatcc aacacccag            49

<210> SEQ ID NO 426
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 426
aagcacttca ccgtgactta gcagcgttcc gtatccaaca cccagactt            49

<210> SEQ ID NO 427
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 427
aagcacttca ccgtgactta gcacgtttcc gtatccaaca cccagactt            49

<210> SEQ ID NO 428
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 428
aagcacttca ccgtgactta gcagagttcc gtatccaaca cccagactt            49

<210> SEQ ID NO 429
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 429
cacttcaccg tgacttagca gacgcgcgta tccaacaccc agacttaatt c          51

<210> SEQ ID NO 430
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 430
cacttcaccg tgacttagca gaccgtcgta tccaacaccc agacttaatt c          51

<210> SEQ ID NO 431
<211> LENGTH: 51
<212> TYPE: DNA

<213> ORGANISM: Artificial Sequence
<220> FEATURE:
<223> OTHER INFORMATION: Synthetic oligonucleotide

<400> SEQUENCE: 431
cacttcaccg tgacttagca gacgagcgta tccaacaccc agacttaatt c            51

<210> SEQ ID NO 432
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 432
ttcaccgtga cttagcagac ttcgcgatcc aacacccaga cttaattctg tta            53

<210> SEQ ID NO 433
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 433
ttcaccgtga cttagcagac ttcaaaatcc aacacccaga cttaattctg tta            53

<210> SEQ ID NO 434
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 434
ttcaccgtga cttagcagac ttcgagatcc aacacccaga cttaattctg tta            53

<210> SEQ ID NO 435
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 435
ccgtgactta gcagacttcc gtgcgcaaca cccagactta attctgttac ag            52

<210> SEQ ID NO 436
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 436
ccgtgactta gcagacttcc gtcgtcaaca cccagactta attctgttac ag            52

<210> SEQ ID NO 437
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 437
ccgtgactta gcagacttcc gtgagcaaca cccagactta attctgttac ag            52

-continued

```
<210> SEQ ID NO 438
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 438
gtgacttagc agacttccgt atcgcgcacc cagacttaat tctgttacag tat          53

<210> SEQ ID NO 439
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 439
gtgacttagc agacttccgt atccgtcacc cagacttaat tctgttacag tat          53

<210> SEQ ID NO 440
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 440
gtgacttagc agacttccgt atcgagcacc cagacttaat tctgttacag tat          53

<210> SEQ ID NO 441
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 441
agcaaaaggc gtatcaggag atcgcgcaag ctttgttgac cgcaccc                  47

<210> SEQ ID NO 442
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 442
agcaaaaggc gtatcaggag atccgtcaag ctttgttgac cgcaccc                  47

<210> SEQ ID NO 443
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 443
agcaaaaggc gtatcaggag atcgagcaag ctttgttgac cgcaccc                  47

<210> SEQ ID NO 444
<211> LENGTH: 46
<212> TYPE: DNA
<213> ORGANISM: Artificial Sequence
<220> FEATURE:
```

<223> OTHER INFORMATION: Synthetic oligonucleotide

<400> SEQUENCE: 444
cgtatcagga gatcaaacaa gctttggcga ccgcacccgc gttggg                        46

<210> SEQ ID NO 445
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 445
cgtatcagga gatcaaacaa gctttgcgta ccgcacccgc gttggg                        46

<210> SEQ ID NO 446
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 446
cgtatcagga gatcaaacaa gctttggaga ccgcacccgc gttggg                        46

<210> SEQ ID NO 447
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 447
gttggctgac tgaagcgcgt gcggagaccg taatggggca gc                           42

<210> SEQ ID NO 448
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 448
gttggctgac tgaagcgcgt cgtgagaccg taatggggca gc                           42

<210> SEQ ID NO 449
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 449
gttggctgac tgaagcgcgt gaggagaccg taatggggca gc                           42

<210> SEQ ID NO 450
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 450
tacgcctaag acgccacgcg cgttgcgtga atttttgggc acagc                        45

-continued

```
<210> SEQ ID NO 451
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 451
tacgcctaag acgccacgcc gtttgcgtga atttttgggc acagc                         45

<210> SEQ ID NO 452
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 452
tacgcctaag acgccacgcg agttgcgtga atttttgggc acagc                         45

<210> SEQ ID NO 453
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 453
gcgtgaattt ttgggcacag cggcgttctg tcgtttatgg attcctggg                     49

<210> SEQ ID NO 454
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 454
gcgtgaattt ttgggcacag cgcgtttctg tcgtttatgg attcctggg                     49

<210> SEQ ID NO 455
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 455
gcgtgaattt ttgggcacag cggagttctg tcgtttatgg attcctggg                     49

<210> SEQ ID NO 456
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 456
gggcacagcg ggattctgtg cgttatggat tcctgggttc gctga                         45

<210> SEQ ID NO 457
<211> LENGTH: 45
<212> TYPE: DNA
<213> ORGANISM: Artificial Sequence
<220> FEATURE:
<223> OTHER INFORMATION: Synthetic oligonucleotide
```

-continued

<400> SEQUENCE: 457
gggcacagcg ggattctgta aattatggat tcctgggttc gctga                45

<210> SEQ ID NO 458
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 458
gggcacagcg ggattctgtg agttatggat tcctgggttc gctga                45

<210> SEQ ID NO 459
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 459
gtcaaaaaca ggtaaagtac cttggggcgt tgctgaaaga aggtcaacgt tgg          53

<210> SEQ ID NO 460
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 460
gtcaaaaaca ggtaaagtac cttgggcgtt tgctgaaaga aggtcaacgt tgg          53

<210> SEQ ID NO 461
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 461
gtcaaaaaca ggtaaagtac cttggggagt tgctgaaaga aggtcaacgt tgg          53

<210> SEQ ID NO 462
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 462
tgctgaaaga aggtcaacgt tgggcgactg aagcgcgtaa ggagacc               47

<210> SEQ ID NO 463
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 463
tgctgaaaga aggtcaacgt tggcgtactg aagcgcgtaa ggagacc               47

<210> SEQ ID NO 464
<211> LENGTH: 47

-continued

```
<212> TYPE: DNA
<213> ORGANISM: Artificial Sequence
<220> FEATURE:
<223> OTHER INFORMATION: Synthetic oligonucleotide

<400> SEQUENCE: 464
tgctgaaaga aggtcaacgt tgggagactg aagcgcgtaa ggagacc                47

<210> SEQ ID NO 465
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 465
tttgttgacc gcacccgcgg cgggtcttcc ggatttaacc aagcc            45

<210> SEQ ID NO 466
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 466
tttgttgacc gcacccgcgc gtggtcttcc ggatttaacc aagcc            45

<210> SEQ ID NO 467
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 467
tttgttgacc gcacccgcgg agggtcttcc ggatttaacc aagcc            45

<210> SEQ ID NO 468
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 468
ctgcacccct gtacccctta gcgaaaacag ggacgctttt caactgg            47

<210> SEQ ID NO 469
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 469
ctgcacccct gtacccctta cgtaaaacag ggacgctttt caactgg            47

<210> SEQ ID NO 470
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 470
```

-continued

```
ctgcacccct gtaccccttta gagaaaacag ggacgctttt caactgg                    47

<210> SEQ ID NO 471
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 471
cccctgtacc ccttaacaaa aacagcgacg cttttcaact ggggggcc                    47

<210> SEQ ID NO 472
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 472
cccctgtacc ccttaacaaa aacacgtacg cttttcaact ggggggcc                    47

<210> SEQ ID NO 473
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 473
cccctgtacc ccttaacaaa aacagagacg cttttcaact ggggggcc                    47

<210> SEQ ID NO 474
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 474 ctgtaccct taacaaaaac aggggcgctt ttcaactggg ggccagac                     48

<210> SEQ ID NO 475
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 475 ctgtaccct taacaaaaac agggcgtctt ttcaactggg ggccagac                     48

<210> SEQ ID NO 476
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 476 ctgtaccct taacaaaaac aggggagctt ttcaactggg ggccagac                     48

<210> SEQ ID NO 477
<211> LENGTH: 48
<212> TYPE: DNA
<213> ORGANISM: Artificial Sequence
```

```
<220> FEATURE:
<223> OTHER INFORMATION: Synthetic oligonucleotide

<400> SEQUENCE: 477
ccttaacaaa aacagggacg cttttcgcgt gggggccaga ccagcaaa                      48

<210> SEQ ID NO 478
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 478
ccttaacaaa aacagggacg cttttccgtt gggggccaga ccagcaaa                      48

<210> SEQ ID NO 479
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 479
cttccggatt taaccaagcc ctttgcgctg ttcgttgatg aaaaacaggg atat             54

<210> SEQ ID NO 480
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 480
cttccggatt taaccaagcc ctttcgtctg ttcgttgatg aaaaacaggg atat             54

<210> SEQ ID NO 481
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 481
cttccggatt taaccaagcc ctttgatctg ttcgttgatg aaaaacaggg atat             54

<210> SEQ ID NO 482
<211> LENGTH: 55
<212> TYPE: DNA
<213> ORGANISM: Artificial Sequence
<220> FEATURE:
<223> OTHER INFORMATION: Synthetic oligonucleotide

<400> SEQUENCE: 482
gatttaacca agccctttga gctggcggtt gatgaaaaac agggatatgc aaaag           55

<210> SEQ ID NO 483
<211> LENGTH: 55
<212> TYPE: DNA
<213> ORGANISM: Artificial Sequence
<220> FEATURE:
<223> OTHER INFORMATION: Synthetic oligonucleotide

<400> SEQUENCE: 483
gatttaacca agccctttga gctgcgtgtt gatgaaaaac agggatatgc aaaag           55
```

-continued

```
<210> SEQ ID NO 484
<211> LENGTH: 55
<212> TYPE: DNA
<213> ORGANISM: Artificial Sequence
<220> FEATURE:
<223> OTHER INFORMATION: Synthetic oligonucleotide

<400> SEQUENCE: 484
gatttaacca agccctttga gctggaggtt gatgaaaaac agggatatgc aaaag        55

<210> SEQ ID NO 485
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 485
cccaaaagtt aggcccgtgg gcgcgccctg ttgcttactt gagtaa             46

<210> SEQ ID NO 486
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 486
cccaaaagtt aggcccgtgg aaacgccctg ttgcttactt gagtaa             46

<210> SEQ ID NO 487
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 487
cccaaaagtt aggcccgtgg gagcgccctg ttgcttactt gagtaa             46

<210> SEQ ID NO 488
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 488
agttgacgat gggtcaaccc ttagcgatct tggctccaca tgctgtaga         49

<210> SEQ ID NO 489
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 489
agttgacgat gggtcaaccc ttacgtatct tggctccaca tgctgtaga         49

<210> SEQ ID NO 490
<211> LENGTH: 49
<212> TYPE: DNA
<213> ORGANISM: Artificial Sequence
<220> FEATURE:
<223> OTHER INFORMATION: Synthetic oligonucleotide
```

-continued

<400> SEQUENCE: 490
agttgacgat gggtcaaccc ttagagatct tggctccaca tgctgtaga                          49

<210> SEQ ID NO 491
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 491
ggatcgtgta caatttggac cagttgcggc tttgaatcca gctactttgc ttc                     53

<210> SEQ ID NO 492
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 492
ggatcgtgta caatttggac cagttcgtgc tttgaatcca gctactttgc ttc                     53

<210> SEQ ID NO 493
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 493
ggatcgtgta caatttggac cagttgaggc tttgaatcca gctactttgc ttc                     53

<210> SEQ ID NO 494
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 494
cgttatgctt ttgcaacagc gcatgcgcat ggcgaaattt accgccgc                          48

<210> SEQ ID NO 495
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 495
cgttatgctt ttgcaacagc gcatcgtcat ggcgaaattt accgccgc                          48

<210> SEQ ID NO 496
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 496
cgttatgctt ttgcaacagc gcatgagcat ggcgaaattt accgccgc                          48

<210> SEQ ID NO 497

<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 497
gcaacagcgc atatccatgg cgcgatttac cgccgccgtg gtc                43

<210> SEQ ID NO 498
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 498
gcaacagcgc atatccatgg ccgtatttac cgccgccgtg gtc                43

<210> SEQ ID NO 499
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 499
gcaacagcgc atatccatgg cgatatttac cgccgccgtg gtc                43

<210> SEQ ID NO 500
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 500
caacagcgca tatccatggc gaagcgtacc gccgccgtgg tctg                44

<210> SEQ ID NO 501
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 501
caacagcgca tatccatggc gaacgttacc gccgccgtgg tctg                44

<210> SEQ ID NO 502
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 502
caacagcgca tatccatggc gaagagtacc gccgccgtgg tctg                44

<210> SEQ ID NO 503
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 503

```
agcggaggct cgtggaaacg cgatggcgga ccaagctgcc c                              41

<210> SEQ ID NO 504
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 504
agcggaggct cgtggaaaca aaatggcgga ccaagctgcc c                              41

<210> SEQ ID NO 505
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 505
agcggaggct cgtggaaacg agatggcgga ccaagctgcc c                              41

<210> SEQ ID NO 506
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 506
gtggaaaccg tatggcggac gcggctgccc gtaaggcggc                               40

<210> SEQ ID NO 507
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 507
gtggaaaccg tatggcggac cgtgctgccc gtaaggcggc                               40

<210> SEQ ID NO 508
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 508
gtggaaaccg tatggcggac gaggctgccc gtaaggcggc                               40

<210> SEQ ID NO 509
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 509
tatggcggac caagctgccg cgaaggcggc gatcacagag ac                            42

<210> SEQ ID NO 510
<211> LENGTH: 42
<212> TYPE: DNA
```

-continued

<213> ORGANISM: Artificial Sequence
<220> FEATURE:
<223> OTHER INFORMATION: Synthetic oligonucleotide

<400> SEQUENCE: 510
tatggcggac caagctgcca aaaaggcggc gatcacagag ac                              42

<210> SEQ ID NO 511
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 511
tatggcggac caagctgccg agaaggcggc gatcacagag ac                              42

<210> SEQ ID NO 512
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 512
gcaagcgctg aatatgtggc ttaatcgcca ggcgggcctc ttgactc                        47

<210> SEQ ID NO 513
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 513
gcaagcgctg aatatgtggc ttaatacgca ggcgggcctc ttgactc                        47

<210> SEQ ID NO 514
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 514
gcaagcgctg aatatgtggc ttaatctcca ggcgggcctc ttgactc                        47

<210> SEQ ID NO 515
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 515
ggtccagcaa gcgctgaata tgcgccttaa tccccaggcg ggcc                           44

<210> SEQ ID NO 516
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 516
ggtccagcaa gcgctgaata tgacgcttaa tccccaggcg ggcc                           44

-continued

```
<210> SEQ ID NO 517
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 517
ggtccagcaa gcgctgaata tgctccttaa tccccaggcg ggcc                     44

<210> SEQ ID NO 518
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 518
ctggtccagc aagcgctgaa tcgctggctt aatccccagg cgg                      43

<210> SEQ ID NO 519
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 519
ctggtccagc aagcgctgaa tacgtggctt aatccccagg cgg                      43

<210> SEQ ID NO 520
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 520
ctggtccagc aagcgctgaa tctctggctt aatccccagg cgg                      43

<210> SEQ ID NO 521
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 521
ggaccaagat cccctggtcc gccaagcgct gaatatgtgg cttaatc                  47

<210> SEQ ID NO 522
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 522
ggaccaagat cccctggtca cgcaagcgct gaatatgtgg cttaatc                  47

<210> SEQ ID NO 523
<211> LENGTH: 47
<212> TYPE: DNA
<213> ORGANISM: Artificial Sequence
<220> FEATURE:
```

<223> OTHER INFORMATION: Synthetic oligonucleotide

<400> SEQUENCE: 523
ggaccaagat cccctggtcc tccaagcgct gaatatgtgg cttaatc                 47

<210> SEQ ID NO 524
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 524
catgggacca agatcccctg cgccagcaag cgctgaatat gtggc                   45

<210> SEQ ID NO 525
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 525
catgggacca agatcccctg acgcagcaag cgctgaatat gtggc                   45

<210> SEQ ID NO 526
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 526
catgggacca agatcccctg ctccagcaag cgctgaatat gtggc                   45

<210> SEQ ID NO 527
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 527
attataagga ttaggtacag tcggatgcgc gtcttctacg cgtttgttga cct          53

<210> SEQ ID NO 528
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 528
attataagga ttaggtacag tcggatgacg gtcttctacg cgtttgttga cct          53

<210> SEQ ID NO 529
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 529
attataagga ttaggtacag tcggatgctc gtcttctacg cgtttgttga cct          53

-continued

<210> SEQ ID NO 530
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 530
gcctgataac agattataag gattaggcgc agtcggatgg atgtcttcta cgc          53

<210> SEQ ID NO 531
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 531
gcctgataac agattataag gattaggacg agtcggatgg atgtcttcta cgc          53

<210> SEQ ID NO 532
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 532
gcctgataac agattataag gattaggctc agtcggatgg atgtcttcta cgc          53

<210> SEQ ID NO 533
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 533
tcacggtgaa gtgcttcatc gaacgctgtg gggctgtttt taaagccct              49

<210> SEQ ID NO 534
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 534
tcacggtgaa gtgcttcatc gaaacgtgtg gggctgtttt taaagccct              49

<210> SEQ ID NO 535
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 535
tcacggtgaa gtgcttcatc gaactctgtg gggctgtttt taaagccct              49

<210> SEQ ID NO 536
<211> LENGTH: 52
<212> TYPE: DNA
<213> ORGANISM: Artificial Sequence
<220> FEATURE:
<223> OTHER INFORMATION: Synthetic oligonucleotide -continued

```
<400> SEQUENCE: 536
ctgctaagtc acggtgaagt gccgcatcga acaatgtggg gctgttttta aa            52

<210> SEQ ID NO 537
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 537
ctgctaagtc acggtgaagt gcacgatcga acaatgtggg gctgttttta aa            52

<210> SEQ ID NO 538
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 538
ctgctaagtc acggtgaagt gcatcatcga acaatgtggg gctgttttta aa            52

<210> SEQ ID NO 539
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 539
tggatacgga agtctgctaa gtccgcgtga agtgcttcat cgaacaatgt g            51

<210> SEQ ID NO 540
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 540
tggatacgga agtctgctaa gtctttgtga agtgcttcat cgaacaatgt g            51

<210> SEQ ID NO 541
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 541
tggatacgga agtctgctaa gtcctcgtga agtgcttcat cgaacaatgt g            51

<210> SEQ ID NO 542
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 542
aagtctgggt gttggatacg gaacgctgct aagtcacggt gaagtgctt              49

<210> SEQ ID NO 543
<211> LENGTH: 49
```

-continued

```
<212> TYPE: DNA
<213> ORGANISM: Artificial Sequence
<220> FEATURE:
<223> OTHER INFORMATION: Synthetic oligonucleotide

<400> SEQUENCE: 543
aagtctgggt gttggatacg gaaacgtgct aagtcacggt gaagtgctt                49

<210> SEQ ID NO 544
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 544
aagtctgggt gttggatacg gaactctgct aagtcacggt gaagtgctt                49

<210> SEQ ID NO 545
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 545
gaattaagtc tgggtgttgg atacgcgcgt ctgctaagtc acggtgaagt g             51

<210> SEQ ID NO 546
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 546
gaattaagtc tgggtgttgg atacgacggt ctgctaagtc acggtgaagt g             51

<210> SEQ ID NO 547
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 547
gaattaagtc tgggtgttgg atacgctcgt ctgctaagtc acggtgaagt g             51

<210> SEQ ID NO 548
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 548
taacagaatt aagtctgggt gttggatcgc gaagtctgct aagtcacggt gaa           53

<210> SEQ ID NO 549
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 549
```

-continued

```
taacagaatt aagtctgggt gttggatttt gaagtctgct aagtcacggt gaa          53

<210> SEQ ID NO 550
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 550
taacagaatt aagtctgggt gttggatctc gaagtctgct aagtcacggt gaa          53

<210> SEQ ID NO 551
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 551
ctgtaacaga attaagtctg ggtgttgcgc acggaagtct gctaagtcac gg           52

<210> SEQ ID NO 552
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 552
ctgtaacaga attaagtctg ggtgttgacg acggaagtct gctaagtcac gg           52

<210> SEQ ID NO 553
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 553
ctgtaacaga attaagtctg ggtgttgctc acggaagtct gctaagtcac gg           52

<210> SEQ ID NO 554
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 554
atactgtaac agaattaagt ctgggtgcgc gatacggaag tctgctaagt cac          53

<210> SEQ ID NO 555
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 555
atactgtaac agaattaagt ctgggtgacg gatacggaag tctgctaagt cac          53

<210> SEQ ID NO 556
<211> LENGTH: 53
<212> TYPE: DNA
<213> ORGANISM: Artificial Sequence
```

-continued

```
<220> FEATURE:
<223> OTHER INFORMATION: Synthetic oligonucleotide

<400> SEQUENCE: 556
atactgtaac agaattaagt ctgggtgctc gatacggaag tctgctaagt cac          53

<210> SEQ ID NO 557
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 557
gggtgcggtc aacaaagctt gcgcgatctc ctgatacgcc ttttgct               47

<210> SEQ ID NO 558
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 558
gggtgcggtc aacaaagctt gacggatctc ctgatacgcc ttttgct               47

<210> SEQ ID NO 559
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 559
gggtgcggtc aacaaagctt gctcgatctc ctgatacgcc ttttgct               47

<210> SEQ ID NO 560
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 560
cccaacgcgg gtgcggtcgc caaagcttgt ttgatctcct gatacg                46

<210> SEQ ID NO 561
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 561
cccaacgcgg gtgcggtacg caaagcttgt ttgatctcct gatacg                46

<210> SEQ ID NO 562
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 562
cccaacgcgg gtgcggtctc caaagcttgt ttgatctcct gatacg                46
```

-continued

```
<210> SEQ ID NO 563
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 563
gctgccccat tacggtctcc gcacgcgctt cagtcagcca ac                          42

<210> SEQ ID NO 564
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 564
gctgccccat tacggtctca cgacgcgctt cagtcagcca ac                          42

<210> SEQ ID NO 565
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 565
gctgccccat tacggtctcc tcacgcgctt cagtcagcca ac                          42

<210> SEQ ID NO 566
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 566
gctgtgccca aaaattcacg caacgcgcgt ggcgtcttag gcgta                       45

<210> SEQ ID NO 567
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 567
gctgtgccca aaaattcacg caaacggcgt ggcgtcttag gcgta                       45

<210> SEQ ID NO 568
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 568
gctgtgccca aaaattcacg caactcgcgt ggcgtcttag gcgta                       45

<210> SEQ ID NO 569
<211> LENGTH: 49
<212> TYPE: DNA
<213> ORGANISM: Artificial Sequence
<220> FEATURE:
<223> OTHER INFORMATION: Synthetic oligonucleotide
```

-continued

```
<400> SEQUENCE: 569
cccaggaatc cataaacgac agaacgccgc tgtgcccaaa aattcacgc              49

<210> SEQ ID NO 570
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 570
cccaggaatc cataaacgac agaaacgcgc tgtgcccaaa aattcacgc              49

<210> SEQ ID NO 571
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 571
cccaggaatc cataaacgac agaactccgc tgtgcccaaa aattcacgc              49

<210> SEQ ID NO 572
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 572
tcagcgaacc caggaatcca taacgcacag aatcccgctg tgccc                 45

<210> SEQ ID NO 573
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 573
tcagcgaacc caggaatcca taatttacag aatcccgctg tgccc                 45

<210> SEQ ID NO 574
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 574
tcagcgaacc caggaatcca taactcacag aatcccgctg tgccc                 45

<210> SEQ ID NO 575
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 575
ccaacgttga ccttctttca gcaacgcccc aaggtacttt acctgttttt gac        53

<210> SEQ ID NO 576
```

-continued

```
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 576
ccaacgttga ccttctttca gcaaacgccc aaggtacttt acctgttttt gac          53

<210> SEQ ID NO 577
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 577
ccaacgttga ccttctttca gcaactcccc aaggtacttt acctgttttt gac          53

<210> SEQ ID NO 578
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 578
ggtctcctta cgcgcttcag tcgcccaacg ttgaccttct ttcagca                 47

<210> SEQ ID NO 579
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 579
ggtctcctta cgcgcttcag tacgccaacg ttgaccttct ttcagca                 47

<210> SEQ ID NO 580
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 580
ggtctcctta cgcgcttcag tctcccaacg ttgaccttct ttcagca                 47

<210> SEQ ID NO 581
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 581
ggcttggtta atccggaag acccgccgcg ggtgcggtca acaaa                     45

<210> SEQ ID NO 582
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 582
```
ggcttggtta aatccggaag accacgcgcg ggtgcggtca acaaa                    45

<210> SEQ ID NO 583
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 583
ggcttggtta aatccggaag accctccgcg ggtgcggtca acaaa                    45

<210> SEQ ID NO 584
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 584
ccagttgaaa agcgtccctg ttttcgctaa ggggtacagg ggtgcag                  47

<210> SEQ ID NO 585
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 585
ccagttgaaa agcgtccctg ttttacgtaa ggggtacagg ggtgcag                  47

<210> SEQ ID NO 586
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 586
ccagttgaaa agcgtccctg ttttctctaa ggggtacagg ggtgcag                  47

<210> SEQ ID NO 587
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 587
ggcccccagt tgaaaagcgt cgctgttttt gttaaggggt acagggg                  47

<210> SEQ ID NO 588
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 588
ggcccccagt tgaaaagcgt acgtgttttt gttaaggggt acagggg                  47

<210> SEQ ID NO 589
<211> LENGTH: 47
<212> TYPE: DNA

<213> ORGANISM: Artificial Sequence
<220> FEATURE:
<223> OTHER INFORMATION: Synthetic oligonucleotide

<400> SEQUENCE: 589
ggcccccagt tgaaaagcgt ctctgttttt gttaaggggt acagggg                    47

<210> SEQ ID NO 590
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 590
gtctggcccc cagttgaaaa gcgcccctgt ttttgttaag gggtacag                   48

<210> SEQ ID NO 591
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 591
gtctggcccc cagttgaaaa gacgccctgt ttttgttaag gggtacag                   48

<210> SEQ ID NO 592
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 592
gtctggcccc cagttgaaaa gctcccctgt ttttgttaag gggtacag                   48

<210> SEQ ID NO 593
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 593
tttgctggtc tggcccccac gcgaaaagcg tccctgtttt tgttaagg                   48

<210> SEQ ID NO 594
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 594
tttgctggtc tggcccccaa cggaaaagcg tccctgtttt tgttaagg                   48

<210> SEQ ID NO 595
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 595
tttgctggtc tggcccccac tcgaaaagcg tccctgtttt tgttaagg                   48

-continued

```
<210> SEQ ID NO 596
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 596
atatccctgt ttttcatcaa cgaacagcgc aaagggcttg gttaaatccg gaag          54

<210> SEQ ID NO 597
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 597
atatccctgt ttttcatcaa cgaacagacg aaagggcttg gttaaatccg gaag          54

<210> SEQ ID NO 598
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 598
atatccctgt ttttcatcaa cgaacagatc aaagggcttg gttaaatccg gaag          54

<210> SEQ ID NO 599
<211> LENGTH: 55
<212> TYPE: DNA
<213> ORGANISM: Artificial Sequence
<220> FEATURE:
<223> OTHER INFORMATION: Synthetic oligonucleotide

<400> SEQUENCE: 599
cttttgcata tccctgtttt tcatcaaccg ccagctcaaa gggcttggtt aaatc          55

<210> SEQ ID NO 600
<211> LENGTH: 55
<212> TYPE: DNA
<213> ORGANISM: Artificial Sequence
<220> FEATURE:
<223> OTHER INFORMATION: Synthetic oligonucleotide

<400> SEQUENCE: 600
cttttgcata tccctgtttt tcatcaacac gcagctcaaa gggcttggtt aaatc          55

<210> SEQ ID NO 601
<211> LENGTH: 55
<212> TYPE: DNA
<213> ORGANISM: Artificial Sequence
<220> FEATURE:
<223> OTHER INFORMATION: Synthetic oligonucleotide

<400> SEQUENCE: 601
cttttgcata tccctgtttt tcatcaacct ccagctcaaa gggcttggtt aaatc          55

<210> SEQ ID NO 602
<211> LENGTH: 46
<212> TYPE: DNA
<213> ORGANISM: Artificial Sequence
<220> FEATURE:
```

-continued

<223> OTHER INFORMATION: Synthetic oligonucleotide

<400> SEQUENCE: 602
ttactcaagt aagcaacagg gcgcgcccac gggcctaact tttggg                46

<210> SEQ ID NO 603
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 603
ttactcaagt aagcaacagg gcgtttccac gggcctaact tttggg                46

<210> SEQ ID NO 604
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 604
ttactcaagt aagcaacagg gcgctcccac gggcctaact tttggg                46

<210> SEQ ID NO 605
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 605
tctacagcat gtggagccaa gatcgctaag ggttgaccca tcgtcaact            49

<210> SEQ ID NO 606
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 606
tctacagcat gtggagccaa gatacgtaag ggttgaccca tcgtcaact            49

<210> SEQ ID NO 607
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 607
tctacagcat gtggagccaa gatctctaag ggttgaccca tcgtcaact            49

<210> SEQ ID NO 608
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 608
gaagcaaagt agctggattc aaagccgcaa ctggtccaaa ttgtacacga tcc        53

-continued

```
<210> SEQ ID NO 609
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 609
gaagcaaagt agctggattc aaagcacgaa ctggtccaaa ttgtacacga tcc            53

<210> SEQ ID NO 610
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 610
gaagcaaagt agctggattc aaagcctcaa ctggtccaaa ttgtacacga tcc            53

<210> SEQ ID NO 611
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 611
gcggcggtaa atttcgccat gcgcatgcgc tgttgcaaaa gcataacg                  48

<210> SEQ ID NO 612
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 612
gcggcggtaa atttcgccat gacgatgcgc tgttgcaaaa gcataacg                  48

<210> SEQ ID NO 613
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 613
gcggcggtaa atttcgccat gctcatgcgc tgttgcaaaa gcataacg                  48

<210> SEQ ID NO 614
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 614
gaccacggcg gcggtaaatc gcgccatgga tatgcgctgt tgc                       43

<210> SEQ ID NO 615
<211> LENGTH: 43
<212> TYPE: DNA
<213> ORGANISM: Artificial Sequence
<220> FEATURE:
<223> OTHER INFORMATION: Synthetic oligonucleotide
```

-continued

```
<400> SEQUENCE: 615
gaccacggcg gcggtaaata cggccatgga tatgcgctgt tgc                    43

<210> SEQ ID NO 616
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 616
gaccacggcg gcggtaaata tcgccatgga tatgcgctgt tgc                    43

<210> SEQ ID NO 617
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 617
cagaccacgg cggcggtacg cttcgccatg gatatgcgct gttg                   44

<210> SEQ ID NO 618
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 618
cagaccacgg cggcggtaac gttcgccatg gatatgcgct gttg                   44

<210> SEQ ID NO 619
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 619
cagaccacgg cggcggtact cttcgccatg gatatgcgct gttg                   44

<210> SEQ ID NO 620
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 620
gggcagcttg gtccgccatc gcgtttccac gagcctccgc t                      41

<210> SEQ ID NO 621
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 621
gggcagcttg gtccgccatt ttgtttccac gagcctccgc t                      41

<210> SEQ ID NO 622
<211> LENGTH: 41
```

-continued

```
<212> TYPE: DNA
<213> ORGANISM: Artificial Sequence
<220> FEATURE:
<223> OTHER INFORMATION: Synthetic oligonucleotide

<400> SEQUENCE: 622
gggcagcttg gtccgccatc tcgtttccac gagcctccgc t                    41

<210> SEQ ID NO 623
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 623
gccgccttac gggcagccgc gtccgccata cggtttccac                      40

<210> SEQ ID NO 624
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 624
gccgccttac gggcagcacg gtccgccata cggtttccac                      40

<210> SEQ ID NO 625
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 625
gccgccttac gggcagcctc gtccgccata cggtttccac                      40

<210> SEQ ID NO 626
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 626
gtctctgtga tcgccgcctt cgcggcagct tggtccgcca ta                   42

<210> SEQ ID NO 627
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 627
gtctctgtga tcgccgcctt tttggcagct tggtccgcca ta                   42

<210> SEQ ID NO 628
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 628
```

-continued

```
gtctctgtga tcgccgcctt ctcggcagct tggtccgcca ta                    42

<210> SEQ ID NO 629
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 629
atttgctgaa agaaggtcaa cgttggcgta ctgatgcgcg taaggagacc           50

<210> SEQ ID NO 630
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 630
ggtctcctta cgcgcatcag tacgccaacg ttgaccttct ttcagcaaat           50

<210> SEQ ID NO 631
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 631
gggattaagc cacatattcg tcgcttgcgt gaccagggga tcttggtccc           50

<210> SEQ ID NO 632
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 632
gggaccaaga tccctggtc acgcaagcga cgaatatgtg gcttaatccc            50

<210> SEQ ID NO 633
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 633
gtcgagtatc tcagaaaaga agaca                                      25

<210> SEQ ID NO 634
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 634
ctcggatgta ggaagtttca cc                                         22

<210> SEQ ID NO 635
<211> LENGTH: 24
<212> TYPE: DNA
<213> ORGANISM: Artificial Sequence
```

-continued

```
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' SUN
<220> FEATURE:
<221> NAME/KEY: misc_feature
<222> LOCATION: (10)..(11)
<223> OTHER INFORMATION: ZEN molecule
<220> FEATURE:
<221> NAME/KEY: misc_feature
<222> LOCATION: (24)..(24)
<223> OTHER INFORMATION: 3' IABkFQ

<400> SEQUENCE: 635
atgccctgcg taaactggat gaca                                           24

<210> SEQ ID NO 636
<211> LENGTH: 2055
<212> TYPE: DNA
<213> ORGANISM: Artificial Sequence
<220> FEATURE:
<223> OTHER INFORMATION: Synthetic oligonucleotide

<400> SEQUENCE: 636
atgactttaa atattgagga tgagcatcgt ttacatgaga catcaaaaga acccgacgtg      60
agcttagggt caacgtggct ttctgacttc ccccaggcgt gggcggagac tggcggaatg     120
gggttagctg tccgccaagc accgttgatc atcccgttaa aggcaacgtc tacacctgtc     180
tctatcaaac agtaccccat gagtcaagag gcccgcctgg ggattaagcc acatattcag     240
cgcttgctgg accaggggat cttggtccca tgtcaatctc cgtggaacac cccccttctg     300
cccgtgaaaa agccaggtac aaacgattat cgtccagttc aagatcttcg cgaggtcaac     360
aaacgcgtag aagacatcca tccgactgta cctaatcctt ataatctgtt atcaggcctg     420
cccccatcgc accaatggta tacagtatta gacttgaaag acgcgttctt ttgcctgcgt     480
ctgcacccaa cgtctcagcc gctgtttgcg ttcgaatggc gtgatcctga aatgggaatt     540
tcgggtcagt taacctggac tcgtctgccc cagggcttta aaaacagccc cacattgttc     600
gatgaagcac ttcaccgtga cttagcagac ttccgtatcc aacacccaga cttaattctg     660
ttacagtatg ttgacgacct tttgttggcg gcaacgtctg aacttgactg tcagcaaggc     720
acacgcgcgt tattacaaac gttaggtaac ttaggatatc gtgcgtccgc gaaaaaggcg     780
caaatttgtc aaaaacaggt aaagtacctt gggtatttgc tgaaagaagg tcaacgttgg     840
ctgactgaag cgcgtaagga gaccgtaatg gggcagccta cgcctaagac gccacgccag     900
ttgcgtgaat ttttgggcac agcgggattc tgtcgtttat ggattcctgg gttcgctgaa     960
atggctgcac ccctgtaccc cttaacaaaa acagggacgc ttttcaactg ggggccagac    1020
cagcaaaagg cgtatcagga gatcaaacaa gctttgttga ccgcacccgc gttgggtctt    1080
ccggatttaa ccaagccctt tgagctgttc gttgatgaaa acagggata tgcaaaagga    1140 gtattaaccc aaaagttagg cccgtggcgt cgccctgttg cttacttgag taaaaaattg    1200
gatcctgtcg cagcaggatg gccaccgtgc ttgcgtatgg tcgcggcaat tgccgttttg    1260
acaaaggatg caggtaagtt gacgatgggt caacccttag taatcttggc tccacatgct    1320
gtagaagcgt tagtaaagca gccccagac cgctggcttt ctaatgcgcg catgacccac    1380
tatcaggcgc ttctgcttga tacggatcgt gtacaatttg gaccagttgt agctttgaat    1440
ccagctactt tgcttccct tccagaagaa ggacttcagc acaattgttt agatattctg    1500
```

-continued

```
gccgaggcac atgggacgcg ccctgatttg acggatcagc cactgcctga tgccgaccat    1560
acatggtata ctggcggcag tagtcttctt caagagggc aacgcaaggc gggagcagcc    1620
gtcactacgg agaccgaagt tatctgggcc aaagcgttac ccgcgggaac atccgcgcaa    1680
cgtgcacagt taatcgctct gacacaggcc ctgaagatgg cagagggcaa aaagttgaat    1740
gtctacacca actcacgtta tgcttttgca acagcgcata tccatggcga aatttaccgc    1800
cgccgtggtc tgctgactag tgagggtaag gaaattaaaa ataaagatga gattcttgcg    1860
ttgttaaaag ctttattctt accaaaacgc ctttcgatca ttcattgccc ggggcatcaa    1920
aagggtcact cagcggaggc tcgtggaaac cgtatggcgg accaagctgc ccgtaaggcg    1980
gcgatcacag agaccccgga tacatcaacg ctgttgatcg aaaacagctc tccctacact    2040
agcgagcatt tttaa                                                     2055
```

<210> SEQ ID NO 637
<211> LENGTH: 684
<212> TYPE: PRT
<213> ORGANISM: Artificial Sequence
<220> FEATURE:
<223> OTHER INFORMATION: RTase mutant

<400> SEQUENCE: 637

```
Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
            195                 200                 205

Ala Asp Phe Arg Ile Gln His Pro Asp Leu Ile Leu Leu Gln Tyr Val
        210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
```

```
                 260              265                270

Leu Leu Lys Glu Gly Gln Arg Trp Leu Thr Glu Ala Arg Lys Glu Thr
         275              280                285

Val Met Gly Gln Pro Thr Pro Lys Thr Pro Arg Gln Leu Arg Glu Phe
         290              295                300

Leu Gly Thr Ala Gly Phe Cys Arg Leu Trp Ile Pro Gly Phe Ala Glu
305              310              315                320

Met Ala Ala Pro Leu Tyr Pro Leu Thr Lys Thr Gly Thr Leu Phe Asn
             325              330                335

Trp Gly Pro Asp Gln Gln Lys Ala Tyr Gln Glu Ile Lys Gln Ala Leu
             340              345                350

Leu Thr Ala Pro Ala Leu Gly Leu Pro Asp Leu Thr Lys Pro Phe Glu
             355              360                365

Leu Phe Val Asp Glu Lys Gln Gly Tyr Ala Lys Gly Val Leu Thr Gln
         370              375                380

Lys Leu Gly Pro Trp Arg Arg Pro Val Ala Tyr Leu Ser Lys Lys Leu
385              390              395                400

Asp Pro Val Ala Ala Gly Trp Pro Pro Cys Leu Arg Met Val Ala Ala
             405              410                415

Ile Ala Val Leu Thr Lys Asp Ala Gly Lys Leu Thr Met Gly Gln Pro
             420              425                430

Leu Val Ile Leu Ala Pro His Ala Val Glu Ala Leu Val Lys Gln Pro
         435              440                445

Pro Asp Arg Trp Leu Ser Asn Ala Arg Met Thr His Tyr Gln Ala Leu
         450              455                460

Leu Leu Asp Thr Asp Arg Val Gln Phe Gly Pro Val Val Ala Leu Asn
465              470              475                480

Pro Ala Thr Leu Leu Pro Leu Pro Glu Glu Gly Leu Gln His Asn Cys
             485              490                495

Leu Asp Ile Leu Ala Glu Ala His Gly Thr Arg Pro Asp Leu Thr Asp
             500              505                510

Gln Pro Leu Pro Asp Ala Asp His Thr Trp Tyr Thr Gly Gly Ser Ser
         515              520                525

Leu Leu Gln Glu Gly Gln Arg Lys Ala Gly Ala Ala Val Thr Thr Glu
         530              535                540

Thr Glu Val Ile Trp Ala Lys Ala Leu Pro Ala Gly Thr Ser Ala Gln
545              550              555                560

Arg Ala Gln Leu Ile Ala Leu Thr Gln Ala Leu Lys Met Ala Glu Gly
             565              570                575

Lys Lys Leu Asn Val Tyr Thr Asn Ser Arg Tyr Ala Phe Ala Thr Ala
             580              585                590

His Ile His Gly Glu Ile Tyr Arg Arg Arg Gly Leu Leu Thr Ser Glu
         595              600                605

Gly Lys Glu Ile Lys Asn Lys Asp Glu Ile Leu Ala Leu Leu Lys Ala
         610              615                620

Leu Phe Leu Pro Lys Arg Leu Ser Ile Ile His Cys Pro Gly His Gln
625              630              635                640

Lys Gly His Ser Ala Glu Ala Arg Gly Asn Arg Met Ala Asp Gln Ala
             645              650                655

Ala Arg Lys Ala Ala Ile Thr Glu Thr Pro Asp Thr Ser Thr Leu Leu
             660              665                670

Ile Glu Asn Ser Ser Pro Tyr Thr Ser Glu His Phe
             675              680
```

```
<210> SEQ ID NO 638
<211> LENGTH: 684
<212> TYPE: PRT
<213> ORGANISM: Artificial Sequence
<220> FEATURE:
<223> OTHER INFORMATION: RTase mutant

<400> SEQUENCE: 638

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Arg Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365
```

-continued

```
Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
                420                 425                 430

Leu Val Ile Leu Ala Pro His Ala Val Glu Ala Leu Val Lys Gln Pro
            435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
                500                 505                 510

Gln Pro Leu Pro Asp Ala Asp His Thr Trp Tyr Thr Gly Gly Ser Ser
            515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
            580                 585                 590

His Ile His Gly Glu Ile Tyr Arg Arg Arg Gly Leu Leu Thr Ser Glu
    595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile Glu Asn Ser Ser Pro Tyr Thr Ser Glu His Phe
    675                 680
```

<210> SEQ ID NO 639
<211> LENGTH: 684
<212> TYPE: PRT
<213> ORGANISM: Artificial Sequence
<220> FEATURE:
<223> OTHER INFORMATION: RTase mutant

<400> SEQUENCE: 639

```
Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45
```

-continued

```
Leu Ile Ile Pro Leu Lys Ala Thr Ser Thr Pro Val Ser Ile Lys Gln
    50                  55                  60

Tyr Pro Met Ser Arg Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
                180                 185                 190

Phe Lys Asn Ser Pro Thr Leu Phe Asp Glu Ala Leu His Arg Asp Leu
            195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
            275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
                340                 345                 350

Leu Thr Ala Pro Ala Leu Gly Leu Pro Asp Leu Thr Lys Pro Phe Glu
            355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460
```

-continued

```
Leu Leu Asp Thr Asp Arg Val Gln Phe Gly Pro Val Val Ala Leu Asn
465             470             475             480

Pro Ala Thr Leu Leu Pro Leu Pro Glu Glu Gly Leu Gln His Asn Cys
            485             490             495

Leu Asp Ile Leu Ala Glu Ala His Gly Thr Arg Pro Asp Leu Thr Asp
            500             505             510

Gln Pro Leu Pro Asp Ala Asp His Thr Trp Tyr Thr Gly Gly Ser Ser
            515             520             525

Leu Leu Gln Glu Gly Gln Arg Lys Ala Gly Ala Ala Val Thr Thr Glu
            530             535             540

Thr Glu Val Ile Trp Ala Lys Ala Leu Pro Ala Gly Thr Ser Ala Gln
545             550             555             560

Arg Ala Gln Leu Ile Ala Leu Thr Gln Ala Leu Lys Met Ala Glu Gly
            565             570             575

Lys Lys Leu Asn Val Tyr Thr Asn Ser Arg Tyr Ala Phe Ala Thr Ala
            580             585             590

His Ile His Gly Glu Ile Tyr Arg Arg Arg Gly Leu Leu Thr Ser Glu
            595             600             605

Gly Lys Glu Ile Lys Asn Lys Asp Glu Ile Leu Ala Leu Leu Lys Ala
            610             615             620

Leu Phe Leu Pro Lys Arg Leu Ser Ile Ile His Cys Pro Gly His Gln
625             630             635             640

Lys Gly His Ser Ala Glu Ala Arg Gly Asn Arg Met Ala Asp Gln Ala
            645             650             655

Ala Arg Lys Ala Ala Ile Thr Glu Thr Pro Asp Thr Ser Thr Leu Leu
            660             665             670

Ile Glu Asn Ser Ser Pro Tyr Thr Ser Glu His Phe
            675             680

<210> SEQ ID NO 640
<211> LENGTH: 684
<212> TYPE: PRT
<213> ORGANISM: Artificial Sequence
<220> FEATURE:
<223> OTHER INFORMATION: RTase mutant

<400> SEQUENCE: 640

Met Thr Leu Asn Ile Glu Asp Glu His Arg Leu His Glu Thr Ser Lys
1               5               10              15

Glu Pro Asp Val Ser Leu Gly Ser Thr Trp Leu Ser Asp Phe Pro Gln
            20              25              30

Ala Trp Ala Glu Thr Gly Gly Met Gly Leu Ala Val Arg Gln Ala Pro
            35              40              45

Leu Ile Ile Pro Leu Lys Ala Thr Ser Thr Pro Val Ser Ile Lys Gln
    50              55              60

Tyr Pro Met Ser Gln Glu Ala Arg Leu Gly Ile Lys Pro His Ile Arg
65              70              75              80

Arg Leu Leu Asp Gln Gly Ile Leu Val Pro Cys Gln Ser Pro Trp Asn
            85              90              95

Thr Pro Leu Leu Pro Val Lys Lys Pro Gly Thr Asn Asp Tyr Arg Pro
            100             105             110

Val Gln Asp Leu Arg Glu Val Asn Lys Arg Val Glu Asp Ile His Pro
            115             120             125

Thr Val Pro Asn Pro Tyr Asn Leu Leu Ser Gly Leu Pro Pro Ser His
    130             135             140
```

-continued

```
Gln Trp Tyr Thr Val Leu Asp Leu Lys Asp Ala Phe Phe Cys Leu Arg
145             150                 155                 160

Leu His Pro Thr Ser Gln Pro Leu Phe Ala Phe Glu Trp Arg Asp Pro
            165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
            195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
            245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
            275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
            325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
            355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
            405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
            435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
            485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Gly Gly Ser Ser
            515                 520                 525

Leu Leu Gln Glu Gly Gln Arg Lys Ala Gly Ala Ala Val Thr Thr Glu
            530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
```

-continued

```
                  565              570              575
Lys Lys Leu Asn Val Tyr Thr Asn Ser Arg Tyr Ala Phe Ala Thr Ala
        580              585              590

His Ile His Gly Glu Ile Tyr Arg Arg Arg Gly Leu Leu Thr Ser Glu
        595              600              605

Gly Lys Glu Ile Lys Asn Lys Asp Glu Ile Leu Ala Leu Leu Lys Ala
    610              615              620

Leu Phe Leu Pro Lys Arg Leu Ser Ile Ile His Cys Pro Gly His Gln
625              630              635              640

Lys Gly His Ser Ala Glu Ala Arg Gly Asn Arg Met Ala Asp Gln Ala
        645              650              655

Ala Arg Lys Ala Ala Ile Thr Glu Thr Pro Asp Thr Ser Thr Leu Leu
        660              665              670

Ile Glu Asn Ser Ser Pro Tyr Thr Ser Glu His Phe
        675              680

<210> SEQ ID NO 641
<211> LENGTH: 684
<212> TYPE: PRT
<213> ORGANISM: Artificial Sequence
<220> FEATURE:
<223> OTHER INFORMATION: RTase mutant

<400> SEQUENCE: 641

Met Thr Leu Asn Ile Glu Asp Glu His Arg Leu His Glu Thr Ser Lys
1               5               10              15

Glu Pro Asp Val Ser Leu Gly Ser Thr Trp Leu Ser Asp Phe Pro Gln
        20              25              30

Ala Trp Ala Glu Thr Gly Gly Met Gly Leu Ala Val Arg Gln Ala Pro
        35              40              45

Leu Ile Ile Pro Leu Lys Ala Thr Ser Thr Pro Val Ser Ile Lys Gln
    50              55              60

Tyr Pro Met Ser Gln Glu Ala Arg Leu Gly Ile Lys Pro His Ile Gln
65              70              75              80

Arg Leu Leu Asp Gln Gly Ile Leu Val Pro Cys Gln Ser Pro Trp Asn
                85              90              95

Thr Pro Arg Leu Pro Val Lys Lys Pro Gly Thr Asn Asp Tyr Arg Pro
        100             105             110

Val Gln Asp Leu Arg Glu Val Asn Lys Arg Val Glu Asp Ile His Pro
        115             120             125

Thr Val Pro Asn Pro Tyr Asn Leu Leu Ser Gly Leu Pro Pro Ser His
    130             135             140

Gln Trp Tyr Thr Val Leu Asp Leu Lys Asp Ala Phe Phe Cys Leu Arg
145             150             155             160

Leu His Pro Thr Ser Gln Pro Leu Phe Ala Phe Glu Trp Arg Asp Pro
                165             170             175

Glu Met Gly Ile Ser Gly Gln Leu Thr Trp Thr Arg Leu Pro Gln Gly
        180             185             190

Phe Lys Asn Ser Pro Thr Leu Phe Asp Glu Ala Leu His Arg Asp Leu
        195             200             205

Ala Asp Phe Arg Ile Gln His Pro Asp Leu Ile Leu Leu Gln Tyr Val
    210             215             220

Asp Asp Leu Leu Leu Ala Ala Thr Ser Glu Leu Asp Cys Gln Gln Gly
225             230             235             240

Thr Arg Ala Leu Leu Gln Thr Leu Gly Asn Leu Gly Tyr Arg Ala Ser
```

-continued

```
                245             250             255

Ala Lys Lys Ala Gln Ile Cys Gln Lys Gln Val Lys Tyr Leu Gly Tyr
            260             265             270

Leu Leu Lys Glu Gly Gln Arg Trp Leu Thr Glu Ala Arg Lys Glu Thr
        275             280             285

Val Met Gly Gln Pro Thr Pro Lys Thr Pro Arg Gln Leu Arg Glu Phe
    290             295             300

Leu Gly Thr Ala Gly Phe Cys Arg Leu Trp Ile Pro Gly Phe Ala Glu
305             310             315             320

Met Ala Ala Pro Leu Tyr Pro Leu Thr Lys Thr Gly Thr Leu Phe Asn
            325             330             335

Trp Gly Pro Asp Gln Gln Lys Ala Tyr Gln Glu Ile Lys Gln Ala Leu
            340             345             350

Leu Thr Ala Pro Ala Leu Gly Leu Pro Asp Leu Thr Lys Pro Phe Glu
        355             360             365

Leu Phe Val Asp Glu Lys Gln Gly Tyr Ala Lys Gly Val Leu Thr Gln
    370             375             380

Lys Leu Gly Pro Trp Arg Arg Pro Val Ala Tyr Leu Ser Lys Lys Leu
385             390             395             400

Asp Pro Val Ala Ala Gly Trp Pro Pro Cys Leu Arg Met Val Ala Ala
            405             410             415

Ile Ala Val Leu Thr Lys Asp Ala Gly Lys Leu Thr Met Gly Gln Pro
            420             425             430

Leu Val Ile Leu Ala Pro His Ala Val Glu Ala Leu Val Lys Gln Pro
            435             440             445

Pro Asp Arg Trp Leu Ser Asn Ala Arg Met Thr His Tyr Gln Ala Leu
    450             455             460

Leu Leu Asp Thr Asp Arg Val Gln Phe Gly Pro Val Val Ala Leu Asn
465             470             475             480

Pro Ala Thr Leu Leu Pro Leu Pro Glu Glu Gly Leu Gln His Asn Cys
            485             490             495

Leu Asp Ile Leu Ala Glu Ala His Gly Thr Arg Pro Asp Leu Thr Asp
            500             505             510

Gln Pro Leu Pro Asp Ala Asp His Thr Trp Tyr Thr Gly Gly Ser Ser
        515             520             525

Leu Leu Gln Glu Gly Gln Arg Lys Ala Gly Ala Ala Val Thr Thr Glu
    530             535             540

Thr Glu Val Ile Trp Ala Lys Ala Leu Pro Ala Gly Thr Ser Ala Gln
545             550             555             560

Arg Ala Gln Leu Ile Ala Leu Thr Gln Ala Leu Lys Met Ala Glu Gly
            565             570             575

Lys Lys Leu Asn Val Tyr Thr Asn Ser Arg Tyr Ala Phe Ala Thr Ala
            580             585             590

His Ile His Gly Glu Ile Tyr Arg Arg Arg Gly Leu Leu Thr Ser Glu
            595             600             605

Gly Lys Glu Ile Lys Asn Lys Asp Glu Ile Leu Ala Leu Leu Lys Ala
    610             615             620

Leu Phe Leu Pro Lys Arg Leu Ser Ile Ile His Cys Pro Gly His Gln
625             630             635             640

Lys Gly His Ser Ala Glu Ala Arg Gly Asn Arg Met Ala Asp Gln Ala
            645             650             655

Ala Arg Lys Ala Ala Ile Thr Glu Thr Pro Asp Thr Ser Thr Leu Leu
            660             665             670
```

-continued

Ile Glu Asn Ser Ser Pro Tyr Thr Ser Glu His Phe
        675                 680

<210> SEQ ID NO 642
<211> LENGTH: 684
<212> TYPE: PRT
<213> ORGANISM: Artificial Sequence
<220> FEATURE:
<223> OTHER INFORMATION: RTase mutant

<400> SEQUENCE: 642

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
            115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
            195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
            245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Asp Ala Arg Lys Glu Thr
            275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
            325                 330                 335

Trp Gly Pro Asp Gln Gln Lys Ala Tyr Gln Glu Ile Lys Gln Ala Leu
            340                 345                 350

-continued

```
Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
                420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
        500                 505                 510

Gln Pro Leu Pro Asp Ala Asp His Thr Trp Tyr Thr Gly Gly Ser Ser
        515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
                580                 585                 590

His Ile His Gly Glu Ile Tyr Arg Arg Arg Gly Leu Leu Thr Ser Glu
        595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
                660                 665                 670

Ile Glu Asn Ser Ser Pro Tyr Thr Ser Glu His Phe
        675                 680
```

```
<210> SEQ ID NO 643
<211> LENGTH: 684
<212> TYPE: PRT
<213> ORGANISM: Artificial Sequence
<220> FEATURE:
<223> OTHER INFORMATION: RTase mutant

<400> SEQUENCE: 643

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
                20                  25                  30
```

-continued

```
Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
        50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
                100                 105                 110

Val Gln Asp Leu Arg Glu Val Asn Lys Arg Val Glu Asp Ile His Pro
                115                 120                 125

Thr Val Pro Asn Pro Tyr Asn Leu Leu Ser Gly Leu Pro Pro Ser His
        130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
                180                 185                 190

Phe Lys Asn Ser Pro Thr Leu Phe Asp Glu Ala Leu His Arg Asp Leu
                195                 200                 205

Ala Asp Phe Arg Ile Gln His Pro Asp Leu Ile Leu Leu Gln Tyr Val
        210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
                260                 265                 270

Leu Leu Lys Glu Gly Gln Arg Trp Leu Thr Glu Ala Arg Lys Glu Thr
        275                 280                 285

Val Met Gly Gln Pro Thr Pro Lys Thr Pro Ala Gln Leu Arg Glu Phe
        290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
                340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
        370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
                420                 425                 430

Leu Val Ile Leu Ala Pro His Ala Val Glu Ala Leu Val Lys Gln Pro
        435                 440                 445
```

-continued

```
Pro Asp Arg Trp Leu Ser Asn Ala Arg Met Thr His Tyr Gln Ala Leu
    450             455             460
```

```
Leu Leu Asp Thr Asp Arg Val Gln Phe Gly Pro Val Val Ala Leu Asn
465             470             475             480
```

```
Pro Ala Thr Leu Leu Pro Leu Pro Glu Glu Gly Leu Gln His Asn Cys
            485             490             495
```

```
Leu Asp Ile Leu Ala Glu Ala His Gly Thr Arg Pro Asp Leu Thr Asp
        500             505             510
```

```
Gln Pro Leu Pro Asp Ala Asp His Thr Trp Tyr Thr Gly Gly Ser Ser
        515             520             525
```

```
Leu Leu Gln Glu Gly Gln Arg Lys Ala Gly Ala Ala Val Thr Thr Glu
        530             535             540
```

```
Thr Glu Val Ile Trp Ala Lys Ala Leu Pro Ala Gly Thr Ser Ala Gln
545             550             555             560
```

```
Arg Ala Gln Leu Ile Ala Leu Thr Gln Ala Leu Lys Met Ala Glu Gly
            565             570             575
```

```
Lys Lys Leu Asn Val Tyr Thr Asn Ser Arg Tyr Ala Phe Ala Thr Ala
            580             585             590
```

```
His Ile His Gly Glu Ile Tyr Arg Arg Arg Gly Leu Leu Thr Ser Glu
            595             600             605
```

```
Gly Lys Glu Ile Lys Asn Lys Asp Glu Ile Leu Ala Leu Leu Lys Ala
        610             615             620
```

```
Leu Phe Leu Pro Lys Arg Leu Ser Ile Ile His Cys Pro Gly His Gln
625             630             635             640
```

```
Lys Gly His Ser Ala Glu Ala Arg Gly Asn Arg Met Ala Asp Gln Ala
            645             650             655
```

```
Ala Arg Lys Ala Ala Ile Thr Glu Thr Pro Asp Thr Ser Thr Leu Leu
            660             665             670
```

```
Ile Glu Asn Ser Ser Pro Tyr Thr Ser Glu His Phe
            675             680
```

```
<210> SEQ ID NO 644
<211> LENGTH: 684
<212> TYPE: PRT
<213> ORGANISM: Artificial Sequence
<220> FEATURE:
<223> OTHER INFORMATION: RTase mutant

<400> SEQUENCE: 644
```

```
Met Thr Leu Asn Ile Glu Asp Glu His Arg Leu His Glu Thr Ser Lys
1               5               10              15
```

```
Glu Pro Asp Val Ser Leu Gly Ser Thr Trp Leu Ser Asp Phe Pro Gln
            20              25              30
```

```
Ala Trp Ala Glu Thr Gly Gly Met Gly Leu Ala Val Arg Gln Ala Pro
        35              40              45
```

```
Leu Ile Ile Pro Leu Lys Ala Thr Ser Thr Pro Val Ser Lys Lys Gln
    50              55              60
```

```
Tyr Pro Met Ser Gln Glu Ala Arg Leu Gly Ile Lys Pro His Ile Gln
65              70              75              80
```

```
Arg Leu Leu Asp Gln Gly Ile Leu Val Pro Cys Gln Ser Pro Trp Asn
            85              90              95
```

```
Thr Pro Leu Leu Pro Val Lys Lys Pro Gly Thr Asn Asp Tyr Arg Pro
            100             105             110
```

```
Val Gln Asp Leu Arg Glu Val Asn Lys Arg Val Glu Asp Ile His Pro
            115             120             125
```

-continued

```
Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
            195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
            275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
            355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
            435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Gly Gly Ser Ser
            515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
```

```
545              550              555              560

Arg Ala Gln Leu Ile Ala Leu Thr Gln Ala Leu Lys Met Ala Glu Gly
                565              570              575

Lys Lys Leu Asn Val Tyr Thr Asn Ser Arg Tyr Ala Phe Ala Thr Ala
            580              585              590

His Ile His Gly Glu Ile Tyr Arg Arg Arg Gly Leu Leu Thr Ser Glu
            595              600              605

Gly Lys Glu Ile Lys Asn Lys Asp Glu Ile Leu Ala Leu Leu Lys Ala
        610              615              620

Leu Phe Leu Pro Lys Arg Leu Ser Ile Ile His Cys Pro Gly His Gln
625              630              635              640

Lys Gly His Ser Ala Glu Ala Arg Gly Asn Arg Met Ala Asp Gln Ala
                645              650              655

Ala Arg Lys Ala Ala Ile Thr Glu Thr Pro Asp Thr Ser Thr Leu Leu
            660              665              670

Ile Glu Asn Ser Ser Pro Tyr Thr Ser Glu His Phe
            675              680

<210> SEQ ID NO 645
<211> LENGTH: 684
<212> TYPE: PRT
<213> ORGANISM: Artificial Sequence
<220> FEATURE:
<223> OTHER INFORMATION: RTase mutant

<400> SEQUENCE: 645

Met Thr Leu Asn Ile Glu Asp Glu His Arg Leu His Glu Thr Ser Lys
1               5               10              15

Glu Pro Asp Val Ser Leu Gly Ser Thr Trp Leu Ser Asp Phe Pro Gln
            20              25              30

Ala Trp Ala Glu Thr Gly Gly Met Gly Leu Ala Val Arg Gln Ala Pro
            35              40              45

Leu Ile Ile Pro Leu Lys Ala Thr Ser Thr Pro Val Ser Met Lys Gln
        50              55              60

Tyr Pro Met Ser Gln Glu Ala Arg Leu Gly Ile Lys Pro His Ile Gln
65              70              75              80

Arg Leu Leu Asp Gln Gly Ile Leu Val Pro Cys Gln Ser Pro Trp Asn
                85              90              95

Thr Pro Leu Leu Pro Val Lys Lys Pro Gly Thr Asn Asp Tyr Arg Pro
            100             105             110

Val Gln Asp Leu Arg Glu Val Asn Lys Arg Val Glu Asp Ile His Pro
            115             120             125

Thr Val Pro Asn Pro Tyr Asn Leu Leu Ser Gly Leu Pro Pro Ser His
        130             135             140

Gln Trp Tyr Thr Val Leu Asp Leu Lys Asp Ala Phe Phe Cys Leu Arg
145             150             155             160

Leu His Pro Thr Ser Gln Pro Leu Phe Ala Phe Glu Trp Arg Asp Pro
                165             170             175

Glu Met Gly Ile Ser Gly Gln Leu Thr Trp Thr Arg Leu Pro Gln Gly
            180             185             190

Phe Lys Asn Ser Pro Thr Leu Phe Asp Glu Ala Leu His Arg Asp Leu
            195             200             205

Ala Asp Phe Arg Ile Gln His Pro Asp Leu Ile Leu Leu Gln Tyr Val
        210             215             220

Asp Asp Leu Leu Leu Ala Ala Thr Ser Glu Leu Asp Cys Gln Gln Gly
```

```
                225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
                260                 265                 270

Leu Leu Lys Glu Gly Gln Arg Trp Leu Thr Glu Ala Arg Lys Glu Thr
                275                 280                 285

Val Met Gly Gln Pro Thr Pro Lys Thr Pro Arg Gln Leu Arg Glu Phe
                290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
                340                 345                 350

Leu Thr Ala Pro Ala Leu Gly Leu Pro Asp Leu Thr Lys Pro Phe Glu
                355                 360                 365

Leu Phe Val Asp Glu Lys Gln Gly Tyr Ala Lys Gly Val Leu Thr Gln
                370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
                420                 425                 430

Leu Val Ile Leu Ala Pro His Ala Val Glu Ala Leu Val Lys Gln Pro
                435                 440                 445

Pro Asp Arg Trp Leu Ser Asn Ala Arg Met Thr His Tyr Gln Ala Leu
                450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
                500                 505                 510

Gln Pro Leu Pro Asp Ala Asp His Thr Trp Tyr Thr Gly Gly Ser Ser
                515                 520                 525

Leu Leu Gln Glu Gly Gln Arg Lys Ala Gly Ala Ala Val Thr Thr Glu
                530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
                580                 585                 590

His Ile His Gly Glu Ile Tyr Arg Arg Arg Gly Leu Leu Thr Ser Glu
                595                 600                 605

Gly Lys Glu Ile Lys Asn Lys Asp Glu Ile Leu Ala Leu Leu Lys Ala
                610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655
```

-continued

```
Ala Arg Lys Ala Ala Ile Thr Glu Thr Pro Asp Thr Ser Thr Leu Leu
            660             665             670

Ile Glu Asn Ser Ser Pro Tyr Thr Ser Glu His Phe
        675                 680

<210> SEQ ID NO 646
<211> LENGTH: 684
<212> TYPE: PRT
<213> ORGANISM: Artificial Sequence
<220> FEATURE:
<223> OTHER INFORMATION: RTase mutant

<400> SEQUENCE: 646

Met Thr Leu Asn Ile Glu Asp Glu His Arg Leu His Glu Thr Ser Lys
1               5               10              15

Glu Pro Asp Val Ser Leu Gly Ser Thr Trp Leu Ser Asp Phe Pro Gln
            20              25              30

Ala Trp Ala Glu Thr Gly Gly Met Gly Leu Ala Val Arg Gln Ala Pro
        35              40              45

Leu Ile Ile Pro Leu Lys Ala Thr Ser Thr Pro Val Ser Ile Lys Gln
    50              55              60

Tyr Pro Met Ser Ile Glu Ala Arg Leu Gly Ile Lys Pro His Ile Gln
65              70              75              80

Arg Leu Leu Asp Gln Gly Ile Leu Val Pro Cys Gln Ser Pro Trp Asn
            85              90              95

Thr Pro Leu Leu Pro Val Lys Lys Pro Gly Thr Asn Asp Tyr Arg Pro
            100             105             110

Val Gln Asp Leu Arg Glu Val Asn Lys Arg Val Glu Asp Ile His Pro
            115             120             125

Thr Val Pro Asn Pro Tyr Asn Leu Leu Ser Gly Leu Pro Pro Ser His
    130             135             140

Gln Trp Tyr Thr Val Leu Asp Leu Lys Asp Ala Phe Phe Cys Leu Arg
145             150             155             160

Leu His Pro Thr Ser Gln Pro Leu Phe Ala Phe Glu Trp Arg Asp Pro
            165             170             175

Glu Met Gly Ile Ser Gly Gln Leu Thr Trp Thr Arg Leu Pro Gln Gly
            180             185             190

Phe Lys Asn Ser Pro Thr Leu Phe Asp Glu Ala Leu His Arg Asp Leu
            195             200             205

Ala Asp Phe Arg Ile Gln His Pro Asp Leu Ile Leu Leu Gln Tyr Val
    210             215             220

Asp Asp Leu Leu Leu Ala Ala Thr Ser Glu Leu Asp Cys Gln Gln Gly
225             230             235             240

Thr Arg Ala Leu Leu Gln Thr Leu Gly Asn Leu Gly Tyr Arg Ala Ser
            245             250             255

Ala Lys Lys Ala Gln Ile Cys Gln Lys Gln Val Lys Tyr Leu Gly Tyr
            260             265             270

Leu Leu Lys Glu Gly Gln Arg Trp Leu Thr Glu Ala Arg Lys Glu Thr
            275             280             285

Val Met Gly Gln Pro Thr Pro Lys Thr Pro Arg Gln Leu Arg Glu Phe
    290             295             300

Leu Gly Thr Ala Gly Phe Cys Arg Leu Trp Ile Pro Gly Phe Ala Glu
305             310             315             320

Met Ala Ala Pro Leu Tyr Pro Leu Thr Lys Thr Gly Thr Leu Phe Asn
            325             330             335
```

-continued

```
Trp Gly Pro Asp Gln Gln Lys Ala Tyr Gln Glu Ile Lys Gln Ala Leu
        340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
        370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
                420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
        450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
                500                 505                 510

Gln Pro Leu Pro Asp Ala Asp His Thr Trp Tyr Thr Gly Gly Ser Ser
        515                 520                 525

Leu Leu Gln Glu Gly Gln Arg Lys Ala Gly Ala Ala Val Thr Thr Glu
        530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
                580                 585                 590

His Ile His Gly Glu Ile Tyr Arg Arg Arg Gly Leu Leu Thr Ser Glu
        595                 600                 605

Gly Lys Glu Ile Lys Asn Lys Asp Glu Ile Leu Ala Leu Leu Lys Ala
        610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
                660                 665                 670

Ile Glu Asn Ser Ser Pro Tyr Thr Ser Glu His Phe
        675                 680
```

```
<210> SEQ ID NO 647
<211> LENGTH: 684
<212> TYPE: PRT
<213> ORGANISM: Artificial Sequence
<220> FEATURE:
<223> OTHER INFORMATION: RTase mutant

<400> SEQUENCE: 647

Met Thr Leu Asn Ile Glu Asp Glu His Arg Leu His Glu Thr Ser Lys
1               5                   10                  15
```

```
Glu Pro Asp Val Ser Leu Gly Ser Thr Trp Leu Ser Asp Phe Pro Gln
        20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Lys Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
            115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
            195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
            275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
            355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430
```

-continued

```
Leu Val Ile Leu Ala Pro His Ala Val Glu Ala Leu Val Lys Gln Pro
        435             440             445

Pro Asp Arg Trp Leu Ser Asn Ala Arg Met Thr His Tyr Gln Ala Leu
        450             455             460

Leu Leu Asp Thr Asp Arg Val Gln Phe Gly Pro Val Val Ala Leu Asn
465             470             475             480

Pro Ala Thr Leu Leu Pro Leu Pro Glu Glu Gly Leu Gln His Asn Cys
        485             490             495

Leu Asp Ile Leu Ala Glu Ala His Gly Thr Arg Pro Asp Leu Thr Asp
        500             505             510

Gln Pro Leu Pro Asp Ala Asp His Thr Trp Tyr Thr Gly Gly Ser Ser
        515             520             525

Leu Leu Gln Glu Gly Gln Arg Lys Ala Gly Ala Ala Val Thr Thr Glu
        530             535             540

Thr Glu Val Ile Trp Ala Lys Ala Leu Pro Ala Gly Thr Ser Ala Gln
545             550             555             560

Arg Ala Gln Leu Ile Ala Leu Thr Gln Ala Leu Lys Met Ala Glu Gly
        565             570             575

Lys Lys Leu Asn Val Tyr Thr Asn Ser Arg Tyr Ala Phe Ala Thr Ala
        580             585             590

His Ile His Gly Glu Ile Tyr Arg Arg Arg Gly Leu Leu Thr Ser Glu
        595             600             605

Gly Lys Glu Ile Lys Asn Lys Asp Glu Ile Leu Ala Leu Leu Lys Ala
        610             615             620

Leu Phe Leu Pro Lys Arg Leu Ser Ile Ile His Cys Pro Gly His Gln
625             630             635             640

Lys Gly His Ser Ala Glu Ala Arg Gly Asn Arg Met Ala Asp Gln Ala
        645             650             655

Ala Arg Lys Ala Ala Ile Thr Glu Thr Pro Asp Thr Ser Thr Leu Leu
        660             665             670

Ile Glu Asn Ser Ser Pro Tyr Thr Ser Glu His Phe
        675             680

<210> SEQ ID NO 648
<211> LENGTH: 684
<212> TYPE: PRT
<213> ORGANISM: Artificial Sequence
<220> FEATURE:
<223> OTHER INFORMATION: RTase mutant

<400> SEQUENCE: 648

Met Thr Leu Asn Ile Glu Asp Glu His Arg Leu His Glu Thr Ser Lys
1               5               10              15

Glu Pro Asp Val Ser Leu Gly Ser Thr Trp Leu Ser Asp Phe Pro Gln
        20              25              30

Ala Trp Ala Glu Thr Gly Gly Met Gly Leu Ala Val Arg Gln Ala Pro
        35              40              45

Leu Ile Ile Pro Leu Lys Ala Thr Ser Thr Pro Val Ser Ile Lys Gln
        50              55              60

Tyr Pro Met Ser Gln Glu Ala Arg Leu Gly Ile Lys Pro His Ile His
65              70              75              80

Arg Leu Leu Asp Gln Gly Ile Leu Val Pro Cys Gln Ser Pro Trp Asn
        85              90              95

Thr Pro Leu Leu Pro Val Lys Lys Pro Gly Thr Asn Asp Tyr Arg Pro
        100             105             110
```

-continued

```
Val Gln Asp Leu Arg Glu Val Asn Lys Arg Val Glu Asp Ile His Pro
    115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
            195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
            275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
            355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
            435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Gly Gly Ser Ser
            515                 520                 525

Leu Leu Gln Glu Gly Gln Arg Lys Ala Gly Ala Ala Val Thr Thr Glu
```

-continued

```
        530              535              540
Thr Glu Val Ile Trp Ala Lys Ala Leu Pro Ala Gly Thr Ser Ala Gln
545              550              555              560

Arg Ala Gln Leu Ile Ala Leu Thr Gln Ala Leu Lys Met Ala Glu Gly
                 565              570              575

Lys Lys Leu Asn Val Tyr Thr Asn Ser Arg Tyr Ala Phe Ala Thr Ala
                 580              585              590

His Ile His Gly Glu Ile Tyr Arg Arg Arg Gly Leu Leu Thr Ser Glu
                 595              600              605

Gly Lys Glu Ile Lys Asn Lys Asp Glu Ile Leu Ala Leu Leu Lys Ala
             610              615              620

Leu Phe Leu Pro Lys Arg Leu Ser Ile Ile His Cys Pro Gly His Gln
625              630              635              640

Lys Gly His Ser Ala Glu Ala Arg Gly Asn Arg Met Ala Asp Gln Ala
                 645              650              655

Ala Arg Lys Ala Ala Ile Thr Glu Thr Pro Asp Thr Ser Thr Leu Leu
                 660              665              670

Ile Glu Asn Ser Ser Pro Tyr Thr Ser Glu His Phe
                 675              680

<210> SEQ ID NO 649
<211> LENGTH: 684
<212> TYPE: PRT
<213> ORGANISM: Artificial Sequence
<220> FEATURE:
<223> OTHER INFORMATION: RTase mutant

<400> SEQUENCE: 649

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
                 20              25                  30

Ala Trp Ala Glu Thr Gly Gly Met Gly Leu Ala Val Arg Gln Ala Pro
             35              40                  45

Leu Ile Ile Pro Leu Lys Ala Thr Ser Thr Pro Val Ser Ile Lys Gln
             50              55                  60

Tyr Pro Met Ser Gln Glu Ala Arg Leu Gly Ile Lys Pro His Ile Ile
65              70                  75                  80

Arg Leu Leu Asp Gln Gly Ile Leu Val Pro Cys Gln Ser Pro Trp Asn
                 85              90                  95

Thr Pro Leu Leu Pro Val Lys Lys Pro Gly Thr Asn Asp Tyr Arg Pro
                 100             105             110

Val Gln Asp Leu Arg Glu Val Asn Lys Arg Val Glu Asp Ile His Pro
                 115             120             125

Thr Val Pro Asn Pro Tyr Asn Leu Leu Ser Gly Leu Pro Pro Ser His
             130             135             140

Gln Trp Tyr Thr Val Leu Asp Leu Lys Asp Ala Phe Phe Cys Leu Arg
145             150             155             160

Leu His Pro Thr Ser Gln Pro Leu Phe Ala Phe Glu Trp Arg Asp Pro
                 165             170             175

Glu Met Gly Ile Ser Gly Gln Leu Thr Trp Thr Arg Leu Pro Gln Gly
                 180             185             190

Phe Lys Asn Ser Pro Thr Leu Phe Asp Glu Ala Leu His Arg Asp Leu
                 195             200             205

Ala Asp Phe Arg Ile Gln His Pro Asp Leu Ile Leu Leu Gln Tyr Val
```

-continued

```
      210                215                220
Asp Asp Leu Leu Leu Ala Ala Thr Ser Glu Leu Asp Cys Gln Gln Gly
225                230                235                240

Thr Arg Ala Leu Leu Gln Thr Leu Gly Asn Leu Gly Tyr Arg Ala Ser
        245                250                255

Ala Lys Lys Ala Gln Ile Cys Gln Lys Gln Val Lys Tyr Leu Gly Tyr
        260                265                270

Leu Leu Lys Glu Gly Gln Arg Trp Leu Thr Glu Ala Arg Lys Glu Thr
        275                280                285

Val Met Gly Gln Pro Thr Pro Lys Thr Pro Arg Gln Leu Arg Glu Phe
        290                295                300

Leu Gly Thr Ala Gly Phe Cys Arg Leu Trp Ile Pro Gly Phe Ala Glu
305                310                315                320

Met Ala Ala Pro Leu Tyr Pro Leu Thr Lys Thr Gly Thr Leu Phe Asn
                325                330                335

Trp Gly Pro Asp Gln Gln Lys Ala Tyr Gln Glu Ile Lys Gln Ala Leu
                340                345                350

Leu Thr Ala Pro Ala Leu Gly Leu Pro Asp Leu Thr Lys Pro Phe Glu
                355                360                365

Leu Phe Val Asp Glu Lys Gln Gly Tyr Ala Lys Gly Val Leu Thr Gln
        370                375                380

Lys Leu Gly Pro Trp Arg Arg Pro Val Ala Tyr Leu Ser Lys Lys Leu
385                390                395                400

Asp Pro Val Ala Ala Gly Trp Pro Pro Cys Leu Arg Met Val Ala Ala
                405                410                415

Ile Ala Val Leu Thr Lys Asp Ala Gly Lys Leu Thr Met Gly Gln Pro
                420                425                430

Leu Val Ile Leu Ala Pro His Ala Val Glu Ala Leu Val Lys Gln Pro
                435                440                445

Pro Asp Arg Trp Leu Ser Asn Ala Arg Met Thr His Tyr Gln Ala Leu
        450                455                460

Leu Leu Asp Thr Asp Arg Val Gln Phe Gly Pro Val Val Ala Leu Asn
465                470                475                480

Pro Ala Thr Leu Leu Pro Leu Pro Glu Glu Gly Leu Gln His Asn Cys
                485                490                495

Leu Asp Ile Leu Ala Glu Ala His Gly Thr Arg Pro Asp Leu Thr Asp
                500                505                510

Gln Pro Leu Pro Asp Ala Asp His Thr Trp Tyr Thr Gly Gly Ser Ser
        515                520                525

Leu Leu Gln Glu Gly Gln Arg Lys Ala Gly Ala Ala Val Thr Thr Glu
        530                535                540

Thr Glu Val Ile Trp Ala Lys Ala Leu Pro Ala Gly Thr Ser Ala Gln
545                550                555                560

Arg Ala Gln Leu Ile Ala Leu Thr Gln Ala Leu Lys Met Ala Glu Gly
                565                570                575

Lys Lys Leu Asn Val Tyr Thr Asn Ser Arg Tyr Ala Phe Ala Thr Ala
                580                585                590

His Ile His Gly Glu Ile Tyr Arg Arg Arg Gly Leu Leu Thr Ser Glu
        595                600                605

Gly Lys Glu Ile Lys Asn Lys Asp Glu Ile Leu Ala Leu Leu Lys Ala
        610                615                620

Leu Phe Leu Pro Lys Arg Leu Ser Ile Ile His Cys Pro Gly His Gln
625                630                635                640
```

-continued

```
Lys Gly His Ser Ala Glu Ala Arg Gly Asn Arg Met Ala Asp Gln Ala
            645             650             655

Ala Arg Lys Ala Ala Ile Thr Glu Thr Pro Asp Thr Ser Thr Leu Leu
            660             665             670

Ile Glu Asn Ser Ser Pro Tyr Thr Ser Glu His Phe
        675             680

<210> SEQ ID NO 650
<211> LENGTH: 684
<212> TYPE: PRT
<213> ORGANISM: Artificial Sequence
<220> FEATURE:
<223> OTHER INFORMATION: RTase mutant

<400> SEQUENCE: 650

Met Thr Leu Asn Ile Glu Asp Glu His Arg Leu His Glu Thr Ser Lys
1               5               10              15

Glu Pro Asp Val Ser Leu Gly Ser Thr Trp Leu Ser Asp Phe Pro Gln
            20              25              30

Ala Trp Ala Glu Thr Gly Gly Met Gly Leu Ala Val Arg Gln Ala Pro
        35              40              45

Leu Ile Ile Pro Leu Lys Ala Thr Ser Thr Pro Val Ser Ile Lys Gln
    50              55              60

Tyr Pro Met Ser Gln Glu Ala Arg Leu Gly Ile Lys Pro His Ile Gln
65              70              75              80

Arg Leu Leu Asp Gln Gly Ile Leu Val Pro Cys Gln Ser Pro Trp Asn
            85              90              95

Thr Pro Leu Lys Pro Val Lys Lys Pro Gly Thr Asn Asp Tyr Arg Pro
            100             105             110

Val Gln Asp Leu Arg Glu Val Asn Lys Arg Val Glu Asp Ile His Pro
            115             120             125

Thr Val Pro Asn Pro Tyr Asn Leu Leu Ser Gly Leu Pro Pro Ser His
    130             135             140

Gln Trp Tyr Thr Val Leu Asp Leu Lys Asp Ala Phe Phe Cys Leu Arg
145             150             155             160

Leu His Pro Thr Ser Gln Pro Leu Phe Ala Phe Glu Trp Arg Asp Pro
            165             170             175

Glu Met Gly Ile Ser Gly Gln Leu Thr Trp Thr Arg Leu Pro Gln Gly
            180             185             190

Phe Lys Asn Ser Pro Thr Leu Phe Asp Glu Ala Leu His Arg Asp Leu
            195             200             205

Ala Asp Phe Arg Ile Gln His Pro Asp Leu Ile Leu Leu Gln Tyr Val
    210             215             220

Asp Asp Leu Leu Leu Ala Ala Thr Ser Glu Leu Asp Cys Gln Gln Gly
225             230             235             240

Thr Arg Ala Leu Leu Gln Thr Leu Gly Asn Leu Gly Tyr Arg Ala Ser
            245             250             255

Ala Lys Lys Ala Gln Ile Cys Gln Lys Gln Val Lys Tyr Leu Gly Tyr
            260             265             270

Leu Leu Lys Glu Gly Gln Arg Trp Leu Thr Glu Ala Arg Lys Glu Thr
            275             280             285

Val Met Gly Gln Pro Thr Pro Lys Thr Pro Arg Gln Leu Arg Glu Phe
    290             295             300

Leu Gly Thr Ala Gly Phe Cys Arg Leu Trp Ile Pro Gly Phe Ala Glu
305             310             315             320
```

-continued

```
Met Ala Ala Pro Leu Tyr Pro Leu Thr Lys Thr Gly Thr Leu Phe Asn
             325             330             335

Trp Gly Pro Asp Gln Gln Lys Ala Tyr Gln Glu Ile Lys Gln Ala Leu
             340             345             350

Leu Thr Ala Pro Ala Leu Gly Leu Pro Asp Leu Thr Lys Pro Phe Glu
             355             360             365

Leu Phe Val Asp Glu Lys Gln Gly Tyr Ala Lys Gly Val Leu Thr Gln
      370             375             380

Lys Leu Gly Pro Trp Arg Arg Pro Val Ala Tyr Leu Ser Lys Lys Leu
385             390             395             400

Asp Pro Val Ala Ala Gly Trp Pro Pro Cys Leu Arg Met Val Ala Ala
             405             410             415

Ile Ala Val Leu Thr Lys Asp Ala Gly Lys Leu Thr Met Gly Gln Pro
             420             425             430

Leu Val Ile Leu Ala Pro His Ala Val Glu Ala Leu Val Lys Gln Pro
             435             440             445

Pro Asp Arg Trp Leu Ser Asn Ala Arg Met Thr His Tyr Gln Ala Leu
      450             455             460

Leu Leu Asp Thr Asp Arg Val Gln Phe Gly Pro Val Val Ala Leu Asn
465             470             475             480

Pro Ala Thr Leu Leu Pro Leu Pro Glu Glu Gly Leu Gln His Asn Cys
             485             490             495

Leu Asp Ile Leu Ala Glu Ala His Gly Thr Arg Pro Asp Leu Thr Asp
             500             505             510

Gln Pro Leu Pro Asp Ala Asp His Thr Trp Tyr Thr Gly Gly Ser Ser
             515             520             525

Leu Leu Gln Glu Gly Gln Arg Lys Ala Gly Ala Ala Val Thr Thr Glu
      530             535             540

Thr Glu Val Ile Trp Ala Lys Ala Leu Pro Ala Gly Thr Ser Ala Gln
545             550             555             560

Arg Ala Gln Leu Ile Ala Leu Thr Gln Ala Leu Lys Met Ala Glu Gly
             565             570             575

Lys Lys Leu Asn Val Tyr Thr Asn Ser Arg Tyr Ala Phe Ala Thr Ala
             580             585             590

His Ile His Gly Glu Ile Tyr Arg Arg Arg Gly Leu Leu Thr Ser Glu
             595             600             605

Gly Lys Glu Ile Lys Asn Lys Asp Glu Ile Leu Ala Leu Leu Lys Ala
      610             615             620

Leu Phe Leu Pro Lys Arg Leu Ser Ile Ile His Cys Pro Gly His Gln
625             630             635             640

Lys Gly His Ser Ala Glu Ala Arg Gly Asn Arg Met Ala Asp Gln Ala
             645             650             655

Ala Arg Lys Ala Ala Ile Thr Glu Thr Pro Asp Thr Ser Thr Leu Leu
             660             665             670

Ile Glu Asn Ser Ser Pro Tyr Thr Ser Glu His Phe
             675             680
```

<210> SEQ ID NO 651
<211> LENGTH: 684
<212> TYPE: PRT
<213> ORGANISM: Artificial Sequence
<220> FEATURE:
<223> OTHER INFORMATION: RTase mutant

<400> SEQUENCE: 651

-continued

```
Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Asn Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
            115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
            165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
            195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
            245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
            275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
            325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
            355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
            405                 410                 415
```

-continued

```
Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
            435                 440                 445

Pro Asp Arg Trp Leu Ser Asn Ala Arg Met Thr His Tyr Gln Ala Leu
            450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                    485                 490                 495

Leu Asp Ile Leu Ala Glu Ala His Gly Thr Arg Pro Asp Leu Thr Asp
                500                 505                 510

Gln Pro Leu Pro Asp Ala Asp His Thr Trp Tyr Thr Gly Gly Ser Ser
            515                 520                 525

Leu Leu Gln Glu Gly Gln Arg Lys Ala Gly Ala Ala Val Thr Thr Glu
            530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
                580                 585                 590

His Ile His Gly Glu Ile Tyr Arg Arg Arg Gly Leu Leu Thr Ser Glu
                595                 600                 605

Gly Lys Glu Ile Lys Asn Lys Asp Glu Ile Leu Ala Leu Leu Lys Ala
            610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                    645                 650                 655

Ala Arg Lys Ala Ala Ile Thr Glu Thr Pro Asp Thr Ser Thr Leu Leu
                660                 665                 670

Ile Glu Asn Ser Ser Pro Tyr Thr Ser Glu His Phe
            675                 680
```

```
<210> SEQ ID NO 652
<211> LENGTH: 684
<212> TYPE: PRT
<213> ORGANISM: Artificial Sequence
<220> FEATURE:
<223> OTHER INFORMATION: RTase mutant

<400> SEQUENCE: 652
```

```
Met Thr Leu Asn Ile Glu Asp Glu His Arg Leu His Glu Thr Ser Lys
1                   5                   10                  15

Glu Pro Asp Val Ser Leu Gly Ser Thr Trp Leu Ser Asp Phe Pro Gln
                20                  25                  30

Ala Trp Ala Glu Thr Gly Gly Met Gly Leu Ala Val Arg Gln Ala Pro
            35                  40                  45

Leu Ile Ile Pro Leu Lys Ala Thr Ser Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                    85                  90                  95
```

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Met Ala Arg Lys Glu Thr
        275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Gly Gly Ser Ser

-continued

```
                515                 520                 525
Leu Leu Gln Glu Gly Gln Arg Lys Ala Gly Ala Ala Val Thr Thr Glu
    530                 535                 540
Thr Glu Val Ile Trp Ala Lys Ala Leu Pro Ala Gly Thr Ser Ala Gln
545                 550                 555                 560
Arg Ala Gln Leu Ile Ala Leu Thr Gln Ala Leu Lys Met Ala Glu Gly
                565                 570                 575
Lys Lys Leu Asn Val Tyr Thr Asn Ser Arg Tyr Ala Phe Ala Thr Ala
                580                 585                 590
His Ile His Gly Glu Ile Tyr Arg Arg Arg Gly Leu Leu Thr Ser Glu
                595                 600                 605
Gly Lys Glu Ile Lys Asn Lys Asp Glu Ile Leu Ala Leu Leu Lys Ala
    610                 615                 620
Leu Phe Leu Pro Lys Arg Leu Ser Ile Ile His Cys Pro Gly His Gln
625                 630                 635                 640
Lys Gly His Ser Ala Glu Ala Arg Gly Asn Arg Met Ala Asp Gln Ala
                645                 650                 655
Ala Arg Lys Ala Ala Ile Thr Glu Thr Pro Asp Thr Ser Thr Leu Leu
                660                 665                 670
Ile Glu Asn Ser Ser Pro Tyr Thr Ser Glu His Phe
                675                 680

<210> SEQ ID NO 653
<211> LENGTH: 684
<212> TYPE: PRT
<213> ORGANISM: Artificial Sequence
<220> FEATURE:
<223> OTHER INFORMATION: RTase mutant

<400> SEQUENCE: 653

Met Thr Leu Asn Ile Glu Asp Glu His Arg Leu His Glu Thr Ser Lys
1               5                   10                  15
Glu Pro Asp Val Ser Leu Gly Ser Thr Trp Leu Ser Asp Phe Pro Gln
                20                  25                  30
Ala Trp Ala Glu Thr Gly Gly Met Gly Leu Ala Val Arg Gln Ala Pro
            35                  40                  45
Leu Ile Ile Pro Leu Lys Ala Thr Ser Thr Pro Val Ser Ile Lys Gln
    50                  55                  60
Tyr Pro Met Ser Gln Glu Ala Arg Leu Gly Ile Lys Pro His Ile Gln
65                  70                  75                  80
Arg Leu Leu Asp Gln Gly Ile Leu Val Pro Cys Gln Ser Pro Trp Asn
                85                  90                  95
Thr Pro Leu Leu Pro Val Lys Lys Pro Gly Thr Asn Asp Tyr Arg Pro
                100                 105                 110
Val Gln Asp Leu Arg Glu Val Asn Lys Arg Val Glu Asp Ile His Pro
            115                 120                 125
Thr Val Pro Asn Pro Tyr Asn Leu Leu Ser Gly Leu Pro Pro Ser His
    130                 135                 140
Gln Trp Tyr Thr Val Leu Asp Leu Lys Asp Ala Phe Phe Cys Leu Arg
145                 150                 155                 160
Leu His Pro Thr Ser Gln Pro Leu Phe Ala Phe Glu Trp Arg Asp Pro
                165                 170                 175
Glu Met Gly Ile Ser Gly Gln Leu Thr Trp Thr Arg Leu Pro Gln Gly
                180                 185                 190
Phe Lys Asn Ser Pro Thr Leu Phe Asp Glu Ala Leu His Arg Asp Leu
```

-continued

```
                195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Trp Ala Arg Lys Glu Thr
            275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
            355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
            435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Gly Gly Ser Ser
            515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
            580                 585                 590

His Ile His Gly Glu Ile Tyr Arg Arg Arg Gly Leu Leu Thr Ser Glu
            595                 600                 605

Gly Lys Glu Ile Lys Asn Lys Asp Glu Ile Leu Ala Leu Leu Lys Ala
    610                 615                 620
```

-continued

```
Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
                660                 665                 670

Ile Glu Asn Ser Ser Pro Tyr Thr Ser Glu His Phe
            675                 680

<210> SEQ ID NO 654
<211> LENGTH: 684
<212> TYPE: PRT
<213> ORGANISM: Artificial Sequence
<220> FEATURE:
<223> OTHER INFORMATION: RTase mutant

<400> SEQUENCE: 654

Met Thr Leu Asn Ile Glu Asp Glu His Arg Leu His Glu Thr Ser Lys
1                   5                   10                  15

Glu Pro Asp Val Ser Leu Gly Ser Thr Trp Leu Ser Asp Phe Pro Gln
                20                  25                  30

Ala Trp Ala Glu Thr Gly Gly Met Gly Leu Ala Val Arg Gln Ala Pro
            35                  40                  45

Leu Ile Ile Pro Leu Lys Ala Thr Ser Thr Pro Val Ser Arg Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
                100                 105                 110

Val Gln Asp Leu Arg Glu Val Asn Lys Arg Val Glu Asp Ile His Pro
            115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
            195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
            245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Asp Ala Arg Lys Glu Thr
            275                 280                 285

Val Met Gly Gln Pro Thr Pro Lys Thr Pro Arg Gln Leu Arg Glu Phe
    290                 295                 300
```

-continued

```
Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
                340                 345                 350

Leu Thr Ala Pro Ala Leu Gly Leu Pro Asp Leu Thr Lys Pro Phe Glu
                355                 360                 365

Leu Phe Val Asp Glu Lys Gln Gly Tyr Ala Lys Gly Val Leu Thr Gln
            370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
                420                 425                 430

Leu Val Ile Leu Ala Pro His Ala Val Glu Ala Leu Val Lys Gln Pro
                435                 440                 445

Pro Asp Arg Trp Leu Ser Asn Ala Arg Met Thr His Tyr Gln Ala Leu
            450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
                500                 505                 510

Gln Pro Leu Pro Asp Ala Asp His Thr Trp Tyr Thr Gly Gly Ser Ser
            515                 520                 525

Leu Leu Gln Glu Gly Gln Arg Lys Ala Gly Ala Ala Val Thr Thr Glu
            530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
                580                 585                 590

His Ile His Gly Glu Ile Tyr Arg Arg Arg Gly Leu Leu Thr Ser Glu
                595                 600                 605

Gly Lys Glu Ile Lys Asn Lys Asp Glu Ile Leu Ala Leu Leu Lys Ala
            610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
                660                 665                 670

Ile Glu Asn Ser Ser Pro Tyr Thr Ser Glu His Phe
            675                 680

<210> SEQ ID NO 655
<211> LENGTH: 684
<212> TYPE: PRT
<213> ORGANISM: Artificial Sequence
<220> FEATURE:
```

-continued

<223> OTHER INFORMATION: RTase mutant

<400> SEQUENCE: 655

```
Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Arg Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Asp Ala Arg Lys Glu Thr
        275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400
```

-continued

```
Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
                420                 425                 430

Leu Val Ile Leu Ala Pro His Ala Val Glu Ala Leu Val Lys Gln Pro
                435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
                500                 505                 510

Gln Pro Leu Pro Asp Ala Asp His Thr Trp Tyr Thr Gly Gly Ser Ser
                515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
                580                 585                 590

His Ile His Gly Glu Ile Tyr Arg Arg Arg Gly Leu Leu Thr Ser Glu
                595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
                660                 665                 670

Ile Glu Asn Ser Ser Pro Tyr Thr Ser Glu His Phe
                675                 680
```

<210> SEQ ID NO 656
<211> LENGTH: 684
<212> TYPE: PRT
<213> ORGANISM: Artificial Sequence
<220> FEATURE:
<223> OTHER INFORMATION: RTase mutant

<400> SEQUENCE: 656

```
Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
                20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Arg Glu Ala Arg Leu Gly Ile Lys Pro His Ile Gln
65                  70                  75                  80
```

-continued

```
Arg Leu Leu Asp Gln Gly Ile Leu Val Pro Cys Gln Ser Pro Trp Asn
            85              90              95

Thr Pro Leu Leu Pro Val Lys Lys Pro Gly Thr Asn Asp Tyr Arg Pro
            100             105             110

Val Gln Asp Leu Arg Glu Val Asn Lys Arg Val Glu Asp Ile His Pro
            115             120             125

Thr Val Pro Asn Pro Tyr Asn Leu Leu Ser Gly Leu Pro Pro Ser His
    130             135             140

Gln Trp Tyr Thr Val Leu Asp Leu Lys Asp Ala Phe Phe Cys Leu Arg
145             150             155             160

Leu His Pro Thr Ser Gln Pro Leu Phe Ala Phe Glu Trp Arg Asp Pro
            165             170             175

Glu Met Gly Ile Ser Gly Gln Leu Thr Trp Thr Arg Leu Pro Gln Gly
            180             185             190

Phe Lys Asn Ser Pro Thr Leu Phe Asp Glu Ala Leu His Arg Asp Leu
            195             200             205

Ala Asp Phe Arg Ile Gln His Pro Asp Leu Ile Leu Leu Gln Tyr Val
    210             215             220

Asp Asp Leu Leu Leu Ala Ala Thr Ser Glu Leu Asp Cys Gln Gln Gly
225             230             235             240

Thr Arg Ala Leu Leu Gln Thr Leu Gly Asn Leu Gly Tyr Arg Ala Ser
            245             250             255

Ala Lys Lys Ala Gln Ile Cys Gln Lys Gln Val Lys Tyr Leu Gly Tyr
            260             265             270

Leu Leu Lys Glu Gly Gln Arg Trp Leu Thr Asp Ala Arg Lys Glu Thr
            275             280             285

Val Met Gly Gln Pro Thr Pro Lys Thr Pro Arg Gln Leu Arg Glu Phe
    290             295             300

Leu Gly Thr Ala Gly Phe Cys Arg Leu Trp Ile Pro Gly Phe Ala Glu
305             310             315             320

Met Ala Ala Pro Leu Tyr Pro Leu Thr Lys Thr Gly Thr Leu Phe Asn
            325             330             335

Trp Gly Pro Asp Gln Gln Lys Ala Tyr Gln Glu Ile Lys Gln Ala Leu
            340             345             350

Leu Thr Ala Pro Ala Leu Gly Leu Pro Asp Leu Thr Lys Pro Phe Glu
            355             360             365

Leu Phe Val Asp Glu Lys Gln Gly Tyr Ala Lys Gly Val Leu Thr Gln
    370             375             380

Lys Leu Gly Pro Trp Arg Arg Pro Val Ala Tyr Leu Ser Lys Lys Leu
385             390             395             400

Asp Pro Val Ala Ala Gly Trp Pro Pro Cys Leu Arg Met Val Ala Ala
            405             410             415

Ile Ala Val Leu Thr Lys Asp Ala Gly Lys Leu Thr Met Gly Gln Pro
            420             425             430

Leu Val Ile Leu Ala Pro His Ala Val Glu Ala Leu Val Lys Gln Pro
            435             440             445

Pro Asp Arg Trp Leu Ser Asn Ala Arg Met Thr His Tyr Gln Ala Leu
    450             455             460

Leu Leu Asp Thr Asp Arg Val Gln Phe Gly Pro Val Val Ala Leu Asn
465             470             475             480

Pro Ala Thr Leu Leu Pro Leu Pro Glu Glu Gly Leu Gln His Asn Cys
            485             490             495

Leu Asp Ile Leu Ala Glu Ala His Gly Thr Arg Pro Asp Leu Thr Asp
```

-continued

```
            500                 505                 510
Gln Pro Leu Pro Asp Ala Asp His Thr Trp Tyr Thr Gly Gly Ser Ser
            515                 520                 525

Leu Leu Gln Glu Gly Gln Arg Lys Ala Gly Ala Ala Val Thr Thr Glu
        530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
                580                 585                 590

His Ile His Gly Glu Ile Tyr Arg Arg Arg Gly Leu Leu Thr Ser Glu
                595                 600                 605

Gly Lys Glu Ile Lys Asn Lys Asp Glu Ile Leu Ala Leu Leu Lys Ala
            610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
                660                 665                 670

Ile Glu Asn Ser Ser Pro Tyr Thr Ser Glu His Phe
            675                 680
```

<210> SEQ ID NO 657
<211> LENGTH: 684
<212> TYPE: PRT
<213> ORGANISM: Artificial Sequence
<220> FEATURE:
<223> OTHER INFORMATION: RTase mutant

<400> SEQUENCE: 657

```
Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Gln Glu Ala Arg Leu Gly Ile Lys Pro His Ile Arg
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
            115                 120                 125

Thr Val Pro Asn Pro Tyr Asn Leu Leu Ser Gly Leu Pro Pro Ser His
        130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
```

-continued

```
                 180               185               190
Phe Lys Asn Ser Pro Thr Leu Phe Asp Glu Ala Leu His Arg Asp Leu
            195               200               205

Ala Asp Phe Arg Ile Gln His Pro Asp Leu Ile Leu Leu Gln Tyr Val
        210               215               220

Asp Asp Leu Leu Leu Ala Ala Thr Ser Glu Leu Asp Cys Gln Gln Gly
225               230               235               240

Thr Arg Ala Leu Leu Gln Thr Leu Gly Asn Leu Gly Tyr Arg Ala Ser
            245               250               255

Ala Lys Lys Ala Gln Ile Cys Gln Lys Gln Val Lys Tyr Leu Gly Tyr
        260               265               270

Leu Leu Lys Glu Gly Gln Arg Trp Leu Thr Asp Ala Arg Lys Glu Thr
        275               280               285

Val Met Gly Gln Pro Thr Pro Lys Thr Pro Arg Gln Leu Arg Glu Phe
        290               295               300

Leu Gly Thr Ala Gly Phe Cys Arg Leu Trp Ile Pro Gly Phe Ala Glu
305               310               315               320

Met Ala Ala Pro Leu Tyr Pro Leu Thr Lys Thr Gly Thr Leu Phe Asn
            325               330               335

Trp Gly Pro Asp Gln Gln Lys Ala Tyr Gln Glu Ile Lys Gln Ala Leu
            340               345               350

Leu Thr Ala Pro Ala Leu Gly Leu Pro Asp Leu Thr Lys Pro Phe Glu
            355               360               365

Leu Phe Val Asp Glu Lys Gln Gly Tyr Ala Lys Gly Val Leu Thr Gln
        370               375               380

Lys Leu Gly Pro Trp Arg Arg Pro Val Ala Tyr Leu Ser Lys Lys Leu
385               390               395               400

Asp Pro Val Ala Ala Gly Trp Pro Pro Cys Leu Arg Met Val Ala Ala
            405               410               415

Ile Ala Val Leu Thr Lys Asp Ala Gly Lys Leu Thr Met Gly Gln Pro
            420               425               430

Leu Val Ile Leu Ala Pro His Ala Val Glu Ala Leu Val Lys Gln Pro
            435               440               445

Pro Asp Arg Trp Leu Ser Asn Ala Arg Met Thr His Tyr Gln Ala Leu
        450               455               460

Leu Leu Asp Thr Asp Arg Val Gln Phe Gly Pro Val Val Ala Leu Asn
465               470               475               480

Pro Ala Thr Leu Leu Pro Leu Pro Glu Glu Gly Leu Gln His Asn Cys
            485               490               495

Leu Asp Ile Leu Ala Glu Ala His Gly Thr Arg Pro Asp Leu Thr Asp
            500               505               510

Gln Pro Leu Pro Asp Ala Asp His Thr Trp Tyr Thr Gly Gly Ser Ser
            515               520               525

Leu Leu Gln Glu Gly Gln Arg Lys Ala Gly Ala Ala Val Thr Thr Glu
        530               535               540

Thr Glu Val Ile Trp Ala Lys Ala Leu Pro Ala Gly Thr Ser Ala Gln
545               550               555               560

Arg Ala Gln Leu Ile Ala Leu Thr Gln Ala Leu Lys Met Ala Glu Gly
            565               570               575

Lys Lys Leu Asn Val Tyr Thr Asn Ser Arg Tyr Ala Phe Ala Thr Ala
            580               585               590

His Ile His Gly Glu Ile Tyr Arg Arg Arg Gly Leu Leu Thr Ser Glu
            595               600               605
```

```
Gly Lys Glu Ile Lys Asn Lys Asp Glu Ile Leu Ala Leu Leu Lys Ala
    610             615             620
```

```
Leu Phe Leu Pro Lys Arg Leu Ser Ile Ile His Cys Pro Gly His Gln
625             630             635             640
```

```
Lys Gly His Ser Ala Glu Ala Arg Gly Asn Arg Met Ala Asp Gln Ala
            645             650             655
```

```
Ala Arg Lys Ala Ala Ile Thr Glu Thr Pro Asp Thr Ser Thr Leu Leu
            660             665             670
```

```
Ile Glu Asn Ser Ser Pro Tyr Thr Ser Glu His Phe
            675             680
```

<210> SEQ ID NO 658
<211> LENGTH: 684
<212> TYPE: PRT
<213> ORGANISM: Artificial Sequence
<220> FEATURE:
<223> OTHER INFORMATION: RTase mutant

<400> SEQUENCE: 658

```
Met Thr Leu Asn Ile Glu Asp Glu His Arg Leu His Glu Thr Ser Lys
1               5               10              15
```

```
Glu Pro Asp Val Ser Leu Gly Ser Thr Trp Leu Ser Asp Phe Pro Gln
            20              25              30
```

```
Ala Trp Ala Glu Thr Gly Gly Met Gly Leu Ala Val Arg Gln Ala Pro
        35              40              45
```

```
Leu Ile Ile Pro Leu Lys Ala Thr Ser Thr Pro Val Ser Ile Lys Gln
    50              55              60
```

```
Tyr Pro Met Ser Gln Glu Ala Arg Leu Gly Ile Lys Pro His Ile Gln
65              70              75              80
```

```
Arg Leu Leu Asp Gln Gly Ile Leu Val Pro Cys Gln Ser Pro Trp Asn
            85              90              95
```

```
Thr Pro Leu Leu Pro Val Lys Lys Pro Gly Thr Asn Asp Tyr Arg Pro
            100             105             110
```

```
Val Gln Asp Leu Arg Glu Val Asn Lys Arg Val Glu Asp Ile His Pro
            115             120             125
```

```
Thr Val Pro Asn Pro Tyr Asn Leu Leu Ser Gly Leu Pro Pro Ser His
    130             135             140
```

```
Gln Trp Tyr Thr Val Leu Asp Leu Lys Asp Ala Phe Phe Cys Leu Arg
145             150             155             160
```

```
Leu His Pro Thr Ser Gln Pro Leu Phe Ala Phe Glu Trp Arg Asp Pro
            165             170             175
```

```
Glu Met Gly Ile Ser Gly Gln Leu Thr Trp Thr Arg Leu Pro Gln Gly
            180             185             190
```

```
Phe Lys Asn Ser Pro Thr Leu Phe Asp Glu Ala Leu His Arg Asp Leu
            195             200             205
```

```
Ala Asp Phe Arg Ile Gln His Pro Asp Leu Ile Leu Leu Gln Tyr Val
    210             215             220
```

```
Asp Asp Leu Leu Leu Ala Ala Thr Ser Glu Leu Asp Cys Gln Gln Gly
225             230             235             240
```

```
Thr Arg Ala Leu Leu Gln Thr Leu Gly Asn Leu Gly Tyr Arg Ala Ser
            245             250             255
```

```
Ala Lys Lys Ala Gln Ile Cys Gln Lys Gln Val Lys Tyr Leu Gly Tyr
            260             265             270
```

```
Leu Leu Lys Glu Gly Gln Arg Trp Leu Thr Asp Ala Arg Lys Glu Thr
            275             280             285
```

-continued

```
Val Met Gly Gln Pro Thr Pro Lys Thr Pro Ala Gln Leu Arg Glu Phe
    290             295             300

Leu Gly Thr Ala Gly Phe Cys Arg Leu Trp Ile Pro Gly Phe Ala Glu
305             310             315             320

Met Ala Ala Pro Leu Tyr Pro Leu Thr Lys Thr Gly Thr Leu Phe Asn
            325             330             335

Trp Gly Pro Asp Gln Gln Lys Ala Tyr Gln Glu Ile Lys Gln Ala Leu
            340             345             350

Leu Thr Ala Pro Ala Leu Gly Leu Pro Asp Leu Thr Lys Pro Phe Glu
            355             360             365

Leu Phe Val Asp Glu Lys Gln Gly Tyr Ala Lys Gly Val Leu Thr Gln
    370             375             380

Lys Leu Gly Pro Trp Arg Arg Pro Val Ala Tyr Leu Ser Lys Lys Leu
385             390             395             400

Asp Pro Val Ala Ala Gly Trp Pro Pro Cys Leu Arg Met Val Ala Ala
            405             410             415

Ile Ala Val Leu Thr Lys Asp Ala Gly Lys Leu Thr Met Gly Gln Pro
            420             425             430

Leu Val Ile Leu Ala Pro His Ala Val Glu Ala Leu Val Lys Gln Pro
            435             440             445

Pro Asp Arg Trp Leu Ser Asn Ala Arg Met Thr His Tyr Gln Ala Leu
    450             455             460

Leu Leu Asp Thr Asp Arg Val Gln Phe Gly Pro Val Val Ala Leu Asn
465             470             475             480

Pro Ala Thr Leu Leu Pro Leu Pro Glu Glu Gly Leu Gln His Asn Cys
            485             490             495

Leu Asp Ile Leu Ala Glu Ala His Gly Thr Arg Pro Asp Leu Thr Asp
            500             505             510

Gln Pro Leu Pro Asp Ala Asp His Thr Trp Tyr Thr Gly Gly Ser Ser
            515             520             525

Leu Leu Gln Glu Gly Gln Arg Lys Ala Gly Ala Ala Val Thr Thr Glu
    530             535             540

Thr Glu Val Ile Trp Ala Lys Ala Leu Pro Ala Gly Thr Ser Ala Gln
545             550             555             560

Arg Ala Gln Leu Ile Ala Leu Thr Gln Ala Leu Lys Met Ala Glu Gly
            565             570             575

Lys Lys Leu Asn Val Tyr Thr Asn Ser Arg Tyr Ala Phe Ala Thr Ala
            580             585             590

His Ile His Gly Glu Ile Tyr Arg Arg Arg Gly Leu Leu Thr Ser Glu
            595             600             605

Gly Lys Glu Ile Lys Asn Lys Asp Glu Ile Leu Ala Leu Leu Lys Ala
    610             615             620

Leu Phe Leu Pro Lys Arg Leu Ser Ile Ile His Cys Pro Gly His Gln
625             630             635             640

Lys Gly His Ser Ala Glu Ala Arg Gly Asn Arg Met Ala Asp Gln Ala
            645             650             655

Ala Arg Lys Ala Ala Ile Thr Glu Thr Pro Asp Thr Ser Thr Leu Leu
            660             665             670

Ile Glu Asn Ser Ser Pro Tyr Thr Ser Glu His Phe
    675             680
```

<210> SEQ ID NO 659
<211> LENGTH: 684

-continued

```
<212> TYPE: PRT
<213> ORGANISM: Artificial Sequence
<220> FEATURE:
<223> OTHER INFORMATION: RTase mutant

<400> SEQUENCE: 659

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Arg Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Arg Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
            115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
            195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
            245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
            325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380
```

-continued

```
Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
                420                 425                 430

Leu Val Ile Leu Ala Pro His Ala Val Glu Ala Leu Val Lys Gln Pro
            435                 440                 445

Pro Asp Arg Trp Leu Ser Asn Ala Arg Met Thr His Tyr Gln Ala Leu
        450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
                500                 505                 510

Gln Pro Leu Pro Asp Ala Asp His Thr Trp Tyr Thr Gly Gly Ser Ser
        515                 520                 525

Leu Leu Gln Glu Gly Gln Arg Lys Ala Gly Ala Ala Val Thr Thr Glu
        530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
                580                 585                 590

His Ile His Gly Glu Ile Tyr Arg Arg Arg Gly Leu Leu Thr Ser Glu
            595                 600                 605

Gly Lys Glu Ile Lys Asn Lys Asp Glu Ile Leu Ala Leu Leu Lys Ala
        610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
                660                 665                 670

Ile Glu Asn Ser Ser Pro Tyr Thr Ser Glu His Phe
                675                 680
```

```
<210> SEQ ID NO 660
<211> LENGTH: 683
<212> TYPE: PRT
<213> ORGANISM: Artificial Sequence
<220> FEATURE:
<223> OTHER INFORMATION: RTase mutant

<400> SEQUENCE: 660
```

```
Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
                20                  25                  30

Ala Trp Ala Glu Thr Gly Gly Met Gly Leu Ala Val Arg Gln Ala Pro
            35                  40                  45

Leu Ile Ile Pro Leu Lys Ala Thr Ser Thr Pro Val Ser Arg Lys Gln
        50                  55                  60
```

-continued

```
Tyr Pro Met Ser Arg Glu Ala Arg Leu Gly Ile Lys Pro His Ile Gln
65              70              75              80

Arg Leu Leu Asp Gln Gly Ile Leu Val Pro Cys Gln Ser Pro Trp Asn
                85              90              95

Thr Pro Leu Leu Pro Val Lys Lys Pro Gly Thr Asn Asp Tyr Arg Pro
            100             105             110

Val Gln Asp Leu Arg Glu Val Asn Lys Arg Val Glu Asp Ile His Pro
        115             120             125

Thr Val Pro Asn Pro Tyr Asn Leu Leu Ser Gly Leu Pro Pro Ser His
    130             135             140

Gln Trp Tyr Thr Val Leu Asp Leu Lys Asp Ala Phe Phe Cys Leu Arg
145             150             155             160

Leu His Pro Thr Ser Gln Pro Leu Phe Ala Phe Glu Trp Arg Asp Pro
            165             170             175

Glu Met Gly Ile Ser Gly Gln Leu Thr Trp Thr Arg Leu Pro Gln Gly
            180             185             190

Phe Lys Asn Ser Pro Thr Leu Phe Asp Glu Ala Leu His Arg Asp Leu
        195             200             205

Ala Asp Phe Arg Ile Gln His Pro Asp Leu Ile Leu Leu Gln Tyr Val
    210             215             220

Asp Asp Leu Leu Leu Ala Ala Thr Ser Glu Leu Asp Cys Gln Gln Gly
225             230             235             240

Thr Arg Ala Leu Leu Gln Thr Leu Gly Asn Leu Gly Tyr Arg Ala Ser
            245             250             255

Ala Lys Lys Ala Gln Ile Cys Gln Lys Gln Val Lys Tyr Leu Gly Tyr
        260             265             270

Leu Leu Lys Glu Gly Gln Arg Trp Leu Thr Glu Ala Arg Lys Glu Thr
        275             280             285

Val Met Gly Gln Pro Thr Pro Lys Thr Pro Arg Gln Leu Arg Glu Phe
    290             295             300

Leu Gly Thr Ala Gly Phe Cys Arg Leu Trp Ile Pro Gly Phe Ala Glu
305             310             315             320

Met Ala Ala Pro Leu Tyr Pro Leu Thr Lys Thr Gly Thr Leu Phe Asn
            325             330             335

Trp Gly Pro Asp Gln Gln Lys Ala Tyr Gln Glu Ile Lys Gln Ala Leu
            340             345             350

Leu Thr Ala Pro Ala Leu Gly Leu Pro Asp Leu Thr Lys Pro Phe Glu
        355             360             365

Leu Phe Val Asp Glu Lys Gln Gly Tyr Ala Lys Gly Val Leu Thr Gln
    370             375             380

Lys Leu Gly Pro Trp Arg Arg Pro Val Ala Tyr Leu Ser Lys Lys Leu
385             390             395             400

Asp Pro Val Ala Ala Gly Trp Pro Pro Cys Leu Arg Met Val Ala Ala
            405             410             415

Ile Ala Val Leu Thr Lys Asp Ala Gly Lys Leu Thr Met Gly Gln Pro
            420             425             430

Leu Val Ile Leu Ala Pro His Ala Val Glu Ala Leu Val Lys Gln Pro
        435             440             445

Pro Asp Arg Trp Leu Ser Asn Ala Arg Met Thr His Tyr Gln Ala Leu
    450             455             460

Leu Leu Asp Thr Asp Arg Val Gln Phe Gly Pro Val Val Ala Leu Asn
465             470             475             480

Pro Ala Thr Leu Leu Pro Leu Pro Glu Glu Gly Leu Gln His Asn Cys
```

-continued

```
                    485                  490                  495
Leu Asp Ile Leu Ala Glu Ala His Gly Thr Arg Pro Asp Leu Thr Asp
            500                  505                  510
Gln Pro Leu Pro Asp Ala Asp His Thr Trp Tyr Thr Gly Gly Ser Ser
            515                  520                  525
Leu Leu Gln Glu Gly Gln Arg Lys Ala Gly Ala Ala Val Thr Thr Glu
            530                  535                  540
Thr Glu Val Ile Trp Ala Lys Ala Leu Pro Ala Gly Thr Ser Ala Gln
545                  550                  555                  560
Arg Ala Gln Leu Ile Ala Leu Thr Gln Ala Leu Lys Met Ala Glu Gly
                    565                  570                  575
Lys Lys Leu Asn Val Tyr Thr Asn Ser Arg Tyr Ala Phe Ala Thr Ala
                    580                  585                  590
His Ile His Gly Glu Ile Tyr Arg Arg Arg Gly Leu Leu Thr Ser Glu
                    595                  600                  605
Gly Lys Glu Ile Lys Asn Lys Asp Glu Ile Leu Ala Leu Leu Lys Ala
            610                  615                  620
Leu Phe Leu Pro Lys Arg Leu Ser Ile Ile His Cys Pro Gly His Gln
625                  630                  635                  640
Lys Gly His Ser Ala Glu Ala Arg Gly Asn Arg Met Ala Asp Gln Ala
                    645                  650                  655
Ala Arg Lys Ala Ala Ile Thr Glu Thr Pro Asp Thr Ser Thr Leu Leu
            660                  665                  670
Ile Glu Asn Ser Ser Pro Tyr Thr Ser Glu His
            675                  680
```

```
<210> SEQ ID NO 661
<211> LENGTH: 684
<212> TYPE: PRT
<213> ORGANISM: Artificial Sequence
<220> FEATURE:
<223> OTHER INFORMATION: RTase mutant

<400> SEQUENCE: 661

Met Thr Leu Asn Ile Glu Asp Glu His Arg Leu His Glu Thr Ser Lys
1                   5                   10                  15
Glu Pro Asp Val Ser Leu Gly Ser Thr Trp Leu Ser Asp Phe Pro Gln
            20                  25                  30
Ala Trp Ala Glu Thr Gly Gly Met Gly Leu Ala Val Arg Gln Ala Pro
            35                  40                  45
Leu Ile Ile Pro Leu Lys Ala Thr Ser Thr Pro Val Ser Arg Lys Gln
            50                  55                  60
Tyr Pro Met Ser Gln Glu Ala Arg Leu Gly Ile Lys Pro His Ile Arg
65                  70                  75                  80
Arg Leu Leu Asp Gln Gly Ile Leu Val Pro Cys Gln Ser Pro Trp Asn
            85                  90                  95
Thr Pro Leu Leu Pro Val Lys Lys Pro Gly Thr Asn Asp Tyr Arg Pro
            100                 105                 110
Val Gln Asp Leu Arg Glu Val Asn Lys Arg Val Glu Asp Ile His Pro
            115                 120                 125
Thr Val Pro Asn Pro Tyr Asn Leu Leu Ser Gly Leu Pro Pro Ser His
            130                 135                 140
Gln Trp Tyr Thr Val Leu Asp Leu Lys Asp Ala Phe Phe Cys Leu Arg
145                 150                 155                 160
Leu His Pro Thr Ser Gln Pro Leu Phe Ala Phe Glu Trp Arg Asp Pro
```

-continued

```
                165                170                175
Glu Met Gly Ile Ser Gly Gln Leu Thr Trp Thr Arg Leu Pro Gln Gly
            180                185                190
Phe Lys Asn Ser Pro Thr Leu Phe Asp Glu Ala Leu His Arg Asp Leu
            195                200                205
Ala Asp Phe Arg Ile Gln His Pro Asp Leu Ile Leu Leu Gln Tyr Val
        210                215                220
Asp Asp Leu Leu Leu Ala Ala Thr Ser Glu Leu Asp Cys Gln Gln Gly
    225                230                235                240
Thr Arg Ala Leu Leu Gln Thr Leu Gly Asn Leu Gly Tyr Arg Ala Ser
                245                250                255
Ala Lys Lys Ala Gln Ile Cys Gln Lys Gln Val Lys Tyr Leu Gly Tyr
            260                265                270
Leu Leu Lys Glu Gly Gln Arg Trp Leu Thr Glu Ala Arg Lys Glu Thr
            275                280                285
Val Met Gly Gln Pro Thr Pro Lys Thr Pro Arg Gln Leu Arg Glu Phe
        290                295                300
Leu Gly Thr Ala Gly Phe Cys Arg Leu Trp Ile Pro Gly Phe Ala Glu
    305                310                315                320
Met Ala Ala Pro Leu Tyr Pro Leu Thr Lys Thr Gly Thr Leu Phe Asn
                325                330                335
Trp Gly Pro Asp Gln Gln Lys Ala Tyr Gln Glu Ile Lys Gln Ala Leu
            340                345                350
Leu Thr Ala Pro Ala Leu Gly Leu Pro Asp Leu Thr Lys Pro Phe Glu
            355                360                365
Leu Phe Val Asp Glu Lys Gln Gly Tyr Ala Lys Gly Val Leu Thr Gln
        370                375                380
Lys Leu Gly Pro Trp Arg Arg Pro Val Ala Tyr Leu Ser Lys Lys Leu
    385                390                395                400
Asp Pro Val Ala Ala Gly Trp Pro Pro Cys Leu Arg Met Val Ala Ala
                405                410                415
Ile Ala Val Leu Thr Lys Asp Ala Gly Lys Leu Thr Met Gly Gln Pro
            420                425                430
Leu Val Ile Leu Ala Pro His Ala Val Glu Ala Leu Val Lys Gln Pro
            435                440                445
Pro Asp Arg Trp Leu Ser Asn Ala Arg Met Thr His Tyr Gln Ala Leu
        450                455                460
Leu Leu Asp Thr Asp Arg Val Gln Phe Gly Pro Val Val Ala Leu Asn
    465                470                475                480
Pro Ala Thr Leu Leu Pro Leu Pro Glu Glu Gly Leu Gln His Asn Cys
            485                490                495
Leu Asp Ile Leu Ala Glu Ala His Gly Thr Arg Pro Asp Leu Thr Asp
            500                505                510
Gln Pro Leu Pro Asp Ala Asp His Thr Trp Tyr Thr Gly Gly Ser Ser
            515                520                525
Leu Leu Gln Glu Gly Gln Arg Lys Ala Gly Ala Ala Val Thr Thr Glu
        530                535                540
Thr Glu Val Ile Trp Ala Lys Ala Leu Pro Ala Gly Thr Ser Ala Gln
    545                550                555                560
Arg Ala Gln Leu Ile Ala Leu Thr Gln Ala Leu Lys Met Ala Glu Gly
                565                570                575
Lys Lys Leu Asn Val Tyr Thr Asn Ser Arg Tyr Ala Phe Ala Thr Ala
            580                585                590
```

-continued

```
His Ile His Gly Glu Ile Tyr Arg Arg Arg Gly Leu Leu Thr Ser Glu
        595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
                660                 665                 670

Ile Glu Asn Ser Ser Pro Tyr Thr Ser Glu His Phe
        675                 680

<210> SEQ ID NO 662
<211> LENGTH: 684
<212> TYPE: PRT
<213> ORGANISM: Artificial Sequence
<220> FEATURE:
<223> OTHER INFORMATION: RTase mutant

<400> SEQUENCE: 662

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
                20                  25                  30

Ala Trp Ala Glu Thr Gly Gly Met Gly Leu Ala Val Arg Gln Ala Pro
            35                  40                  45

Leu Ile Ile Pro Leu Lys Ala Thr Ser Thr Pro Val Ser Arg Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
                100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
                260                 265                 270
```

-continued

```
Leu Leu Lys Glu Gly Gln Arg Trp Leu Thr Glu Ala Arg Lys Glu Thr
    275                 280                 285

Val Met Gly Gln Pro Thr Pro Lys Thr Pro Ala Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
                340                 345                 350

Leu Thr Ala Pro Ala Leu Gly Leu Pro Asp Leu Thr Lys Pro Phe Glu
                355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
                420                 425                 430

Leu Val Ile Leu Ala Pro His Ala Val Glu Ala Leu Val Lys Gln Pro
                435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
                500                 505                 510

Gln Pro Leu Pro Asp Ala Asp His Thr Trp Tyr Thr Gly Gly Ser Ser
    515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
                580                 585                 590

His Ile His Gly Glu Ile Tyr Arg Arg Arg Gly Leu Leu Thr Ser Glu
                595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
                660                 665                 670

Ile Glu Asn Ser Ser Pro Tyr Thr Ser Glu His Phe
    675                 680
```

-continued

<210> SEQ ID NO 663
<211> LENGTH: 684
<212> TYPE: PRT
<213> ORGANISM: Artificial Sequence
<220> FEATURE:
<223> OTHER INFORMATION: RTase mutant

<400> SEQUENCE: 663

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
                20                  25                  30

Ala Trp Ala Glu Thr Gly Gly Met Gly Leu Ala Val Arg Gln Ala Pro
            35                  40                  45

Leu Ile Ile Pro Leu Lys Ala Thr Ser Thr Pro Val Ser Ile Lys Gln
        50                  55                  60

Tyr Pro Met Ser Arg Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Arg Pro Val Lys Lys Pro Gly Thr Asn Asp Tyr Arg Pro
                100                 105                 110

Val Gln Asp Leu Arg Glu Val Asn Lys Arg Val Glu Asp Ile His Pro
                115                 120                 125

Thr Val Pro Asn Pro Tyr Asn Leu Leu Ser Gly Leu Pro Pro Ser His
        130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
                180                 185                 190

Phe Lys Asn Ser Pro Thr Leu Phe Asp Glu Ala Leu His Arg Asp Leu
                195                 200                 205

Ala Asp Phe Arg Ile Gln His Pro Asp Leu Ile Leu Leu Gln Tyr Val
        210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
                260                 265                 270

Leu Leu Lys Glu Gly Gln Arg Trp Leu Thr Glu Ala Arg Lys Glu Thr
                275                 280                 285

Val Met Gly Gln Pro Thr Pro Lys Thr Pro Arg Gln Leu Arg Glu Phe
        290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
                340                 345                 350

Leu Thr Ala Pro Ala Leu Gly Leu Pro Asp Leu Thr Lys Pro Phe Glu
        355                 360                 365

-continued

```
Leu Phe Val Asp Glu Lys Gln Gly Tyr Ala Lys Gly Val Leu Thr Gln
    370             375             380

Lys Leu Gly Pro Trp Arg Arg Pro Val Ala Tyr Leu Ser Lys Lys Leu
385             390             395             400

Asp Pro Val Ala Ala Gly Trp Pro Pro Cys Leu Arg Met Val Ala Ala
            405             410             415

Ile Ala Val Leu Thr Lys Asp Ala Gly Lys Leu Thr Met Gly Gln Pro
            420             425             430

Leu Val Ile Leu Ala Pro His Ala Val Glu Ala Leu Val Lys Gln Pro
            435             440             445

Pro Asp Arg Trp Leu Ser Asn Ala Arg Met Thr His Tyr Gln Ala Leu
    450             455             460

Leu Leu Asp Thr Asp Arg Val Gln Phe Gly Pro Val Val Ala Leu Asn
465             470             475             480

Pro Ala Thr Leu Leu Pro Leu Pro Glu Glu Gly Leu Gln His Asn Cys
            485             490             495

Leu Asp Ile Leu Ala Glu Ala His Gly Thr Arg Pro Asp Leu Thr Asp
            500             505             510

Gln Pro Leu Pro Asp Ala Asp His Thr Trp Tyr Thr Gly Gly Ser Ser
    515             520             525

Leu Leu Gln Glu Gly Gln Arg Lys Ala Gly Ala Ala Val Thr Thr Glu
    530             535             540

Thr Glu Val Ile Trp Ala Lys Ala Leu Pro Ala Gly Thr Ser Ala Gln
545             550             555             560

Arg Ala Gln Leu Ile Ala Leu Thr Gln Ala Leu Lys Met Ala Glu Gly
            565             570             575

Lys Lys Leu Asn Val Tyr Thr Asn Ser Arg Tyr Ala Phe Ala Thr Ala
            580             585             590

His Ile His Gly Glu Ile Tyr Arg Arg Arg Gly Leu Leu Thr Ser Glu
    595             600             605

Gly Lys Glu Ile Lys Asn Lys Asp Glu Ile Leu Ala Leu Leu Lys Ala
    610             615             620

Leu Phe Leu Pro Lys Arg Leu Ser Ile Ile His Cys Pro Gly His Gln
625             630             635             640

Lys Gly His Ser Ala Glu Ala Arg Gly Asn Arg Met Ala Asp Gln Ala
            645             650             655

Ala Arg Lys Ala Ala Ile Thr Glu Thr Pro Asp Thr Ser Thr Leu Leu
            660             665             670

Ile Glu Asn Ser Ser Pro Tyr Thr Ser Glu His Phe
    675             680
```

```
<210> SEQ ID NO 664
<211> LENGTH: 684
<212> TYPE: PRT
<213> ORGANISM: Artificial Sequence
<220> FEATURE:
<223> OTHER INFORMATION: RTase mutant

<400> SEQUENCE: 664

Met Thr Leu Asn Ile Glu Asp Glu His Arg Leu His Glu Thr Ser Lys
1               5               10              15

Glu Pro Asp Val Ser Leu Gly Ser Thr Trp Leu Ser Asp Phe Pro Gln
                20              25              30

Ala Trp Ala Glu Thr Gly Gly Met Gly Leu Ala Val Arg Gln Ala Pro
        35              40              45
```

-continued

```
Leu Ile Ile Pro Leu Lys Ala Thr Ser Thr Pro Val Ser Ile Lys Gln
    50                  55                  60

Tyr Pro Met Ser Gln Glu Ala Arg Leu Gly Ile Lys Pro His Ile Arg
65                  70                  75                  80

Arg Leu Leu Asp Gln Gly Ile Leu Val Pro Cys Gln Ser Pro Trp Asn
                85                  90                  95

Thr Pro Leu Arg Pro Val Lys Lys Pro Gly Thr Asn Asp Tyr Arg Pro
                100                 105                 110

Val Gln Asp Leu Arg Glu Val Asn Lys Arg Val Glu Asp Ile His Pro
                115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
                180                 185                 190

Phe Lys Asn Ser Pro Thr Leu Phe Asp Glu Ala Leu His Arg Asp Leu
                195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
                260                 265                 270

Leu Leu Lys Glu Gly Gln Arg Trp Leu Thr Glu Ala Arg Lys Glu Thr
                275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
                340                 345                 350

Leu Thr Ala Pro Ala Leu Gly Leu Pro Asp Leu Thr Lys Pro Phe Glu
                355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
                420                 425                 430

Leu Val Ile Leu Ala Pro His Ala Val Glu Ala Leu Val Lys Gln Pro
                435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
```

-continued

```
465                     470                     475                     480
Pro Ala Thr Leu Leu Pro Leu Pro Glu Glu Gly Leu Gln His Asn Cys
                485                     490                     495

Leu Asp Ile Leu Ala Glu Ala His Gly Thr Arg Pro Asp Leu Thr Asp
                500                     505                     510

Gln Pro Leu Pro Asp Ala Asp His Thr Trp Tyr Thr Gly Gly Ser Ser
                515                     520                     525

Leu Leu Gln Glu Gly Gln Arg Lys Ala Gly Ala Ala Val Thr Thr Glu
                530                     535                     540

Thr Glu Val Ile Trp Ala Lys Ala Leu Pro Ala Gly Thr Ser Ala Gln
545                     550                     555                     560

Arg Ala Gln Leu Ile Ala Leu Thr Gln Ala Leu Lys Met Ala Glu Gly
                565                     570                     575

Lys Lys Leu Asn Val Tyr Thr Asn Ser Arg Tyr Ala Phe Ala Thr Ala
                580                     585                     590

His Ile His Gly Glu Ile Tyr Arg Arg Arg Gly Leu Leu Thr Ser Glu
                595                     600                     605

Gly Lys Glu Ile Lys Asn Lys Asp Glu Ile Leu Ala Leu Leu Lys Ala
                610                     615                     620

Leu Phe Leu Pro Lys Arg Leu Ser Ile Ile His Cys Pro Gly His Gln
625                     630                     635                     640

Lys Gly His Ser Ala Glu Ala Arg Gly Asn Arg Met Ala Asp Gln Ala
                645                     650                     655

Ala Arg Lys Ala Ala Ile Thr Glu Thr Pro Asp Thr Ser Thr Leu Leu
                660                     665                     670

Ile Glu Asn Ser Ser Pro Tyr Thr Ser Glu His Phe
                675                     680
```

<210> SEQ ID NO 665
<211> LENGTH: 684
<212> TYPE: PRT
<213> ORGANISM: Artificial Sequence
<220> FEATURE:
<223> OTHER INFORMATION: RTase mutant

<400> SEQUENCE: 665

```
Met Thr Leu Asn Ile Glu Asp Glu His Arg Leu His Glu Thr Ser Lys
1               5                       10                      15

Glu Pro Asp Val Ser Leu Gly Ser Thr Trp Leu Ser Asp Phe Pro Gln
                20                      25                      30

Ala Trp Ala Glu Thr Gly Gly Met Gly Leu Ala Val Arg Gln Ala Pro
                35                      40                      45

Leu Ile Ile Pro Leu Lys Ala Thr Ser Thr Pro Val Ser Ile Lys Gln
                50                      55                      60

Tyr Pro Met Ser Gln Glu Ala Arg Leu Gly Ile Lys Pro His Ile Gln
65                      70                      75                      80

Arg Leu Leu Asp Gln Gly Ile Leu Val Pro Cys Gln Ser Pro Trp Asn
                85                      90                      95

Thr Pro Leu Arg Pro Val Lys Lys Pro Gly Thr Asn Asp Tyr Arg Pro
                100                     105                     110

Val Gln Asp Leu Arg Glu Val Asn Lys Arg Val Glu Asp Ile His Pro
                115                     120                     125

Thr Val Pro Asn Pro Tyr Asn Leu Leu Ser Gly Leu Pro Pro Ser His
                130                     135                     140

Gln Trp Tyr Thr Val Leu Asp Leu Lys Asp Ala Phe Phe Cys Leu Arg
```

-continued

```
145                150                155                160

Leu His Pro Thr Ser Gln Pro Leu Phe Ala Phe Glu Trp Arg Asp Pro
                165                170                175

Glu Met Gly Ile Ser Gly Gln Leu Thr Trp Thr Arg Leu Pro Gln Gly
                180                185                190

Phe Lys Asn Ser Pro Thr Leu Phe Asp Glu Ala Leu His Arg Asp Leu
                195                200                205

Ala Asp Phe Arg Ile Gln His Pro Asp Leu Ile Leu Leu Gln Tyr Val
        210                215                220

Asp Asp Leu Leu Leu Ala Ala Thr Ser Glu Leu Asp Cys Gln Gln Gly
225                230                235                240

Thr Arg Ala Leu Leu Gln Thr Leu Gly Asn Leu Gly Tyr Arg Ala Ser
                245                250                255

Ala Lys Lys Ala Gln Ile Cys Gln Lys Gln Val Lys Tyr Leu Gly Tyr
                260                265                270

Leu Leu Lys Glu Gly Gln Arg Trp Leu Thr Glu Ala Arg Lys Glu Thr
                275                280                285

Val Met Gly Gln Pro Thr Pro Lys Thr Pro Ala Gln Leu Arg Glu Phe
        290                295                300

Leu Gly Thr Ala Gly Phe Cys Arg Leu Trp Ile Pro Gly Phe Ala Glu
305                310                315                320

Met Ala Ala Pro Leu Tyr Pro Leu Thr Lys Thr Gly Thr Leu Phe Asn
                325                330                335

Trp Gly Pro Asp Gln Gln Lys Ala Tyr Gln Glu Ile Lys Gln Ala Leu
                340                345                350

Leu Thr Ala Pro Ala Leu Gly Leu Pro Asp Leu Thr Lys Pro Phe Glu
                355                360                365

Leu Phe Val Asp Glu Lys Gln Gly Tyr Ala Lys Gly Val Leu Thr Gln
        370                375                380

Lys Leu Gly Pro Trp Arg Arg Pro Val Ala Tyr Leu Ser Lys Lys Leu
385                390                395                400

Asp Pro Val Ala Ala Gly Trp Pro Pro Cys Leu Arg Met Val Ala Ala
                405                410                415

Ile Ala Val Leu Thr Lys Asp Ala Gly Lys Leu Thr Met Gly Gln Pro
                420                425                430

Leu Val Ile Leu Ala Pro His Ala Val Glu Ala Leu Val Lys Gln Pro
                435                440                445

Pro Asp Arg Trp Leu Ser Asn Ala Arg Met Thr His Tyr Gln Ala Leu
        450                455                460

Leu Leu Asp Thr Asp Arg Val Gln Phe Gly Pro Val Val Ala Leu Asn
465                470                475                480

Pro Ala Thr Leu Leu Pro Leu Pro Glu Glu Gly Leu Gln His Asn Cys
                485                490                495

Leu Asp Ile Leu Ala Glu Ala His Gly Thr Arg Pro Asp Leu Thr Asp
                500                505                510

Gln Pro Leu Pro Asp Ala Asp His Thr Trp Tyr Thr Gly Gly Ser Ser
                515                520                525

Leu Leu Gln Glu Gly Gln Arg Lys Ala Gly Ala Ala Val Thr Thr Glu
        530                535                540

Thr Glu Val Ile Trp Ala Lys Ala Leu Pro Ala Gly Thr Ser Ala Gln
545                550                555                560

Arg Ala Gln Leu Ile Ala Leu Thr Gln Ala Leu Lys Met Ala Glu Gly
                565                570                575
```

-continued

```
Lys Lys Leu Asn Val Tyr Thr Asn Ser Arg Tyr Ala Phe Ala Thr Ala
        580                 585                 590

His Ile His Gly Glu Ile Tyr Arg Arg Arg Gly Leu Leu Thr Ser Glu
        595                 600                 605

Gly Lys Glu Ile Lys Asn Lys Asp Glu Ile Leu Ala Leu Leu Lys Ala
        610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
                660                 665                 670

Ile Glu Asn Ser Ser Pro Tyr Thr Ser Glu His Phe
        675                 680

<210> SEQ ID NO 666
<211> LENGTH: 684
<212> TYPE: PRT
<213> ORGANISM: Artificial Sequence
<220> FEATURE:
<223> OTHER INFORMATION: RTase mutant

<400> SEQUENCE: 666

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
                20                  25                  30

Ala Trp Ala Glu Thr Gly Gly Met Gly Leu Ala Val Arg Gln Ala Pro
            35                  40                  45

Leu Ile Ile Pro Leu Lys Ala Thr Ser Thr Pro Val Ser Ile Lys Gln
        50                  55                  60

Tyr Pro Met Ser Arg Glu Ala Arg Leu Gly Ile Lys Pro His Ile Arg
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
                100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
        130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
                180                 185                 190

Phe Lys Asn Ser Pro Thr Leu Phe Asp Glu Ala Leu His Arg Asp Leu
        195                 200                 205

Ala Asp Phe Arg Ile Gln His Pro Asp Leu Ile Leu Leu Gln Tyr Val
        210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255
```

-continued

```
Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
            275                 280                 285

Val Met Gly Gln Pro Thr Pro Lys Thr Pro Arg Gln Leu Arg Glu Phe
            290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
            355                 360                 365

Leu Phe Val Asp Glu Lys Gln Gly Tyr Ala Lys Gly Val Leu Thr Gln
            370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
                420                 425                 430

Leu Val Ile Leu Ala Pro His Ala Val Glu Ala Leu Val Lys Gln Pro
            435                 440                 445

Pro Asp Arg Trp Leu Ser Asn Ala Arg Met Thr His Tyr Gln Ala Leu
            450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
                500                 505                 510

Gln Pro Leu Pro Asp Ala Asp His Thr Trp Tyr Thr Gly Gly Ser Ser
            515                 520                 525

Leu Leu Gln Glu Gly Gln Arg Lys Ala Gly Ala Ala Val Thr Thr Glu
            530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
                580                 585                 590

His Ile His Gly Glu Ile Tyr Arg Arg Arg Gly Leu Leu Thr Ser Glu
            595                 600                 605

Gly Lys Glu Ile Lys Asn Lys Asp Glu Ile Leu Ala Leu Leu Lys Ala
            610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670
```

```
Ile Glu Asn Ser Ser Pro Tyr Thr Ser Glu His Phe
        675                 680

<210> SEQ ID NO 667
<211> LENGTH: 684
<212> TYPE: PRT
<213> ORGANISM: Artificial Sequence
<220> FEATURE:
<223> OTHER INFORMATION: RTase mutant

<400> SEQUENCE: 667

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Arg Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
            115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
            195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
            275                 280                 285

Val Met Gly Gln Pro Thr Pro Lys Thr Pro Ala Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350
```

-continued

```
Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
        370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
                420                 425                 430

Leu Val Ile Leu Ala Pro His Ala Val Glu Ala Leu Val Lys Gln Pro
                435                 440                 445

Pro Asp Arg Trp Leu Ser Asn Ala Arg Met Thr His Tyr Gln Ala Leu
        450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
                500                 505                 510

Gln Pro Leu Pro Asp Ala Asp His Thr Trp Tyr Thr Gly Gly Ser Ser
        515                 520                 525

Leu Leu Gln Glu Gly Gln Arg Lys Ala Gly Ala Ala Val Thr Thr Glu
        530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
                580                 585                 590

His Ile His Gly Glu Ile Tyr Arg Arg Arg Gly Leu Leu Thr Ser Glu
                595                 600                 605

Gly Lys Glu Ile Lys Asn Lys Asp Glu Ile Leu Ala Leu Leu Lys Ala
        610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
                660                 665                 670

Ile Glu Asn Ser Ser Pro Tyr Thr Ser Glu His Phe
        675                 680
```

<210> SEQ ID NO 668
<211> LENGTH: 684
<212> TYPE: PRT
<213> ORGANISM: Artificial Sequence
<220> FEATURE:
<223> OTHER INFORMATION: RTase mutant

<400> SEQUENCE: 668

```
Met Thr Leu Asn Ile Glu Asp Glu His Arg Leu His Glu Thr Ser Lys
1                 5                   10                  15

Glu Pro Asp Val Ser Leu Gly Ser Thr Trp Leu Ser Asp Phe Pro Gln
                20                  25                  30
```

-continued

```
Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Gln Glu Ala Arg Leu Gly Ile Lys Pro His Ile Arg
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
                100                 105                 110

Val Gln Asp Leu Arg Glu Val Asn Lys Arg Val Glu Asp Ile His Pro
                115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
                180                 185                 190

Phe Lys Asn Ser Pro Thr Leu Phe Asp Glu Ala Leu His Arg Asp Leu
                195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
                260                 265                 270

Leu Leu Lys Glu Gly Gln Arg Trp Leu Thr Glu Ala Arg Lys Glu Thr
                275                 280                 285

Val Met Gly Gln Pro Thr Pro Lys Thr Pro Ala Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
                340                 345                 350

Leu Thr Ala Pro Ala Leu Gly Leu Pro Asp Leu Thr Lys Pro Phe Glu
                355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
                420                 425                 430

Leu Val Ile Leu Ala Pro His Ala Val Glu Ala Leu Val Lys Gln Pro
    435                 440                 445

Pro Asp Arg Trp Leu Ser Asn Ala Arg Met Thr His Tyr Gln Ala Leu
```

-continued

```
           450             455             460

Leu Leu Asp Thr Asp Arg Val Gln Phe Gly Pro Val Val Ala Leu Asn
465             470             475             480

Pro Ala Thr Leu Leu Pro Leu Pro Glu Glu Gly Leu Gln His Asn Cys
            485             490             495

Leu Asp Ile Leu Ala Glu Ala His Gly Thr Arg Pro Asp Leu Thr Asp
            500             505             510

Gln Pro Leu Pro Asp Ala Asp His Thr Trp Tyr Thr Gly Gly Ser Ser
            515             520             525

Leu Leu Gln Glu Gly Gln Arg Lys Ala Gly Ala Ala Val Thr Thr Glu
            530             535             540

Thr Glu Val Ile Trp Ala Lys Ala Leu Pro Ala Gly Thr Ser Ala Gln
545             550             555             560

Arg Ala Gln Leu Ile Ala Leu Thr Gln Ala Leu Lys Met Ala Glu Gly
            565             570             575

Lys Lys Leu Asn Val Tyr Thr Asn Ser Arg Tyr Ala Phe Ala Thr Ala
            580             585             590

His Ile His Gly Glu Ile Tyr Arg Arg Arg Gly Leu Leu Thr Ser Glu
            595             600             605

Gly Lys Glu Ile Lys Asn Lys Asp Glu Ile Leu Ala Leu Leu Lys Ala
            610             615             620

Leu Phe Leu Pro Lys Arg Leu Ser Ile Ile His Cys Pro Gly His Gln
625             630             635             640

Lys Gly His Ser Ala Glu Ala Arg Gly Asn Arg Met Ala Asp Gln Ala
            645             650             655

Ala Arg Lys Ala Ala Ile Thr Glu Thr Pro Asp Thr Ser Thr Leu Leu
            660             665             670

Ile Glu Asn Ser Ser Pro Tyr Thr Ser Glu His Phe
            675             680
```

```
<210> SEQ ID NO 669
<211> LENGTH: 684
<212> TYPE: PRT
<213> ORGANISM: Artificial Sequence
<220> FEATURE:
<223> OTHER INFORMATION: RTase mutant

<400> SEQUENCE: 669

Met Thr Leu Asn Ile Glu Asp Glu His Arg Leu His Glu Thr Ser Lys
1               5               10              15

Glu Pro Asp Val Ser Leu Gly Ser Thr Trp Leu Ser Asp Phe Pro Gln
            20              25              30

Ala Trp Ala Glu Thr Gly Gly Met Gly Leu Ala Val Arg Gln Ala Pro
            35              40              45

Leu Ile Ile Pro Leu Lys Ala Thr Ser Thr Pro Val Ser Ile Lys Gln
            50              55              60

Tyr Pro Met Ser Arg Glu Ala Arg Leu Gly Ile Lys Pro His Ile Gln
65              70              75              80

Arg Leu Leu Asp Gln Gly Ile Leu Val Pro Cys Gln Ser Pro Trp Asn
            85              90              95

Thr Pro Leu Arg Pro Val Lys Lys Pro Gly Thr Asn Asp Tyr Arg Pro
            100             105             110

Val Gln Asp Leu Arg Glu Val Asn Lys Arg Val Glu Asp Ile His Pro
            115             120             125

Thr Val Pro Asn Pro Tyr Asn Leu Leu Ser Gly Leu Pro Pro Ser His
```

```
                 130                  135                  140

Gln Trp Tyr Thr Val Leu Asp Leu Lys Asp Ala Phe Phe Cys Leu Arg
145                  150                  155                  160

Leu His Pro Thr Ser Gln Pro Leu Phe Ala Phe Glu Trp Arg Asp Pro
                 165                  170                  175

Glu Met Gly Ile Ser Gly Gln Leu Thr Trp Thr Arg Leu Pro Gln Gly
                 180                  185                  190

Phe Lys Asn Ser Pro Thr Leu Phe Asp Glu Ala Leu His Arg Asp Leu
                 195                  200                  205

Ala Asp Phe Arg Ile Gln His Pro Asp Leu Ile Leu Leu Gln Tyr Val
         210                  215                  220

Asp Asp Leu Leu Leu Ala Ala Thr Ser Glu Leu Asp Cys Gln Gln Gly
225                  230                  235                  240

Thr Arg Ala Leu Leu Gln Thr Leu Gly Asn Leu Gly Tyr Arg Ala Ser
                 245                  250                  255

Ala Lys Lys Ala Gln Ile Cys Gln Lys Gln Val Lys Tyr Leu Gly Tyr
                 260                  265                  270

Leu Leu Lys Glu Gly Gln Arg Trp Leu Thr Asp Ala Arg Lys Glu Thr
                 275                  280                  285

Val Met Gly Gln Pro Thr Pro Lys Thr Pro Arg Gln Leu Arg Glu Phe
         290                  295                  300

Leu Gly Thr Ala Gly Phe Cys Arg Leu Trp Ile Pro Gly Phe Ala Glu
305                  310                  315                  320

Met Ala Ala Pro Leu Tyr Pro Leu Thr Lys Thr Gly Thr Leu Phe Asn
                 325                  330                  335

Trp Gly Pro Asp Gln Gln Lys Ala Tyr Gln Glu Ile Lys Gln Ala Leu
                 340                  345                  350

Leu Thr Ala Pro Ala Leu Gly Leu Pro Asp Leu Thr Lys Pro Phe Glu
                 355                  360                  365

Leu Phe Val Asp Glu Lys Gln Gly Tyr Ala Lys Gly Val Leu Thr Gln
         370                  375                  380

Lys Leu Gly Pro Trp Arg Arg Pro Val Ala Tyr Leu Ser Lys Lys Leu
385                  390                  395                  400

Asp Pro Val Ala Ala Gly Trp Pro Pro Cys Leu Arg Met Val Ala Ala
                 405                  410                  415

Ile Ala Val Leu Thr Lys Asp Ala Gly Lys Leu Thr Met Gly Gln Pro
                 420                  425                  430

Leu Val Ile Leu Ala Pro His Ala Val Glu Ala Leu Val Lys Gln Pro
                 435                  440                  445

Pro Asp Arg Trp Leu Ser Asn Ala Arg Met Thr His Tyr Gln Ala Leu
         450                  455                  460

Leu Leu Asp Thr Asp Arg Val Gln Phe Gly Pro Val Val Ala Leu Asn
465                  470                  475                  480

Pro Ala Thr Leu Leu Pro Leu Pro Glu Glu Gly Leu Gln His Asn Cys
                 485                  490                  495

Leu Asp Ile Leu Ala Glu Ala His Gly Thr Arg Pro Asp Leu Thr Asp
                 500                  505                  510

Gln Pro Leu Pro Asp Ala Asp His Thr Trp Tyr Thr Gly Gly Ser Ser
                 515                  520                  525

Leu Leu Gln Glu Gly Gln Arg Lys Ala Gly Ala Ala Val Thr Thr Glu
         530                  535                  540

Thr Glu Val Ile Trp Ala Lys Ala Leu Pro Ala Gly Thr Ser Ala Gln
545                  550                  555                  560
```

```
Arg Ala Gln Leu Ile Ala Leu Thr Gln Ala Leu Lys Met Ala Glu Gly
            565             570             575

Lys Lys Leu Asn Val Tyr Thr Asn Ser Arg Tyr Ala Phe Ala Thr Ala
            580             585             590

His Ile His Gly Glu Ile Tyr Arg Arg Arg Gly Leu Leu Thr Ser Glu
            595             600             605

Gly Lys Glu Ile Lys Asn Lys Asp Glu Ile Leu Ala Leu Leu Lys Ala
            610             615             620

Leu Phe Leu Pro Lys Arg Leu Ser Ile Ile His Cys Pro Gly His Gln
625             630             635             640

Lys Gly His Ser Ala Glu Ala Arg Gly Asn Arg Met Ala Asp Gln Ala
            645             650             655

Ala Arg Lys Ala Ala Ile Thr Glu Thr Pro Asp Thr Ser Thr Leu Leu
            660             665             670

Ile Glu Asn Ser Ser Pro Tyr Thr Ser Glu His Phe
            675             680

<210> SEQ ID NO 670
<211> LENGTH: 684
<212> TYPE: PRT
<213> ORGANISM: Artificial Sequence
<220> FEATURE:
<223> OTHER INFORMATION: RTase mutant

<400> SEQUENCE: 670

Met Thr Leu Asn Ile Glu Asp Glu His Arg Leu His Glu Thr Ser Lys
1               5               10              15

Glu Pro Asp Val Ser Leu Gly Ser Thr Trp Leu Ser Asp Phe Pro Gln
            20              25              30

Ala Trp Ala Glu Thr Gly Gly Met Gly Leu Ala Val Arg Gln Ala Pro
            35              40              45

Leu Ile Ile Pro Leu Lys Ala Thr Ser Thr Pro Val Ser Ile Lys Gln
            50              55              60

Tyr Pro Met Ser Gln Glu Ala Arg Leu Gly Ile Lys Pro His Ile Arg
65              70              75              80

Arg Leu Leu Asp Gln Gly Ile Leu Val Pro Cys Gln Ser Pro Trp Asn
            85              90              95

Thr Pro Leu Arg Pro Val Lys Lys Pro Gly Thr Asn Asp Tyr Arg Pro
            100             105             110

Val Gln Asp Leu Arg Glu Val Asn Lys Arg Val Glu Asp Ile His Pro
            115             120             125

Thr Val Pro Asn Pro Tyr Asn Leu Leu Ser Gly Leu Pro Pro Ser His
            130             135             140

Gln Trp Tyr Thr Val Leu Asp Leu Lys Asp Ala Phe Phe Cys Leu Arg
145             150             155             160

Leu His Pro Thr Ser Gln Pro Leu Phe Ala Phe Glu Trp Arg Asp Pro
            165             170             175

Glu Met Gly Ile Ser Gly Gln Leu Thr Trp Thr Arg Leu Pro Gln Gly
            180             185             190

Phe Lys Asn Ser Pro Thr Leu Phe Asp Glu Ala Leu His Arg Asp Leu
            195             200             205

Ala Asp Phe Arg Ile Gln His Pro Asp Leu Ile Leu Leu Gln Tyr Val
            210             215             220

Asp Asp Leu Leu Leu Ala Ala Thr Ser Glu Leu Asp Cys Gln Gln Gly
225             230             235             240
```

Thr Arg Ala Leu Leu Gln Thr Leu Gly Asn Leu Gly Tyr Arg Ala Ser
        245                 250                 255

Ala Lys Lys Ala Gln Ile Cys Gln Lys Gln Val Lys Tyr Leu Gly Tyr
        260                 265                 270

Leu Leu Lys Glu Gly Gln Arg Trp Leu Thr Asp Ala Arg Lys Glu Thr
        275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
                340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
                420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
        500                 505                 510

Gln Pro Leu Pro Asp Ala Asp His Thr Trp Tyr Thr Gly Gly Ser Ser
        515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
                580                 585                 590

His Ile His Gly Glu Ile Tyr Arg Arg Arg Gly Leu Leu Thr Ser Glu
        595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

-continued

Ala Arg Lys Ala Ala Ile Thr Glu Thr Pro Asp Thr Ser Thr Leu Leu
        660                     665                 670

Ile Glu Asn Ser Ser Pro Tyr Thr Ser Glu His Phe
        675                 680

<210> SEQ ID NO 671
<211> LENGTH: 684
<212> TYPE: PRT
<213> ORGANISM: Artificial Sequence
<220> FEATURE:
<223> OTHER INFORMATION: RTase mutant

<400> SEQUENCE: 671

Met Thr Leu Asn Ile Glu Asp Glu His Arg Leu His Glu Thr Ser Lys
1                   5                   10                  15

Glu Pro Asp Val Ser Leu Gly Ser Thr Trp Leu Ser Asp Phe Pro Gln
                20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Arg Glu Ala Arg Leu Gly Ile Lys Pro His Ile Arg
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
                100                 105                 110

Val Gln Asp Leu Arg Glu Val Asn Lys Arg Val Glu Asp Ile His Pro
            115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
            195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Asp Ala Arg Lys Glu Thr
            275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
                340                 345                 350

Leu Thr Ala Pro Ala Leu Gly Leu Pro Asp Leu Thr Lys Pro Phe Glu
            355                 360                 365

Leu Phe Val Asp Glu Lys Gln Gly Tyr Ala Lys Gly Val Leu Thr Gln
        370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Gly Gly Ser Ser
        515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
            565                 570                 575

Lys Lys Leu Asn Val Tyr Thr Asn Ser Arg Tyr Ala Phe Ala Thr Ala
            580                 585                 590

His Ile His Gly Glu Ile Tyr Arg Arg Arg Gly Leu Leu Thr Ser Glu
        595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
            645                 650                 655

Ala Arg Lys Ala Ala Ile Thr Glu Thr Pro Asp Thr Ser Thr Leu Leu
            660                 665                 670

Ile Glu Asn Ser Ser Pro Tyr Thr Ser Glu His Phe
        675                 680

<210> SEQ ID NO 672
<211> LENGTH: 684
<212> TYPE: PRT
<213> ORGANISM: Artificial Sequence
<220> FEATURE:
<223> OTHER INFORMATION: RTase mutant

<400> SEQUENCE: 672

Met Thr Leu Asn Ile Glu Asp Glu His Arg Leu His Glu Thr Ser Lys
1               5                   10                  15

-continued

```
Glu Pro Asp Val Ser Leu Gly Ser Thr Trp Leu Ser Asp Phe Pro Gln
            20              25                  30

Ala Trp Ala Glu Thr Gly Gly Met Gly Leu Ala Val Arg Gln Ala Pro
        35              40                  45

Leu Ile Ile Pro Leu Lys Ala Thr Ser Thr Pro Val Ser Ile Lys Gln
    50              55                  60

Tyr Pro Met Ser Arg Glu Ala Arg Leu Gly Ile Lys Pro His Ile Arg
65                  70              75                  80

Arg Leu Leu Asp Gln Gly Ile Leu Val Pro Cys Gln Ser Pro Trp Asn
                85              90                  95

Thr Pro Leu Arg Pro Val Lys Lys Pro Gly Thr Asn Asp Tyr Arg Pro
            100             105             110

Val Gln Asp Leu Arg Glu Val Asn Lys Arg Val Glu Asp Ile His Pro
        115             120             125

Thr Val Pro Asn Pro Tyr Asn Leu Leu Ser Gly Leu Pro Pro Ser His
    130             135             140

Gln Trp Tyr Thr Val Leu Asp Leu Lys Asp Ala Phe Phe Cys Leu Arg
145             150             155             160

Leu His Pro Thr Ser Gln Pro Leu Phe Ala Phe Glu Trp Arg Asp Pro
            165             170             175

Glu Met Gly Ile Ser Gly Gln Leu Thr Trp Thr Arg Leu Pro Gln Gly
            180             185             190

Phe Lys Asn Ser Pro Thr Leu Phe Asp Glu Ala Leu His Arg Asp Leu
            195             200             205

Ala Asp Phe Arg Ile Gln His Pro Asp Leu Ile Leu Leu Gln Tyr Val
    210             215             220

Asp Asp Leu Leu Leu Ala Ala Thr Ser Glu Leu Asp Cys Gln Gln Gly
225             230             235             240

Thr Arg Ala Leu Leu Gln Thr Leu Gly Asn Leu Gly Tyr Arg Ala Ser
            245             250             255

Ala Lys Lys Ala Gln Ile Cys Gln Lys Gln Val Lys Tyr Leu Gly Tyr
            260             265             270

Leu Leu Lys Glu Gly Gln Arg Trp Leu Thr Glu Ala Arg Lys Glu Thr
            275             280             285

Val Met Gly Gln Pro Thr Pro Lys Thr Pro Arg Gln Leu Arg Glu Phe
    290             295             300

Leu Gly Thr Ala Gly Phe Cys Arg Leu Trp Ile Pro Gly Phe Ala Glu
305             310             315             320

Met Ala Ala Pro Leu Tyr Pro Leu Thr Lys Thr Gly Thr Leu Phe Asn
            325             330             335

Trp Gly Pro Asp Gln Gln Lys Ala Tyr Gln Glu Ile Lys Gln Ala Leu
            340             345             350

Leu Thr Ala Pro Ala Leu Gly Leu Pro Asp Leu Thr Lys Pro Phe Glu
            355             360             365

Leu Phe Val Asp Glu Lys Gln Gly Tyr Ala Lys Gly Val Leu Thr Gln
    370             375             380

Lys Leu Gly Pro Trp Arg Arg Pro Val Ala Tyr Leu Ser Lys Lys Leu
385             390             395             400

Asp Pro Val Ala Ala Gly Trp Pro Pro Cys Leu Arg Met Val Ala Ala
            405             410             415

Ile Ala Val Leu Thr Lys Asp Ala Gly Lys Leu Thr Met Gly Gln Pro
            420             425             430

Leu Val Ile Leu Ala Pro His Ala Val Glu Ala Leu Val Lys Gln Pro
```

-continued

```
              435                440                445

Pro Asp Arg Trp Leu Ser Asn Ala Arg Met Thr His Tyr Gln Ala Leu
    450                455                460

Leu Leu Asp Thr Asp Arg Val Gln Phe Gly Pro Val Val Ala Leu Asn
465                470                475                480

Pro Ala Thr Leu Leu Pro Leu Pro Glu Glu Gly Leu Gln His Asn Cys
                485                490                495

Leu Asp Ile Leu Ala Glu Ala His Gly Thr Arg Pro Asp Leu Thr Asp
                500                505                510

Gln Pro Leu Pro Asp Ala Asp His Thr Trp Tyr Thr Gly Gly Ser Ser
            515                520                525

Leu Leu Gln Glu Gly Gln Arg Lys Ala Gly Ala Ala Val Thr Thr Glu
    530                535                540

Thr Glu Val Ile Trp Ala Lys Ala Leu Pro Ala Gly Thr Ser Ala Gln
545                550                555                560

Arg Ala Gln Leu Ile Ala Leu Thr Gln Ala Leu Lys Met Ala Glu Gly
            565                570                575

Lys Lys Leu Asn Val Tyr Thr Asn Ser Arg Tyr Ala Phe Ala Thr Ala
            580                585                590

His Ile His Gly Glu Ile Tyr Arg Arg Arg Gly Leu Leu Thr Ser Glu
            595                600                605

Gly Lys Glu Ile Lys Asn Lys Asp Glu Ile Leu Ala Leu Leu Lys Ala
    610                615                620

Leu Phe Leu Pro Lys Arg Leu Ser Ile Ile His Cys Pro Gly His Gln
625                630                635                640

Lys Gly His Ser Ala Glu Ala Arg Gly Asn Arg Met Ala Asp Gln Ala
                645                650                655

Ala Arg Lys Ala Ala Ile Thr Glu Thr Pro Asp Thr Ser Thr Leu Leu
            660                665                670

Ile Glu Asn Ser Ser Pro Tyr Thr Ser Glu His Phe
            675                680

<210> SEQ ID NO 673
<211> LENGTH: 684
<212> TYPE: PRT
<213> ORGANISM: Artificial Sequence
<220> FEATURE:
<223> OTHER INFORMATION: RTase mutant

<400> SEQUENCE: 673

Met Thr Leu Asn Ile Glu Asp Glu His Arg Leu His Glu Thr Ser Lys
1               5                  10                 15

Glu Pro Asp Val Ser Leu Gly Ser Thr Trp Leu Ser Asp Phe Pro Gln
                20                 25                 30

Ala Trp Ala Glu Thr Gly Gly Met Gly Leu Ala Val Arg Gln Ala Pro
            35                 40                 45

Leu Ile Ile Pro Leu Lys Ala Thr Ser Thr Pro Val Ser Ile Lys Gln
    50                 55                 60

Tyr Pro Met Ser Arg Glu Ala Arg Leu Gly Ile Lys Pro His Ile Arg
65                 70                 75                 80

Arg Leu Leu Asp Gln Gly Ile Leu Val Pro Cys Gln Ser Pro Trp Asn
                85                 90                 95

Thr Pro Leu Arg Pro Val Lys Lys Pro Gly Thr Asn Asp Tyr Arg Pro
                100                105                110

Val Gln Asp Leu Arg Glu Val Asn Lys Arg Val Glu Asp Ile His Pro
```

```
              115                 120                 125
Thr Val Pro Asn Pro Tyr Asn Leu Leu Ser Gly Leu Pro Pro Ser His
    130                 135                 140
Gln Trp Tyr Thr Val Leu Asp Leu Lys Asp Ala Phe Phe Cys Leu Arg
145                 150                 155                 160
Leu His Pro Thr Ser Gln Pro Leu Phe Ala Phe Glu Trp Arg Asp Pro
                165                 170                 175
Glu Met Gly Ile Ser Gly Gln Leu Thr Trp Thr Arg Leu Pro Gln Gly
                180                 185                 190
Phe Lys Asn Ser Pro Thr Leu Phe Asp Glu Ala Leu His Arg Asp Leu
                195                 200                 205
Ala Asp Phe Arg Ile Gln His Pro Asp Leu Ile Leu Leu Gln Tyr Val
    210                 215                 220
Asp Asp Leu Leu Leu Ala Ala Thr Ser Glu Leu Asp Cys Gln Gln Gly
225                 230                 235                 240
Thr Arg Ala Leu Leu Gln Thr Leu Gly Asn Leu Gly Tyr Arg Ala Ser
                245                 250                 255
Ala Lys Lys Ala Gln Ile Cys Gln Lys Gln Val Lys Tyr Leu Gly Tyr
                260                 265                 270
Leu Leu Lys Glu Gly Gln Arg Trp Leu Thr Asp Ala Arg Lys Glu Thr
                275                 280                 285
Val Met Gly Gln Pro Thr Pro Lys Thr Pro Arg Gln Leu Arg Glu Phe
    290                 295                 300
Leu Gly Thr Ala Gly Phe Cys Arg Leu Trp Ile Pro Gly Phe Ala Glu
305                 310                 315                 320
Met Ala Ala Pro Leu Tyr Pro Leu Thr Lys Thr Gly Thr Leu Phe Asn
                325                 330                 335
Trp Gly Pro Asp Gln Gln Lys Ala Tyr Gln Glu Ile Lys Gln Ala Leu
                340                 345                 350
Leu Thr Ala Pro Ala Leu Gly Leu Pro Asp Leu Thr Lys Pro Phe Glu
                355                 360                 365
Leu Phe Val Asp Glu Lys Gln Gly Tyr Ala Lys Gly Val Leu Thr Gln
    370                 375                 380
Lys Leu Gly Pro Trp Arg Arg Pro Val Ala Tyr Leu Ser Lys Lys Leu
385                 390                 395                 400
Asp Pro Val Ala Ala Gly Trp Pro Pro Cys Leu Arg Met Val Ala Ala
                405                 410                 415
Ile Ala Val Leu Thr Lys Asp Ala Gly Lys Leu Thr Met Gly Gln Pro
                420                 425                 430
Leu Val Ile Leu Ala Pro His Ala Val Glu Ala Leu Val Lys Gln Pro
                435                 440                 445
Pro Asp Arg Trp Leu Ser Asn Ala Arg Met Thr His Tyr Gln Ala Leu
    450                 455                 460
Leu Leu Asp Thr Asp Arg Val Gln Phe Gly Pro Val Val Ala Leu Asn
465                 470                 475                 480
Pro Ala Thr Leu Leu Pro Leu Pro Glu Glu Gly Leu Gln His Asn Cys
                485                 490                 495
Leu Asp Ile Leu Ala Glu Ala His Gly Thr Arg Pro Asp Leu Thr Asp
                500                 505                 510
Gln Pro Leu Pro Asp Ala Asp His Thr Trp Tyr Thr Gly Gly Ser Ser
                515                 520                 525
Leu Leu Gln Glu Gly Gln Arg Lys Ala Gly Ala Ala Val Thr Thr Glu
    530                 535                 540
```

-continued

```
Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
                580                 585                 590

His Ile His Gly Glu Ile Tyr Arg Arg Arg Gly Leu Leu Thr Ser Glu
            595                 600                 605

Gly Lys Glu Ile Lys Asn Lys Asp Glu Ile Leu Ala Leu Leu Lys Ala
        610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile Glu Asn Ser Ser Pro Tyr Thr Ser Glu His Phe
            675                 680
```

```
<210> SEQ ID NO 674
<211> LENGTH: 684
<212> TYPE: PRT
<213> ORGANISM: Artificial Sequence
<220> FEATURE:
<223> OTHER INFORMATION: RTase mutant

<400> SEQUENCE: 674

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
                20                  25                  30

Ala Trp Ala Glu Thr Gly Gly Met Gly Leu Ala Val Arg Gln Ala Pro
            35                  40                  45

Leu Ile Ile Pro Leu Lys Ala Thr Ser Thr Pro Val Ser Ile Lys Gln
        50                  55                  60

Tyr Pro Met Ser Arg Glu Ala Arg Leu Gly Ile Lys Pro His Ile Arg
65                  70                  75                  80

Arg Leu Leu Asp Gln Gly Ile Leu Val Pro Cys Gln Ser Pro Trp Asn
                85                  90                  95

Thr Pro Leu Lys Pro Val Lys Lys Pro Gly Thr Asn Asp Tyr Arg Pro
                100                 105                 110

Val Gln Asp Leu Arg Glu Val Asn Lys Arg Val Glu Asp Ile His Pro
            115                 120                 125

Thr Val Pro Asn Pro Tyr Asn Leu Leu Ser Gly Leu Pro Pro Ser His
        130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
                180                 185                 190

Phe Lys Asn Ser Pro Thr Leu Phe Asp Glu Ala Leu His Arg Asp Leu
                195                 200                 205

Ala Asp Phe Arg Ile Gln His Pro Asp Leu Ile Leu Leu Gln Tyr Val
        210                 215                 220
```

-continued

```
Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
                260                 265                 270

Leu Leu Lys Glu Gly Gln Arg Trp Leu Thr Asp Ala Arg Lys Glu Thr
                275                 280                 285

Val Met Gly Gln Pro Thr Pro Lys Thr Pro Arg Gln Leu Arg Glu Phe
                290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
                340                 345                 350

Leu Thr Ala Pro Ala Leu Gly Leu Pro Asp Leu Thr Lys Pro Phe Glu
                355                 360                 365

Leu Phe Val Asp Glu Lys Gln Gly Tyr Ala Lys Gly Val Leu Thr Gln
                370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
                420                 425                 430

Leu Val Ile Leu Ala Pro His Ala Val Glu Ala Leu Val Lys Gln Pro
                435                 440                 445

Pro Asp Arg Trp Leu Ser Asn Ala Arg Met Thr His Tyr Gln Ala Leu
                450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
                500                 505                 510

Gln Pro Leu Pro Asp Ala Asp His Thr Trp Tyr Thr Gly Gly Ser Ser
                515                 520                 525

Leu Leu Gln Glu Gly Gln Arg Lys Ala Gly Ala Ala Val Thr Thr Glu
                530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
                580                 585                 590

His Ile His Gly Glu Ile Tyr Arg Arg Arg Gly Leu Leu Thr Ser Glu
                595                 600                 605

Gly Lys Glu Ile Lys Asn Lys Asp Glu Ile Leu Ala Leu Leu Lys Ala
                610                 615                 620

Leu Phe Leu Pro Lys Arg Leu Ser Ile Ile His Cys Pro Gly His Gln
625                 630                 635                 640
```

-continued

```
Lys Gly His Ser Ala Glu Ala Arg Gly Asn Arg Met Ala Asp Gln Ala
            645                 650                 655

Ala Arg Lys Ala Ala Ile Thr Glu Thr Pro Asp Thr Ser Thr Leu Leu
            660                 665                 670

Ile Glu Asn Ser Ser Pro Tyr Thr Ser Glu His Phe
        675                 680

<210> SEQ ID NO 675
<211> LENGTH: 684
<212> TYPE: PRT
<213> ORGANISM: Artificial Sequence
<220> FEATURE:
<223> OTHER INFORMATION: RTase mutant

<400> SEQUENCE: 675

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Arg Glu Ala Arg Leu Gly Ile Lys Pro His Ile Arg
65                  70                  75                  80

Arg Leu Leu Asp Gln Gly Ile Leu Val Pro Cys Gln Ser Pro Trp Asn
                85                  90                  95

Thr Pro Leu Asn Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
            115                 120                 125

Thr Val Pro Asn Pro Tyr Asn Leu Leu Ser Gly Leu Pro Pro Ser His
        130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
            195                 200                 205

Ala Asp Phe Arg Ile Gln His Pro Asp Leu Ile Leu Leu Gln Tyr Val
        210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
            245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Asp Ala Arg Lys Glu Thr
        275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320
```

-continued

```
Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
            355                 360                 365

Leu Phe Val Asp Glu Lys Gln Gly Tyr Ala Lys Gly Val Leu Thr Gln
        370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
            405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
            435                 440                 445

Pro Asp Arg Trp Leu Ser Asn Ala Arg Met Thr His Tyr Gln Ala Leu
        450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
            485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Gly Gly Ser Ser
            515                 520                 525

Leu Leu Gln Glu Gly Gln Arg Lys Ala Gly Ala Ala Val Thr Thr Glu
        530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
            565                 570                 575

Lys Lys Leu Asn Val Tyr Thr Asn Ser Arg Tyr Ala Phe Ala Thr Ala
            580                 585                 590

His Ile His Gly Glu Ile Tyr Arg Arg Arg Gly Leu Leu Thr Ser Glu
            595                 600                 605

Gly Lys Glu Ile Lys Asn Lys Asp Glu Ile Leu Ala Leu Leu Lys Ala
        610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
            645                 650                 655

Ala Arg Lys Ala Ala Ile Thr Glu Thr Pro Asp Thr Ser Thr Leu Leu
            660                 665                 670

Ile Glu Asn Ser Ser Pro Tyr Thr Ser Glu His Phe
            675                 680
```

<210> SEQ ID NO 676
<211> LENGTH: 684
<212> TYPE: PRT
<213> ORGANISM: Artificial Sequence
<220> FEATURE:
<223> OTHER INFORMATION: RTase mutant

<400> SEQUENCE: 676

-continued

```
Met Thr Leu Asn Ile Glu Asp Glu His Arg Leu His Glu Thr Ser Lys
1               5               10              15

Glu Pro Asp Val Ser Leu Gly Ser Thr Trp Leu Ser Asp Phe Pro Gln
            20              25              30

Ala Trp Ala Glu Thr Gly Gly Met Gly Leu Ala Val Arg Gln Ala Pro
        35              40              45

Leu Ile Ile Pro Leu Lys Ala Thr Ser Thr Pro Val Ser Ile Lys Gln
    50              55              60

Tyr Pro Met Ser Ile Glu Ala Arg Leu Gly Ile Lys Pro His Ile Arg
65              70              75              80

Arg Leu Leu Asp Gln Gly Ile Leu Val Pro Cys Gln Ser Pro Trp Asn
            85              90              95

Thr Pro Leu Arg Pro Val Lys Lys Pro Gly Thr Asn Asp Tyr Arg Pro
            100             105             110

Val Gln Asp Leu Arg Glu Val Asn Lys Arg Val Glu Asp Ile His Pro
        115             120             125

Thr Val Pro Asn Pro Tyr Asn Leu Leu Ser Gly Leu Pro Pro Ser His
    130             135             140

Gln Trp Tyr Thr Val Leu Asp Leu Lys Asp Ala Phe Phe Cys Leu Arg
145             150             155             160

Leu His Pro Thr Ser Gln Pro Leu Phe Ala Phe Glu Trp Arg Asp Pro
            165             170             175

Glu Met Gly Ile Ser Gly Gln Leu Thr Trp Thr Arg Leu Pro Gln Gly
            180             185             190

Phe Lys Asn Ser Pro Thr Leu Phe Asp Glu Ala Leu His Arg Asp Leu
        195             200             205

Ala Asp Phe Arg Ile Gln His Pro Asp Leu Ile Leu Leu Gln Tyr Val
    210             215             220

Asp Asp Leu Leu Leu Ala Ala Thr Ser Glu Leu Asp Cys Gln Gln Gly
225             230             235             240

Thr Arg Ala Leu Leu Gln Thr Leu Gly Asn Leu Gly Tyr Arg Ala Ser
            245             250             255

Ala Lys Lys Ala Gln Ile Cys Gln Lys Gln Val Lys Tyr Leu Gly Tyr
        260             265             270

Leu Leu Lys Glu Gly Gln Arg Trp Leu Thr Asp Ala Arg Lys Glu Thr
        275             280             285

Val Met Gly Gln Pro Thr Pro Lys Thr Pro Arg Gln Leu Arg Glu Phe
    290             295             300

Leu Gly Thr Ala Gly Phe Cys Arg Leu Trp Ile Pro Gly Phe Ala Glu
305             310             315             320

Met Ala Ala Pro Leu Tyr Pro Leu Thr Lys Thr Gly Thr Leu Phe Asn
            325             330             335

Trp Gly Pro Asp Gln Gln Lys Ala Tyr Gln Glu Ile Lys Gln Ala Leu
            340             345             350

Leu Thr Ala Pro Ala Leu Gly Leu Pro Asp Leu Thr Lys Pro Phe Glu
        355             360             365

Leu Phe Val Asp Glu Lys Gln Gly Tyr Ala Lys Gly Val Leu Thr Gln
    370             375             380

Lys Leu Gly Pro Trp Arg Arg Pro Val Ala Tyr Leu Ser Lys Lys Leu
385             390             395             400

Asp Pro Val Ala Ala Gly Trp Pro Pro Cys Leu Arg Met Val Ala Ala
            405             410             415

Ile Ala Val Leu Thr Lys Asp Ala Gly Lys Leu Thr Met Gly Gln Pro
```

-continued

```
                420              425              430
Leu Val Ile Leu Ala Pro His Ala Val Glu Ala Leu Val Lys Gln Pro
            435              440              445
Pro Asp Arg Trp Leu Ser Asn Ala Arg Met Thr His Tyr Gln Ala Leu
    450              455              460
Leu Leu Asp Thr Asp Arg Val Gln Phe Gly Pro Val Val Ala Leu Asn
465              470              475              480
Pro Ala Thr Leu Leu Pro Leu Pro Glu Glu Gly Leu Gln His Asn Cys
                485              490              495
Leu Asp Ile Leu Ala Glu Ala His Gly Thr Arg Pro Asp Leu Thr Asp
            500              505              510
Gln Pro Leu Pro Asp Ala Asp His Thr Trp Tyr Thr Gly Gly Ser Ser
            515              520              525
Leu Leu Gln Glu Gly Gln Arg Lys Ala Gly Ala Ala Val Thr Thr Glu
            530              535              540
Thr Glu Val Ile Trp Ala Lys Ala Leu Pro Ala Gly Thr Ser Ala Gln
545              550              555              560
Arg Ala Gln Leu Ile Ala Leu Thr Gln Ala Leu Lys Met Ala Glu Gly
            565              570              575
Lys Lys Leu Asn Val Tyr Thr Asn Ser Arg Tyr Ala Phe Ala Thr Ala
            580              585              590
His Ile His Gly Glu Ile Tyr Arg Arg Arg Gly Leu Leu Thr Ser Glu
            595              600              605
Gly Lys Glu Ile Lys Asn Lys Asp Glu Ile Leu Ala Leu Leu Lys Ala
    610              615              620
Leu Phe Leu Pro Lys Arg Leu Ser Ile Ile His Cys Pro Gly His Gln
625              630              635              640
Lys Gly His Ser Ala Glu Ala Arg Gly Asn Arg Met Ala Asp Gln Ala
            645              650              655
Ala Arg Lys Ala Ala Ile Thr Glu Thr Pro Asp Thr Ser Thr Leu Leu
            660              665              670
Ile Glu Asn Ser Ser Pro Tyr Thr Ser Glu His Phe
            675              680

<210> SEQ ID NO 677
<211> LENGTH: 684
<212> TYPE: PRT
<213> ORGANISM: Artificial Sequence
<220> FEATURE:
<223> OTHER INFORMATION: RTase mutant

<400> SEQUENCE: 677

Met Thr Leu Asn Ile Glu Asp Glu His Arg Leu His Glu Thr Ser Lys
1               5                   10                  15
Glu Pro Asp Val Ser Leu Gly Ser Thr Trp Leu Ser Asp Phe Pro Gln
                20                  25                  30
Ala Trp Ala Glu Thr Gly Gly Met Gly Leu Ala Val Arg Gln Ala Pro
            35                  40                  45
Leu Ile Ile Pro Leu Lys Ala Thr Ser Thr Pro Val Ser Ile Lys Gln
    50                  55                  60
Tyr Pro Met Ser Lys Glu Ala Arg Leu Gly Ile Lys Pro His Ile Arg
65                  70                  75                  80
Arg Leu Leu Asp Gln Gly Ile Leu Val Pro Cys Gln Ser Pro Trp Asn
                85                  90                  95
Thr Pro Leu Arg Pro Val Lys Lys Pro Gly Thr Asn Asp Tyr Arg Pro
```

-continued

```
                100               105               110
Val Gln Asp Leu Arg Glu Val Asn Lys Arg Val Glu Asp Ile His Pro
            115               120               125

Thr Val Pro Asn Pro Tyr Asn Leu Leu Ser Gly Leu Pro Pro Ser His
        130               135               140

Gln Trp Tyr Thr Val Leu Asp Leu Lys Asp Ala Phe Phe Cys Leu Arg
145               150               155               160

Leu His Pro Thr Ser Gln Pro Leu Phe Ala Phe Glu Trp Arg Asp Pro
                165               170               175

Glu Met Gly Ile Ser Gly Gln Leu Thr Trp Thr Arg Leu Pro Gln Gly
            180               185               190

Phe Lys Asn Ser Pro Thr Leu Phe Asp Glu Ala Leu His Arg Asp Leu
            195               200               205

Ala Asp Phe Arg Ile Gln His Pro Asp Leu Ile Leu Leu Gln Tyr Val
            210               215               220

Asp Asp Leu Leu Leu Ala Ala Thr Ser Glu Leu Asp Cys Gln Gln Gly
225               230               235               240

Thr Arg Ala Leu Leu Gln Thr Leu Gly Asn Leu Gly Tyr Arg Ala Ser
            245               250               255

Ala Lys Lys Ala Gln Ile Cys Gln Lys Gln Val Lys Tyr Leu Gly Tyr
            260               265               270

Leu Leu Lys Glu Gly Gln Arg Trp Leu Thr Asp Ala Arg Lys Glu Thr
            275               280               285

Val Met Gly Gln Pro Thr Pro Lys Thr Pro Arg Gln Leu Arg Glu Phe
            290               295               300

Leu Gly Thr Ala Gly Phe Cys Arg Leu Trp Ile Pro Gly Phe Ala Glu
305               310               315               320

Met Ala Ala Pro Leu Tyr Pro Leu Thr Lys Thr Gly Thr Leu Phe Asn
                325               330               335

Trp Gly Pro Asp Gln Gln Lys Ala Tyr Gln Glu Ile Lys Gln Ala Leu
            340               345               350

Leu Thr Ala Pro Ala Leu Gly Leu Pro Asp Leu Thr Lys Pro Phe Glu
            355               360               365

Leu Phe Val Asp Glu Lys Gln Gly Tyr Ala Lys Gly Val Leu Thr Gln
            370               375               380

Lys Leu Gly Pro Trp Arg Arg Pro Val Ala Tyr Leu Ser Lys Lys Leu
385               390               395               400

Asp Pro Val Ala Ala Gly Trp Pro Pro Cys Leu Arg Met Val Ala Ala
                405               410               415

Ile Ala Val Leu Thr Lys Asp Ala Gly Lys Leu Thr Met Gly Gln Pro
            420               425               430

Leu Val Ile Leu Ala Pro His Ala Val Glu Ala Leu Val Lys Gln Pro
            435               440               445

Pro Asp Arg Trp Leu Ser Asn Ala Arg Met Thr His Tyr Gln Ala Leu
            450               455               460

Leu Leu Asp Thr Asp Arg Val Gln Phe Gly Pro Val Val Ala Leu Asn
465               470               475               480

Pro Ala Thr Leu Leu Pro Leu Pro Glu Glu Gly Leu Gln His Asn Cys
                485               490               495

Leu Asp Ile Leu Ala Glu Ala His Gly Thr Arg Pro Asp Leu Thr Asp
            500               505               510

Gln Pro Leu Pro Asp Ala Asp His Thr Trp Tyr Thr Gly Gly Ser Ser
            515               520               525
```

-continued

Leu Leu Gln Glu Gly Gln Arg Lys Ala Gly Ala Ala Val Thr Thr Glu
    530             535         540

Thr Glu Val Ile Trp Ala Lys Ala Leu Pro Ala Gly Thr Ser Ala Gln
545             550         555                 560

Arg Ala Gln Leu Ile Ala Leu Thr Gln Ala Leu Lys Met Ala Glu Gly
                565             570         575

Lys Lys Leu Asn Val Tyr Thr Asn Ser Arg Tyr Ala Phe Ala Thr Ala
            580             585         590

His Ile His Gly Glu Ile Tyr Arg Arg Arg Gly Leu Leu Thr Ser Glu
        595         600             605

Gly Lys Glu Ile Lys Asn Lys Asp Glu Ile Leu Ala Leu Leu Lys Ala
    610             615             620

Leu Phe Leu Pro Lys Arg Leu Ser Ile Ile His Cys Pro Gly His Gln
625             630             635             640

Lys Gly His Ser Ala Glu Ala Arg Gly Asn Arg Met Ala Asp Gln Ala
            645             650             655

Ala Arg Lys Ala Ala Ile Thr Glu Thr Pro Asp Thr Ser Thr Leu Leu
            660             665             670

Ile Glu Asn Ser Ser Pro Tyr Thr Ser Glu His Phe
            675             680

<210> SEQ ID NO 678
<211> LENGTH: 684
<212> TYPE: PRT
<213> ORGANISM: Artificial Sequence
<220> FEATURE:
<223> OTHER INFORMATION: RTase mutant

<400> SEQUENCE: 678

Met Thr Leu Asn Ile Glu Asp Glu His Arg Leu His Glu Thr Ser Lys
1               5               10              15

Glu Pro Asp Val Ser Leu Gly Ser Thr Trp Leu Ser Asp Phe Pro Gln
            20              25              30

Ala Trp Ala Glu Thr Gly Gly Met Gly Leu Ala Val Arg Gln Ala Pro
        35              40              45

Leu Ile Ile Pro Leu Lys Ala Thr Ser Thr Pro Val Ser Ile Lys Gln
    50              55              60

Tyr Pro Met Ser Arg Glu Ala Arg Leu Gly Ile Lys Pro His Ile His
65              70              75              80

Arg Leu Leu Asp Gln Gly Ile Leu Val Pro Cys Gln Ser Pro Trp Asn
            85              90              95

Thr Pro Leu Arg Pro Val Lys Lys Pro Gly Thr Asn Asp Tyr Arg Pro
            100             105             110

Val Gln Asp Leu Arg Glu Val Asn Lys Arg Val Glu Asp Ile His Pro
            115             120             125

Thr Val Pro Asn Pro Tyr Asn Leu Leu Ser Gly Leu Pro Pro Ser His
    130             135             140

Gln Trp Tyr Thr Val Leu Asp Leu Lys Asp Ala Phe Phe Cys Leu Arg
145             150             155             160

Leu His Pro Thr Ser Gln Pro Leu Phe Ala Phe Glu Trp Arg Asp Pro
                165             170             175

Glu Met Gly Ile Ser Gly Gln Leu Thr Trp Thr Arg Leu Pro Gln Gly
            180             185             190

Phe Lys Asn Ser Pro Thr Leu Phe Asp Glu Ala Leu His Arg Asp Leu
            195             200             205

-continued

```
Ala Asp Phe Arg Ile Gln His Pro Asp Leu Ile Leu Leu Gln Tyr Val
    210             215             220

Asp Asp Leu Leu Leu Ala Ala Thr Ser Glu Leu Asp Cys Gln Gln Gly
225             230             235             240

Thr Arg Ala Leu Leu Gln Thr Leu Gly Asn Leu Gly Tyr Arg Ala Ser
            245             250             255

Ala Lys Lys Ala Gln Ile Cys Gln Lys Gln Val Lys Tyr Leu Gly Tyr
            260             265             270

Leu Leu Lys Glu Gly Gln Arg Trp Leu Thr Asp Ala Arg Lys Glu Thr
            275             280             285

Val Met Gly Gln Pro Thr Pro Lys Thr Pro Arg Gln Leu Arg Glu Phe
    290             295             300

Leu Gly Thr Ala Gly Phe Cys Arg Leu Trp Ile Pro Gly Phe Ala Glu
305             310             315             320

Met Ala Ala Pro Leu Tyr Pro Leu Thr Lys Thr Gly Thr Leu Phe Asn
            325             330             335

Trp Gly Pro Asp Gln Gln Lys Ala Tyr Gln Glu Ile Lys Gln Ala Leu
            340             345             350

Leu Thr Ala Pro Ala Leu Gly Leu Pro Asp Leu Thr Lys Pro Phe Glu
            355             360             365

Leu Phe Val Asp Glu Lys Gln Gly Tyr Ala Lys Gly Val Leu Thr Gln
    370             375             380

Lys Leu Gly Pro Trp Arg Arg Pro Val Ala Tyr Leu Ser Lys Lys Leu
385             390             395             400

Asp Pro Val Ala Ala Gly Trp Pro Pro Cys Leu Arg Met Val Ala Ala
            405             410             415

Ile Ala Val Leu Thr Lys Asp Ala Gly Lys Leu Thr Met Gly Gln Pro
            420             425             430

Leu Val Ile Leu Ala Pro His Ala Val Glu Ala Leu Val Lys Gln Pro
            435             440             445

Pro Asp Arg Trp Leu Ser Asn Ala Arg Met Thr His Tyr Gln Ala Leu
    450             455             460

Leu Leu Asp Thr Asp Arg Val Gln Phe Gly Pro Val Val Ala Leu Asn
465             470             475             480

Pro Ala Thr Leu Leu Pro Leu Pro Glu Glu Gly Leu Gln His Asn Cys
            485             490             495

Leu Asp Ile Leu Ala Glu Ala His Gly Thr Arg Pro Asp Leu Thr Asp
            500             505             510

Gln Pro Leu Pro Asp Ala Asp His Thr Trp Tyr Thr Gly Gly Ser Ser
    515             520             525

Leu Leu Gln Glu Gly Gln Arg Lys Ala Gly Ala Ala Val Thr Thr Glu
    530             535             540

Thr Glu Val Ile Trp Ala Lys Ala Leu Pro Ala Gly Thr Ser Ala Gln
545             550             555             560

Arg Ala Gln Leu Ile Ala Leu Thr Gln Ala Leu Lys Met Ala Glu Gly
            565             570             575

Lys Lys Leu Asn Val Tyr Thr Asn Ser Arg Tyr Ala Phe Ala Thr Ala
            580             585             590

His Ile His Gly Glu Ile Tyr Arg Arg Arg Gly Leu Leu Thr Ser Glu
            595             600             605

Gly Lys Glu Ile Lys Asn Lys Asp Glu Ile Leu Ala Leu Leu Lys Ala
    610             615             620
```

```
Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
                660                 665                 670

Ile Glu Asn Ser Ser Pro Tyr Thr Ser Glu His Phe
            675                 680

<210> SEQ ID NO 679
<211> LENGTH: 684
<212> TYPE: PRT
<213> ORGANISM: Artificial Sequence
<220> FEATURE:
<223> OTHER INFORMATION: RTase mutant

<400> SEQUENCE: 679

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
                20                  25                  30

Ala Trp Ala Glu Thr Gly Gly Met Gly Leu Ala Val Arg Gln Ala Pro
            35                  40                  45

Leu Ile Ile Pro Leu Lys Ala Thr Ser Thr Pro Val Ser Ile Lys Gln
        50                  55                  60

Tyr Pro Met Ser Arg Glu Ala Arg Leu Gly Ile Lys Pro His Ile Ile
65                  70                  75                  80

Arg Leu Leu Asp Gln Gly Ile Leu Val Pro Cys Gln Ser Pro Trp Asn
                85                  90                  95

Thr Pro Leu Arg Pro Val Lys Lys Pro Gly Thr Asn Asp Tyr Arg Pro
                100                 105                 110

Val Gln Asp Leu Arg Glu Val Asn Lys Arg Val Glu Asp Ile His Pro
            115                 120                 125

Thr Val Pro Asn Pro Tyr Asn Leu Leu Ser Gly Leu Pro Pro Ser His
        130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
                180                 185                 190

Phe Lys Asn Ser Pro Thr Leu Phe Asp Glu Ala Leu His Arg Asp Leu
            195                 200                 205

Ala Asp Phe Arg Ile Gln His Pro Asp Leu Ile Leu Leu Gln Tyr Val
        210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
                260                 265                 270

Leu Leu Lys Glu Gly Gln Arg Trp Leu Thr Asp Ala Arg Lys Glu Thr
            275                 280                 285

Val Met Gly Gln Pro Thr Pro Lys Thr Pro Arg Gln Leu Arg Glu Phe
        290                 295                 300
```

-continued

```
Leu Gly Thr Ala Gly Phe Cys Arg Leu Trp Ile Pro Gly Phe Ala Glu
305             310             315             320

Met Ala Ala Pro Leu Tyr Pro Leu Thr Lys Thr Gly Thr Leu Phe Asn
            325             330             335

Trp Gly Pro Asp Gln Gln Lys Ala Tyr Gln Glu Ile Lys Gln Ala Leu
            340             345             350

Leu Thr Ala Pro Ala Leu Gly Leu Pro Asp Leu Thr Lys Pro Phe Glu
            355             360             365

Leu Phe Val Asp Glu Lys Gln Gly Tyr Ala Lys Gly Val Leu Thr Gln
            370             375             380

Lys Leu Gly Pro Trp Arg Arg Pro Val Ala Tyr Leu Ser Lys Lys Leu
385             390             395             400

Asp Pro Val Ala Ala Gly Trp Pro Pro Cys Leu Arg Met Val Ala Ala
            405             410             415

Ile Ala Val Leu Thr Lys Asp Ala Gly Lys Leu Thr Met Gly Gln Pro
            420             425             430

Leu Val Ile Leu Ala Pro His Ala Val Glu Ala Leu Val Lys Gln Pro
            435             440             445

Pro Asp Arg Trp Leu Ser Asn Ala Arg Met Thr His Tyr Gln Ala Leu
            450             455             460

Leu Leu Asp Thr Asp Arg Val Gln Phe Gly Pro Val Val Ala Leu Asn
465             470             475             480

Pro Ala Thr Leu Leu Pro Leu Pro Glu Glu Gly Leu Gln His Asn Cys
            485             490             495

Leu Asp Ile Leu Ala Glu Ala His Gly Thr Arg Pro Asp Leu Thr Asp
            500             505             510

Gln Pro Leu Pro Asp Ala Asp His Thr Trp Tyr Thr Gly Gly Ser Ser
            515             520             525

Leu Leu Gln Glu Gly Gln Arg Lys Ala Gly Ala Ala Val Thr Thr Glu
            530             535             540

Thr Glu Val Ile Trp Ala Lys Ala Leu Pro Ala Gly Thr Ser Ala Gln
545             550             555             560

Arg Ala Gln Leu Ile Ala Leu Thr Gln Ala Leu Lys Met Ala Glu Gly
            565             570             575

Lys Lys Leu Asn Val Tyr Thr Asn Ser Arg Tyr Ala Phe Ala Thr Ala
            580             585             590

His Ile His Gly Glu Ile Tyr Arg Arg Arg Gly Leu Leu Thr Ser Glu
            595             600             605

Gly Lys Glu Ile Lys Asn Lys Asp Glu Ile Leu Ala Leu Leu Lys Ala
            610             615             620

Leu Phe Leu Pro Lys Arg Leu Ser Ile Ile His Cys Pro Gly His Gln
625             630             635             640

Lys Gly His Ser Ala Glu Ala Arg Gly Asn Arg Met Ala Asp Gln Ala
            645             650             655

Ala Arg Lys Ala Ala Ile Thr Glu Thr Pro Asp Thr Ser Thr Leu Leu
            660             665             670

Ile Glu Asn Ser Ser Pro Tyr Thr Ser Glu His Phe
            675             680
```

<210> SEQ ID NO 680
<211> LENGTH: 684
<212> TYPE: PRT
<213> ORGANISM: Artificial Sequence
<220> FEATURE:
<223> OTHER INFORMATION: RTase mutant -continued

```
<400> SEQUENCE: 680

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Arg Glu Ala Arg Leu Gly Ile Lys Pro His Ile Arg
65                  70                  75                  80

Arg Leu Leu Asp Gln Gly Ile Leu Val Pro Cys Gln Ser Pro Trp Asn
                85                  90                  95

Thr Pro Leu Arg Pro Val Lys Lys Pro Gly Thr Asn Asp Tyr Arg Pro
                100                 105                 110

Val Gln Asp Leu Arg Glu Val Asn Lys Arg Val Glu Asp Ile His Pro
            115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
            195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Met Ala Arg Lys Glu Thr
            275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
            355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
```

-continued

```
                405                 410                 415
Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
            435                 440                 445

Pro Asp Arg Trp Leu Ser Asn Ala Arg Met Thr His Tyr Gln Ala Leu
            450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
                500                 505                 510

Gln Pro Leu Pro Asp Ala Asp His Thr Trp Tyr Thr Gly Gly Ser Ser
            515                 520                 525

Leu Leu Gln Glu Gly Gln Arg Lys Ala Gly Ala Ala Val Thr Thr Glu
            530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
                580                 585                 590

His Ile His Gly Glu Ile Tyr Arg Arg Arg Gly Leu Leu Thr Ser Glu
                595                 600                 605

Gly Lys Glu Ile Lys Asn Lys Asp Glu Ile Leu Ala Leu Leu Lys Ala
            610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
                660                 665                 670

Ile Glu Asn Ser Ser Pro Tyr Thr Ser Glu His Phe
                675                 680

<210> SEQ ID NO 681
<211> LENGTH: 684
<212> TYPE: PRT
<213> ORGANISM: Artificial Sequence
<220> FEATURE:
<223> OTHER INFORMATION: RTase mutant

<400> SEQUENCE: 681

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
            35                  40                  45

Leu Ile Ile Pro Leu Lys Ala Thr Ser Thr Pro Val Ser Ile Lys Gln
            50                  55                  60

Tyr Pro Met Ser Arg Glu Ala Arg Leu Gly Ile Lys Pro His Ile Arg
65                  70                  75                  80

Arg Leu Leu Asp Gln Gly Ile Leu Val Pro Cys Gln Ser Pro Trp Asn
```

-continued

```
                85                90                95

Thr Pro Leu Arg Pro Val Lys Lys Pro Gly Thr Asn Asp Tyr Arg Pro
            100               105               110

Val Gln Asp Leu Arg Glu Val Asn Lys Arg Val Glu Asp Ile His Pro
            115               120               125

Thr Val Pro Asn Pro Tyr Asn Leu Leu Ser Gly Leu Pro Pro Ser His
            130               135               140

Gln Trp Tyr Thr Val Leu Asp Leu Lys Asp Ala Phe Phe Cys Leu Arg
145               150               155               160

Leu His Pro Thr Ser Gln Pro Leu Phe Ala Phe Glu Trp Arg Asp Pro
                165               170               175

Glu Met Gly Ile Ser Gly Gln Leu Thr Trp Thr Arg Leu Pro Gln Gly
                180               185               190

Phe Lys Asn Ser Pro Thr Leu Phe Asp Glu Ala Leu His Arg Asp Leu
                195               200               205

Ala Asp Phe Arg Ile Gln His Pro Asp Leu Ile Leu Leu Gln Tyr Val
            210               215               220

Asp Asp Leu Leu Leu Ala Ala Thr Ser Glu Leu Asp Cys Gln Gln Gly
225               230               235               240

Thr Arg Ala Leu Leu Gln Thr Leu Gly Asn Leu Gly Tyr Arg Ala Ser
                245               250               255

Ala Lys Lys Ala Gln Ile Cys Gln Lys Gln Val Lys Tyr Leu Gly Tyr
                260               265               270

Leu Leu Lys Glu Gly Gln Arg Trp Leu Thr Trp Ala Arg Lys Glu Thr
                275               280               285

Val Met Gly Gln Pro Thr Pro Lys Thr Pro Arg Gln Leu Arg Glu Phe
            290               295               300

Leu Gly Thr Ala Gly Phe Cys Arg Leu Trp Ile Pro Gly Phe Ala Glu
305               310               315               320

Met Ala Ala Pro Leu Tyr Pro Leu Thr Lys Thr Gly Thr Leu Phe Asn
                325               330               335

Trp Gly Pro Asp Gln Gln Lys Ala Tyr Gln Glu Ile Lys Gln Ala Leu
                340               345               350

Leu Thr Ala Pro Ala Leu Gly Leu Pro Asp Leu Thr Lys Pro Phe Glu
                355               360               365

Leu Phe Val Asp Glu Lys Gln Gly Tyr Ala Lys Gly Val Leu Thr Gln
            370               375               380

Lys Leu Gly Pro Trp Arg Arg Pro Val Ala Tyr Leu Ser Lys Lys Leu
385               390               395               400

Asp Pro Val Ala Ala Gly Trp Pro Pro Cys Leu Arg Met Val Ala Ala
                405               410               415

Ile Ala Val Leu Thr Lys Asp Ala Gly Lys Leu Thr Met Gly Gln Pro
                420               425               430

Leu Val Ile Leu Ala Pro His Ala Val Glu Ala Leu Val Lys Gln Pro
                435               440               445

Pro Asp Arg Trp Leu Ser Asn Ala Arg Met Thr His Tyr Gln Ala Leu
            450               455               460

Leu Leu Asp Thr Asp Arg Val Gln Phe Gly Pro Val Val Ala Leu Asn
465               470               475               480

Pro Ala Thr Leu Leu Pro Leu Pro Glu Glu Gly Leu Gln His Asn Cys
                485               490               495

Leu Asp Ile Leu Ala Glu Ala His Gly Thr Arg Pro Asp Leu Thr Asp
                500               505               510
```

-continued

```
Gln Pro Leu Pro Asp Ala Asp His Thr Trp Tyr Thr Gly Gly Ser Ser
        515             520             525

Leu Leu Gln Glu Gly Gln Arg Lys Ala Gly Ala Ala Val Thr Thr Glu
    530             535             540

Thr Glu Val Ile Trp Ala Lys Ala Leu Pro Ala Gly Thr Ser Ala Gln
545             550             555             560

Arg Ala Gln Leu Ile Ala Leu Thr Gln Ala Leu Lys Met Ala Glu Gly
            565             570             575

Lys Lys Leu Asn Val Tyr Thr Asn Ser Arg Tyr Ala Phe Ala Thr Ala
            580             585             590

His Ile His Gly Glu Ile Tyr Arg Arg Arg Gly Leu Leu Thr Ser Glu
            595             600             605

Gly Lys Glu Ile Lys Asn Lys Asp Glu Ile Leu Ala Leu Leu Lys Ala
    610             615             620

Leu Phe Leu Pro Lys Arg Leu Ser Ile Ile His Cys Pro Gly His Gln
625             630             635             640

Lys Gly His Ser Ala Glu Ala Arg Gly Asn Arg Met Ala Asp Gln Ala
            645             650             655

Ala Arg Lys Ala Ala Ile Thr Glu Thr Pro Asp Thr Ser Thr Leu Leu
            660             665             670

Ile Glu Asn Ser Ser Pro Tyr Thr Ser Glu His Phe
        675             680
```

```
<210> SEQ ID NO 682
<211> LENGTH: 684
<212> TYPE: PRT
<213> ORGANISM: Artificial Sequence
<220> FEATURE:
<223> OTHER INFORMATION: RTase mutant

<400> SEQUENCE: 682
```

```
Met Thr Leu Asn Ile Glu Asp Glu His Arg Leu His Glu Thr Ser Lys
1               5               10              15

Glu Pro Asp Val Ser Leu Gly Ser Thr Trp Leu Ser Asp Phe Pro Gln
            20              25              30

Ala Trp Ala Glu Thr Gly Gly Met Gly Leu Ala Val Arg Gln Ala Pro
        35              40              45

Leu Ile Ile Pro Leu Lys Ala Thr Ser Thr Pro Val Ser Lys Lys Gln
    50              55              60

Tyr Pro Met Ser Arg Glu Ala Arg Leu Gly Ile Lys Pro His Ile Arg
65              70              75              80

Arg Leu Leu Asp Gln Gly Ile Leu Val Pro Cys Gln Ser Pro Trp Asn
            85              90              95

Thr Pro Leu Arg Pro Val Lys Lys Pro Gly Thr Asn Asp Tyr Arg Pro
            100             105             110

Val Gln Asp Leu Arg Glu Val Asn Lys Arg Val Glu Asp Ile His Pro
            115             120             125

Thr Val Pro Asn Pro Tyr Asn Leu Leu Ser Gly Leu Pro Pro Ser His
    130             135             140

Gln Trp Tyr Thr Val Leu Asp Leu Lys Asp Ala Phe Phe Cys Leu Arg
145             150             155             160

Leu His Pro Thr Ser Gln Pro Leu Phe Ala Phe Glu Trp Arg Asp Pro
            165             170             175

Glu Met Gly Ile Ser Gly Gln Leu Thr Trp Thr Arg Leu Pro Gln Gly
        180             185             190
```

-continued

```
Phe Lys Asn Ser Pro Thr Leu Phe Asp Glu Ala Leu His Arg Asp Leu
        195                 200                 205

Ala Asp Phe Arg Ile Gln His Pro Asp Leu Ile Leu Leu Gln Tyr Val
        210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
                260                 265                 270

Leu Leu Lys Glu Gly Gln Arg Trp Leu Thr Asp Ala Arg Lys Glu Thr
                275                 280                 285

Val Met Gly Gln Pro Thr Pro Lys Thr Pro Arg Gln Leu Arg Glu Phe
        290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
                340                 345                 350

Leu Thr Ala Pro Ala Leu Gly Leu Pro Asp Leu Thr Lys Pro Phe Glu
                355                 360                 365

Leu Phe Val Asp Glu Lys Gln Gly Tyr Ala Lys Gly Val Leu Thr Gln
        370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
                420                 425                 430

Leu Val Ile Leu Ala Pro His Ala Val Glu Ala Leu Val Lys Gln Pro
                435                 440                 445

Pro Asp Arg Trp Leu Ser Asn Ala Arg Met Thr His Tyr Gln Ala Leu
        450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
                500                 505                 510

Gln Pro Leu Pro Asp Ala Asp His Thr Trp Tyr Thr Gly Gly Ser Ser
        515                 520                 525

Leu Leu Gln Glu Gly Gln Arg Lys Ala Gly Ala Ala Val Thr Thr Glu
        530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
                580                 585                 590

His Ile His Gly Glu Ile Tyr Arg Arg Arg Gly Leu Leu Thr Ser Glu
        595                 600                 605
```

```
Gly Lys Glu Ile Lys Asn Lys Asp Glu Ile Leu Ala Leu Leu Lys Ala
    610             615             620
Leu Phe Leu Pro Lys Arg Leu Ser Ile Ile His Cys Pro Gly His Gln
625             630             635             640
Lys Gly His Ser Ala Glu Ala Arg Gly Asn Arg Met Ala Asp Gln Ala
                645             650             655
Ala Arg Lys Ala Ala Ile Thr Glu Thr Pro Asp Thr Ser Thr Leu Leu
            660             665             670
Ile Glu Asn Ser Ser Pro Tyr Thr Ser Glu His Phe
        675             680

<210> SEQ ID NO 683
<211> LENGTH: 684
<212> TYPE: PRT
<213> ORGANISM: Artificial Sequence
<220> FEATURE:
<223> OTHER INFORMATION: RTase mutant

<400> SEQUENCE: 683

Met Thr Leu Asn Ile Glu Asp Glu His Arg Leu His Glu Thr Ser Lys
1               5               10              15
Glu Pro Asp Val Ser Leu Gly Ser Thr Trp Leu Ser Asp Phe Pro Gln
            20              25              30
Ala Trp Ala Glu Thr Gly Gly Met Gly Leu Ala Val Arg Gln Ala Pro
        35              40              45
Leu Ile Ile Pro Leu Lys Ala Thr Ser Thr Pro Val Ser Met Lys Gln
    50              55              60
Tyr Pro Met Ser Arg Glu Ala Arg Leu Gly Ile Lys Pro His Ile Arg
65              70              75              80
Arg Leu Leu Asp Gln Gly Ile Leu Val Pro Cys Gln Ser Pro Trp Asn
            85              90              95
Thr Pro Leu Arg Pro Val Lys Lys Pro Gly Thr Asn Asp Tyr Arg Pro
            100             105             110
Val Gln Asp Leu Arg Glu Val Asn Lys Arg Val Glu Asp Ile His Pro
        115             120             125
Thr Val Pro Asn Pro Tyr Asn Leu Leu Ser Gly Leu Pro Pro Ser His
    130             135             140
Gln Trp Tyr Thr Val Leu Asp Leu Lys Asp Ala Phe Phe Cys Leu Arg
145             150             155             160
Leu His Pro Thr Ser Gln Pro Leu Phe Ala Phe Glu Trp Arg Asp Pro
            165             170             175
Glu Met Gly Ile Ser Gly Gln Leu Thr Trp Thr Arg Leu Pro Gln Gly
            180             185             190
Phe Lys Asn Ser Pro Thr Leu Phe Asp Glu Ala Leu His Arg Asp Leu
            195             200             205
Ala Asp Phe Arg Ile Gln His Pro Asp Leu Ile Leu Leu Gln Tyr Val
    210             215             220
Asp Asp Leu Leu Leu Ala Ala Thr Ser Glu Leu Asp Cys Gln Gln Gly
225             230             235             240
Thr Arg Ala Leu Leu Gln Thr Leu Gly Asn Leu Gly Tyr Arg Ala Ser
            245             250             255
Ala Lys Lys Ala Gln Ile Cys Gln Lys Gln Val Lys Tyr Leu Gly Tyr
            260             265             270
Leu Leu Lys Glu Gly Gln Arg Trp Leu Thr Asp Ala Arg Lys Glu Thr
            275             280             285
```

-continued

```
Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
                340                 345                 350

Leu Thr Ala Pro Ala Leu Gly Leu Pro Asp Leu Thr Lys Pro Phe Glu
                355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
                420                 425                 430

Leu Val Ile Leu Ala Pro His Ala Val Glu Ala Leu Val Lys Gln Pro
                435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
                500                 505                 510

Gln Pro Leu Pro Asp Ala Asp His Thr Trp Tyr Thr Gly Gly Ser Ser
    515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
                580                 585                 590

His Ile His Gly Glu Ile Tyr Arg Arg Arg Gly Leu Leu Thr Ser Glu
    595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
                660                 665                 670

Ile Glu Asn Ser Ser Pro Tyr Thr Ser Glu His Phe
    675                 680
```

<210> SEQ ID NO 684
<211> LENGTH: 684
<212> TYPE: PRT

<210> ORGANISM: Artificial Sequence
<220> FEATURE:
<223> OTHER INFORMATION: RTase mutant
<213> ORGANISM: Artificial Sequence
<220> FEATURE:
<223> OTHER INFORMATION: RTase mutant

<400> SEQUENCE: 684

```
Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Ile Glu Ala Arg Leu Gly Ile Lys Pro His Ile His
65                  70                  75                  80

Arg Leu Leu Asp Gln Gly Ile Leu Val Pro Cys Gln Ser Pro Trp Asn
                85                  90                  95

Thr Pro Leu Lys Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
            115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
                180                 185                 190

Phe Lys Asn Ser Pro Thr Leu Phe Asp Glu Ala Leu His Arg Asp Leu
            195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Met Ala Arg Lys Glu Thr
            275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
            355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
```

-continued

```
         385                390                395                400

Asp Pro Val Ala Ala Gly Trp Pro Pro Cys Leu Arg Met Val Ala Ala
            405                410                415

Ile Ala Val Leu Thr Lys Asp Ala Gly Lys Leu Thr Met Gly Gln Pro
            420                425                430

Leu Val Ile Leu Ala Pro His Ala Val Glu Ala Leu Val Lys Gln Pro
            435                440                445

Pro Asp Arg Trp Leu Ser Asn Ala Arg Met Thr His Tyr Gln Ala Leu
            450                455                460

Leu Leu Asp Thr Asp Arg Val Gln Phe Gly Pro Val Val Ala Leu Asn
        465                470                475                480

Pro Ala Thr Leu Leu Pro Leu Pro Glu Glu Gly Leu Gln His Asn Cys
            485                490                495

Leu Asp Ile Leu Ala Glu Ala His Gly Thr Arg Pro Asp Leu Thr Asp
            500                505                510

Gln Pro Leu Pro Asp Ala Asp His Thr Trp Tyr Thr Gly Gly Ser Ser
            515                520                525

Leu Leu Gln Glu Gly Gln Arg Lys Ala Gly Ala Ala Val Thr Thr Glu
            530                535                540

Thr Glu Val Ile Trp Ala Lys Ala Leu Pro Ala Gly Thr Ser Ala Gln
        545                550                555                560

Arg Ala Gln Leu Ile Ala Leu Thr Gln Ala Leu Lys Met Ala Glu Gly
            565                570                575

Lys Lys Leu Asn Val Tyr Thr Asn Ser Arg Tyr Ala Phe Ala Thr Ala
            580                585                590

His Ile His Gly Glu Ile Tyr Arg Arg Arg Gly Leu Leu Thr Ser Glu
            595                600                605

Gly Lys Glu Ile Lys Asn Lys Asp Glu Ile Leu Ala Leu Leu Lys Ala
            610                615                620

Leu Phe Leu Pro Lys Arg Leu Ser Ile Ile His Cys Pro Gly His Gln
        625                630                635                640

Lys Gly His Ser Ala Glu Ala Arg Gly Asn Arg Met Ala Asp Gln Ala
            645                650                655

Ala Arg Lys Ala Ala Ile Thr Glu Thr Pro Asp Thr Ser Thr Leu Leu
            660                665                670

Ile Glu Asn Ser Ser Pro Tyr Thr Ser Glu His Phe
            675                680
```

<210> SEQ ID NO 685
<211> LENGTH: 684
<212> TYPE: PRT
<213> ORGANISM: Artificial Sequence
<220> FEATURE:
<223> OTHER INFORMATION: RTase mutant

<400> SEQUENCE: 685

```
Met Thr Leu Asn Ile Glu Asp Glu His Arg Leu His Glu Thr Ser Lys
1               5                  10                 15

Glu Pro Asp Val Ser Leu Gly Ser Thr Trp Leu Ser Asp Phe Pro Gln
            20                 25                 30

Ala Trp Ala Glu Thr Gly Gly Met Gly Leu Ala Val Arg Gln Ala Pro
            35                 40                 45

Leu Ile Ile Pro Leu Lys Ala Thr Ser Thr Pro Val Ser Met Lys Gln
        50                 55                 60

Tyr Pro Met Ser Ile Glu Ala Arg Leu Gly Ile Lys Pro His Ile His
```

-continued

```
65                  70                  75                  80

Arg Leu Leu Asp Gln Gly Ile Leu Val Pro Cys Gln Ser Pro Trp Asn
                 85                  90                  95

Thr Pro Leu Lys Pro Val Lys Lys Pro Gly Thr Asn Asp Tyr Arg Pro
                100                 105                 110

Val Gln Asp Leu Arg Glu Val Asn Lys Arg Val Glu Asp Ile His Pro
                115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
                180                 185                 190

Phe Lys Asn Ser Pro Thr Leu Phe Asp Glu Ala Leu His Arg Asp Leu
                195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
                260                 265                 270

Leu Leu Lys Glu Gly Gln Arg Trp Leu Thr Met Ala Arg Lys Glu Thr
                275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
                340                 345                 350

Leu Thr Ala Pro Ala Leu Gly Leu Pro Asp Leu Thr Lys Pro Phe Glu
                355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
                420                 425                 430

Leu Val Ile Leu Ala Pro His Ala Val Glu Ala Leu Val Lys Gln Pro
                435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495
```

-continued

```
Leu Asp Ile Leu Ala Glu Ala His Gly Thr Arg Pro Asp Leu Thr Asp
        500                 505                 510

Gln Pro Leu Pro Asp Ala Asp His Thr Trp Tyr Thr Gly Gly Ser Ser
        515                 520                 525

Leu Leu Gln Glu Gly Gln Arg Lys Ala Gly Ala Ala Val Thr Thr Glu
        530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
                580                 585                 590

His Ile His Gly Glu Ile Tyr Arg Arg Arg Gly Leu Leu Thr Ser Glu
                595                 600                 605

Gly Lys Glu Ile Lys Asn Lys Asp Glu Ile Leu Ala Leu Leu Lys Ala
        610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
                660                 665                 670

Ile Glu Asn Ser Ser Pro Tyr Thr Ser Glu His Phe
        675                 680
```

```
<210> SEQ ID NO 686
<211> LENGTH: 683
<212> TYPE: PRT
<213> ORGANISM: Artificial Sequence
<220> FEATURE:
<223> OTHER INFORMATION: RTase mutant

<400> SEQUENCE: 686

Thr Leu Asn Ile Glu Asp Glu His Arg Leu His Glu Thr Ser Lys Glu
1               5                   10                  15

Pro Asp Val Ser Leu Gly Ser Thr Trp Leu Ser Asp Phe Pro Gln Ala
                20                  25                  30

Trp Ala Glu Thr Gly Gly Met Gly Leu Ala Val Arg Gln Ala Pro Leu
        35                  40                  45

Ile Ile Pro Leu Lys Ala Thr Ser Thr Pro Val Ser Ile Lys Gln Tyr
        50                  55                  60

Pro Met Ser Arg Glu Ala Arg Leu Gly Ile Lys Pro His Ile Arg Arg
65                  70                  75                  80

Leu Leu Asp Gln Gly Ile Leu Val Pro Cys Gln Ser Pro Trp Asn Thr
                85                  90                  95

Pro Leu Arg Pro Val Lys Lys Pro Gly Thr Asn Asp Tyr Arg Pro Val
                100                 105                 110

Gln Asp Leu Arg Glu Val Asn Lys Arg Val Glu Asp Ile His Pro Thr
        115                 120                 125

Val Pro Asn Pro Tyr Asn Leu Leu Ser Gly Leu Pro Pro Ser His Gln
        130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175
```

-continued

```
Met Gly Ile Ser Gly Gln Leu Thr Trp Thr Arg Leu Pro Gln Gly Phe
        180                 185                 190

Lys Asn Ser Pro Thr Leu Phe Asp Glu Ala Leu His Arg Asp Leu Ala
        195                 200                 205

Asp Phe Arg Ile Gln His Pro Asp Leu Ile Leu Leu Gln Tyr Val Asp
        210                 215                 220

Asp Leu Leu Leu Ala Ala Thr Ser Glu Leu Asp Cys Gln Gln Gly Thr
225                 230                 235                 240

Arg Ala Leu Leu Gln Thr Leu Gly Asn Leu Gly Tyr Arg Ala Ser Ala
                245                 250                 255

Lys Lys Ala Gln Ile Cys Gln Lys Gln Val Lys Tyr Leu Gly Tyr Leu
        260                 265                 270

Leu Lys Glu Gly Gln Arg Trp Leu Thr Asp Ala Arg Lys Glu Thr Val
        275                 280                 285

Met Gly Gln Pro Thr Pro Lys Thr Pro Arg Gln Leu Arg Glu Phe Leu
        290                 295                 300

Gly Thr Ala Gly Phe Cys Arg Leu Trp Ile Pro Gly Phe Ala Glu Met
305                 310                 315                 320

Ala Ala Pro Leu Tyr Pro Leu Thr Lys Thr Gly Thr Leu Phe Asn Trp
                325                 330                 335

Gly Pro Asp Gln Gln Lys Ala Tyr Gln Glu Ile Lys Gln Ala Leu Leu
                340                 345                 350

Thr Ala Pro Ala Leu Gly Leu Pro Asp Leu Thr Lys Pro Phe Glu Leu
                355                 360                 365

Phe Val Asp Glu Lys Gln Gly Tyr Ala Lys Gly Val Leu Thr Gln Lys
        370                 375                 380

Leu Gly Pro Trp Arg Arg Pro Val Ala Tyr Leu Ser Lys Lys Leu Asp
385                 390                 395                 400

Pro Val Ala Ala Gly Trp Pro Pro Cys Leu Arg Met Val Ala Ala Ile
                405                 410                 415

Ala Val Leu Thr Lys Asp Ala Gly Lys Leu Thr Met Gly Gln Pro Leu
                420                 425                 430

Arg Ile Leu Ala Pro His Ala Val Glu Ala Leu Val Lys Gln Pro Pro
        435                 440                 445

Asp Arg Trp Leu Ser Asn Ala Arg Met Thr His Tyr Gln Ala Leu Leu
        450                 455                 460

Leu Asp Thr Asp Arg Val Gln Phe Gly Pro Val Val Ala Leu Asn Pro
465                 470                 475                 480

Ala Thr Leu Leu Pro Leu Pro Glu Glu Gly Leu Gln His Asn Cys Leu
                485                 490                 495

Asp Ile Leu Ala Glu Ala His Gly Thr Arg Pro Asp Leu Thr Asp Gln
                500                 505                 510

Pro Leu Pro Asp Ala Asp His Thr Trp Tyr Thr Gly Gly Ser Ser Leu
        515                 520                 525

Leu Gln Glu Gly Gln Arg Lys Ala Gly Ala Ala Val Thr Thr Glu Thr
        530                 535                 540

Glu Val Ile Trp Ala Lys Ala Leu Pro Ala Gly Thr Ser Ala Gln Arg
545                 550                 555                 560

Ala Gln Leu Ile Ala Leu Thr Gln Ala Leu Lys Met Ala Glu Gly Lys
                565                 570                 575

Lys Leu Asn Val Tyr Thr Asn Ser Arg Tyr Ala Phe Ala Thr Ala His
                580                 585                 590
```

```
Ile His Gly Glu Ile Tyr Arg Arg Arg Gly Leu Leu Thr Ser Glu Gly
        595                 600                 605

Lys Glu Ile Lys Asn Lys Asp Glu Ile Leu Ala Leu Leu Lys Ala Leu
        610                 615                 620

Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asp Gln Ala Ala
                645                 650                 655

Arg Lys Ala Ala Ile Thr Glu Thr Pro Asp Thr Ser Thr Leu Leu Ile
                660                 665                 670

Glu Asn Ser Ser Pro Tyr Thr Ser Glu His Phe
        675                 680
```

```
<210> SEQ ID NO 687
<211> LENGTH: 683
<212> TYPE: PRT
<213> ORGANISM: Artificial Sequence
<220> FEATURE:
<223> OTHER INFORMATION: RTase mutant

<400> SEQUENCE: 687
```

```
Thr Leu Asn Ile Glu Asp Glu His Arg Leu His Glu Thr Ser Lys Glu
1               5                   10                  15

Pro Asp Val Ser Leu Gly Ser Thr Trp Leu Ser Asp Phe Pro Gln Ala
                20                  25                  30

Trp Ala Glu Thr Gly Gly Met Gly Leu Ala Val Arg Gln Ala Pro Leu
        35                  40                  45

Ile Ile Pro Leu Lys Ala Thr Ser Thr Pro Val Ser Ile Lys Gln Tyr
        50                  55                  60

Pro Met Ser Arg Glu Ala Arg Leu Gly Ile Lys Pro His Ile Arg Arg
65                  70                  75                  80

Leu Leu Asp Gln Gly Ile Leu Val Pro Cys Gln Ser Pro Trp Asn Thr
                85                  90                  95

Pro Leu Arg Pro Val Lys Lys Pro Gly Thr Asn Asp Tyr Arg Pro Val
                100                 105                 110

Gln Asp Leu Arg Glu Val Asn Lys Arg Val Glu Asp Ile His Pro Thr
        115                 120                 125

Val Pro Asn Pro Tyr Asn Leu Leu Ser Gly Leu Pro Pro Ser His Gln
        130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175

Met Gly Ile Ser Gly Gln Leu Thr Trp Thr Arg Leu Pro Gln Gly Phe
                180                 185                 190

Lys Asn Ser Pro Thr Leu Phe Asp Glu Ala Leu His Arg Asp Leu Ala
        195                 200                 205

Asp Phe Arg Ile Gln His Pro Asp Leu Ile Leu Leu Gln Tyr Val Asp
        210                 215                 220

Asp Leu Leu Leu Ala Ala Thr Ser Glu Leu Asp Cys Gln Gln Gly Thr
225                 230                 235                 240

Arg Ala Leu Leu Gln Thr Leu Gly Asn Leu Gly Tyr Arg Ala Ser Ala
                245                 250                 255

Lys Lys Ala Gln Ile Cys Gln Lys Gln Val Lys Tyr Leu Gly Tyr Leu
        260                 265                 270
```

```
Leu Lys Glu Gly Gln Arg Trp Leu Thr Asp Ala Arg Lys Glu Thr Val
    275                 280                 285

Met Gly Gln Pro Thr Pro Lys Thr Pro Arg Gln Leu Arg Glu Phe Leu
    290                 295                 300

Gly Thr Ala Gly Phe Cys Arg Leu Trp Ile Pro Gly Phe Ala Glu Met
305                 310                 315                 320

Ala Ala Pro Leu Tyr Pro Leu Thr Lys Thr Gly Thr Leu Phe Asn Trp
                325                 330                 335

Gly Pro Asp Gln Gln Lys Ala Tyr Gln Glu Ile Lys Gln Ala Leu Leu
                340                 345                 350

Thr Ala Pro Ala Leu Gly Leu Pro Asp Leu Thr Lys Pro Phe Glu Leu
                355                 360                 365

Phe Val Asp Glu Lys Gln Gly Tyr Ala Lys Gly Val Leu Thr Gln Lys
    370                 375                 380

Leu Gly Pro Trp Arg Arg Pro Val Ala Tyr Leu Ser Lys Lys Leu Asp
385                 390                 395                 400

Pro Val Ala Ala Gly Trp Pro Pro Cys Leu Arg Met Val Ala Ala Ile
                405                 410                 415

Ala Val Leu Thr Lys Asp Ala Gly Lys Leu Thr Met Gly Gln Pro Leu
                420                 425                 430

Val Ile Leu Ala Pro His Ala Val Glu Ala Leu Val Lys Gln Pro Pro
                435                 440                 445

Asp Arg Trp Leu Ser Asn Ala Arg Met Thr His Tyr Gln Ala Leu Leu
    450                 455                 460

Leu Asp Thr Asp Arg Val Gln Phe Gly Pro Val Val Ala Leu Asn Pro
465                 470                 475                 480

Ala Thr Leu Leu Pro Leu Pro Glu Glu Gly Leu Gln His Asn Cys Leu
                485                 490                 495

Asp Ile Leu Ala Glu Ala His Gly Thr Arg Pro Asp Leu Thr Asp Gln
                500                 505                 510

Pro Leu Pro Asp Ala Asp His Thr Trp Tyr Thr Gly Gly Ser Ser Leu
    515                 520                 525

Leu Gln Glu Gly Gln Arg Lys Ala Gly Ala Ala Val Thr Thr Glu Thr
    530                 535                 540

Glu Val Ile Trp Ala Lys Ala Leu Pro Ala Gly Thr Ser Ala Gln Arg
545                 550                 555                 560

Ala Gln Leu Ile Ala Leu Thr Gln Ala Leu Lys Met Ala Glu Gly Lys
                565                 570                 575

Lys Leu Asn Val Tyr Thr Asn Ser Arg Tyr Ala Phe Ala Thr Ala His
                580                 585                 590

Glu His Gly Glu Ile Tyr Arg Arg Gly Leu Leu Thr Ser Glu Gly
    595                 600                 605

Lys Glu Ile Lys Asn Lys Asp Glu Ile Leu Ala Leu Leu Lys Ala Leu
    610                 615                 620

Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asp Gln Ala Ala
                645                 650                 655

Arg Lys Ala Ala Ile Thr Glu Thr Pro Asp Thr Ser Thr Leu Leu Ile
                660                 665                 670

Glu Asn Ser Ser Pro Tyr Thr Ser Glu His Phe
    675                 680
```

```
<210> SEQ ID NO 688
<211> LENGTH: 683
<212> TYPE: PRT
<213> ORGANISM: Artificial Sequence
<220> FEATURE:
<223> OTHER INFORMATION: RTase mutant

<400> SEQUENCE: 688

Thr Leu Asn Ile Glu Asp Glu His Arg Leu His Glu Thr Ser Lys Glu
1               5                   10                  15

Pro Asp Val Ser Leu Gly Ser Thr Trp Leu Ser Asp Phe Pro Gln Ala
            20                  25                  30

Trp Ala Glu Thr Gly Gly Met Gly Leu Ala Val Arg Gln Ala Pro Leu
        35                  40                  45

Ile Ile Pro Leu Lys Ala Thr Ser Thr Pro Val Ser Ile Lys Gln Tyr
    50                  55                  60

Pro Met Ser Arg Glu Ala Arg Leu Gly Ile Lys Pro His Ile Arg Arg
65                  70                  75                  80

Leu Leu Asp Gln Gly Ile Leu Val Pro Cys Gln Ser Pro Trp Asn Thr
                85                  90                  95

Pro Leu Arg Pro Val Lys Lys Pro Gly Thr Asn Asp Tyr Arg Pro Val
            100                 105                 110

Gln Asp Leu Arg Glu Val Asn Lys Arg Val Glu Asp Ile His Pro Thr
            115                 120                 125

Val Pro Asn Pro Tyr Asn Leu Leu Ser Gly Leu Pro Pro Ser His Gln
        130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175

Met Gly Ile Ser Gly Gln Leu Thr Trp Thr Arg Leu Pro Gln Gly Phe
            180                 185                 190

Lys Asn Ser Pro Thr Leu Phe Asp Glu Ala Leu His Arg Asp Leu Ala
            195                 200                 205

Asp Phe Arg Ile Gln His Pro Asp Leu Ile Leu Leu Gln Tyr Val Asp
        210                 215                 220

Asp Leu Leu Leu Ala Ala Thr Ser Glu Leu Asp Cys Gln Gln Gly Thr
225                 230                 235                 240

Arg Ala Leu Leu Gln Thr Leu Gly Asn Leu Gly Tyr Arg Ala Ser Ala
                245                 250                 255

Lys Lys Ala Gln Ile Cys Gln Lys Gln Val Lys Tyr Leu Gly Tyr Leu
            260                 265                 270

Leu Lys Glu Gly Gln Arg Trp Leu Thr Asp Ala Arg Lys Glu Thr Val
        275                 280                 285

Met Gly Gln Pro Thr Pro Lys Thr Pro Arg Glu Leu Arg Glu Phe Leu
    290                 295                 300

Gly Thr Ala Gly Phe Cys Arg Leu Trp Ile Pro Gly Phe Ala Glu Met
305                 310                 315                 320

Ala Ala Pro Leu Tyr Pro Leu Thr Lys Thr Gly Thr Leu Phe Asn Trp
                325                 330                 335

Gly Pro Asp Gln Gln Lys Ala Tyr Gln Glu Ile Lys Gln Ala Leu Leu
            340                 345                 350

Thr Ala Pro Ala Leu Gly Leu Pro Asp Leu Thr Lys Pro Phe Glu Leu
        355                 360                 365

Phe Val Asp Glu Lys Gln Gly Tyr Ala Lys Gly Val Leu Thr Gln Lys
```

-continued

```
       370               375               380

Leu Gly Pro Trp Arg Arg Pro Val Ala Tyr Leu Ser Lys Lys Leu Asp
385               390               395               400

Pro Val Ala Ala Gly Trp Pro Pro Cys Leu Arg Met Val Ala Ala Ile
              405               410               415

Ala Val Leu Thr Lys Asp Ala Gly Lys Leu Thr Met Gly Gln Pro Leu
              420               425               430

Val Ile Leu Ala Pro His Ala Val Glu Ala Leu Val Lys Gln Pro Pro
              435               440               445

Asp Arg Trp Leu Ser Asn Ala Arg Met Thr His Tyr Gln Ala Leu Leu
              450               455               460

Leu Asp Thr Asp Arg Val Gln Phe Gly Pro Val Val Ala Leu Asn Pro
465               470               475               480

Ala Thr Leu Leu Pro Leu Pro Glu Glu Gly Leu Gln His Asn Cys Leu
              485               490               495

Asp Ile Leu Ala Glu Ala His Gly Thr Arg Pro Asp Leu Thr Asp Gln
              500               505               510

Pro Leu Pro Asp Ala Asp His Thr Trp Tyr Thr Gly Gly Ser Ser Leu
              515               520               525

Leu Gln Glu Gly Gln Arg Lys Ala Gly Ala Ala Val Thr Thr Glu Thr
              530               535               540

Glu Val Ile Trp Ala Lys Ala Leu Pro Ala Gly Thr Ser Ala Gln Arg
545               550               555               560

Ala Gln Leu Ile Ala Leu Thr Gln Ala Leu Lys Met Ala Glu Gly Lys
              565               570               575

Lys Leu Asn Val Tyr Thr Asn Ser Arg Tyr Ala Phe Ala Thr Ala His
              580               585               590

Ile His Gly Glu Ile Tyr Arg Arg Arg Gly Leu Leu Thr Ser Glu Gly
              595               600               605

Lys Glu Ile Lys Asn Lys Asp Glu Ile Leu Ala Leu Leu Lys Ala Leu
              610               615               620

Phe Leu Pro Lys Arg Leu Ser Ile Ile His Cys Pro Gly His Gln Lys
625               630               635               640

Gly His Ser Ala Glu Ala Arg Gly Asn Arg Met Ala Asp Gln Ala Ala
              645               650               655

Arg Lys Ala Ala Ile Thr Glu Thr Pro Asp Thr Ser Thr Leu Leu Ile
              660               665               670

Glu Asn Ser Ser Pro Tyr Thr Ser Glu His Phe
              675               680
```

```
<210> SEQ ID NO 689
<211> LENGTH: 683
<212> TYPE: PRT
<213> ORGANISM: Artificial Sequence
<220> FEATURE:
<223> OTHER INFORMATION: RTase mutant

<400> SEQUENCE: 689

Thr Leu Asn Ile Glu Asp Glu His Arg Leu His Glu Thr Ser Lys Glu
1               5               10               15

Pro Asp Val Ser Leu Gly Ser Thr Trp Leu Ser Asp Phe Pro Gln Ala
              20               25               30

Trp Ala Glu Thr Gly Gly Met Gly Leu Ala Val Arg Gln Ala Pro Leu
              35               40               45

Ile Ile Pro Leu Lys Ala Thr Ser Thr Pro Val Ser Ile Lys Gln Tyr
```

-continued

```
         50              55              60

Pro Met Ser Arg Glu Ala Arg Leu Gly Ile Lys Pro His Ile Arg Arg
65              70              75              80

Leu Leu Asp Gln Gly Ile Leu Val Pro Cys Gln Ser Pro Trp Asn Thr
                85              90              95

Pro Leu Arg Pro Val Lys Lys Pro Gly Thr Asn Asp Tyr Arg Pro Val
            100             105             110

Gln Asp Leu Arg Glu Val Asn Lys Arg Val Glu Asp Ile His Pro Thr
            115             120             125

Val Pro Asn Pro Tyr Asn Leu Leu Ser Gly Leu Pro Pro Ser His Gln
        130             135             140

Trp Tyr Thr Val Leu Asp Leu Lys Asp Ala Phe Phe Cys Leu Arg Leu
145             150             155             160

His Pro Thr Ser Gln Pro Leu Phe Ala Phe Glu Trp Arg Asp Pro Glu
                165             170             175

Met Gly Ile Ser Gly Gln Leu Thr Trp Thr Arg Leu Pro Gln Gly Phe
                180             185             190

Lys Asn Ser Pro Thr Leu Phe Asp Glu Ala Leu His Arg Asp Leu Ala
            195             200             205

Asp Phe Arg Ile Gln His Pro Asp Leu Ile Leu Leu Gln Tyr Val Asp
        210             215             220

Asp Leu Leu Leu Ala Ala Thr Ser Glu Leu Asp Cys Gln Gln Gly Thr
225             230             235             240

Arg Ala Leu Leu Gln Thr Leu Gly Asn Leu Gly Tyr Arg Ala Ser Ala
            245             250             255

Lys Lys Ala Gln Ile Cys Gln Lys Gln Val Lys Tyr Leu Gly Tyr Leu
            260             265             270

Leu Lys Glu Gly Gln Arg Trp Leu Thr Asp Ala Arg Lys Glu Thr Val
            275             280             285

Met Gly Gln Pro Thr Pro Lys Thr Pro Arg Gln Leu Arg Glu Phe Leu
        290             295             300

Gly Thr Ala Gly Phe Cys Arg Leu Trp Ile Pro Gly Phe Ala Glu Met
305             310             315             320

Ala Ala Pro Leu Tyr Pro Leu Thr Lys Thr Gly Glu Leu Phe Asn Trp
                325             330             335

Gly Pro Asp Gln Gln Lys Ala Tyr Gln Glu Ile Lys Gln Ala Leu Leu
            340             345             350

Thr Ala Pro Ala Leu Gly Leu Pro Asp Leu Thr Lys Pro Phe Glu Leu
            355             360             365

Phe Val Asp Glu Lys Gln Gly Tyr Ala Lys Gly Val Leu Thr Gln Lys
        370             375             380

Leu Gly Pro Trp Arg Arg Pro Val Ala Tyr Leu Ser Lys Lys Leu Asp
385             390             395             400

Pro Val Ala Ala Gly Trp Pro Pro Cys Leu Arg Met Val Ala Ala Ile
                405             410             415

Ala Val Leu Thr Lys Asp Ala Gly Lys Leu Thr Met Gly Gln Pro Leu
            420             425             430

Val Ile Leu Ala Pro His Ala Val Glu Ala Leu Val Lys Gln Pro Pro
            435             440             445

Asp Arg Trp Leu Ser Asn Ala Arg Met Thr His Tyr Gln Ala Leu Leu
        450             455             460

Leu Asp Thr Asp Arg Val Gln Phe Gly Pro Val Val Ala Leu Asn Pro
465             470             475             480
```

-continued

```
Ala Thr Leu Leu Pro Leu Pro Glu Glu Gly Leu Gln His Asn Cys Leu
            485             490             495

Asp Ile Leu Ala Glu Ala His Gly Thr Arg Pro Asp Leu Thr Asp Gln
            500             505             510

Pro Leu Pro Asp Ala Asp His Thr Trp Tyr Thr Gly Gly Ser Ser Leu
            515             520             525

Leu Gln Glu Gly Gln Arg Lys Ala Gly Ala Ala Val Thr Thr Glu Thr
        530             535             540

Glu Val Ile Trp Ala Lys Ala Leu Pro Ala Gly Thr Ser Ala Gln Arg
545             550             555             560

Ala Gln Leu Ile Ala Leu Thr Gln Ala Leu Lys Met Ala Glu Gly Lys
            565             570             575

Lys Leu Asn Val Tyr Thr Asn Ser Arg Tyr Ala Phe Ala Thr Ala His
            580             585             590

Ile His Gly Glu Ile Tyr Arg Arg Arg Gly Leu Leu Thr Ser Glu Gly
            595             600             605

Lys Glu Ile Lys Asn Lys Asp Glu Ile Leu Ala Leu Leu Lys Ala Leu
        610             615             620

Phe Leu Pro Lys Arg Leu Ser Ile Ile His Cys Pro Gly His Gln Lys
625             630             635             640

Gly His Ser Ala Glu Ala Arg Gly Asn Arg Met Ala Asp Gln Ala Ala
            645             650             655

Arg Lys Ala Ala Ile Thr Glu Thr Pro Asp Thr Ser Thr Leu Leu Ile
            660             665             670

Glu Asn Ser Ser Pro Tyr Thr Ser Glu His Phe
            675             680
```

```
<210> SEQ ID NO 690
<211> LENGTH: 683
<212> TYPE: PRT
<213> ORGANISM: Artificial Sequence
<220> FEATURE:
<223> OTHER INFORMATION: RTase mutant

<400> SEQUENCE: 690
```

```
Thr Leu Asn Ile Glu Asp Glu His Arg Leu His Glu Thr Ser Lys Glu
1               5               10              15

Pro Asp Val Ser Leu Gly Ser Thr Trp Leu Ser Asp Phe Pro Gln Ala
            20              25              30

Trp Ala Glu Thr Gly Gly Met Gly Leu Ala Val Arg Gln Ala Pro Leu
        35              40              45

Ile Ile Pro Leu Lys Ala Thr Ser Thr Pro Val Ser Ile Lys Gln Tyr
    50              55              60

Pro Met Ser Arg Glu Ala Arg Leu Gly Ile Lys Pro His Ile Arg Arg
65              70              75              80

Leu Leu Asp Gln Gly Ile Leu Val Pro Cys Gln Ser Pro Trp Asn Thr
            85              90              95

Pro Leu Arg Pro Val Lys Lys Pro Gly Thr Asn Asp Tyr Arg Pro Val
            100             105             110

Gln Asp Leu Arg Glu Val Asn Lys Arg Val Glu Asp Ile His Pro Thr
            115             120             125

Val Pro Asn Pro Tyr Asn Leu Leu Ser Gly Leu Pro Pro Ser His Gln
        130             135             140

Trp Tyr Thr Val Leu Asp Leu Lys Asp Ala Phe Phe Cys Leu Arg Leu
145             150             155             160
```

-continued

```
His Pro Thr Ser Gln Pro Leu Phe Ala Phe Glu Trp Arg Asp Pro Glu
             165             170             175

Met Gly Ile Ser Gly Gln Leu Thr Trp Thr Arg Leu Pro Gln Gly Phe
             180             185             190

Lys Asn Ser Pro Thr Leu Phe Asp Glu Ala Leu His Arg Asp Leu Ala
             195             200             205

Asp Phe Arg Ile Gln His Pro Asp Leu Ile Leu Leu Gln Tyr Val Asp
    210             215             220

Asp Leu Leu Leu Ala Ala Thr Ser Glu Leu Asp Cys Gln Gln Gly Thr
225             230             235             240

Arg Ala Leu Leu Gln Thr Leu Gly Asn Leu Gly Tyr Arg Ala Ser Ala
             245             250             255

Lys Lys Ala Gln Ile Cys Gln Lys Gln Val Lys Tyr Leu Gly Tyr Leu
             260             265             270

Leu Lys Glu Gly Gln Arg Trp Arg Thr Glu Ala Arg Lys Glu Thr Val
             275             280             285

Met Gly Gln Pro Thr Pro Lys Thr Pro Arg Gln Leu Arg Glu Phe Leu
    290             295             300

Gly Thr Ala Gly Phe Cys Arg Leu Trp Ile Pro Gly Phe Ala Glu Met
305             310             315             320

Ala Ala Pro Leu Tyr Pro Leu Thr Lys Thr Gly Thr Leu Phe Asn Trp
             325             330             335

Gly Pro Asp Gln Gln Lys Ala Tyr Gln Glu Ile Lys Gln Ala Leu Leu
             340             345             350

Thr Ala Pro Ala Leu Gly Leu Pro Asp Leu Thr Lys Pro Phe Glu Leu
             355             360             365

Phe Val Asp Glu Lys Gln Gly Tyr Ala Lys Gly Val Leu Thr Gln Lys
    370             375             380

Leu Gly Pro Trp Arg Arg Pro Val Ala Tyr Leu Ser Lys Lys Leu Asp
385             390             395             400

Pro Val Ala Ala Gly Trp Pro Pro Cys Leu Arg Met Val Ala Ala Ile
             405             410             415

Ala Val Leu Thr Lys Asp Ala Gly Lys Leu Thr Met Gly Gln Pro Leu
             420             425             430

Val Ile Leu Ala Pro His Ala Val Glu Ala Leu Val Lys Gln Pro Pro
             435             440             445

Asp Arg Trp Leu Ser Asn Ala Arg Met Thr His Tyr Gln Ala Leu Leu
    450             455             460

Leu Asp Thr Asp Arg Val Gln Phe Gly Pro Val Val Ala Leu Asn Pro
465             470             475             480

Ala Thr Leu Leu Pro Leu Pro Glu Glu Gly Leu Gln His Asn Cys Leu
             485             490             495

Asp Ile Leu Ala Glu Ala His Gly Thr Arg Pro Asp Leu Thr Asp Gln
             500             505             510

Pro Leu Pro Asp Ala Asp His Thr Trp Tyr Thr Gly Gly Ser Ser Leu
             515             520             525

Leu Gln Glu Gly Gln Arg Lys Ala Gly Ala Ala Val Thr Thr Glu Thr
             530             535             540

Glu Val Ile Trp Ala Lys Ala Leu Pro Ala Gly Thr Ser Ala Gln Arg
545             550             555             560

Ala Gln Leu Ile Ala Leu Thr Gln Ala Leu Lys Met Ala Glu Gly Lys
             565             570             575
```

-continued

```
Lys Leu Asn Val Tyr Thr Asn Ser Arg Tyr Ala Phe Ala Thr Ala His
            580                 585                 590

Ile His Gly Glu Ile Tyr Arg Arg Arg Gly Leu Leu Thr Ser Glu Gly
        595                 600                 605

Lys Glu Ile Lys Asn Lys Asp Glu Ile Leu Ala Leu Leu Lys Ala Leu
    610                 615                 620

Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asp Gln Ala Ala
                645                 650                 655

Arg Lys Ala Ala Ile Thr Glu Thr Pro Asp Thr Ser Thr Leu Leu Ile
            660                 665                 670

Glu Asn Ser Ser Pro Tyr Thr Ser Glu His Phe
        675                 680

<210> SEQ ID NO 691
<211> LENGTH: 683
<212> TYPE: PRT
<213> ORGANISM: Artificial Sequence
<220> FEATURE:
<223> OTHER INFORMATION: RTase mutant

<400> SEQUENCE: 691

Thr Leu Asn Ile Glu Asp Glu His Arg Leu His Glu Thr Ser Lys Glu
1               5                   10                  15

Pro Asp Val Ser Leu Gly Ser Thr Trp Leu Ser Asp Phe Pro Gln Ala
            20                  25                  30

Trp Ala Glu Thr Gly Gly Met Gly Leu Ala Val Arg Gln Ala Pro Leu
        35                  40                  45

Ile Ile Pro Leu Lys Ala Thr Ser Thr Pro Val Ser Ile Lys Gln Tyr
    50                  55                  60

Pro Met Ser Arg Glu Ala Arg Leu Gly Ile Lys Pro His Ile Arg Arg
65                  70                  75                  80

Leu Leu Asp Gln Gly Ile Leu Val Pro Cys Gln Ser Pro Trp Asn Thr
                85                  90                  95

Pro Leu Arg Pro Val Lys Lys Pro Gly Thr Asn Asp Tyr Arg Pro Val
            100                 105                 110

Gln Asp Leu Arg Glu Val Asn Lys Arg Val Glu Asp Ile His Pro Thr
        115                 120                 125

Val Pro Asn Pro Tyr Asn Leu Leu Ser Gly Leu Pro Pro Ser His Gln
    130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175

Met Gly Ile Ser Gly Gln Leu Thr Trp Thr Arg Leu Pro Gln Gly Phe
            180                 185                 190

Lys Asn Ser Pro Thr Leu Phe Asp Glu Ala Leu His Arg Asp Leu Ala
        195                 200                 205

Asp Phe Arg Ile Gln His Pro Asp Leu Ile Leu Leu Gln Tyr Val Asp
    210                 215                 220

Asp Leu Leu Leu Ala Ala Thr Ser Glu Leu Asp Cys Gln Gln Gly Thr
225                 230                 235                 240

Arg Ala Leu Leu Gln Thr Leu Gly Asn Leu Gly Tyr Arg Ala Ser Ala
                245                 250                 255
```

-continued

```
Lys Lys Ala Gln Ile Cys Gln Lys Gln Val Lys Tyr Leu Gly Tyr Leu
            260             265             270

Leu Lys Glu Gly Gln Arg Trp Arg Thr Asp Ala Arg Lys Glu Thr Val
        275             280             285

Met Gly Gln Pro Thr Pro Lys Thr Pro Arg Gln Leu Arg Glu Phe Leu
    290             295             300

Gly Thr Ala Gly Phe Cys Arg Leu Trp Ile Pro Gly Phe Ala Glu Met
305             310             315             320

Ala Ala Pro Leu Tyr Pro Leu Thr Lys Thr Gly Thr Leu Phe Asn Trp
            325             330             335

Gly Pro Asp Gln Gln Lys Ala Tyr Gln Glu Ile Lys Gln Ala Leu Leu
            340             345             350

Thr Ala Pro Ala Leu Gly Leu Pro Asp Leu Thr Lys Pro Phe Glu Leu
            355             360             365

Phe Val Asp Glu Lys Gln Gly Tyr Ala Lys Gly Val Leu Thr Gln Lys
    370             375             380

Leu Gly Pro Trp Arg Arg Pro Val Ala Tyr Leu Ser Lys Lys Leu Asp
385             390             395             400

Pro Val Ala Ala Gly Trp Pro Pro Cys Leu Arg Met Val Ala Ala Ile
            405             410             415

Ala Val Leu Thr Lys Asp Ala Gly Lys Leu Thr Met Gly Gln Pro Leu
            420             425             430

Val Ile Leu Ala Pro His Ala Val Glu Ala Leu Val Lys Gln Pro Pro
            435             440             445

Asp Arg Trp Leu Ser Asn Ala Arg Met Thr His Tyr Gln Ala Leu Leu
    450             455             460

Leu Asp Thr Asp Arg Val Gln Phe Gly Pro Val Val Ala Leu Asn Pro
465             470             475             480

Ala Thr Leu Leu Pro Leu Pro Glu Glu Gly Leu Gln His Asn Cys Leu
            485             490             495

Asp Ile Leu Ala Glu Ala His Gly Thr Arg Pro Asp Leu Thr Asp Gln
            500             505             510

Pro Leu Pro Asp Ala Asp His Thr Trp Tyr Thr Gly Gly Ser Ser Leu
            515             520             525

Leu Gln Glu Gly Gln Arg Lys Ala Gly Ala Ala Val Thr Thr Glu Thr
    530             535             540

Glu Val Ile Trp Ala Lys Ala Leu Pro Ala Gly Thr Ser Ala Gln Arg
545             550             555             560

Ala Gln Leu Ile Ala Leu Thr Gln Ala Leu Lys Met Ala Glu Gly Lys
            565             570             575

Lys Leu Asn Val Tyr Thr Asn Ser Arg Tyr Ala Phe Ala Thr Ala His
            580             585             590

Ile His Gly Glu Ile Tyr Arg Arg Arg Gly Leu Leu Thr Ser Glu Gly
            595             600             605

Lys Glu Ile Lys Asn Lys Asp Glu Ile Leu Ala Leu Leu Lys Ala Leu
    610             615             620

Phe Leu Pro Lys Arg Leu Ser Ile Ile His Cys Pro Gly His Gln Lys
625             630             635             640

Gly His Ser Ala Glu Ala Arg Gly Asn Arg Met Ala Asp Gln Ala Ala
            645             650             655

Arg Lys Ala Ala Ile Thr Glu Thr Pro Asp Thr Ser Thr Leu Leu Ile
            660             665             670

Glu Asn Ser Ser Pro Tyr Thr Ser Glu His Phe
```

```
              675                 680

<210> SEQ ID NO 692
<211> LENGTH: 683
<212> TYPE: PRT
<213> ORGANISM: Artificial Sequence
<220> FEATURE:
<223> OTHER INFORMATION: RTase mutant

<400> SEQUENCE: 692

Thr Leu Asn Ile Glu Asp Glu His Arg Leu His Glu Thr Ser Lys Glu
1               5                   10                  15

Pro Asp Val Ser Leu Gly Ser Thr Trp Leu Ser Asp Phe Pro Gln Ala
            20                  25                  30

Trp Ala Glu Thr Gly Gly Met Gly Leu Ala Val Arg Gln Ala Pro Leu
        35                  40                  45

Ile Ile Pro Leu Lys Ala Thr Ser Thr Pro Val Ser Ile Lys Gln Tyr
    50                  55                  60

Pro Met Ser Arg Glu Ala Arg Leu Gly Ile Lys Pro His Ile Gln Arg
65                  70                  75                  80

Leu Arg Asp Gln Gly Ile Leu Val Pro Cys Gln Ser Pro Trp Asn Thr
                85                  90                  95

Pro Leu Arg Pro Val Lys Lys Pro Gly Thr Asn Asp Tyr Arg Pro Val
            100                 105                 110

Gln Asp Leu Arg Glu Val Asn Lys Arg Val Glu Asp Ile His Pro Thr
            115                 120                 125

Val Pro Asn Pro Tyr Asn Leu Leu Ser Gly Leu Pro Pro Ser His Gln
    130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175

Met Gly Ile Ser Gly Gln Leu Thr Trp Thr Arg Leu Pro Gln Gly Phe
            180                 185                 190

Lys Asn Ser Pro Thr Leu Phe Asp Glu Ala Leu His Arg Asp Leu Ala
            195                 200                 205

Asp Phe Arg Ile Gln His Pro Asp Leu Ile Leu Leu Gln Tyr Val Asp
    210                 215                 220

Asp Leu Leu Leu Ala Ala Thr Ser Glu Leu Asp Cys Gln Gln Gly Thr
225                 230                 235                 240

Arg Ala Leu Leu Gln Thr Leu Gly Asn Leu Gly Tyr Arg Ala Ser Ala
                245                 250                 255

Lys Lys Ala Gln Ile Cys Gln Lys Gln Val Lys Tyr Leu Gly Tyr Leu
            260                 265                 270

Leu Lys Glu Gly Gln Arg Trp Leu Thr Asp Ala Arg Lys Glu Thr Val
            275                 280                 285

Met Gly Gln Pro Thr Pro Lys Thr Pro Arg Gln Leu Arg Glu Phe Leu
    290                 295                 300

Gly Thr Ala Gly Phe Cys Arg Leu Trp Ile Pro Gly Phe Ala Glu Met
305                 310                 315                 320

Ala Ala Pro Leu Tyr Pro Leu Thr Lys Thr Gly Thr Leu Phe Asn Trp
                325                 330                 335

Gly Pro Asp Gln Gln Lys Ala Tyr Gln Glu Ile Lys Gln Ala Leu Leu
            340                 345                 350

Thr Ala Pro Ala Leu Gly Leu Pro Asp Leu Thr Lys Pro Phe Glu Leu
```

-continued

```
                355                  360                  365

Phe Val Asp Glu Lys Gln Gly Tyr Ala Lys Gly Val Leu Thr Gln Lys
    370                  375                  380

Leu Gly Pro Trp Arg Arg Pro Val Ala Tyr Leu Ser Lys Lys Leu Asp
385                  390                  395                  400

Pro Val Ala Ala Gly Trp Pro Pro Cys Leu Arg Met Val Ala Ala Ile
                405                  410                  415

Ala Val Leu Thr Lys Asp Ala Gly Lys Leu Thr Met Gly Gln Pro Leu
                420                  425                  430

Val Ile Leu Ala Pro His Ala Val Glu Ala Leu Val Lys Gln Pro Pro
                435                  440                  445

Asp Arg Trp Leu Ser Asn Ala Arg Met Thr His Tyr Gln Ala Leu Leu
    450                  455                  460

Leu Asp Thr Asp Arg Val Gln Phe Gly Pro Val Val Ala Leu Asn Pro
465                  470                  475                  480

Ala Thr Leu Leu Pro Leu Pro Glu Glu Gly Leu Gln His Asn Cys Leu
                485                  490                  495

Asp Ile Leu Ala Glu Ala His Gly Thr Arg Pro Asp Leu Thr Asp Gln
                500                  505                  510

Pro Leu Pro Asp Ala Asp His Thr Trp Tyr Thr Gly Gly Ser Ser Leu
                515                  520                  525

Leu Gln Glu Gly Gln Arg Lys Ala Gly Ala Ala Val Thr Thr Glu Thr
    530                  535                  540

Glu Val Ile Trp Ala Lys Ala Leu Pro Ala Gly Thr Ser Ala Gln Arg
545                  550                  555                  560

Ala Gln Leu Ile Ala Leu Thr Gln Ala Leu Lys Met Ala Glu Gly Lys
                565                  570                  575

Lys Leu Asn Val Tyr Thr Asn Ser Arg Tyr Ala Phe Ala Thr Ala His
                580                  585                  590

Ile His Gly Glu Ile Tyr Arg Arg Arg Gly Leu Leu Thr Ser Glu Gly
    595                  600                  605

Lys Glu Ile Lys Asn Lys Asp Glu Ile Leu Ala Leu Leu Lys Ala Leu
    610                  615                  620

Phe Leu Pro Lys Arg Leu Ser Ile Ile His Cys Pro Gly His Gln Lys
625                  630                  635                  640

Gly His Ser Ala Glu Ala Arg Gly Asn Arg Met Ala Asp Gln Ala Ala
                645                  650                  655

Arg Lys Ala Ala Ile Thr Glu Thr Pro Asp Thr Ser Thr Leu Leu Ile
                660                  665                  670

Glu Asn Ser Ser Pro Tyr Thr Ser Glu His Phe
    675                  680
```

```
<210> SEQ ID NO 693
<211> LENGTH: 683
<212> TYPE: PRT
<213> ORGANISM: Artificial Sequence
<220> FEATURE:
<223> OTHER INFORMATION: RTase mutant

<400> SEQUENCE: 693

Thr Leu Asn Ile Glu Asp Glu His Arg Leu His Glu Thr Ser Lys Glu
1               5                   10                  15

Pro Asp Val Ser Leu Gly Ser Thr Trp Leu Ser Asp Phe Pro Gln Ala
                20                  25                  30

Trp Ala Glu Thr Gly Gly Met Gly Leu Ala Val Arg Gln Ala Pro Leu
```

-continued

```
                 35                  40                  45
Ile Ile Pro Leu Lys Ala Thr Ser Thr Pro Val Ser Ile Lys Gln Tyr
    50                  55                  60

Pro Met Ser Arg Glu Ala Arg Leu Gly Ile Lys Pro His Ile Arg Arg
65                  70                  75                  80

Leu Arg Asp Gln Gly Ile Leu Val Pro Cys Gln Ser Pro Trp Asn Thr
                85                  90                  95

Pro Leu Arg Pro Val Lys Lys Pro Gly Thr Asn Asp Tyr Arg Pro Val
                100                 105                 110

Gln Asp Leu Arg Glu Val Asn Lys Arg Val Glu Asp Ile His Pro Thr
                115                 120                 125

Val Pro Asn Pro Tyr Asn Leu Leu Ser Gly Leu Pro Pro Ser His Gln
    130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175

Met Gly Ile Ser Gly Gln Leu Thr Trp Thr Arg Leu Pro Gln Gly Phe
                180                 185                 190

Lys Asn Ser Pro Thr Leu Phe Asp Glu Ala Leu His Arg Asp Leu Ala
                195                 200                 205

Asp Phe Arg Ile Gln His Pro Asp Leu Ile Leu Leu Gln Tyr Val Asp
    210                 215                 220

Asp Leu Leu Leu Ala Ala Thr Ser Glu Leu Asp Cys Gln Gln Gly Thr
225                 230                 235                 240

Arg Ala Leu Leu Gln Thr Leu Gly Asn Leu Gly Tyr Arg Ala Ser Ala
                245                 250                 255

Lys Lys Ala Gln Ile Cys Gln Lys Gln Val Lys Tyr Leu Gly Tyr Leu
                260                 265                 270

Leu Lys Glu Gly Gln Arg Trp Leu Thr Asp Ala Arg Lys Glu Thr Val
                275                 280                 285

Met Gly Gln Pro Thr Pro Lys Thr Pro Arg Gln Leu Arg Glu Phe Leu
    290                 295                 300

Gly Thr Ala Gly Phe Cys Arg Leu Trp Ile Pro Gly Phe Ala Glu Met
305                 310                 315                 320

Ala Ala Pro Leu Tyr Pro Leu Thr Lys Thr Gly Thr Leu Phe Asn Trp
                325                 330                 335

Gly Pro Asp Gln Gln Lys Ala Tyr Gln Glu Ile Lys Gln Ala Leu Leu
                340                 345                 350

Thr Ala Pro Ala Leu Gly Leu Pro Asp Leu Thr Lys Pro Phe Glu Leu
                355                 360                 365

Phe Val Asp Glu Lys Gln Gly Tyr Ala Lys Gly Val Leu Thr Gln Lys
    370                 375                 380

Leu Gly Pro Trp Arg Arg Pro Val Ala Tyr Leu Ser Lys Lys Leu Asp
385                 390                 395                 400

Pro Val Ala Ala Gly Trp Pro Pro Cys Leu Arg Met Val Ala Ala Ile
                405                 410                 415

Ala Val Leu Thr Lys Asp Ala Gly Lys Leu Thr Met Gly Gln Pro Leu
                420                 425                 430

Val Ile Leu Ala Pro His Ala Val Glu Ala Leu Val Lys Gln Pro Pro
    435                 440                 445

Asp Arg Trp Leu Ser Asn Ala Arg Met Thr His Tyr Gln Ala Leu Leu
    450                 455                 460
```

-continued

```
Leu Asp Thr Asp Arg Val Gln Phe Gly Pro Val Val Ala Leu Asn Pro
465                 470                 475                 480

Ala Thr Leu Leu Pro Leu Pro Glu Glu Gly Leu Gln His Asn Cys Leu
                485                 490                 495

Asp Ile Leu Ala Glu Ala His Gly Thr Arg Pro Asp Leu Thr Asp Gln
                500                 505                 510

Pro Leu Pro Asp Ala Asp His Thr Trp Tyr Thr Gly Gly Ser Ser Leu
                515                 520                 525

Leu Gln Glu Gly Gln Arg Lys Ala Gly Ala Ala Val Thr Thr Glu Thr
            530                 535                 540

Glu Val Ile Trp Ala Lys Ala Leu Pro Ala Gly Thr Ser Ala Gln Arg
545                 550                 555                 560

Ala Gln Leu Ile Ala Leu Thr Gln Ala Leu Lys Met Ala Glu Gly Lys
                565                 570                 575

Lys Leu Asn Val Tyr Thr Asn Ser Arg Tyr Ala Phe Ala Thr Ala His
                580                 585                 590

Ile His Gly Glu Ile Tyr Arg Arg Arg Gly Leu Leu Thr Ser Glu Gly
            595                 600                 605

Lys Glu Ile Lys Asn Lys Asp Glu Ile Leu Ala Leu Leu Lys Ala Leu
        610                 615                 620

Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asp Gln Ala Ala
                645                 650                 655

Arg Lys Ala Ala Ile Thr Glu Thr Pro Asp Thr Ser Thr Leu Leu Ile
                660                 665                 670

Glu Asn Ser Ser Pro Tyr Thr Ser Glu His Phe
                675                 680
```

```
<210> SEQ ID NO 694
<211> LENGTH: 683
<212> TYPE: PRT
<213> ORGANISM: Artificial Sequence
<220> FEATURE:
<223> OTHER INFORMATION: RTase mutant

<400> SEQUENCE: 694
```

```
Thr Leu Asn Ile Glu Asp Glu His Arg Leu His Glu Thr Ser Lys Glu
1               5                   10                  15

Pro Asp Val Ser Leu Gly Ser Thr Trp Leu Ser Asp Phe Pro Gln Ala
                20                  25                  30

Trp Ala Glu Thr Gly Gly Met Gly Leu Ala Val Arg Gln Ala Pro Leu
            35                  40                  45

Ile Ile Pro Leu Lys Ala Thr Ser Thr Pro Val Ser Ile Lys Gln Tyr
        50                  55                  60

Pro Met Ser Arg Glu Ala Arg Leu Gly Ile Lys Pro His Ile Arg Arg
65                  70                  75                  80

Leu Leu Asp Gln Gly Ile Leu Val Pro Cys Gln Ser Pro Trp Asn Thr
                85                  90                  95

Pro Leu Arg Pro Val Lys Lys Pro Gly Thr Asn Asp Tyr Arg Pro Val
                100                 105                 110

Gln Asp Leu Arg Glu Val Asn Lys Arg Val Glu Asp Ile His Pro Thr
            115                 120                 125

Val Pro Asn Pro Tyr Asn Leu Leu Ser Gly Leu Pro Pro Ser His Gln
        130                 135                 140
```

-continued

```
Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175

Met Gly Ile Ser Gly Gln Leu Thr Trp Thr Arg Leu Pro Gln Gly Phe
                180                 185                 190

Lys Asn Ser Pro Thr Leu Phe Asp Glu Ala Leu His Arg Asp Leu Ala
                195                 200                 205

Asp Phe Arg Ile Gln His Pro Asp Leu Ile Leu Leu Gln Tyr Val Asp
            210                 215                 220

Asp Leu Leu Leu Ala Ala Thr Ser Glu Leu Asp Cys Gln Gln Gly Thr
225                 230                 235                 240

Arg Ala Leu Leu Gln Thr Leu Gly Asn Leu Gly Tyr Arg Ala Ser Ala
                245                 250                 255

Lys Lys Ala Gln Ile Cys Gln Lys Gln Val Lys Tyr Leu Gly Tyr Leu
                260                 265                 270

Leu Lys Glu Gly Gln Arg Trp Leu Thr Asp Ala Arg Lys Glu Thr Val
            275                 280                 285

Met Gly Gln Pro Thr Pro Lys Thr Pro Arg Glu Leu Arg Glu Phe Leu
            290                 295                 300

Gly Thr Ala Gly Phe Cys Arg Leu Trp Ile Pro Gly Phe Ala Glu Met
305                 310                 315                 320

Ala Ala Pro Leu Tyr Pro Leu Thr Lys Thr Gly Thr Leu Phe Asn Trp
                325                 330                 335

Gly Pro Asp Gln Gln Lys Ala Tyr Gln Glu Ile Lys Gln Ala Leu Leu
            340                 345                 350

Thr Ala Pro Ala Leu Gly Leu Pro Asp Leu Thr Lys Pro Phe Glu Leu
            355                 360                 365

Phe Val Asp Glu Lys Gln Gly Tyr Ala Lys Gly Val Leu Thr Gln Lys
            370                 375                 380

Leu Gly Pro Trp Arg Arg Pro Val Ala Tyr Leu Ser Lys Lys Leu Asp
385                 390                 395                 400

Pro Val Ala Ala Gly Trp Pro Pro Cys Leu Arg Met Val Ala Ala Ile
                405                 410                 415

Ala Val Leu Thr Lys Asp Ala Gly Lys Leu Thr Met Gly Gln Pro Leu
                420                 425                 430

Val Ile Leu Ala Pro His Ala Val Glu Ala Leu Val Lys Gln Pro Pro
            435                 440                 445

Asp Arg Trp Leu Ser Asn Ala Arg Met Thr His Tyr Gln Ala Leu Leu
            450                 455                 460

Leu Asp Thr Asp Arg Val Gln Phe Gly Pro Val Val Ala Leu Asn Pro
465                 470                 475                 480

Ala Thr Leu Leu Pro Leu Pro Glu Glu Gly Leu Gln His Asn Cys Leu
                485                 490                 495

Asp Ile Leu Ala Glu Ala His Gly Thr Arg Pro Asp Leu Thr Asp Gln
            500                 505                 510

Pro Leu Pro Asp Ala Asp His Thr Trp Tyr Thr Gly Gly Ser Ser Leu
            515                 520                 525

Leu Gln Glu Gly Gln Arg Lys Ala Gly Ala Ala Val Thr Thr Glu Thr
            530                 535                 540

Glu Val Ile Trp Ala Lys Ala Leu Pro Ala Gly Thr Ser Ala Gln Arg
545                 550                 555                 560
```

-continued

---

Ala Gln Leu Ile Ala Leu Thr Gln Ala Leu Lys Met Ala Glu Gly Lys
                565                 570                 575

Lys Leu Asn Val Tyr Thr Asn Ser Arg Tyr Ala Phe Ala Thr Ala His
            580                 585                 590

Glu His Gly Glu Ile Tyr Arg Arg Gly Leu Leu Thr Ser Glu Gly
            595                 600                 605

Lys Glu Ile Lys Asn Lys Asp Glu Ile Leu Ala Leu Leu Lys Ala Leu
        610                 615                 620

Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asp Gln Ala Ala
                645                 650                 655

Arg Lys Ala Ala Ile Thr Glu Thr Pro Asp Thr Ser Thr Leu Leu Ile
                660                 665                 670

Glu Asn Ser Ser Pro Tyr Thr Ser Glu His Phe
                675                 680

<210> SEQ ID NO 695
<211> LENGTH: 683
<212> TYPE: PRT
<213> ORGANISM: Artificial Sequence
<220> FEATURE:
<223> OTHER INFORMATION: RTase mutant

<400> SEQUENCE: 695

Thr Leu Asn Ile Glu Asp Glu His Arg Leu His Glu Thr Ser Lys Glu
1               5                   10                  15

Pro Asp Val Ser Leu Gly Ser Thr Trp Leu Ser Asp Phe Pro Gln Ala
            20                  25                  30

Trp Ala Glu Thr Gly Gly Met Gly Leu Ala Val Arg Gln Ala Pro Leu
            35                  40                  45

Ile Ile Pro Leu Lys Ala Thr Ser Thr Pro Val Ser Ile Lys Gln Tyr
        50                  55                  60

Pro Met Ser Arg Glu Ala Arg Leu Gly Ile Lys Pro His Ile Arg Arg
65                  70                  75                  80

Leu Arg Asp Gln Gly Ile Leu Val Pro Cys Gln Ser Pro Trp Asn Thr
                85                  90                  95

Pro Leu Arg Pro Val Lys Lys Pro Gly Thr Asn Asp Tyr Arg Pro Val
            100                 105                 110

Gln Asp Leu Arg Glu Val Asn Lys Arg Val Glu Asp Ile His Pro Thr
            115                 120                 125

Val Pro Asn Pro Tyr Asn Leu Leu Ser Gly Leu Pro Pro Ser His Gln
        130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175

Met Gly Ile Ser Gly Gln Leu Thr Trp Thr Arg Leu Pro Gln Gly Phe
            180                 185                 190

Lys Asn Ser Pro Thr Leu Phe Asp Glu Ala Leu His Arg Asp Leu Ala
            195                 200                 205

Asp Phe Arg Ile Gln His Pro Asp Leu Ile Leu Leu Gln Tyr Val Asp
        210                 215                 220

Asp Leu Leu Leu Ala Ala Thr Ser Glu Leu Asp Cys Gln Gln Gly Thr
225                 230                 235                 240

-continued

```
Arg Ala Leu Leu Gln Thr Leu Gly Asn Leu Gly Tyr Arg Ala Ser Ala
            245             250             255

Lys Lys Ala Gln Ile Cys Gln Lys Gln Val Lys Tyr Leu Gly Tyr Leu
            260             265             270

Leu Lys Glu Gly Gln Arg Trp Leu Thr Asp Ala Arg Lys Glu Thr Val
            275             280             285

Met Gly Gln Pro Thr Pro Lys Thr Pro Arg Glu Leu Arg Glu Phe Leu
    290             295             300

Gly Thr Ala Gly Phe Cys Arg Leu Trp Ile Pro Gly Phe Ala Glu Met
305             310             315             320

Ala Ala Pro Leu Tyr Pro Leu Thr Lys Thr Gly Thr Leu Phe Asn Trp
            325             330             335

Gly Pro Asp Gln Gln Lys Ala Tyr Gln Glu Ile Lys Gln Ala Leu Leu
            340             345             350

Thr Ala Pro Ala Leu Gly Leu Pro Asp Leu Thr Lys Pro Phe Glu Leu
            355             360             365

Phe Val Asp Glu Lys Gln Gly Tyr Ala Lys Gly Val Leu Thr Gln Lys
    370             375             380

Leu Gly Pro Trp Arg Arg Pro Val Ala Tyr Leu Ser Lys Lys Leu Asp
385             390             395             400

Pro Val Ala Ala Gly Trp Pro Pro Cys Leu Arg Met Val Ala Ala Ile
            405             410             415

Ala Val Leu Thr Lys Asp Ala Gly Lys Leu Thr Met Gly Gln Pro Leu
            420             425             430

Val Ile Leu Ala Pro His Ala Val Glu Ala Leu Val Lys Gln Pro Pro
            435             440             445

Asp Arg Trp Leu Ser Asn Ala Arg Met Thr His Tyr Gln Ala Leu Leu
    450             455             460

Leu Asp Thr Asp Arg Val Gln Phe Gly Pro Val Val Ala Leu Asn Pro
465             470             475             480

Ala Thr Leu Leu Pro Leu Pro Glu Glu Gly Leu Gln His Asn Cys Leu
            485             490             495

Asp Ile Leu Ala Glu Ala His Gly Thr Arg Pro Asp Leu Thr Asp Gln
            500             505             510

Pro Leu Pro Asp Ala Asp His Thr Trp Tyr Thr Gly Gly Ser Ser Leu
            515             520             525

Leu Gln Glu Gly Gln Arg Lys Ala Gly Ala Ala Val Thr Thr Glu Thr
    530             535             540

Glu Val Ile Trp Ala Lys Ala Leu Pro Ala Gly Thr Ser Ala Gln Arg
545             550             555             560

Ala Gln Leu Ile Ala Leu Thr Gln Ala Leu Lys Met Ala Glu Gly Lys
            565             570             575

Lys Leu Asn Val Tyr Thr Asn Ser Arg Tyr Ala Phe Ala Thr Ala His
            580             585             590

Glu His Gly Glu Ile Tyr Arg Arg Arg Gly Leu Leu Thr Ser Glu Gly
            595             600             605

Lys Glu Ile Lys Asn Lys Asp Glu Ile Leu Ala Leu Leu Lys Ala Leu
            610             615             620

Phe Leu Pro Lys Arg Leu Ser Ile Ile His Cys Pro Gly His Gln Lys
625             630             635             640

Gly His Ser Ala Glu Ala Arg Gly Asn Arg Met Ala Asp Gln Ala Ala
            645             650             655

Arg Lys Ala Ala Ile Thr Glu Thr Pro Asp Thr Ser Thr Leu Leu Ile
```

```
                660              665              670
Glu Asn Ser Ser Pro Tyr Thr Ser Glu His Phe
        675              680

<210> SEQ ID NO 696
<211> LENGTH: 683
<212> TYPE: PRT
<213> ORGANISM: Artificial Sequence
<220> FEATURE:
<223> OTHER INFORMATION: RTase mutant

<400> SEQUENCE: 696

Thr Leu Asn Ile Glu Asp Glu His Arg Leu His Glu Thr Ser Lys Glu
1               5                   10                  15

Pro Asp Val Ser Leu Gly Ser Thr Trp Leu Ser Asp Phe Pro Gln Ala
            20                  25                  30

Trp Ala Glu Thr Gly Gly Met Gly Leu Ala Val Arg Gln Ala Pro Leu
        35                  40                  45

Ile Ile Pro Leu Lys Ala Thr Ser Thr Pro Val Ser Ile Lys Gln Tyr
    50                  55                  60

Pro Met Ser Arg Glu Ala Arg Leu Gly Ile Lys Pro His Ile Arg Arg
65                  70                  75                  80

Leu Leu Asp Gln Gly Ile Leu Val Pro Cys Gln Ser Pro Trp Asn Thr
                85                  90                  95

Pro Leu Arg Pro Val Lys Lys Pro Gly Thr Asn Asp Tyr Arg Pro Val
            100                 105                 110

Gln Asp Leu Arg Glu Val Asn Lys Arg Val Glu Asp Ile His Pro Thr
        115                 120                 125

Val Pro Asn Pro Tyr Asn Leu Leu Ser Gly Leu Pro Pro Ser His Gln
    130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175

Met Gly Ile Ser Gly Gln Leu Thr Trp Thr Arg Leu Pro Gln Gly Phe
            180                 185                 190

Lys Asn Ser Pro Thr Leu Phe Asp Glu Ala Leu His Arg Asp Leu Ala
        195                 200                 205

Asp Phe Arg Ile Gln His Pro Asp Leu Ile Leu Leu Gln Tyr Val Asp
    210                 215                 220

Asp Leu Leu Leu Ala Ala Thr Ser Glu Leu Asp Cys Gln Gln Gly Thr
225                 230                 235                 240

Arg Ala Leu Leu Gln Thr Leu Gly Asn Leu Gly Tyr Arg Ala Ser Ala
                245                 250                 255

Lys Lys Ala Gln Ile Cys Gln Lys Gln Val Lys Tyr Leu Gly Tyr Leu
            260                 265                 270

Leu Lys Glu Gly Gln Arg Trp Leu Thr Asp Ala Arg Lys Glu Thr Val
        275                 280                 285

Met Gly Gln Pro Thr Pro Lys Thr Pro Arg Glu Leu Arg Glu Phe Leu
    290                 295                 300

Gly Thr Ala Gly Phe Cys Arg Leu Trp Ile Pro Gly Phe Ala Glu Met
305                 310                 315                 320

Ala Ala Pro Leu Tyr Pro Leu Thr Lys Thr Gly Thr Leu Phe Asn Trp
                325                 330                 335

Gly Pro Asp Gln Gln Lys Ala Tyr Gln Glu Ile Lys Gln Ala Leu Leu
```

-continued

```
                340               345               350

Thr Ala Pro Ala Leu Gly Leu Pro Asp Leu Thr Lys Pro Phe Glu Leu
            355               360               365

Phe Val Asp Glu Lys Gln Gly Tyr Ala Lys Gly Val Leu Thr Gln Lys
            370               375               380

Leu Gly Pro Trp Arg Arg Pro Val Ala Tyr Leu Ser Lys Lys Leu Asp
385               390               395               400

Pro Val Ala Ala Gly Trp Pro Pro Cys Leu Arg Met Val Ala Ala Ile
                405               410               415

Ala Val Leu Thr Lys Asp Ala Gly Lys Leu Thr Met Gly Gln Pro Leu
            420               425               430

Arg Ile Leu Ala Pro His Ala Val Glu Ala Leu Val Lys Gln Pro Pro
            435               440               445

Asp Arg Trp Leu Ser Asn Ala Arg Met Thr His Tyr Gln Ala Leu Leu
            450               455               460

Leu Asp Thr Asp Arg Val Gln Phe Gly Pro Val Val Ala Leu Asn Pro
465               470               475               480

Ala Thr Leu Leu Pro Leu Pro Glu Glu Gly Leu Gln His Asn Cys Leu
                485               490               495

Asp Ile Leu Ala Glu Ala His Gly Thr Arg Pro Asp Leu Thr Asp Gln
            500               505               510

Pro Leu Pro Asp Ala Asp His Thr Trp Tyr Thr Gly Gly Ser Ser Leu
            515               520               525

Leu Gln Glu Gly Gln Arg Lys Ala Gly Ala Ala Val Thr Thr Glu Thr
            530               535               540

Glu Val Ile Trp Ala Lys Ala Leu Pro Ala Gly Thr Ser Ala Gln Arg
545               550               555               560

Ala Gln Leu Ile Ala Leu Thr Gln Ala Leu Lys Met Ala Glu Gly Lys
                565               570               575

Lys Leu Asn Val Tyr Thr Asn Ser Arg Tyr Ala Phe Ala Thr Ala His
            580               585               590

Glu His Gly Glu Ile Tyr Arg Arg Arg Gly Leu Leu Thr Ser Glu Gly
            595               600               605

Lys Glu Ile Lys Asn Lys Asp Glu Ile Leu Ala Leu Leu Lys Ala Leu
            610               615               620

Phe Leu Pro Lys Arg Leu Ser Ile Ile His Cys Pro Gly His Gln Lys
625               630               635               640

Gly His Ser Ala Glu Ala Arg Gly Asn Arg Met Ala Asp Gln Ala Ala
                645               650               655

Arg Lys Ala Ala Ile Thr Glu Thr Pro Asp Thr Ser Thr Leu Leu Ile
            660               665               670

Glu Asn Ser Ser Pro Tyr Thr Ser Glu His Phe
            675               680
```

```
<210> SEQ ID NO 697
<211> LENGTH: 683
<212> TYPE: PRT
<213> ORGANISM: Artificial Sequence
<220> FEATURE:
<223> OTHER INFORMATION: RTase mutant

<400> SEQUENCE: 697

Thr Leu Asn Ile Glu Asp Glu His Arg Leu His Glu Thr Ser Lys Glu
1               5               10               15

Pro Asp Val Ser Leu Gly Ser Thr Trp Leu Ser Asp Phe Pro Gln Ala
```

-continued

```
                20              25              30
Trp Ala Glu Thr Gly Gly Met Gly Leu Ala Val Arg Gln Ala Pro Leu
            35              40              45
Ile Ile Pro Leu Lys Ala Thr Ser Thr Pro Val Ser Ile Lys Gln Tyr
        50              55              60
Pro Met Ser Arg Glu Ala Arg Leu Gly Ile Lys Pro His Ile Arg Arg
65              70              75              80
Leu Arg Asp Gln Gly Ile Leu Val Pro Cys Gln Ser Pro Trp Asn Thr
            85              90              95
Pro Leu Arg Pro Val Lys Lys Pro Gly Thr Asn Asp Tyr Arg Pro Val
            100             105             110
Gln Asp Leu Arg Glu Val Asn Lys Arg Val Glu Asp Ile His Pro Thr
        115             120             125
Val Pro Asn Pro Tyr Asn Leu Leu Ser Gly Leu Pro Pro Ser His Gln
        130             135             140
Trp Tyr Thr Val Leu Asp Leu Lys Asp Ala Phe Phe Cys Leu Arg Leu
145             150             155             160
His Pro Thr Ser Gln Pro Leu Phe Ala Phe Glu Trp Arg Asp Pro Glu
            165             170             175
Met Gly Ile Ser Gly Gln Leu Thr Trp Thr Arg Leu Pro Gln Gly Phe
            180             185             190
Lys Asn Ser Pro Thr Leu Phe Asp Glu Ala Leu His Arg Asp Leu Ala
            195             200             205
Asp Phe Arg Ile Gln His Pro Asp Leu Ile Leu Leu Gln Tyr Val Asp
        210             215             220
Asp Leu Leu Leu Ala Ala Thr Ser Glu Leu Asp Cys Gln Gln Gly Thr
225             230             235             240
Arg Ala Leu Leu Gln Thr Leu Gly Asn Leu Gly Tyr Arg Ala Ser Ala
            245             250             255
Lys Lys Ala Gln Ile Cys Gln Lys Gln Val Lys Tyr Leu Gly Tyr Leu
            260             265             270
Leu Lys Glu Gly Gln Arg Trp Leu Thr Asp Ala Arg Lys Glu Thr Val
        275             280             285
Met Gly Gln Pro Thr Pro Lys Thr Pro Arg Glu Leu Arg Glu Phe Leu
    290             295             300
Gly Thr Ala Gly Phe Cys Arg Leu Trp Ile Pro Gly Phe Ala Glu Met
305             310             315             320
Ala Ala Pro Leu Tyr Pro Leu Thr Lys Thr Gly Thr Leu Phe Asn Trp
            325             330             335
Gly Pro Asp Gln Gln Lys Ala Tyr Gln Glu Ile Lys Gln Ala Leu Leu
        340             345             350
Thr Ala Pro Ala Leu Gly Leu Pro Asp Leu Thr Lys Pro Phe Glu Leu
        355             360             365
Phe Val Asp Glu Lys Gln Gly Tyr Ala Lys Gly Val Leu Thr Gln Lys
    370             375             380
Leu Gly Pro Trp Arg Arg Pro Val Ala Tyr Leu Ser Lys Lys Leu Asp
385             390             395             400
Pro Val Ala Ala Gly Trp Pro Pro Cys Leu Arg Met Val Ala Ala Ile
            405             410             415
Ala Val Leu Thr Lys Asp Ala Gly Lys Leu Thr Met Gly Gln Pro Leu
        420             425             430
Arg Ile Leu Ala Pro His Ala Val Glu Ala Leu Val Lys Gln Pro Pro
        435             440             445
```

-continued

```
Asp Arg Trp Leu Ser Asn Ala Arg Met Thr His Tyr Gln Ala Leu Leu
    450                 455                 460

Leu Asp Thr Asp Arg Val Gln Phe Gly Pro Val Val Ala Leu Asn Pro
465                 470                 475                 480

Ala Thr Leu Leu Pro Leu Pro Glu Glu Gly Leu Gln His Asn Cys Leu
                485                 490                 495

Asp Ile Leu Ala Glu Ala His Gly Thr Arg Pro Asp Leu Thr Asp Gln
                500                 505                 510

Pro Leu Pro Asp Ala Asp His Thr Trp Tyr Thr Gly Gly Ser Ser Leu
                515                 520                 525

Leu Gln Glu Gly Gln Arg Lys Ala Gly Ala Ala Val Thr Thr Glu Thr
    530                 535                 540

Glu Val Ile Trp Ala Lys Ala Leu Pro Ala Gly Thr Ser Ala Gln Arg
545                 550                 555                 560

Ala Gln Leu Ile Ala Leu Thr Gln Ala Leu Lys Met Ala Glu Gly Lys
                565                 570                 575

Lys Leu Asn Val Tyr Thr Asn Ser Arg Tyr Ala Phe Ala Thr Ala His
                580                 585                 590

Glu His Gly Glu Ile Tyr Arg Arg Arg Gly Leu Leu Thr Ser Glu Gly
                595                 600                 605

Lys Glu Ile Lys Asn Lys Asp Glu Ile Leu Ala Leu Leu Lys Ala Leu
    610                 615                 620

Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asp Gln Ala Ala
                645                 650                 655

Arg Lys Ala Ala Ile Thr Glu Thr Pro Asp Thr Ser Thr Leu Leu Ile
                660                 665                 670

Glu Asn Ser Ser Pro Tyr Thr Ser Glu His Phe
            675                 680
```

```
<210> SEQ ID NO 698
<211> LENGTH: 683
<212> TYPE: PRT
<213> ORGANISM: Artificial Sequence
<220> FEATURE:
<223> OTHER INFORMATION: RTase mutant

<400> SEQUENCE: 698

Thr Leu Asn Ile Glu Asp Glu His Arg Leu His Glu Thr Ser Lys Glu
1               5                   10                  15

Pro Asp Val Ser Leu Gly Ser Thr Trp Leu Ser Asp Phe Pro Gln Ala
                20                  25                  30

Trp Ala Glu Thr Gly Gly Met Gly Leu Ala Val Arg Gln Ala Pro Leu
            35                  40                  45

Ile Ile Pro Leu Lys Ala Thr Ser Thr Pro Val Ser Ile Lys Gln Tyr
    50                  55                  60

Pro Met Ser Arg Glu Ala Arg Leu Gly Ile Lys Pro His Ile Arg Arg
65                  70                  75                  80

Leu Arg Asp Gln Gly Ile Leu Val Pro Cys Gln Ser Pro Trp Asn Thr
                85                  90                  95

Pro Leu Arg Pro Val Lys Lys Pro Gly Thr Asn Asp Tyr Arg Pro Val
            100                 105                 110

Gln Asp Leu Arg Glu Val Asn Lys Arg Val Glu Asp Ile His Pro Thr
    115                 120                 125
```

-continued

```
Val Pro Asn Pro Tyr Asn Leu Leu Ser Gly Leu Pro Pro Ser His Gln
    130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175

Met Gly Ile Ser Gly Gln Leu Thr Trp Thr Arg Leu Pro Gln Gly Phe
                180                 185                 190

Lys Asn Ser Pro Thr Leu Phe Asp Glu Ala Leu His Arg Asp Leu Ala
                195                 200                 205

Asp Phe Arg Ile Gln His Pro Asp Leu Ile Leu Leu Gln Tyr Val Asp
    210                 215                 220

Asp Leu Leu Leu Ala Ala Thr Ser Glu Leu Asp Cys Gln Gln Gly Thr
225                 230                 235                 240

Arg Ala Leu Leu Gln Thr Leu Gly Asn Leu Gly Tyr Arg Ala Ser Ala
                245                 250                 255

Lys Lys Ala Gln Ile Cys Gln Lys Gln Val Lys Tyr Leu Gly Tyr Leu
                260                 265                 270

Leu Lys Glu Gly Gln Arg Trp Leu Thr Asp Ala Arg Lys Glu Thr Val
                275                 280                 285

Met Gly Gln Pro Thr Pro Lys Thr Pro Arg Glu Leu Arg Glu Phe Leu
    290                 295                 300

Gly Thr Ala Gly Phe Cys Arg Leu Trp Ile Pro Gly Phe Ala Glu Met
305                 310                 315                 320

Ala Ala Pro Leu Tyr Pro Leu Thr Lys Thr Gly Glu Leu Phe Asn Trp
                325                 330                 335

Gly Pro Asp Gln Gln Lys Ala Tyr Gln Glu Ile Lys Gln Ala Leu Leu
                340                 345                 350

Thr Ala Pro Ala Leu Gly Leu Pro Asp Leu Thr Lys Pro Phe Glu Leu
                355                 360                 365

Phe Val Asp Glu Lys Gln Gly Tyr Ala Lys Gly Val Leu Thr Gln Lys
    370                 375                 380

Leu Gly Pro Trp Arg Arg Pro Val Ala Tyr Leu Ser Lys Lys Leu Asp
385                 390                 395                 400

Pro Val Ala Ala Gly Trp Pro Pro Cys Leu Arg Met Val Ala Ala Ile
                405                 410                 415

Ala Val Leu Thr Lys Asp Ala Gly Lys Leu Thr Met Gly Gln Pro Leu
                420                 425                 430

Val Ile Leu Ala Pro His Ala Val Glu Ala Leu Val Lys Gln Pro Pro
    435                 440                 445

Asp Arg Trp Leu Ser Asn Ala Arg Met Thr His Tyr Gln Ala Leu Leu
    450                 455                 460

Leu Asp Thr Asp Arg Val Gln Phe Gly Pro Val Val Ala Leu Asn Pro
465                 470                 475                 480

Ala Thr Leu Leu Pro Leu Pro Glu Glu Gly Leu Gln His Asn Cys Leu
                485                 490                 495

Asp Ile Leu Ala Glu Ala His Gly Thr Arg Pro Asp Leu Thr Asp Gln
                500                 505                 510

Pro Leu Pro Asp Ala Asp His Thr Trp Tyr Thr Gly Gly Ser Ser Leu
                515                 520                 525

Leu Gln Glu Gly Gln Arg Lys Ala Gly Ala Ala Val Thr Thr Glu Thr
    530                 535                 540
```

-continued

Glu Val Ile Trp Ala Lys Ala Leu Pro Ala Gly Thr Ser Ala Gln Arg
545                 550                 555                 560

Ala Gln Leu Ile Ala Leu Thr Gln Ala Leu Lys Met Ala Glu Gly Lys
                565                 570                 575

Lys Leu Asn Val Tyr Thr Asn Ser Arg Tyr Ala Phe Ala Thr Ala His
                580                 585                 590

Glu His Gly Glu Ile Tyr Arg Arg Gly Leu Leu Thr Ser Glu Gly
            595                 600                 605

Lys Glu Ile Lys Asn Lys Asp Glu Ile Leu Ala Leu Leu Lys Ala Leu
            610                 615                 620

Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asp Gln Ala Ala
                645                 650                 655

Arg Lys Ala Ala Ile Thr Glu Thr Pro Asp Thr Ser Thr Leu Leu Ile
                660                 665                 670

Glu Asn Ser Ser Pro Tyr Thr Ser Glu His Phe
            675                 680

<210> SEQ ID NO 699
<211> LENGTH: 683
<212> TYPE: PRT
<213> ORGANISM: Artificial Sequence
<220> FEATURE:
<223> OTHER INFORMATION: RTase mutant

<400> SEQUENCE: 699

Thr Leu Asn Ile Glu Asp Glu His Arg Leu His Glu Thr Ser Lys Glu
1                   5                   10                  15

Pro Asp Val Ser Leu Gly Ser Thr Trp Leu Ser Asp Phe Pro Gln Ala
                20                  25                  30

Trp Ala Glu Thr Gly Gly Met Gly Leu Ala Val Arg Gln Ala Pro Leu
            35                  40                  45

Ile Ile Pro Leu Lys Ala Thr Ser Thr Pro Val Ser Ile Lys Gln Tyr
        50                  55                  60

Pro Met Ser Arg Glu Ala Arg Leu Gly Ile Lys Pro His Ile Arg Arg
65                  70                  75                  80

Leu Arg Asp Gln Gly Ile Leu Val Pro Cys Gln Ser Pro Trp Asn Thr
                85                  90                  95

Pro Leu Arg Pro Val Lys Lys Pro Gly Thr Asn Asp Tyr Arg Pro Val
                100                 105                 110

Gln Asp Leu Arg Glu Val Asn Lys Arg Val Glu Asp Ile His Pro Thr
            115                 120                 125

Val Pro Asn Pro Tyr Asn Leu Leu Ser Gly Leu Pro Pro Ser His Gln
        130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175

Met Gly Ile Ser Gly Gln Leu Thr Trp Thr Arg Leu Pro Gln Gly Phe
                180                 185                 190

Lys Asn Ser Pro Thr Leu Phe Asp Glu Ala Leu His Arg Asp Leu Ala
            195                 200                 205

Asp Phe Arg Ile Gln His Pro Asp Leu Ile Leu Leu Gln Tyr Val Asp
        210                 215                 220

-continued

Asp Leu Leu Leu Ala Ala Thr Ser Glu Leu Asp Cys Gln Gln Gly Thr
225                 230                 235                 240

Arg Ala Leu Leu Gln Thr Leu Gly Asn Leu Gly Tyr Arg Ala Ser Ala
                245                 250                 255

Lys Lys Ala Gln Ile Cys Gln Lys Gln Val Lys Tyr Leu Gly Tyr Leu
                260                 265                 270

Leu Lys Glu Gly Gln Arg Trp Leu Thr Asp Ala Arg Lys Glu Thr Val
                275                 280                 285

Met Gly Gln Pro Thr Pro Lys Thr Pro Arg Glu Leu Arg Glu Phe Leu
290                 295                 300

Gly Thr Ala Gly Phe Cys Arg Leu Trp Ile Pro Gly Phe Ala Glu Met
305                 310                 315                 320

Ala Ala Pro Leu Tyr Pro Leu Thr Lys Thr Gly Glu Leu Phe Asn Trp
                325                 330                 335

Gly Pro Asp Gln Gln Lys Ala Tyr Gln Glu Ile Lys Gln Ala Leu Leu
                340                 345                 350

Thr Ala Pro Ala Leu Gly Leu Pro Asp Leu Thr Lys Pro Phe Glu Leu
                355                 360                 365

Phe Val Asp Glu Lys Gln Gly Tyr Ala Lys Gly Val Leu Thr Gln Lys
370                 375                 380

Leu Gly Pro Trp Arg Arg Pro Val Ala Tyr Leu Ser Lys Lys Leu Asp
385                 390                 395                 400

Pro Val Ala Ala Gly Trp Pro Pro Cys Leu Arg Met Val Ala Ala Ile
                405                 410                 415

Ala Val Leu Thr Lys Asp Ala Gly Lys Leu Thr Met Gly Gln Pro Leu
                420                 425                 430

Arg Ile Leu Ala Pro His Ala Val Glu Ala Leu Val Lys Gln Pro Pro
                435                 440                 445

Asp Arg Trp Leu Ser Asn Ala Arg Met Thr His Tyr Gln Ala Leu Leu
                450                 455                 460

Leu Asp Thr Asp Arg Val Gln Phe Gly Pro Val Val Ala Leu Asn Pro
465                 470                 475                 480

Ala Thr Leu Leu Pro Leu Pro Glu Glu Gly Leu Gln His Asn Cys Leu
                485                 490                 495

Asp Ile Leu Ala Glu Ala His Gly Thr Arg Pro Asp Leu Thr Asp Gln
                500                 505                 510

Pro Leu Pro Asp Ala Asp His Thr Trp Tyr Thr Gly Gly Ser Ser Leu
                515                 520                 525

Leu Gln Glu Gly Gln Arg Lys Ala Gly Ala Ala Val Thr Thr Glu Thr
                530                 535                 540

Glu Val Ile Trp Ala Lys Ala Leu Pro Ala Gly Thr Ser Ala Gln Arg
545                 550                 555                 560

Ala Gln Leu Ile Ala Leu Thr Gln Ala Leu Lys Met Ala Glu Gly Lys
                565                 570                 575

Lys Leu Asn Val Tyr Thr Asn Ser Arg Tyr Ala Phe Ala Thr Ala His
                580                 585                 590

Glu His Gly Glu Ile Tyr Arg Arg Arg Gly Leu Leu Thr Ser Glu Gly
                595                 600                 605

Lys Glu Ile Lys Asn Lys Asp Glu Ile Leu Ala Leu Leu Lys Ala Leu
                610                 615                 620

Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asp Gln Ala Ala

-continued

```
                  645               650               655
Arg Lys Ala Ala Ile Thr Glu Thr Pro Asp Thr Ser Thr Leu Leu Ile
          660               665               670

Glu Asn Ser Ser Pro Tyr Thr Ser Glu His Phe
        675               680
```

```
<210> SEQ ID NO 700
<211> LENGTH: 49
<212> TYPE: DNA
<213> ORGANISM: Artificial Sequence
<220> FEATURE:
<223> OTHER INFORMATION: Synthetic Oligonucleotide

<400> SEQUENCE: 700
agttgacgat gggtcaaccc ttacgtatct tggctccaca tgctgtaga                49

<210> SEQ ID NO 701
<211> LENGTH: 49
<212> TYPE: DNA
<213> ORGANISM: Artificial Sequence
<220> FEATURE:
<223> OTHER INFORMATION: Synthetic Oligonucleotide

<400> SEQUENCE: 701
tctacagcat gtggagccaa gatacgtaag ggttgaccca tcgtcaact                49

<210> SEQ ID NO 702
<211> LENGTH: 48
<212> TYPE: DNA
<213> ORGANISM: Artificial Sequence
<220> FEATURE:
<223> OTHER INFORMATION: Synthetic Oligonucleotide

<400> SEQUENCE: 702
cgttatgctt ttgcaacagc gcatgagcat ggcgaaattt accgccgc                 48

<210> SEQ ID NO 703
<211> LENGTH: 48
<212> TYPE: DNA
<213> ORGANISM: Artificial Sequence
<220> FEATURE:
<223> OTHER INFORMATION: Synthetic Oligonucleotide

<400> SEQUENCE: 703
gcggcggtaa atttcgccat gctcatgcgc tgttgcaaaa gcataacg                 48

<210> SEQ ID NO 704
<211> LENGTH: 45
<212> TYPE: DNA
<213> ORGANISM: Artificial Sequence
<220> FEATURE:
<223> OTHER INFORMATION: Synthetic Oligonucleotide

<400> SEQUENCE: 704
tacgcctaag acgccacgcg agttgcgtga atttttgggc acagc                    45

<210> SEQ ID NO 705
<211> LENGTH: 45
<212> TYPE: DNA
<213> ORGANISM: Artificial Sequence
<220> FEATURE:
<223> OTHER INFORMATION: Synthetic Oligonucleotide

<400> SEQUENCE: 705
gctgtgccca aaaattcacg caactcgcgt ggcgtcttag gcgta                    45
```

-continued

```
<210> SEQ ID NO 706
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 706
gattaagcca catattcagc gcttgtatga ccaggggatc ttggtcc                47

<210> SEQ ID NO 707
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 707
ggaccaagat cccctggtca tacaagcgct gaatatgtgg cttaatc                47

<210> SEQ ID NO 708
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 708
tgctgaaaga aggtcaacgt tggatcactg aagcgcgtaa ggagacc                47

<210> SEQ ID NO 709
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 709
ggtctcctta cgcgcttcag tgatccaacg ttgaccttct ttcagca                47

<210> SEQ ID NO 710
<211> LENGTH: 49
<212> TYPE: DNA
<213> ORGANISM: Artificial Sequence
<220> FEATURE:
<223> OTHER INFORMATION: Synthetic Oligonucleotide

<400> SEQUENCE: 710
agttgacgat gggtcaaccc ttaaacatct tggctccaca tgctgtaga             49

<210> SEQ ID NO 711
<211> LENGTH: 49
<212> TYPE: DNA
<213> ORGANISM: Artificial Sequence
<220> FEATURE:
<223> OTHER INFORMATION: Synthetic Oligonucleotide

<400> SEQUENCE: 711
tctacagcat gtggagccaa gatgtttaag ggttgaccca tcgtcaact             49

<210> SEQ ID NO 712
<211> LENGTH: 48
<212> TYPE: DNA
<213> ORGANISM: Artificial Sequence
<220> FEATURE:
```

<223> OTHER INFORMATION: Synthetic Oligonucleotide

<400> SEQUENCE: 712
cgttatgctt ttgcaacagc gcattggcat ggcgaaattt accgccgc          48

<210> SEQ ID NO 713
<211> LENGTH: 48
<212> TYPE: DNA
<213> ORGANISM: Artificial Sequence
<220> FEATURE:
<223> OTHER INFORMATION: Synthetic Oligonucleotide

<400> SEQUENCE: 713
gcggcggtaa atttcgccat gccaatgcgc tgttgcaaaa gcataacg          48

<210> SEQ ID NO 714
<211> LENGTH: 52
<212> TYPE: DNA
<213> ORGANISM: Artificial Sequence
<220> FEATURE:
<223> OTHER INFORMATION: Synthetic Oligonucleotide

<400> SEQUENCE: 714
gccagttgcg tgaatttttg ggcaaagcgg gattctgtcg tttatggatt cc          52

<210> SEQ ID NO 715
<211> LENGTH: 52
<212> TYPE: DNA
<213> ORGANISM: Artificial Sequence
<220> FEATURE:
<223> OTHER INFORMATION: Synthetic Oligonucleotide

<400> SEQUENCE: 715
ggaatccata aacgacagaa tcccgctttg cccaaaaatt cacgcaactg gc          52

<210> SEQ ID NO 716
<211> LENGTH: 2055
<212> TYPE: DNA
<213> ORGANISM: Artificial Sequence
<220> FEATURE:
<223> OTHER INFORMATION: Synthetic Oligonucleotide

<400> SEQUENCE: 716
atgactttaa atattgagga tgagcatcgt ttacatgaga catcaaaaga acccgacgtg          60
agcttagggt caacgtggct ttctgacttc ccccaggcgt gggcggagac tggcggaatg          120
gggttagctg tccgccaagc accgttgatc atcccgttaa aggcaacgtc tacacctgtc          180
tctatcaaac agtaccccat gagtcaagag gcccgcctgg ggattaagcc acatattcag          240
cgcttgctgg accaggggat cttggtccca tgtcaatctc cgtggaacac ccccttctg          300 cccgtgaaaa agccaggtac aaacgattat cgtccagttc aagatcttcg cgaggtcaac          360
aaacgcgtag aagacatcca tccgactgta cctaatcctt ataatctgtt atcaggcctg          420
cccccatcgc accaatggta tacagtatta gacttgaaag acgcgttctt ttgcctgcgt          480
ctgcacccaa cgtctcagcc gctgtttgcg ttcgaatggc gtgatcctga aatgggaatt          540
tcgggtcagt taacctggac tcgtctgccc cagggcttta aaaacagccc cacattgttc          600
gatgaagcac ttcaccgtga cttagcagac ttccgtatcc aacacccaga cttaattctg          660
ttacagtatg ttgacgacct tttgttggcg gcaacgtctg aacttgactg tcagcaaggc          720
acacgcgcgt tattacaaac gttaggtaac ttaggatatc gtgcgtccgc gaaaaaggcg          780
caaatttgtc aaaaacaggt aaagtacctt gggtatttgc tgaaagaagg tcaacgttgg          840

```
ctgactgaag cgcgtaagga gaccgtaatg gggcagccta cgcctaagac gccacgccag    900
ttgcgtgaat ttttgggcac agcgggattc tgtcgtttat ggattcctgg gttcgctgaa    960
atggctgcac ccctgtaccc cttaacaaaa acagggacgc ttttcaactg ggggccagac   1020
cagcaaaagg cgtatcagga gatcaaacaa gctttgttga ccgcacccgc gttgggtctt   1080
ccggatttaa ccaagccctt tgagctgttc gttgatgaaa aacagggata tgcaaaagga   1140
gtattaaccc aaaagttagg cccgtggcgt cgccctgttg cttacttgag taaaaaattg   1200
gatcctgtcg cagcaggatg gccaccgtgc ttgcgtatgg tcgcggcaat tgccgttttg   1260
acaaaggatg caggtaagtt gacgatgggt caacccttag taatcttggc tccacatgct   1320
gtagaagcgt tagtaaagca gcccccagac cgctggcttt ctaatgcgcg catgacccac   1380
tatcaggcgc ttctgcttga tacggatcgt gtacaatttg gaccagttgt agctttgaat   1440
ccagctactt tgcttcccct tccagaagaa ggacttcagc acaattgttt agatattctg   1500
gccgaggcac atgggacgcg ccctgatttg acggatcagc cactgcctga tgccgaccat   1560
acatggtata ctggcggcag tagtcttctt caagaggggc aacgcaaggc gggagcagcc   1620
gtcactacgg agaccgaagt tatctgggcc aaagcgttac ccgcgggaac atccgcgcaa   1680
cgtgcacagt taatcgctct gacacaggcc ctgaagatgg cagagggcaa aaagttgaat   1740
gtctacacca actcacgtta tgcttttgca acagcgcata tccatggcga aatttaccgc   1800
cgccgtggtc tgctgactag tgagggtaag gaaattaaaa ataaagatga gattcttgcg   1860
ttgttaaaag ctttattctt accaaaacgc ctttcgatca ttcattgccc ggggcatcaa   1920
aagggtcact cagcggaggc tcgtggaaac cgtatggcgg accaagctgc ccgtaaggcg   1980
gcgatcacag agaccccgga tacatcaacg ctgttgatcg aaaacagctc tccctacact   2040
agcgagcatt tttaa                                                     2055
```

```
<210> SEQ ID NO 717
<211> LENGTH: 684
<212> TYPE: PRT
<213> ORGANISM: Artificial Sequence
<220> FEATURE:
<223> OTHER INFORMATION: Synthetic Peptide

<400> SEQUENCE: 717

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140
```

-continued

```
Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
                180                 185                 190

Phe Lys Asn Ser Pro Thr Leu Phe Asp Glu Ala Leu His Arg Asp Leu
                195                 200                 205

Ala Asp Phe Arg Ile Gln His Pro Asp Leu Ile Leu Leu Gln Tyr Val
            210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
                260                 265                 270

Leu Leu Lys Glu Gly Gln Arg Trp Leu Thr Glu Ala Arg Lys Glu Thr
                275                 280                 285

Val Met Gly Gln Pro Thr Pro Lys Thr Pro Arg Gln Leu Arg Glu Phe
            290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
                340                 345                 350

Leu Thr Ala Pro Ala Leu Gly Leu Pro Asp Leu Thr Lys Pro Phe Glu
                355                 360                 365

Leu Phe Val Asp Glu Lys Gln Gly Tyr Ala Lys Gly Val Leu Thr Gln
            370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
                420                 425                 430

Leu Val Ile Leu Ala Pro His Ala Val Glu Ala Leu Val Lys Gln Pro
                435                 440                 445

Pro Asp Arg Trp Leu Ser Asn Ala Arg Met Thr His Tyr Gln Ala Leu
            450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
                500                 505                 510

Gln Pro Leu Pro Asp Ala Asp His Thr Trp Tyr Thr Gly Gly Ser Ser
                515                 520                 525

Leu Leu Gln Glu Gly Gln Arg Lys Ala Gly Ala Ala Val Thr Thr Glu
            530                 535                 540

Thr Glu Val Ile Trp Ala Lys Ala Leu Pro Ala Gly Thr Ser Ala Gln
545                 550                 555                 560
```

-continued

```
Arg Ala Gln Leu Ile Ala Leu Thr Gln Ala Leu Lys Met Ala Glu Gly
            565                 570                 575

Lys Lys Leu Asn Val Tyr Thr Asn Ser Arg Tyr Ala Phe Ala Thr Ala
            580                 585                 590

His Ile His Gly Glu Ile Tyr Arg Arg Arg Gly Leu Leu Thr Ser Glu
            595                 600                 605

Gly Lys Glu Ile Lys Asn Lys Asp Glu Ile Leu Ala Leu Leu Lys Ala
        610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile Glu Asn Ser Ser Pro Tyr Thr Ser Glu His Phe
            675                 680
```

<210> SEQ ID NO 718
<211> LENGTH: 2052
<212> TYPE: DNA
<213> ORGANISM: Artificial Sequence
<220> FEATURE:
<223> OTHER INFORMATION: Synthetic Oligonucleotide

<400> SEQUENCE: 718

```
atgactttaa atattgagga tgagcatcgt ttacatgaga catcaaaaga acccgacgtg      60
agcttagggt caacgtggct ttctgacttc ccccaggcgt gggcggagac tggcggaatg     120
gggttagctg tccgccaagc accgttgatc atcccgttaa aggcaacgtc tacacctgtc     180
tctatcaaac agtaccccat gagtcgtgag gcccgcctgg ggattaagcc acatattcgt     240
cgcttgctgg accaggggat cttggtccca tgtcaatctc cgtggaacac ccccccttcgt     300 cccgtgaaaa agccaggtac aaacgattat cgtccagttc aagatcttcg cgaggtcaac     360
aaacgcgtag aagacatcca tccgactgta cctaatcctt ataatctgtt atcaggcctg     420
cccccatcgc accaatggta tacagtatta gacttgaaag acgcgttctt ttgcctgcgt     480
ctgcacccaa cgtctcagcc gctgtttgcg ttcgaatggc gtgatcctga atgggaatt      540 tcgggtcagt taacctggac tcgtctgccc cagggcttta aaaacagccc cacattgttc     600
gatgaagcac ttcaccgtga cttagcagac ttccgtatcc aacacccaga cttaattctg     660
ttacagtatg ttgacgacct tttgttggcg gcaacgtctg aacttgactg tcagcaaggc     720
acacgcgcgt tattacaaac gttaggtaac ttaggatatc gtgcgtccgc gaaaaaggcg     780
caaatttgtc aaaaacaggt aaagtacctt gggtatttgc tgaaagaagg tcaacgttgg     840
ctgactgatg cgcgtaagga gaccgtaatg gggcagccta cgcctaagac gccacgcgaa     900
ttgcgtgaat ttttgggcac agcgggattc tgtcgtttat ggattcctgg gttcgctgaa     960
atggctgcac ccctgtaccc cttaacaaaa acagggacgc tttttcaactg ggggccagac    1020 cagcaaaagg cgtatcagga gatcaaacaa gctttgttga ccgcacccgc gttgggtctt    1080
ccggatttaa ccaagcccct tgagctgttc gttgatgaaa aacagggata tgcaaaagga    1140
gtattaaccc aaaagttagg cccgtggcgt cgccctgttg cttacttgag taaaaaattg    1200
gatcctgtcg cagcaggatg ccaccgtgc ttgcgtatgg tcgcggcaat tgccgttttg    1260
acaaaggatg caggtaagtt gacgatgggt caacccttac gtatcttggc tccacatgct    1320
gtagaagcgt tagtaaagca gcccccagac cgctggcttt ctaatgcgcg catgacccac    1380
```

```
tatcaggcgc ttctgcttga tacggatcgt gtacaatttg gaccagttgt agctttgaat    1440
ccagctactt tgcttcccct tccagaagaa ggacttcagc acaattgttt agatattctg    1500
gccgaggcac atgggacgcg ccctgatttg acggatcagc cactgcctga tgccgaccat    1560
acatggtata ctggcggcag tagtcttctt caagaggggc aacgcaaggc gggagcagcc    1620
gtcactacgg agaccgaagt tatctgggcc aaagcgttac ccgcgggaac atccgcgcaa    1680
cgtgcacagt taatcgctct gacacaggcc ctgaagatgg cagagggcaa aaagttgaat    1740
gtctacacca actcacgtta tgcttttgca acagcgcatt ggcatggcga aatttaccgc    1800
cgccgtggtc tgctgactag tgagggtaag gaaattaaaa ataaagatga gattcttgcg    1860
ttgttaaaag ctttattctt accaaaacgc ctttcgatca ttcattgccc ggggcatcaa    1920
aagggtcact cagcggaggc tcgtggaaac cgtatggcgg accaagctgc ccgtaaggcg    1980
gcgatcacag agaccccgga tacatcaacg ctgttgatcg aaaacagctc tccctacact    2040
agcgagcatt tt                                                        2052
```

```
<210> SEQ ID NO 719
<211> LENGTH: 684
<212> TYPE: PRT
<213> ORGANISM: Artificial Sequence
<220> FEATURE:
<223> OTHER INFORMATION: Synthetic Peptide

<400> SEQUENCE: 719

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
                20                  25                  30

Ala Trp Ala Glu Thr Gly Gly Met Gly Leu Ala Val Arg Gln Ala Pro
            35                  40                  45

Leu Ile Ile Pro Leu Lys Ala Thr Ser Thr Pro Val Ser Ile Lys Gln
        50                  55                  60

Tyr Pro Met Ser Arg Glu Ala Arg Leu Gly Ile Lys Pro His Ile Arg
65                  70                  75                  80

Arg Leu Leu Asp Gln Gly Ile Leu Val Pro Cys Gln Ser Pro Trp Asn
                85                  90                  95

Thr Pro Leu Arg Pro Val Lys Lys Pro Gly Thr Asn Asp Tyr Arg Pro
                100                 105                 110

Val Gln Asp Leu Arg Glu Val Asn Lys Arg Val Glu Asp Ile His Pro
            115                 120                 125

Thr Val Pro Asn Pro Tyr Asn Leu Leu Ser Gly Leu Pro Pro Ser His
        130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
                180                 185                 190

Phe Lys Asn Ser Pro Thr Leu Phe Asp Glu Ala Leu His Arg Asp Leu
            195                 200                 205

Ala Asp Phe Arg Ile Gln His Pro Asp Leu Ile Leu Leu Gln Tyr Val
        210                 215                 220

Asp Asp Leu Leu Leu Ala Ala Thr Ser Glu Leu Asp Cys Gln Gln Gly
225                 230                 235                 240
```

-continued

```
Thr Arg Ala Leu Leu Gln Thr Leu Gly Asn Leu Gly Tyr Arg Ala Ser
            245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Asp Ala Arg Lys Glu Thr
            275                 280                 285

Val Met Gly Gln Pro Thr Pro Lys Thr Pro Arg Glu Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
                340                 345                 350

Leu Thr Ala Pro Ala Leu Gly Leu Pro Asp Leu Thr Lys Pro Phe Glu
                355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
                420                 425                 430

Leu Arg Ile Leu Ala Pro His Ala Val Glu Ala Leu Val Lys Gln Pro
                435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
                500                 505                 510

Gln Pro Leu Pro Asp Ala Asp His Thr Trp Tyr Thr Gly Gly Ser Ser
            515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
                580                 585                 590

His Trp His Gly Glu Ile Tyr Arg Arg Arg Gly Leu Leu Thr Ser Glu
            595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655
```

Ala Arg Lys Ala Ala Ile Thr Glu Thr Pro Asp Thr Ser Thr Leu Leu
            660                 665                 670

Ile Glu Asn Ser Ser Pro Tyr Thr Ser Glu His Phe
            675                 680

<210> SEQ ID NO 720
<211> LENGTH: 2052
<212> TYPE: DNA
<213> ORGANISM: Artificial Sequence
<220> FEATURE:
<223> OTHER INFORMATION: Synthetic Oligonucleotide

<400> SEQUENCE: 720
atgactttaa atattgagga tgagcatcgt ttacatgaga catcaaaaga acccgacgtg        60
agcttagggt caacgtggct ttctgacttc ccccaggcgt gggcggagac tggcggaatg       120
gggttagctg tccgccaagc accgttgatc atcccgttaa aggcaacgtc tacacctgtc       180
tctatcaaac agtaccccat gagtcgtgag gcccgcctgg ggattaagcc acatattcgt       240
cgcttgctgg accaggggat cttggtccca tgtcaatctc cgtggaacac ccccccttcgt       300 cccgtgaaaa agccaggtac aaacgattat cgtccagttc aagatcttcg cgaggtcaac       360
aaacgcgtag aagacatcca tccgactgta cctaatcctt ataatctgtt atcaggcctg       420
cccccatcgc accaatggta tacagtatta gacttgaaag acgcgttctt ttgcctgcgt       480
ctgcacccaa cgtctcagcc gctgtttgcg ttcgaatggc gtgatcctga aatgggaatt       540
tcgggtcagt taacctggac tcgtctgccc cagggcttta aaaacagccc cacattgttc       600
gatgaagcac ttcaccgtga cttagcagac ttccgtatcc aacacccaga cttaattctg       660
ttacagtatg ttgacgacct tttgttggcg gcaacgtctg aacttgactg tcagcaaggc       720
acacgcgcgt tattacaaac gttaggtaac ttaggatatc gtgcgtccgc gaaaaaggcg       780
caaatttgtc aaaaacaggt aaagtacctt gggtatttgc tgaaagaagg tcaacgttgg       840
attactgatg cgcgtaagga gaccgtaatg gggcagccta cgcctaagac gccacgcgaa       900
ttgcgtgaat ttttgggcac agcgggattc tgtcgtttat ggattcctgg gttcgctgaa       960
atggctgcac ccctgtaccc cttaacaaaa acagggacgc ttttcaactg ggggccagac      1020
cagcaaaagg cgtatcagga gatcaaacaa gctttgttga ccgcacccgc gttgggtctt      1080
ccggatttaa ccaagcccct tgagctgttc gttgatgaaa acagggata tgcaaaagga      1140 gtattaaccc aaaagttagg cccgtggcgt cgccctgttg cttacttgag taaaaaattg      1200
gatcctgtcg cagcaggatg gccaccgtgc ttgcgtatgg tcgcggcaat tgccgttttg      1260
acaaaggatg caggtaagtt gacgatgggt caacccttac gtatcttggc tccacatgct      1320
gtagaagcgt tagtaaagca gccccccagac cgctggcttt ctaatgcgcg catgacccac      1380
tatcaggcgc ttctgcttga tacggatcgt gtacaatttg gaccagttgt agctttgaat      1440
ccagctactt tgcttcccct tccagaagaa ggacttcagc acaattgttt agatattctg      1500
gccgaggcac atgggacgcg ccctgatttg acggatcagc cactgcctga tgccgaccat      1560
acatggtata ctggcggcag tagtcttctt caagaggggc aacgcaaggc gggagcagcc      1620
gtcactacgg agaccgaagt tatctgggcc aaagcgttac ccgcgggaac atccgcgcaa      1680
cgtgcacagt taatcgctct gacacaggcc ctgaagatgg cagagggcaa aaagttgaat      1740
gtctacacca actcacgtta tgcttttgca acagcgcatt ggcatggcga aatttaccgc      1800
cgccgtggtc tgctgactag tgagggtaag gaaattaaaa ataaagatga gattcttgcg      1860
ttgttaaaag ctttattctt accaaaacgc ctttcgatca ttcattgccc ggggcatcaa      1920

-continued

```
aagggtcact cagcggaggc tcgtggaaac cgtatggcgg accaagctgc ccgtaaggcg      1980
gcgatcacag agaccccgga tacatcaacg ctgttgatcg aaaacagctc tccctacact      2040
agcgagcatt tt                                                          2052
```

<210> SEQ ID NO 721
<211> LENGTH: 684
<212> TYPE: PRT
<213> ORGANISM: Artificial Sequence
<220> FEATURE:
<223> OTHER INFORMATION: Synthetic Peptide

<400> SEQUENCE: 721

```
Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Arg Glu Ala Arg Leu Gly Ile Lys Pro His Ile Arg
65                  70                  75                  80

Arg Leu Leu Asp Gln Gly Ile Leu Val Pro Cys Gln Ser Pro Trp Asn
                85                  90                  95

Thr Pro Leu Arg Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
            115                 120                 125

Thr Val Pro Asn Pro Tyr Asn Leu Leu Ser Gly Leu Pro Pro Ser His
        130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
                180                 185                 190

Phe Lys Asn Ser Pro Thr Leu Phe Asp Glu Ala Leu His Arg Asp Leu
            195                 200                 205

Ala Asp Phe Arg Ile Gln His Pro Asp Leu Ile Leu Leu Gln Tyr Val
        210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Ile Thr Asp Ala Arg Lys Glu Thr
        275                 280                 285

Val Met Gly Gln Pro Thr Pro Lys Thr Pro Arg Glu Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335
```

```
Trp Gly Pro Asp Gln Gln Lys Ala Tyr Gln Glu Ile Lys Gln Ala Leu
        340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
        370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
                420                 425                 430

Leu Arg Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
        450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
                500                 505                 510

Gln Pro Leu Pro Asp Ala Asp His Thr Trp Tyr Thr Gly Gly Ser Ser
        515                 520                 525

Leu Leu Gln Glu Gly Gln Arg Lys Ala Gly Ala Ala Val Thr Thr Glu
        530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
                580                 585                 590

His Trp His Gly Glu Ile Tyr Arg Arg Arg Gly Leu Leu Thr Ser Glu
        595                 600                 605

Gly Lys Glu Ile Lys Asn Lys Asp Glu Ile Leu Ala Leu Leu Lys Ala
        610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
                660                 665                 670

Ile Glu Asn Ser Ser Pro Tyr Thr Ser Glu His Phe
        675                 680
```

```
<210> SEQ ID NO 722
<211> LENGTH: 2052
<212> TYPE: DNA
<213> ORGANISM: Artificial Sequence
<220> FEATURE:
<223> OTHER INFORMATION: Synthetic Oligonucleotide

<400> SEQUENCE: 722
atgactttaa atattgagga tgagcatcgt ttacatgaga catcaaaaga acccgacgtg      60
```

```
agcttagggt caacgtggct ttctgacttc ccccaggcgt gggcggagac tggcggaatg        120
gggttagctg tccgccaagc accgttgatc atcccgttaa aggcaacgtc tacacctgtc        180
tctatcaaac agtaccccat gagtcgtgag gcccgcctgg ggattaagcc acatattcgt        240
cgcttgtatg accaggggat cttggtccca tgtcaatctc cgtggaacac ccccttcgt         300 cccgtgaaaa agccaggtac aaacgattat cgtccagttc aagatcttcg cgaggtcaac        360
aaacgcgtag aagacatcca tccgactgta cctaatcctt ataatctgtt atcaggcctg        420
cccccatcgc accaatggta tacagtatta gacttgaaag acgcgttctt ttgcctgcgt        480
ctgcacccaa cgtctcagcc gctgtttgcg ttcgaatggc gtgatcctga aatgggaatt        540
tcgggtcagt taacctggac tcgtctgccc cagggcttta aaaacagccc cacattgttc        600
gatgaagcac ttcaccgtga cttagcagac ttccgtatcc aacacccaga cttaattctg        660
ttacagtatg ttgacgacct tttgttggcg gcaacgtctg aacttgactg tcagcaaggc        720
acacgcgcgt tattacaaac gttaggtaac ttaggatatc gtgcgtccgc gaaaaaggcg        780
caaatttgtc aaaaacaggt aaagtacctt gggtatttgc tgaaagaagg tcaacgttgg        840
attactgatg cgcgtaagga accgtaatg gggcagccta cgcctaagac gccacgcgaa         900
ttgcgtgaat ttttgggcac agcgggattc tgtcgtttat ggattcctgg gttcgctgaa        960
atggctgcac ccctgtaccc cttaacaaaa acagggacgc ttttcaactg ggggccagac       1020
cagcaaaagg cgtatcagga gatcaaacaa gctttgttga ccgcacccgc gttgggtctt       1080
ccggatttaa ccaagcccct tgagctgttc gttgatgaaa acagggata tgcaaaagga        1140 gtattaaccc aaaagttagg cccgtggcgt cgccctgttg cttacttgag taaaaaattg       1200
gatcctgtcg cagcaggatg gccaccgtgc ttgcgtatgg tcgcggcaat tgccgttttg       1260
acaaaggatg caggtaagtt gacgatgggt caacccttac gtatcttggc tccacatgct       1320
gtagaagcgt tagtaaagca gcccccagac cgctggcttt ctaatgcgcg catgacccac       1380
tatcaggcgc ttctgcttga tacgatcgt gtacaatttg accagttgt agctttgaat        1440 ccagctactt tgcttcccct tccagaagaa ggacttcagc acaattgttt agatattctg       1500
gccgaggcac atgggacgcg ccctgatttg acggatcagc cactgcctga tgccgaccat       1560
acatggtata ctggcggcag tagtcttctt caagaggggc aacgcaaggc gggagcagcc       1620
gtcactacgg agaccgaagt tatctgggcc aaagcgttac ccgcgggaac atccgcgcaa       1680
cgtgcacagt taatcgctct gacacaggcc ctgaagatgg cagagggcaa aaagttgaat       1740
gtctacacca actcacgtta tgcttttgca acagcgcatt ggcatggcga aatttaccgc       1800
cgccgtggtc tgctgactag tgagggtaag gaaattaaaa ataaagatga gattcttgcg       1860
ttgttaaaag ctttattctt accaaaacgc ctttcgatca ttcattgccc ggggcatcaa       1920
aagggtcact cagcggaggc tcgtggaaac cgtatggcgg accaagctgc ccgtaaggcg       1980
gcgatcacag agaccccgga tacatcaacg ctgttgatcg aaaacagctc tccctacact       2040
agcgagcatt tt                                                           2052
```

<210> SEQ ID NO 723
<211> LENGTH: 684
<212> TYPE: PRT
<213> ORGANISM: Artificial Sequence
<220> FEATURE:
<223> OTHER INFORMATION: Synthetic Peptide

<400> SEQUENCE: 723

Met Thr Leu Asn Ile Glu Asp Glu His Arg Leu His Glu Thr Ser Lys

```
1                5                      10                     15

Glu Pro Asp Val Ser Leu Gly Ser Thr Trp Leu Ser Asp Phe Pro Gln
             20                 25                 30

Ala Trp Ala Glu Thr Gly Gly Met Gly Leu Ala Val Arg Gln Ala Pro
             35                 40                 45

Leu Ile Ile Pro Leu Lys Ala Thr Ser Thr Pro Val Ser Ile Lys Gln
     50                 55                 60

Tyr Pro Met Ser Arg Glu Ala Arg Leu Gly Ile Lys Pro His Ile Arg
65                 70                 75                 80

Arg Leu Tyr Asp Gln Gly Ile Leu Val Pro Cys Gln Ser Pro Trp Asn
             85                 90                 95

Thr Pro Leu Arg Pro Val Lys Lys Pro Gly Thr Asn Asp Tyr Arg Pro
             100                105                110

Val Gln Asp Leu Arg Glu Val Asn Lys Arg Val Glu Asp Ile His Pro
             115                120                125

Thr Val Pro Asn Pro Tyr Asn Leu Leu Ser Gly Leu Pro Pro Ser His
     130                135                140

Gln Trp Tyr Thr Val Leu Asp Leu Lys Asp Ala Phe Phe Cys Leu Arg
145                150                155                160

Leu His Pro Thr Ser Gln Pro Leu Phe Ala Phe Glu Trp Arg Asp Pro
             165                170                175

Glu Met Gly Ile Ser Gly Gln Leu Thr Trp Thr Arg Leu Pro Gln Gly
             180                185                190

Phe Lys Asn Ser Pro Thr Leu Phe Asp Glu Ala Leu His Arg Asp Leu
             195                200                205

Ala Asp Phe Arg Ile Gln His Pro Asp Leu Ile Leu Leu Gln Tyr Val
     210                215                220

Asp Asp Leu Leu Leu Ala Ala Thr Ser Glu Leu Asp Cys Gln Gln Gly
225                230                235                240

Thr Arg Ala Leu Leu Gln Thr Leu Gly Asn Leu Gly Tyr Arg Ala Ser
             245                250                255

Ala Lys Lys Ala Gln Ile Cys Gln Lys Gln Val Lys Tyr Leu Gly Tyr
             260                265                270

Leu Leu Lys Glu Gly Gln Arg Trp Ile Thr Asp Ala Arg Lys Glu Thr
             275                280                285

Val Met Gly Gln Pro Thr Pro Lys Thr Pro Arg Glu Leu Arg Glu Phe
     290                295                300

Leu Gly Thr Ala Gly Phe Cys Arg Leu Trp Ile Pro Gly Phe Ala Glu
305                310                315                320

Met Ala Ala Pro Leu Tyr Pro Leu Thr Lys Thr Gly Thr Leu Phe Asn
             325                330                335

Trp Gly Pro Asp Gln Gln Lys Ala Tyr Gln Glu Ile Lys Gln Ala Leu
             340                345                350

Leu Thr Ala Pro Ala Leu Gly Leu Pro Asp Leu Thr Lys Pro Phe Glu
             355                360                365

Leu Phe Val Asp Glu Lys Gln Gly Tyr Ala Lys Gly Val Leu Thr Gln
     370                375                380

Lys Leu Gly Pro Trp Arg Arg Pro Val Ala Tyr Leu Ser Lys Lys Leu
385                390                395                400

Asp Pro Val Ala Ala Gly Trp Pro Pro Cys Leu Arg Met Val Ala Ala
             405                410                415

Ile Ala Val Leu Thr Lys Asp Ala Gly Lys Leu Thr Met Gly Gln Pro
     420                425                430
```

-continued

```
Leu Arg Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Gly Gly Ser Ser
        515                 520                 525

Leu Leu Gln Glu Gly Gln Arg Lys Ala Gly Ala Ala Val Thr Thr Glu
        530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
            580                 585                 590

His Trp His Gly Glu Ile Tyr Arg Arg Arg Gly Leu Leu Thr Ser Glu
        595                 600                 605

Gly Lys Glu Ile Lys Asn Lys Asp Glu Ile Leu Ala Leu Leu Lys Ala
        610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
                660                 665                 670

Ile Glu Asn Ser Ser Pro Tyr Thr Ser Glu His Phe
            675                 680
```

```
<210> SEQ ID NO 724
<211> LENGTH: 2052
<212> TYPE: DNA
<213> ORGANISM: Artificial Sequence
<220> FEATURE:
<223> OTHER INFORMATION: Synthetic Oligonucleotide

<400> SEQUENCE: 724
atgactttaa atattgagga tgagcatcgt ttacatgaga catcaaaaga acccgacgtg      60
agcttagggt caacgtggct ttctgacttc ccccaggcgt gggcggagac tggcggaatg     120
gggttagctg tccgccaagc accgttgatc atcccgttaa aggcaacgtc tacacctgtc     180
tctatcaaac agtaccccat gagtcgtgag gcccgcctgg ggattaagcc acatattcgt     240
cgcttgtatg accaggggat cttggtccca tgtcaatctc cgtggaacac cccccttcgt     300
cccgtgaaaa agccaggtac aaacgattat cgtccagttc aagatcttcg cgaggtcaac     360
aaacgcgtag aagacatcca tccgactgta cctaatcctt ataatctgtt atcaggcctg     420
cccccatcgc accaatggta tacagtatta gacttgaaag acgcgttctt ttgcctgcgt     480
ctgcacccaa cgtctcagcc gctgtttgcg ttcgaatggc gtgatcctga aatgggaatt     540
tcgggtcagt taacctggac tcgtctgccc cagggcttta aaaacagccc cacattgttc     600
```

-continued

```
gatgaagcac ttcaccgtga cttagcagac ttccgtatcc aacacccaga cttaattctg     660
ttacagtatg ttgacgacct tttgttggcg gcaacgtctg aacttgactg tcagcaaggc     720
acacgcgcgt tattacaaac gttaggtaac ttaggatatc gtgcgtccgc gaaaaaggcg     780
caaatttgtc aaaaacaggt aaagtacctt gggtatttgc tgaaagaagg tcaacgttgg     840
attactgatg cgcgtaagga gaccgtaatg gggcagccta cgcctaagac gccacgcgaa     900
ttgcgtgaat ttttgggcaa agcgggattc tgtcgtttat ggattcctgg gttcgctgaa     960
atggctgcac ccctgtaccc cttaacaaaa acagggacgc ttttcaactg ggggccagac    1020
cagcaaaagg cgtatcagga gatcaaacaa gctttgttga ccgcacccgc gttgggtctt    1080
ccggatttaa ccaagccctt tgagctgttc gttgatgaaa acagggata tgcaaaagga     1140 gtattaaccc aaaagttagg cccgtggcgt cgccctgttg cttacttgag taaaaaattg    1200
gatcctgtcg cagcaggatg gccaccgtgc ttgcgtatgg tcgcggcaat tgccgttttg    1260
acaaaggatg caggtaagtt gacgatgggt caacccttaa acatcttggc tccacatgct    1320
gtagaagcgt tagtaaagca gcccccagac cgctggcttt ctaatgcgcg catgacccac    1380
tatcaggcgc ttctgcttga tacggatcgt gtacaatttg gaccagttgt agctttgaat    1440
ccagctactt tgcttcccct tccagaagaa ggacttcagc acaattgttt agatattctg    1500
gccgaggcac atgggacgcg ccctgatttg acggatcagc cactgcctga tgccgaccat    1560
acatggtata ctggcggcag tagtcttctt caagaggggc aacgcaaggc gggagcagcc    1620
gtcactacgg agaccgaagt tatctgggcc aaagcgttac ccgcgggaac atccgcgcaa    1680
cgtgcacagt taatcgctct gacacaggcc ctgaagatgg cagagggcaa aaagttgaat    1740
gtctacacca actcacgtta tgcttttgca acagcgcatt ggcatggcga aatttaccgc    1800
cgccgtggtc tgctgactag tgagggtaag gaaattaaaa ataaagatga gattcttgcg    1860
ttgttaaaag ctttattctt accaaaacgc ctttcgatca ttcattgccc ggggcatcaa    1920
aagggtcact cagcggaggc tcgtggaaac cgtatggcgg accaagctgc ccgtaaggcg    1980
gcgatcacag agacccccgga tacatcaacg ctgttgatcg aaaacagctc tccctacact    2040
agcgagcatt tt                                                         2052
```

```
<210> SEQ ID NO 725
<211> LENGTH: 684
<212> TYPE: PRT
<213> ORGANISM: Artificial Sequence
<220> FEATURE:
<223> OTHER INFORMATION: Synthetic Peptide

<400> SEQUENCE: 725

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
                20                  25                  30

Ala Trp Ala Glu Thr Gly Gly Met Gly Leu Ala Val Arg Gln Ala Pro
            35                  40                  45

Leu Ile Ile Pro Leu Lys Ala Thr Ser Thr Pro Val Ser Ile Lys Gln
        50                  55                  60

Tyr Pro Met Ser Arg Glu Ala Arg Leu Gly Ile Lys Pro His Ile Arg
65                  70                  75                  80

Arg Leu Tyr Asp Gln Gly Ile Leu Val Pro Cys Gln Ser Pro Trp Asn
                85                  90                  95

Thr Pro Leu Arg Pro Val Lys Lys Pro Gly Thr Asn Asp Tyr Arg Pro
```

-continued

```
                100             105             110

Val Gln Asp Leu Arg Glu Val Asn Lys Arg Val Glu Asp Ile His Pro
            115             120             125

Thr Val Pro Asn Pro Tyr Asn Leu Leu Ser Gly Leu Pro Pro Ser His
        130             135             140

Gln Trp Tyr Thr Val Leu Asp Leu Lys Asp Ala Phe Phe Cys Leu Arg
145             150             155             160

Leu His Pro Thr Ser Gln Pro Leu Phe Ala Phe Glu Trp Arg Asp Pro
            165             170             175

Glu Met Gly Ile Ser Gly Gln Leu Thr Trp Thr Arg Leu Pro Gln Gly
        180             185             190

Phe Lys Asn Ser Pro Thr Leu Phe Asp Glu Ala Leu His Arg Asp Leu
        195             200             205

Ala Asp Phe Arg Ile Gln His Pro Asp Leu Ile Leu Leu Gln Tyr Val
        210             215             220

Asp Asp Leu Leu Leu Ala Ala Thr Ser Glu Leu Asp Cys Gln Gln Gly
225             230             235             240

Thr Arg Ala Leu Leu Gln Thr Leu Gly Asn Leu Gly Tyr Arg Ala Ser
            245             250             255

Ala Lys Lys Ala Gln Ile Cys Gln Lys Gln Val Lys Tyr Leu Gly Tyr
            260             265             270

Leu Leu Lys Glu Gly Gln Arg Trp Ile Thr Asp Ala Arg Lys Glu Thr
            275             280             285

Val Met Gly Gln Pro Thr Pro Lys Thr Pro Arg Glu Leu Arg Glu Phe
    290             295             300

Leu Gly Lys Ala Gly Phe Cys Arg Leu Trp Ile Pro Gly Phe Ala Glu
305             310             315             320

Met Ala Ala Pro Leu Tyr Pro Leu Thr Lys Thr Gly Thr Leu Phe Asn
            325             330             335

Trp Gly Pro Asp Gln Gln Lys Ala Tyr Gln Glu Ile Lys Gln Ala Leu
            340             345             350

Leu Thr Ala Pro Ala Leu Gly Leu Pro Asp Leu Thr Lys Pro Phe Glu
            355             360             365

Leu Phe Val Asp Glu Lys Gln Gly Tyr Ala Lys Gly Val Leu Thr Gln
    370             375             380

Lys Leu Gly Pro Trp Arg Arg Pro Val Ala Tyr Leu Ser Lys Lys Leu
385             390             395             400

Asp Pro Val Ala Ala Gly Trp Pro Pro Cys Leu Arg Met Val Ala Ala
            405             410             415

Ile Ala Val Leu Thr Lys Asp Ala Gly Lys Leu Thr Met Gly Gln Pro
            420             425             430

Leu Asn Ile Leu Ala Pro His Ala Val Glu Ala Leu Val Lys Gln Pro
            435             440             445

Pro Asp Arg Trp Leu Ser Asn Ala Arg Met Thr His Tyr Gln Ala Leu
    450             455             460

Leu Leu Asp Thr Asp Arg Val Gln Phe Gly Pro Val Val Ala Leu Asn
465             470             475             480

Pro Ala Thr Leu Leu Pro Leu Pro Glu Glu Gly Leu Gln His Asn Cys
            485             490             495

Leu Asp Ile Leu Ala Glu Ala His Gly Thr Arg Pro Asp Leu Thr Asp
            500             505             510

Gln Pro Leu Pro Asp Ala Asp His Thr Trp Tyr Thr Gly Gly Ser Ser
            515             520             525
```

-continued

```
Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
                580                 585                 590

His Trp His Gly Glu Ile Tyr Arg Arg Arg Gly Leu Leu Thr Ser Glu
                595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
                660                 665                 670

Ile Glu Asn Ser Ser Pro Tyr Thr Ser Glu His Phe
                675                 680
```

```
<210> SEQ ID NO 726
<211> LENGTH: 2052
<212> TYPE: DNA
<213> ORGANISM: Artificial Sequence
<220> FEATURE:
<223> OTHER INFORMATION: Synthetic Oligonucleotide

<400> SEQUENCE: 726 atgacttaa atattgagga tgagcatcgt ttacatgaga catcaaaaga acccgacgtg        60
agcttagggt caacgtggct ttctgacttc ccccaggcgt gggcggagac tggcggaatg       120
gggttagctg tccgccaagc accgttgatc atcccgttaa aggcaacgtc tacacctgtc       180
tctatcaaac agtaccccat gagtcgtgag gcccgcctgg ggattaagcc acatattcgt       240
cgcttgctgg accaggggat cttggtccca tgtcaatctc cgtggaacac cccccttcgt       300
cccgtgaaaa agccaggtac aaacgattat cgtccagttc aagatcttcg cgaggtcaac       360
aaacgcgtag aagacatcca tccgactgta cctaatcctt ataatctgtt atcaggcctg       420
cccccatcgc accaatggta tacagtatta gacttgaaag acgcgttctt ttgcctgcgt       480
ctgcacccaa cgtctcagcc gctgtttgcg ttcgaatggc gtgatcctga atgggaatt        540 tcgggtcagt taacctggac tcgtctgccc cagggcttta aaaacagccc cacattgttc       600
gatgaagcac ttcaccgtga cttagcagac ttccgtatcc aacacccaga cttaattctg       660
ttacagtatg ttgacgacct tttgttggcg gcaacgtctg aacttgactg tcagcaaggc       720
acacgcgcgt tattacaaac gttaggtaac ttaggatatc gtgcgtccgc gaaaaaggcg       780
caaatttgtc aaaaacaggt aaagtacctt gggtatttgc tgaaagaagg tcaacgttgg       840
ctgactgatg cgcgtaagga gaccgtaatg gggcagccta cgcctaagac gccacgcgaa       900
ttgcgtgaat ttttgggcaa agcgggattc tgtcgtttat ggattcctgg gttcgctgaa       960
atggctgcac ccctgtaccc cttaacaaaa acagggacgc ttttcaactg ggggccagac      1020
cagcaaaagg cgtatcagga gatcaaacaa gctttgttga ccgcacccgc gttgggtctt      1080
ccggatttaa ccaagccctt tgagctgttc gttgatgaaa acagggata tgcaaaagga      1140
```

-continued

```
gtattaaccc aaaagttagg cccgtggcgt cgccctgttg cttacttgag taaaaaattg   1200
gatcctgtcg cagcaggatg gccaccgtgc ttgcgtatgg tcgcggcaat tgccgttttg   1260
acaaaggatg caggtaagtt gacgatgggt caacccttac gtatcttggc tccacatgct   1320
gtagaagcgt tagtaaagca gcccccagac cgctggcttt ctaatgcgcg catgacccac   1380
tatcaggcgc ttctgcttga tacggatcgt gtacaatttg gaccagttgt agctttgaat   1440
ccagctactt tgcttcccct tccagaagaa ggacttcagc acaattgttt agatattctg   1500
gccgaggcac atgggacgcg ccctgatttg acggatcagc cactgcctga tgccgaccat   1560
acatggtata ctggcggcag tagtcttctt caagaggggc aacgcaaggc gggagcagcc   1620
gtcactacgg agaccgaagt tatctgggcc aaagcgttac ccgcgggaac atccgcgcaa   1680
cgtgcacagt taatcgctct gacacaggcc ctgaagatgg cagagggcaa aaagttgaat   1740
gtctacacca actcacgtta tgcttttgca acagcgcatg aacatggcga aatttaccgc   1800
cgccgtggtc tgctgactag tgagggtaag gaaattaaaa ataaagatga gattcttgcg   1860
ttgttaaaag ctttattctt accaaaacgc ctttcgatca ttcattgccc ggggcatcaa   1920
aagggtcact cagcggaggc tcgtggaaac cgtatggcgg accaagctgc ccgtaaggcg   1980
gcgatcacag agaccccgga tacatcaacg ctgttgatcg aaaacagctc tccctacact   2040
agcgagcatt tt                                                        2052
```

```
<210> SEQ ID NO 727
<211> LENGTH: 684
<212> TYPE: PRT
<213> ORGANISM: Artificial Sequence
<220> FEATURE:
<223> OTHER INFORMATION: Synthetic Peptide

<400> SEQUENCE: 727

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Arg Glu Ala Arg Leu Gly Ile Lys Pro His Ile Arg
65                  70                  75                  80

Arg Leu Leu Asp Gln Gly Ile Leu Val Pro Cys Gln Ser Pro Trp Asn
                85                  90                  95

Thr Pro Leu Arg Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
```

-continued

```
            195                  200                  205

Ala Asp Phe Arg Ile Gln His Pro Asp Leu Ile Leu Leu Gln Tyr Val
    210                  215                  220

Asp Asp Leu Leu Leu Ala Ala Thr Ser Glu Leu Asp Cys Gln Gln Gly
225                  230                  235                  240

Thr Arg Ala Leu Leu Gln Thr Leu Gly Asn Leu Gly Tyr Arg Ala Ser
                245                  250                  255

Ala Lys Lys Ala Gln Ile Cys Gln Lys Gln Val Lys Tyr Leu Gly Tyr
            260                  265                  270

Leu Leu Lys Glu Gly Gln Arg Trp Leu Thr Asp Ala Arg Lys Glu Thr
        275                  280                  285

Val Met Gly Gln Pro Thr Pro Lys Thr Pro Arg Glu Leu Arg Glu Phe
    290                  295                  300

Leu Gly Lys Ala Gly Phe Cys Arg Leu Trp Ile Pro Gly Phe Ala Glu
305                  310                  315                  320

Met Ala Ala Pro Leu Tyr Pro Leu Thr Lys Thr Gly Thr Leu Phe Asn
                325                  330                  335

Trp Gly Pro Asp Gln Gln Lys Ala Tyr Gln Glu Ile Lys Gln Ala Leu
            340                  345                  350

Leu Thr Ala Pro Ala Leu Gly Leu Pro Asp Leu Thr Lys Pro Phe Glu
        355                  360                  365

Leu Phe Val Asp Glu Lys Gln Gly Tyr Ala Lys Gly Val Leu Thr Gln
    370                  375                  380

Lys Leu Gly Pro Trp Arg Arg Pro Val Ala Tyr Leu Ser Lys Lys Leu
385                  390                  395                  400

Asp Pro Val Ala Ala Gly Trp Pro Pro Cys Leu Arg Met Val Ala Ala
                405                  410                  415

Ile Ala Val Leu Thr Lys Asp Ala Gly Lys Leu Thr Met Gly Gln Pro
            420                  425                  430

Leu Arg Ile Leu Ala Pro His Ala Val Glu Ala Leu Val Lys Gln Pro
        435                  440                  445

Pro Asp Arg Trp Leu Ser Asn Ala Arg Met Thr His Tyr Gln Ala Leu
    450                  455                  460

Leu Leu Asp Thr Asp Arg Val Gln Phe Gly Pro Val Val Ala Leu Asn
465                  470                  475                  480

Pro Ala Thr Leu Leu Pro Leu Pro Glu Glu Gly Leu Gln His Asn Cys
                485                  490                  495

Leu Asp Ile Leu Ala Glu Ala His Gly Thr Arg Pro Asp Leu Thr Asp
            500                  505                  510

Gln Pro Leu Pro Asp Ala Asp His Thr Trp Tyr Thr Gly Gly Ser Ser
        515                  520                  525

Leu Leu Gln Glu Gly Gln Arg Lys Ala Gly Ala Ala Val Thr Thr Glu
    530                  535                  540

Thr Glu Val Ile Trp Ala Lys Ala Leu Pro Ala Gly Thr Ser Ala Gln
545                  550                  555                  560

Arg Ala Gln Leu Ile Ala Leu Thr Gln Ala Leu Lys Met Ala Glu Gly
                565                  570                  575

Lys Lys Leu Asn Val Tyr Thr Asn Ser Arg Tyr Ala Phe Ala Thr Ala
            580                  585                  590

His Glu His Gly Glu Ile Tyr Arg Arg Arg Gly Leu Leu Thr Ser Glu
        595                  600                  605

Gly Lys Glu Ile Lys Asn Lys Asp Glu Ile Leu Ala Leu Leu Lys Ala
    610                  615                  620
```

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile Glu Asn Ser Ser Pro Tyr Thr Ser Glu His Phe
        675                 680

<210> SEQ ID NO 728
<211> LENGTH: 2052
<212> TYPE: DNA
<213> ORGANISM: Artificial Sequence
<220> FEATURE:
<223> OTHER INFORMATION: Synthetic Oligonucleotide

<400> SEQUENCE: 728
atgactttaa atattgagga tgagcatcgt ttacatgaga catcaaaaga acccgacgtg      60
agcttagggt caacgtggct ttctgacttc ccccaggcgt gggcggagac tggcggaatg     120
gggttagctg tccgccaagc accgttgatc atcccgttaa aggcaacgtc tacacctgtc     180
tctatcaaac agtaccccat gagtcgtgag gcccgcctgg ggattaagcc acatattcgt     240
cgcttgtatg accaggggat cttggtccca tgtcaatctc cgtggaacac cccccttcgt     300
cccgtgaaaa agccaggtac aaacgattat cgtccagttc aagatcttcg cgaggtcaac     360
aaacgcgtag aagacatcca tccgactgta cctaatcctt ataatctgtt atcaggcctg     420
cccccatcgc accaatggta tacagtatta gacttgaaag acgcgttctt ttgcctgcgt     480
ctgcacccaa cgtctcagcc gctgtttgcg ttcgaatggc gtgatcctga aatgggaatt     540
tcgggtcagt taacctggac tcgtctgccc cagggcttta aaaacagccc cacattgttc     600
gatgaagcac ttcaccgtga cttagcagac ttccgtatcc aacacccaga cttaattctg     660
ttacagtatg ttgacgacct tttgttggcg gcaacgtctg aacttgactg tcagcaaggc     720
acacgcgcgt tattacaaac gttaggtaac ttaggatatc gtgcgtccgc gaaaaaggcg     780
caaatttgtc aaaaacaggt aaagtacctt gggtatttgc tgaaagaagg tcaacgttgg     840
attactgatg cgcgtaagga gaccgtaatg gggcagccta cgcctaagac gccacgcgaa     900
ttgcgtgaat ttttgggcac agcgggattc tgtcgtttat ggattcctgg gttcgctgaa     960
atggctgcac ccctgtaccc cttaacaaaa acagggacgc ttttcaactg ggggccagac    1020
cagcaaaagg cgtatcagga gatcaaacaa gctttgttga ccgcacccgc gttgggtctt    1080
ccggatttaa ccaagcccct tgagctgttc gttgatgaaa acagggata tgcaaaagga    1140 gtattaaccc aaaagttagg cccgtggcgt cgccctgttg cttacttgag taaaaaattg    1200
gatcctgtcg cagcaggatg gccaccgtgc ttgcgtatgg tcgcggcaat tgccgttttg    1260
acaaaggatg caggtaagtt gacgatgggt caacccttac gtatcttggc tccacatgct    1320
gtagaagcgt tagtaaagca gccccagac cgctggcttt ctaatgcgcg catgacccac    1380
tatcaggcgc ttctgcttga tacggatcgt gtacaatttg gaccagttgt agctttgaat    1440
ccagctactt tgcttcccct tccagaagaa ggacttcagc acaattgttt agatattctg    1500
gccgaggcac atgggacgcg ccctgatttg acggatcagc cactgcctga tgccgaccat    1560
acatggtata ctggcggcag tagtcttctt caagagggc aacgcaaggc gggagcagcc    1620
gtcactacgg agaccgaagt tatctgggcc aaagcgttac ccgcgggaac atccgcgcaa    1680

```
cgtgcacagt taatcgctct gacacaggcc ctgaagatgg cagagggcaa aaagttgaat    1740
gtctacacca actcacgtta tgcttttgca acagcgcatg aacatggcga aatttaccgc    1800
cgccgtggtc tgctgactag tgagggtaag gaaattaaaa ataaagatga gattcttgcg    1860
ttgttaaaag ctttattctt accaaaacgc ctttcgatca ttcattgccc ggggcatcaa    1920
aagggtcact cagcggaggc tcgtggaaac cgtatggcgg accagctgc ccgtaaggcg     1980 gcgatcacag agaccccgga tacatcaacg ctgttgatcg aaaacagctc tccctacact    2040
agcgagcatt tt                                                        2052
```

<210> SEQ ID NO 729
<211> LENGTH: 684
<212> TYPE: PRT
<213> ORGANISM: Artificial Sequence
<220> FEATURE:
<223> OTHER INFORMATION: Synthetic Peptide

<400> SEQUENCE: 729

```
Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Arg Glu Ala Arg Leu Gly Ile Lys Pro His Ile Arg
65                  70                  75                  80

Arg Leu Tyr Asp Gln Gly Ile Leu Val Pro Cys Gln Ser Pro Trp Asn
                85                  90                  95

Thr Pro Leu Arg Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
            115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
            195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Ile Thr Asp Ala Arg Lys Glu Thr
            275                 280                 285

Val Met Gly Gln Pro Thr Pro Lys Thr Pro Arg Glu Leu Arg Glu Phe
```

```
        290              295              300

Leu Gly Thr Ala Gly Phe Cys Arg Leu Trp Ile Pro Gly Phe Ala Glu
305              310              315              320

Met Ala Ala Pro Leu Tyr Pro Leu Thr Lys Thr Gly Thr Leu Phe Asn
                 325              330              335

Trp Gly Pro Asp Gln Gln Lys Ala Tyr Gln Glu Ile Lys Gln Ala Leu
                 340              345              350

Leu Thr Ala Pro Ala Leu Gly Leu Pro Asp Leu Thr Lys Pro Phe Glu
                 355              360              365

Leu Phe Val Asp Glu Lys Gln Gly Tyr Ala Lys Gly Val Leu Thr Gln
                 370              375              380

Lys Leu Gly Pro Trp Arg Arg Pro Val Ala Tyr Leu Ser Lys Lys Leu
385              390              395              400

Asp Pro Val Ala Ala Gly Trp Pro Pro Cys Leu Arg Met Val Ala Ala
                 405              410              415

Ile Ala Val Leu Thr Lys Asp Ala Gly Lys Leu Thr Met Gly Gln Pro
                 420              425              430

Leu Arg Ile Leu Ala Pro His Ala Val Glu Ala Leu Val Lys Gln Pro
                 435              440              445

Pro Asp Arg Trp Leu Ser Asn Ala Arg Met Thr His Tyr Gln Ala Leu
                 450              455              460

Leu Leu Asp Thr Asp Arg Val Gln Phe Gly Pro Val Val Ala Leu Asn
465              470              475              480

Pro Ala Thr Leu Leu Pro Leu Pro Glu Glu Gly Leu Gln His Asn Cys
                 485              490              495

Leu Asp Ile Leu Ala Glu Ala His Gly Thr Arg Pro Asp Leu Thr Asp
                 500              505              510

Gln Pro Leu Pro Asp Ala Asp His Thr Trp Tyr Thr Gly Gly Ser Ser
                 515              520              525

Leu Leu Gln Glu Gly Gln Arg Lys Ala Gly Ala Ala Val Thr Thr Glu
                 530              535              540

Thr Glu Val Ile Trp Ala Lys Ala Leu Pro Ala Gly Thr Ser Ala Gln
545              550              555              560

Arg Ala Gln Leu Ile Ala Leu Thr Gln Ala Leu Lys Met Ala Glu Gly
                 565              570              575

Lys Lys Leu Asn Val Tyr Thr Asn Ser Arg Tyr Ala Phe Ala Thr Ala
                 580              585              590

His Glu His Gly Glu Ile Tyr Arg Arg Arg Gly Leu Leu Thr Ser Glu
                 595              600              605

Gly Lys Glu Ile Lys Asn Lys Asp Glu Ile Leu Ala Leu Leu Lys Ala
                 610              615              620

Leu Phe Leu Pro Lys Arg Leu Ser Ile Ile His Cys Pro Gly His Gln
625              630              635              640

Lys Gly His Ser Ala Glu Ala Arg Gly Asn Arg Met Ala Asp Gln Ala
                 645              650              655

Ala Arg Lys Ala Ala Ile Thr Glu Thr Pro Asp Thr Ser Thr Leu Leu
                 660              665              670

Ile Glu Asn Ser Ser Pro Tyr Thr Ser Glu His Phe
                 675              680
```

```
<210> SEQ ID NO 730
<211> LENGTH: 2052
<212> TYPE: DNA
<213> ORGANISM: Artificial Sequence
```

<220> FEATURE:
<223> OTHER INFORMATION: Synthetic Oligonucleotide

<400> SEQUENCE: 730

```
atgactttaa atattgagga tgagcatcgt ttacatgaga catcaaaaga acccgacgtg         60
agcttagggt caacgtggct ttctgacttc ccccaggcgt gggcggagac tggcggaatg        120
gggttagctg tccgccaagc accgttgatc atcccgttaa aggcaacgtc tacacctgtc        180
tctatcaaac agtaccccat gagtcgtgag gcccgcctgg ggattaagcc acatattcgt        240
cgcttgtatg accaggggat cttggtccca tgtcaatctc cgtggaacac ccccccttcgt       300 cccgtgaaaa agccaggtac aaacgattat cgtccagttc aagatcttcg cgaggtcaac        360
aaacgcgtag aagacatcca tccgactgta cctaatcctt ataatctgtt atcaggcctg        420
cccccatcgc accaatggta tacagtatta gacttgaaag acgcgttctt ttgcctgcgt        480
ctgcacccaa cgtctcagcc gctgtttgcg ttcgaatggc gtgatcctga aatgggaatt       540
tcgggtcagt taacctggac tcgtctgccc cagggcttta aaaacagccc cacattgttc        600
gatgaagcac ttcaccgtga cttagcagac ttccgtatcc aacacccaga cttaattctg        660
ttacagtatg ttgacgacct tttgttggcg gcaacgtctg aacttgactg tcagcaaggc        720
acacgcgcgt tattacaaac gttaggtaac ttaggatatc gtgcgtccgc gaaaaaggcg        780
caaatttgtc aaaaacaggt aaagtacctt gggtatttgc tgaaagaagg tcaacgttgg        840
attactgatg cgcgtaagga gaccgtaatg gggcagccta cgcctaagac gccacgcgaa        900
ttgcgtgaat ttttgggcaa agcgggattc tgtcgtttat ggattcctgg gttcgctgaa        960
atggctgcac ccctgtaccc cttaacaaaa acagggacgc ttttcaactg ggggccagac       1020
cagcaaaagg cgtatcagga gatcaaacaa gctttgttga ccgcacccgc gttgggtctt       1080
ccggatttaa ccaagccctt tgagctgttc gttgatgaaa aacagggata tgcaaaagga       1140
gtattaaccc aaaagttagg cccgtggcgt cgccctgttg cttacttgag taaaaaattg       1200
gatcctgtcg cagcaggatg gccaccgtgc ttgcgtatgg tcgcggcaat tgccgttttg       1260
acaaaggatg caggtaagtt gacgatgggt caacccttac gtatcttggc tccacatgct       1320
gtagaagcgt tagtaaagca gcccccagac cgctggcttt ctaatgcgcg catgacccac       1380
tatcaggcgc ttctgcttga tacggatcgt gtacaatttg gaccagttgt agctttgaat       1440
ccagctactt tgcttcccct tccagaagaa ggacttcagc acaattgttt agatattctg       1500
gccgaggcac atgggacgcg ccctgatttg acggatcagc cactgcctga tgccgaccat       1560
acatggtata ctggcggcag tagtcttctt caagaggggc aacgcaaggc gggagcagcc       1620
gtcactacgg agaccgaagt tatctgggcc aaagcgttac ccgcgggaac atccgcgcaa       1680
cgtgcacagt taatcgctct gacacaggcc ctgaagatgg cagagggcaa aaagttgaat       1740
gtctacacca actcacgtta tgcttttgca acagcgcatg aacatggcga aatttaccgc       1800
cgccgtggtc tgctgactag tgagggtaag gaaattaaaa ataaagatga gattcttgcg       1860
ttgttaaaag ctttattctt accaaaacgc ctttcgatca ttcattgccc ggggcatcaa       1920
aagggtcact cagcggaggc tcgtggaaac cgtatggcgg accaagctgc ccgtaaggcg       1980
gcgatcacag agacccccgga tacatcaacg ctgttgatcg aaaacagctc tccctacact       2040
agcgagcatt tt                                                          2052
```

<210> SEQ ID NO 731
<211> LENGTH: 684
<212> TYPE: PRT

```
<213> ORGANISM: Artificial Sequence
<220> FEATURE:
<223> OTHER INFORMATION: Synthetic Peptide

<400> SEQUENCE: 731

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
                20                  25                  30

Ala Trp Ala Glu Thr Gly Gly Met Gly Leu Ala Val Arg Gln Ala Pro
            35                  40                  45

Leu Ile Ile Pro Leu Lys Ala Thr Ser Thr Pro Val Ser Ile Lys Gln
        50                  55                  60

Tyr Pro Met Ser Arg Glu Ala Arg Leu Gly Ile Lys Pro His Ile Arg
65                  70                  75                  80

Arg Leu Tyr Asp Gln Gly Ile Leu Val Pro Cys Gln Ser Pro Trp Asn
                85                  90                  95

Thr Pro Leu Arg Pro Val Lys Lys Pro Gly Thr Asn Asp Tyr Arg Pro
                100                 105                 110

Val Gln Asp Leu Arg Glu Val Asn Lys Arg Val Glu Asp Ile His Pro
            115                 120                 125

Thr Val Pro Asn Pro Tyr Asn Leu Leu Ser Gly Leu Pro Pro Ser His
        130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
                180                 185                 190

Phe Lys Asn Ser Pro Thr Leu Phe Asp Glu Ala Leu His Arg Asp Leu
            195                 200                 205

Ala Asp Phe Arg Ile Gln His Pro Asp Leu Ile Leu Leu Gln Tyr Val
        210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
                260                 265                 270

Leu Leu Lys Glu Gly Gln Arg Trp Ile Thr Asp Ala Arg Lys Glu Thr
            275                 280                 285

Val Met Gly Gln Pro Thr Pro Lys Thr Pro Arg Glu Leu Arg Glu Phe
        290                 295                 300

Leu Gly Lys Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
                340                 345                 350

Leu Thr Ala Pro Ala Leu Gly Leu Pro Asp Leu Thr Lys Pro Phe Glu
            355                 360                 365

Leu Phe Val Asp Glu Lys Gln Gly Tyr Ala Lys Gly Val Leu Thr Gln
        370                 375                 380

Lys Leu Gly Pro Trp Arg Arg Pro Val Ala Tyr Leu Ser Lys Lys Leu
```

-continued

```
385                     390                     395                     400

Asp Pro Val Ala Ala Gly Trp Pro Pro Cys Leu Arg Met Val Ala Ala
                405                     410                     415

Ile Ala Val Leu Thr Lys Asp Ala Gly Lys Leu Thr Met Gly Gln Pro
                420                     425                     430

Leu Arg Ile Leu Ala Pro His Ala Val Glu Ala Leu Val Lys Gln Pro
            435                     440                     445

Pro Asp Arg Trp Leu Ser Asn Ala Arg Met Thr His Tyr Gln Ala Leu
        450                     455                     460

Leu Leu Asp Thr Asp Arg Val Gln Phe Gly Pro Val Val Ala Leu Asn
465                     470                     475                     480

Pro Ala Thr Leu Leu Pro Leu Pro Glu Glu Gly Leu Gln His Asn Cys
                485                     490                     495

Leu Asp Ile Leu Ala Glu Ala His Gly Thr Arg Pro Asp Leu Thr Asp
            500                     505                     510

Gln Pro Leu Pro Asp Ala Asp His Thr Trp Tyr Thr Gly Gly Ser Ser
            515                     520                     525

Leu Leu Gln Glu Gly Gln Arg Lys Ala Gly Ala Ala Val Thr Thr Glu
        530                     535                     540

Thr Glu Val Ile Trp Ala Lys Ala Leu Pro Ala Gly Thr Ser Ala Gln
545                     550                     555                     560

Arg Ala Gln Leu Ile Ala Leu Thr Gln Ala Leu Lys Met Ala Glu Gly
            565                     570                     575

Lys Lys Leu Asn Val Tyr Thr Asn Ser Arg Tyr Ala Phe Ala Thr Ala
            580                     585                     590

His Glu His Gly Glu Ile Tyr Arg Arg Arg Gly Leu Leu Thr Ser Glu
        595                     600                     605

Gly Lys Glu Ile Lys Asn Lys Asp Glu Ile Leu Ala Leu Leu Lys Ala
        610                     615                     620

Leu Phe Leu Pro Lys Arg Leu Ser Ile Ile His Cys Pro Gly His Gln
625                     630                     635                     640

Lys Gly His Ser Ala Glu Ala Arg Gly Asn Arg Met Ala Asp Gln Ala
            645                     650                     655

Ala Arg Lys Ala Ala Ile Thr Glu Thr Pro Asp Thr Ser Thr Leu Leu
            660                     665                     670

Ile Glu Asn Ser Ser Pro Tyr Thr Ser Glu His Phe
            675                     680
```